United States Patent
Lopes et al.

(10) Patent No.: US 11,286,490 B2
(45) Date of Patent: Mar. 29, 2022

(54) FORMATION OF ALKENES THROUGH ENZYMATIC DEHYDRATION OF ALKANOLS

(71) Applicant: BRASKEM S.A., Sao Paulo (BR)

(72) Inventors: Mateus Schreiner Lopes, Campinas (BR); Daniel Johannes Koch, Campinas (BR); Iuri Estrada Gouvea, Campinas (BR); Debora Noma Okamoto, Campinas (BR); Veronica Leite Queiroz, Campinas (BR)

(73) Assignee: BRASKEM S.A., Sao Paulo (BR)

( * ) Notice: Subject to any disclaimer, the term of this patent is extended or adjusted under 35 U.S.C. 154(b) by 0 days.

(21) Appl. No.: 16/317,406

(22) PCT Filed: Jul. 12, 2017

(86) PCT No.: PCT/US2017/041732
§ 371 (c)(1),
(2) Date: Jan. 11, 2019

(87) PCT Pub. No.: WO2018/013701
PCT Pub. Date: Jan. 18, 2018

(65) Prior Publication Data
US 2019/0323016 A1    Oct. 24, 2019

Related U.S. Application Data

(60) Provisional application No. 62/361,109, filed on Jul. 12, 2016.

(51) Int. Cl.
| | | |
|---|---|---|
| *C12P 5/02* | (2006.01) | |
| *C12N 9/90* | (2006.01) | |
| *C12N 9/88* | (2006.01) | |
| *C12N 15/52* | (2006.01) | |
| *C12P 7/04* | (2006.01) | |

(52) U.S. Cl.
CPC ............... *C12N 15/52* (2013.01); *C12N 9/88* (2013.01); *C12N 9/90* (2013.01); *C12P 5/026* (2013.01); *C12P 7/04* (2013.01); *C12Y 402/01127* (2013.01); *C12Y 504/04004* (2013.01)

(58) Field of Classification Search
CPC .......... C12N 9/88; C12N 9/90; C12N 9/0008; C12N 9/1025; C12P 5/026; C12P 7/04; C12P 2203/00; C12P 7/26; C12Y 207/01047; C12Y 203/01009
USPC .... 435/252.2, 166, 167, 160, 157, 189, 195, 435/233
See application file for complete search history.

(56) References Cited

U.S. PATENT DOCUMENTS

| | | |
|---|---|---|
| 2007/0092957 A1 | 4/2007 | Donaldson et al. |
| 2009/0081746 A1 | 3/2009 | Liao et al. |
| 2009/0246842 A1 | 10/2009 | Hawkins et al. |
| 2011/0165644 A1 | 7/2011 | Marliere |
| 2013/0109064 A1 | 5/2013 | Osterhout et al. |
| 2014/0065686 A1 | 3/2014 | Marliere |
| 2014/0141482 A1 | 5/2014 | Pearlman et al. |

FOREIGN PATENT DOCUMENTS

| | | |
|---|---|---|
| EP | 2336341 A1 | 6/2011 |
| WO | WO 2008/067627 A2 | 6/2008 |
| WO | WO 2009/008377 A1 | 1/2009 |
| WO | WO 2009/103026 A1 | 8/2009 |
| WO | WO 2010/099201 A1 | 9/2010 |
| WO | WO 2011/022651 A1 | 2/2011 |
| WO | WO 2011/076691 A1 | 6/2011 |
| WO | 2012174439 A2 | 12/2012 |
| WO | 2013082542 A2 | 6/2013 |
| WO | WO 2013/090915 A1 | 6/2013 |
| WO | 2013188546 A2 | 12/2013 |
| WO | 2014033129 A1 | 3/2014 |
| WO | WO 2014/064198 A1 | 5/2014 |
| WO | WO 2014/184345 A1 | 11/2014 |
| WO | WO 2015/002977 A1 | 1/2015 |
| WO | WO 2015/042588 A1 | 3/2015 |
| WO | WO 2015/082447 A1 | 6/2015 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Bermejo et al., "Expression of Clostridium acetobutylicum ATCC 824 Genes in *Escherichia coli* for Acetone Production and Acetate Detoxification," Applied and Enviromental Microbiology, Mar. 1998, 64(3):1079-1085.
Brodkorb et al., "Linalool dehydratase-isomerase, a bifunctional enzyme in the anaerobic degradation of monoterpenes," The Journal of Biological Chemistry (2010) 285(40):30436-30442.
Cameron et al., "Metabolic Engineering of Propanediol Pathways," Biotechnol. Prog. (1998) 14: 116-125.
Ehrenberger et al., "Structure-Guided Engineering of Xylitol Dehydrogenase Cosubstrate Specificity," Structure, Mar. 2006, 14: 567-575.

(Continued)

*Primary Examiner* — Robert B Mondesi
*Assistant Examiner* — Mohammad Y Meah
(74) *Attorney, Agent, or Firm* — Morgan, Lewis & Bockius LLP

(57) ABSTRACT

The present application relates to recombinant microorganisms expressing a dehydratase useful in a one-step, direct fermentative production of one or more primary alkenes from one or more saturated primary or secondary alcohols. Known, well developed high-yielding pathways that use renewable feedstock can be introduced into the recombinant microorganisms to obtain the alcohol precursors. Also provided are methods of producing one or more primary alkenes using the recombinant microorganisms, as well as compositions comprising the recombinant microorganisms and/or optionally the primary alkene products.

13 Claims, 12 Drawing Sheets
Specification includes a Sequence Listing.

(56) References Cited

OTHER PUBLICATIONS

Extended European Search Report for European Application No. 17828392.5 dated Jan. 27, 2020.

Hao and Berry, "A thermostable variant of fructose bisphosphate aldolase constructed by directed evolution also shows increased stability in organic solvents," Protein Engineering, Design & Selection, 2004, vol. 17, No. 9, pp. 689-697.

International Search Report and Written Opinion of International Searching Authority for International Application No. PCT/US2017/041732 dated Nov. 20, 2017.

Jang et al., "Bio-Based Production of C2-C6 Platform Chemicals," Biotechnology and Bioengineering, 2012, 109:2437-2459.

Jarboe, L.R., "YqhD: a broad-substrate range aldehyde reductase with various applications in production of biorenewable fuels and chemicals," Applied Microbiology and Biotechnology, 2011, 89:249-257.

Jones and Woods, "Acetone-butanol fermentation revisited," Microbiol Rev. (1986) 50(4): 484-524.

Jung et al., "Oxidative Dehydrogenation of $C_4$ Raffinate-3 to 1,3-Butadiene in a Dual-bed Reaction System Comprising $ZnFe_2O_4$ and $CoᎮFe_3Bi_1Mo_{12}O_{51}$ Catalysts: A Synergistic Effect of $ZnFe_2O_4$ and $CoᎮFe_3Bi_1Mo_{12}O_{51}$," Catalysis Letters (2008) 123, pp. 239-245.

Lamed and Zeikus, "Novel NADP-linked alcohol-aldehyde/ketone oxidoreductase in thermophilic ethanologenic bacteria," Biochem. J. (1981) 195: 183-190.

Lee et al., "Metabolic engineering of Clostridium acetobutylicum ATCC 824 for isopropanol-butanol-ethanol fermentation," Applied and Environmental Microbiology (2012) 78(5): 1416-1423.

Li et al., "Enhanced activity of yqhD oxidoreductase in synthesis of 1,3-propanediol by error-prone PCR," Progress in Natural Science, 2008, 18: 1519-1524.

Marmulla et al. "Linalool isomerase, a membrane-anchored enzyme in the anaerobic monoterpene degradation in Thauera linaloolentis 47Lol," BMC Biochemistry, (2016) 17:6, 11 pages.

Patel et al., "Engineering of the catalytic site of xylose isomerase to enhance bioconversion of a non-preferential substrate," Protein Engineering, Design & Selection, 2012, vol. 25, No. 7, pp. 331-336.

Plumridge et al., "The decarboxylation of the weak-acid preservative, sorbic acid, is encoded by linked genes in *Aspergillus* spp," Fungal Genetics and Biology, (2010) 47: 683-692.

Sulzenbacher et al., "Crystal Structure of *E. coli* Alcohol Dehydrogenase YqhD: Evidence of a Covalently Modified NADP Coenzyme," J. Mol. Biol. 2004, 342(2):489-502.

Xue et al., "Exogenous or L-Rhamnose-Derived 1,2-Propanediol Is Metabolized via a pduD-Dependent Pathway in Listeria innocua," Applied and Environmental Microbiology, (2008) 74(22):7073-7079.

Communication from the European Patent Office dated Jan. 27, 2020, regarding extended European search report for European Application No. 17828392.5-1111 (4 pages).

Invitation from the European Patent Office dated Jun. 30, 2021, for European Patent Application No. 17828392.5-1111 (4 pages).

Notice of Reasons for Rejection from Japanese Patent Office dated Aug. 18, 2021, for Japanese Patent Application No. 2019-501517 (8 pages).

\* cited by examiner

FORMATION OF ALKENES THROUGH ENZYMATIC DEHYDRATION OF ALKANOLS

CROSS-REFERENCE TO RELATED APPLICATIONS

This application is the U.S. national stage application to International Patent Application No. PCT/US2017/041732, filed Jul. 12, 2017, which claims the benefit of priority under 35 U.S.C 119(e) to U.S. Provisional Application No. 62/361,109, filed Jul. 12, 2016, the contents of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BRSK-002-01US_SeqList_ST25.txt. The text file is about 115 KB, was created on Jan. 11, 2019, and is being submitted electronically via EFS-Web.

TECHNICAL FIELD

This application relates to recombinant microorganisms useful in the biosynthesis of one or more primary alkenes from one or more saturated primary or secondary alcohols by a one-step enzymatic dehydration. The application further relates to methods of producing one or more primary alkenes from one or more saturated primary or secondary alcohols by expressing one or more linalool dehydratases/isomerases, as well as compositions comprising one or more of these primary alkenes and/or the recombinant microorganisms.

BACKGROUND

Primary alkenes such as propene (propylene) and butene (1-butene, 1-butylene) are valuable as starting compounds for a variety of products. Propene is needed for the production of films, packaging, caps and closures as well as for other applications. Propene is also used for the production of important chemicals such as propylene oxide, acrylonitrile, cumene, butyraldehyde, and acrylic acid. Over 85 million tons of propene are processed worldwide. Butene can serve as a comonomer in the production of certain kinds of polyethylene, such as linear low-density polyethylene (LL-DPE). Butene has also been used as a precursor to polypropylene resins, butylene oxide, and butanone.

However, these primary alkenes are currently obtained from chemical, multi-step synthesis using non-renewable fossil feedstocks, which contribute to climate change. Additionally, the chemical synthesis involves harsh conditions such as acidic conditions, high temperatures and/or high pressures and can require an often difficult separation of product from substrate. To develop more environmentally friendly processes, researchers have engineered microorganisms with biosynthetic pathways to produce these primary alkenes. However, these pathways are challenging to implement. Loss of product yield and requirements for activated substrate and energetic co-factors are some major obstacles to overcome.

Thus, there exists a need for improved biosynthesis pathways for the production of primary alkenes such as propene and butene.

SUMMARY OF THE DISCLOSURE

The present application relates to recombinant microorganisms useful in the biosynthesis of one or more primary alkenes from one or more saturated primary or secondary alcohols by a one-step enzymatic dehydration. In some embodiments, the dehydration step is catalyzed by one or more linalool dehydratases/isomerases. In further embodiments, methods of producing one or more primary alkenes from one or more saturated primary or secondary alcohols by expressing one or more linalool dehydratases/isomerases in a microorganism are provided, as well as compositions comprising one or more of these primary alkenes and/or the recombinant microorganisms.

In one aspect, the present application relates to a recombinant microorganism capable of producing one or more primary alkenes, each primary alkene having a structure as shown in Structure B, from one or more saturated primary or secondary alcohols, each primary or secondary alcohol having a structure as shown in Structure A,

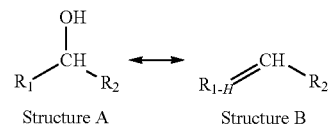

Structure A      Structure B wherein $R_1=C_nH_{2n+1}$ with $1 \leq n \leq 11$; $R_2=C_mH_{2m+1}$ with $0 \leq m \leq 10$ and $n+m \leq 11$; and wherein the recombinant microorganism expresses one or more exogenous nucleic acid molecules encoding one or more linalool dehydratases/isomerases that catalyzes the conversion of the one or more saturated primary or secondary alcohols to one or more corresponding primary alkenes.

In one embodiment, the recombinant microorganism further expresses one or more endogenous or exogenous nucleic acid molecules encoding one or more enzymes for the production of the one or more saturated primary or secondary alcohols from a renewable feedstock. In another embodiment, the renewable feedstock is one or more sugars.

In one embodiment, the corresponding primary alkene is propene and the primary alcohol is 1-propanol. In another embodiment, the corresponding primary alkene is propene and the secondary alcohol is 2-propanol. In some embodiments, the corresponding primary alkene is butene and the primary alcohol is 1-butanol. In further embodiments, the corresponding primary alkene is butene and the secondary alcohol is 2-butanol.

In one embodiment, one or more primary alkenes is produced from the one or more saturated primary or secondary alcohols via a single enzymatic step. In some embodiments, the production of one or more corresponding primary alkenes from one or more saturated primary or secondary alcohols comprises a dehydration step. In further embodiments, the dehydration step is substrate activation independent. In a yet further embodiment, the dehydration step is cofactor independent.

In one embodiment, the linalool dehydratase/isomerase is obtained from a microorganism selected from the group consisting of *Castellaniella defragrans* species. In some embodiments, the linalool dehydratase/isomerase comprises an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63. In some embodiments, the linalool dehydratase/isomerase is encoded by a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62. In further embodiments, the linalool dehydratase/isomerase is LinD. In some embodiments, the linalool dehydratase/isomerase is not comprised of an amino acid sequence selected from the group consisting of SEQ ID NOs: 64, 65, 66, 67 and 68.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a D-tagatose 3-epimerase that catalyzes the conversion of D-xylulose to D-ribulose;

(b) at least one endogenous or exogenous nucleic acid molecule encoding a D-ribulokinase that catalyzes the conversion of D-ribulose from (a) to D-ribulose-1-phosphate;

(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

(d) at least one endogenous or exogenous nucleic acid molecule encoding a glycolaldehyde reductase that catalyzes the conversion of glycolaldehyde from (c) to monoethylene glycol (MEG);

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one endogenous or exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

In one embodiment, the enzyme that catalyzes the conversion of D-xylulose to D-ribulose is an enzyme having D-tagatose 3-epimerase activity. In a further embodiment, the enzyme that catalyzes the conversion of D-xylulose to D-ribulose is encoded by one or more endogenous nucleic acid molecules. In an alternative embodiment, the enzyme that catalyzes the conversion of D-xylulose to D-ribulose is encoded by one or more exogenous nucleic acid molecules. In another embodiment, the enzyme having D-tagatose 3-epimerase activity is encoded by a nucleic acid molecule obtained from a microorganism selected from *Pseudomonas* sp., *Mesorhizobium* sp. and *Rhodobacter* sp. In some embodiments, the nucleic acid molecule encoding an enzyme having D-tagatose 3-epimerase activity is obtained from a microorganism selected from *Pseudomonas cichorii*, *Pseudomonas* sp. ST-24, *Mesorhizobium loti* and *Rhodobacter sphaeroides*. In some embodiments, the nucleic acid molecule encoding an enzyme having D-tagatose 3-epimerase activity is dte, C1KKR1, or homolog thereof. In some embodiments, the one or more nucleic acid molecules is FJ851309.1 or homolog thereof. In a further embodiment, the enzyme having D-tagatose 3-epimerase activity comprises an amino acid sequence selected from the group consisting of SEQ ID NOs: 71 and 73. In yet a further embodiment, the enzyme having D-tagatose 3-epimerase activity is encoded by a nucleic acid sequence selected from the group consisting of SEQ ID NOs: 69, 70 and 72.

In one embodiment, the enzyme that catalyzes the conversion of D-ribulose to D-ribulose-1-phosphate is an enzyme having D-ribulokinase activity. In a further embodiment, the enzyme that catalyzes the conversion of D-ribulose to D-ribulose-1-phosphate is encoded by one or more endogenous nucleic acid molecules. In an alternative embodiment, the enzyme that catalyzes the conversion of D-ribulose to D-ribulose-1-phosphate is encoded by one or more exogenous nucleic acid molecules. In another embodiment, the enzyme having D-ribulokinase activity is encoded by a nucleic acid molecule obtained from *E. coli*. In some embodiments, the nucleic acid molecule encoding an enzyme having D-ribulokinase activity is fucK, or homolog thereof. In a further embodiment, the enzyme having D-ribulokinase activity comprises an amino acid sequence set forth in SEQ ID NO: 76. In yet a further embodiment, the enzyme having D-ribulokinase activity is encoded by a nucleic acid sequence selected from the group consisting of SEQ ID NOs: 74 and 75.

In one embodiment, the enzyme that catalyzes the conversion of D-ribulose-1-phosphate to glycolaldehyde and dihydroxyacetonephosphate (DHAP) is an enzyme having D-ribulose-1-phosphate aldolase activity. In a further embodiment, the enzyme that catalyzes the conversion of D-ribulose-1-phosphate to glycolaldehyde and DHAP is encoded by one or more endogenous nucleic acid molecules. In an alternative embodiment, the enzyme that catalyzes the conversion of D-ribulose-1-phosphate to glycolaldehyde and DHAP is encoded by one or more exogenous nucleic acid molecules. In another embodiment, the enzyme having D-ribulose-1-phosphate aldolase activity is encoded by a nucleic acid molecule obtained from *E. coli*. In some embodiments, the nucleic acid molecule encoding an enzyme having D-ribulose-1-phosphate aldolase activity is fucA, or homolog thereof. In a further embodiment, the enzyme having D-ribulose-1-phosphate aldolase activity comprises an amino acid sequence set forth in SEQ ID NO: 79. In yet a further embodiment, the enzyme having D-ribulose-1-phosphate aldolase activity is encoded by a nucleic acid sequence selected from the group consisting of SEQ ID NOs: 77 and 78.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a D-xylulose 1-kinase that catalyzes the conversion of D-xylulose to D-xylulose-1-phosphate;

(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);

(c) at least one endogenous or exogenous nucleic acid molecule encoding a glycolaldehyde reductase that catalyzes the conversion of glycolaldehyde from (b) to MEG;

(d) at least one endogenous or exogenous nucleic acid molecule encoding a thiolase that catalyzes the conversion of acetyl-CoA to acetoacetyl-CoA;

(e) at least one endogenous or exogenous nucleic acid molecule encoding an acetate:acetoacetyl-CoA transferase or hydrolase that catalyzes the conversion of acetoacetyl-CoA from (d) to acetoacetate;

(f) at least one endogenous or exogenous nucleic acid molecule encoding an acetoacetate decarboxylase that catalyzes the conversion of acetoacetate from (e) to acetone; and/or (g) at least one endogenous or exogenous nucleic acid molecule encoding a secondary alcohol dehydrogenase that catalyzes the conversion of acetone from (f) to isopropanol.

In one embodiment, the enzyme that catalyzes the conversion of D-xylulose to D-xylulose-1-phosphate is an enzyme having D-xylulose 1-kinase activity. In a further embodiment, the enzyme that catalyzes the conversion of D-xylulose to D-xylulose-1-phosphate is encoded by one or more endogenous nucleic acid molecules. In an alternative embodiment, the enzyme that catalyzes the conversion of D-xylulose to D-xylulose-1-phosphate is encoded by one or more exogenous nucleic acid molecules. In another embodiment, the enzyme having D-xylulose 1-kinase activity is encoded by a nucleic acid molecule obtained from *Homo sapiens*. In one embodiment, the *Homo sapiens* enzyme having D-xylulose 1-kinase activity is a ketohexokinase C. In some embodiments, the nucleic acid molecule encoding human ketohexokinase C is khk-C, or homolog thereof. In another embodiment, the one or more nucleic acid molecules encoding the enzyme having D-xylulose 1-kinase activity comprises an amino acid sequence set forth in SEQ ID NO: 123. In a further embodiment, the one or more nucleic acid molecules encoding the enzyme having D-xylulose 1-kinase activity is encoded by a nucleic acid sequence selected from the group consisting of SEQ ID NOs: 121 and 122.

In one embodiment, the enzyme that catalyzes the conversion of D-xylulose-1-phosphate to glycolaldehyde and dihydroxyacetonephosphate (DHAP) is a D-xylulose-1-phosphate aldolase. In a further embodiment, the enzyme that catalyzes the conversion of D-xylulose-1-phosphate to glycolaldehyde and DHAP is encoded by one or more endogenous nucleic acid molecules. In an alternative embodiment, the enzyme that catalyzes the conversion of D-xylulose-1-phosphate to glycolaldehyde and DHAP is encoded by one or more exogenous nucleic acid molecules. In another embodiment, the enzyme is a D-xylulose-1-phosphate aldolase that is encoded by a nucleic acid molecule obtained from *Homo sapiens*. In one embodiment, the *Homo sapiens* D-xylulose 1-phosphate aldolase is an aldolase B. In some embodiments, the nucleic acid molecule encoding human aldolase B is ALDOB, or homolog thereof. In some embodiments, the one or more nucleic acid molecules encoding the D-xylulose-1-phosphate aldolase comprises an amino acid sequence set forth in SEQ ID NO: 126. In some embodiments, the one or more nucleic acid molecules encoding the D-xylulose-1-phosphate aldolase is encoded by a nucleic acid sequence selected from the group consisting of SEQ ID NOs: 124 and 125.

In one embodiment, the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In some embodiments, an endogenous D-xylose isomerase catalyzes the conversion of D-xylose to D-xylulose.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a xylose dehydrogenase that catalyzes the conversion of D-xylose to D-xylonolactone;

(b) at least one endogenous or exogenous nucleic acid molecule encoding a xylonolactonase that catalyzes the conversion of D-xylonolactone from (a) to D-xylonate;

(c) at least one endogenous or exogenous nucleic acid molecule encoding a xylonate dehydratase that catalyzes the conversion of D-xylonate from (b) to 2-keto-3-deoxy-xylonate;

(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;

(e) at least one endogenous or exogenous nucleic acid molecule encoding a glycolaldehyde reductase that catalyzes the conversion of glycolaldehyde from (d) to MEG;

(f) at least one exogenous nucleic acid molecule encoding a thiolase that catalyzes the conversion of acetyl-CoA to acetoacetyl-CoA;

(g) at least one exogenous nucleic acid molecule encoding an acetate:acetoacetyl-CoA transferase or hydrolase that catalyzes the conversion of acetoacetyl-CoA from (f) to acetoacetate;

(h) at least one exogenous nucleic acid molecule encoding an acetoacetate decarboxylase that catalyzes the conversion of acetoacetate from (g) to acetone; and/or (i) at least one endogenous or exogenous nucleic acid molecule encoding a secondary alcohol dehydrogenase that catalyzes the conversion of acetone from (h) to isopropanol.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a xylose dehydrogenase that catalyzes the conversion of D-xylose to D-xylonate;

(b) at least one endogenous or exogenous nucleic acid molecule encoding a xylonate dehydratase that catalyzes the conversion of D-xylonate from (a) to 2-keto-3-deoxy-xylonate;

(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;

(d) at least one exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

In one embodiment, the enzyme that catalyzes the conversion of D-xylose to D-xylonolactone is an enzyme having xylose dehydrogenase activity. In a further embodiment, the enzyme that catalyzes the conversion of D-xylose to D-xylonolactone is encoded by one or more endogenous nucleic acid molecules. In an alternative embodiment, the enzyme that catalyzes the conversion of D-xylose to D-xylonolactone is encoded by one or more exogenous nucleic acid molecules. In another embodiment, the enzyme having xylose dehydrogenase activity is encoded by a nucleic acid molecule obtained from a microorganism selected from *Caulobacter* sp., *Haloarcula* sp., *Haloferax* sp., *Halorubrum* sp. and *Trichoderma* sp.

In some embodiments, the nucleic acid molecule encoding the enzyme having xylose dehydrogenase activity is obtained from a microorganism selected from *Caulobacter crescentus, Haloarcula marismortui, Haloferax volcanii, Halorubrum lacusprofundi* and *Trichoderma reesei*. In some embodiments, the nucleic acid molecule encoding an enzyme having xylose dehydrogenase activity is selected from xylB, xdh (HVO_B0028), xyd1, or homolog thereof. In a further embodiment, the one or more nucleic acid molecules encoding the enzyme having xylose dehydrogenase activity comprises an amino acid sequence selected from the group consisting of SEQ ID NOs: 129, 131 and 133. In yet another embodiment, the one or more nucleic acid molecules encoding the enzyme having xylose dehydrogenase activity is encoded by a nucleic acid sequence selected from the group consisting of SEQ ID NOs: 127, 128, 130 and 132.

In one embodiment, the enzyme that catalyzes the conversion of D-xylonolactone to D-xylonate is an enzyme having xylonolactonase activity. In a further embodiment, the enzyme that catalyzes the conversion of D-xylonolactone to D-xylonate is encoded by one or more endogenous nucleic acid molecules. In an alternative embodiment, the enzyme that catalyzes the conversion of D-xylonolactone to D-xylonate is encoded by one or more exogenous nucleic acid molecules. In another embodiment, the enzyme having xylonolactonase activity is encoded by a nucleic acid molecule obtained from a microorganism selected from *Caulobacter* sp. and *Haloferax* sp. In some embodiments, the nucleic acid molecule encoding the enzyme having xylonolactonase activity is obtained from a microorganism selected from *Caulobacter crescentus, Haloferax volcanii* and *Haloferax gibbonsii*. In some embodiments, the nucleic acid molecule encoding an enzyme having xylonolactonase activity is xylC, or homolog thereof. In a further embodiment, the one or more nucleic acid molecules encoding the enzyme having xylonolactonase activity comprises an amino acid sequence set forth in SEQ ID NO: 135. In yet another embodiment, the one or more nucleic acid molecules encoding the enzyme having xylonolactonase activity is encoded by a nucleic acid sequence set forth in SEQ ID NO: 134.

In one embodiment, the enzyme that catalyzes the conversion of D-xylonate to 2-keto-3-deoxy-xylonate is an enzyme having xylonate dehydratase activity. In a further embodiment, the enzyme that catalyzes the conversion of D-xylonate to 2-keto-3-deoxy-xylonate is encoded by one or more endogenous nucleic acid molecules. In an alternative embodiment, the enzyme that catalyzes the conversion of D-xylonate to 2-keto-3-deoxy-xylonate is encoded by one or more exogenous nucleic acid molecules. In another embodiment, the enzyme having xylonate dehydratase activity is encoded by a nucleic acid molecule obtained from a microorganism selected from *Caulobacter* sp., *Haloferax* sp., *Sulfolobus* sp. and *E. coli*. In some embodiments, the nucleic acid molecule encoding the enzyme having xylonate dehydratase activity is obtained from a microorganism selected from *Caulobacter crescentus, Haloferax volcanii, E. coli* and *Sulfolobus solfataricus*. In some embodiments, the nucleic acid molecule encoding an enzyme having xylonate dehydratase activity is selected from xylD, yjhG, yagF, xad, or homolog thereof. In a further embodiment, the one or more nucleic acid molecules encoding the enzyme having xylonate dehydratase activity comprises an amino acid sequence selected from the group consisting of SEQ ID NOs: 137, 140 and 143. In yet another embodiment, the one or more nucleic acid molecules encoding the enzyme having xylonate dehydratase activity is encoded by a nucleic acid sequence selected from the group consisting of SEQ ID NOs: 136, 138, 139, 141 and 142.

In one embodiment, the enzyme that catalyzes the conversion of 2-keto-3-deoxy-xylonate to glycolaldehyde and pyruvate is an enzyme having 2-keto-3-deoxy-D-pentonate aldolase activity. In a further embodiment, the enzyme that catalyzes the conversion of 2-keto-3-deoxy-xylonate to glycolaldehyde and pyruvate is encoded by one or more endogenous nucleic acid molecules. In an alternative embodiment, the enzyme that catalyzes the conversion of 2-keto-3-deoxy-xylonate to glycolaldehyde and pyruvate is encoded by one or more exogenous nucleic acid molecules. In another embodiment, the enzyme having 2-keto-3-deoxy-D-pentonate aldolase activity is encoded by a nucleic acid molecule obtained from a microorganism selected from *Pseudomonas* sp. and *E. coli*. In some embodiments, the nucleic acid molecule encoding an enzyme having 2-keto-3-deoxy-D-pentonate aldolase activity is selected from yjhH, yagE, or homolog thereof. In a further embodiment, the one or more nucleic acid molecules encoding the enzyme having 2-keto-3-deoxy-D-pentonate aldolase activity comprises an amino acid sequence selected from the group consisting of SEQ ID NOs: 146 and 149. In yet another embodiment, the one or more nucleic acid molecules encoding the enzyme having 2-keto-3-deoxy-D-pentonate aldolase activity is encoded by a nucleic acid sequence selected from the group consisting of SEQ ID NOs: 144, 145, 147 and 148.

In some embodiments, the recombinant microorganism further comprises one or more modifications selected from the group consisting of:

(a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In one embodiment, the recombinant microorganism is capable of co-producing monoethylene glycol (MEG) and isopropanol from exogenous D-xylose and glucose and expresses one or more of the following:

(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;

(b) at least one exogenous nucleic acid molecule encoding a D-xylose isomerase that catalyzes the conversion of D-xylose to D-xylulose, and wherein the microorganism further expresses one or more of the following:

(c) at least one endogenous or exogenous nucleic acid molecule encoding a D-tagatose 3-epimerase that catalyzes the conversion of D-xylulose from (a) or (b) to D-ribulose;

(d) at least one endogenous or exogenous nucleic acid molecule encoding a D-ribulokinase that catalyzes the conversion of D-ribulose from (c) to D-ribulose-1-phosphate;

(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);

(f) at least one endogenous or exogenous nucleic acid molecule encoding a glycolaldehyde reductase or methylglyoxal reductase that catalyzes the conversion of glycolaldehyde from (e) to MEG;

(g) at least one endogenous or exogenous nucleic acid molecule encoding a thiolase that catalyzes the conversion of acetyl-CoA to acetoacetyl-CoA;

(h) at least one endogenous or exogenous nucleic acid molecule encoding an acetate:acetoacetyl-CoA transferase or hydrolase that catalyzes the conversion of acetoacetyl-CoA from (g) to acetoacetate;

(i) at least one endogenous or exogenous nucleic acid molecule encoding an acetoacetate decarboxylase that catalyzes the conversion of acetoacetate from (h) to acetone; and/or (j) at least one endogenous or exogenous nucleic acid molecule encoding a secondary alcohol dehydrogenase that catalyzes the conversion of acetone from (i) to isopropanol.

In one embodiment, the enzyme that catalyzes the conversion of D-xylose to xylitol is an enzyme having xylose reductase or aldose reductase activity. In a further embodiment, the enzyme that catalyzes the conversion of D-xylose to xylitol is encoded by one or more endogenous nucleic acid molecules. In an alternative embodiment, the enzyme that catalyzes the conversion of D-xylose to xylitol is encoded by one or more exogenous nucleic acid molecules. In another embodiment, the enzyme having xylose reductase or aldose reductase activity is encoded by a nucleic acid molecule obtained from a microorganism selected from *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the nucleic acid molecule encoding the enzyme having xylose reductase or aldose reductase activity is obtained from a microorganism selected from *Hypocrea jecorina, Scheffersomyces stipitis, S. cerevisiae, Pachysolen tannophilus, Pichia stipitis, Pichia quercuum, Candida shehatae, Candida tenuis, Candida tropicalis, Aspergillus niger, Neurospora crassa* and *Cyptococcus lactativorus*. In some embodiments, the nucleic acid molecule encoding an enzyme having xylose reductase or aldose reductase activity is xyl1, GRE3, or homolog thereof. In some embodiments, the one or more nucleic acid molecules encoding the enzyme having xylose reductase or aldose reductase activity comprises an amino acid sequence selected from the group consisting of SEQ ID NOs: 152 and 155. In some embodiments, the one or more nucleic acid molecules encoding the enzyme having xylose reductase or aldose reductase activity is encoded by a nucleic acid sequence selected from the group consisting of SEQ ID NOs: 150, 151, 153 and 154.

In one embodiment, the enzyme that catalyzes the conversion of xylitol to D-xylulose is an enzyme having xylitol dehydrogenase activity. In a further embodiment, the enzyme that catalyzes the conversion of xylitol to D-xylulose is encoded by one or more endogenous nucleic acid molecules. In an alternative embodiment, the enzyme that catalyzes the conversion of xylitol to D-xylulose is encoded by one or more exogenous nucleic acid molecules. In another embodiment, the enzyme having xylitol dehydrogenase activity is encoded by a nucleic acid molecule obtained from a microorganism selected from *Scheffersomyces* sp., *Trichoderma* sp., *Pichia* sp., *Saccharomyces* sp., *Gluconobacter* sp., *Galactocandida* sp., *Neurospora* sp., and *Serratia* sp. In some embodiments, the nucleic acid molecule encoding the enzyme having xylitol dehydrogenase activity is obtained from a microorganism selected from *Scheffersomyces stipitis, Trichoderma reesei, Pichia stipitis, S. cerevisiae, Gluconobacter oxydans, Galactocandida mastotermitis, Neurospora crassa* and *Serratia marcescens*. In some embodiments, the one or more nucleic acid molecule encoding an enzyme having xylitol dehydrogenase activity is xyl2, xdh1, or homolog thereof. In some embodiments, the one or more nucleic acid molecules encoding the enzyme having xylitol dehydrogenase activity comprises an amino acid sequence selected from the group consisting of SEQ ID NOs: 158 and 160. In some embodiments, the one or more nucleic acid molecules encoding the enzyme having xylitol dehydrogenase activity is encoded by a nucleic acid sequence selected from the group consisting of SEQ ID NOs: 156, 157 and 159.

In one embodiment, the enzyme that catalyzes the conversion of D-xylose to D-xylulose is an enzyme having D-xylose isomerase activity. In a further embodiment, the enzyme that catalyzes the conversion of D-xylose to D-xylulose is encoded by one or more endogenous nucleic acid molecules. In an alternative embodiment, the enzyme that catalyzes the conversion of D-xylose to D-xylulose is encoded by one or more exogenous nucleic acid molecules. In another embodiment, the enzyme having D-xylose isomerase activity is encoded by a nucleic acid molecule obtained from *E. coli*. In another embodiment, the enzyme having xylose isomerase activity is encoded by one or more nucleic acid molecules obtained from *Pyromyces* sp. In some embodiments, the nucleic acid molecule encoding an enzyme having D-xylose isomerase activity is xylA, or homolog thereof. In yet another embodiment, the one or more nucleic acid molecules encoding the enzyme having xylose isomerase activity comprises an amino acid sequence selected from SEQ ID NOs: 163 and 190. In a further embodiment, the one or more nucleic acid molecules encoding the enzyme having xylose isomerase activity is encoded by a nucleic acid sequence selected from SEQ ID NOs: 161, 162 and 189.

In some embodiments, the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate; and (b) a deletion, insertion, or loss of function mutation in a gene encoding an alkaline phosphatase that catalyzes the conversion of D-xylulose-5-phosphate to D-xylose.

In any of the above embodiments, the DHAP is converted to acetyl-CoA through the endogenous glycolysis pathway in the microorganism.

In any of the above embodiments, the enzyme that catalyzes the conversion of glycolaldehyde to MEG is an enzyme having glycolaldehyde reductase or aldehyde reductase activity. In a further embodiment, the enzyme that catalyzes the conversion of glycolaldehyde to MEG is encoded by one or more endogenous nucleic acid molecules.

In an alternative embodiment, the enzyme that catalyzes the conversion of glycolaldehyde to MEG is encoded by one or more exogenous nucleic acid molecules. In another embodiment, the enzyme having glycolaldehyde reductase or aldehyde reductase activity is encoded by a nucleic acid molecule obtained from a microorganism selected from E. coli or S. cerevisiae. In some embodiments, the nucleic acid molecule encoding an enzyme having glycolaldehyde reductase or aldehyde reductase activity is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 81, 83, 85, 88, 91, 93, 96, 98 and 100. In yet a further embodiment, the glycolaldehyde reductase is encoded by a nucleic acid sequence selected from the group consisting of SEQ ID NOs: 80, 82, 84, 86, 87, 89, 90, 92, 94, 95, 97 and 99.

In any of the above embodiments, the enzyme that catalyzes the conversion of acetyl-CoA to acetoacetyl-CoA is an enzyme having thiolase or acetyl coenzyme A acetyltransferase activity. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is an enzyme having thiolase or acetyl coenzyme A acetyltransferase activity that is encoded by a nucleic acid molecule obtained from a microorganism selected from Clostridium sp., Bacillus sp., E. coli, Saccharomyces sp. and Marinobacter sp. In some embodiments, the nucleic acid molecule encoding an enzyme having thiolase or acetyl coenzyme A acetyltransferase activity is obtained from a microorganism selected from Clostridium acetobutylicum, Clostridium thermosaccharolyticum, Bacillus cereus, E. coli, Saccharomyces cerevisiae and Marinobacter hydrocarbonoclasticus. In some embodiments, the nucleic acid molecule encoding an enzyme having thiolase or acetyl coenzyme A acetyltransferase activity is thlA, atoB and/or ERG10, or homolog thereof. In a further embodiment, the enzyme having thiolase or acetyl coenzyme A acetyltransferase activity comprises an amino acid sequence selected from the group consisting of SEQ ID NOs: 103, 105 and 108. In yet a further embodiment, the enzyme having thiolase or acetyl coenzyme A acetyltransferase activity is encoded by a nucleic acid sequence selected from the group consisting of SEQ ID NOs: 101, 102, 104, 106 and 107.

In any of the above embodiments, the enzyme that catalyzes the conversion of acetoacetyl-CoA to acetoacetate is an enzyme having acetate:acetoacetyl-CoA transferase or hydrolase activity. In some embodiments, the enzyme having transferase activity is an enzyme having acetyl-CoA:acetoacetate-CoA transferase activity. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme having acetate:acetoacetyl-CoA transferase or hydrolase activity is encoded by one or more nucleic acid molecule obtained from a microorganism selected from Clostridium sp. and E. coli. In some embodiments, the nucleic acid molecules encoding an enzyme having acetate:acetoacetyl-CoA hydrolase activity is obtained from Clostridium acetobutylicum. In some embodiments, the nucleic acid molecules encoding an enzyme having acetate:acetoacetyl-CoA transferase activity is obtained from E. coli. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the enzyme having acetyl-CoA:acetoacetate-CoA transferase activity or acetate:acetoacetyl-CoA hydrolase activity comprises an amino acid sequence selected from the group consisting of SEQ ID NOs: 111, 114, 165, 167, 169 and 171. In yet a further embodiment, the enzyme having acetyl-CoA:acetoacetate-CoA transferase activity or acetate:acetoacetyl-CoA hydrolase activity is encoded by a nucleic acid sequence selected from the group consisting of SEQ ID NOs: 109, 110, 112, 113, 164, 166, 168 and 170.

In any of the above embodiments, the enzyme that catalyzes the conversion of acetoacetate to acetone is an enzyme having acetoacetate decarboxylase activity. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme having acetoacetate decarboxylase activity is encoded by a nucleic acid molecule obtained from a microorganism selected from Clostridium sp., Bacillus sp., Chromobacterium sp. and Pseudomonas sp. In some embodiments, the nucleic acid molecule encoding an enzyme having acetoacetate decarboxylase activity is obtained from a microorganism selected from Clostridium acetobutylicum, Clostridium beierinckii, Clostridium cellulolyticum, Bacillus polymyxa, Chromobacterium violaceum and Pseudomonas putida. In some embodiments, the nucleic acid molecule encoding an enzyme having acetoacetate decarboxylase activity is adc, or homolog thereof. In a further embodiment, the enzyme having acetoacetate decarboxylase activity comprises an amino acid sequence selected from the group consisting of SEQ ID NOs: 117 and 120. In yet another embodiment, the enzyme having acetoacetate decarboxylase activity is encoded by a nucleic acid sequence selected from the group consisting of SEQ ID NOs: 115, 116, 118 and 119.

In any of the above embodiments, the recombinant microorganism may comprise at least one nucleic acid molecule encoding an enzyme that catalyzes the conversion of acetone to isopropanol. In one embodiment, the enzyme that catalyzes the conversion of acetone to isopropanol is encoded by one or more endogenous nucleic acid molecules. In an alternative embodiment, the enzyme that catalyzes the conversion of acetone to isopropanol is encoded by one or more exogenous nucleic acid molecules. In one embodiment, the enzyme that catalyzes the conversion of acetone to isopropanol is a secondary alcohol dehydrogenase (S-ADH). In another embodiment, the enzyme having secondary alcohol dehydrogenase activity is encoded by a nucleic acid molecule obtained from a microorganism selected from Burkholderia sp, Alcaligenes sp., Clostridium sp., Thermoanaerobacter sp., Phytomonas sp., Rhodococcus sp., Methanobacterium sp., Methanogenium sp., Entamoeba sp., Trichomonas sp., and Tritrichomonas sp.

In some embodiments, the nucleic acid molecule encoding the enzyme having secondary alcohol dehydrogenase activity is obtained from a microorganism selected from *Burkholderia* sp. AIU 652, *Alcaligenes eutrophus*, *Clostridium ragsdalei*, *Clostridium beijennckii*, *Clostridium carboxidivorans*, *Thermoanaerobacter brockii*, *Thermoanaerobacter ethanolicus* (*Clostridium thermohydrosulfuricum*), *Rhodococcus ruber*, *Methanobacterium palustre*, methanogenic archaea *Methanogenium liminatans*, parasitic protist *Entamoeba histolytica*, parasitic protozoan *Tritrichomonas foetus* and human parasite *Trichomonas vaginalis*. In some embodiments, the one or more nucleic acid molecule encoding an enzyme having secondary alcohol dehydrogenase activity is adh, adhB, EhAdh1, or homolog thereof. In some embodiments, the S-ADH is predicted from homology and can be from *Thermoanaerobacter mathranii*, *Micrococcus luteus*, *Nocardiopsis alba*, *Mycobacterium hassiacum*, *Helicobacter suis*, *Candida albicans*, *Candida parapsilosis*, *Candida orthopsilosis*, *Candida metapsilosis*, *Grosmannia clavigera* and *Scheffersomyces stipitis*. In a further embodiment, the enzyme having alcohol dehydrogenase activity comprises an amino acid sequence selected from the group consisting of SEQ ID NOs: 174 and 176. In yet another embodiment, the alcohol dehydrogenase is encoded by a nucleic acid sequence selected from the group consisting of SEQ ID NOs: 172, 173 and 175.

In any of the above embodiments, the enzyme that catalyzes the conversion of D-xylulose to D-xylulose-5-phosphate is a D-xylulose-5-kinase. In some embodiments, the D-xylulose-5-kinase is from *Escherichia coli*. In some embodiments, the D-xylulose-5-kinase is encoded by the xylB gene, or homolog thereof. In some embodiments, a recombinant microorganism producing MEG and isopropanol comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

In any of the above embodiments, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene, or homolog thereof. In some embodiments, a recombinant microorganism producing MEG and isopropanol comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

In any of the above embodiments, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof. In some embodiments, a recombinant microorganism producing MEG and isopropanol comprises a deletion, insertion, or loss of function mutation in a gene encoding a lactate dehydrogenase to prevent the production of lactate from pyruvate and instead shunt the reaction toward production of isopropanol.

In any of the above embodiments, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof. In some embodiments, a recombinant microorganism producing MEG and isopropanol comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the recombinant microorganism is capable of producing isopropanol and expresses one or more of the following:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and/or (d) at least one endogenous or exogenous nucleic acid molecule encoding a secondary alcohol dehydrogenase that catalyzes the conversion of acetone from (c) to isopropanol.

In some embodiments, the recombinant microorganism further comprises a deletion, insertion, or loss of function mutation in a gene encoding a lactate dehydrogenase that catalyzes the conversion of pyruvate to lactate.

In one embodiment, the recombinant microorganism is capable of co-producing n-propanol and isopropanol and expresses one or more of the following:

(a) at least one endogenous or exogenous nucleic acid molecule encoding a methylglyoxal synthase that catalyzes the conversion of dihydroxyacetone phosphate (DHAP) to methylglyoxal;

(b) at least one endogenous or exogenous nucleic acid molecule encoding an aldo-keto reductase that catalyzes the conversion of methylglyoxal from (a) to acetol;

(c) at least one endogenous or exogenous nucleic acid molecule encoding a glyoxylate reductase, a methylglyoxal dehydrogenase or an aldehyde dehydrogenase that catalyzes the conversion of methylglyoxal from (a) to lactaldehyde;

(d) at least one endogenous or exogenous nucleic acid molecule encoding an aldo-keto reductase that catalyzes the conversion of acetol from (b) to 1,2-propanediol;

(e) at least one endogenous or exogenous nucleic acid molecule encoding an aldehyde reductase that catalyzes the conversion of lactaldehyde from (c) to 1,2-propanediol;

(f) at least one endogenous or exogenous nucleic acid molecule encoding a diol-dehydratase that catalyzes the conversion of 1,2-propanediol from (d) or (e) to propanal;

(g) at least one endogenous or exogenous nucleic acid molecule encoding a dehydrogenase that catalyzes the conversion of propanal from (f) to n-propanol;

(h) at least one endogenous or exogenous nucleic acid molecule encoding a pyruvate formate lyase that catalyzes the conversion of pyruvate to acetyl-CoA;

(i) at least one endogenous or exogenous nucleic acid molecule encoding a thiolase that catalyzes the conversion of acetyl-CoA from (h) to acetoacetyl-CoA;

(j) at least one endogenous or exogenous nucleic acid molecule encoding an acetate:acetoacetyl-CoA transferase or hydrolase that catalyzes the conversion of acetoacetyl-CoA from (i) to acetoacetate;

(k) at least one endogenous or exogenous nucleic acid molecule encoding an acetoacetate decarboxylase that catalyzes the conversion of acetoacetate from (j) to acetone; and/or (l) at least one endogenous or exogenous nucleic acid molecule encoding a secondary alcohol dehydrogenase that catalyzes the conversion of acetone from (k) to isopropanol; and wherein the DHAP and pyruvate are produced from glycolysis in the microorganism.

In some embodiments, the recombinant microorganism further comprises one or more modifications selected from the group consisting of:

(a) a deletion, insertion, or loss of function mutation in a gene encoding an acetaldehyde dehydrogenase that catalyzes the conversion of lactaldehyde to lactate; and (b) a deletion, insertion, or loss of function mutation in a gene encoding a lactate dehydrogenase that catalyzes the conversion of pyruvate to lactate.

In one embodiment, the recombinant microorganism is capable of co-producing acetone, butanol and ethanol, and expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetaldehyde from (e) to ethanol or butyraldehyde from (i) to butanol;
and wherein the pyruvate is produced from glycolysis in the microorganism.

In some embodiments, the recombinant microorganism further comprises a deletion, insertion, or loss of function mutation in a gene encoding a lactate dehydrogenase that catalyzes the conversion of pyruvate to lactate.

In one embodiment, the recombinant microorganism is capable of co-producing isopropanol, butanol and ethanol, and expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetone from (d) to isopropanol, acetaldehyde from (e) to ethanol or butyraldehyde from (i) to butanol; and wherein the pyruvate is produced from glycolysis in the microorganism.

In some embodiments, the recombinant microorganism further comprises a deletion, insertion, or loss of function mutation in a gene encoding a butyrate kinase that catalyzes the conversion of butyryl phosphate to butyrate.

In one embodiment, the recombinant microorganism is capable of producing isobutanol and expresses one or more of the following:

(a) at least one endogenous or exogenous nucleic acid molecule encoding an acetohydroxy acid synthase that catalyzes the conversion of pyruvate to acetolactate;

(b) at least one endogenous or exogenous nucleic acid molecule encoding an acetohydroxy acid isomeroreductase that catalyzes the conversion of acetolactate from (a) to 2,3-dihydroxy-isovalerate;

(c) at least one endogenous or exogenous nucleic acid molecule encoding a dihydroxy-acid dehydratase that catalyzes the conversion of 2,3-dihydroxy-isovalerate from (b) to α-keto-isovalerate;

(d) at least one endogenous or exogenous nucleic acid molecule encoding a 2-keto-acid decarboxylase that catalyzes the conversion of α-keto-isovalerate from (c) to isobutyraldehyde; and/or (e) at least one endogenous or exogenous nucleic acid molecule encoding an alcohol dehydrogenase that catalyzes the conversion of isobutyraldehyde from (d) to isobutanol; and wherein the pyruvate is produced from glycolysis in the microorganism.

In some embodiments, the recombinant microorganism further comprises one or more modifications selected from the group consisting of:

(a) a deletion, insertion, or loss of function mutation in a gene encoding an ethanol dehydrogenase that catalyzes the conversion of acetaldehyde to ethanol; and (b) a deletion, insertion, or loss of function mutation in a gene encoding a lactate dehydrogenase that catalyzes the conversion of pyruvate to lactate.

In yet another aspect, the present application provides a method of producing one or more primary alkenes from one or more saturated primary or secondary alcohols using a recombinant microorganism as described above, wherein the method comprises cultivating the recombinant microorganism in a culture medium containing a feedstock providing a carbon source until the one or more primary alkenes is produced. In one embodiment, the one or more primary alkenes is propene and the one or more saturated primary alcohol is 1-propanol. In another embodiment, the one or more primary alkenes is propene and the one or more saturated secondary alcohol is 2-propanol. In some embodiments, the one or more primary alkenes is butene and the one or more saturated primary alcohol is 1-butanol. In further embodiments, the one or more primary alkenes is butene and the one or more saturated secondary alcohol is 2-butanol.

In yet another aspect, the present application provides a method of producing a recombinant microorganism that produces or accumulates one or more primary alkenes from one or more saturated primary or secondary alcohols. In one embodiment, the one or more primary alkenes is propene and the one or more saturated primary alcohol is 1-propanol. In another embodiment, the one or more primary alkenes is propene and the one or more saturated secondary alcohol is 2-propanol. In some embodiments, the one or more primary alkenes is butene and the one or more saturated primary alcohol is 1-butanol. In further embodiments, the one or more primary alkenes is butene and the one or more saturated secondary alcohol is 2-butanol.

BRIEF DESCRIPTION OF DRAWINGS

Illustrative embodiments of the disclosure are illustrated in the drawings, in which.

DETAILED DESCRIPTION

Definitions

Figure 1:
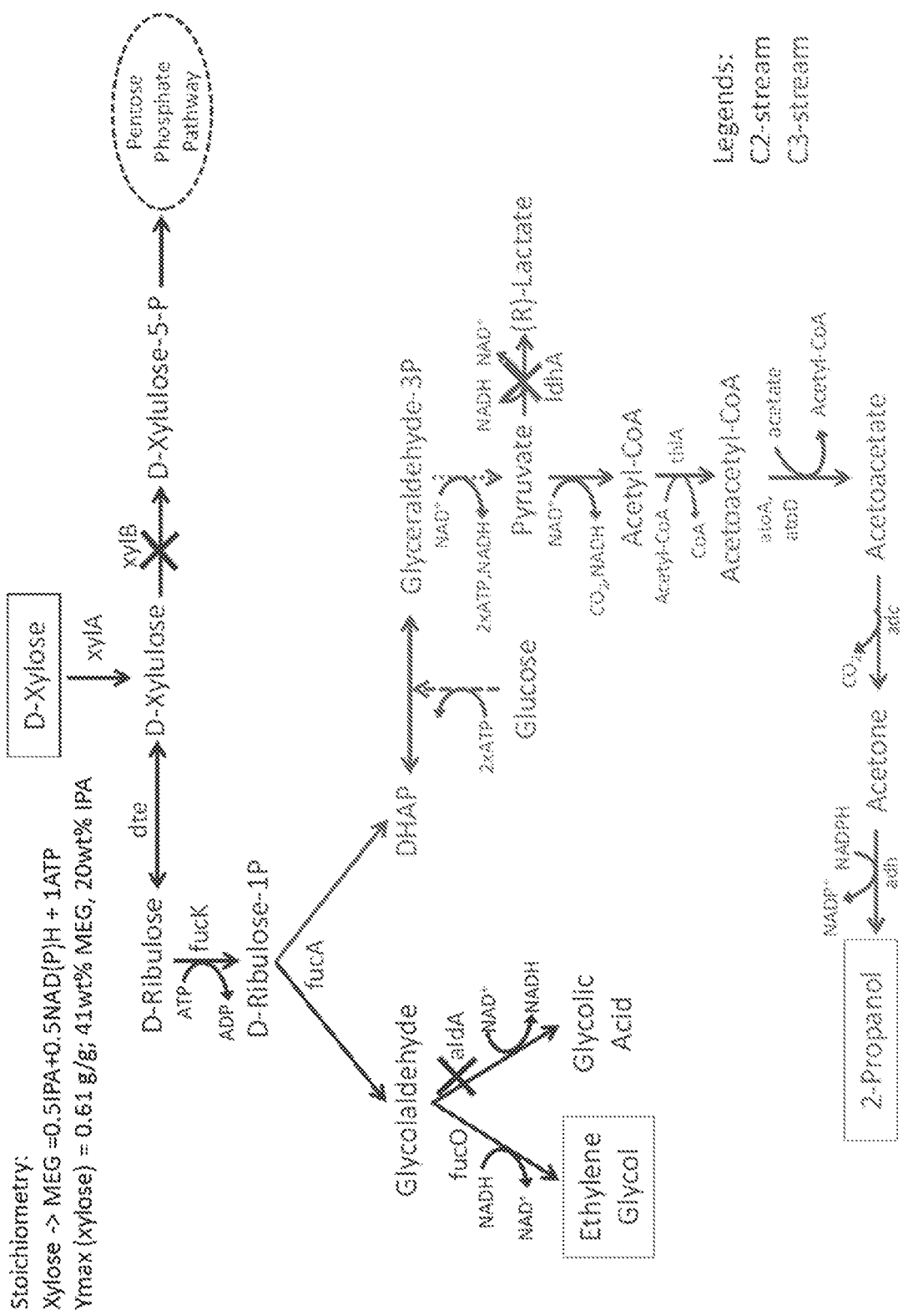
FIG. 1 illustrates MEG and isopropanol co-production pathway via ribulose-1-phosphate.

The following definitions and abbreviations are to be used for the interpretation of the disclosure.

As used herein and in the appended claims, the singular forms "a," "an," and "the" include plural referents unless the context clearly dictates otherwise. Thus, for example, reference to "a three-carbon compound" includes a plurality of such three-carbon compounds and reference to "the microorganism" includes reference to one or more microorganisms, and so forth.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1 X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobactenum, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynudeotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.).

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, a linalool dehydratase/isomerase enzyme may be a "variant" relative to a reference linalool dehydratase/isomerase enzyme by virtue of alteration(s) in any part of the polypeptide sequence encoding the reference linalool dehydratase/isomerase enzyme. A variant of a reference linalool dehydratase/isomerase enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference linalool dehydratase/isomerase enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed linalool dehydratase/isomerase enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed linalool dehydratase/isomerase enzymes of the present disclosure.

The term "signal sequence" as used herein refers to an amino acid sequence that targets peptides and polypeptides to cellular locations or to the extracellular environment Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

The term "yield potential" as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balanced" refers to a set of reactions, which taken together produce as much redox cofactors as they consume. Designing metabolic pathways and engineering an organism such that the redox cofactors are balanced or close to being balanced usually results in a more efficient, higher yield production of the desired compounds. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. Biological energy is frequently stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide (NAD+), which then contributes to the creation of a proton gradient, which drives the synthesis of adenosine triphosphate (ATP) and is maintained by the reduction of oxygen. The term redox state is often used to describe the balance of GSH/GSSG, NAD+/NADH and NADP+/NADPH in a biological system such as a cell or organ. The redox state is reflected in the balance of several sets of metabolites (e.g., lactate and pyruvate, beta-hydroxybutyrate, and acetoacetate), whose interconversion is dependent on these ratios. An abnormal redox state can develop in a variety of deleterious situations, such as hypoxia, shock, and sepsis.

The terms "C2 pathway", "C2 branch pathway" or "C2 stream" as used herein refers to a biochemical pathway wherein MEG can be produced via glycolaldehyde.

The terms "C3 pathway", "C3 branch pathway" or "C3 stream" as used herein refers to a biochemical pathway wherein MEG or one or more three-carbon compounds such as isopropanol can be produced via pyruvate or dihydroxyacetonephosphate (DHAP).

The term "olefin" as used herein is interchangeable with "alkene" and refers to an unsaturated hydrocarbon that contains at least one carbon-carbon double bond.

INTRODUCTION

The present disclosure relates to the production of important primary alkene bulk chemicals, such as propylene (propene) and butylene (butene), via enzymatic dehydration of the linear primary or secondary alkanols, allowing for a one-step, direct fermentative production of propylene (propene) or butylene (butene) from renewable resources like glucose.

The inventors of the present disclosure unexpectedly found that non-activated, saturated primary or secondary alcohols such as 1-propanol, 2-propanol, and 1-butanol can be directly dehydrated to primary alkenes, such as propene or 1-butene.

In some embodiments, each primary alkene has a structure as shown in Structure B and is produced from one or more saturated primary or secondary alcohols, each primary or secondary alcohol having a structure as shown in Structure A,

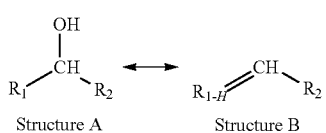

Structure A    Structure B wherein $R_1=C_nH_{2n+1}$ with $1 \leq n \leq 11$; $R_2=C_mH_{2m+1}$ with $0 \leq m \leq 10$ and $n+m \leq 11$. In some embodiments, the conversion of the one or more saturated primary or secondary alcohols to one or more corresponding primary alkenes is catalyzed by one or more nucleic acid molecules encoding one or more linalool dehydratases/isomerases.

Exemplary alcohol substrates ($C_nH_{2n+2}O$) with $3 \leq n \leq 12$ which can be converted into the corresponding alkene ($C_nH_{2n}$) using linalool dehydratase/isomerase are listed in Table 1. In other embodiments, possible alcohol substrates are furthermore all the possible branched-chain isomers of all the alcohol substrates mentioned in Table 1. Branched-chain isomers for butanol and pentanol and their appropriate LinD dehydration products are mentioned in Table 1.

TABLE 1

Examples for LinD substrates $C_nH_{2n+2}O$ with $3 \leq n \leq 12$ and their appropriate products $C_nH_{2n}$ after enzymatic dehydration (isomer examples are in italics).

| n | LinD Alcohol ($C_nH_{2n+2}O$) Substrate | LinD Alkene ($C_nH_{2n}$) product |
|---|---|---|
| 3 | 1-propanol | propylene |
|   | 2-propanol | propylene |
| 4 | 1-butanol | 1-butene |
|   | 2-butanol | 1-butene |
|   |   | 2 butene |
|   | *isobutanol* | *isobutene* |
| 5 | 1 pentanol | 1 pentene |
|   | 2 pentanol | 1 pentene |
|   |   | 2 pentene |
|   | 3 pentanol | 2 pentene |
|   | *3-methyl-1-butanol* | *3-methyl-1-butene* |
|   | *3-methyl-2-butanol* | *3-methyl-2-butene* |
|   |   | *2-methyl-1-butene* |
|   | *2-methyl-1-butanol* | *2-methyl-2-butene* |
| 6 | 1-hexanol | 1-hexene |
|   | 2-hexanol | 1-hexene |
|   |   | 2-hexene |
|   | 3-hexanol | 2-hexene |
|   |   | 3-hexene |
| 7 | 1-heptanol | 1-heptene |
|   | 2-heptanol | 2-heptene |
|   | 3-heptanol | 3-heptene |
|   | 4-heptanol | 4-heptene |
| 8 | 1-octanol | 1-octene |
|   | 2- octanol | 2-octene |
|   | 3- octanol | 3-octene |
|   | 4- octanol | 4-octene |
| 9 | 1-nonanol | 1-nonene |
|   | 2-nonanol | 2-nonene |
|   | 3-nonanol | 3-nonene |
|   | 4-nonanol | 4-nonene |
|   | 5-nonanol | 5-nonene |
| 10 | 1-decanol | 1-decene |
|   | 2-decanol | 2-decene |
|   | 3-decanol | 3-decene |
|   | 4-decanol | 4-decene |
|   | 5-decanol | 5-decene |
| 11 | 1-undecanol | 1-undecene |
|   | 2-undecanol | 2-undecene |
|   | 3-undecanol | 3-undecene |
|   | 4-undecanol | 4-undecene |
|   | 5-undecanol | 5-undecene |
|   | 6-undecanol | 6-undecene |
| 12 | 1-dodecanol | 1-dodecene |
|   | 2-dodecanol | 2-dodecene |
|   | 3-dodecanol | 3-dodecene |
|   | 4-dodecanol | 4-dodecene |
|   | 5-dodecanol | 5-dodecene |
|   | 6-dodecanol | 6-dodecene |

Previous work on chemical synthesis and/or biosynthesis pathways for the production of primary alkenes presents challenges and drawbacks, which are summarized below.

WO2008067627A2 describes that olefins can be obtained from gasification of lignocellulosic materials or other organic substrates, followed by the formation of methanol and its subsequent transformation, either directly or indirectly from the intermediate dimethyl ether, into propylene. This reaction step may further generate ethylene and/or butylene as co-products.

WO2010099201A10100 describes a conventional petrochemical process for preparing butadiene, during the steam cracking of naphtha and gas-oil fractions, or production by catalytic dehydrogenation of n-butane or n-butene (which themselves are obtained by steam cracking). The crude 1,3-butadiene-containing fraction includes various C3-C5 hydrocarbons, including propylene, propane, isobutylene, 1-butene, n-butane, trans-2-butene, cis-2-butene, C4 acetylenes, 1,2-butadiene, various C5 hydrocarbons, etc., depending upon the particulars of the process and conditions.

In other conventional processes of alkene production, the dehydration of alcohols is carried out in both gas and liquid phases with both heterogeneous and homogeneous catalyst systems in many different reactor configurations. Typically, the catalysts used are stable to the water that is a product of the reaction. The resulting alkenes either exit the reactor in the gas or liquid phase, depending upon the conditions, and are captured by a downstream purification process or are further converted in the reactor to other compounds. Typical dehydration catalysts require acid treatment using phosphoric acid, sulfuric acid or neutral alumina and zeolites and generally work at higher temperatures and pressures than the acidic versions of these catalysts. Dehydrogenation catalysts convert saturated carbon-carbon bonds in organic molecules into unsaturated double bonds. Typical dehydrogenation catalysts are mixtures of metal oxides with varying degrees of selectivity towards specific olefins (e.g., Jung J C, et al, Catalysis Letters 2008, 123, p. 239).

For example when 1-butanol, 2-butanol, or isobutanol are dehydrated, a mixture of four C4 olefins-1-butene, cis-2-butene, trans-2-butene, and isobutene—is formed. The starting material determines the exact concentration of each olefin by thermodynamics and by the reaction conditions and catalysts used. It is possible to understand how these factors affect the distribution of olefins in the final product and use this knowledge to obtain mixtures enriched in a particular olefin. However, production of a single olefin by the dehydration of one of these alcohols is generally difficult.

Propylene is obtained mainly as a by-product of catalytical or thermal oil cracking, or as a co-product of ethylene production from natural gas (Propylene, Jamie G. Lacson, CEH Marketing Research Report-2004, Chemical Economics Handbook-SRI International). Propylene can also be produced by dimerization of ethylene to yield butylene followed by metathesis with additional ethylene to produce propylene. Another route is biobutanol production by sugar fermentation followed by dehydration and metathesis with ethylene. Some thermal routes are also being evaluated such as gasification of biomass to produce a syngas followed by synthesis of methanol, which will then produce green propylene via methanol-to-olefin technology.

The use of alternative routes for the production of propylene, butylene and other dienes has been explored using a wide range of renewable raw materials. Some publications refer to the possibility to convert an alcohol enzymatically by the use of a (de)hydratase into an alkene. The oleate hydratase (EC 4.2.1.53) is described as dehydrating its natural substrate, 10-hydroxy-stearic acid. However, the hydroxyl group is in the middle of the molecule, thus requiring far less activation energy for dehydration than a terminal or α- or β-sub-terminal group. EP2336341A1 describes using oleate hydratase for the dehydration of propanol (1- or 2-propanol) or butanol to produce propene and butane, respectively.

US20110165644A1, WO2014064198A1 and WO2015082447A1 describe a potential biosynthetic pathway for terminal alkene production based on the decarboxylation of 3-hydroxyalkanoates to the respective terminal alkene using a member of the phylogenetic superfamily of mevalonate diphosphate decarboxylase (MDD) (EC 4.1.1.33).

Another common type of activated substrate utilized by a dehydratase is a CoA activated α- or β-hydroxyalkanoate. For instance, 3-hydroxybutyryl-CoA is dehydrated by 3-hydroxybutyryl-CoA dehydratase to crotonyl-CoA, an intermediate steps in the generation of n-butanol.

Enoic acid (alkenoate) decarboxylase enzymes can catalyze decarboxylation reactions of enoic acids to alkenes. Different classes of enoic acid decarboxylases are described, such as sorbic acid decarboxylase, aconitate decarboxylase, 4-oxalocrotonate decarboxylase and cinnamate decarboxylase. US2013010906A1 describes the prophetic use of such enoic acid decarboxylases to convert crotonic acid to propylene. WO2013090915A1 describes the conversion of Crotyl-OH to butadiene by a linalool dehydratase, and WO2014184345A1 describes variants of linalool dehydratase isomerase having improved activity in catalyzing not only the conversion of crotyl-OH to butadiene but also 3-methylbut-2-en1-ol into isoprene, indicating that the enzyme can accept small substrates. As described in Brodkorb et al. (2010) (Brodkorb D et al. (2010) Linalool Dehydratase-Isomerase, a Bifunctional Enzyme in the Anaerobic Degradation of Monoterpenes. The Journal of Biological Chemistry 285(40): 30436-30442), linalool dehydratase isomerase is an enzyme that catalyzes in vitro an isomerization of the primary allyl-alcohol geraniol to its stereoisomer linalool and a subsequent dehydration of this tertiary alcohol to the corresponding acyclic monoterpene myrcene.

Sorbic acid decarboxylase converts sorbic acid to 1,3-pentadiene. Three genes are required for the decarboxylation: padAI, ohbAI, and sdrA (Plumridge et al. (2010) Fung. Genet. Bio, 47:683-692).

The present disclosure is based on the dehydration of saturated primary or secondary alcohols to the respective primary alkene using an enzymatic dehydration. The production of an olefin by this method avoids several drawbacks of existing chemical or described biotechnological routes:

Through bioconversion, no chemical catalysis is necessary. No harsh conditions, acid addition, high temperature or pressure is required.

The present disclosure describes a one-step fermentative production. This is in contrast to complex, multiple-step synthesis or combination of fermentation with chemical derivatization (i.e. dehydration), requiring multiple purifications and separate reaction facilities.

The fermentative process of the present disclosure allows use of renewable resources in contrast to the many chemical synthesis methods which often require non-renewable, fossil feedstocks.

In the case of the gaseous product propene, it easily separates from the substrate (i.e. glucose or 2-propanol) and biocatalyst (i.e. cells or enzyme) in the liquid phase; this is in contrast to a chemical process using gaseous substrates to produce a gaseous product, requiring an often difficult separation, or a process with a liquid intermediate (propanol), also requiring purification from solubilized substrates before final conversion is possible (dehydration to propene).

In contrast to a biotechnological route using enoic acid decarboxylase, no carbon ($CO_2$) is lost in the reaction; loss of carbon means a reduction in yield of product per precursor/substrate.

In contrast to a biotechnological route using mevalonate diphosphate decarboxylase on 3-hydroxyalkanoates (i.e. 3-hydroxybutyrate+ATP→propene+$CO_2$+ADP+Pi), no activation energy (ATP) is needed and no carbon ($CO_2$) is lost in the reaction.

Known, well developed high-yielding pathways for the production of precursors such as n-butanol, 1- or 2-propanol exist and can be utilized, in contrast to, for example, enoic acid based alkene biosynthesis, where highly performing pathways for pre-cursor generation would first have to be developed.

Surprisingly, no activation of the alcohol substrate or use of energetic cofactor is required for the dehydration, in contrast to other dehydratases requiring ATP, NAD(P)H or CoA activation of the substrate.

Surprisingly, short-chain three carbon molecules are accepted by linalool dehydratase/isomerase (LinD) as substrates, in contrast to the natural 10 carbon long-chained substrates or medium-chain length four carbon non-natural substrates (crotyl alcohol) described so far.

Surprisingly, primary or secondary alkanols were accepted by LinD as substrates; this is a distinctly different class of compounds compared to all natural or non-natural substrates of LinD described so far, which are enols. These enols have an unsaturated carbon-carbon double-bond neighboring the targeted alcohol group, which is presumed to take part in the active mechanism as electron donor. As described in Brodkorb et al. (2010), the presence of a double bond at the C2-carbon atom suggests a highly specific binding site for substrates. Citronellol compared to geraniol lacks the double bond and is impossible to isomerize.

In some embodiments, the alkene can be produced in a one-step fermentation directly from a sugar. In certain embodiments, the direct conversion (dehydration) of an alcohol to the respective alkene, mediated by an enzyme of the linalool dehydratase/isomerase family, can be done in conjunction with a pathway generating the alcohol substrate from a renewable resource. High yielding pathways and appropriate production strains for the production of 1- or 2-propanol or 1-butanol from sugars have been developed and/or described in literature.

Exemplary Pathways to Generate Alcohols

Pathways for the production of alcohols from renewable feedstocks in microorganisms expressing one or more endogenous or exogenous nucleic acid molecules encoding one or more enzymes for the production of the one or more saturated primary or secondary alcohols are known. Exemplary pathways are listed in Table 2 and described below. The described alcohol pathways are exemplary and are not intended to limit the alcohol pathway(s) that can be used to produce alcohol substrates for the present disclosure. Any pathway producing an alcohol as described in Table 1 and in the present disclosure may be used to obtain one or more alcohol substrates for dehydration with a dehydratase/isomerase to one or more primary alkenes.

TABLE 2

Pathways to produce one or more alcohols from one or more renewable feedstocks

| Pathway | Reference[a] |
|---|---|
| Mono ethylene glycol and isopropanol co-production from xylose, via ribulose-1-phosphate | Present application |
| Mono ethylene glycol and isopropanol co-production from xylose, via xylulose-1-phosphate | Present application |
| Mono ethylene glycol and isopropanol co-production from xylose, via xylonate, two-step process using a xylose dehydrogenase to convert D-xylose to D-xylonolactone followed by conversion of D-xylonolactone to D-xylonate with a xylonolactonase enzyme | Present application |
| Mono ethylene glycol and isopropanol co-production from xylose, via xylonate, one-step process using a xylose dehydrogenase to convert D-xylose directly to D-xylonate | Present application |
| Mono ethylene glycol and isopropanol co-production from xylose and glucose | Present application |
| Isopropanol from renewable feedstock | WO 2009/008377 (Mitsui et al.) |
| Isopropanol and n-propanol co-production | WO 2011/022651 (McBride et al.) |
| acetone, butanol, ethanol (ABE) fermentation | Jones D T and Woods D R (1986) Acetone-butanol fermentation revisited. Microbiol Rev. 50(4): 484-524 |
| Isopropanol, butanol, ethanol (IBE) fermentation | Lee J et al. (2012) Metabolic engineering of *Clostridium acetobutylicum* ATCC 824 for isopropanol-butanol-ethanol fermentation. Applied and Environmental Microbiology 78(5): 1416-1423 |
| Fermentative isobutanol production | U.S. 2009/0081746 (Liao et al.) and U.S. 2007/0092957 (Donaldson et al.) |

[a]The contents of each of the references in this table are herein incorporated by reference in their entireties for all purposes.

Pathways for Co-Production of Mono Ethylene Glycol (MEG) and Isopropanol (IPA)

In some embodiments, a pathway to generate an isopropanol (IPA) substrate combines one of three easy to implement, high yield C2 streams for mono ethylene glycol (MEG) production from xylose with an easy to implement IPA production stream via the dihydroxy acetone phosphate (DHAP) pathway. The problem of the IPA pathway, excess NADH production, complements the NADH requiring C2 part of MEG production. The combination of these pathways leads to a high total yield potential of 61 wt %, which is close to the maximum energetic yield of 65 wt % for degradation of xylose into MEG and IPA, assuming these products are produced in a 2:1 ratio. This high yield potential stems from the synergies of coupling the IPA pathway with the C2-branch of MEG production from xylose.

The proposed pathway in its basic form is not redox neutral, but has a small excess of 0.5 mol NADH per mol of consumed xylose. In an aerobic fermentation, oxidation of NADH can deliver just enough ATP to obtain sufficient, but not excessive, ATP required for growth and maintenance during the production phase without having a significantly negative impact on product formation.

Pathways for the co-production of MEG and IPA from xylose solve a number of problems associated with MEG and/or IPA production. In one embodiment, the problem of a difficult to implement C3 pathway in production of MEG from xylose is solved. In another embodiment, the problem of ATP shortage in production of MEG from xylose is solved. In another embodiment, the problem of loss of yield potential in production of MEG from glucose is solved. In another embodiment, the problem of ATP shortage in production of MEG from glucose is solved. In another embodiment, the problem of excess NADH production in production of MEG from glucose is solved. In another embodiment, the problem of loss of yield potential in production of IPA from glucose is solved. In another embodiment, the problem of excess NADH production in production of IPA from glucose is solved.

In some embodiments, the co-production of MEG and IPA from xylose proceeds via ribulose-1-phosphate. In one embodiment, the pathway for MEG+IPA co-production in *E. coli* comprises the following enzymes for IPA production: thiolase, acetate:acetoacetyl-CoA transferase or hydrolase, acetoacetate decarboxylase and secondary alcohol dehydrogenase. The MEG pathway via ribulose-1-phosphate comprises the following enzymes: D-tagatose 3-epimerase, D-ribulokinase, D-ribulose-phosphate aldolase and glycolaldehyde reductase. In order to increase carbon flux to the desired pathway, three specific genes that could divert carbon flux were identified and deleted: xylB gene coding for a xylulokinase (this enzyme can divert carbon flux into the pentose phosphate pathway), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

The first step of the pathway (FIG. 1) is the natural conversion of D-xylose into D-xylulose. D-xylulose normally enters the pentose phosphate pathway for energy and biomass generation, which is inhibited by the deletion of the xylB gene.

Figure 4:
FIG. 4 illustrates the conversion of acetoacetate to propene through the activities of acetoacetate decarboxylase (adc), alcohol dehydrogenase (adh) and linalool dehydratase/isomerase (linD).
Figure 5:
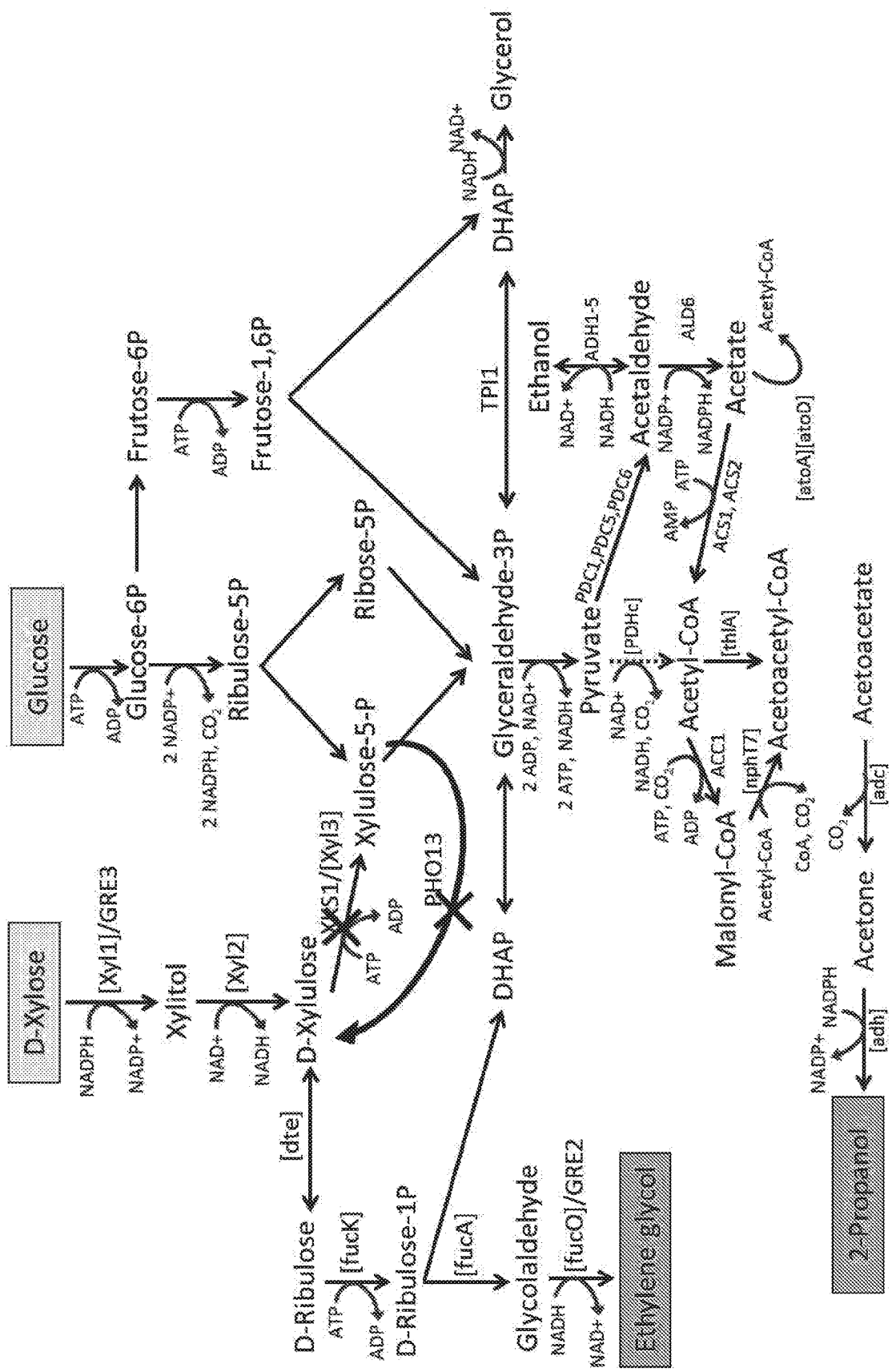
FIG. 5 illustrates MEG and isopropanol co-production pathway from xylose and glucose, via ribulose-1-phosphate, in S. cerevisiae.

In the engineered pathway, all carbon will be re-directed to D-ribulose by the D-tagatose 3-epimerase enzyme. D-ribulose is them converted to D-Ribulose-1-phosphate by the native *E. coli* enzyme D-ribulokinase. D-Ribulose-1-phosphate is cleaved into glycolaldehyde and dihydroxy acetone phosphate (DHAP) by D-ribulose-phosphate aldolase. The further degradation of DHAP is termed the C3 branch, leading to IPA production. Degradation of glycolaldehyde, termed the C2-branch, can lead to ethylene glycol or glycolate formation. Glycolate is the undesired by-product that can be produced by the aldA gene product. Ethylene glycol can be produced from glycolaldehyde using the enzyme glycolaldehyde reductase. The conversion of DHAP to acetyl-CoA (through glyceraldehyde-3P and pyruvate) is part of natural *E. coli* metabolism. One molecule of acetyl-CoA is condensed to another molecule of acetyl-CoA by the enzyme thiolase to produce acetoacetyl-CoA. The CoA from acetoacetyl-CoA is recycled to a molecule of acetate by acetate:acetoacetyl-CoA transferase or hydrolase, generating acetyl-CoA and acetoacetate. Acetoacetate is decarboxylated by acetoacetate decarboxylase to acetone which is further reduced to IPA by a secondary alcohol dehydrogenase enzyme. IPA can further be converted to propene by a linalool dehydratase/isomerase of the present disclosure (FIG. 4).

In some embodiments, the co-production of MEG and IPA from xylose proceeds via D-xylulose-1-phosphate. In some embodiments, the pathway for MEG+IPA co-production in *E. coli* comprises the following enzymes for IPA production: thiolase, acetate:acetoacetyl-CoA transferase or hydrolase, acetoacetate decarboxylase and secondary alcohol dehydrogenase. The MEG pathway via D-xylulose-1-phosphate comprises the following enzymes: D-xylulose 1-kinase, D-xylulose-1-phosphate aldolase and glycolaldehyde reductase. In order to increase carbon flux to the desired pathway, three specific genes that could divert carbon flux were identified and deleted: xylB gene coding for a xylulokinase (this enzyme can divert carbon flux into the pentose phosphate pathway), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

Figure 2:
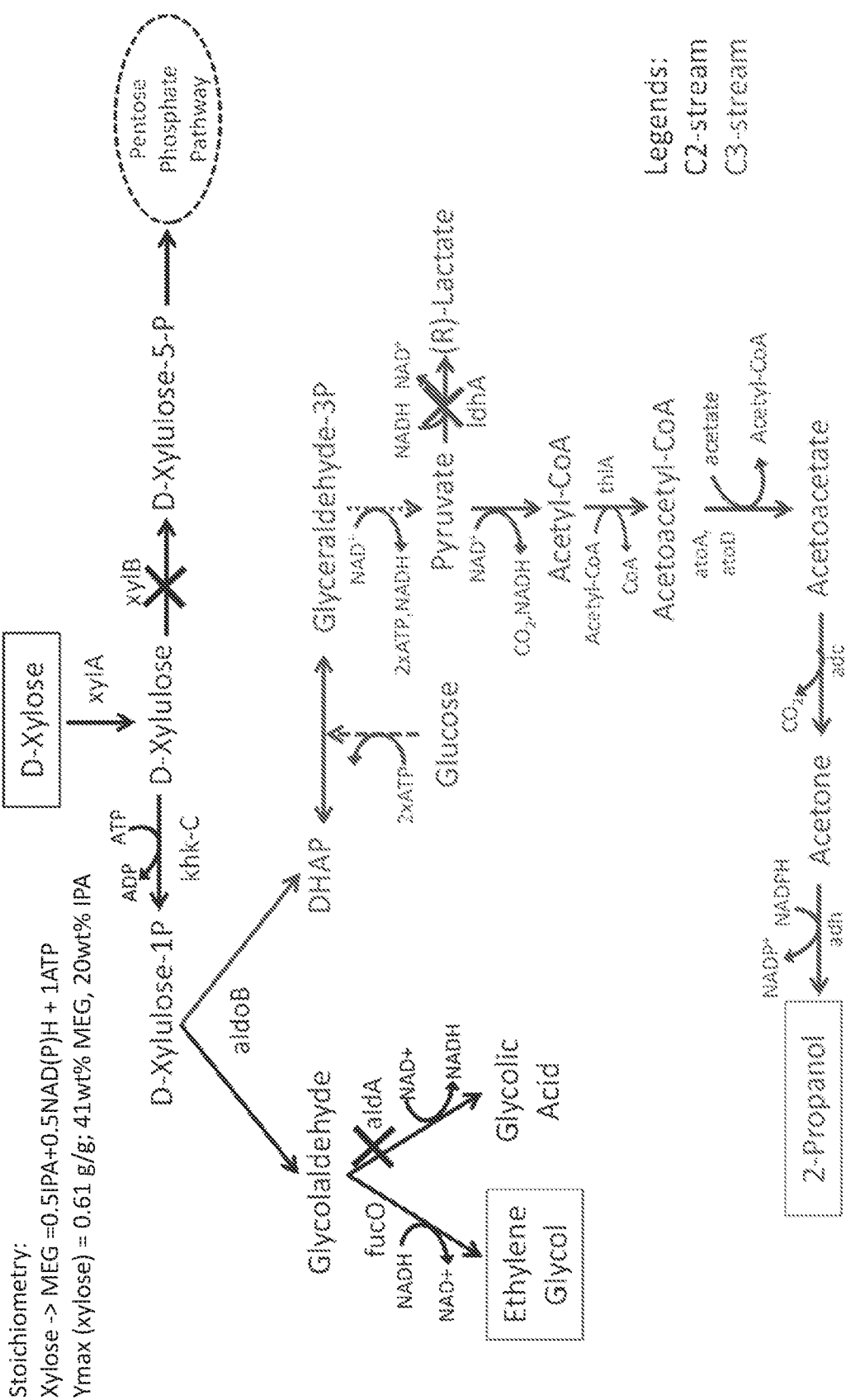
FIG. 2 illustrates MEG and isopropanol co-production pathway via xylulose-1-phosphate.

The first step of the pathway (FIG. 2) is the natural conversion of D-xylose into D-xylulose. D-xylulose normally enters the pentose phosphate pathway for energy and biomass generation, which is inhibited by the deletion of the xylB gene. In the engineered pathway, all carbon will be re-directed to D-xylulose-1-phosphate by the D-xylulose 1-kinase enzyme. D-xylulose-1-phosphate is then cleaved into glycolaldehyde and dihydroxy acetone phosphate (DHAP) by D-xylulose-1-phosphate aldolase. Production of MEG from glycolaldehyde and a three carbon compound from DHAP (for example, acetone, IPA and/or propene) proceeds as described for FIG. 1.

In some embodiments, the co-production of MEG and IPA from xylose proceeds via D-xylonate. In some embodiments, the pathway for MEG+IPA co-production in *E. coli* comprises the following enzymes for IPA production: thiolase, acetate:acetoacetyl-CoA transferase or hydrolase, acetoacetate decarboxylase and secondary alcohol dehydrogenase. The MEG pathway via D-xylonate comprises the following enzymes: xylose dehydrogenase, optionally xylonolactonase, xylonate dehydratase, 2-keto-3-deoxy-D-xylonate aldolase and glycolaldehyde reductase. In order to increase carbon flux to the desired pathway, three specific genes that could divert carbon flux were identified and deleted: xylA gene coding for a D-xylose isomerase (this enzyme can divert carbon flux from D-xylose to D-xylulose instead of to D-xylonate or D-xylonolactone), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

Figure 3:
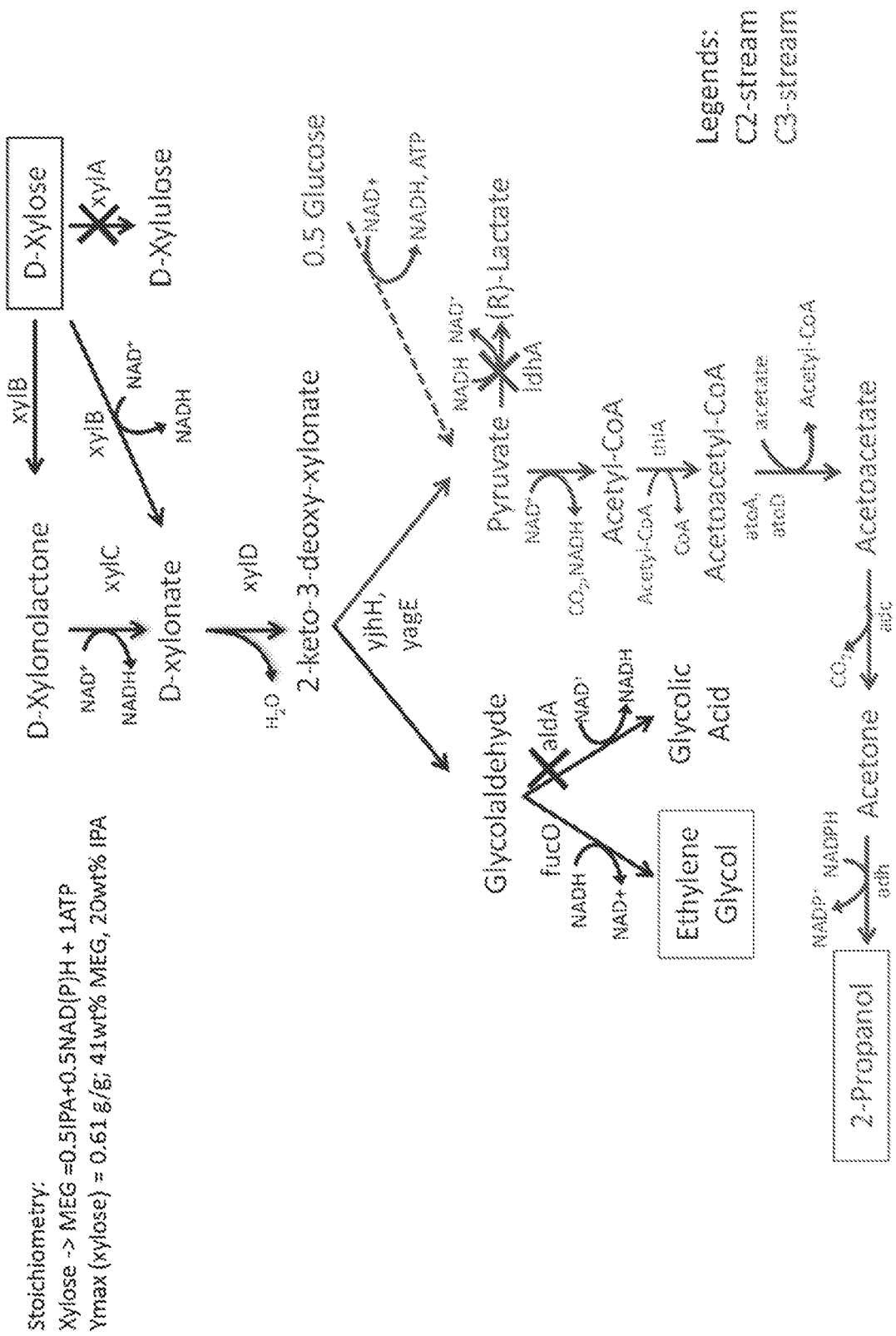
FIG. 3 illustrates MEG and isopropanol co-production pathway via xylonate.

The first step of the pathway (FIG. 3) is the conversion of D-xylose into D-xylonate, either by a two-step process using a xylose dehydrogenase to convert D-xylose to D-xylonolactone followed by conversion of D-xylonolactone to D-xylonate with a xylonolactonase enzyme, or by a one-step process using a xylose dehydrogenase to convert D-xylose directly to D-xylonate. The conversion of D-xylose to D-xylulose is inhibited by the deletion of the xylA gene. D-xylonate is then converted to 2-keto-3-deoxy-xylonate by a xylonate dehydratase. 2-keto-3-deoxy-xylonate is then cleaved into glycolaldehyde and pyruvate by 2-keto-3-deoxy-D-xylonate aldolase. Production of MEG from glycolaldehyde and a three carbon compound from pyruvate (for example, acetone, IPA and/or propene) proceeds as described for FIG. 1.

The pathway for MEG+IPA co-production in S. cerevisiae (FIG. 6) comprises the following enzymes for IPA production: thiolase, acetate:acetoacetyl-CoA transferase or hydrolase, acetoacetate decarboxylase and secondary alcohol dehydrogenase. The MEG pathway via D-ribulose-1-phosphate comprises the following enzymes: D-tagatose 3-epimerase, D-ribulokinase, D-ribulose-phosphate aldolase and glycolaldehyde reductase. Besides the two main pathways, S. cerevisiae is not capable of consuming xylose, so two different pathways were tested for xylose consumption. Pathway 1 comprises 2 genes: Xyl1 converts D-Xylose to xylitol, and Xyl2 converts Xylitol to D-xylulose. Pathway 2 comprises only one gene: XylA that directly converts D-xylose to D-xylulose. In order to increase carbon flux to the desired pathway, two specific genes that could divert carbon flux were identified and deleted: XKS1 gene coding for a xylulokinase (this enzyme can divert carbon flux into the pentose phosphate pathway) and PHO13 gene coding for alkaline phosphatase (can divert carbon from pentose phosphate pathway).

The first step of the pathway is the conversion of D-xylose into D-xylulose, directly or via the intermediate xylitol. D-xylulose is converted to D-ribulose by the D-tagatose 3-epimerase enzyme. D-ribulose is then converted to D-Ribulose-1-phosphate by D-ribulokinase. D-Ribulose-1-phosphate is cleaved into glycolaldehyde and DHAP by D-ribulose-phosphate aldolase. DHAP enters the C3 branch for IPA production and glycolaldehyde can be converted to ethylene glycol using glycolaldehyde reductase. The conversion of DHAP to acetyl-CoA (through glyceraldehyde-3P and pyruvate) is part of the natural S. cerevisiae metabolism. One molecule of acetyl-CoA is condensed to another molecule of acetyl-CoA by thiolase, producing acetoacetyl-CoA. The CoA from acetoacetyl-CoA is recycled to a molecule of acetate by acetate:acetoacetyl-CoA transferase or hydrolase, generating one molecule of acetyl-CoA and one of acetoacetate. Acetoacetate is further decarboxylated by acetoacetate decarboxylase to acetone, which is further converted to IPA by a secondary alcohol dehydrogenase enzyme. IPA can further be converted to propene by a linalool dehydratase/isomerase of the present disclosure (FIG. 4).

The main problem of the IPA pathway, excess NADH production, is highly synergistic with a C2-stream for MEG production by complementing the NADH requirement of the C2 branch, while leaving just enough NADH to generate required ATP in an aerobic process, without excess ATP production.

The synergy of coupling IPA with MEG production is such that, without necessity of $CO_2$ fixation, the combined products' yield potential of 61 wt % is very close (94%) to the energetic (=theoretic, pathway independent) maximum yield potential of 65 wt %.

The MEG and IPA co-production pathways also avoid the biggest metabolic engineering and technical challenges of both MEG and IPA fermentation processes: C3-stream MEG fermentation and carbon fixation for IPA process.

In one embodiment, MEG is produced through the conversion of glycolaldehyde in a C2 branch pathway and IPA is produced through the conversion of DHAP or pyruvate in a C3 branch pathway. In a further embodiment, the IPA is converted to propene by a linalool dehydratase/isomerase.

In one embodiment, at least a portion of the excess NADH produced in the C3 branch is used as a source of reducing equivalents in the C2 branch. In another embodiment, at least a portion of the excess NADH produced in the C3 branch is used to produce ATP.

In one embodiment, the co-produced MEG and IPA comprise a yield potential greater than 90% of the theoretical maximum yield potential without carbon fixation. In another embodiment, excess biomass formation is minimized and production of MEG and IPA is maximized.

Isopropanol from Renewable Feedstock

In one embodiment, an isopropanol substrate can be produced in a microorganism according to the disclosure of Mitsui et al. (WO 2009/008377). In some embodiments, an isopropanol substrate can be produced in a microorganism to which an acetoacetate decarboxylase activity, an isopropanol dehydrogenase activity, a CoA transferase activity and a thiolase activity have been imparted. In some embodiments, a recombinant microorganism capable of producing isopropanol from a renewable feedstock expresses one or more of the following:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and/or (d) at least one endogenous or exogenous nucleic acid molecule encoding a secondary alcohol dehydrogenase that catalyzes the conversion of acetone from (c) to isopropanol.

In a further embodiment, the recombinant microorganism further comprises a deletion, insertion, or loss of function mutation in a gene encoding a lactate dehydrogenase that catalyzes the conversion of pyruvate to lactate.

In some embodiments, the renewable feedstock is glucose.

All of the four kinds of isopropanol-producing enzymes, that is, acetoacetate decarboxylase, isopropyl alcohol dehydrogenase, CoA transferase and thiolase has been imparted to the isopropanol-producing microorganism. The production of isopropanol using this isopropanol-producing microorganism does not generate alcohols such as butanol and ethanol as by-products. Thereby, collection of isopropanol can be made remarkably simple compared to uses of a conventional isopropanol-producing microorganism.

In some embodiments, the starting material for production of isopropanol may be from one or more renewable feedstocks. In some embodiments, the starting material for production of isopropanol may be a plant organ such as a root, stem, stalk, branch, leaf, flower or seed, a plant body containing these, or a degradation product of each of these plant organs, and, in addition, among the carbon sources obtained from plant bodies or plant organs or degradation products thereof, those capable of being used by microorganisms as carbon sources for culturing are also included in the material.

Examples of the carbon sources that may be used as starting material for production of isopropanol generally include saccharides such as starch, glucose, fructose, sucrose, xylose and arabinose; plant degradation products containing large amounts of these components; and hydrolysates of cellulose. In other embodiments, glycerin and fatty acids also can be carbon sources.

Preferable embodiments of starting material used for production of isopropanol include crops such as cereals, maize, rice, wheat, soybean, sugarcane, beet and cotton. Examples of the forms of their usage as raw materials include, but are not limited to, crude products, juices and ground products.

The isopropanol-producing microorganism may be any one as long as it has an ability to produce isopropanol from one or more renewable feedstocks, and examples thereof include bacteria which utilize plant-derived materials when cultured and secrete isopropanol into the culture medium after certain time periods.

Four kinds of isopropanol-producing activities, that is, an acetoacetate decarboxylase activity, an isopropyl alcohol dehydrogenase activity, a CoA transferase activity and a thiolase activity are imparted to the isopropanol-producing microorganism.

In the disclosure, "impart(ing)" an activity, in addition to introducing a gene encoding an enzyme from the outside of a host microorganism into the inside thereof (introducing an exogenous nucleic acid sequence encoding an enzyme), also includes enhancing the activity of a promoter of an endogenous gene encoding an enzyme in the genome of a host microorganism, and replacing a promoter with another promoter to cause overexpression of an endogenous gene encoding an enzyme.

Acetoacetate decarboxylase referred to in the present disclosure is the collective name of enzymes which are classified with enzyme code 4.1.1.4 according to the report by International Union of Biochemistry (I.U.B.) Enzyme Commission and catalyze reactions producing acetone from acetoacetic acid.

Examples of such enzymes include those derived from bacteria of the genus *Clostridium* such as *Clostridium acetobutylicum* and *Clostridium beijerinckii*; and those derived from bacteria of the genus *Bacillus* such as *Bacillus polymyxa*.

In some embodiments, the acetoacetate decarboxylase is exogenous to the microorganism. In some embodiments, a nucleic acid sequence encoding acetoacetate decarboxylase can be obtained from each of the above-mentioned organisms, or a synthetic nucleic acid sequence can be synthesized based on a known nucleic acid sequence(s) of the gene encoding acetoacetate decarboxylase.

Preferable examples of the gene include those derived from bacteria of the genus *Clostridium* or bacteria of the genus *Bacillus*, and examples thereof include nucleic acid sequences of the gene derived from *Clostridium acetobutylicum* or *Bacillus polymyxa*. A nucleic acid sequence of the gene derived from *Clostridium acetobutylicum* is especially preferable.

Isopropyl alcohol dehydrogenase referred to in the present disclosure is the collective name of enzymes which are classified with enzyme code 1.1.1.80 according to the report by International Union of Biochemistry (I.U.B.) Enzyme Commission and catalyze reactions producing isopropanol from acetone.

Examples of such enzymes include those derived from bacteria of the genus *Clostridium* such as *Clostridium* beijerinckii.

In some embodiments, the isopropanol dehydrogenase is exogenous to the microorganism. In some embodiments, a nucleic acid sequence encoding isopropanol dehydrogenase can be obtained from each of the above-mentioned organisms, or a synthetic nucleic acid sequence can be synthesized based on a known nucleic acid sequence(s) of the gene encoding isopropanol dehydrogenase. Preferable examples of the gene include those derived from bacteria of the genus *Clostridium*, and examples thereof include nucleic acid sequences of the gene derived from *Clostridium beijerinckii*.

The CoA transferase referred to in the present disclosure is the collective name of enzymes which are classified with enzyme code 2.8.3.8 according to the report by International Union of Biochemistry (I.U.B.) Enzyme Commission and catalyze reactions producing acetoacetic acid from acetoacetyl-CoA.

Examples of such enzymes include those derived from bacteria of the genus *Clostridium* such as *Clostridium acetobutylicum* and *Clostridium beijerinckii*, bacteria of the genus *Roseburia* such as *Roseburia intestinalis*, bacteria of the genus *Faecalibacterium* such as *Faecalibacterium prausnitzii*, bacteria of the genus *Coprococcus*, trypanosomes such as *Trypanosoma brucei* and bacteria of the genus *Escherichia* such as *Escherichia coli* (*E. coli*).

In some embodiments, the CoA transferase is exogenous to the microorganism. In some embodiments, a nucleic acid sequence encoding CoA transferase can be obtained from each of the above-mentioned organisms, or a synthetic nucleic acid sequence can be synthesized based on a known nucleic acid sequence(s) of the gene encoding CoA transferase. Preferable examples of the gene include nucleic acid sequences of the gene derived from bacteria of the genus *Clostridium* such as *Clostridium acetobutylicum*, bacteria of the genus *Roseburia* such as *Roseburia intestinalis*, bacteria of the genus *Faecalibacterium* such as *Faecalibacterium prausnitzii*, bacteria of the genus *Coprococcus*, trypanosomes such as *Typanosoma brucei* and bacteria of the genus *Escherichia* such as *Escherichia coli*. More preferable examples thereof include those derived from bacteria of the genus *Clostridium* and bacteria of the genus *Escherichia*. A nucleic acid sequence of the gene derived from *Clostridium acetobutylicum* or *Escherichia coli* is especially preferable.

In some embodiments, the thiolase referred to in the present disclosure is the collective name of enzymes which are classified with enzyme code 2.3.1.9 according to the report by International Union of Biochemistry (I.U.B.) Enzyme Commission and catalyze reactions producing acetoacetyl-CoA from acetyl-CoA.

Examples of thiolases include those derived from bacteria of the genus *Clostridium* such as *Clostridium acetobutylicum* and *Clostridium beijerinckii*, bacteria of the genus *Escherichia* such as *Escherichia coli*, bacteria of *Halobacterium* sp., bacteria of the genus *Zoogloea* such as *Zoogloea ramigera*, bacteria of *Rhizobium* sp., bacteria of the genus *Bradyrhizobium* such as *Bradyrhizobium japonicum*, bacteria of the genus *Caulobacter* such as *Caulobacter crescentus*, bacteria of the genus *Streptomyces* such as *Streptomyces collinus*, bacteria of the genus *Enterococcus* such as *Enterococcus faecalis*, yeasts of the genus *Candida* such as *Candida tropicalis*, the genus *Helianthus* (Asteraceae) such as *Helianthus annuus*, the genus *Gallus* (Phasianidae) such as *Gallus gallus*, the genus *Rattus* (Muridae) such as *Rattus norvegicus*, the genus *Sus* (Suidae) such as *Sus scrofa* and the genus *Bos* (Bovidae) such as *Bos taurus*.

In some embodiments, the thiolase is exogenous to the microorganism. In some embodiments, a nucleic acid sequence encoding thiolase can be obtained from each of the above-mentioned organisms, or a synthetic nucleic acid sequence can be synthesized based on a known nucleic acid sequence(s) of the gene encoding thiolase. Preferable examples of the gene include nucleic acid sequences of the gene derived from bacteria of the genus *Clostridium* such as *Clostridium acetobutylicum* and *Clostridium beijennckii*, bacteria of the genus *Escherichia* such as *Escherichia coli*, bacteria of *Halobacterium* sp., bacteria of the genus *Zoogloea* such as *Zoogloea ramigera*, bacteria of *Rhizobium* sp., bacteria of the genus *Bradyrhizobium* such as *Bradyrhizobium japonicum*, bacteria of the genus *Caulobacter* such as *Caulobacter crescentus*, bacteria of the genus *Streptomyces* such as *Streptomyces collinus*, bacteria of the genus *Enterococcus* such as *Enterococcus faecalis*, yeasts of the genus *Candida* such as *Candida tropicalis*, the genus *Helianthus* (Asteraceae) such as *Helianthus annuus*, the genus *Gallus* (Phasianidae) such as *Gallus gallus*, the genus *Rattus* (Muridae) such as *Rattus norvegicus*, the genus *Sus* (Suidae) such as *Sus scrofa* and the genus *Bos* (Bovidae) such as *Bos taurus*. More preferable examples thereof include those derived from bacteria of the genus *Clostridium* and bacteria of the genus *Escherichia*; and a nucleic acid sequence of the gene derived from *Clostridium acetobutylicum* or *Escherichia coli* is especially preferable.

Each of the above four kinds of enzymes is preferably derived from at least one species selected from the group consisting of bacteria of the genus *Clostridium*, bacteria of the genus *Bacillus* and bacteria of the genus *Escherichia* in view of the enzyme activity, and, in particular, more preferable are the cases where acetoacetate decarboxylase and isopropanol dehydrogenase are derived from a bacterium/bacteria of the genus *Clostridium* and the CoA transferase activity and thiolase activity are derived from a bacterium/bacteria of the genus *Escherichia*, and the cases where all of these four kinds of enzymes are derived from a bacterium/bacteria of the genus *Clostridium*.

In certain embodiments, each of the four kinds of enzymes according to the present disclosure is preferably derived from any of *Clostridium acetobutylicum*, *Clostridium beijennckii* and *Escherichia coli* in view of the enzyme activity. More preferably, acetoacetate decarboxylase is the enzyme derived from *Clostridium acetobutylicum*; each of CoA transferase and thiolase is the enzyme derived from *Clostridium acetobutylicum* or *Escherichia coli*; and isopropanol dehydrogenase is the enzyme derived from *Clostridium beijerinckii*. Especially preferably, in view of the enzyme activities of the above-described four kinds of enzymes, the acetoacetate decarboxylase activity is derived from *Clostridium acetobutylicum*; the isopropanol dehydrogenase activity is derived from *Clostridium beijerinckii*; and the CoA transferase activity and thiolase activity are derived from *Escherichia coli*.

The activity of each of these enzymes of the present disclosure may be introduced as one or more exogenous nucleic acid sequences encoding one or more of these enzymes into the host microorganism, or alternatively, the activity of each of these enzymes of the present disclosure may be realized by overexpression of the endogenous gene(s) encoding each of these enzymes in the host microorganism. Overexpression of the endogenous gene(s) can be by enhancement of activity of a promoter(s) of the endogenous gene(s) of the host microorganism or replacement of the promoter(s) with another promoter(s) to cause overexpression of the endogenous gene(s).

Introduction of the enzyme activities may be carried out, for example, by introduction of the exogenous nucleic acid sequences encoding those four kinds of enzymes into the host microorganism using gene recombination technology. In this case, the introduced nucleic acid sequences may be either the same or different from the species of the host microorganism. Preparation of the nucleic acid sequence, cleavage and ligation of DNA molecules, transformation, PCR (Polymerase Chain Reaction), design and synthesis of oligonucleotides used as primers, and the like may be carried out by the conventional methods well-known by persons skilled in the art. These methods are described in, for example, Sambrook, J., et al., "Molecular Cloning A Laboratory Manual, Second Edition", Cold Spring Harbor Laboratory Press (1989).

Any promoter may be used as the promoter used for enhancement of the promoter activity or overexpression of the nucleic acid sequence encoding an enzyme as long as it can be expressed in a host microorganism. For example, promoters derived from *E. coli* or phages, such as the trp promoter, lac promoter, $P_L$ promoter and $P_R$ promoter are used. Promoters artificially designed or modified, such as the tac promoter may also be used. In some embodiments, the glyceraldehyde-3-phosphate dehydrogenase (GAPDH) promoter, glutamate decarboxylase A (gadA) promoter and serine hydroxymethyltransferase (glyA) promoter may also be used. These may be appropriately selected depending on the origins and types of the enzymes used.

For example, for enhancement of the activity of thiolase or CoA transferase derived from *Escherichia coli*, any promoter(s) may be used as long as it/they allow(s) expression of the enzyme in a host such as *E. coli*, and one or more of the promoter may be appropriately selected from the group of exemplary promoters consisting of the trp promoter, lac promoter, $P_L$ promoter, $P_R$ promoter, tac promoter, glyceraldehyde-3-phosphate dehydrogenase (GAPDH) promoter, glutamate decarboxylase A (gadA) promoter and serine hydroxymethyltransferase (glyA) promoter. Promoters such as the trp promoter, lac promoter, $P_L$ promoter, $P_R$ promoter, tac promoter, glyceraldehyde-3-phosphate dehydrogenase (GAPDH) promoter, glutamate decarboxylase A (gadA) promoter and serine hydroxymethyltransferase (glyA) promoter may be used to replace the promoter for thiolase or CoA transferase derived from *Escherichia* coli.

These promoters may be introduced into the host cell according to a conventional method such that the target gene encoding an enzyme may be expressed by, for example, ligating the promoter(s) into a vector that contains the target gene, followed by introduction of the vector into the host microorganism.

In some embodiments the host microorganism used for introduction of the genes encoding the four kinds of enzymes of acetoacetate decarboxylase, isopropanol dehydrogenase, CoA transferase and thiolase is a prokaryote. In some embodiments, a prokaryote is the target of either enhancement of activity of promoter(s) of these enzymes or replacement of the promoter(s). In certain embodiments, the prokaryote is a bacterium. Examples of such a bacterium include bacteria of the genus *Escherichia*, bacteria of the genus *Bacillus* and bacteria of the genus *Corynebacterium*; and *Escherichia coli*, which is especially convenient and has yielded plenty of results in industrial uses, is preferably used.

Isopropanol and n-Propanol Co-Production

In one embodiment, n-propanol and isopropanol substrates can be produced in a microorganism according to the disclosure of McBride et al. (WO 2011/022651). Recombinant microorganisms have been described where the microorganism expresses one or more native and/or heterologous enzymes; where the one or more enzymes function in one or more engineered metabolic pathways to achieve conversion of a carbohydrate source to n-propanol and isopropanol.

In some embodiments, a recombinant microorganism capable of co-producing n-propanol and isopropanol from a renewable feedstock expresses one or more of the following:

(a) at least one endogenous or exogenous nucleic acid molecule encoding a methylglyoxal synthase that catalyzes the conversion of dihydroxyacetone phosphate (DHAP) to methylglyoxal;

(b) at least one endogenous or exogenous nucleic acid molecule encoding an aldo-keto reductase that catalyzes the conversion of methylglyoxal from (a) to acetol;

(c) at least one endogenous or exogenous nucleic acid molecule encoding a glyoxylate reductase, a methylglyoxal dehydrogenase or an aldehyde dehydrogenase that catalyzes the conversion of methylglyoxal from (a) to lactaldehyde;

(d) at least one endogenous or exogenous nucleic acid molecule encoding an aldo-keto reductase that catalyzes the conversion of acetol from (b) to 1,2-propanediol;

(e) at least one endogenous or exogenous nucleic acid molecule encoding an aldehyde reductase that catalyzes the conversion of lactaldehyde from (c) to 1,2-propanediol;

(f) at least one endogenous or exogenous nucleic acid molecule encoding a diol-dehydratase that catalyzes the conversion of 1,2-propanediol from (d) or (e) to propanal;

(g) at least one endogenous or exogenous nucleic acid molecule encoding a dehydrogenase that catalyzes the conversion of propanal from (f) to n-propanol;

(h) at least one endogenous or exogenous nucleic acid molecule encoding a pyruvate formate lyase that catalyzes the conversion of pyruvate to acetyl-CoA;

(i) at least one endogenous or exogenous nucleic acid molecule encoding a thiolase that catalyzes the conversion of acetyl-CoA from (h) to acetoacetyl-CoA;

(j) at least one endogenous or exogenous nucleic acid molecule encoding an acetate:acetoacetyl-CoA transferase or hydrolase that catalyzes the conversion of acetoacetyl-CoA from (i) to acetoacetate;

(k) at least one endogenous or exogenous nucleic acid molecule encoding an acetoacetate decarboxylase that catalyzes the conversion of acetoacetate from (j) to acetone; and/or (l) at least one endogenous or exogenous nucleic acid molecule encoding a secondary alcohol dehydrogenase that catalyzes the conversion of acetone from (k) to isopropanol; wherein the DHAP and pyruvate are produced from glycolysis in the microorganism.

In a further embodiment, the recombinant microorganism further comprises one or more modifications selected from the group consisting of:

(a) a deletion, insertion, or loss of function mutation in a gene encoding an acetaldehyde dehydrogenase that catalyzes the conversion of lactaldehyde to lactate; and (b) a deletion, insertion, or loss of function mutation in a gene encoding a lactate dehydrogenase that catalyzes the conversion of pyruvate to lactate.

In some embodiments, the renewable feedstock is one or more pentose and/or hexose sugars.

In some embodiments, a pathway for the co-production of isopropanol and n-propanol in a microorganism is used to generate the alcohol substrates for dehydration to primary alkenes. In certain embodiments, isopropanol production serves in an ATP generating capacity, while n-propanol production serves as an electron sink to balance the anaerobic fermentation. This pathway allows for a balanced fermentation equation that is thermodynamically feasible. In one embodiment, the microorganism can be used in consolidated bio-processing.

Consolidated Bio-Processing (CBP) describes a mode of operation where biocatalysts produce enzymes that can break down inexpensive cellulose into usable sugars and then simultaneously ferment them into value added products in a single vessel.

Both products can be recovered from the fermentation broth via distillation, reducing downstream processing complexity. Isopropanol is a product natively produced by solventogenic Clostridia, and is rapidly produced by *Thermoanaerobacter* species when fed with acetone, indicating the presence of a native alcohol dehydrogenase with high activity for the desired reaction (Lamed R J and Zeikus J G (1981) The Biochemical J 195(1):183-190). Acetone production has been extensively studied, and the Clostridial pathway has been heterologously expressed in *E. coli* (Bermejo L L et al. (1998) Appl. Environ. Microbiol. 64(3): 1079-85). n-propanol is a natural product of propanediol degradation, with many microorganisms reported to perform this catalysis under anaerobic conditions. Recently, the genes involved in this conversion have been identified in one species, *Listeria innocula*, which will facilitate the expression of this pathway in bacterial CBP organisms (Xue J et al. (2008) Applied and Environmental Microbiol. 74(22):7073-7079). Propanediol, a key intermediate of the n-propanol pathway, is a natural fermentation product of thermophilic bacteria. *T. thermosaccharolyticum* HG-8, the organism reported to produce the highest titer of propanediol, can be engineered for the production of n-propanol.

The combined production of n-propanol and isopropanol from glucose or xylose requires the activity of several distinct enzymes (Table 3).

TABLE 3

List of native and non-native gene candidates pertaining to engineering of n-propanol and isopropanol in the CBP bacterial platform.

| Activity | EC | *C. thermocellum* | *T. saccharolyticum* | Non-native bacteria |
|---|---|---|---|---|
| triose phosphate isomerase | 5.3.1.1 | 139 | or2687 | |
| methylglyoxal synthase | 4.2.3.3 | 95 | or2316 | |
| aldo-keto reductase | 1.1.1.— | 152 | or1401 | |

TABLE 3-continued

List of native and non-native gene candidates pertaining to engineering of n-propanol and isopropanol in the CBP bacterial platform.

| Activity | EC | C. thermocellum | T. saccharolyticum | Non-native bacteria |
|---|---|---|---|---|
| (methylglyoxal to acetol) | | 236<br>283 | or1402<br>or785<br>or414<br>or2491 | |
| aldo-keto reductase (methylglyoxal to propanediol) | 1.1.1.— | 101<br>394<br>423<br>2445<br>2579 | or1043<br>or2289<br>or411<br>or2426<br>or0286 | |
| propanediol dehydratase | 4.2.1.28 | | or0222,<br>or0224-<br>or0226 | T. sacch genes can be expressed in C. therm |
| propanaldehyde dehydrogenase | 1.1.1.202 | 101<br>394<br>423<br>2579 | 0411<br>1043<br>2426<br>2289<br>0286 | |
| phosphotransacetylase | 2.3.1.8 | 1029 | or1741 | |
| acetate kinase | 2.7.2.1 | 1028 | or1742 | |
| thiolase | 2.3.1.9 | | | C. acetobutylicum |
| CoA transferase | 2.8.3.8 | | | C. acetobutylicum CtfAB |
| acetoacetate decarboxylase | 4.1.1.4 | | | C. acetobutylicum Adc, Aad |
| PFOR (oxidoreductase) | 1.2.7.1 | 2390-93 | or0047 | |
| Genes to knock out or down-regulate | | | | |
| Alcohol dehydrogenase | 1.1.1.1 | 423 | or411 | |
| Lactate dehydrogenase | 1.1.1.27 | 1053 | or180 | |
| hydrogenase | 1.12.7.2 | 425-31 | or1545-48 | |

The combined production of n-propanol and isopropanol from 3 glucose molecules during bacterial metabolism is governed by the overall stoichiometric equation:

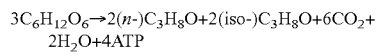

$$3C_6H_{12}O_6 \rightarrow 2(n\text{-})C_3H_8O + 2(iso\text{-})C_3H_8O + 6CO_2 + 2H_2O + 4ATP$$

The theoretical yield of propanols on a hexose sugar for the above pathway is 0.44 g propanols/g hexose.

The combined production of n-propanol and isopropanol from 9 xylose molecules during bacterial metabolism is governed by the overall stoichiometric equation:

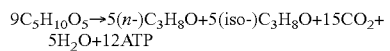

$$9C_5H_{10}O_5 \rightarrow 5(n\text{-})C_3H_8O + 5(iso\text{-})C_3H_8O + 15CO_2 + 5H_2O + 12ATP$$

The theoretical yield of propanols on a pentose sugar for the above pathway is 0.44 g propanols/g hexose.

For this metabolic pathway, product yields are identical for hexose, e.g., glucose, and pentose, e.g., xylose, carbohydrates due to the activity of triose phosphate isomerase (tpi) (E.C. 5.3.1.1). Pentose fermentation produces more of the isomer glyceraldehyde 3-phosphate (GAP) than dihydroxyacetone phosphate (DHAP) compared to hexose fermentation, which produces equimolar ratios of the two compounds. However, tpi allows for the conversion of GAP to DHAP and vice-versa, creating equal product yields for both carbohydrates.

The metabolic pathways for the production of n-propanol and isopropanol can be subdivided into two distinct production routes: (i) the conversion of dihydroxyacetone phosphate into n-propanol; and (ii) the conversion of pyruvate into isopropanol.

For the n-propanol route, route (i), dihydroxyacetone phosphate is converted to methyglyoxal by methylglyoxal synthase (E.C. 4.2.3.3). Methylglyoxal is subsequently converted to acetol by an oxidoreductase (E.C. 1.1.1.-) or to lactaldehyde by a keto-reductase (1.1.1.79 or 1.1.1.-). These intermediates are then further reduced to propanediol by enzymes from (E.C. 1.1.1.-). Propanediol is then dehydrated to propanal by a diol-hydrolase (E.C. 4.2.1.28) and reduced to n-propanol by a dehydrogenase (E.C. 1.1.1.202).

All the required enzymatic activities for the production of propanediol have been demonstrated in C. thermosaccharolyticum, a strain that can be genetically engineered (Cameron D C et al. (1998) Biotechnol. Prog. 14: 116-125). Relevant endogenous enzymes in the bacterial CBP platform production strains that exhibit high levels of homology to the desired enzymatic domains have also been identified (Table 3). The enzymes leading to propanediol in the bacterial CBP platform production strains can be characterized for implementation in route (i).

For the isopropanol route, route (ii), glyceraldehyde 3-phosphate is further metabolized to pyruvate through standard glycolysis reactions, producing ATP to power cellular reactions and reducing equivalents needed to balance n-propanol production during anaerobic fermentation. Pyruvate is then metabolized to acetyl-CoA, reduced ferredoxin, and $CO_2$ by pyruvate ferredoxin oxidoreductase (E.C. 1.2.7.1). NADH and $H_2$ are subsequently produced during the oxidation of ferredoxin.

Acetyl-CoA is then converted to acetate by phosphate acetyltransferase (EC 2.3.1.8) and acetate kinase (E.C. 2.7.2.1) in an ATP generating reaction. Two acetyl-CoA molecules are converted to acetoacetyl-CoA by thiolase (E.C. 2.3.1.9). Acetoacetyl-CoA is then converted to acetoacetate by Coenzyme A transferase (E.C. 2.8.3.8), where the CoA species is transferred from acetoacetyl-CoA to acetate, replenishing the acetyl-CoA consumed during the thiolase reaction. Acetoacetate is then converted to acetone by acetoacetate decarboxylase (E.C. 4.1.1.4). The reduction of acetone to isopropanol can be accomplished by alcohol dehydrogenases (E.C. 1.1.1.80).

The enzymes catalyzing the production of acetone from acetyl-CoA have been identified in the literature from *C. acetobutylicum* (Bermejo L L et al. (1998) Appl. Environ. Microbiol. 64(3): 1079-85). The conversion of acetone to isopropanol has been shown by multiple alcohol dehydrogenases and endogenous bacterial enzymes can be screened for their capability to accept acetone as a substrate.

Gene deletions will also be required to achieve high yields of propanol production. These include deletion of L-lactate dehydrogenase, ldh (E.C. 1.1.1.27); hydrogenase, hyd (E.C. 1.12.7.2); and acetaldehyde dehydrogenase, acdh (E.C. 1.2.1.10).

The term "methylglyoxal synthase" or "mgs" refers to an enzyme that catalyzes the chemical reaction glycerone phosphate methylglyoxal+phosphate.

The term "aldo-keto reductase" can refer to any number of related monomeric NADPH-dependent oxidoreductases, such as aldose reductase, prostaglandin F synthase, xylose reductase, and many others.

The term "oxidoreductase" refers to an enzyme that catalyzes the transfer of electrons from one molecule (the reductant, also called the hydrogen or electron donor) to another (the oxidant, also called the hydrogen or electron acceptor).

The term "glyoxylate reductase" refers to an enzyme that catalyzes the chemical reaction glycolate+$NAD^+$⇌glyoxylate+$NADH+H^+$. This enzyme belongs to the family of oxidoreductases, specifically those acting on the CH—OH group of donor with NAD+ or NADP+ as acceptor.

The term "methylglyoxal dehydrogenase" refers to an enzyme that oxidizes methylglyoxal to pyruvate.

The term "CoA transferase" is an enzyme, for example, such as acetyl CoA transferase that catalyzes the chemical reaction acyl-CoA+acetate a fatty acid anion+acetyl-CoA. The term "CoA transferase" also refers to an enzyme that catalyzes the chemical reaction acetoacetyl-CoA+acetate⇌acetoacetate+acetyl-CoA.

The term "acetoacetate decarboxylase" or "ADC" refers to an enzyme involved in both the ketone body production pathway in humans and other mammals, and solventogenesis in certain bacteria. Its reaction involves a decarboxylation of acetoacetate, forming acetone and carbon dioxide.

The term "aldehyde dehydrogenase" refers to an enzyme that catalyzes the oxidation (dehydrogenation) of aldehydes.

The term "dehydrogenase" refers to an enzyme that oxidizes a substrate by transferring one or more hydrides ($H^-$) to an acceptor, usually $NAD^+/NAD^+$.

The term "alcohol dehydrogenase" or "ADH" is intended to include the enzyme capable of converting aldehydes, such as acetaldehyde and propionaldehyde, and ketones, such as acetone, into an alcohol, such as ethanol, n-propanol, or isopropanol.

The term "phosphotransacetylase" or "PTA" is intended to include the enzyme capable of converting acetyl CoA into acetyl phosphate.

The term "diol dehydratase" is intended to include the enzyme capable of converting propanediol to propanal.

Acetone, Butanol, Ethanol (ABE) Fermentation

In one embodiment, butanol and ethanol substrates can be produced in a microorganism according to the acetone, butanol, ethanol (ABE) fermentation process described by Jones and Woods (Jones D T and Woods D R (1986) Acetone-butanol fermentation revisited. Microbiol Rev. 50(4): 484-524).

Acetone-butanol-ethanol (ABE) fermentation of sugar using solventogenic strains of *Clostridium* is a well-known industrial process, and it was used during the early and middle 20th century for the production of solvents. Hexose sugars (including mono-, di-, tri-, and polysaccharides) are metabolized via the Embden-Meyerhof pathway with the conversion of 1 mol of hexose to 2 mol of pyruvate, with the net production of 2 mol of adenosine triphosphate (ATP) and 2 mol of reduced nicotinamide adenine dinucleotide (NADH). The solvent-producing clostridia metabolize pentose sugars by way of the pentose phosphate pathway. The pentoses fermented are converted to pentose 5-phosphate and dissimilated by means of the transketolase-transaldolase sequence, resulting in the production of fructose 6-phosphate and glyceraldehyde 3-phosphate, which enter the glycolytic pathway. The fermentation of 3 mol of pentose yields 5 mol of ATP and 5 mol of NADH.

The pyruvate resulting from glycolysis is cleaved by pyruvate ferredoxin oxidoreductase in the presence of coenzyme A (CoA) to yield carbon dioxide, acetyl-CoA, and reduced ferredoxin. Acetyl-CoA produced by the phosphoroclastic cleavage is the central intermediate in the branched fermentation pathways leading to both acid and solvent production.

The onset of solvent production involves a switch in the carbon flow from the acid-producing pathways to the solvent-producing pathways. During solvent production, acetyl-CoA and butyryl-CoA function as the key intermediates for ethanol and butanol production. These pathways produce acetylaldehyde and butyraldehyde, respectively, as intermediates, and the pathway requires the function of two sets of dehydrogenases to accomplish the necessary reduction to produce ethanol and butanol.

The reduction of butyryl-CoA to butanol is mediated by butyraldehyde dehydrogenase and butanol dehydrogenase. In both *C. acetobutylicum* and *C. beijerinckii*, the activity of butanol dehydrogenase has been reported to be NADPH dependent rather than NADH dependent. The analogous acetaldehyde dehydrogenase and ethanol dehydrogenase are responsible for ethanol production from acetyl-CoA. Ethanol can be produced independently from acetone and butanol by *C. acetobutylicum* under certain culture conditions.

In some embodiments, a recombinant microorganism capable of co-producing acetone, butanol and ethanol from a renewable feedstock expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetaldehyde from (e) to ethanol or butyraldehyde from (i) to butanol;

wherein the pyruvate is produced from glycolysis in the microorganism.

In a further embodiment, the recombinant microorganism further comprises a deletion, insertion, or loss of function mutation in a gene encoding a lactate dehydrogenase that catalyzes the conversion of pyruvate to lactate.

In some embodiments, the renewable feedstock is one or more pentose and/or hexose sugars.

Isopropanol, Butanol, Ethanol (IBE) Fermentation

*C. acetobutylicum* and other solventogenic strains have been used in large-scale butanol production in the acetone-butanol-ethanol (ABE) fermentation process. Theoretical analysis of organisms' pathway stoichiometry and cellular energetic needs and some experimental results suggest that it is possible to convert most of a sugar substrate into butanol alone. However, attempts to reduce acetone production by metabolic engineering resulted in decreased butanol production and the accumulation of acetic and butyric acids.

A microorganism can be engineered to produce isopropanol instead of acetone during an ABE fermentation process. The process whereby the acetone is converted to isopropanol is called IBE (isopropanol-butanol-ethanol) fermentation and is described here. In the IBE fermentation strategy, the acetone production pathway is not disrupted, and thus it is expected that butanol production will not be compromised.

In one embodiment, isopropanol, butanol and ethanol substrates can be produced in a microorganism according to the isopropanol, butanol, ethanol (IBE) fermentation process described by Lee et al. (Lee J et al. (2012) Metabolic engineering of *Clostridium acetobutylicum* ATCC 824 for isopropanol-butanol-ethanol fermentation. Applied and Environmental Microbiology 78(5): 1416-1423).

In some embodiments, a microorganism can be engineered to produce isopropanol-butanol-ethanol (IBE) by introducing into the microorganism a secondary alcohol dehydrogenase (SADH). In certain embodiments, the secondary alcohol dehydrogenase is encoded by the $adh_{B-593}$ gene of *Clostridium beijerinckii* NRRL B-593. In some embodiments, the microorganism further comprises a synthetic acetone operon consisting of the acetoacetate decarboxylase (adc) and coenzyme A transferase genes (ctfA and ctfB). In certain embodiments, the synthetic acetone operon increases the flux toward isopropanol formation. In some embodiments, the microorganism further comprises a deletion, insertion, or loss of function mutation in a gene encoding a butyrate kinase (buk) which catalyzes the conversion of butyryl phosphate to butyrate. In some embodiments, the microorganism is *Clostridium* acetobutylicum.

In some embodiments, a recombinant microorganism capable of co-producing isopropanol, butanol and ethanol from a renewable feedstock expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetone from (d) to isopropanol, acetaldehyde from (e) to ethanol or butyraldehyde from (i) to butanol; wherein the pyruvate is produced from glycolysis in the microorganism.

In a further embodiment, the recombinant microorganism further comprises a deletion, insertion, or loss of function mutation in a gene encoding a butyrate kinase that catalyzes the conversion of butyryl phosphate to butyrate.

In some embodiments, the renewable feedstock is one or more pentose and/or hexose sugars.

Fermentative Isobutanol Production

In one embodiment, an isobutanol substrate can be produced in a microorganism according to the isobutanol fermentation process described by Liao et al. (US 2009/0081746) and/or Donaldson et al. (US 2007/0092957).

In one embodiment, a microorganism can be engineered to produce isobutanol from a suitable substrate or metabolic intermediate by introducing into the microorganism one or more nucleic acid molecules encoding polypeptides comprising acetohydroxy acid synthase activity, acetohydroxy acid isomeroreductase activity, dihydroxy-acid dehydratase activity, 2-keto-acid decarboxylase activity, and alcohol dehydrogenase activity.

The disclosure includes metabolically engineered biosynthetic pathways that utilize a microorganism's native amino acid pathway. Alcohol production utilizing the organism's native amino acid pathways offers several advantages. Not only does it avoid the difficulty of expressing a large set of foreign genes but it also minimizes the possible accumulation of toxic intermediates and circumvents the need to involve oxygen-sensitive enzymes and CoA-dependent intermediates. The disclosure provides a system utilizing the microorganism's native metabolites in the amino acid biosynthetic pathway to produce isobutanol.

Accordingly, provided herein are recombinant microorganisms that produce isobutanol and in some aspects may include the elevated expression of target enzymes such as acetohydroxy acid synthase (e.g., ilvIH operon), acetohydroxy acid isomeroreductase (e.g., ilvC), dihydroxy-acid dehydratase (e.g., ilvD), 2-keto-acid decarboxylase (e.g., PDC6, ARO10, THI3, kivd, or pdc), and alcohol dehydrogenase (e.g., ADH2). The microorganism may further include the deletion or inhibition of expression of an ethanol dehydrogenase (e.g., an adhE), ldh (e.g., an ldhA), frd (e.g., an frdB, an frdC or an frdBC), fnr, leuA, ilvE, poxB, ilvA, pflB, or pta gene, or any combination thereof, to increase the availability of pyruvate or reduce enzymes that compete for a metabolite in a desired biosynthetic pathway.

In some aspects the recombinant microorganism may include the elevated expression of acetolactate synthase (e.g., alsS), acteohydroxy acid isomeroreductase (e.g., ilvC), dihydroxy-acid dehydratase (e.g., ilvD), 2-keto acid decarboxylase (e.g., PDC6, ARO10, TH13, kivd, or pdc), and alcohol dehydrogenase (e.g., ADH2). With reference to alcohol dehydrogenases, although ethanol dehydrogenase is an alcohol dehydrogenase, the synthesis of ethanol is undesirable as a by-product in fermentative isobutanol production. Accordingly, reference to an increase in alcohol dehydrogenase activity or expression in a microorganism specifically excludes ethanol dehydrogenase activity.

In some embodiments, acetohydroxy acid synthase can be encoded by a polynucleotide derived from an ilvH operon. In some embodiments, acetohydroxy acid isomeroreductase can be encoded by a polynucleotide derived from an ilvC gene. In some embodiments, dihydroxy-acid dehydratase can be encoded by a polynucleotide derived from an ilvD gene. In some embodiments, 2-keto-acid decarboxylase can be encoded by a polynucleotide derived from a PDC6, ARO10, THI3, kivd, and/or pdc gene. In some embodiments, alcohol dehydrogenase can be encoded by a polynucleotide derived from an ADH2 gene.

The term "operon" refers two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alterative substrates and/or the ability to function in alterative environmental conditions.

Acetohydroxy acid synthases (e.g. ilvH) and acetolactate synthases (e.g., alsS, ilvB, ilv) catalyze the synthesis of the branched-chain amino acids (valine, leucine, and isoleucine). IlvH encodes an acetohydroxy acid synthase in E. coli (see, e.g., acetohydroxy acid synthase AHAS III (IlvH) (*Escherichia coli*) gi|40846|emb|CAA38855.1|(40846), incorporated herein by reference). Homologs and variants as well as operons comprising ilvH are known and include, for example, ilvH (*Microcystis aeruginosa* PCC 7806) gi|59026908|emb|CAO89159.1|(159026908); IlvH (*Bacillus amyloliquefaciens* FZB42) gi|154686966|ref|YP.sub.--001422127.1|(154686966); IlvH (*Bacillus amyloliquefaciens* FZB42) gi|154352817|gb|ABS74896.1| (154352817); IlvH (*Xenorhabdus nematophila*) gi|131054140|gb|ABO32787.1|(131054140); IlvH (*Salmonella typhimurium*) gi|7631124|gb|AAF65177.1|AF117227.sub.--2(7631124), ilvN (*Listeria innocua*) gi|16414606|emb|CAC97322.1| (16414606); ilvN (*Listeria monocytogenes*) gi|16411438|emb|CAD0063.1|(16411438); acetohydroxy acid synthase (*Caulobacter crescentus*) gi|408939|gb|AAA23048.1|(408939); acetohydroxy acid synthase I, small subunit (*Salmonella enterica* subsp. *enterica* serovar *Typhi*) gi|16504830|emb|CAD03199.1| (16504830); acetohydroxy acid synthase, small subunit (*Tropheryma whipplei* TW08/27) gi|28572714|ref|NP.sub.--789494.1|(28572714); acetohydroxy acid synthase, small subunit (*Tropheryma whipplei* TW08/27) gi|28410846|emb|CAD67232.1|(28410846); acetohydroxy acid synthase I, small subunit (*Salmonella enterica* subsp. *enterica* serovar *Paratyphi* A str. ATCC 9150) gi|56129933|gb|AAV79439.1i(56129933); acetohydroxy acid synthase small subunit; acetohydroxy acid synthase, small subunit gi|551779|gb|AAA62430.1|(551779); acetohydroxy acid synthase I, small subunit (*Salmonella enterica* subsp. *enterica* serovar *Typhi* Ty2) gi|29139650|gb|AA071216.1(29139650); acetohydroxy acid synthase small subunit (*Streptomyces cinnamonensis*) gi|5733116|gb|AAD49432.1|AF175526.sub.--1(5733116); acetohydroxy acid synthase large subunit; and acetohydroxy acid synthase, large subunit gi|400334|gb|AAA62429.1 (400334), the sequences associated with the accession numbers are incorporated herein by reference. Acetolactate synthase genes include alsS and ilvl. Homologs of ilvl and alsS are known and include, for example, acetolactate synthase small subunit (*Bifidobacterium longum* NCC2705) gi|23325489|gb|AAN24137.1|(23325489); acetolactate synthase small subunit (*Geobacillus stearothermophilus*) gi|19918933|gb|AAL99357.1|(19918933); acetolactate synthase (*Azoarcus* sp. BH72) gi|119671178|emb|CAL95091.1|(119671178); Acetolactate synthase small subunit (*Corynebacterium diphtheriae*) gi|38199954|emb|CAE49622.1|(38199954); acetolactate synthase (*Azoarcus* sp. BH72) gi|119669739|emb|CAL93652.1|(119669739); acetolactate synthase small subunit (*Corynebacterium jeikeium* K411) gi|68263981|emb|CAI37469.1|(68263981); acetolactate synthase small subunit (*Bacillus subtilis*) gi|1770067|emb|CAA99562.1|(1770067); Acetolactate synthase isozyme 1 small subunit (AHAS-I) (Acetohydroxyacid synthase I small subunit) (ALS-I) gi|83309006|sp|P0ADF8.1|ILVN_ECOLI(83309006); acetolactate synthase large subunit (*Geobacillus stearothermophilus*) gi|19918932|gb|AAL99356.1|(19918932); and Acetolactate synthase, small subunit (*Thermoanaerobacter tengcongensis* MB4) gi|20806556|ref|NP.sub.--621727.1| (20806556), the sequences associated with the accession numbers are incorporated herein by reference. There are approximately 1120 ilvB homologs and variants listed in NCBI.

Acetohydroxy acid isomeroreductase is the second enzyme in parallel pathways for the biosynthesis of isoleucine and valine. llvC encodes an acetohydroxy acid isomeroreductase in E. coli. Homologs and variants of ilvC are known and include, for example, acetohydroxyacid reductoisomerase (Schizosaccharomyces pombe 972h-) gi|162312317|ref|NP.sub.--001018845.21(162312317); acetohydroxyacid reductoisomerase (Schizosaccharomyces pombe) gi|3116142|emb|CAA18891.1|(3116142); acetohydroxyacid reductoisomerase (Saccharomyces cerevisiae YJM789) gi|151940879|gb|EDN59261.1|(151940879); llv5p: acetohydroxyacid reductoisomerase (Saccharomyces cerevisiae) gi|609403|gb|AAB67753.1|(609403); ACL198Wp (Ashbya gossypii ATCC 10895) gi|45185490|ref|NP.sub.--983206.1|(45185490); ACL198Wp (Ashbya gossypii ATCC 10895) gi|44981208|gb|AAS51030.1|(44981208); acetohydroxyacid isomeroreductase; llv5x (Saccharomyces cerevisiae) gi|957238|gb|AAB33579.1.parallel.bbm|369068|bbs|165406 (957238); acetohydroxy-acid isomeroreductase; llv5g (Saccharomyces cerevisiae) gi|957236|gb|AAB33578.1.parallel.bbm|369064|bbs|165405 (957236); and ketol-acid reductoisomerase (Schizosaccharomyces pombe) gi|2696654|dbj|BAA24000.1|(2696654), each sequence associated with the accession number is incorporated herein by reference.

Dihydroxy-acid dehydratases catalyzes the fourth step in the biosynthesis of isoleucine and valine, the dehydratation of 2,3-dihydroxy-isovaleic acid into alpha-ketoisovaleric acid. llvD and ilv3 encode a dihydroxy-acid dehydratase. Homologs and variants of dihydroxy-acid dehydratases are known and include, for example, llvD (Mycobacterium leprae) gi|2104594|emb|CAB08798.1|(2104594); dihydroxy-acid dehydratase (Tropheryma whipplei TWO8/27) gi|28410848|emb|CAD67234.1|(28410848); dihydroxy-acid dehydratase (Mycobacterium leprae) gi|13093837|emb|CAC32140.1|(13093837); dihydroxy-acid dehydratase (Rhodopirellula baltica SH 1) gi|32447871|emb|CAD77389.1|(32447871); and putative dihydroxy-acid dehydratase (Staphylococcus aureus subsp. aureus MRSA252) gi|49242408|emb|CAG41121.1| (49242408), each sequence associated with the accession numbers are incorporated herein by reference.

2-ketoacid decarboxylases catalyze the conversion of a 2-ketoacid to the respective aldehyde. For example, 2-ketoisovalerate decarboxylase catalyzes the conversion of 2-ketoisovalerate to isobutyraldehyde. A number of 2-ketoacid decarboxylases are known and are exemplified by the pdc, pdc1, pdc5, pdc6, aro10, thl3, kdcA and kivd genes. Exemplary homologs and variants useful for the conversion of a 2-ketoacid to the respective aldehyde comprise sequences designated by the following accession numbers and identified enzymatic activity: gi|44921617|gb|AAS49166.1| branched-chain alpha-keto acid decarboxylase (Lactococcus lactis); gi|15004729|ref|NP.sub.--149189.1| Pyruvate decarboxylase (Clostridium acetobutylicum ATCC 824); gi|82749898|ref|YP.sub.--415639.1| probable pyruvate decarboxylase (Staphylococcus aureus RF122); gi|77961217|ref|ZP.sub.--00825060.1|COG3961: Pyruvate decarboxylase and related thiamine pyrophosphate-requiring enzymes (Yersinia mollaretii ATCC 43969); gi|71065418|ref|YP.sub.--264145.1| putative pyruvate decarboxylase (Psychrobacter arcticus 273-4); gi|16761331|ref|NP.sub.--456948.1| putative decarboxylase (Salmonella entenca subsp. entenca serovar Typhi str. CT18); gi|93005792|ref|YP.sub.--580229.1 Pyruvate decarboxylase (Psychrobacter cryohalolentis K5); gi|23129016|ref|ZP.sub.--00110850.1| COG3961: Pyruvate decarboxylase and related thiamine pyrophosphate-requiring enzymes (Nostoc punctiforme PCC 73102); gi|16417060|gb|AAL18557.1|AF354297.sub.--1 pyruvate decarboxylase (Sarcina ventriculi); gi|15607993|ref|NP.sub.--215368.1 PROBABLE PYRUVATE OR INDOLE-3-PYRUVATE DECARBOXYLASE PDC (Mycobacterium tuberculosis H37Rv); gi|41406881|ref|NP.sub.--959717.1| Pdc (Mycobacterium avium subsp. paratuberculosis K-10); gi|91779968|ref|YP.sub.--555176.1 putative pyruvate decarboxylase (Burkholderia xenovorans LB400); gi|1582816|ref|NP.sub.--302424.1| pyruvate (or indolepyruvate) decarboxylase (Mycobacterium leprae TN); gi|118616174|ref|YP.sub.--904506.1 pyruvate or indole-3-pyruvate decarboxylase Pdc (Mycobacterium ulcerans Agy99); gi|67989660|ref|NP.sub.--001018185.1| hypothetical protein SPAC3H8.01 (Schizosaccharomyces pombe 972h-); gi|21666011|gb|AAM73540.1AF282847.sub.--1 pyruvate decarboxylase PdcB (Rhizopus oryzae); gi|69291130|ref|ZP.sub.--00619161.1| Pyruvate decarboxylase:Pyruvate decarboxylase (Kineococcus radiotolerans SRS30216); gi|66363022|ref|XP.sub.--628477.1| pyruvate decarboxylase (Cryptosporidium parvum Iowa II); gi|70981398|ref|XP.sub.--731481.1| pyruvate decarboxylase (Aspergillus fumigatus Af293); gi|121704274|ref|XP.sub.--001270401.1| pyruvate decarboxylase, putative (Aspergillus clavatus NRRL 1); gi|119467089|ref|XP.sub.--001257351.1| pyruvate decarboxylase, putative (Neosartorya fischeri NRRL 181); gi|26554143|ref|NP.sub.--758077.1| pyruvate decarboxylase (Mycoplasma penetrans HF-2); gi|21666009|gb|AAM73539.1|AF282846.sub.--1 pyruvate decarboxylase PdcA (Rhizopus oryzae).

Alcohol dehydrogenases (adh) catalyze the final step of amino acid catabolism, conversion of an aldehyde to a long chain or complex alcohol. Various adh genes are known in the art. As indicated herein adh1 homologs and variants include, for example, adh2, adh3, adh4, adh5, adh 6 and sfa1 (see, e.g., SFA (Saccharomyces cerevisiae) gi|288591|emb|CAA48161.1|(288591); the sequence associated with the accession number is incorporated herein by reference).

In some embodiments, a recombinant microorganism capable of producing isobutanol from a renewable feedstock expresses one or more of the following:

(a) at least one endogenous or exogenous nucleic acid molecule encoding an acetohydroxy acid synthase that catalyzes the conversion of pyruvate to acetolactate;

(b) at least one endogenous or exogenous nucleic acid molecule encoding an acetohydroxy acid isomeroreductase that catalyzes the conversion of acetolactate from (a) to 2,3-dihydroxy-isovalerate;

(c) at least one endogenous or exogenous nucleic acid molecule encoding a dihydroxy-acid dehydratase that catalyzes the conversion of 2,3-dihydroxy-isovalerate from (b) to α-keto-isovalerate;

(d) at least one endogenous or exogenous nucleic acid molecule encoding a 2-keto-acid decarboxylase that catalyzes the conversion of α-keto-isovalerate from (c) to isobutyraldehyde; and/or (e) at least one endogenous or exogenous nucleic acid molecule encoding an alcohol dehydrogenase that catalyzes the conversion of isobutyraldehyde from (d) to isobutanol; wherein the pyruvate is produced from glycolysis in the microorganism.

In a further embodiment, the recombinant microorganism further comprises one or more modifications selected from the group consisting of:

(a) a deletion, insertion, or loss of function mutation in a gene encoding an ethanol dehydrogenase that catalyzes the conversion of acetaldehyde to ethanol; and (b) a deletion, insertion, or loss of function mutation in a gene encoding a lactate dehydrogenase that catalyzes the conversion of pyruvate to lactate.

In some embodiments, the renewable feedstock is one or more pentose and/or hexose sugars.

Enzymes

Dehydratase-Isomerase (EC 4.2.1.-)

The present disclosure describes enzymes that can catalyze the following reactions:

geraniol⇌(3S)-linalool     (reversible reaction, EC 5.4.4.4)

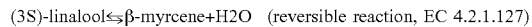

(3S)-linalool⇌β-myrcene+H2O     (reversible reaction, EC 4.2.1.127)

In one embodiment, the enzymes are dehydratase/isomerases that can catalyze the conversion of one or more saturated primary or secondary alcohols to one or more corresponding primary alkenes. In some embodiments, each primary alkene has a structure as shown in Structure B and is produced from one or more saturated primary or secondary alcohols, each primary or secondary alcohol having a structure as shown in Structure A,

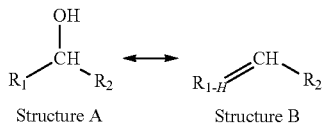

Structure A          Structure B wherein $R_1=C_nH_{2n+1}$ with $1\leq n\leq 11$; $R_2=C_mH_{2m+1}$ with $0\leq m\leq 10$ and $n+m\leq 11$.

Linalool dehydratase/isomerase has been purified to homogeneity from *Castellaniella defragrans* and found to be a homotetramer. The enzyme is present in cells grown on monoterpenes, but not in cells grown on acetate. The enzyme is inactivated by oxygen, but can be reactivated by a reducing agent under anaerobic conditions.

The bifunctional enzyme can catalyze two reactions—the isomerization of geraniol to (3S)-linalool and the hydration of β-myrcene to linalool (3,7-dimethyl-1,6-octadien-3-ol).

The gene encoding the enzyme was isolated and sequenced, and shown to encode a precursor protein containing a signal peptide for transport into the periplasm.

In some embodiments, the dehydratase/isomerase is a linalool dehydratase/isomerase. In one embodiment, the linalool dehydratase/isomerase is obtained from a microorganism selected from the group consisting of *Castellaniella defragrans* species.

In some embodiments, an amino acid sequence of a linalool dehydratase/isomerase has at least 50%, preferably at least 60%, more preferably at least 70%, more preferably at least 75%, most preferably at least 80%, most preferably at least 85%, even more preferably at least 90%, and even most preferably at least 95% sequence identity to an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63. In some embodiments, a nucleic acid sequence encoding a linalool dehydratase/isomerase has at least 50%, preferably at least 60%, more preferably at least 70%, more preferably at least 75%, most preferably at least 80%, most preferably at least 85%, even more preferably at least 90%, and even most preferably at least 95% sequence identity to a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62.

In some embodiments, the linalool dehydratase/isomerase comprises an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63. In some embodiments, the linalool dehydratase/isomerase is encoded by a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62. In further embodiments, the linalool dehydratase/isomerase is LinD. In some embodiments, the linalool dehydratase/isomerase is not comprised of an amino acid sequence selected from the group consisting of SEQ ID NOs: 64, 65, 66, 67 and 68.

In one embodiment, the linalool dehydratase/isomerase catalyzes the conversion of an alcohol listed in Table 1 to the corresponding alkene listed in Table 1. In one embodiment, the linalool dehydratase/isomerase catalyzes the conversion of 1-propanol to propene. In another embodiment, the linalool dehydratase/isomerase catalyzes the conversion of 2-propanol to propene. In some embodiments, the linalool dehydratase/isomerase catalyzes the conversion of 1-butanol to butene. In further embodiments, the linalool dehydratase/isomerase catalyzes the conversion of 2-butanol to butene.

D-tagatose 3-epimerase (EC 5.1.3.31)

The present disclosure describes enzymes that can catalyze the epimerization of various ketoses at the C3 position, interconverting D-fructose and D-psicose, D-tagatose and D-sorbose, D-ribulose and D-xylulose, and L-ribulose and L-xylulose. The specificity depends on the species. The enzymes from *Pseudomonas cichorii* and *Rhodobacter sphaeroides* require $Mn^{2+}$. In one embodiment, the enzyme is D-tagatose 3-epimerase (dte). In another embodiment, the D-tagatose 3-epimerase catalyzes the conversion of D-xylulose to D-ribulose.

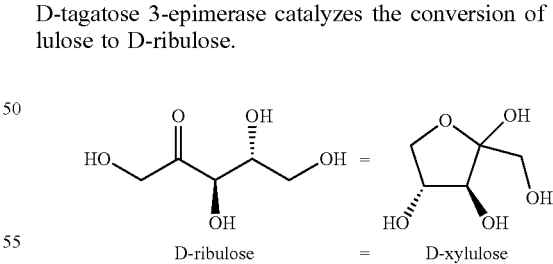

D-ribulose     =     D-xylulose

In some embodiments, the D-tagatose 3-epimerase is from *Pseudomonas* spp. In another embodiment, the D-tagatose 3-epimerase is from *Pseudomonas cichorii*. In another embodiment, the D-tagatose 3-epimerase is from *Pseudomonas* sp. ST-24. In another embodiment, the D-tagatose 3-epimerase is from *Mesorhizobium loti*. In another embodiment, the D-tagatose 3-epimerase is from *Rhodobacter sphaeroides* (C1KKR1).

D-tagatose 3-epimerase may also be known as L-ribulose 3-epimerase or ketose 3-epimerase.

In one embodiment, the enzyme that catalyzes the conversion of D-xylulose to D-ribulose is an enzyme having D-tagatose 3-epimerase activity. In a further embodiment, the enzyme that catalyzes the conversion of D-xylulose to D-ribulose is encoded by one or more endogenous nucleic acid molecules. In an alternative embodiment, the enzyme that catalyzes the conversion of D-xylulose to D-ribulose is encoded by one or more exogenous nucleic acid molecules. In another embodiment, the enzyme having D-tagatose 3-epimerase activity is encoded by a nucleic acid molecule obtained from a microorganism selected from *Pseudomonas* sp., *Mesorhizobium* sp. and *Rhodobacter* sp. In some embodiments, the nucleic acid molecule encoding an enzyme having D-tagatose 3-epimerase activity is obtained from a microorganism selected from *Pseudomonas cichorii, Pseudomonas* sp. ST-24, *Mesorhizobium loti* and *Rhodobacter sphaeroides*. In some embodiments, the nucleic acid molecule encoding an enzyme having D-tagatose 3-epimerase activity is dte, C1KKR1, or homolog thereof. In some embodiments, the one or more nucleic acid molecules is FJ851309.1 or homolog thereof. In a further embodiment, the enzyme having D-tagatose 3-epimerase activity comprises an amino acid sequence selected from the group consisting of SEQ ID NOs: 71 and 73. In yet a further embodiment, the enzyme having D-tagatose 3-epimerase activity is encoded by a nucleic acid sequence selected from the group consisting of SEQ ID NOs: 69, 70 and 72.

D-ribulokinase (EC 2.7.1.16)

The present disclosure describes enzymes that can catalyze the following reactions:

D-ribulokinase may also be known as L-fuculokinase, fuculokinase, ATP: L-fuculose 1-phosphotransferase or L-fuculose kinase.

Thus, in some embodiments, the disclosure provides for an enzyme that plays roles in the fucose degradation pathway, the super pathway of fucose and rhamnose degradation and/or the D-arabinose degradation|pathway.

In some embodiments, the enzyme can function as both an L-fucolokinase and a D-ribulokinase, the second enzyme of the L-fucose and D-arabinose degradation pathways, respectively.

In particular embodiments, the enzyme converts D-ribulose to D-ribulose-1-phosphate. In some embodiments, the D-ribulokinase is from *Escherichia coli*. In some embodiments, the D-ribulokinase is encoded by the fucK gene.

In one embodiment, the enzyme that catalyzes the conversion of D-ribulose to D-ribulose-1-phosphate is an enzyme having D-ribulokinase activity. In a further embodiment, the enzyme that catalyzes the conversion of D-ribulose to D-ribulose-1-phosphate is encoded by one or more endogenous nucleic acid molecules. In an alternative embodiment, the enzyme that catalyzes the conversion of D-ribulose to D-ribulose-1-phosphate is encoded by one or more exogenous nucleic acid molecules. In another embodiment, the enzyme having D-ribulokinase activity is encoded by a nucleic acid molecule obtained from *E. coli*. In some embodiments, the nucleic acid molecule encoding an enzyme having D-ribulokinase activity is fucK, or homolog thereof. In a further embodiment, the enzyme having D-ribulokinase activity comprises an amino acid sequence set forth in SEQ ID NO: 76. In yet a further embodiment, the enzyme having D-ribulokinase activity is encoded by a nucleic acid sequence selected from the group consisting of SEQ ID NOs: 74 and 75.

D-ribulose-1-phosphate aldolase (EC 4.1.2.17)

The present disclosure describes enzymes that can catalyze the following reversible reactions:

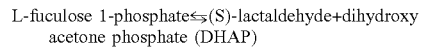

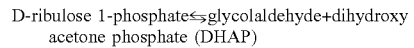

D-ribulose-1-phosphate aldolase may also be known as L-fuculose-phosphate aldolase, L-fuculose 1-phosphate aldolase or L-fuculose-1-phosphate (S)-lactaldehyde-lyase.

Thus, in some embodiments, the disclosure provides for an enzyme that plays roles in the fucose degradation pathway, the super pathway of fucose and rhamnose degradation and/or the D-arabinose degradation|pathway. In one embodiment, the enzyme may use $Zn^{2+}$ as a cofactor. In another embodiment, an inhibitor of this enzyme may be phosphoglycolohydroxamate.

In some embodiments, the enzyme can function as both an L-fuculose-phosphate aldolase and a D-ribulose-phosphate aldolase, the third enzyme of the L-fucose and D-arabinose degradation pathways, respectively.

The substrate specificity of the enzyme has been tested with a partially purified preparation from an *E. coli* strain.

Crystal structures of the enzyme and a number of point mutants have been solved. The combination of structural data and enzymatic activity of mutants allowed modelling and refinement of the catalytic mechanism of the enzyme. The enantiomeric selectivity of the enzyme has been studied.

In particular embodiments, the enzyme converts D-ribulose-1-phosphate to glycolaldehyde and DHAP. In some embodiments, the D-ribulose-1-phosphate aldolase is from *Escherichia coli*. In some embodiments, the D-ribulose-1-phosphate aldolase is encoded by the fucA gene.

In one embodiment, the enzyme that catalyzes the conversion of D-ribulose-1-phosphate to glycolaldehyde and dihydroxyacetonephosphate (DHAP) is an enzyme having D-ribulose-1-phosphate aldolase activity. In a further embodiment, the enzyme that catalyzes the conversion of D-ribulose-1-phosphate to glycolaldehyde and DHAP is encoded by one or more endogenous nucleic acid molecules. In an alternative embodiment, the enzyme that catalyzes the conversion of D-ribulose-1-phosphate to glycolaldehyde and DHAP is encoded by one or more exogenous nucleic acid molecules. In another embodiment, the enzyme having D-ribulose-1-phosphate aldolase activity is encoded by a nucleic acid molecule obtained from *E. coli*. In some embodiments, the nucleic acid molecule encoding an enzyme having D-ribulose-1-phosphate aldolase activity is fucA, or homolog thereof. In a further embodiment, the enzyme having D-ribulose-1-phosphate aldolase activity comprises an amino acid sequence set forth in SEQ ID NO: 79. In yet a further embodiment, the enzyme having D-ribulose-1-phosphate aldolase activity is encoded by a nucleic acid sequence selected from the group consisting of SEQ ID NOs: 77 and 78.

Glycolaldehyde Reductase (EC 1.1.1.77)

The present disclosure describes enzymes that can catalyze the following reversible reactions:

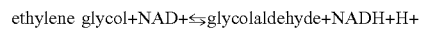

Glycolaldehyde reductase may also be known as lactaldehyde reductase, propanediol oxidoreductase, (R) [or (S)]-propane-1,2-diol:NAD+ oxidoreductase or L-1,2-propanediol oxidoreductase.

Thus, in some embodiments, the disclosure provides for an enzyme that plays roles in the ethylene glycol degradation pathway, the super pathway of glycol metabolism and degradation, the anaerobic L-lactaldehyde degradation pathway and/or the super pathway of fucose and rhamnose degradation. In one embodiment, the enzyme may use $Fe^{2+}$ as a cofactor.

L-1,2-propanediol oxidoreductase is an iron-dependent group III dehydrogenase. It anaerobically reduces L-lactaldehyde, a product of both the L-fucose and L-rhamnose catabolic pathways, to L-1,2-propanediol, which is then excreted from the cell.

Crystal structures of the enzyme have been solved, showing a domain-swapped dimer in which the metal, cofactor and substrate binding sites could be located. An aspartate and three conserved histidine residues are required for $Fe^{2+}$ binding and enzymatic activity.

In vitro, the enzyme can be reactivated by high concentrations of NAD+ and efficiently inactivated by a mixture of $Fe^{3+}$ and ascorbate or $Fe^{2+}$ and $H_2O_2$. Metal-catalyzed oxidation of the conserved His277 residue is proposed to be the cause of the inactivation.

Expression of FucO enables engineered one-turn reversal of the β-oxidation cycle. FucO activity contributes to the conversion of isobutyraldehyde to isobutanol in an engineered strain.

In particular embodiments, the enzyme converts glycolaldehyde to MEG. In some embodiments, the glycolaldehyde reductase is from *Escherichia coli*. In some embodiments, the glycolaldehyde reductase is encoded by the fucO gene.

In some embodiments, the enzyme that catalyzes the conversion of glycolaldehyde to MEG is an enzyme having glycolaldehyde reductase or aldehyde reductase activity. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme having glycolaldehyde reductase or aldehyde reductase activity is encoded by a nucleic acid molecule obtained from a microorganism selected from *E. coli* or *S. cerevisiae*. In some embodiments, the nucleic acid molecule encoding an enzyme having glycolaldehyde reductase or aldehyde reductase activity is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 81, 83, 85, 88, 91, 93, 96, 98 and 100. In yet a further embodiment, the glycolaldehyde reductase is encoded by a nucleic acid sequence selected from the group consisting of SEQ ID NOs: 80, 82, 84, 86, 87, 89, 90, 92, 94, 95, 97 and 99.

Aldehyde Reductases

A number of aldehyde reductases may be used to convert glycolaldehyde to MEG.

An NADPH-dependent aldehyde reductase (YqhD) can catalyze the following reactions:

acetol+NADP+⇌methylglyoxal+NADPH+H+(reversible, EC1.1.1.-)

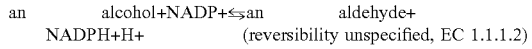

an alcohol+NADP+⇌an aldehyde+ NADPH+H+ (reversibility unspecified, EC 1.1.1.2)

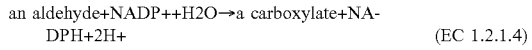

an aldehyde+NADP++H2O→a carboxylate+NADPH+2H+ (EC 1.2.1.4)

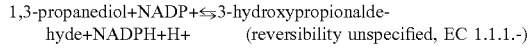

1,3-propanediol+NADP+⇌3-hydroxypropionaldehyde+NADPH+H+ (reversibility unspecified, EC 1.1.1.-)

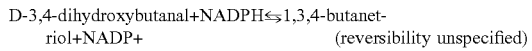

D-3,4-dihydroxybutanal+NADPH⇌1,3,4-butanetriol+NADP+ (reversibility unspecified)

YqhD is an NADPH-dependent aldehyde reductase that may be involved in glyoxal detoxification and/or be part of a glutathione-independent response to lipid peroxidation.

It has been reported that various alcohols, aldehydes, amino acids, sugars and α-hydroxy acids have been tested as substrates for YqhD. The purified protein only shows NADP-dependent alcohol dehydrogenase activity, with a preference for alcohols longer than C(3), but with Km values in the millimolar range, suggesting that they are not the physiological substrates. In contrast, YqhD does exhibit short-chain aldehyde reductase activity with substrates such as propanaldehyde, acetaldehyde, and butanaldehyde, as well as acrolein and malondialdehyde. In a metabolically engineered strain, phenylacetaldehyde and 4-hydroxyphenylacetaldehyde are reduced to 2-phenylethanol and 2-(4-hydroxyphenyl)ethanol by the endogenous aldehyde reductases YqhD, YjgB, and YahK.

Overexpression of YqhD increases 1,3-propanediol oxidoreductase activity of the cell. *E. coli* has been engineered to express YqhD for the industrial production of 1,3-propanediol. YqhD activity contributes to the production of isobutanol, 1,2-propanediol, 1,2,4-butanetriol and acetol as well. Mutation of yqhD enables production of butanol by an engineered one-turn reversal of the β-oxidation cycle.

YqhD has furfural reductase activity, which appears to cause growth inhibition due to depletion of NADPH in metabolically engineered strains that produce alcohol from lignocellulosic biomass.

The crystal structure of YqhD has been solved at 2 Å resolution. YqhD is an asymmetric dimer of dimers, and the active site contains a $Zn^{2+}$ ion. The NADPH cofactor is modified by hydroxyl groups at positions 5 and 6 in the nicotinamide ring.

Overexpression of yqhD leads to increased resistance to reactive oxygen-generating compounds such as hydrogen peroxide, paraquat, chromate and potassium tellurite. A yqhD deletion mutant shows increased sensitivity to these compounds and to glyoxal, and contains increased levels of reactive aldehydes that are generated during lipid peroxidation. Conversely, yqhD deletion leads to increased furfural tolerance.

In particular embodiments, an NADPH-dependent aldehyde reductase converts glycolaldehyde to MEG. In some embodiments, the NADPH-dependent aldehyde reductase is from *Escherichia coli*. In some embodiments, the NADPH-dependent aldehyde reductase is encoded by the yqhD gene.

A multi-functional methylglyoxal reductase (DkgA) can catalyze the following reactions:

acetol+NADP+⇌methylglyoxal+
 NADPH+
(the reaction is physiologically favored in the opposite direction, EC 1.1.1.-)

isobutanol+NADP+⇌isobutanal+
 NADPH+H+         (reversibility unspecified, EC 1.1.1.-)

ethyl-(2R)-methyl-(3S)-hydroxybutanoate+NADP+
 ⇌ethyl-2-methylacetoacetate+
 NADPH+H+         (reversibility unspecified, EC 1.1.1.-)

2-keto-L-gulonate+NADP+←2,5-didehydro-D-gluconate+
 NADPH+
(the reaction is favored in the opposite direction, EC 1.1.1.346)

DkgA (YqhE) belongs to the aldo-keto reductase (AKR) family and has been shown to have methylglyoxal reductase and beta-keto ester reductase activity.

dkgA is reported to encode a 2,5-diketo-D-gluconate reductase (25DKGR) A, one of two 25DKG reductases in *E. coli*. The enzyme uses NADPH as the preferred electron donor and is thought to be involved in ketogluconate metabolism. The specific activity of the enzyme towards 2,5-diketo-D-gluconate is reported to be almost 1000-fold lower than its activity towards methylglyoxal.

Due to its low Km for NADPH, reduction of furans by DkgA may deplete NADPH pools and thereby limit cellular biosynthesis. A broad survey of aldehyde reductases showed that DkgA was one of several endogenous aldehyde reductases that contribute to the degradation of desired aldehyde end products of metabolic engineering.

A crystal structure of DkgA has been solved at 2.16 Å resolution.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgA gene.

A multi-functional methylglyoxal reductase (DkgB) can catalyze the following reactions:

acetol+NADP+
 ⇌methylglyoxal+
(the  NADPH+H+   reaction   is
 physiologically favored in the opposite direction, EC 1.1.1.-)

4-nitrobenzyl alcohol+NADP+⇌-nitrobenzaldehyde+NADPH+H+   (reversibility unspecified, EC 1.1.1.91)

2-keto-L-gulonate+NADP+←2,5-didehydro-D-gluconate+
 NADPH+
(the reaction is favored in the opposite direction, EC 1.1.1.346)

DkgB (YafB) is a member of the aldo-keto reductase (AKR) subfamily 3F. DkgB was shown to have 2,5-diketo-D-gluconate reductase, methylglyoxal reductase and 4-nitrobenzaldehyde reductase activities.

dkgB is reported to encode 2,5-diketo-D-gluconate reductase (25DKGR) B, one of two 25DKG reductases in *E. coli*. The enzyme uses NADPH as the preferred electron donor and is thought to be involved in ketogluconate metabolism. However, the specific activity of the enzyme towards 2,5-diketo-D-gluconate is reported to be almost 1000-fold lower than its activity towards methylglyoxal.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgB gene.

A methylglyoxal reductase (YeaE) can catalyze the following reaction:

acetol+NADP+⇌methylglyoxal+
(the  NADPH+H+   reaction   is
 physiologically favored in the opposite direction, EC 1.1.1.-)

YeaE has been shown to have methylglyoxal reductase activity.

The subunit structure of YeaE has not been determined, but its amino acid sequence similarity to the aldo-keto reductases DkgA (YqhE) and DkgB (YafB) suggests that it may be monomeric.

In particular embodiments, a methylglyoxal reductase converts glycolaldehyde to MEG. In some embodiments, the methylglyoxal reductase is from *Escherichia coli*. In some embodiments, the methylglyoxal reductase is encoded by the yeaE gene.

A L-glyceraldehyde 3-phosphate reductase (yghZ) can catalyze the following reactions:

L-glyceraldehyde 3-phosphate+NADPH+H+→sn-
 glycerol 3-phosphate+NADP+         (EC 1.1.1.-)

acetol+
 NADP+⇌methylglyoxal+
(the  NADPH+H+   reaction   is
 physiologically favored in the opposite direction, EC 1.1.1.-)

YghZ is an L-glyceraldehyde 3-phosphate (L-GAP) reductase. The enzyme is also able to detoxify methylglyoxal at a low rate. YghZ defines the AKR14 (aldo-keto reductase 14) protein family.

L-GAP is not a natural metabolite and is toxic to *E. coli*. L-GAP is a substrate of both the glycerol-3-phosphate and hexose phosphate transport systems of *E. coli* K-12. It has been postulated that the physiological role of YghZ is the detoxification of L-GAP, which may be formed by non-enzymatic racemization of GAP or by an unknown cellular process.

The crystal structure of the *E. coli* enzyme has been determined and is suggested to be a tetramer. However, others have found that the protein forms an octamer based on gel filtration and electron microscopy studies.

In particular embodiments, a L-glyceraldehyde 3-phosphate reductase converts glycolaldehyde to MEG. In some embodiments, the L-glyceraldehyde 3-phosphate reductase is from *Escherichia coli*. In some embodiments, the L-glyceraldehyde 3-phosphate reductase is encoded by the yghZ gene.

An L-1,2-propanediol dehydrogenase/glycerol dehydrogenase (GldA) can catalyze the following reactions:

(S)-propane-1,2-diol+NAD+⇌acetol+NADH+H+(reversible reaction)

aminoacetone+NADH+H+→(R)-1-aminopropan-2-
 ol+NAD+         (EC 1.1.1.75)

glycerol+NAD+⇌dihydroxyacetone+
 NADH+H+         (reversible reaction, EC 1.1.1.6)

The physiological function of the GldA enzyme has long been unclear. The enzyme was independently isolated as a glycerol dehydrogenase and a D-1-amino-2-propanol: NAD+ oxidoreductase. At that time, D-1-amino-2-propanol was thought to be an intermediate for the biosynthesis of vitamin B12, and although *E. coli* is unable to synthesize vitamin B12 de novo, enzymes catalyzing the synthesis of this compound were sought. It was later found that GldA was responsible for both activities.

The primary in vivo role of GldA was recently proposed to be the removal of dihydroxyacetone by converting it to glycerol. However, a dual role in the fermentation of glycerol has also recently been established. Glycerol dissimilation in *E. coli* can be accomplished by two different pathways. The glycerol and glycerophosphodiester degradation pathway requires the presence of a terminal electron acceptor and utilizes an ATP-dependent kinase of the Glp system, which phosphorylates glycerol to glycerol-3-phosphate. However, upon inactivation of the kinase and selection for growth on glycerol, it was found that an NAD+-linked dehydrogenase, GldA, was able to support glycerol fermentation. Recently, it was shown that GldA was involved in glycerol fermentation both as a glycerol dehydrogenase, producing dihydroxyacetone, and as a 1,2-propanediol dehydrogenase, regenerating NAD+ by producing 1,2-propanediol from acetol.

The enzyme is found in two catalytically active forms, a large form of eight subunits and a small form of two subunits. The large form appears to be the major species.

In particular embodiments, an L-1,2-propanediol dehydrogenase/glycerol dehydrogenase converts glycolaldehyde to MEG. In some embodiments, the L-1,2-propanediol dehydrogenase/glycerol dehydrogenase is from *Escherichia coli*. In some embodiments, the L-1,2-propanediol dehydrogenase/glycerol dehydrogenase is encoded by the gldA gene.

An NADPH-dependent methylglyoxal reductase (GRE2) from *Saccharomyces cerevisiae* can catalyze the following reactions:

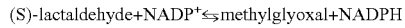

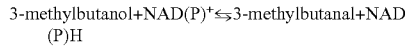

Gre2 is a versatile enzyme that catalyzes the stereoselective reduction of a broad range of substrates including aliphatic and aromatic ketones, diketones, as well as aldehydes, using NADPH as the cofactor.

The crystal structures of Gre2 from *S. cerevisiae* in an apo-form at 2.00 Å and NADPH-complexed form at 2.40 Å resolution have been solved. Gre2 forms a homodimer, each subunit of which contains an N-terminal Rossmann-fold domain and a variable C-terminal domain, which participates in substrate recognition. The induced fit upon binding to the cofactor NADPH makes the two domains shift toward each other, producing an interdomain cleft that better fits the substrate. Computational simulation combined with site-directed mutagenesis and enzymatic activity analysis enabled characterization of a potential substrate-binding pocket that determines the stringent substrate stereoselectivity for catalysis.

Gre2 catalyzes the irreversible reduction of the cytotoxic compound methylglyoxal (MG) to (S)-lactaldehyde as an alternative to detoxification of MG by glyoxalase|GLO1. MG is synthesized via a bypath of glycolysis from dihydroxyacetone phosphate and is believed to play a role in cell cycle regulation and stress adaptation. GRE2 also catalyzes the reduction of isovaleraldehyde to isoamylalcohol. The enzyme serves to suppress isoamylalcohol-induced filamentation by modulating the levels of isovaleraldehyde, the signal to which cells respond by filamentation. GRE2 is also involved in ergosterol metabolism.

In particular embodiments, an NADPH-dependent methylglyoxal reductase converts glycolaldehyde to MEG. In some embodiments, the NADPH-dependent methylglyoxal reductase is from *S. cerevisiae*. In some embodiments, the NADPH-dependent methylglyoxal reductase is encoded by the GRE2 gene.

Thiolase/Acetyl Coenzyme A Acetyltransferase (EC 2.3.1.9)

The present disclosure describes enzymes that can catalyze the following reaction:

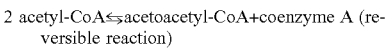

Thiolase/Acetyl coenzyme A acetyltransferase may also be known as acetyl-CoA-C-acetyltransferase, acetoacetyl-CoA thiolase, acetyl-CoA:acetyl-CoA C-acetyltransferase or thiolase II.

Thus, in some embodiments, the disclosure provides for an enzyme that plays a role in acetoacetate degradation (to acetyl CoA). In one embodiment, an inhibitor of this enzyme may be acetoacetyl-CoA.

In particular embodiments, the enzyme converts acetyl-CoA to acetoacetyl-CoA. In some embodiments, the thiolase/acetyl coenzyme A acetyltransferase is from *Clostridium* spp. In some embodiments, the thiolase/acetyl coenzyme A acetyltransferase is from *Clostridium acetobutylicum*. In some embodiments, the thiolase/acetyl coenzyme A acetyltransferase is from *Clostridium thermosaccharolyticum*. In some embodiments, the thiolase/acetyl coenzyme A acetyltransferase is from *Bacillus cereus*. In some embodiments, the thiolase/acetyl coenzyme A acetyltransferase is from *Marinobacter hydrocarbonoclasticus* ATCC 49840. In some embodiments, the thiolase/acetyl coenzyme A acetyltransferase is encoded by the thlA gene. In some embodiments, the thiolase/acetyl coenzyme A acetyltransferase is from *Escherichia coli*. In some embodiments, the thiolase/acetyl coenzyme A acetyltransferase is encoded by the atoB gene.

In some embodiments, the enzyme that catalyzes the conversion of acetyl-CoA to acetoacetyl-CoA is an enzyme having thiolase or acetyl coenzyme A acetyltransferase activity. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is an enzyme having thiolase or acetyl coenzyme A acetyltransferase activity that is encoded by a nucleic acid molecule obtained from a microorganism selected from *Clostridium* sp., *Bacillus* sp., *E. coli*, *Saccharomyces* sp. and *Marinobacter* sp. In some embodiments, the nucleic acid molecule encoding an enzyme having thiolase or acetyl coenzyme A acetyltransferase activity is obtained from a microorganism selected from *Clostridium acetobutylicum, Clostridium thermosaccharolyticum, Bacillus cereus, E. coli, Saccharomyces cerevisiae* and *Marinobacter hydrocarbonoclasticus*. In some embodiments, the nucleic acid molecule encoding an enzyme having thiolase or acetyl coenzyme A acetyltransferase activity is thlA, atoB and/or ERG10, or homolog thereof. In a further embodiment, the enzyme having thiolase or acetyl coenzyme A acetyltransferase activity comprises an amino acid sequence selected from the group consisting of SEQ ID NOs: 103, 105 and 108. In yet a further embodiment, the enzyme having thiolase or acetyl coenzyme A acetyltransferase activity is encoded by a nucleic acid sequence selected from the group consisting of SEQ ID NOs: 101, 102, 104, 106 and 107.

Acetate:Acetoacetyl-CoA Transferase (EC 2.8.3.-)

The present disclosure describes enzymes that can catalyze the following reaction:

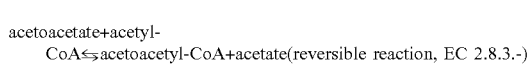

Acetate:Acetoacetyl-CoA transferase may also be known as acetoacetyl-CoA transferase or acetyl-CoA:acetoacetate-CoA transferase.

Thus, in some embodiments, the disclosure provides for an enzyme that plays a role in acetoacetate degradation (to acetyl CoA). In one embodiment, inhibitors of this enzyme may include acetyl-CoA and coenzyme A.

The growth of *E. coli* on short-chain fatty acids (C3-C6) requires the activation of the acids to their respective thioesters. This activation is catalyzed by acetoacetyl-CoA transferase. The reaction takes place in two half-reactions which involves a covalent enzyme-CoA. The enzyme undergoes two detectable conformational changes during the reaction. It is thought likely that the reaction proceeds by a ping-pong mechanism. The enzyme can utilize a variety of short-chain acyl-CoA and carboxylic acid substrates but exhibits maximal activity with normal and 3-keto substrates.

In particular embodiments, the enzyme converts acetoacetyl-CoA to acetoacetate. In some embodiments, the acetate:acetoacetyl-CoA transferase is from *Clostridium* spp. In some embodiments, the acetate:acetoacetyl-CoA transferase is from *Clostridium acetobutylicum*. In some embodiments, the acetate:acetoacetyl-CoA transferase is from *Escherichia coli*. In some embodiments, the acetate:acetoacetyl-CoA transferase is encoded by the atoA and atoD genes. In another embodiment, the subunit composition of acetoacetyl-CoA transferase is $[(AtoA)_2][(AtoD)_2]$, with $(AtoA)_2$ being the β complex and $(AtoD)_2$ being the α complex. In one embodiment, the acetate:acetoacetyl-CoA transferase is a fused acetate:acetoacetyl-CoA transferase: α subunit/β subunit. In another embodiment, the acetate:acetoacetyl-CoA transferase is encoded by the ydiF gene.

In any of the above embodiments, the enzyme that catalyzes the conversion of acetoacetyl-CoA to acetoacetate is an enzyme having acetate:acetoacetyl-CoA transferase or hydrolase activity. In some embodiments, the enzyme having transferase activity is an enzyme having acetyl-CoA:acetoacetate-CoA transferase activity. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme having acetate:acetoacetyl-CoA transferase or hydrolase activity is encoded by one or more nucleic acid molecule obtained from a microorganism selected from *Clostridium* sp. and *E. coli*. In some embodiments, the nucleic acid molecules encoding an enzyme having acetate:acetoacetyl-CoA hydrolase activity is obtained from *Clostridium acetobutylicum*. In some embodiments, the nucleic acid molecules encoding an enzyme having acetate:acetoacetyl-CoA transferase activity is obtained from *E. coli*. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the enzyme having acetyl-CoA:acetoacetate-CoA transferase activity or acetate:acetoacetyl-CoA hydrolase activity comprises an amino acid sequence selected from the group consisting of SEQ ID NOs: 111, 114, 165, 167, 169 and 171. In yet a further embodiment, the enzyme having acetyl-CoA:acetoacetate-CoA transferase activity or acetate:acetoacetyl-CoA hydrolase activity is encoded by a nucleic acid sequence selected from the group consisting of SEQ ID NOs: 109, 110, 112, 113, 164, 166, 168 and 170.

Acetate:Acetoacetyl-CoA Hydrolase (EC 3.1.2.11)

The present disclosure describes enzymes that can catalyze the following reaction:

acetoacetyl-CoA+H$_2$O ⇌ CoA+acetoacetate

Acetoacetyl-CoA hydrolase may also be known as acetoacetyl coenzyme A hydrolase, acetoacetyl CoA deacylase or acetoacetyl coenzyme A deacylase.

This enzyme belongs to the family of hydrolases, specifically those acting on thioester bonds.

In particular embodiments, the enzyme converts acetoacetyl-CoA to acetoacetate. In some embodiments, the acetate:acetoacetyl-CoA hydrolase is from *Clostridium* spp. In some embodiments, the acetate:acetoacetyl-CoA hydrolase is from *Clostridium acetobutylicum*. In another embodiment, the Acetoacetyl-CoA hydrolase is encoded by the ctfA (subunit A) and ctfB (subunit B) genes.

Acetoacetate Decarboxylase (EC 4.1.1.4)

The present disclosure describes enzymes that can catalyze the following reaction:

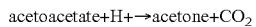

acetoacetate+H+→acetone+CO$_2$

Acetoacetate decarboxylase may also be known as ADC, AADC or acetoacetate carboxy-lyase.

Thus, in some embodiments, the disclosure provides for an enzyme that plays roles in isopropanol biosynthesis, pyruvate fermentation to acetone, the super pathway of *Clostridium acetobutylicum* acidogenic and solventogenic fermentation and/or the super pathway of *Clostridium acetobutylicum* solventogenic fermentation.

Acetoacetate decarboxylase (ADC) plays a key role in solvent production in *Clostridium acetobutylicum*. During the acidogenic phase of growth, acids accumulate causing a metabolic shift to solvent production. In this phase acids are re-assimilated and metabolized to produce acetone, butanol and ethanol.

Preliminary purification and crystallization of the enzyme has revealed that a lysine residue is implicated in the active site. The enzyme is a large complex composed of 12 copies of a single type of subunit.

The enzyme of *Clostridium acetobutylicum* ATCC 824 has been purified and the adc gene encoding it cloned. The enzyme has also been purified from the related strain *Clostridium acetobutylicum* DSM 792 and the gene cloned and sequenced. The decarboxylation reaction proceeds by the formation of a Schiff base intermediate.

ADC is a key enzyme in acid uptake, effectively pulling the CoA-transferase reaction in the direction of acetoacetate formation.

In particular embodiments, the enzyme converts acetoacetate to acetone. In some embodiments, the acetoacetate decarboxylase is from *Clostridium* spp. In some embodiments, the acetoacetate decarboxylase is from *Clostridium acetobutylicum*. In some embodiments, the acetoacetate decarboxylase is from *Clostridium beijerinckii*. In some embodiments, the acetoacetate decarboxylase is from *Clostridium cellulolyticum*. In some embodiments, the acetoacetate decarboxylase is from *Bacillus polymyxa*. In some embodiments, the acetoacetate decarboxylase is from *Chromobacterium violaceum*. In some embodiments, the acetoacetate decarboxylase is from *Pseudomonas putida*. In another embodiment, the acetoacetate decarboxylase is encoded by the adc gene.

In some embodiments, the enzyme that catalyzes the conversion of acetoacetate to acetone is an enzyme having acetoacetate decarboxylase activity. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme having acetoacetate decarboxylase activity is encoded by a nucleic acid molecule obtained from a microorganism selected from *Clostridium* sp., *Bacillus* sp., *Chromobacterium* sp. and *Pseudomonas* sp. In some embodiments, the nucleic acid molecule encoding an enzyme having acetoacetate decarboxylase activity is obtained from a microorganism selected from *Clostridium acetobutylicum*, *Clostridium beijerinckii*, *Clostridium cellulolyticum*, *Bacillus polymyxa*, *Chromobacterium violaceum* and *Pseudomonas putida*. In some embodiments, the nucleic acid molecule encoding an enzyme having acetoacetate decarboxylase activity is adc, or homolog thereof. In a further embodiment, the enzyme having acetoacetate decarboxylase activity comprises an amino acid sequence selected from the group consisting of SEQ ID NOs: 117 and 120. In yet another embodiment, the enzyme having acetoacetate decarboxylase activity is encoded by a nucleic acid sequence selected from the group consisting of SEQ ID NOs: 115, 116, 118 and 119.

Alcohol Dehydrogenase (EC 1.1.1.-)

The present disclosure describes enzymes that can catalyze the reversible oxidation of primary or secondary alcohols to aldehydes or ketones, respectively. In one embodiment, the enzyme is a secondary alcohol dehydrogenase (S-ADH) and catalyzes the reduction of ketones such as acetone into secondary alcohols such as 2-propanol (isopropanol).

In some embodiments the S-ADH is from *Burkholderia* sp. In some embodiments, the S-ADH is from *Burkholderia* sp. AIU 652. In some embodiments, the S-ADH is from *Alcaligenes* sp. In some embodiments, the S-ADH is from *Alcaligenes eutrophus*. In some embodiments, the S-ADH is from *Clostridium* sp. In some embodiments, the S-ADH is from *Clostridium ragsdalei*. In some embodiments, the S-ADH is from *Clostridium beijerinckii*. In some embodiments, the S-ADH is from *Thermoanaerobacter* sp. In some embodiments, the S-ADH is from *Thermoanaerobacter brockii*. In some embodiments, the S-ADH is from *Thermoanaerobacter ethanolicus* (*Clostridium thermohydrosulfuricum*). In some embodiments, the S-ADH is encoded by the adhB gene. In some embodiments, the S-ADH is from the trypanosomatid *Phytomonas* sp. In some embodiments, the S-ADH is from *Rhodococcus* sp. In some embodiments, the S-ADH is from *Rhodococcus ruber*. In some embodiments, the S-ADH is from *Methanobacterium palustre*. In some embodiments, the S-ADH is from methanogenic archaea *Methanogenium liminatans*. In some embodiments, the S-ADH is from the parasitic protist *Entamoeba histolytica* (EhAdh1). In some embodiments, the S-ADH is from parasitic protozoan *Tritrichomonas foetus*. In some embodiments, the S-ADH is from human parasite *Trichomonas vaginalis*.

In some embodiments, the S-ADH is predicted from homology and can be from *Thermoanaerobacter mathranii*, *Micrococcus luteus*, *Nocardiopsis alba*, *Mycobacterium hassiacum*, *Helicobacter suis*, *Candida albicans*, *Candida parapsilosis*, *Candida orthopsilosis*, *Candida metapsilosis*, *Grosmannia clavigera* and *Scheffersomyces stipitis*.

In some embodiments, the recombinant microorganism may comprise at least one nucleic acid molecule encoding an enzyme that catalyzes the conversion of acetone to isopropanol. In one embodiment, the enzyme that catalyzes the conversion of acetone to isopropanol is encoded by one or more endogenous nucleic acid molecules. In an alternative embodiment, the enzyme that catalyzes the conversion of acetone to isopropanol is encoded by one or more exogenous nucleic acid molecules. In one embodiment, the enzyme that catalyzes the conversion of acetone to isopropanol is a secondary alcohol dehydrogenase (S-ADH). In another embodiment, the enzyme having secondary alcohol dehydrogenase activity is encoded by a nucleic acid molecule obtained from a microorganism selected from *Burkholderia* sp, *Alcaligenes* sp., *Clostridium* sp., *Thermoanaerobacter* sp., *Phytomonas* sp., *Rhodococcus* sp., *Methanobacterium* sp., *Methanogenium* sp., *Entamoeba* sp., *Trichomonas* sp., and *Tritrichomonas* sp. In some embodiments, the nucleic acid molecule encoding the enzyme having secondary alcohol dehydrogenase activity is obtained from a microorganism selected from *Burkholderia* sp. AIU 652, *Alcaligenes eutrophus*, *Clostridium ragsdalei*, *Clostridium beijerinckii*, *Clostridium carboxidivorans*, *Thermoanaerobacter brockii*, *Thermoanaerobacter ethanolicus* (*Clostridium thermohydrosulfuricum*), *Rhodococcus ruber*, *Methanobacterium palustre*, methanogenic archaea *Methanogenium liminatans*, parasitic protist *Entamoeba histolytica*, parasitic protozoan *Tritrichomonas foetus* and human parasite *Trichomonas vaginalis*. In some embodiments, the one or more nucleic acid molecule encoding an enzyme having secondary alcohol dehydrogenase activity is adh, adhB, EhAdh1, or homolog thereof. In some embodiments, the S-ADH is predicted from homology and can be from *Thermoanaerobacter mathranii*, *Micrococcus luteus*, *Nocardiopsis alba*, *Mycobacterium hassiacum*, *Helicobacter suis*, *Candida albicans*, *Candida parapsilosis*, *Candida orthopsilosis*, *Candida metapsilosis*, *Grosmannia clavigera* and *Scheffersomyces stipitis*. In a further embodiment, the enzyme having alcohol dehydrogenase activity comprises an amino acid sequence selected from the group consisting of SEQ ID NOs: 174 and 176. In yet another embodiment, the alcohol dehydrogenase is encoded by a nucleic acid sequence selected from the group consisting of SEQ ID NOs: 172, 173 and 175.

D-xylulose 1-kinase (EC 2.7.1.-)

The present disclosure describes enzymes that can catalyze the conversion of D-xylulose to D-xylulose-1-phosphate. In some embodiments, the conversion can be catalyzed by a human ketohexokinase C (khk-C), also known as fructokinase.

Ketohexokinase, or fructokinase, phosphorylates fructose to fructose-1-phosphate. The enzyme is involved in fructose metabolism, which is part of carbohydrate metabolism. It is found in the liver, intestine and kidney cortex.

In human liver, purified fructokinase, when coupled with aldolase, has been discovered to contribute to an alternative mechanism to produce oxalate from xylitol. In coupled sequence, fructokinase and aldolase produce glycolaldehyde, a precursor to oxalate, from D-xylulose via D-xylulose 1-phosphate.

In particular embodiments, the enzyme converts D-xylulose to D-xylulose-1-phosphate. In some embodiments, the D-xylulose 1-kinase is a ketohexokinase C. In some embodiments, the ketohexokinase C is from *Homo sapiens*. In some embodiments, the human ketohexokinase C is encoded by the khk-C gene.

In one embodiment, the enzyme that catalyzes the conversion of D-xylulose to D-xylulose-1-phosphate is an enzyme having D-xylulose 1-kinase activity. In a further embodiment, the enzyme that catalyzes the conversion of D-xylulose to D-xylulose-1-phosphate is encoded by one or more endogenous nucleic acid molecules. In an alternative embodiment, the enzyme that catalyzes the conversion of D-xylulose to D-xylulose-1-phosphate is encoded by one or more exogenous nucleic acid molecules. In another embodiment, the enzyme having D-xylulose 1-kinase activity is encoded by a nucleic acid molecule obtained from *Homo sapiens*. In one embodiment, the *Homo sapiens* enzyme having D-xylulose 1-kinase activity is a ketohexokinase C. In some embodiments, the nucleic acid molecule encoding human ketohexokinase C is khk-C, or homolog thereof. In another embodiment, the one or more nucleic acid molecules encoding the enzyme having D-xylulose 1-kinase activity comprises an amino acid sequence set forth in SEQ ID NO: 123. In a further embodiment, the one or more nucleic acid molecules encoding the enzyme having D-xylulose 1-kinase activity is encoded by a nucleic acid sequence selected from the group consisting of SEQ ID NOs: 121 and 122.

D-xylulose-1-phosphate aldolase

The present disclosure describes enzymes that can catalyze the conversion of D-xylulose-1-phosphate to glycolaldehyde and DHAP. In some embodiments, the conversion can be catalyzed by a human aldolase B, which is also known as fructose-bisphosphate aldolase B or liver-type aldolase.

Aldolase B is one of three isoenzymes (A, B, and C) of the class I fructose 1,6-bisphosphate aldolase enzyme (EC 4.1.2.13), and plays a key role in both glycolysis and gluconeogenesis. The generic fructose 1,6-bisphosphate aldolase enzyme catalyzes the reversible cleavage of fructose 1,6-bisphosphate (FBP) into glyceraldehyde 3-phosphate and dihydroxyacetone phosphate (DHAP) as well as the reversible cleavage of fructose 1-phosphate (F1P) into glyceraldehyde and dihydroxyacetone phosphate. In mammals, aldolase B is preferentially expressed in the liver, while aldolase A is expressed in muscle and erythrocytes and aldolase C is expressed in the brain. Slight differences in isozyme structure result in different activities for the two substrate molecules: FBP and fructose 1-phosphate. Aldolase B exhibits no preference and thus catalyzes both reactions, while aldolases A and C prefer FBP.

Aldolase B is a homotetrameric enzyme, composed of four subunits. Each subunit has a molecular weight of 36 kDa and contains an eight-stranded a/3 barrel, which encloses lysine 229 (the Schiff-base forming amino acid that is key for catalysis).

In particular embodiments, the enzyme converts D-xylulose-1-phosphate to glycolaldehyde and DHAP. In some embodiments, the D-xylulose-1-phosphate aldolase is an aldolase B. In some embodiments, the aldolase B is from *Homo sapiens*. In some embodiments, the human aldolase B is encoded by the ALDOB gene.

In one embodiment, the enzyme that catalyzes the conversion of D-xylulose-1-phosphate to glycolaldehyde and dihydroxyacetonephosphate (DHAP) is a D-xylulose-1-phosphate aldolase. In a further embodiment, the enzyme that catalyzes the conversion of D-xylulose-1-phosphate to glycolaldehyde and DHAP is encoded by one or more endogenous nucleic acid molecules. In an alternative embodiment, the enzyme that catalyzes the conversion of D-xylulose-1-phosphate to glycolaldehyde and DHAP is encoded by one or more exogenous nucleic acid molecules.

In another embodiment, the enzyme is a D-xylulose-1-phosphate aldolase that is encoded by a nucleic acid molecule obtained from *Homo sapiens*. In one embodiment, the *Homo sapiens* D-xylulose 1-phosphate aldolase is an aldolase B. In some embodiments, the nucleic acid molecule encoding human aldolase B is ALDOB, or homolog thereof. In some embodiments, the one or more nucleic acid molecules encoding the D-xylulose-1-phosphate aldolase comprises an amino acid sequence set forth in SEQ ID NO: 126. In some embodiments, the one or more nucleic acid molecules encoding the D-xylulose-1-phosphate aldolase is encoded by a nucleic acid sequence selected from the group consisting of SEQ ID NOs: 124 and 125.

D-xylose Isomerase (EC 5.3.1.5)

The present disclosure describes enzymes that can catalyze the following reversible reaction:

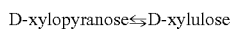

D-xylose isomerase may also be known as xylose isomerase or D-xylose ketol-isomerase.

Thus, in some embodiments, the disclosure provides for an enzyme that plays a role in xylose degradation.

Xylose isomerase catalyzes the first reaction in the catabolism of D-xylose.

Two conserved histidine residues, H101 and H271, were shown to be essential for catalytic activity. The fluorescence of two conserved tryptophan residues, W49 and W188, is quenched during binding of xylose, and W49 was shown to be essential for catalytic activity. The presence of $Mg^{2+}$, $Mn^{2+}$ or $Co^{2+}$ protects the enzyme from thermal denaturation.

The subunit composition has not been established experimentally.

In particular embodiments, the enzyme converts D-xylose to D-xylulose. In some embodiments, the D-xylose isomerase is from *Escherichia coli*. In some embodiments, the D-xylose isomerase is encoded by the xylA gene.

In some embodiments, a recombinant microorganism producing MEG and an alcohol comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the enzyme that catalyzes the conversion of D-xylose to D-xylulose is an enzyme having D-xylose isomerase activity. In a further embodiment, the enzyme that catalyzes the conversion of D-xylose to D-xylulose is encoded by one or more endogenous nucleic acid molecules. In an alternative embodiment, the enzyme that catalyzes the conversion of D-xylose to D-xylulose is encoded by one or more exogenous nucleic acid molecules. In another embodiment, the enzyme having D-xylose isomerase activity is encoded by a nucleic acid molecule obtained from *E. coli*. In another embodiment, the enzyme having xylose isomerase activity is encoded by one or more nucleic acid molecules obtained from *Pyromyces* sp. In some embodiments, the nucleic acid molecule encoding an enzyme having D-xylose isomerase activity is xylA, or homolog thereof. In yet another embodiment, the one or more nucleic acid molecules encoding the enzyme having xylose isomerase activity comprises an amino acid sequence selected from SEQ ID NOs: 163 and 190. In a further embodiment, the one or more nucleic acid molecules encoding the enzyme having xylose isomerase activity is encoded by a nucleic acid sequence selected from SEQ ID NOs: 161, 162 and 189.

In some embodiments, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof. In some embodiments, a recombinant microorganism producing MEG and isopropanol comprises a deletion, insertion, or loss of function mutation in a gene encoding a D-xylose isomerase to prevent conversion of D-xylose to D-xylulose and instead shunt the reaction toward the conversion of D-xylose to D-xylonate.

D-xylulose-5-kinase/xylulokinase

The present disclosure describes enzymes that can catalyze the following reactions:

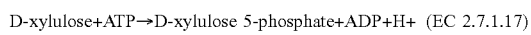

D-xylose+ATP→D-xylulose 5-phosphate+ADP+H+ (EC 2.7.1.17)

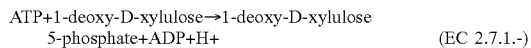

ATP+1-deoxy-D-xylulose→1-deoxy-D-xylulose 5-phosphate+ADP+H+ (EC 2.7.1.-)

D-xylulose-5-kinase may also be known as xylulose kinase or xylulokinase.

Xylulokinase catalyzes the phosphorylation of D-xylulose, the second step in the xylose degradation pathway, producing D-xylulose-5-phosphate, an intermediate of the pentose phosphate pathway.

In the absence of substrate, xylulokinase has weak ATPase activity. Xylulokinase can also catalyze the phosphorylation of 1-deoxy-D-xylulose. This would allow a potential salvage pathway for generating 1-deoxy-D-xylulose 5-phosphate for use in the biosynthesis of terpenoids, thiamine and pyridoxal. The rate of phosphorylation of 1-deoxy-D-xylulose is 32-fold lower than the rate of phosphorylation of D-xylulose.

The kinetic mechanism of the bacterial enzyme has been studied, suggesting a predominantly ordered reaction mechanism. The enzyme undergoes significant conformational changes upon binding of the substrate and of ATP. Two conserved aspartate residues, D6 and D233, were found to be essential for catalytic activity, and a catalytic mechanism has been proposed.

Crystal structures of bacterial xylulokinase in the apo form and bound to D-xylulose have been determined at 2.7 and 2.1 Å resolution, respectively.

In particular embodiments, the enzyme converts D-xylulose to D-xylulose-5-phosphate. In some embodiments, the D-xylulose-5-kinase is from *Escherichia coli*. In some embodiments, the D-xylulose-5-kinase is encoded by the xylB gene. In some embodiments, the D-xylulose-5-kinase is from *Saccharomyces cerevisiae*. In some embodiments the D-xylulose-5-kinase is encoded by the XKS1 gene. In some embodiments, the D-xylulose-5-kinase is from *Pichia stipitis*. In some embodiments the D-xylulose-5-kinase is encoded by the XYL3 gene.

In some embodiments, a recombinant microorganism producing MEG and an alcohol comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

Xylose Dehydrogenase

The present disclosure describes enzymes that can catalyze the following reactions:

aldehydo-D-xylose+NAD++H2O→D-xylonate+ NADH+2H+

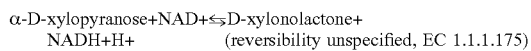

α-D-xylopyranose+NAD+⇌D-xylonolactone+ NADH+H+  (reversibility unspecified, EC 1.1.1.175)

Xylose dehydrogenase may also be known as D-xylose dehydrogenase, D-xylose 1-dehydrogenase, (NAD+)-linked D-xylose dehydrogenase, NAD+-D-xylose dehydrogenase, D-xylose:NAD+1-oxidoreductase D-Xylose dehydrogenase catalyzes the NAD+-dependent oxidation of D-xylose to D-xylonolactone. This is the first reaction in the oxidative, non-phosphorylative pathway for the degradation of D-xylose in *Caulobacter crescentus*. This pathway is similar to the pathway for L-arabinose degradation in *Azospirillum brasilense*. The amino acid sequence of the *C. crescentus* enzyme is unrelated to that of xylose dehydrogenase from the archaeon *Haloarcula marismortui*, or the L-arabinose 1-dehydrogenase of *Azospirillum brasilense*.

D-xylose is the preferred substrate for recombinant D-xylose dehydrogenase from *Caulobacter crescentus*. The enzyme can use L-arabinose, but it is a poorer substrate. The Km for L-arabinose is 166 mM. Other substrates such as D-arabinose, L-xylose, D-ribose, D-galactose, D-glucose and D-glucose-6-phosphate showed little or no activity in the assay, as measured by NADH production. *C. crescentus* D-xylose dehydrogenase can convert D-xylose to D-xylonate directly.

Partially purified, native D-xylose dehydrogenase from *C. crescentus* had a Km of 70 µM for D-xylose. This value was lower than the Km of 760 µM for the recombinant, His-tagged enzyme.

In some embodiments, the D-Xylose dehydrogenase is from the halophilic archaeon *Haloferax volcanii*. The *Haloferax volcanii* D-Xylose dehydrogenase catalyzes the first reaction in the oxidative xylose degradation pathway of the halophilic archaeon *Haloferax volcanii*. The *H. volcanii* D-Xylose dehydrogenase shows 59% amino acid sequence identity to a functionally characterized xylose dehydrogenase from *Haloarcula marismortui* and 56% identity to an ortholog in *Halorubrum lacusprofundi*, but is only 11% identical to the bacterial NAD+-dependent xylose dehydrogenase from *Caulobacter crescentus* CB15.

In particular embodiments, the enzyme converts D-xylose to D-xylonolactone. In some embodiments, the D-Xylose dehydrogenase is from *Caulobacter crescentus*. In some embodiments, the D-Xylose dehydrogenase is encoded by the xylB gene. In some embodiments, the D-Xylose dehydrogenase is from *Haloferax volcanii*. In some embodiments, the D-Xylose dehydrogenase is from *Haloarcula marismortui*. In some embodiments, the D-Xylose dehydrogenase is from *Halorubrum lacusprofundi*. In some embodiments, the D-Xylose dehydrogenase is encoded by the xdh gene.

In one embodiment, the enzyme that catalyzes the conversion of D-xylose to D-xylonolactone is an enzyme having xylose dehydrogenase activity. In a further embodiment, the enzyme that catalyzes the conversion of D-xylose to D-xylonolactone is encoded by one or more endogenous nucleic acid molecules. In an alternative embodiment, the enzyme that catalyzes the conversion of D-xylose to D-xylonolactone is encoded by one or more exogenous nucleic acid molecules. In another embodiment, the enzyme having xylose dehydrogenase activity is encoded by a nucleic acid molecule obtained from a microorganism selected from *Caulobacter* sp., *Haloarcula* sp., *Haloferax* sp., *Halorubrum* sp. and *Trichoderma* sp. In some embodiments, the nucleic acid molecule encoding the enzyme having xylose dehydrogenase activity is obtained from a microorganism selected from *Caulobacter crescentus*, *Haloarcula marismortui*, *Haloferax volcanii*, *Halorubrum lacusprofundi* and *Trichoderma reesei*. In some embodiments, the nucleic acid molecule encoding an enzyme having xylose dehydrogenase activity is selected from xylB, xdh (HVO_B0028), xyd1, or homolog thereof. In a further embodiment, the one or more nucleic acid molecules encoding the enzyme having xylose dehydrogenase activity comprises an amino acid sequence selected from the group consisting of SEQ ID NOs: 129, 131 and 133. In yet another embodiment, the one or more nucleic acid molecules encoding the enzyme having xylose dehydrogenase activity is encoded by a nucleic acid sequence selected from the group consisting of SEQ ID NOs: 127, 128, 130 and 132.

Xylonolactonase (3.1.1.68)

The present disclosure describes enzymes that can catalyze the following reaction:

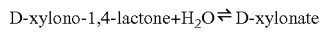
D-xylono-1,4-lactone+H₂O ⇌ D-xylonate

This enzyme belongs to the family of hydrolases, specifically those acting on carboxylic ester bonds. This enzyme participates in pentose and glucuronate interconversions.

Xylonolactonase may also be known as D-xylonolactonase, xylono-1,4-lactonase, xylono-gamma-lactonase or D-xylono-1,4-lactone lactonohydrolase.

In particular embodiments, the enzyme converts D-xylonolactone to D-xylonate. In some embodiments, the D-xylonolactonase is from *Haloferax* sp. In some embodiments, the D-xylonolactonase is from *Haloferax volcanii*. In some embodiments, the D-xylonolactonase is from *Haloferax gibbonsii*. In some embodiments, the D-xylonolactonase is from *Caulobacter crescentus*. In some embodiments, the D-xylonolactonase is encoded by the xylC gene.

In one embodiment, the enzyme that catalyzes the conversion of D-xylonolactone to D-xylonate is an enzyme having xylonolactonase activity. In a further embodiment, the enzyme that catalyzes the conversion of D-xylonolactone to D-xylonate is encoded by one or more endogenous nucleic acid molecules. In an alternative embodiment, the enzyme that catalyzes the conversion of D-xylonolactone to D-xylonate is encoded by one or more exogenous nucleic acid molecules. In another embodiment, the enzyme having xylonolactonase activity is encoded by a nucleic acid molecule obtained from a microorganism selected from *Caulobacter* sp. and *Haloferax* sp. In some embodiments, the nucleic acid molecule encoding the enzyme having xylonolactonase activity is obtained from a microorganism selected from *Caulobacter crescentus, Haloferax volcanii* and *Haloferax gibbonsii*. In some embodiments, the nucleic acid molecule encoding an enzyme having xylonolactonase activity is xylC, or homolog thereof. In a further embodiment, the one or more nucleic acid molecules encoding the enzyme having xylonolactonase activity comprises an amino acid sequence set forth in SEQ ID NO: 135. In yet another embodiment, the one or more nucleic acid molecules encoding the enzyme having xylonolactonase activity is encoded by a nucleic acid sequence set forth in SEQ ID NO: 134.

Xylonate Dehydratase (EC 4.2.1.82)

The present disclosure describes enzymes that can catalyze the following reaction:

D-xylonate ⇌ 2-keto-3-deoxy-D-xylonate+H₂O

This enzyme belongs to the family of lyases, specifically the hydro-lyases, which cleave carbon-oxygen bonds. This enzyme participates in pentose and glucuronate interconversions.

Xylonate dehydratase may also be known as D-xylonate hydro-lyase, D-xylo-aldonate dehydratase or D-xylonate dehydratase.

In particular embodiments, the enzyme converts D-xylonate to 2-keto-3-deoxy-D-xylonate. In some embodiments, the xylonate dehydratase is from *Caulobacter crescentus*. In some embodiments, the xylonate dehydratase is encoded by the xylD gene. In some embodiments, the xylonate dehydratase is from *Escherichia coli*. In some embodiments, the xylonate dehydratase is encoded by the yjhG gene. In some embodiments, the xylonate dehydratase is encoded by the yagF gene. In some embodiments, the xylonate dehydratase is from *Haloferax volcanii*. In some embodiments, the xylonate dehydratase is encoded by the xad gene. In some embodiments, the xylonate dehydratase is from *Sulfolobus solfataricus*.

In one embodiment, the enzyme that catalyzes the conversion of D-xylonate to 2-keto-3-deoxy-xylonate is an enzyme having xylonate dehydratase activity. In a further embodiment, the enzyme that catalyzes the conversion of D-xylonate to 2-keto-3-deoxy-xylonate is encoded by one or more endogenous nucleic acid molecules. In an alternative embodiment, the enzyme that catalyzes the conversion of D-xylonate to 2-keto-3-deoxy-xylonate is encoded by one or more exogenous nucleic acid molecules. In another embodiment, the enzyme having xylonate dehydratase activity is encoded by a nucleic acid molecule obtained from a microorganism selected from *Caulobacter* sp., *Haloferax* sp., *Sulfolobus* sp. and *E. coli*. In some embodiments, the nucleic acid molecule encoding the enzyme having xylonate dehydratase activity is obtained from a microorganism selected from *Caulobacter crescentus, Haloferax volcanii, E. coli* and *Sulfolobus solfataricus*. In some embodiments, the nucleic acid molecule encoding an enzyme having xylonate dehydratase activity is selected from xylD, yjhG, yagF, xad, or homolog thereof. In a further embodiment, the one or more nucleic acid molecules encoding the enzyme having xylonate dehydratase activity comprises an amino acid sequence selected from the group consisting of SEQ ID NOs: 137, 140 and 143. In yet another embodiment, the one or more nucleic acid molecules encoding the enzyme having xylonate dehydratase activity is encoded by a nucleic acid sequence selected from the group consisting of SEQ ID NOs: 136, 138, 139, 141 and 142.

2-keto-3-deoxy-D-pentonate aldolase (4.1.2.28)

The present disclosure describes enzymes that can catalyze the following reaction:

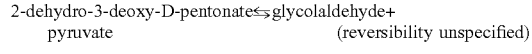
2-dehydro-3-deoxy-D-pentonate ⇌ glycolaldehyde+pyruvate  (reversibility unspecified)

This enzyme belongs to the family of lyases, specifically the aldehyde-lyases, which cleave carbon-carbon bonds. This enzyme participates in pentose and glucuronate interconversions.

2-keto-3-deoxy-D-pentonate aldolase may also be known as 2-dehydro-3-deoxy-D-pentonate glycolaldehyde-lyase (pyruvate-forming), 2-dehydro-3-deoxy-D-pentonate aldolase, 3-deoxy-D-pentulosonic acid aldolase, and 2-dehydro-3-deoxy-D-pentonate glycolaldehyde-lyase.

YjhH appears to be a 2-dehydro-3-deoxy-D-pentonate aldolase. Genetic evidence suggests that YagE may also function as a 2-dehydro-3-deoxy-D-pentonate aldolase. yagE is part of the prophage CP4-6.

A yjhH yagE double mutant cannot use D-xylonate as the sole source of carbon, and crude cell extracts do not contain 2-dehydro-3-deoxy-D-pentonate aldolase activity. Both phenotypes are complemented by providing yjhH on a plasmid.

ArcA appears to activate yjhH gene expression under anaerobiosis. Two putative ArcA binding sites were identified 211 and 597 bp upstream of this gene, but no promoter upstream of it has been identified.

The crystal structure of YagE suggests that the protein is a homotetramer. Co-crystal structures of YagE in the presence of pyruvate and 2-keto-3-deoxygalactonate have been solved.

In particular embodiments, the enzyme converts 2-keto-3-deoxy-xylonate to glycolaldehyde and pyruvate. In some embodiments, the 2-keto-3-deoxy-D-pentonate aldolase is from *Pseudomonas* sp. In some embodiments, the 2-keto-3-deoxy-D-pentonate aldolase is from *Escherichia coli*. In some embodiments, the 2-keto-3-deoxy-D-pentonate aldolase is encoded by the yjhH gene. In some embodiments, the 2-keto-3-deoxy-D-pentonate aldolase is encoded by the yagE gene.

In one embodiment, the enzyme that catalyzes the conversion of 2-keto-3-deoxy-xylonate to glycolaldehyde and pyruvate is an enzyme having 2-keto-3-deoxy-D-pentonate aldolase activity. In a further embodiment, the enzyme that catalyzes the conversion of 2-keto-3-deoxy-xylonate to glycolaldehyde and pyruvate is encoded by one or more endogenous nucleic acid molecules. In an alternative embodiment, the enzyme that catalyzes the conversion of 2-keto-3-deoxy-xylonate to glycolaldehyde and pyruvate is encoded by one or more exogenous nucleic acid molecules. In another embodiment, the enzyme having 2-keto-3-deoxy-D-pentonate aldolase activity is encoded by a nucleic acid molecule obtained from a microorganism selected from *Pseudomonas* sp. and *E. coli*. In some embodiments, the nucleic acid molecule encoding an enzyme having 2-keto-3-deoxy-D-pentonate aldolase activity is selected from yjhH, yagE, or homolog thereof. In a further embodiment, the one or more nucleic acid molecules encoding the enzyme having 2-keto-3-deoxy-D-pentonate aldolase activity comprises an amino acid sequence selected from the group consisting of SEQ ID NOs: 146 and 149. In yet another embodiment, the one or more nucleic acid molecules encoding the enzyme having 2-keto-3-deoxy-D-pentonate aldolase activity is encoded by a nucleic acid sequence selected from the group consisting of SEQ ID NOs: 144, 145, 147 and 148.

Glycolaldehyde Dehydrogenase (1.2.1.21)

The present disclosure describes enzymes that can catalyze the following reaction:

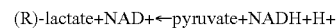

glycolaldehyde+NAD$^+$+H$_2$O ⇌ glycolate+NADH+2H$^+$

This enzyme belongs to the family of oxidoreductases, specifically those acting on the aldehyde or oxo group of donor with NAD+ or NADP+ as acceptor. This enzyme participates in glyoxylate and dicarboxylate metabolism.

Glycolaldehyde dehydrogenase may also be known as glycolaldehyde:NAD+ oxidoreductase or glycol aldehyde dehydrogenase.

In *E. coli* aldehyde dehydrogenase A (AldA) is an enzyme of relatively broad substrate specificity for small α-hydroxy-aldehyde substrates. It is thus utilized in several metabolic pathways.

L-fucose and L-rhamnose are metabolized through parallel pathways which converge after their corresponding aldolase reactions yielding the same products: dihydoxy-acetone phosphate and L-lactaldehyde. Aerobically, aldehyde dehydrogenase A oxidizes L-lactaldehyde to L-lactate.

In parallel pathways utilizing the same enzymes, D-arabinose and L-xylose can be metabolized to dihydoxy-acetone phosphate and glycolaldehyde, which is oxidized to glycolate by aldehyde dehydrogenase A.

Crystal structures of the enzyme alone and in ternary and binary complexes have been solved.

Aldehyde dehydrogenase A is only present under aerobic conditions and is most highly induced by the presence of fucose, rhamnose or glutamate. The enzyme is inhibited by NADH, which may act as a switch to shift from oxidation of lactaldehyde to its reduction by propanediol oxidoreductase. AldA is upregulated during short-term adaptation to glucose limitation.

Based on sequence similarity, AldA was predicted to be a succinate-semialdehyde dehydrogenase.

Regulation of aldA expression has been investigated. The gene is regulated by catabolite repression, repression under anaerobic conditions via ArcA, and induction by the carbon source.

In particular embodiments, the enzyme converts glycolaldehyde to glycolate. In some embodiments, the glycolaldehyde dehydrogenase is from *Escherichia coli*. In some embodiments, the glycolaldehyde dehydrogenase is encoded by the aldA gene.

In some embodiments, a recombinant microorganism producing MEG and an alcohol comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

Lactate Dehydrogenase (1.1.1.28)

The present disclosure describes enzymes that can catalyze the following reaction:

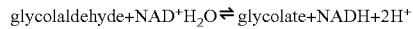

(R)-lactate+NAD+ ⇌ pyruvate+NADH+H+

Lactate dehydrogenase (LDH) is an enzyme found in nearly all living cells such as in animals, plants and prokaryotes. LDH catalyzes the conversion of lactate to pyruvic acid and back, as it converts NADH to NAD+ and back. A dehydrogenase is an enzyme that transfers a hydride from one molecule to another.

LDH exist in four distinct enzyme classes. The most common one is NAD(P)-dependent L-lactate dehydrogenase. Other LDHs act on D-lactate and/or are dependent on cytochrome c: D-lactate dehydrogenase (cytochrome) and L-lactate dehydrogenase (cytochrome).

LDH has been of medical significance because it is found extensively in body tissues, such as blood cells and heart muscle. Because it is released during tissue damage, it is a marker of common injuries and disease such as heart failure.

Lactate dehydrogenase may also be known as lactic acid dehydrogenase, (R)-lactate:NAD+ oxidoreductase or D-lactate dehydrogenase-fermentative.

In *E. coli*, lactate dehydrogenase (LdhA) is a soluble NAD-linked lactate dehydrogenase (LDH) that is specific for the production of D-lactate. LdhA is a homotetramer and shows positive homotropic cooperativity under higher pH conditions.

*E. coli* contains two other lactate dehydrogenases: D-lactate dehydrogenase and L-lactate dehydrogenase. Both are membrane-associated flavoproteins required for aerobic growth on lactate.

LdhA is present under aerobic conditions but is induced when *E. coli* is grown on a variety of sugars under anaerobic conditions at acidic pH. Unlike most of the genes involved in anaerobic respiration, ldhA is not activated by Fnr rather the ArcAB system and several genes involved in the control of carbohydrate metabolism (csrAB and mlc) appear to regulate expression. The expression of ldhA is negatively affected by the transcriptional regulator ArcA. ldhA belongs to the σ32 regulon.

The ldhA gene is a frequent target for mutations in metabolic engineering, most often to eliminate production of undesirable fermentation side products, but also to specifically produce D-lactate.

In particular embodiments, the enzyme converts pyruvate to lactate. In some embodiments, the lactate dehydrogenase is from *Escherichia coli*. In some embodiments, the lactate dehydrogenase is encoded by the ldhA gene.

In some embodiments, a recombinant microorganism producing MEG and an alcohol comprises a deletion, insertion, or loss of function mutation in a gene encoding a lactate dehydrogenase to prevent the production of lactate from pyruvate and instead shunt the reaction toward production of an alcohol.

Xylose Reductase or Aldose Reductase (EC 1.1.1.21)

The present disclosure describes enzymes that can catalyze the following reactions:

α-D-xylose+NADPH+H+ ⇌ xylitol+NADP an alditol+NAD(P)+ ⇌ AD(P)H+aldose

Aldose reductase may also be known as alditol:NAD(P)+ 1-oxidoreductase, polyol dehydrogenase or aldehyde reductase.

Aldose reductase is a cytosolic oxidoreductase that catalyzes the reduction of a variety of aldehydes and carbonyls, including monosaccharides.

Aldose reductase may be considered a prototypical enzyme of the aldo-keto reductase enzyme superfamily. The enzyme comprises 315 amino acid residues and folds into a β/α-barrel structural motif composed of eight parallel β strands. Adjacent strands are connected by eight peripheral α-helical segments running anti-parallel to the β sheet. The catalytic active site is situated in the barrel core. The NADPH cofactor is situated at the top of the β/α barrel, with the nicotinamide ring projecting down in the center of the barrel and pyrophosphate straddling the barrel lip.

The reaction mechanism of aldose reductase in the direction of aldehyde reduction follows a sequential ordered path where NADPH binds, followed by the substrate. Binding of NADPH induces a conformational change (Enzyme.NADPH→Enzyme*.NADPH) that involves hinge-like movement of a surface loop (residues 213-217) so as to cover a portion of the NADPH in a manner similar to that of a safety belt. The alcohol product is formed via a transfer of the pro-R hydride of NADPH to the face of the substrate's carbonyl carbon. Following release of the alcohol product, another conformational change occurs (E*.NAD(P)+→E.NAD(P)+) in order to release NADP+. Kinetic studies have shown that reorientation of this loop to permit release of NADP+ appears to represent the rate-limiting step in the direction of aldehyde reduction. As the rate of coenzyme release limits the catalytic rate, it can be seen that perturbation of interactions that stabilize coenzyme binding can have dramatic effects on the maximum velocity (Vmax).

D-xylose-fermenting *Pichia stipitis* and *Candida shehatae* were shown to produce one single aldose reductase (ALR) that is active both with NADPH and NADH. Other yeasts such as *Pachysolen tannophilus* and *C. tropicalis* synthesize multiple forms of ALR with different coenzyme specificities. The significant dual coenzyme specificity distinguishes the *P. stipitis* and the *C. shehatae* enzymes from most other ALRs so far isolated from mammalian or microbial sources. The yeast *Candida tenuis* CBS 4435 produces comparable NADH- and NADPH-linked aldehyde-reducing activities during growth on D-xylose.

In particular embodiments, the enzyme converts D-xylose to xylitol. In some embodiments, the xylose reductase or aldose reductase is from *Hypocrea jecorina*. In some embodiments, the xylose reductase or aldose reductase is encoded by the xyl1 gene. In some embodiments, the xylose reductase or aldose reductase is from *Saccharomyces cerevisiae*. In some embodiments, the xylose reductase or aldose reductase is encoded by the GRE3 gene. In some embodiments, the xylose reductase or aldose reductase is from *Pachysolen tannophilus*. In some embodiments, the xylose reductase or aldose reductase is from *Pichia* sp. In some embodiments, the xylose reductase or aldose reductase is from *Pichia stipitis*. In some embodiments, the xylose reductase or aldose reductase is from *Pichia quercuum*. In some embodiments, the xylose reductase or aldose reductase is from *Candida* sp. In some embodiments, the xylose reductase or aldose reductase is from *Candida shehatae*. In some embodiments, the xylose reductase or aldose reductase is from *Candida tenuis*. In some embodiments, the xylose reductase or aldose reductase is from *Candida tropicalis*. In some embodiments, the xylose reductase or aldose reductase is from *Aspergillus niger*. In some embodiments, the xylose reductase or aldose reductase is from *Neurospora crassa*. In some embodiments, the xylose reductase or aldose reductase is from Cryptococcus lactativorus.

In one embodiment, the enzyme that catalyzes the conversion of D-xylose to xylitol is an enzyme having xylose reductase or aldose reductase activity. In a further embodiment, the enzyme that catalyzes the conversion of D-xylose to xylitol is encoded by one or more endogenous nucleic acid molecules. In an alternative embodiment, the enzyme that catalyzes the conversion of D-xylose to xylitol is encoded by one or more exogenous nucleic acid molecules. In another embodiment, the enzyme having xylose reductase or aldose reductase activity is encoded by a nucleic acid molecule obtained from a microorganism selected from *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the nucleic acid molecule encoding the enzyme having xylose reductase or aldose reductase activity is obtained from a microorganism selected from *Hypocrea jecorina, Scheffersomyces stipitis, S. cerevisiae, Pachysolen tannophilus, Pichia stipitis, Pichia quercuum, Candida shehatae, Candida tenuis, Candida tropicalis, Aspergillus niger, Neurospora crassa* and *Cyptococcus lactativorus*. In some embodiments, the nucleic acid molecule encoding an enzyme having xylose reductase or aldose reductase activity is xyl1, GRE3, or homolog thereof. In some embodiments, the one or more nucleic acid molecules encoding the enzyme having xylose reductase or aldose reductase activity comprises an amino acid sequence selected from the group consisting of SEQ ID NOs: 152 and 155. In some embodiments, the one or more nucleic acid molecules encoding the enzyme having xylose reductase or aldose reductase activity is encoded by a nucleic acid sequence selected from the group consisting of SEQ ID NOs: 150, 151, 153 and 154.

Xylitol Dehydrogenase (1.1.1.9)

The present disclosure describes enzymes that can catalyze the following reaction:

xylitol+NAD+ ⇌ D-xylulose+NADH+H+

Xylitol dehydrogenase may also be known as D-xylulose reductase, NAD+-dependent xylitol dehydrogenase, erythritol dehydrogenase, 2,3-cis-polyol(DPN) dehydrogenase (C3-5), pentitol-DPN dehydrogenase, xylitol-2-dehydrogenase or xylitol:NAD+2-oxidoreductase (D-xylulose-forming).

Xylitol dehydrogenase (XDH) is one of several enzymes responsible for assimilating xylose into eukaryotic metabolism and is useful for fermentation of xylose contained in agricultural byproducts to produce ethanol. For efficient xylose utilization at high flux rates, cosubstrates should be recycled between the NAD+-specific XDH and the NADPH-preferring xylose reductase, another enzyme in the pathway.

In particular embodiments, the enzyme converts xylitol to D-xylulose. In some embodiments, the xylitol dehydrogenase is from yeast. In some embodiments, the xylitol dehydrogenase is from *Pichia* sp., *Saccharomyces* sp., *Gluconobacter* sp., *Galactocandida* sp., *Neurospora* sp. or *Serratia* sp. In some embodiments, the xylitol dehydrogenase is from *Pichia stipitis*, *S. cerevisiae*, *Gluconobacter oxydans*, *Galactocandida mastotermitis*, *Neurospora crassa* or *Serratia marcescens*. In some embodiments, the xylitol dehydrogenase is encoded by xyl2 or xdh1.

In one embodiment, the enzyme that catalyzes the conversion of xylitol to D-xylulose is an enzyme having xylitol dehydrogenase activity. In a further embodiment, the enzyme that catalyzes the conversion of xylitol to D-xylulose is encoded by one or more endogenous nucleic acid molecules. In an alternative embodiment, the enzyme that catalyzes the conversion of xylitol to D-xylulose is encoded by one or more exogenous nucleic acid molecules. In another embodiment, the enzyme having xylitol dehydrogenase activity is encoded by a nucleic acid molecule obtained from a microorganism selected from *Scheffersomyces* sp., *Trichoderma* sp., *Pichia* sp., *Saccharomyces* sp., *Gluconobacter* sp., *Galactocandida* sp., *Neurospora* sp., and *Serratia* sp. In some embodiments, the nucleic acid molecule encoding the enzyme having xylitol dehydrogenase activity is obtained from a microorganism selected from *Scheffersomyces stipitis*, *Trichoderma reesei*, *Pichia stipitis*, *S. cerevisiae*, *Gluconobacter oxydans*, *Galactocandida mastotermitis*, *Neurospora crassa* and *Serratia marcescens*. In some embodiments, the one or more nucleic acid molecule encoding an enzyme having xylitol dehydrogenase activity is xyl2, xdh1, or homolog thereof. In some embodiments, the one or more nucleic acid molecules encoding the enzyme having xylitol dehydrogenase activity comprises an amino acid sequence selected from the group consisting of SEQ ID NOs: 158 and 160. In some embodiments, the one or more nucleic acid molecules encoding the enzyme having xylitol dehydrogenase activity is encoded by a nucleic acid sequence selected from the group consisting of SEQ ID NOs: 156, 157 and 159.

Alkaline Phosphatase (EC 3.1.3.1)

Alkaline phosphatase is a hydrolase enzyme responsible for removing phosphate groups from many types of molecules, including nucleotides, proteins, and alkaloids. As the name suggests, alkaline phosphatases are most effective in an alkaline environment. It is sometimes used synonymously as basic phosphatase.

The *S. cerevisiae* Pho13 alkaline phosphatase enzyme is a monomeric protein with molecular mass of 60 kDa and hydrolyzes p-nitrophenyl phosphate with maximal activity at pH 8.2 with strong dependence on Mg2+ ions and an apparent Km of 3.6×10(−5) M. No other substrates tested except phosphorylated histone II-A and casein were hydrolyzed at any significant rate. These data suggest that the physiological role of the p-nitrophenyl phosphate-specific phosphatase may involve participation in reversible protein phosphorylation.

In particular embodiments, the enzyme converts D-xylulose-5-phosphate to D-xylulose. In some embodiments, the alkaline phosphatase is from yeast. In some embodiments, the alkaline phosphatase is from *Saccharomyces* sp. In some embodiments, the alkaline phosphatase is from *S. cerevisiae*. In some embodiments, the alkaline phosphatase is encoded by the PHO13 gene.

In some embodiments, a recombinant microorganism producing MEG and an alcohol comprises a deletion, insertion, or loss of function mutation in a gene encoding an alkaline phosphatase to prevent the conversion of D-xylulose-5-phosphate to D-xylulose.

Production of One or More Primary Alkenes Using a Recombinant Microorganism

As discussed above, in a first aspect, the present disclosure relates to a recombinant microorganism capable of producing one or more primary alkenes, each primary alkene having a structure as shown in Structure B, from one or more saturated primary or secondary alcohols, each primary or secondary alcohol having a structure as shown in Structure A,

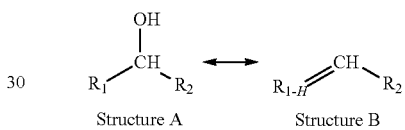

Structure A          Structure B wherein $R_1=C_nH_{2n+1}$ with $1 \le n \le 11$; $R_2=C_mH_{2m+1}$ with $0 \le m \le 10$ and $n+m \le 11$; and wherein the recombinant microorganism expresses one or more exogenous nucleic acid molecules encoding one or more linalool dehydratases/isomerases that catalyzes the conversion of the one or more saturated primary or secondary alcohols to one or more corresponding primary alkenes.

In one embodiment, the recombinant microorganism further expresses one or more endogenous or exogenous nucleic acid molecules encoding one or more enzymes for the production of the one or more saturated primary or secondary alcohols from a renewable feedstock.

In one embodiment, the corresponding primary alkene is propene and the primary alcohol is 1-propanol. In another embodiment, the corresponding primary alkene is propene and the secondary alcohol is 2-propanol. In some embodiments, the corresponding primary alkene is butene and the primary alcohol is 1-butanol. In further embodiments, the corresponding primary alkene is butene and the secondary alcohol is 2-butanol.

In one embodiment, one or more primary alkenes is produced from the one or more saturated primary or secondary alcohols via a single enzymatic step. In some embodiments, the production of one or more corresponding primary alkenes from one or more saturated primary or secondary alcohols comprises a dehydration step. In further embodiments, the dehydration step is substrate activation independent. In a yet further embodiment, the dehydration step is cofactor independent.

In one embodiment, the linalool dehydratase/isomerase is obtained from a microorganism selected from the group consisting of *Castellaniella defragrans* species.

In some embodiments, an amino acid sequence of a linalool dehydratase/isomerase has at least 50%, preferably at least 60%, more preferably at least 70%, more preferably at least 75%, most preferably at least 80%, most preferably at least 85%, even more preferably at least 90%, and even most preferably at least 95% sequence identity to an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63. In some embodiments, a nucleic acid sequence encoding a linalool dehydratase/isomerase has at least 50%, preferably at least 60%, more preferably at least 70%, more preferably at least 75%, most preferably at least 80%, most preferably at least 85%, even more preferably at least 90%, and even most preferably at least 95% sequence identity to a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62.

In some embodiments, the linalool dehydratase/isomerase comprises an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63. In some embodiments, the linalool dehydratase/isomerase is encoded by a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62. In further embodiments, the linalool dehydratase/isomerase is LinD. In some embodiments, the linalool dehydratase/isomerase is not comprised of an amino acid sequence selected from the group consisting of SEQ ID NOs: 64, 65, 66, 67 and 68.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a D-tagatose 3-epimerase that catalyzes the conversion of D-xylulose to D-ribulose;

(b) at least one endogenous or exogenous nucleic acid molecule encoding a D-ribulokinase that catalyzes the conversion of D-ribulose from (a) to D-ribulose-1-phosphate;

(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

(d) at least one endogenous or exogenous nucleic acid molecule encoding a glycolaldehyde reductase that catalyzes the conversion of glycolaldehyde from (c) to mono ethylene glycol (MEG);

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one endogenous or exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

In one embodiment, the enzyme that catalyzes the conversion of D-xylulose to D-ribulose is an enzyme having D-tagatose 3-epimerase activity. In a further embodiment, the enzyme that catalyzes the conversion of D-xylulose to D-ribulose is encoded by one or more endogenous nucleic acid molecules. In an alternative embodiment, the enzyme that catalyzes the conversion of D-xylulose to D-ribulose is encoded by one or more exogenous nucleic acid molecules. In another embodiment, the enzyme having D-tagatose 3-epimerase activity is encoded by a nucleic acid molecule obtained from a microorganism selected from *Pseudomonas* sp., *Mesorhizobium* sp. and *Rhodobacter* sp. In some embodiments, the nucleic acid molecule encoding an enzyme having D-tagatose 3-epimerase activity is obtained from a microorganism selected from *Pseudomonas cichorii, Pseudomonas* sp. ST-24, *Mesorhizobium loti* and *Rhodobacter sphaeroides*. In some embodiments, the nucleic acid molecule encoding an enzyme having D-tagatose 3-epimerase activity is dte, C1KKR1, or homolog thereof. In some embodiments, the one or more nucleic acid molecules is FJ851309.1 or homolog thereof. In a further embodiment, the enzyme having D-tagatose 3-epimerase activity comprises an amino acid sequence selected from the group consisting of SEQ ID NOs: 71 and 73. In yet a further embodiment, the enzyme having D-tagatose 3-epimerase activity is encoded by a nucleic acid sequence selected from the group consisting of SEQ ID NOs: 69, 70 and 72.

In one embodiment, the enzyme that catalyzes the conversion of D-ribulose to D-ribulose-1-phosphate is an enzyme having D-ribulokinase activity. In a further embodiment, the enzyme that catalyzes the conversion of D-ribulose to D-ribulose-1-phosphate is encoded by one or more endogenous nucleic acid molecules. In an alternative embodiment, the enzyme that catalyzes the conversion of D-ribulose to D-ribulose-1-phosphate is encoded by one or more exogenous nucleic acid molecules. In another embodiment, the enzyme having D-ribulokinase activity is encoded by a nucleic acid molecule obtained from *E. coli*. In some embodiments, the nucleic acid molecule encoding an enzyme having D-ribulokinase activity is fucK, or homolog thereof. In a further embodiment, the enzyme having D-ribulokinase activity comprises an amino acid sequence set forth in SEQ ID NO: 76. In yet a further embodiment, the enzyme having D-ribulokinase activity is encoded by a nucleic acid sequence selected from the group consisting of SEQ ID NOs: 74 and 75.

In one embodiment, the enzyme that catalyzes the conversion of D-ribulose-1-phosphate to glycolaldehyde and dihydroxyacetonephosphate (DHAP) is an enzyme having D-ribulose-1-phosphate aldolase activity. In a further embodiment, the enzyme that catalyzes the conversion of D-ribulose-1-phosphate to glycolaldehyde and DHAP is encoded by one or more endogenous nucleic acid molecules. In an alternative embodiment, the enzyme that catalyzes the conversion of D-ribulose-1-phosphate to glycolaldehyde and DHAP is encoded by one or more exogenous nucleic acid molecules. In another embodiment, the enzyme having D-ribulose-1-phosphate aldolase activity is encoded by a nucleic acid molecule obtained from *E. coli*. In some embodiments, the nucleic acid molecule encoding an enzyme having D-ribulose-1-phosphate aldolase activity is fucA, or homolog thereof. In a further embodiment, the enzyme having D-ribulose-1-phosphate aldolase activity comprises an amino acid sequence set forth in SEQ ID NO: 79. In yet a further embodiment, the enzyme having D-ribulose-1-phosphate aldolase activity is encoded by a nucleic acid sequence selected from the group consisting of SEQ ID NOs: 77 and 78.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a D-xylulose 1-kinase that catalyzes the conversion of D-xylulose to D-xylulose-1-phosphate;

(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);

(c) at least one endogenous or exogenous nucleic acid molecule encoding a glycolaldehyde reductase that catalyzes the conversion of glycolaldehyde from (b) to MEG;

(d) at least one endogenous or exogenous nucleic acid molecule encoding a thiolase that catalyzes the conversion of acetyl-CoA to acetoacetyl-CoA;

(e) at least one endogenous or exogenous nucleic acid molecule encoding an acetate:acetoacetyl-CoA transferase or hydrolase that catalyzes the conversion of acetoacetyl-CoA from (d) to acetoacetate;

(f) at least one endogenous or exogenous nucleic acid molecule encoding an acetoacetate decarboxylase that catalyzes the conversion of acetoacetate from (e) to acetone; and/or (g) at least one endogenous or exogenous nucleic acid molecule encoding a secondary alcohol dehydrogenase that catalyzes the conversion of acetone from (f) to isopropanol.

In one embodiment, the enzyme that catalyzes the conversion of D-xylulose to D-xylulose-1-phosphate is an enzyme having D-xylulose 1-kinase activity. In a further embodiment, the enzyme that catalyzes the conversion of D-xylulose to D-xylulose-1-phosphate is encoded by one or more endogenous nucleic acid molecules. In an alternative embodiment, the enzyme that catalyzes the conversion of D-xylulose to D-xylulose-1-phosphate is encoded by one or more exogenous nucleic acid molecules. In another embodiment, the enzyme having D-xylulose 1-kinase activity is encoded by a nucleic acid molecule obtained from Homo sapiens. In one embodiment, the Homo sapiens enzyme having D-xylulose 1-kinase activity is a ketohexokinase C. In some embodiments, the nucleic acid molecule encoding human ketohexokinase C is khk-C, or homolog thereof. In another embodiment, the one or more nucleic acid molecules encoding the enzyme having D-xylulose 1-kinase activity comprises an amino acid sequence set forth in SEQ ID NO: 123. In a further embodiment, the one or more nucleic acid molecules encoding the enzyme having D-xylulose 1-kinase activity is encoded by a nucleic acid sequence selected from the group consisting of SEQ ID NOs: 121 and 122.

In one embodiment, the enzyme that catalyzes the conversion of D-xylulose-1-phosphate to glycolaldehyde and dihydroxyacetonephosphate (DHAP) is a D-xylulose-1-phosphate aldolase. In a further embodiment, the enzyme that catalyzes the conversion of D-xylulose-1-phosphate to glycolaldehyde and DHAP is encoded by one or more endogenous nucleic acid molecules. In an alternative embodiment, the enzyme that catalyzes the conversion of D-xylulose-1-phosphate to glycolaldehyde and DHAP is encoded by one or more exogenous nucleic acid molecules. In another embodiment, the enzyme is a D-xylulose-1-phosphate aldolase that is encoded by a nucleic acid molecule obtained from Homo sapiens. In one embodiment, the Homo sapiens D-xylulose 1-phosphate aldolase is an aldolase B. In some embodiments, the nucleic acid molecule encoding human aldolase B is ALDOB, or homolog thereof. In some embodiments, the one or more nucleic acid molecules encoding the D-xylulose-1-phosphate aldolase comprises an amino acid sequence set forth in SEQ ID NO: 126. In some embodiments, the one or more nucleic acid molecules encoding the D-xylulose-1-phosphate aldolase is encoded by a nucleic acid sequence selected from the group consisting of SEQ ID NOs: 124 and 125.

In one embodiment, the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In some embodiments, an endogenous D-xylose isomerase catalyzes the conversion of D-xylose to D-xylulose.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a xylose dehydrogenase that catalyzes the conversion of D-xylose to D-xylonolactone;

(b) at least one endogenous or exogenous nucleic acid molecule encoding a xylonolactonase that catalyzes the conversion of D-xylonolactone from (a) to D-xylonate;

(c) at least one endogenous or exogenous nucleic acid molecule encoding a xylonate dehydratase that catalyzes the conversion of D-xylonate from (b) to 2-keto-3-deoxy-xylonate;

(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;

(e) at least one endogenous or exogenous nucleic acid molecule encoding a glycolaldehyde reductase that catalyzes the conversion of glycolaldehyde from (d) to MEG;

(f) at least one exogenous nucleic acid molecule encoding a thiolase that catalyzes the conversion of acetyl-CoA to acetoacetyl-CoA;

(g) at least one endogenous or exogenous nucleic acid molecule encoding an acetate:acetoacetyl-CoA transferase or hydrolase that catalyzes the conversion of acetoacetyl-CoA from (f) to acetoacetate;

(h) at least one exogenous nucleic acid molecule encoding an acetoacetate decarboxylase that catalyzes the conversion of acetoacetate from (g) to acetone; and/or (i) at least one endogenous or exogenous nucleic acid molecule encoding a secondary alcohol dehydrogenase that catalyzes the conversion of acetone from (h) to isopropanol.

In one embodiment, the recombinant microorganism is capable of co-producing monoethylene glycol (MEG) and isopropanol from exogenous D-xylose and expresses one or more of the following:

(a) at least one endogenous or exogenous nucleic acid molecule encoding a xylose dehydrogenase that catalyzes the conversion of D-xylose to D-xylonate;

(b) at least one endogenous or exogenous nucleic acid molecule encoding a xylonate dehydratase that catalyzes the conversion of D-xylonate from (a) to 2-keto-3-deoxy-xylonate;

(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;

(d) at least one exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

In one embodiment, the enzyme that catalyzes the conversion of D-xylose to D-xylonolactone is an enzyme having xylose dehydrogenase activity. In a further embodiment, the enzyme that catalyzes the conversion of D-xylose to D-xylonolactone is encoded by one or more endogenous nucleic acid molecules. In an alternative embodiment, the enzyme that catalyzes the conversion of D-xylose to D-xylonolactone is encoded by one or more exogenous nucleic acid molecules. In another embodiment, the enzyme having xylose dehydrogenase activity is encoded by a nucleic acid molecule obtained from a microorganism selected from *Caulobacter* sp., *Haloarcula* sp., *Haloferax* sp., *Halorubrum* sp. and *Trichoderma* sp. In some embodiments, the nucleic acid molecule encoding the enzyme having xylose dehydrogenase activity is obtained from a microorganism selected from *Caulobacter crescentus, Haloarcula marismortui, Haloferax volcanii, Halorubrum lacusprofundi* and *Trichoderma reesei*. In some embodiments, the nucleic acid molecule encoding an enzyme having xylose dehydrogenase activity is selected from xylB, xdh (HVO_B0028), xyd1, or homolog thereof. In a further embodiment, the one or more nucleic acid molecules encoding the enzyme having xylose dehydrogenase activity comprises an amino acid sequence selected from the group consisting of SEQ ID NOs: 129, 131 and 133. In yet another embodiment, the one or more nucleic acid molecules encoding the enzyme having xylose dehydrogenase activity is encoded by a nucleic acid sequence selected from the group consisting of SEQ ID NOs: 127, 128, 130 and 132.

In one embodiment, the enzyme that catalyzes the conversion of D-xylonolactone to D-xylonate is an enzyme having xylonolactonase activity. In a further embodiment, the enzyme that catalyzes the conversion of D-xylonolactone to D-xylonate is encoded by one or more endogenous nucleic acid molecules. In an alternative embodiment, the enzyme that catalyzes the conversion of D-xylonolactone to D-xylonate is encoded by one or more exogenous nucleic acid molecules. In another embodiment, the enzyme having xylonolactonase activity is encoded by a nucleic acid molecule obtained from a microorganism selected from *Caulobacter* sp. and *Haloferax* sp. In some embodiments, the nucleic acid molecule encoding the enzyme having xylonolactonase activity is obtained from a microorganism selected from *Caulobacter crescentus, Haloferax volcanii* and *Haloferax gibbonsii*. In some embodiments, the nucleic acid molecule encoding an enzyme having xylonolactonase activity is xylC, or homolog thereof. In a further embodiment, the one or more nucleic acid molecules encoding the enzyme having xylonolactonase activity comprises an amino acid sequence set forth in SEQ ID NO: 135. In yet another embodiment, the one or more nucleic acid molecules encoding the enzyme having xylonolactonase activity is encoded by a nucleic acid sequence set forth in SEQ ID NO: 134.

In one embodiment, the enzyme that catalyzes the conversion of D-xylonate to 2-keto-3-deoxy-xylonate is an enzyme having xylonate dehydratase activity. In a further embodiment, the enzyme that catalyzes the conversion of D-xylonate to 2-keto-3-deoxy-xylonate is encoded by one or more endogenous nucleic acid molecules. In an alternative embodiment, the enzyme that catalyzes the conversion of D-xylonate to 2-keto-3-deoxy-xylonate is encoded by one or more exogenous nucleic acid molecules. In another embodiment, the enzyme having xylonate dehydratase activity is encoded by a nucleic acid molecule obtained from a microorganism selected from *Caulobacter* sp., *Haloferax* sp., *Sulfolobus* sp. and *E. coli*. In some embodiments, the nucleic acid molecule encoding the enzyme having xylonate dehydratase activity is obtained from a microorganism selected from *Caulobacter crescentus, Haloferax volcanii, E. coli* and *Sulfolobus solfataricus*. In some embodiments, the nucleic acid molecule encoding an enzyme having xylonate dehydratase activity is selected from xylD, yjhG, yagF, xad, or homolog thereof. In a further embodiment, the one or more nucleic acid molecules encoding the enzyme having xylonate dehydratase activity comprises an amino acid sequence selected from the group consisting of SEQ ID NOs: 137, 140 and 143. In yet another embodiment, the one or more nucleic acid molecules encoding the enzyme having xylonate dehydratase activity is encoded by a nucleic acid sequence selected from the group consisting of SEQ ID NOs: 136, 138, 139, 141 and 142.

In one embodiment, the enzyme that catalyzes the conversion of 2-keto-3-deoxy-xylonate to glycolaldehyde and pyruvate is an enzyme having 2-keto-3-deoxy-D-pentonate aldolase activity. In a further embodiment, the enzyme that catalyzes the conversion of 2-keto-3-deoxy-xylonate to glycolaldehyde and pyruvate is encoded by one or more endogenous nucleic acid molecules. In an alternative embodiment, the enzyme that catalyzes the conversion of 2-keto-3-deoxy-xylonate to glycolaldehyde and pyruvate is encoded by one or more exogenous nucleic acid molecules. In another embodiment, the enzyme having 2-keto-3-deoxy-D-pentonate aldolase activity is encoded by a nucleic acid molecule obtained from a microorganism selected from *Pseudomonas* sp. and *E. coli*. In some embodiments, the nucleic acid molecule encoding an enzyme having 2-keto-3-deoxy-D-pentonate aldolase activity is selected from yjhH, yagE, or homolog thereof. In a further embodiment, the one or more nucleic acid molecules encoding the enzyme having 2-keto-3-deoxy-D-pentonate aldolase activity comprises an amino acid sequence selected from the group consisting of SEQ ID NOs: 146 and 149. In yet another embodiment, the one or more nucleic acid molecules encoding the enzyme having 2-keto-3-deoxy-D-pentonate aldolase activity is encoded by a nucleic acid sequence selected from the group consisting of SEQ ID NOs: 144, 145, 147 and 148.

In some embodiments, the recombinant microorganism further comprises one or more modifications selected from the group consisting of:

(a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In one embodiment, the recombinant microorganism is capable of co-producing monoethylene glycol (MEG) and isopropanol from exogenous D-xylose and glucose and expresses one or more of the following:

(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;

(b) at least one exogenous nucleic acid molecule encoding a D-xylose isomerase that catalyzes the conversion of D-xylose to D-xylulose, and wherein the microorganism further expresses one or more of the following:

(c) at least one endogenous or exogenous nucleic acid molecule encoding a D-tagatose 3-epimerase that catalyzes the conversion of D-xylulose from (a) or (b) to D-ribulose;

(d) at least one endogenous or exogenous nucleic acid molecule encoding a D-ribulokinase that catalyzes the conversion of D-ribulose from (c) to D-ribulose-1-phosphate;

(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);

(f) at least one endogenous or exogenous nucleic acid molecule encoding a glycolaldehyde reductase or methylglyoxal reductase that catalyzes the conversion of glycolaldehyde from (e) to MEG;

(g) at least one endogenous or exogenous nucleic acid molecule encoding a thiolase that catalyzes the conversion of acetyl-CoA to acetoacetyl-CoA;

(h) at least one endogenous or exogenous nucleic acid molecule encoding an acetate:acetoacetyl-CoA transferase or hydrolase that catalyzes the conversion of acetoacetyl-CoA from (g) to acetoacetate;

(i) at least one endogenous or exogenous nucleic acid molecule encoding an acetoacetate decarboxylase that catalyzes the conversion of acetoacetate from (h) to acetone; and/or (j) at least one endogenous or exogenous nucleic acid molecule encoding a secondary alcohol dehydrogenase that catalyzes the conversion of acetone from (i) to isopropanol.

In one embodiment, the enzyme that catalyzes the conversion of D-xylose to xylitol is an enzyme having xylose reductase or aldose reductase activity. In a further embodiment, the enzyme that catalyzes the conversion of D-xylose to xylitol is encoded by one or more endogenous nucleic acid molecules. In an alternative embodiment, the enzyme that catalyzes the conversion of D-xylose to xylitol is encoded by one or more exogenous nucleic acid molecules. In another embodiment, the enzyme having xylose reductase or aldose reductase activity is encoded by a nucleic acid molecule obtained from a microorganism selected from *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the nucleic acid molecule encoding the enzyme having xylose reductase or aldose reductase activity is obtained from a microorganism selected from *Hypocrea jecorina*, *Scheffersomyces stipitis*, *S. cerevisiae*, *Pachysolen tannophilus*, *Pichia stipitis*, *Pichia quercuum*, *Candida shehatae*, *Candida tenuis*, *Candida tropicalis*, *Aspergillus niger*, *Neurospora crassa* and *Cyptococcus lactativorus*. In some embodiments, the nucleic acid molecule encoding an enzyme having xylose reductase or aldose reductase activity is xyl1, GRE3, or homolog thereof. In some embodiments, the one or more nucleic acid molecules encoding the enzyme having xylose reductase or aldose reductase activity comprises an amino acid sequence selected from the group consisting of SEQ ID NOs: 152 and 155. In some embodiments, the one or more nucleic acid molecules encoding the enzyme having xylose reductase or aldose reductase activity is encoded by a nucleic acid sequence selected from the group consisting of SEQ ID NOs: 150, 151, 153 and 154.

In one embodiment, the enzyme that catalyzes the conversion of xylitol to D-xylulose is an enzyme having xylitol dehydrogenase activity. In a further embodiment, the enzyme that catalyzes the conversion of xylitol to D-xylulose is encoded by one or more endogenous nucleic acid molecules. In an alternative embodiment, the enzyme that catalyzes the conversion of xylitol to D-xylulose is encoded by one or more exogenous nucleic acid molecules. In another embodiment, the enzyme having xylitol dehydrogenase activity is encoded by a nucleic acid molecule obtained from a microorganism selected from *Scheffersomyces* sp., *Trichoderma* sp., *Pichia* sp., *Saccharomyces* sp., *Gluconobacter* sp., *Galactocandida* sp., *Neurospora* sp., and *Serratia* sp. In some embodiments, the nucleic acid molecule encoding the enzyme having xylitol dehydrogenase activity is obtained from a microorganism selected from *Scheffersomyces stipitis*, *Trichoderma reesei*, *Pichia stipitis*, *S. cerevisiae*, *Gluconobacter oxydans*, *Galactocandida mastotermitis*, *Neurospora crassa* and *Serratia marcescens*. In some embodiments, the one or more nucleic acid molecule encoding an enzyme having xylitol dehydrogenase activity is xyl2, xdh1, or homolog thereof. In some embodiments, the one or more nucleic acid molecules encoding the enzyme having xylitol dehydrogenase activity comprises an amino acid sequence selected from the group consisting of SEQ ID NOs: 158 and 160. In some embodiments, the one or more nucleic acid molecules encoding the enzyme having xylitol dehydrogenase activity is encoded by a nucleic acid sequence selected from the group consisting of SEQ ID NOs: 156, 157 and 159.

In one embodiment, the enzyme that catalyzes the conversion of D-xylose to D-xylulose is an enzyme having D-xylose isomerase activity. In a further embodiment, the enzyme that catalyzes the conversion of D-xylose to D-xylulose is encoded by one or more endogenous nucleic acid molecules. In an alternative embodiment, the enzyme that catalyzes the conversion of D-xylose to D-xylulose is encoded by one or more exogenous nucleic acid molecules. In another embodiment, the enzyme having D-xylose isomerase activity is encoded by a nucleic acid molecule obtained from *E. coli*. In another embodiment, the enzyme having xylose isomerase activity is encoded by one or more nucleic acid molecules obtained from *Pyromyces* sp. In some embodiments, the nucleic acid molecule encoding an enzyme having D-xylose isomerase activity is xylA, or homolog thereof. In yet another embodiment, the one or more nucleic acid molecules encoding the enzyme having xylose isomerase activity comprises an amino acid sequence selected from SEQ ID NOs: 163 and 190. In a further embodiment, the one or more nucleic acid molecules encoding the enzyme having xylose isomerase activity is encoded by a nucleic acid sequence selected from SEQ ID NOs: 161, 162 and 189.

In some embodiments, the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate; and (b) a deletion, insertion, or loss of function mutation in a gene encoding an alkaline phosphatase that catalyzes the conversion of D-xylulose-5-phosphate to D-xylulose.

In any of the above embodiments, the DHAP is converted to acetyl-CoA through the endogenous glycolysis pathway in the microorganism.

In any of the above embodiments, the enzyme that catalyzes the conversion of glycolaldehyde to MEG is an enzyme having glycolaldehyde reductase or aldehyde reductase activity. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme having glycolaldehyde reductase or aldehyde reductase activity is encoded by a nucleic acid molecule obtained from a microorganism selected from *E. coli* or *S. cerevisiae*. In some embodiments, the nucleic acid molecule encoding an enzyme having glycolaldehyde reductase or aldehyde reductase activity is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 81, 83, 85, 88, 91, 93, 96, 98 and 100. In yet a further embodiment, the glycolaldehyde reductase is encoded by a nucleic acid sequence selected from the group consisting of SEQ ID NOs: 80, 82, 84, 86, 87, 89, 90, 92, 94, 95, 97 and 99.

In any of the above embodiments, the enzyme that catalyzes the conversion of acetyl-CoA to acetoacetyl-CoA is an enzyme having thiolase or acetyl coenzyme A acetyltransferase activity. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is an enzyme having thiolase or acetyl coenzyme A acetyltransferase activity that is encoded by a nucleic acid molecule obtained from a microorganism selected from *Clostridium* sp., *Bacillus* sp., *E. coli*, *Saccharomyces* sp. and *Marinobacter* sp. In some embodiments, the nucleic acid molecule encoding an enzyme having thiolase or acetyl coenzyme A acetyltransferase activity is obtained from a microorganism selected from *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the nucleic acid molecule encoding an enzyme having thiolase or acetyl coenzyme A acetyltransferase activity is thlA, atoB and/or ERG10, or homolog thereof. In a further embodiment, the enzyme having thiolase or acetyl coenzyme A acetyltransferase activity comprises an amino acid sequence selected from the group consisting of SEQ ID NOs: 103, 105 and 108. In yet a further embodiment, the enzyme having thiolase or acetyl coenzyme A acetyltransferase activity is encoded by a nucleic acid sequence selected from the group consisting of SEQ ID NOs: 101, 102, 104, 106 and 107.

In any of the above embodiments, the enzyme that catalyzes the conversion of acetoacetyl-CoA to acetoacetate is an enzyme having acetate:acetoacetyl-CoA transferase or hydrolase activity. In some embodiments, the enzyme having transferase activity is an enzyme having acetyl-CoA:acetoacetate-CoA transferase activity. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme having acetate:acetoacetyl-CoA transferase or hydrolase activity is encoded by one or more nucleic acid molecule obtained from a microorganism selected from *Clostridium* sp. and *E. coli*. In some embodiments, the nucleic acid molecules encoding an enzyme having acetate:acetoacetyl-CoA hydrolase activity is obtained from *Clostridium acetobutylicum*. In some embodiments, the nucleic acid molecules encoding an enzyme having acetate:acetoacetyl-CoA transferase activity is obtained from *E. coli*. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the enzyme having acetyl-CoA:acetoacetate-CoA transferase activity or acetate:acetoacetyl-CoA hydrolase activity comprises an amino acid sequence selected from the group consisting of SEQ ID NOs: 111, 114, 165, 167, 169 and 171. In yet a further embodiment, the enzyme having acetyl-CoA:acetoacetate-CoA transferase activity or acetate:acetoacetyl-CoA hydrolase activity is encoded by a nucleic acid sequence selected from the group consisting of SEQ ID NOs: 109, 110, 112, 113, 164, 166, 168 and 170.

In any of the above embodiments, the enzyme that catalyzes the conversion of acetoacetate to acetone is an enzyme having acetoacetate decarboxylase activity. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme having acetoacetate decarboxylase activity is encoded by a nucleic acid molecule obtained from a microorganism selected from *Clostridium* sp., *Bacillus* sp., *Chromobacterium* sp. and *Pseudomonas* sp. In some embodiments, the nucleic acid molecule encoding an enzyme having acetoacetate decarboxylase activity is obtained from a microorganism selected from *Clostridium acetobutylicum*, *Clostridium beierinckii*, *Clostridium cellulolyticum*, *Bacillus polymyxa*, *Chromobacterium violaceum* and *Pseudomonas putida*. In some embodiments, the nucleic acid molecule encoding an enzyme having acetoacetate decarboxylase activity is adc, or homolog thereof. In a further embodiment, the enzyme having acetoacetate decarboxylase activity comprises an amino acid sequence selected from the group consisting of SEQ ID NOs: 117 and 120. In yet another embodiment, the enzyme having acetoacetate decarboxylase activity is encoded by a nucleic acid sequence selected from the group consisting of SEQ ID NOs: 115, 116, 118 and 119.

In any of the above embodiments, the recombinant microorganism may comprise at least one nucleic acid molecule encoding an enzyme that catalyzes the conversion of acetone to isopropanol. In one embodiment, the enzyme that catalyzes the conversion of acetone to isopropanol is encoded by one or more endogenous nucleic acid molecules. In an alternative embodiment, the enzyme that catalyzes the conversion of acetone to isopropanol is encoded by one or more exogenous nucleic acid molecules. In one embodiment, the enzyme that catalyzes the conversion of acetone to isopropanol is a secondary alcohol dehydrogenase (S-ADH). In another embodiment, the enzyme having secondary alcohol dehydrogenase activity is encoded by a nucleic acid molecule obtained from a microorganism selected from *Burkholderia* sp, *Alcaligenes* sp., *Clostridium* sp., *Thermoanaerobacter* sp., *Phytomonas* sp., *Rhodococcus* sp., *Methanobacterium* sp., *Methanogenium* sp., *Entamoeba* sp., *Trichomonas* sp., and *Tritrichomonas* sp. In some embodiments, the nucleic acid molecule encoding the enzyme having secondary alcohol dehydrogenase activity is obtained from a microorganism selected from *Burkholderia* sp. AIU 652, *Alcaligenes eutrophus, Clostridium ragsdalei, Clostridium beijennckii, Clostridium carboxidivorans, Thermoanaerobacter brockii, Thermoanaerobacter ethanolicus* (*Clostridium thermohydrosulfuricum*), *Rhodococcus ruber, Methanobacterium palustre*, methanogenic archaea *Methanogenium liminatans*, parasitic protist *Entamoeba histolytica*, parasitic protozoan *Tritrichomonas foetus* and human parasite *Trichomonas vaginalis*. In some embodiments, the one or more nucleic acid molecule encoding an enzyme having secondary alcohol dehydrogenase activity is adh, adhB, EhAdh1, or homolog thereof. In some embodiments, the S-ADH is predicted from homology and can be from *Thermoanaerobacter mathranii, Micrococcus luteus, Nocardiopsis alba, Mycobacterium hassiacum, Helicobacter suis, Candida albicans, Candida parapsilosis, Candida orthopsilosis, Candida metapsilosis, Grosmannia clavigera* and *Scheffersomyces stipitis*. In a further embodiment, the enzyme having alcohol dehydrogenase activity comprises an amino acid sequence selected from the group consisting of SEQ ID NOs: 174 and 176. In yet another embodiment, the alcohol dehydrogenase is encoded by a nucleic acid sequence selected from the group consisting of SEQ ID NOs: 172, 173 and 175.

In any of the above embodiments, the enzyme that catalyzes the conversion of D-xylulose to D-xylulose-5-phosphate is a D-xylulose-5-kinase. In some embodiments, the D-xylulose-5-kinase is from *Escherichia coli*. In some embodiments, the D-xylulose-5-kinase is encoded by the xylB gene, or homolog thereof. In some embodiments, a recombinant microorganism producing MEG and isopropanol comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

In any of the above embodiments, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene, or homolog thereof. In some embodiments, a recombinant microorganism producing MEG and isopropanol comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

In any of the above embodiments, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof. In some embodiments, a recombinant microorganism producing MEG and isopropanol comprises a deletion, insertion, or loss of function mutation in a gene encoding a lactate dehydrogenase to prevent the production of lactate from pyruvate and instead shunt the reaction toward production of isopropanol.

In any of the above embodiments, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof. In some embodiments, a recombinant microorganism producing MEG and isopropanol comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the recombinant microorganism is capable of producing isopropanol and expresses one or more of the following:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and/or (d) at least one endogenous or exogenous nucleic acid molecule encoding a secondary alcohol dehydrogenase that catalyzes the conversion of acetone from (c) to isopropanol.

In some embodiments, the recombinant microorganism further comprises a deletion, insertion, or loss of function mutation in a gene encoding a lactate dehydrogenase that catalyzes the conversion of pyruvate to lactate.

In one embodiment, the recombinant microorganism is capable of co-producing n-propanol and isopropanol and expresses one or more of the following:

(a) at least one endogenous or exogenous nucleic acid molecule encoding a methylglyoxal synthase that catalyzes the conversion of dihydroxyacetone phosphate (DHAP) to methylglyoxal;

(b) at least one endogenous or exogenous nucleic acid molecule encoding an aldo-keto reductase that catalyzes the conversion of methylglyoxal from (a) to acetol;

(c) at least one endogenous or exogenous nucleic acid molecule encoding a glyoxylate reductase, a methylglyoxal dehydrogenase or an aldehyde dehydrogenase that catalyzes the conversion of methylglyoxal from (a) to lactaldehyde;

(d) at least one endogenous or exogenous nucleic acid molecule encoding an aldo-keto reductase that catalyzes the conversion of acetol from (b) to 1,2-propanediol;

(e) at least one endogenous or exogenous nucleic acid molecule encoding an aldehyde reductase that catalyzes the conversion of lactaldehyde from (c) to 1,2-propanediol;

(f) at least one endogenous or exogenous nucleic acid molecule encoding a diol-dehydratase that catalyzes the conversion of 1,2-propanediol from (d) or (e) to propanal;

(g) at least one endogenous or exogenous nucleic acid molecule encoding a dehydrogenase that catalyzes the conversion of propanal from (f) to n-propanol;

(h) at least one endogenous or exogenous nucleic acid molecule encoding a pyruvate formate lyase that catalyzes the conversion of pyruvate to acetyl-CoA;

(i) at least one endogenous or exogenous nucleic acid molecule encoding a thiolase that catalyzes the conversion of acetyl-CoA from (h) to acetoacetyl-CoA;

(j) at least one endogenous or exogenous nucleic acid molecule encoding an acetate:acetoacetyl-CoA transferase or hydrolase that catalyzes the conversion of acetoacetyl-CoA from (i) to acetoacetate;

(k) at least one endogenous or exogenous nucleic acid molecule encoding an acetoacetate decarboxylase that catalyzes the conversion of acetoacetate from (j) to acetone; and/or (l) at least one endogenous or exogenous nucleic acid molecule encoding a secondary alcohol dehydrogenase that catalyzes the conversion of acetone from (k) to isopropanol; and wherein the DHAP and pyruvate are produced from glycolysis in the microorganism.

In some embodiments, the recombinant microorganism further comprises one or more modifications selected from the group consisting of:

(a) a deletion, insertion, or loss of function mutation in a gene encoding an acetaldehyde dehydrogenase that catalyzes the conversion of lactaldehyde to lactate; and (b) a deletion, insertion, or loss of function mutation in a gene encoding a lactate dehydrogenase that catalyzes the conversion of pyruvate to lactate.

In one embodiment, the recombinant microorganism is capable of co-producing acetone, butanol and ethanol, and expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetaldehyde from (e) to ethanol or butyraldehyde from (i) to butanol;

and wherein the pyruvate is produced from glycolysis in the microorganism.

In some embodiments, the recombinant microorganism further comprises a deletion, insertion, or loss of function mutation in a gene encoding a lactate dehydrogenase that catalyzes the conversion of pyruvate to lactate.

In one embodiment, the recombinant microorganism is capable of co-producing isopropanol, butanol and ethanol, and expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetone from (d) to isopropanol, acetaldehyde from (e) to ethanol or butyraldehyde from (i) to butanol;

and wherein the pyruvate is produced from glycolysis in the microorganism.

In some embodiments, the recombinant microorganism further comprises a deletion, insertion, or loss of function mutation in a gene encoding a butyrate kinase that catalyzes the conversion of butyryl phosphate to butyrate.

In one embodiment, the recombinant microorganism is capable of producing isobutanol and expresses one or more of the following:

(a) at least one endogenous or exogenous nucleic acid molecule encoding an acetohydroxy acid synthase that catalyzes the conversion of pyruvate to acetolactate;

(b) at least one endogenous or exogenous nucleic acid molecule encoding an acetohydroxy acid isomeroreductase that catalyzes the conversion of acetolactate from (a) to 2,3-dihydroxy-isovalerate;

(c) at least one endogenous or exogenous nucleic acid molecule encoding a dihydroxy-acid dehydratase that catalyzes the conversion of 2,3-dihydroxy-isovalerate from (b) to α-keto-isovalerate;

(d) at least one endogenous or exogenous nucleic acid molecule encoding a 2-keto-acid decarboxylase that catalyzes the conversion of α-keto-isovalerate from (c) to isobutyraldehyde; and/or (e) at least one endogenous or exogenous nucleic acid molecule encoding an alcohol dehydrogenase that catalyzes the conversion of isobutyraldehyde from (d) to isobutanol; and wherein the pyruvate is produced from glycolysis in the microorganism.

In some embodiments, the recombinant microorganism further comprises one or more modifications selected from the group consisting of:

(a) a deletion, insertion, or loss of function mutation in a gene encoding an ethanol dehydrogenase that catalyzes the conversion of acetaldehyde to ethanol; and (b) a deletion, insertion, or loss of function mutation in a gene encoding a lactate dehydrogenase that catalyzes the conversion of pyruvate to lactate.

In yet another aspect, the present disclosure provides a method of producing a recombinant microorganism that produces one or more primary alkenes from one or more saturated primary or secondary alcohols as described above in any of the embodiments.

Recombinant Microorganism

The disclosure provides microorganisms that can be engineered to express various endogenous or exogenous enzymes.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Tnchosporon, Rhodotorula*, and *Myxozyma*.

In some embodiments, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium*.

In some embodiments, the recombinant microorganism is used to produce one or more primary alkenes disclosed herein. In some embodiments, the recombinant microorganism is used to produce one or more saturated primary or secondary alcohols that are converted to one or more primary alkenes.

Accordingly, in another aspect, the present invention provides a method of producing one or more primary alkenes using a recombinant microorganism described herein. In one embodiment, the method comprises cultivating the recombinant microorganism in a culture medium containing a feedstock providing a carbon source until one or more primary alkenes is produced. In a further embodiment, the one or more primary alkenes is recovered. Recovery can be by methods known in the art, such as distillation, membrane-based separation gas stripping, solvent extraction, and expanded bed adsorption. In an exemplary embodiment, the one or more primary alkenes is selected from propene, butene, and any alkene listed in Table 1.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In an exemplary embodiment, the carbon source is a sugar. In a further exemplary embodiment, the sugar is glucose. In alternative embodiments, the sugar is selected from the group consisting of glucose, fructose, xylose and sucrose.

Methods of Producing One or More Primary Alkenes

As discussed above, in another aspect, the present disclosure relates to a method of producing one or more primary alkenes, each primary alkene having a structure as shown in Structure B, from one or more saturated primary or secondary alcohols, each primary or secondary alcohol having a structure as shown in Structure A,

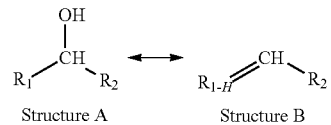

Structure A            Structure B wherein $R_1=C_nH_{2n+1}$ with $1 \leq n \leq 11$; $R_2=C_mH_{2m+1}$ with $0 \leq m \leq 10$ and $n+m \leq 11$; and wherein the method comprises expressing in a recombinant microorganism one or more exogenous nucleic acid molecules encoding one or more linalool dehydratase/isomerases that catalyzes the conversion of the one or more saturated primary or secondary alcohols to one or more corresponding primary alkenes.

In one embodiment, the method further comprises expressing in the recombinant microorganism one or more endogenous or exogenous nucleic acid molecules encoding one or more enzymes for the production of the one or more saturated primary or secondary alcohols from a renewable feedstock. In a further embodiment, the renewable feedstock is one or more sugars.

In one embodiment, the corresponding primary alkene is propene and the primary alcohol is 1-propanol. In another embodiment, the corresponding primary alkene is propene and the secondary alcohol is 2-propanol. In some embodiments, the corresponding primary alkene is butene and the primary alcohol is 1-butanol. In further embodiments, the corresponding primary alkene is butene and the secondary alcohol is 2-butanol.

In one embodiment, one or more primary alkenes is produced from the one or more saturated primary or secondary alcohols via a single enzymatic step. In some embodiments, the production of one or more corresponding primary alkenes from one or more saturated primary or secondary alcohols comprises a dehydration step. In further embodiments, the dehydration step is substrate activation independent. In a yet further embodiment, the dehydration step is cofactor independent.

In one embodiment, the linalool dehydratase/isomerase is obtained from a microorganism selected from the group consisting of *Castellaniella defragrans* species.

In some embodiments, an amino acid sequence of a linalool dehydratase/isomerase has at least 50%, preferably at least 60%, more preferably at least 70%, more preferably at least 75%, most preferably at least 80%, most preferably at least 85%, even more preferably at least 90%, and even most preferably at least 95% sequence identity to an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63. In some embodiments, a nucleic acid sequence encoding a linalool dehydratase/isomerase has at least 50%, preferably at least 60%, more preferably at least 70%, more preferably at least 75%, most preferably at least 80%, most preferably at least 85%, even more preferably at least 90%, and even most preferably at least 95% sequence identity to a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62.

In some embodiments, the linalool dehydratase/isomerase comprises an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63. In some embodiments, the linalool dehydratase/isomerase is encoded by a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62. In further embodiments, the linalool dehydratase/isomerase is LinD. In some embodiments, the linalool dehydratase/isomerase is not comprised of an amino acid sequence selected from the group consisting of SEQ ID NOs: 64, 65, 66, 67 and 68.

In one embodiment, the method comprises expressing one or more of the following in a recombinant microorganism capable of co-producing monoethylene glycol (MEG) and isopropanol from exogenous D-xylose:

(a) at least one endogenous or exogenous nucleic acid molecule encoding a D-tagatose 3-epimerase that catalyzes the conversion of D-xylulose to D-ribulose;

(b) at least one endogenous or exogenous nucleic acid molecule encoding a D-ribulokinase that catalyzes the conversion of D-ribulose from (a) to D-ribulose-1-phosphate;

(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

(d) at least one endogenous or exogenous nucleic acid molecule encoding a glycolaldehyde reductase that catalyzes the conversion of glycolaldehyde from (c) to mono ethylene glycol (MEG);

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one endogenous or exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

In one embodiment, the enzyme that catalyzes the conversion of D-xylulose to D-ribulose is an enzyme having D-tagatose 3-epimerase activity. In a further embodiment, the enzyme that catalyzes the conversion of D-xylulose to D-ribulose is encoded by one or more endogenous nucleic acid molecules. In an alternative embodiment, the enzyme that catalyzes the conversion of D-xylulose to D-ribulose is encoded by one or more exogenous nucleic acid molecules. In another embodiment, the enzyme having D-tagatose 3-epimerase activity is encoded by a nucleic acid molecule obtained from a microorganism selected from *Pseudomonas* sp., *Mesorhizobium* sp. and *Rhodobacter* sp. In some embodiments, the nucleic acid molecule encoding an enzyme having D-tagatose 3-epimerase activity is obtained from a microorganism selected from *Pseudomonas cichorii*, *Pseudomonas* sp. ST-24, *Mesorhizobium loti* and *Rhodobacter sphaeroides*. In some embodiments, the nucleic acid molecule encoding an enzyme having D-tagatose 3-epimerase activity is dte, C1KKR1, or homolog thereof. In some embodiments, the one or more nucleic acid molecules is FJ851309.1 or homolog thereof. In a further embodiment, the enzyme having D-tagatose 3-epimerase activity comprises an amino acid sequence selected from the group consisting of SEQ ID NOs: 71 and 73. In yet a further embodiment, the enzyme having D-tagatose 3-epimerase activity is encoded by a nucleic acid sequence selected from the group consisting of SEQ ID NOs: 69, 70 and 72.

In one embodiment, the enzyme that catalyzes the conversion of D-ribulose to D-ribulose-1-phosphate is an enzyme having D-ribulokinase activity. In a further embodiment, the enzyme that catalyzes the conversion of D-ribulose to D-ribulose-1-phosphate is encoded by one or more endogenous nucleic acid molecules. In an alternative embodiment, the enzyme that catalyzes the conversion of D-ribulose to D-ribulose-1-phosphate is encoded by one or more exogenous nucleic acid molecules. In another embodiment, the enzyme having D-ribulokinase activity is encoded by a nucleic acid molecule obtained from *E. coli*. In some embodiments, the nucleic acid molecule encoding an enzyme having D-ribulokinase activity is fucK, or homolog thereof. In a further embodiment, the enzyme having D-ribulokinase activity comprises an amino acid sequence set forth in SEQ ID NO: 76. In yet a further embodiment, the enzyme having D-ribulokinase activity is encoded by a nucleic acid sequence selected from the group consisting of SEQ ID NOs: 74 and 75.

In one embodiment, the enzyme that catalyzes the conversion of D-ribulose-1-phosphate to glycolaldehyde and dihydroxyacetonephosphate (DHAP) is an enzyme having D-ribulose-1-phosphate aldolase activity. In a further embodiment, the enzyme that catalyzes the conversion of D-ribulose-1-phosphate to glycolaldehyde and DHAP is encoded by one or more endogenous nucleic acid molecules. In an alternative embodiment, the enzyme that catalyzes the conversion of D-ribulose-1-phosphate to glycolaldehyde and DHAP is encoded by one or more exogenous nucleic acid molecules. In another embodiment, the enzyme having D-ribulose-1-phosphate aldolase activity is encoded by a nucleic acid molecule obtained from *E. coli*. In some embodiments, the nucleic acid molecule encoding an enzyme having D-ribulose-1-phosphate aldolase activity is fucA, or homolog thereof. In a further embodiment, the enzyme having D-ribulose-1-phosphate aldolase activity comprises an amino acid sequence set forth in SEQ ID NO: 79. In yet a further embodiment, the enzyme having D-ribulose-1-phosphate aldolase activity is encoded by a nucleic acid sequence selected from the group consisting of SEQ ID NOs: 77 and 78.

In one embodiment, the method comprises expressing one or more of the following in a recombinant microorganism capable of co-producing monoethylene glycol (MEG) and isopropanol from exogenous D-xylose:

(a) at least one endogenous or exogenous nucleic acid molecule encoding a D-xylulose 1-kinase that catalyzes the conversion of D-xylulose to D-xylulose-1-phosphate;

(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);

(c) at least one endogenous or exogenous nucleic acid molecule encoding a glycolaldehyde reductase that catalyzes the conversion of glycolaldehyde from (b) to MEG;

(d) at least one endogenous or exogenous nucleic acid molecule encoding a thiolase that catalyzes the conversion of acetyl-CoA to acetoacetyl-CoA;

(e) at least one endogenous or exogenous nucleic acid molecule encoding an acetate:acetoacetyl-CoA transferase or hydrolase that catalyzes the conversion of acetoacetyl-CoA from (d) to acetoacetate;

(f) at least one endogenous or exogenous nucleic acid molecule encoding an acetoacetate decarboxylase that catalyzes the conversion of acetoacetate from (e) to acetone; and/or (g) at least one endogenous or exogenous nucleic acid molecule encoding a secondary alcohol dehydrogenase that catalyzes the conversion of acetone from (f) to isopropanol.

In one embodiment, the enzyme that catalyzes the conversion of D-xylulose to D-xylulose-1-phosphate is an enzyme having D-xylulose 1-kinase activity. In a further embodiment, the enzyme that catalyzes the conversion of D-xylulose to D-xylulose-1-phosphate is encoded by one or more endogenous nucleic acid molecules. In an alternative embodiment, the enzyme that catalyzes the conversion of D-xylulose to D-xylulose-1-phosphate is encoded by one or more exogenous nucleic acid molecules. In another embodiment, the enzyme having D-xylulose 1-kinase activity is encoded by a nucleic acid molecule obtained from *Homo sapiens*. In one embodiment, the *Homo sapiens* enzyme having D-xylulose 1-kinase activity is a ketohexokinase C. In some embodiments, the nucleic acid molecule encoding human ketohexokinase C is khk-C, or homolog thereof. In another embodiment, the one or more nucleic acid molecules encoding the enzyme having D-xylulose 1-kinase activity comprises an amino acid sequence set forth in SEQ ID NO: 123. In a further embodiment, the one or more nucleic acid molecules encoding the enzyme having D-xylulose 1-kinase activity is encoded by a nucleic acid sequence selected from the group consisting of SEQ ID NOs: 121 and 122.

In one embodiment, the enzyme that catalyzes the conversion of D-xylulose-1-phosphate to glycolaldehyde and dihydroxyacetonephosphate (DHAP) is a D-xylulose-1-phosphate aldolase. In a further embodiment, the enzyme that catalyzes the conversion of D-xylulose-1-phosphate to glycolaldehyde and DHAP is encoded by one or more endogenous nucleic acid molecules. In an alternative embodiment, the enzyme that catalyzes the conversion of D-xylulose-1-phosphate to glycolaldehyde and DHAP is encoded by one or more exogenous nucleic acid molecules. In another embodiment, the enzyme is a D-xylulose-1-phosphate aldolase that is encoded by a nucleic acid molecule obtained from *Homo sapiens*. In one embodiment, the *Homo sapiens* D-xylulose 1-phosphate aldolase is an aldolase B. In some embodiments, the nucleic acid molecule encoding human aldolase B is ALDOB, or homolog thereof. In some embodiments, the one or more nucleic acid molecules encoding the D-xylulose-1-phosphate aldolase comprises an amino acid sequence set forth in SEQ ID NO: 126. In some embodiments, the one or more nucleic acid molecules encoding the D-xylulose-1-phosphate aldolase is encoded by a nucleic acid sequence selected from the group consisting of SEQ ID NOs: 124 and 125.

In one embodiment, the method further comprises introducing into the recombinant microorganism one or more modifications selected from the group consisting of:

(a) a deletion, insertion, or loss of function mutation in a gene encoding a D-xylulose-5-kinase that catalyzes the conversion of D-xylulose to D-xylulose-5-phosphate;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In some embodiments, an endogenous D-xylose isomerase catalyzes the conversion of D-xylose to D-xylulose.

In one embodiment, the method comprises expressing one or more of the following in a recombinant microorganism capable of co-producing monoethylene glycol (MEG) and isopropanol from exogenous D-xylose:

(a) at least one endogenous or exogenous nucleic acid molecule encoding a xylose dehydrogenase that catalyzes the conversion of D-xylose to D-xylonolactone;

(b) at least one endogenous or exogenous nucleic acid molecule encoding a xylonolactonase that catalyzes the conversion of D-xylonolactone from (a) to D-xylonate;

(c) at least one endogenous or exogenous nucleic acid molecule encoding a xylonate dehydratase that catalyzes the conversion of D-xylonate from (b) to 2-keto-3-deoxy-xylonate;

(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;

(e) at least one endogenous or exogenous nucleic acid molecule encoding a glycolaldehyde reductase that catalyzes the conversion of glycolaldehyde from (d) to MEG;

(f) at least one exogenous nucleic acid molecule encoding a thiolase that catalyzes the conversion of acetyl-CoA to acetoacetyl-CoA;

(g) at least one endogenous or exogenous nucleic acid molecule encoding an acetate:acetoacetyl-CoA transferase or hydrolase that catalyzes the conversion of acetoacetyl-CoA from (f) to acetoacetate;

(h) at least one exogenous nucleic acid molecule encoding an acetoacetate decarboxylase that catalyzes the conversion of acetoacetate from (g) to acetone; and/or (i) at least one endogenous or exogenous nucleic acid molecule encoding a secondary alcohol dehydrogenase that catalyzes the conversion of acetone from (h) to isopropanol.

In one embodiment, the method comprises expressing one or more of the following in a recombinant microorganism capable of co-producing monoethylene glycol (MEG) and isopropanol from exogenous D-xylose:

(a) at least one endogenous or exogenous nucleic acid molecule encoding a xylose dehydrogenase that catalyzes the conversion of D-xylose to D-xylonate;

(b) at least one endogenous or exogenous nucleic acid molecule encoding a xylonate dehydratase that catalyzes the conversion of D-xylonate from (a) to 2-keto-3-deoxy-xylonate;

(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;

(d) at least one exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

In one embodiment, the enzyme that catalyzes the conversion of D-xylose to D-xylonolactone is an enzyme having xylose dehydrogenase activity. In a further embodiment, the enzyme that catalyzes the conversion of D-xylose to D-xylonolactone is encoded by one or more endogenous nucleic acid molecules. In an alternative embodiment, the enzyme that catalyzes the conversion of D-xylose to D-xylonolactone is encoded by one or more exogenous nucleic acid molecules. In another embodiment, the enzyme having xylose dehydrogenase activity is encoded by a nucleic acid molecule obtained from a microorganism selected from *Caulobacter* sp., *Haloarcula* sp., *Haloferax* sp., *Halorubrum* sp. and *Trichoderma* sp. In some embodiments, the nucleic acid molecule encoding the enzyme having xylose dehydrogenase activity is obtained from a microorganism selected from *Caulobacter crescentus, Haloarcula marismortui, Haloferax volcanii, Halorubrum lacusprofundi* and *Trichoderma reesei*. In some embodiments, the nucleic acid molecule encoding an enzyme having xylose dehydrogenase activity is selected from xylB, xdh (HVO_B0028), xyd1, or homolog thereof. In a further embodiment, the one or more nucleic acid molecules encoding the enzyme having xylose dehydrogenase activity comprises an amino acid sequence selected from the group consisting of SEQ ID NOs: 129, 131 and 133. In yet another embodiment, the one or more nucleic acid molecules encoding the enzyme having xylose dehydrogenase activity is encoded by a nucleic acid sequence selected from the group consisting of SEQ ID NOs: 127, 128, 130 and 132.

In one embodiment, the enzyme that catalyzes the conversion of D-xylonolactone to D-xylonate is an enzyme having xylonolactonase activity. In a further embodiment, the enzyme that catalyzes the conversion of D-xylonolactone to D-xylonate is encoded by one or more endogenous nucleic acid molecules. In an alternative embodiment, the enzyme that catalyzes the conversion of D-xylonolactone to D-xylonate is encoded by one or more exogenous nucleic acid molecules. In another embodiment, the enzyme having xylonolactonase activity is encoded by a nucleic acid molecule obtained from a microorganism selected from *Caulobacter* sp. and *Haloferax* sp. In some embodiments, the nucleic acid molecule encoding the enzyme having xylonolactonase activity is obtained from a microorganism selected from *Caulobacter crescentus, Haloferax volcanii* and *Haloferax gibbonsii*. In some embodiments, the nucleic acid molecule encoding an enzyme having xylonolactonase activity is xylC, or homolog thereof. In a further embodiment, the one or more nucleic acid molecules encoding the enzyme having xylonolactonase activity comprises an amino acid sequence set forth in SEQ ID NO: 135. In yet another embodiment, the one or more nucleic acid molecules encoding the enzyme having xylonolactonase activity is encoded by a nucleic acid sequence set forth in SEQ ID NO: 134.

In one embodiment, the enzyme that catalyzes the conversion of D-xylonate to 2-keto-3-deoxy-xylonate is an enzyme having xylonate dehydratase activity. In a further embodiment, the enzyme that catalyzes the conversion of D-xylonate to 2-keto-3-deoxy-xylonate is encoded by one or more endogenous nucleic acid molecules. In an alternative embodiment, the enzyme that catalyzes the conversion of D-xylonate to 2-keto-3-deoxy-xylonate is encoded by one or more exogenous nucleic acid molecules. In another embodiment, the enzyme having xylonate dehydratase activity is encoded by a nucleic acid molecule obtained from a microorganism selected from *Caulobacter* sp., *Haloferax* sp., *Sulfolobus* sp. and *E. coli*. In some embodiments, the nucleic acid molecule encoding the enzyme having xylonate dehydratase activity is obtained from a microorganism selected from *Caulobacter crescentus, Haloferax volcanii, E. coli* and *Sulfolobus solfataricus*. In some embodiments, the nucleic acid molecule encoding an enzyme having xylonate dehydratase activity is selected from xylD, yjhG, yagF, xad, or homolog thereof. In a further embodiment, the one or more nucleic acid molecules encoding the enzyme having xylonate dehydratase activity comprises an amino acid sequence selected from the group consisting of SEQ ID NOs: 137, 140 and 143. In yet another embodiment, the one or more nucleic acid molecules encoding the enzyme having xylonate dehydratase activity is encoded by a nucleic acid sequence selected from the group consisting of SEQ ID NOs: 136, 138, 139, 141 and 142.

In one embodiment, the enzyme that catalyzes the conversion of 2-keto-3-deoxy-xylonate to glycolaldehyde and pyruvate is an enzyme having 2-keto-3-deoxy-D-pentonate aldolase activity. In a further embodiment, the enzyme that catalyzes the conversion of 2-keto-3-deoxy-xylonate to glycolaldehyde and pyruvate is encoded by one or more endogenous nucleic acid molecules. In an alternative embodiment, the enzyme that catalyzes the conversion of 2-keto-3-deoxy-xylonate to glycolaldehyde and pyruvate is encoded by one or more exogenous nucleic acid molecules. In another embodiment, the enzyme having 2-keto-3-deoxy-D-pentonate aldolase activity is encoded by a nucleic acid molecule obtained from a microorganism selected from *Pseudomonas* sp. and *E. coli*. In some embodiments, the nucleic acid molecule encoding an enzyme having 2-keto-3-deoxy-D-pentonate aldolase activity is selected from yjhH, yagE, or homolog thereof. In a further embodiment, the one or more nucleic acid molecules encoding the enzyme having 2-keto-3-deoxy-D-pentonate aldolase activity comprises an amino acid sequence selected from the group consisting of SEQ ID NOs: 146 and 149. In yet another embodiment, the one or more nucleic acid molecules encoding the enzyme having 2-keto-3-deoxy-D-pentonate aldolase activity is encoded by a nucleic acid sequence selected from the group consisting of SEQ ID NOs: 144, 145, 147 and 148.

In some embodiments, the method further comprises introducing into the recombinant microorganism one or more modifications selected from the group consisting of:

(a) a deletion, insertion, or loss of function mutation in a gene encoding a D-xylose isomerase that catalyzes the conversion of D-xylose to D-xylulose; (b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

In one embodiment, the method comprises expressing one or more of the following in a recombinant microorganism capable of co-producing monoethylene glycol (MEG) and isopropanol from exogenous D-xylose and glucose:

(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;

(b) at least one exogenous nucleic acid molecule encoding a D-xylose isomerase that catalyzes the conversion of D-xylose to D-xylulose, and wherein the microorganism further expresses one or more of the following:

(c) at least one endogenous or exogenous nucleic acid molecule encoding a D-tagatose 3-epimerase that catalyzes the conversion of D-xylulose from (a) or (b) to D-ribulose;

(d) at least one endogenous or exogenous nucleic acid molecule encoding a D-ribulokinase that catalyzes the conversion of D-ribulose from (c) to D-ribulose-1-phosphate;

(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);

(f) at least one endogenous or exogenous nucleic acid molecule encoding a glycolaldehyde reductase or methylglyoxal reductase that catalyzes the conversion of glycolaldehyde from (e) to MEG;

(g) at least one endogenous or exogenous nucleic acid molecule encoding a thiolase that catalyzes the conversion of acetyl-CoA to acetoacetyl-CoA;

(h) at least one endogenous or exogenous nucleic acid molecule encoding an acetate:acetoacetyl-CoA transferase or hydrolase that catalyzes the conversion of acetoacetyl-CoA from (g) to acetoacetate;

(i) at least one endogenous or exogenous nucleic acid molecule encoding an acetoacetate decarboxylase that catalyzes the conversion of acetoacetate from (h) to acetone; and/or (j) at least one endogenous or exogenous nucleic acid molecule encoding a secondary alcohol dehydrogenase that catalyzes the conversion of acetone from (i) to isopropanol.

In one embodiment, the enzyme that catalyzes the conversion of D-xylose to xylitol is an enzyme having xylose reductase or aldose reductase activity. In a further embodiment, the enzyme that catalyzes the conversion of D-xylose to xylitol is encoded by one or more endogenous nucleic acid molecules. In an alternative embodiment, the enzyme that catalyzes the conversion of D-xylose to xylitol is encoded by one or more exogenous nucleic acid molecules. In another embodiment, the enzyme having xylose reductase or aldose reductase activity is encoded by a nucleic acid molecule obtained from a microorganism selected from *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the nucleic acid molecule encoding the enzyme having xylose reductase or aldose reductase activity is obtained from a microorganism selected from *Hypocrea jecorina, Scheffersomyces stipitis, S. cerevisiae, Pachysolen tannophilus, Pichia stipitis, Pichia quercuum, Candida shehatae, Candida tenuis, Candida tropicalis, Aspergillus niger, Neurospora crassa* and *Cyptococcus lactativorus*. In some embodiments, the nucleic acid molecule encoding an enzyme having xylose reductase or aldose reductase activity is xyl1, GRE3, or homolog thereof. In some embodiments, the one or more nucleic acid molecules encoding the enzyme having xylose reductase or aldose reductase activity comprises an amino acid sequence selected from the group consisting of SEQ ID NOs: 152 and 155. In some embodiments, the one or more nucleic acid molecules encoding the enzyme having xylose reductase or aldose reductase activity is encoded by a nucleic acid sequence selected from the group consisting of SEQ ID NOs: 150, 151, 153 and 154.

In one embodiment, the enzyme that catalyzes the conversion of xylitol to D-xylulose is an enzyme having xylitol dehydrogenase activity. In a further embodiment, the enzyme that catalyzes the conversion of xylitol to D-xylulose is encoded by one or more endogenous nucleic acid molecules. In an alternative embodiment, the enzyme that catalyzes the conversion of xylitol to D-xylulose is encoded by one or more exogenous nucleic acid molecules. In another embodiment, the enzyme having xylitol dehydrogenase activity is encoded by a nucleic acid molecule obtained from a microorganism selected from *Scheffersomyces* sp., *Trichoderma* sp., *Pichia* sp., *Saccharomyces* sp., *Gluconobacter* sp., *Galactocandida* sp., *Neurospora* sp., and *Serratia* sp. In some embodiments, the nucleic acid molecule encoding the enzyme having xylitol dehydrogenase activity is obtained from a microorganism selected from *Scheffersomyces stipitis, Trichoderma reesei, Pichia stipitis, S. cerevisiae, Gluconobacter oxydans, Galactocandida mastotermitis, Neurospora crassa* and *Serratia marcescens*. In some embodiments, the one or more nucleic acid molecule encoding an enzyme having xylitol dehydrogenase activity is xyl2, xdh1, or homolog thereof. In some embodiments, the one or more nucleic acid molecules encoding the enzyme having xylitol dehydrogenase activity comprises an amino acid sequence selected from the group consisting of SEQ ID NOs: 158 and 160. In some embodiments, the one or more nucleic acid molecules encoding the enzyme having xylitol dehydrogenase activity is encoded by a nucleic acid sequence selected from the group consisting of SEQ ID NOs: 156, 157 and 159.

In one embodiment, the enzyme that catalyzes the conversion of D-xylose to D-xylulose is an enzyme having D-xylose isomerase activity. In a further embodiment, the enzyme that catalyzes the conversion of D-xylose to D-xylulose is encoded by one or more endogenous nucleic acid molecules. In an alternative embodiment, the enzyme that catalyzes the conversion of D-xylose to D-xylulose is encoded by one or more exogenous nucleic acid molecules. In another embodiment, the enzyme having D-xylose isomerase activity is encoded by a nucleic acid molecule obtained from *E. coli*. In another embodiment, the enzyme having xylose isomerase activity is encoded by one or more nucleic acid molecules obtained from *Pyromyces* sp. In some embodiments, the nucleic acid molecule encoding an enzyme having D-xylose isomerase activity is xylA, or homolog thereof. In yet another embodiment, the one or more nucleic acid molecules encoding the enzyme having xylose isomerase activity comprises an amino acid sequence selected from SEQ ID NOs: 163 and 190. In a further embodiment, the one or more nucleic acid molecules encoding the enzyme having xylose isomerase activity is encoded by a nucleic acid sequence selected from SEQ ID NOs: 161, 162 and 189.

In some embodiments, the method further comprises introducing into the recombinant microorganism one or more modifications selected from the group consisting of:

(a) a deletion, insertion, or loss of function mutation in a gene encoding a D-xylulose-5-kinase that catalyzes the conversion of D-xylulose to D-xylulose-5-phosphate; and (b) a deletion, insertion, or loss of function mutation in a gene encoding an alkaline phosphatase that catalyzes the conversion of D-xylulose-5-phosphate to D-xylulose.

In any of the above embodiments, the DHAP is converted to acetyl-CoA through the endogenous glycolysis pathway in the microorganism.

In any of the above embodiments, the enzyme that catalyzes the conversion of glycolaldehyde to MEG is an enzyme having glycolaldehyde reductase or aldehyde reductase activity. In a further embodiment, the enzyme that catalyzes the conversion of glycolaldehyde to MEG is encoded by one or more endogenous nucleic acid molecules. In an alternative embodiment, the enzyme that catalyzes the conversion of glycolaldehyde to MEG is encoded by one or more exogenous nucleic acid molecules. In another embodiment, the enzyme having glycolaldehyde reductase or aldehyde reductase activity is encoded by a nucleic acid molecule obtained from a microorganism selected from *E. coli* or *S. cerevisiae*. In some embodiments, the nucleic acid molecule encoding an enzyme having glycolaldehyde reductase or aldehyde reductase activity is selected from fucO, yqhD, dkgA (yqhE), dkgB (yafB), yeaE, yghZ, gldA, GRE2, or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 81, 83, 85, 88, 91, 93, 96, 98 and 100. In yet a further embodiment, the glycolaldehyde reductase is encoded by a nucleic acid sequence selected from the group consisting of SEQ ID NOs: 80, 82, 84, 86, 87, 89, 90, 92, 94, 95, 97 and 99.

In any of the above embodiments, the enzyme that catalyzes the conversion of acetyl-CoA to acetoacetyl-CoA is an enzyme having thiolase or acetyl coenzyme A acetyltransferase activity. In a further embodiment, the enzyme that catalyzes the conversion of acetyl-CoA to acetoacetyl-CoA is encoded by one or more endogenous nucleic acid molecules. In an alternative embodiment, the enzyme that catalyzes the conversion of acetyl-CoA to acetoacetyl-CoA is encoded by one or more exogenous nucleic acid molecules. In another embodiment, the enzyme is an enzyme having thiolase or acetyl coenzyme A acetyltransferase activity that is encoded by a nucleic acid molecule obtained from a microorganism selected from *Clostridium* sp., *Bacillus* sp., *E. coli*, *Saccharomyces* sp. and *Marinobacter* sp. In some embodiments, the nucleic acid molecule encoding an enzyme having thiolase or acetyl coenzyme A acetyltransferase activity is obtained from a microorganism selected from *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the nucleic acid molecule encoding an enzyme having thiolase or acetyl coenzyme A acetyltransferase activity is thlA, atoB and/or ERG10, or homolog thereof. In a further embodiment, the enzyme having thiolase or acetyl coenzyme A acetyltransferase activity comprises an amino acid sequence selected from the group consisting of SEQ ID NOs: 103, 105 and 108. In yet a further embodiment, the enzyme having thiolase or acetyl coenzyme A acetyltransferase activity is encoded by a nucleic acid sequence selected from the group consisting of SEQ ID NOs: 101, 102, 104, 106 and 107.

In any of the above embodiments, the enzyme that catalyzes the conversion of acetoacetyl-CoA to acetoacetate is an enzyme having acetate:acetoacetyl-CoA transferase or hydrolase activity. In some embodiments, the enzyme having transferase activity is an enzyme having acetyl-CoA:acetoacetate-CoA transferase activity. In a further embodiment, the enzyme that catalyzes the conversion of acetoacetyl-CoA to acetoacetate is encoded by one or more endogenous nucleic acid molecules. In an alternative embodiment, the enzyme that catalyzes the conversion of acetoacetyl-CoA to acetoacetate is encoded by one or more exogenous nucleic acid molecules. In another embodiment, the enzyme having acetate:acetoacetyl-CoA transferase or hydrolase activity is encoded by one or more nucleic acid molecule obtained from a microorganism selected from *Clostridium* sp. and *E. coli*. In some embodiments, the nucleic acid molecules encoding an enzyme having acetate:acetoacetyl-CoA hydrolase activity is obtained from *Clostridium acetobutylicum*. In some embodiments, the nucleic acid molecules encoding an enzyme having acetate:acetoacetyl-CoA transferase activity is obtained from *E. coli*. In some embodiments, the nucleic acid molecules encoding acetate:acetoacetyl-CoA transferase subunits are atoA and atoD, or homologs thereof. In some embodiments, the nucleic acid molecules encoding acetate:acetoacetyl-CoA hydrolase subunits are ctfA and ctfB, or homologs thereof. In a further embodiment, the enzyme having acetyl-CoA:acetoacetate-CoA transferase activity or acetate:acetoacetyl-CoA hydrolase activity comprises an amino acid sequence selected from the group consisting of SEQ ID NOs: 111, 114, 165, 167, 169 and 171. In yet a further embodiment, the enzyme having acetyl-CoA:acetoacetate-CoA transferase activity or acetate:acetoacetyl-CoA hydrolase activity is encoded by a nucleic acid sequence selected from the group consisting of SEQ ID NOs: 109, 110, 112, 113, 164, 166, 168 and 170.

In any of the above embodiments, the enzyme that catalyzes the conversion of acetoacetate to acetone is an enzyme having acetoacetate decarboxylase activity. In a further embodiment, the enzyme that catalyzes the conversion of acetoacetate to acetone is encoded by one or more endogenous nucleic acid molecules. In an alternative embodiment, the enzyme that catalyzes the conversion of acetoacetate to acetone is encoded by one or more exogenous nucleic acid molecules. In another embodiment, the enzyme having acetoacetate decarboxylase activity is encoded by a nucleic acid molecule obtained from a microorganism selected from *Clostridium* sp., *Bacillus* sp., *Chromobacterium* sp. and *Pseudomonas* sp. In some embodiments, the nucleic acid molecule encoding an enzyme having acetoacetate decarboxylase activity is obtained from a microorganism selected from *Clostridium acetobutylicum*, *Clostridium beijerinckii*, *Clostridium cellulolyticum*, *Bacillus polymyxa*, *Chromobacterium violaceum* and *Pseudomonas putida*. In some embodiments, the nucleic acid molecule encoding an enzyme having acetoacetate decarboxylase activity is adc, or homolog thereof. In a further embodiment, the enzyme having acetoacetate decarboxylase activity comprises an amino acid sequence selected from the group consisting of SEQ ID NOs: 117 and 120. In yet another embodiment, the enzyme having acetoacetate decarboxylase activity is encoded by a nucleic acid sequence selected from the group consisting of SEQ ID NOs: 115, 116, 118 and 119.

In any of the above embodiments, the recombinant microorganism may comprise at least one nucleic acid molecule encoding an enzyme that catalyzes the conversion of acetone to isopropanol. In one embodiment, the enzyme that catalyzes the conversion of acetone to isopropanol is encoded by one or more endogenous nucleic acid molecules. In an alternative embodiment, the enzyme that catalyzes the conversion of acetone to isopropanol is encoded by one or more exogenous nucleic acid molecules. In one embodiment, the enzyme that catalyzes the conversion of acetone to isopropanol is a secondary alcohol dehydrogenase (S-ADH). In another embodiment, the enzyme having secondary alcohol dehydrogenase activity is encoded by a nucleic acid molecule obtained from a microorganism selected from Burkholderia sp, Alcaligenes sp., Clostridium sp., Thermoanaerobacter sp., Phytomonas sp., Rhodococcus sp., Methanobacterium sp., Methanogenium sp., Entamoeba sp., Trichomonas sp., and Tritrichomonas sp. In some embodiments, the nucleic acid molecule encoding the enzyme having secondary alcohol dehydrogenase activity is obtained from a microorganism selected from Burkholderia sp. AIU 652, Alcaligenes eutrophus, Clostridium ragsdalei, Clostridium beijennckii, Clostridium carboxidivorans, Thermoanaerobacter brockii, Thermoanaerobacter ethanolicus (Clostridium thermohydrosulfuricum), Rhodococcus ruber, Methanobacterium palustre, methanogenic archaea Methanogenium liminatans, parasitic protist Entamoeba histolytica, parasitic protozoan Tritrichomonas foetus and human parasite Trichomonas vaginalis. In some embodiments, the one or more nucleic acid molecule encoding an enzyme having secondary alcohol dehydrogenase activity is adh, adhB, EhAdh1, or homolog thereof. In some embodiments, the S-ADH is predicted from homology and can be from Thermoanaerobacter mathranii, Micrococcus luteus, Nocardiopsis alba, Mycobacterium hassiacum, Helicobacter suis, Candida albicans, Candida parapsilosis, Candida orthopsilosis, Candida metapsilosis, Grosmanmia clavigera and Scheffersomyces stipitis. In a further embodiment, the enzyme having alcohol dehydrogenase activity comprises an amino acid sequence selected from the group consisting of SEQ ID NOs: 174 and 176. In yet another embodiment, the alcohol dehydrogenase is encoded by a nucleic acid sequence selected from the group consisting of SEQ ID NOs: 172, 173 and 175.

In any of the above embodiments, the enzyme that catalyzes the conversion of D-xylulose to D-xylulose-5-phosphate is a D-xylulose-5-kinase. In some embodiments, the D-xylulose-5-kinase is from Escherichia coli. In some embodiments, the D-xylulose-5-kinase is encoded by the xylB gene, or homolog thereof. In some embodiments, a recombinant microorganism producing MEG and isopropanol comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

In any of the above embodiments, the enzyme that catalyzes the conversion of glycolaldehyde to glycolic acid is a glycolaldehyde dehydrogenase. In some embodiments, the glycolaldehyde dehydrogenase is from Escherichia coli. In some embodiments, the glycolaldehyde dehydrogenase is encoded by the aldA gene, or homolog thereof. In some embodiments, a recombinant microorganism producing MEG and isopropanol comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

In any of the above embodiments, the enzyme that catalyzes the conversion of pyruvate to lactate is a lactate dehydrogenase. In particular embodiments, the enzyme converts pyruvate to lactate. In some embodiments, the lactate dehydrogenase is from Escherichia coli. In some embodiments, the lactate dehydrogenase is encoded by the ldhA gene, or homolog thereof. In some embodiments, a recombinant microorganism producing MEG and isopropanol comprises a deletion, insertion, or loss of function mutation in a gene encoding a lactate dehydrogenase to prevent the production of lactate from pyruvate and instead shunt the reaction toward production of isopropanol.

In any of the above embodiments, the enzyme that catalyzes the conversion of D-xylose to D-xylulose is a D-xylose isomerase. In some embodiments, the D-xylose isomerase is from Escherichia coli. In some embodiments, the D-xylose isomerase is encoded by the xylA gene, or homolog thereof. In some embodiments, a recombinant microorganism producing MEG and isopropanol comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the method comprises expressing one or more of the following in a recombinant microorganism capable of producing isopropanol:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and/or (d) at least one endogenous or exogenous nucleic acid molecule encoding a secondary alcohol dehydrogenase that catalyzes the conversion of acetone from (c) to isopropanol.

In some embodiments, the recombinant microorganism further comprises a deletion, insertion, or loss of function mutation in a gene encoding a lactate dehydrogenase that catalyzes the conversion of pyruvate to lactate.

In one embodiment, the method comprises expressing one or more of the following in a recombinant microorganism capable of co-producing n-propanol and isopropanol:

(a) at least one endogenous or exogenous nucleic acid molecule encoding a methylglyoxal synthase that catalyzes the conversion of dihydroxyacetone phosphate (DHAP) to methylglyoxal;

(b) at least one endogenous or exogenous nucleic acid molecule encoding an aldo-keto reductase that catalyzes the conversion of methylglyoxal from (a) to acetol;

(c) at least one endogenous or exogenous nucleic acid molecule encoding a glyoxylate reductase, a methylglyoxal dehydrogenase or an aldehyde dehydrogenase that catalyzes the conversion of methylglyoxal from (a) to lactaldehyde;

(d) at least one endogenous or exogenous nucleic acid molecule encoding an aldo-keto reductase that catalyzes the conversion of acetol from (b) to 1,2-propanediol;

(e) at least one endogenous or exogenous nucleic acid molecule encoding an aldehyde reductase that catalyzes the conversion of lactaldehyde from (c) to 1,2-propanediol;

(f) at least one endogenous or exogenous nucleic acid molecule encoding a diol-dehydratase that catalyzes the conversion of 1,2-propanediol from (d) or (e) to propanal;

(g) at least one endogenous or exogenous nucleic acid molecule encoding a dehydrogenase that catalyzes the conversion of propanal from (f) to n-propanol;

(h) at least one endogenous or exogenous nucleic acid molecule encoding a pyruvate formate lyase that catalyzes the conversion of pyruvate to acetyl-CoA;

(i) at least one endogenous or exogenous nucleic acid molecule encoding a thiolase that catalyzes the conversion of acetyl-CoA from (h) to acetoacetyl-CoA;

(j) at least one endogenous or exogenous nucleic acid molecule encoding an acetate:acetoacetyl-CoA transferase or hydrolase that catalyzes the conversion of acetoacetyl-CoA from (i) to acetoacetate;

(k) at least one endogenous or exogenous nucleic acid molecule encoding an acetoacetate decarboxylase that catalyzes the conversion of acetoacetate from (j) to acetone; and/or (l at least one endogenous or exogenous nucleic acid molecule encoding a secondary alcohol dehydrogenase that catalyzes the conversion of acetone from (k) to isopropanol; wherein the DHAP and pyruvate are produced from glycolysis in the microorganism.

In some embodiments, the method further comprises introducing into the recombinant microorganism one or more modifications selected from the group consisting of:

(a) a deletion, insertion, or loss of function mutation in a gene encoding an acetaldehyde dehydrogenase that catalyzes the conversion of lactaldehyde to lactate; and (b) a deletion, insertion, or loss of function mutation in a gene encoding a lactate dehydrogenase that catalyzes the conversion of pyruvate to lactate.

In one embodiment, the method comprises expressing one or more of the following in a recombinant microorganism capable of co-producing acetone, butanol and ethanol:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetaldehyde from (e) to ethanol or butyraldehyde from (i) to butanol;
wherein the pyruvate is produced from glycolysis in the microorganism.

In some embodiments, the recombinant microorganism further comprises a deletion, insertion, or loss of function mutation in a gene encoding a lactate dehydrogenase that catalyzes the conversion of pyruvate to lactate.

In one embodiment, the method comprises expressing one or more of the following in a recombinant microorganism capable of co-producing isopropanol, butanol and ethanol:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetone from (d) to isopropanol, acetaldehyde from (e) to ethanol or butyraldehyde from (i) to butanol.
wherein the pyruvate is produced from glycolysis in the microorganism.

In some embodiments, the method further comprises a deletion, insertion, or loss of function mutation in a gene encoding a butyrate kinase that catalyzes the conversion of butyryl phosphate to butyrate.

In one embodiment, the method comprises expressing one or more of the following in a recombinant microorganism capable of producing isobutanol:

(a) at least one endogenous or exogenous nucleic acid molecule encoding an acetohydroxy acid synthase that catalyzes the conversion of pyruvate to acetolactate;

(b) at least one endogenous or exogenous nucleic acid molecule encoding an acetohydroxy acid isomeroreductase that catalyzes the conversion of acetolactate from (a) to 2,3-dihydroxy-isovalerate;

(c) at least one endogenous or exogenous nucleic acid molecule encoding a dihydroxy-acid dehydratase that catalyzes the conversion of 2,3-dihydroxy-isovalerate from (b) to α-keto-isovalerate;

(d) at least one endogenous or exogenous nucleic acid molecule encoding a 2-keto-acid decarboxylase that catalyzes the conversion of α-keto-isovalerate from (c) to isobutyraldehyde; and/or (e) at least one endogenous or exogenous nucleic acid molecule encoding an alcohol dehydrogenase that catalyzes the conversion of isobutyraldehyde from (d) to isobutanol. wherein the pyruvate is produced from glycolysis in the microorganism.

In some embodiments, the method further comprises one or more modifications selected from the group consisting of:

(a) a deletion, insertion, or loss of function mutation in a gene encoding an ethanol dehydrogenase that catalyzes the conversion of acetaldehyde to ethanol; and (b) a deletion, insertion, or loss of function mutation in a gene encoding a lactate dehydrogenase that catalyzes the conversion of pyruvate to lactate.

Enzyme Engineering

The enzymes in the recombinant microorganism can be engineered to improve one or more aspects of the substrate to product conversion. Non-limiting examples of enzymes that can be further engineered for use in methods of the disclosure include an aldolase, an aldehyde reductase, an acetoacetyl coenzyme A hydrolase, a xylose isomerase, a xylitol dehydrogenase and combinations thereof. These enzymes can be engineered for improved catalytic activity, improved selectivity, improved stability, improved tolerance to various fermentation conditions (temperature, pH, etc.), or improved tolerance to various metabolic substrates, products, by-products, intermediates, etc. The term "improved catalytic activity" as used herein with respect to a particular enzymatic activity refers to a higher level of enzymatic activity than that measured relative to a comparable non-engineered enzyme.

For example, engineering methods have been used to alter the stability, substrate specificity and stereospecificity of aldolases to produce excellent enzymes for biocatalytic processes. The thermostability and solvent tolerance of fructose-1,6-bisphosphate aldolase (FBP-aldolase) was increased using family DNA shuffling of the fda genes from *Escherichia coli* and *Edwardsiella ictaluri*. A fourth generation variant was identified which displayed an average 280-fold higher half-life at 53° C. than either parent. The same variant also displayed enhanced activity in various polar and non-polar organic solvents (Hao and Berry 2004 Protein Eng Des Sel 17:689-697).

As another example, acetoacetyl coenzyme A hydrolase can convert acetoacetyl-CoA to acetoacetate. However, the hydrolase is unspecific in that it also reacts with the same magnitude of order with acetyl-CoA, which is the substrate required for acetoacetyl-CoA formation by the enzyme thiolase. Thus, to create more efficient acetoacetyl-CoA hydrolases, these enzymes have been engineered to have at least 10× higher activity for the acetoacetyl-CoA substrate than for acetyl-CoA substrate by replacing several glutamic acid residues in the enzyme beta subunit that is important for catalysis (WO 2015/042588).

As another example, the *E. coli* YqhD enzyme is a broad substrate aldehyde reductase with NADPH-dependent reductase activity for more than 10 aldehyde substrates and is a useful enzyme to produce biorenewable fuels and chemicals (Jarboe 2010 *Applied Microbiology and Biotechnology* 89:249). Though YqhD enzyme activity is beneficial through its scavenging of toxic aldehydes, the enzyme is also NADPH-dependent and contributes to NADPH depletion and growth inhibition of organisms. Error-prone PCR of YqhD was performed in order to improve 1,3-propanediol production from 3-hydroxypropionaldehyde (3-HPA). This directed engineering yielded two mutants, D99QN147H and Q202A, with decreased Km and increased kcat for certain aldehydes, particularly 3-HPA (Li et al. 2008 Prog. Nat. Sci. 18 (12):1519-1524). The improved catalytic activity of the D99QN147H mutant is consistent with what is known about the structure of YqhD (Sulzenbacher et al. 2004 J. Mol. Biol. 342 (2):489-502), as residues Asp99 and Asn147 both interact with NADPH. Use of the D99QN147H mutant increased 1,3-propanediol production from 3-HPA 2-fold.

As another example, xylose isomerase is a metal-dependent enzyme that catalyzes the interconversion of aldose and ketose sugars, primarily between xylose to xylulose and glucose to fructose. It has lower affinity for lyxose, arabinose and mannose sugars. The hydroxyl groups of sugars may define the substrate preference of sugar isomerases. The aspartate at residue 256 of *Thermus thermophilus* xylose isomerase was replaced with arginine (Patel et al. 2012 Protein Engineering, Design & Selection vol. 25 no. 7 pp. 331-336). This mutant xylose isomerase exhibited an increase in specificity for D-lyxose, L-arabinose and D-mannose. The catalytic efficiency of the D256R xylose isomerase mutant was also higher for these 3 substrates compared to the wild type enzyme. It was hypothesized that the arginine at residue 256 in the mutant enzyme may play a role in the catalytic reaction or influence changes in substrate orientation.

As another example, the enzyme xylitol dehydrogenase plays a role in the utilization of xylose along with xylose reductase. Xylose reductase (XR) reduces xylose to xylitol and then xylitol dehydrogenase (XDH) reoxidizes xylitol to form xylulose. However, since XR prefers NADPH as cosubstrate, while XDH exclusively uses NAD+ as cosubstrate, a cosubstrate recycling problem is encountered. One solution is to engineer XDH such that its cosubstrate specificity is altered from NAD+ to NADP+ (Ehrensberger et al. 2006 Structure 14: 567-575). A crystal structure of the *Gluconobacter oxydans* holoenzyme revealed that Asp38 is largely responsible for the NAD+ specificity of XDH. Asp38 interacts with the hydroxyls of the adenosine ribose, and Met39 stacks under the purine ring and is also located near the 2' hydroxyl. A double mutant (D38S/M39R) XDH was constructed that exclusively used NADP+ without loss of enzyme activity.

Metabolic Engineering—Enzyme Overexpression or Enzyme Downregulation/Deletion for Increased Pathway Flux In various embodiments described herein, the exogenous and endogenous enzymes in the recombinant microorganism participating in the biosynthesis pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, a recombinant microorganism of the disclosure is generated from a host that contains the enzymatic capability to synthesize substrates such as saturated primary or secondary alcohols. In some embodiments, it can be useful to increase the synthesis or accumulation of, for example, 1-propanol, 2-propanol, 1-butanol, 2-butanol or any alcohol listed in Table 1, to increase the production of the corresponding primary alkenes.

In some embodiments, it may be useful to increase the expression of endogenous or exogenous enzymes involved in the biosynthesis of saturated primary or secondary alcohols, thereby resulting in increased substrate for the one-step dehydration reaction catalyzed by one or more linalool dehydratase/isomerases to produce one or more primary alkenes. In some embodiments, it may be useful to increase the expression of the one or more linalool dehydratase/isomerases involved in the dehydration of saturated primary or secondary alcohols to the corresponding primary alkenes.

Increased synthesis or accumulation can be accomplished by, for example, overexpression of nucleic acids encoding one or more of the above-described alcohol biosynthesis pathway enzymes and/or overexpression of nucleic acids encoding one or more linalool dehydratase/isomerases. Overexpression of one or more alcohol biosynthesis pathway enzymes and/or one or more linalool dehydratase/isomerases can occur, for example, through increased expression of an endogenous gene or genes, or through the expression, or increased expression, of an exogenous gene or genes. Therefore, naturally occurring organisms can be readily modified to generate non-natural, primary alkene producing microorganisms through overexpression of one or more nucleic acid molecules encoding one or more alcohol biosynthesis pathway enzymes and/or one or more linalool dehydratase/isomerases. In addition, a non-naturally occurring organism can be generated by mutagenesis of an endogenous gene that results in an increase in activity of one or more alcohol biosynthesis pathway enzymes described above.

Equipped with the present disclosure, the skilled artisan will be able to readily construct the recombinant microorganisms described herein, as the recombinant microorganisms of the disclosure can be constructed using methods well known in the art as exemplified above to exogenously express one or more nucleic acids encoding one or more alcohol biosynthesis pathway enzymes and/or one or more linalool dehydratase/isomerases in sufficient amounts to produce one or more primary alkenes.

Methods for constructing and testing the expression levels of a non-naturally occurring primary alkene-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more nucleic acids encoding one or more alcohol biosynthesis pathway enzymes and/or one or more linalool dehydratase/isomerases as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218).

Those of skill in the art will recognize that, due to the degenerate nature of the genetic code, a variety of nucleic acid sequences can be used to encode a given enzyme of the disclosure. The nucleic acid sequences encoding the biosynthetic enzymes are referenced herein merely to illustrate an embodiment of the disclosure, and the disclosure includes any nucleic acid sequences that encode the amino acid sequences of the polypeptides and proteins of the enzymes of the present disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the nucleic acid sequences shown herein merely illustrate embodiments of the disclosure.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., Science, 236: 1237-1245 (1987)). Exemplary expression control sequences are described in, for example, Goeddel, *Gene*

*Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes that catalyzes a reaction in a pathway that competes with the biosynthesis pathway for the production of one or more saturated primary or secondary alcohol substrates converted by one or more linalool dehydratase/isomerases into the corresponding primary alkenes.

In some embodiments, the recombinant microorganism is manipulated to delete, disrupt, mutate, and/or reduce the activity of one or more endogenous enzymes that catalyzes the conversion of D-xylulose to D-xylulose-5-phosphate. In some such embodiments, the enzyme that catalyzes the conversion of D-xylulose to D-xylulose-5-phosphate is a D-xylulose-5-kinase. In some embodiments, the D-xylulose-5-kinase is from *Escherichia coli*. In some embodiments, the D-xylulose-5-kinase is encoded by the xylB gene or homologs thereof. In some embodiments, the manipulation prevents the conversion of D-xylulose to D-xylulose-5-phosphate and instead shunts the reaction toward conversion of D-xylulose to D-xylulose-1-phosphate.

In some embodiments, the recombinant microorganism is manipulated to delete, disrupt, mutate, and/or reduce the activity of one or more endogenous enzymes that catalyzes the conversion of glycolaldehyde to glycolic acid. In some such embodiments, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene or homologs thereof. In some embodiments, the manipulation prevents the production of glycolic acid from glycolaldehyde and instead shunts the reaction toward conversion of glycolaldehyde to MEG.

In some embodiments, the recombinant microorganism is manipulated to delete, disrupt, mutate, and/or reduce the activity of one or more endogenous enzymes that catalyzes the conversion of lactaldehyde to lactate. In some embodiments, the enzyme that catalyzes the conversion of lactaldehyde to lactate is an acetaldehyde dehydrogenase. In some embodiments, the acetaldehyde dehydrogenase is encoded by the aldA gene or homologs thereof. In some embodiments, the manipulation prevents the production of lactate from lactaldehyde and instead shunts the reaction toward conversion of lactaldehyde to 1,2-propanediol.

In some embodiments, the recombinant microorganism is manipulated to delete, disrupt, mutate, and/or reduce the activity of one or more endogenous enzymes that catalyzes the conversion of pyruvate to lactate. In some such embodiments, the enzyme that catalyzes the conversion of pyruvate to lactate is a lactate dehydrogenase. In some embodiments, the lactate dehydrogenase is from *Escherichia coli*. In some embodiments, the lactate dehydrogenase is encoded by the ldhA gene or homologs thereof. In some embodiments, the manipulation prevents the production of lactate from pyruvate and instead shunts the reaction toward production of an alcohol.

In some embodiments, the recombinant microorganism is manipulated to delete, disrupt, mutate, and/or reduce the activity of one or more endogenous enzymes that catalyzes the conversion of D-xylulose to D-xylulose-5-phosphate. In some such embodiments, the enzyme that catalyzes the conversion of D-xylulose to D-xylulose-5-phosphate is a D-xylulose-5-kinase. In some embodiments, the D-xylulose-5-kinase is from *Saccharomyces cerevisiae*. In some embodiments the D-xylulose-5-kinase is encoded by the XKS1 gene or homologs thereof. In some embodiments, the D-xylulose-5-kinase is from *Pichia stipitis*. In some embodiments the D-xylulose-5-kinase is encoded by the XYL3 gene or homologs thereof. In some embodiments, the manipulation prevents the conversion of D-xylulose to D-xylulose-5-phosphate and instead shunts the reaction toward conversion of D-xylulose to D-xylulose-1-phosphate.

In some embodiments, the recombinant microorganism is manipulated to delete, disrupt, mutate, and/or reduce the activity of one or more endogenous enzymes that catalyzes the conversion of D-xylulose-5-phosphate to D-xylulose. In some such embodiments, the enzyme that catalyzes the conversion of D-xylulose-5-phosphate to D-xylulose is an alkaline phosphatase. In some embodiments, the alkaline phosphatase is from *S. cerevisiae*. In some embodiments, the alkaline phosphatase is encoded by the PHO13 gene or homologs thereof. In some embodiments, the manipulation prevents the conversion of D-xylulose-5-phosphate to D-xylulose.

In some embodiments, the recombinant microorganism is manipulated to delete, disrupt, mutate, and/or reduce the activity of one or more endogenous enzymes that catalyzes the conversion of D-xylose to D-xylulose. In some such embodiments, the enzyme that catalyzes the conversion of D-xylose to D-xylulose is a D-xylose isomerase. In some embodiments, the D-xylose isomerase is from *E. coli*. In some embodiments, the D-xylose isomerase is encoded by the xylA gene or homologs thereof. In some embodiments, the manipulation prevents conversion of D-xylose to D-xylulose and instead shunts the reaction toward the conversion of D-xylose to D-xylonate.

In some embodiments, the recombinant microorganism is manipulated to delete, disrupt, mutate, and/or reduce the activity of one or more endogenous enzymes that catalyzes the conversion of butyryl phosphate to butyrate. In some embodiments, the enzyme that catalyzes the conversion of butyryl phosphate to butyrate is a butyrate kinase. In some embodiments, the butyrate kinase is encoded by the buk gene or homologs thereof. In some embodiments, the manipulation prevents the production of butyrate from butyryl phosphate and instead shunts the reaction toward conversion of butyryl phosphate to butyryl-CoA.

In some embodiments, the recombinant microorganism is manipulated to delete, disrupt, mutate, and/or reduce the activity of one or more endogenous enzymes that catalyzes the conversion of acetaldehyde to ethanol. In some embodiments, the enzyme that catalyzes the conversion of acetaldehyde to ethanol is an ethanol dehydrogenase. In some embodiments, the ethanol dehydrogenase is encoded by the adhE gene or homologs thereof. In some embodiments, the manipulation prevents the production of ethanol from acetaldehyde and instead shunts the reaction toward conversion of acetaldehyde to acetyl-CoA.

EXAMPLES

Example 1: Propylene Production from Propanol by Whole Cell Assay

The synthesized gene of linalool dehydratase-isomerase (SEQ ID NO: 63) was cloned in a pET28a (+) expression vector, then transformed using a heat shock protocol into competent *E. coli* BL21 (DE3) cells. The negative control used in the assay was prepared by transforming the empty vector into *E. coli* BL21 (DE3) cells.

The enzymatic assays with whole cells was carried out under the following conditions:

1 mL of a culture of OD 2 containing cells expressing the recombinant linalool dehydratase-isomerase was incubated with shaking for 24 h at 37° C. in a 2 mL sealed glass vial with 2 mM DTT, 1 mM IPTG and 0-50 mM 1- or 2-propanol. As a control 1 mL of a culture of OD 2 without the recombinant linalool dehydratase-isomerase was also incubated using the same conditions described above.

Figure 6:
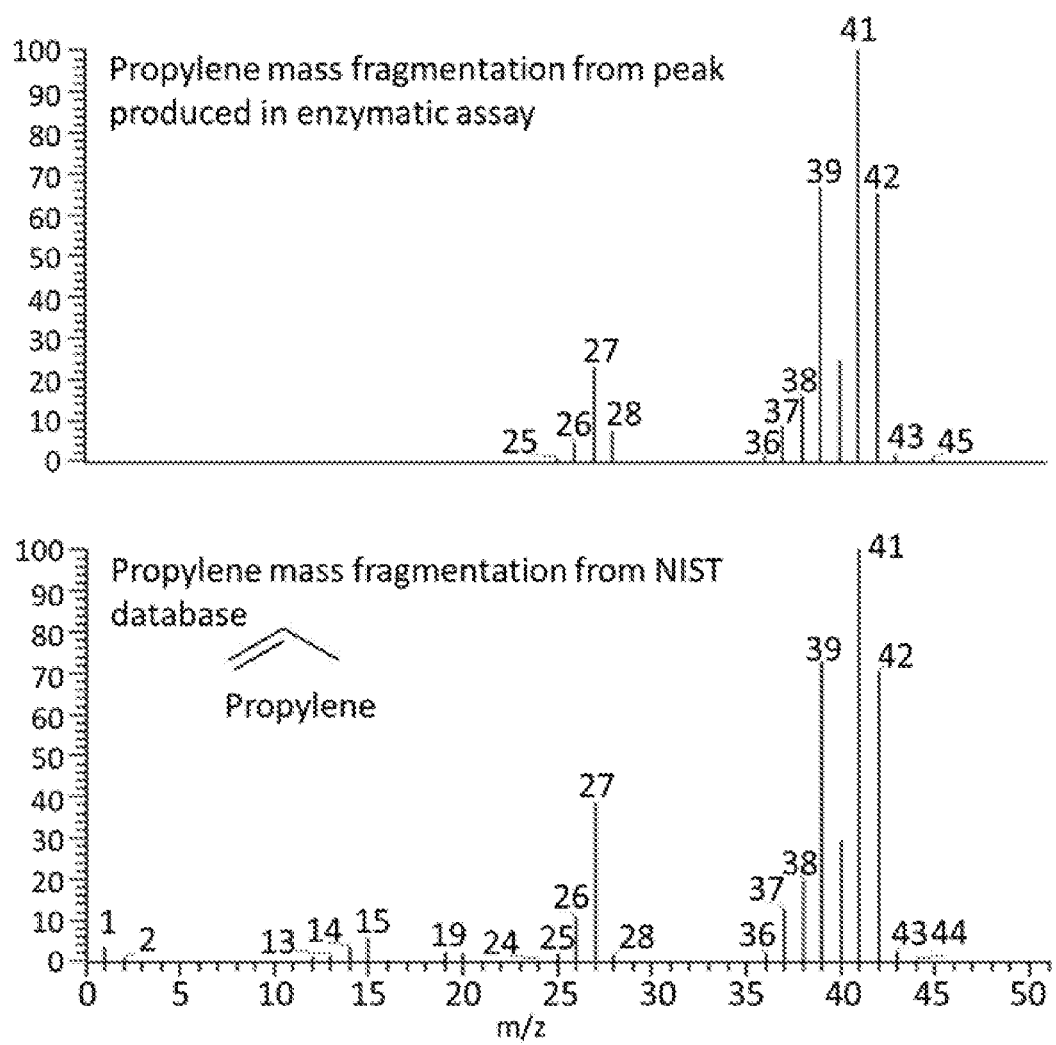
FIG. 6 shows propylene mass fragmentation comparison between the propylene produced by E. coli expressing a linalool dehydratase/isomerase and a database of mass fragmentation.

0.5 mL of the headspace phase was injected into a gas chromatograph (Focus GC—Thermo) equipped with electron impact mass spectrometer detector (ISQ—Thermo). Helium was used as a carrier gas with a flow rate of 1.5 mL/min; the split rate used was 10 with a split flow of 15 mL/min. The volatile compounds were separated in a HP-Plot/Q column (Agilent) with initial temperature held at 60° C. for 1.5 min followed by a ramp at 15° C./min to 150° C. held for 1 min. The retention time of propylene under these conditions was 4.82 min. The product reaction was identified both by comparison with a propylene standard and by comparison with a data base of mass fragmentation (FIG. 6).

Figure 7:
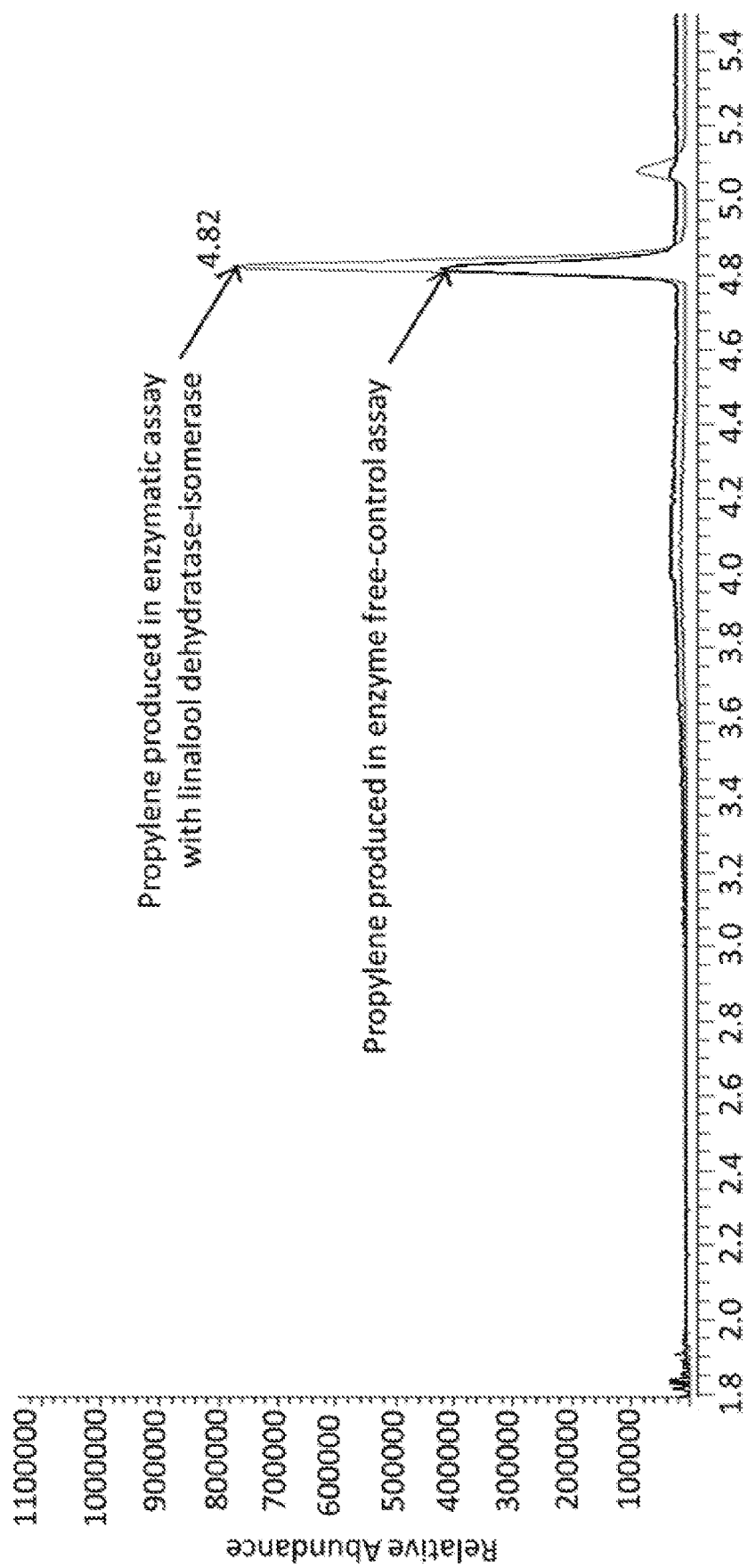
FIG. 7 shows GC-MS chromatograms obtained for enzymatic and enzyme-free assays as described in Example 1 (whole cell assay using 2-propanol).
Figure 8:
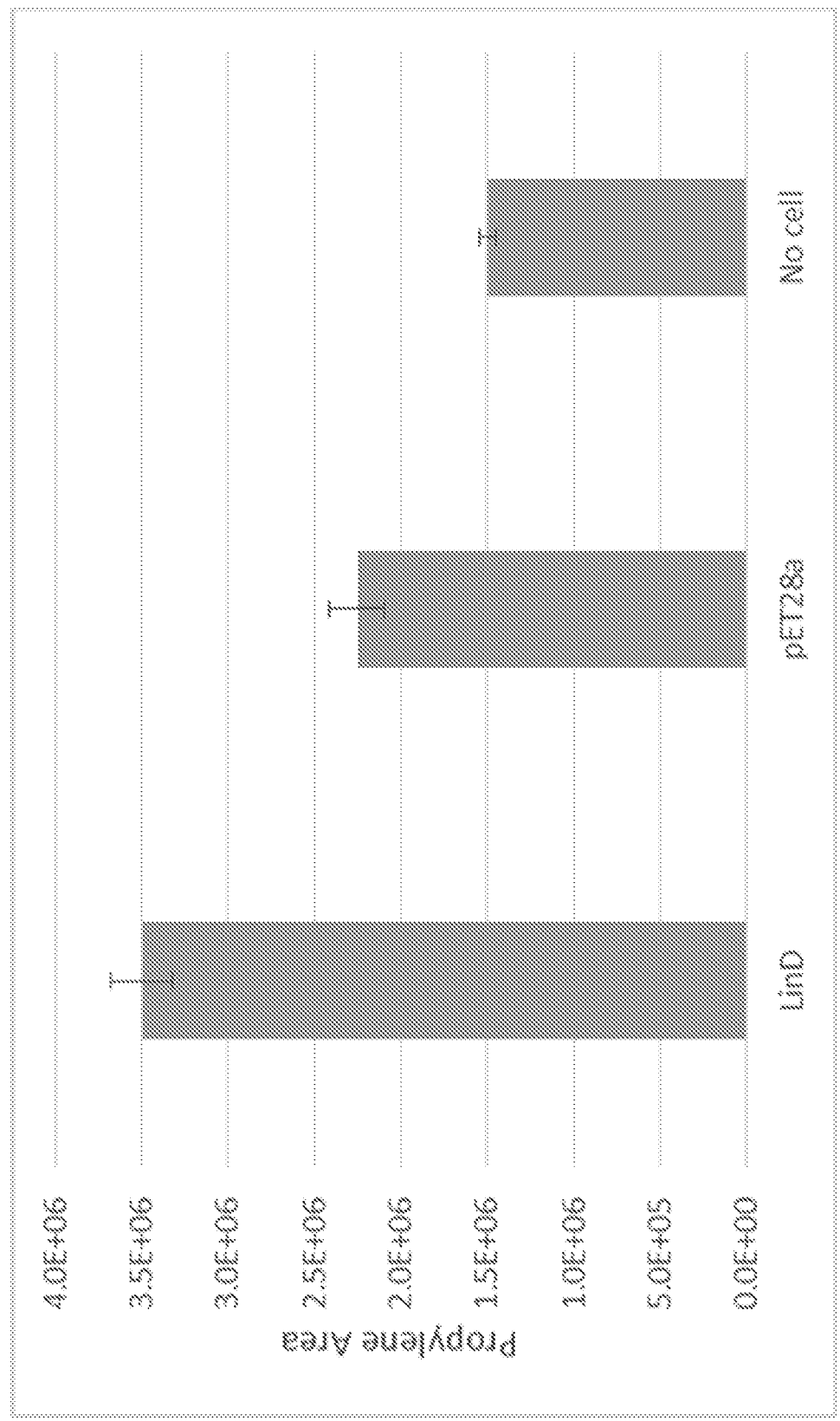
FIG. 8 shows a comparison of propylene production from linalool dehydratase-isomerase (LinD) and controls (pET-28 without LinD insert and no cell) for whole cell enzymatic assay, using 2-propanol.

A significant production of propylene was observed in the assay with the linalool dehydratase-isomerase. A small amount of propylene was observed in the control reaction that contained culture without the linalool enzyme (FIG. 7 and FIG. 8, Table 4).

TABLE 4

Propylene production after 24 h incubation in whole cell assay with propanol.

| Assay | Propylene peak area (arbitrary units) |
|---|---|
| Enzymatic assay with linalool dehydratase-isomerase | 3561535 ± 79279 |
| Enzyme free control assay | 1481575 ± 29950 |

Example 2. Propylene Production from Propanol Using Lysates

The synthesized gene of linalool dehydratase-isomerase (SEQ ID NO: 63) was cloned into a pET28a(+) expression vector, then transformed using heat shock protocol into competent *E. coli* BL21 (DE3) cells. The negative control used in the assay was prepared by transforming the empty vector into *E. coli* BL21 (DE3) cells.

The pre-inoculum of a single transformant was grown at 37° C. and 220 rpm overnight in TB media. An inoculum starting with OD 0.1 was also grown in TB media at 37° C. and 220 rpm until it reached OD 0.9, when 1 mM of IPTG was added for overnight expression at 18° C. and 220 rpm.

The cells were collected by centrifugation at 5000 rpm for 20 min and 4° C. The pellet was kept in −80° C. for 1 hour, then thawed on ice and resuspended in 10% of original volume in Tris-HCl 50 mM pH 7.5. The lysis was done by sonication (3-5 cycles, 10 s ON/10 s OFF, 500 W machine, 25% amplitude) on ice. Afterwards, to separate the soluble fraction, the suspension was centrifuged at 5000 rpm for 30 min at 4° C. The protein concentration was determined using the Bradford method.

The enzymatic assays with lysates from *E. coli* BL21 (DE3) containing the plasmid pET-28+LinD were carried out under the following conditions:

1 mL of the lysate (normalized by total protein amount) containing the recombinant linalool dehydratase-isomerase was incubated with shaking for 24 h and 37° C. in a 2 mL sealed glass vial with 2 mM DTT and 0-50 mM propanol. As a control, 1 mL of the lysate without the recombinant linalool dehydratase-isomerase was also incubated using the same conditions as described above.

0.5 mL of the headspace phase was injected into a gas chromatograph (Focus GC—Thermo) equipped with electron impact mass spectrometer detector (ISQ—Thermo). Helium was used as a carrier gas with a flow rate of 1.5 mL/min; the split rate used was 10 with a split flow of 15 mL/min. The volatile compounds were separated in a HP-Plot/Q column (Agilent) with initial temperature held at 60° C. for 1.5 min followed by a ramp at 15° C./min to 150° C. held for 1 min. The retention time of propylene under these conditions was 4.82 min. The product reaction was identified both by comparison with a propylene standard and by comparison with a database of mass fragmentation.

A significant production of propylene was observed in the assay with the linalool dehydratase-isomerase. A small amount of propylene was observed in the control reaction that contained culture without the linalool enzyme (Table 5).

TABLE 5

Propylene production after 24 h incubation in lysate assay with 1-propanol and 2-propanol.

| Assay | 1-propanol as substrate Propylene peak area (arbitrary units) | 2-propanol as substrate Propylene peak area (arbitrary units) |
|---|---|---|
| Enzymatic assay with linalool dehydratase-isomerase | 87064 ± 7004 | 62335 ± 2018 |
| Enzyme free control assay | 22394 ± 3526 | 4038 ± 1009 |

Example 3: Butylene Production from Butanol by Whole Cell Assay

The synthesized gene of linalool dehydratase-isomerase (SEQ ID NO: 63) was cloned into a pET28a(+) expression vector, then transformed using heat shock protocol in competent *E. coli* BL21 (DE3) cells. The negative control used in the assay was prepared by transforming the empty vector into *E. coli* BL21 (DE3) cells.

The enzymatic assays with whole cells were carried out under the following conditions:

1 mL of a culture with OD 2 containing the recombinant linalool dehydratase-isomerase was incubated with shaking for 24 h and 37° C. in a 2 mL sealed glass vial with 2 mM DTT, 1 mM IPTG and 0-50 mM butanol. As a control 1 mL of a culture with OD 2 without the recombinant linalool dehydratase-isomerase was also incubated using the same conditions described above.

Figure 9:
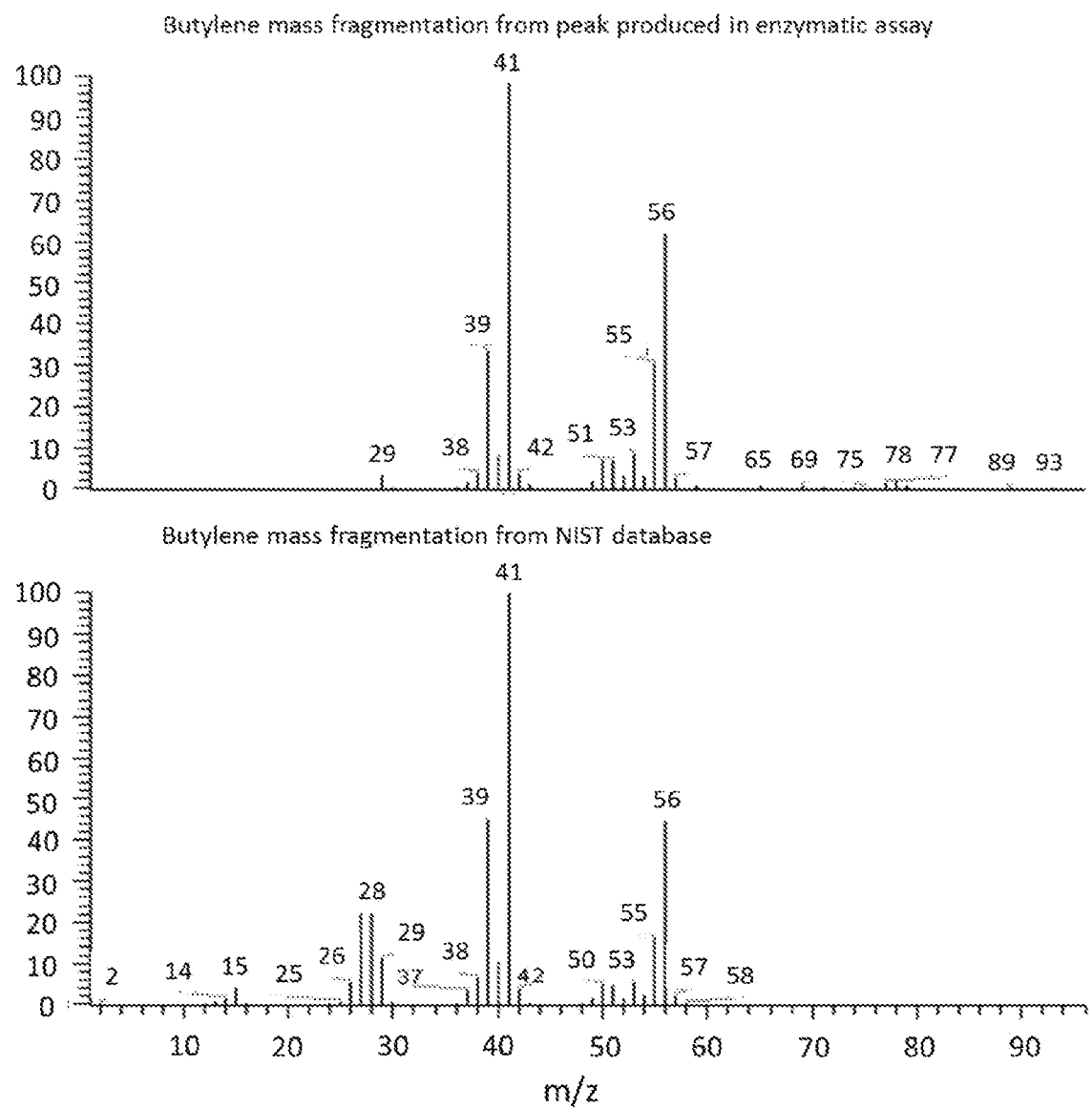
FIG. 9 shows butylene mass fragmentation comparison between the butylene produced by E. coli expressing a linalool dehydratase/isomerase and a database of mass fragmentation.

0.5 mL of the headspace phase was injected into a gas chromatograph (Focus GC—Thermo) equipped with electron impact mass spectrometer detector (ISQ—Thermo). Helium was used as a carrier gas with a flow rate of 1.5 mL/min; the split rate used was 10 with a split flow of 15 mL/min. The volatile compounds were separated in a HP-Plot/Q column (Agilent) with initial temperature held at 60° C. for 0.5 min followed by a ramp at 50° C./min to 250° C. held for 2 min. The retention time of butylene under these conditions was 3.9 min. The product reaction was identified both by comparison with a butylene standard and by comparison with a database of mass fragmentation (FIG. 9).

Figure 10:
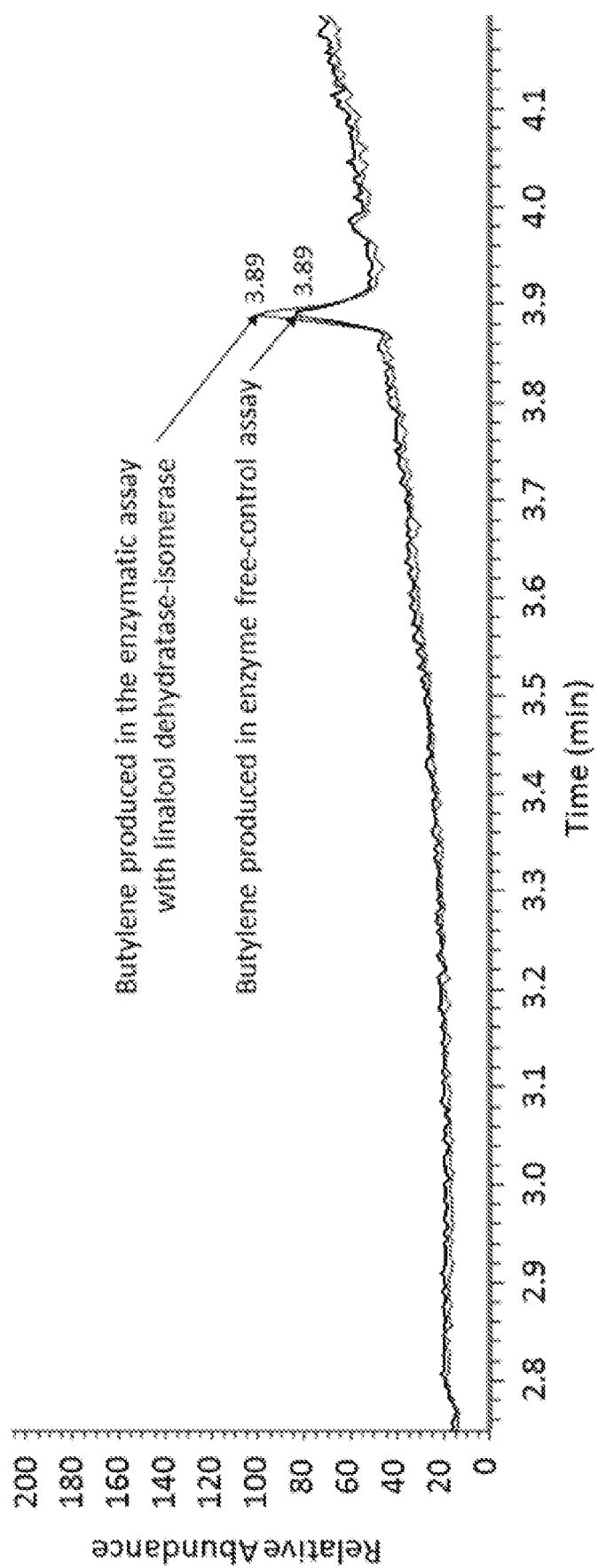
FIG. 10 shows GC-MS chromatograms obtained for enzymatic and enzyme-free assays as described in Example 3 for whole cell assay.

A significant production of butylene was observed in the assay with the linalool dehydratase-isomerase. A small amount of butylene was observed in the control reaction that contained culture without the enzyme (FIG. 10, Table 6).

TABLE 6

Butylene production in whole cell assay after 24 h incubation with butanol.

| Assay | Butylene peak area (arbitrary units) |
|---|---|
| Enzymatic assay with linalool dehydratase-isomerase | 1516521 ± 125190 |
| Enzyme free control assay | 1030898 ± 112778 |

Example 4: Butylene Production from Butanol Using Lysates

The synthesized gene of linalool dehydratase-isomerase (SEQ ID NO: 63) was cloned into a pET28a(+) expression vector, then transformed using heat shock protocol into competent E. coli BL21 (DE3) cells. The negative control used in the assay was prepared by transforming the empty vector into E. coli BL21 (DE3) cells.

The pre-inoculum of the cells was grown at 37° C. and 220 rpm overnight in TB media, an inoculum starting with OD 0.1 was also grown in TB media at 37° C. and 220 rpm until it reached OD 0.9, when 1 mM of IPTG was added for overnight expression at 18° C. and 220 rpm.

The cells were collected by centrifugation at 5000 rpm for 20 min at 4° C. The pellet was kept at −80° C. for 1 hour, then thawed on ice and resuspended in 10% of original volume in Tris-HCl 50 mM pH 7.5. The lysis was done by sonication (3-5 cycles, 10 s ON/10 s OFF, 25% amplitude, 500 W) on ice. Afterwards, to separate the soluble fraction, the suspension was centrifuged at 5000 rpm for 30 min at 4° C. The protein concentration was determined using the Bradford method.

The enzymatic assays with lysates from E. coli BL21 (DE3) containing the plasmid pET-28+LinD were carried out under the following conditions:

1 mL of the lysate (normalized by total protein amount) containing the recombinant linalool dehydratase-isomerase was incubated with shaking for 24 h at 37° C. in a 2 mL sealed glass vial with 2 mM DTT and 0-50 mM butanol. As a control, 1 mL of the lysate without the recombinant linalool dehydratase-isomerase was also incubated using the same conditions as described above.

0.5 mL of the headspace phase was injected into a gas chromatograph (Focus GC—Thermo) equipped with electron impact mass spectrometer detector (ISQ—Thermo). Helium was used as a carrier gas with a flow rate of 1.5 mL/min; the split rate used was 10 with a split flow of 15 mL/min. The volatile compounds were separated in a HP-Plot/Q column (Agilent) with initial temperature held at 60° C. for 0.5 min followed by a ramp at 50° C./min to 250° C. held for 2 min. The retention time of butylene under these conditions was 3.9 min. The product reaction was identified both by comparison with a butylene standard and by comparison with a database of mass fragmentation.

A significant production of butylene was observed in the assay with the linalool dehydratase-isomerase. A small amount of butylene was observed in the control reaction that contained culture without the linalool enzyme (Table 7).

TABLE 7

Butylene production in lysate assay after 24 h incubation with butanol.

| Assay | Butylene peak area (arbitrary units) |
|---|---|
| Enzymatic assay with linalool dehydratase-isomerase | 1258661 ± 66460 |
| Enzyme free control assay | 674903 ± 194931 |

Surprisingly, the enzyme linalool dehydratase isomerase (EC 4.2.1.127) does not require a double bond (enol group) in the substrate, as would be expected. The natural reaction is an isomerization of geraniol to linalool and then dehydration to myrcene (3-methyl-2-en-1-ol group). For non-natural substrates, isomerization of crotyl alcohol to methylvinyl carbinol and dehydration to 1,3 butadiene has been described (2-en-1-ol group). The very similar isomerization of 3-methyl-3-buten-1-ol (isoprenol) to 3-methyl-3-buten-2-ol and dehydration to isoprene has been described.

The results given here as related to dehydration of a primary alcohol, demonstrated for the reaction of 1- or 2-propanol to propene and 1-butanol to butene, show a number of unexpected features:

No tertiary methyl group in the substrate is needed.

No double-bond in the substrate is needed, in contrast to all reported substrates so far.

A very short substrate is accepted (C3), well below the known natural substrate (C10) and the smallest reported non-natural substrate (C5, C4).

Example 5. Direct Production of Propylene from Glucose

Vectors pZs*13 containing an IPA pathway in an operon under pILacO promoter and pET28a containing LinD gene were co-transformed into BL21Star (DE3) using electroporation. Production of isopropanol requires the expression of five genes: thl (thiolase), atoA/D (acetate:acetoacetyl-CoA transferase), adc (acetoacetate decarboxylase) and adh (secondary alcohol dehydrogenase). atoA/D gene is native from E. coli and was PCR amplified (Forward Primer CTGTTGT-TATATTGTAATGATGTATGCAAGAGGGATAAA (SEQ ID NO: 183) and Reverse Primer TATATCTCCTTCT-TAAAGTTCATAAATCACCCCGTTGC (SEQ ID NO: 184)). thl (Thl amino acid sequence set forth in SEQ ID NO: 103), adc (Adc amino acid sequence set forth in SEQ ID NO: 117) and adh (Adh amino acid sequence set forth in SEQ ID NO: 174) were codon optimized for E. coli and synthesized. An operon containing thl (thiolase), adh (secondary alcohol dehydrogenase), adc (acetoacetate decarboxylase), atoA/D (acetate:acetoacetyl-CoA transferase) genes and T1 terminator under the control of the inducible promoter pLLacO was constructed in a pZS*13 backbone. The candidate selection was done using kanamycin and ampicillin in LB medium. The strain herein was referred to as IPA+LinD.

This combination of plasmids provides a strain capable of producing isopropanol from glucose and also expressing linalool isomerase dehydratase enzyme.

One single colony of IPA+LinD, pZs*13_IPA and pET28a_LinD was inoculated in TB medium containing 10 g/L glycerol supplemented with kanamycin (50 µg/mL) and ampicillin (100 µg/mL) at 37° C., 220 rpm. After 20 hours, a new inoculation was done using optical density of 0.2 in TB medium containing 1.5 g/L glycerol supplemented with appropriate antibiotics at 37° C., 220 rpm. After 3 hours, the OD achieved 1.0 at 600 nm and IPTG was added to a final concentration of 1 mM. The flasks were incubated at 18° C., 220 rpm.

After 16 hours, the OD was measured and the cultures were concentrated to reach OD 20 using the following media as described for each assay:

(a) pZs*13_IPA in TB 20 g/L glucose (control for isopropanol production),
(b) IPA+LinD in TB 10 g/L glycerol and 3 g/L isopropanol (control for propylene production),
(c) IPA+LinD in TB 20 g/L glucose and 3 g/L isopropanol (control for propylene production),
(d) IPA+LinD in TB 20 g/L glucose (candidate 1 for propylene production),
(e) IPA+LinD in TB 20 g/L glucose (candidate 2 for propylene production)

Figure 11:
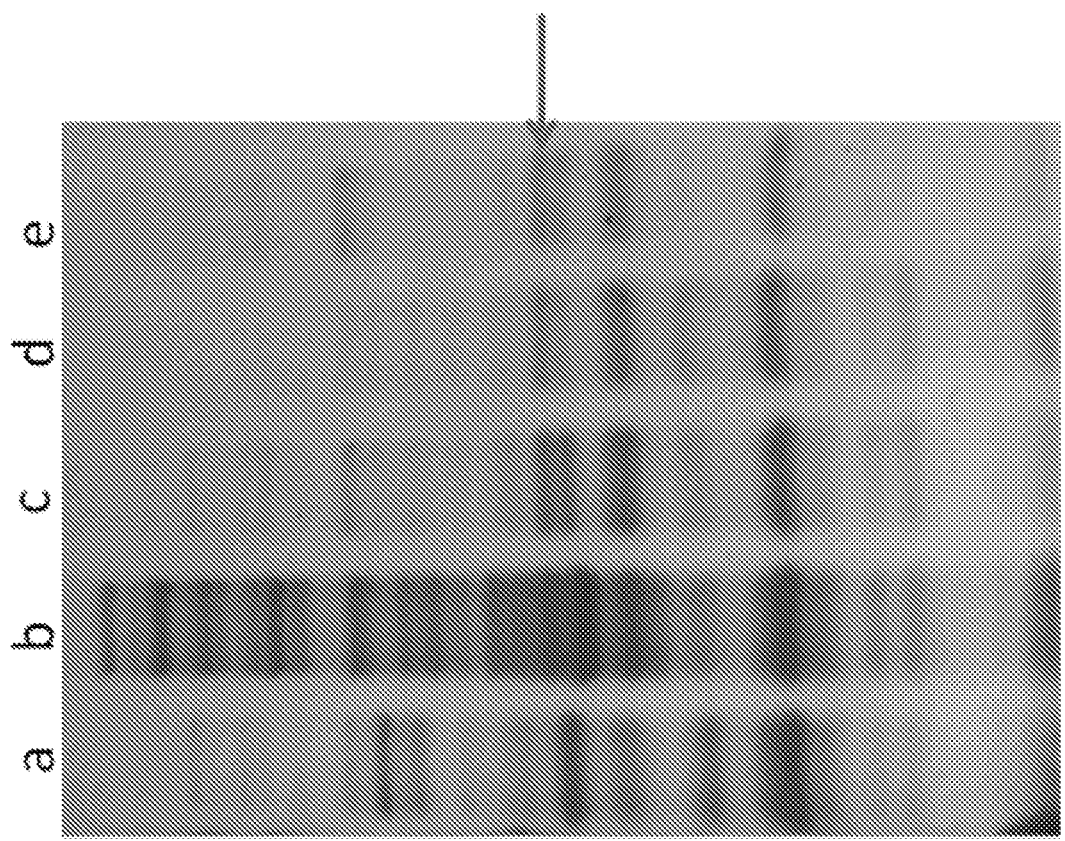
FIG. 11 shows an SDS-PAGE of soluble fraction of assays (a) to (e) as described in Example 5. The arrow indicates LinD expression in (b), (c), (d) and (e).

One aliquot of all cultures were lysate for expression analysis and the cells were collected by centrifugation at 5000 rpm for 20 min and 4° C. The pellet was kept in −80° C. for 1 hour then it was thawed on ice and ressuspended in 10% of original volume in Tris-HCl 50 mM pH 7.5. The lysis was done by sonication (3-5 cycles, 10/10 minutes, 25% amplitude) on ice after that to separate the soluble fraction it was centrifuged at 5000 rpm for 30 min at 4° C. The samples were heated at 95° C. for 10 minutes and analyzed in SDS-PAGE (FIG. 11).

1.0 mL aliquots of each culture were placed in 2 mL headspace vials in triplicate and incubated at 37° C., 225 rpm. At the end of 116 hours of incubation the vials were removed from the shaking incubator and the propylene and isopropanol concentration was analyzed in GC-MS. A control containing only TB medium 20 g/L glucose was done in order to verify contamination in the end of incubation period. 1.0 mL of the headspace phase was injected in gas chromatograph (Focus GC—Thermo) equipped with electron impact mass spectrometer detector (ISQ—Thermo). Helium was used as a carrier gas with a flow rate of 1.5 mL/min, the split rate used was 10 with a split flow of 15 mL/min. The volatile compounds were separated in a HP-Plot/Q column (Agilent) with initial temperature held at 90° C. for 1.0 min followed by a first ramp at 13.3° C./min to 130° C. and a second one at 45° C./min to 200° C. held for 1 min. The retention time of propylene under these conditions was 1.51 min and of isopropanol was 4.3 min. The product reaction was identified both by comparison with propylene and isopropanol standards and by comparison with a data base of mass fragmentation.

Figure 12:
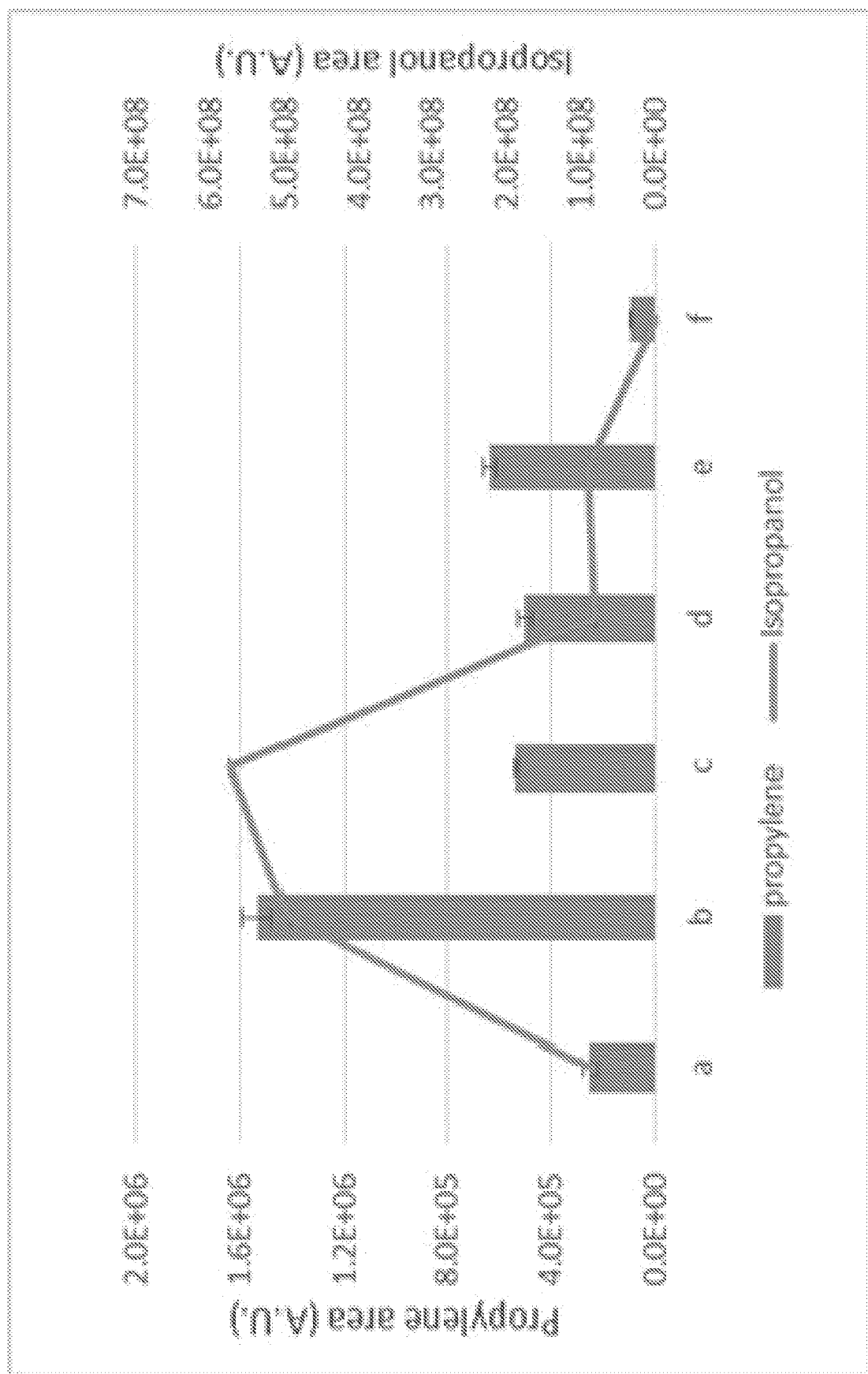
FIG. 12 illustrates that assays (d) and (e) showed the production of propylene and isopropanol in IPA+LinD candidates. Assay (a) showed isopropanol production of pZs*13_IPA and a small amount of propylene. Assays (b) and (c) showed propylene production in medium supplemented with 3.0 g/L isopropanol using glycerol and glucose as carbon source, respectively.

The production of isopropanol in assays (a), (d) and (e) were 0.5 g/L and in (b) and (c) 3.0 g/L as expected. The production of 4 $10^{-5}$ mM of propylene was observed in the assay (b) positive control for propylene and a significant production was observed in the assays (d) and (e), candidates with IPA+LinD co-transformed (FIG. 12). No amount of propylene was observed in the control reaction that contained only TB medium.

Summary Exemplary Sequences:

Linalool Dehydratase (LinD) from *Castellaniella defragrans* 65Phen (Designated LinD-1).

SEQ ID NO: 1: Native nucleic acid sequence encoding wild type (WT) linalool dehydratase polypeptide SEQ ID NO: 2; including signal peptide encoding sequence.

SEQ ID NO: 2: Native full-length wild type linalool dehydratase polypeptide, designated LinD-1.

SEQ ID NO: 3: Codon optimized nucleic acid encoding SEQ ID NO: 2.

SEQ ID NO: 4: Native nucleic acid encoding processed (mature) form of LinD-1.

SEQ ID NO: 5: Mature (processed) form of SEQ ID NO: 2 wild type linalool dehydratase.

SEQ ID NO: 6: Nucleic acid encoding SEQ ID NO: 7; differs from SEQ ID NO: 3 by having 12 codon substitutions.

SEQ ID NO: 7: Full-length polypeptide variant of LinD-1, designated LinD-1N, having 12 substitutions (A18I, F20L, Y70F, G73S, G132M, R170K, I181L, V195F, D199N, F324S, G364S, L367F).

Linalool Dehydratase (LinD) from *Castellaniella Defragrans* 62Car: Designated LinD-2.

SEQ ID NO: 8: Native nucleic acid encoding SEQ ID NO: 9; including signal peptide.

SEQ ID NO: 9: Full-length wild type LinD from *C. defragrans* 62Car, with signal peptide, designated LinD-2.

SEQ ID NO: 10: codon optimized nucleic acid encoding full length LinD-2.

SEQ ID NO: 11: Native nucleic acid encoding processed (mature) form of SEQ ID NO 12.

SEQ ID NO: 12: Mature, processed form of LinD polypeptide LinD-2.

SEQ ID NO: 13: Nucleic acid encoding full-length variant SEQ ID NO: 14; differs from wild type SED ID NO: 10 by having 11 codon substitutions.

SEQ ID NO: 14: Full-length variant LinD-2 with 11 amino acid substitutions (V19I, Y71F, G74S, G133M, R171K, I182L, V196F, D200N, F325S, G365S, L368F; designated LinD-2C).

Linalool Dehydratase (LinD) from Metagenomics on Activated Sludge from Padre Dam Enriched on Myrcene: Designated LinD-3.

SEQ ID NO: 15: Native nucleic acid encoding SEQ ID NO: 16, which is unprocessed and includes its signal peptide.

SEQ ID NO: 16: Native, or unprocessed, LinD enzyme, including signal peptide, designated LinD-3.

SEQ ID NO: 17: Nucleic acid encoding processed SEQ ID NO: 18 LinD enzyme, no signal peptide.

SEQ ID NO: 18: Processed LinD-3 LinD enzyme, no signal peptide.

Full length SEQ ID NO: 16 polypeptide has 99% sequence identity to full length SEQ ID NO: 2; and the mature, or processed, GNM SEQ ID NO: 18 polypeptide has 99% sequence identity to processed SEQ ID NO: 5.

Full length SEQ ID NO: 16 polypeptide has 94% sequence identity to full length SEQ ID NO: 9; and the mature, or processed, SEQ ID NO: 18 polypeptide has 96% sequence identity to processed SEQ ID NO: 12.

Linalool Dehydratase (LinD) from Metagenomics on Activated Sludge from Camp Pendleton Enriched on Myrcene (Secondary Enrichment): Designated LinD-4.

SEQ ID NO: 19: Native nucleic acid encoding SEQ ID NO: 20, which is unprocessed and includes its signal peptide.

SEQ ID NO: 20: Native, or unprocessed, LinD enzyme, including signal peptide, designated LinD-4.

SEQ ID NO: 21: Nucleic acid encoding processed SEQ ID NO: 22 LinD enzyme, no signal peptide.

SEQ ID NO: 22: Processed LinD-4 LinD enzyme, no signal peptide.

Full length SEQ ID NO: 20 polypeptide has 75% sequence identity to full length SEQ ID NO: 2; and the mature, or processed, SEQ ID NO: 22 polypeptide has 79% sequence identity to processed SEQ ID NO: 5.

Full length SEQ ID NO: 20 polypeptide has 75% sequence identity to full length SEQ ID NO: 9; and the mature, or processed, SEQ ID NO: 22 polypeptide has 79% sequence identity to processed SEQ ID NO: 12.

Linalool Dehydratase (LinD) from Metagenomics on Activated Sludge from Camp Pendleton Enriched on Myrcene (Primary Enrichment): Designated LinD-5.

SEQ ID NO: 23: Native nucleic acid encoding SEQ ID NO: 24, which is unprocessed and includes its signal peptide.

SEQ ID NO: 24: Native, or unprocessed, LinD enzyme, including signal peptide, designated LinD-5.

SEQ ID NO: 25: Nucleic acid encoding processed SEQ ID NO: 26 LinD enzyme, no signal peptide.

SEQ ID NO: 26: Processed LinD-5 LinD enzyme, no signal peptide.

Full length SEQ ID NO: 24 polypeptide has 78% sequence identity to full length SEQ ID NO: 2; and the mature, or processed, SEQ ID NO: 26 polypeptide has 82% sequence identity to processed SEQ ID NO: 5.

Full length SEQ ID NO: 24 polypeptide has 78% sequence identity to full length SEQ ID NO: 9; and the mature, or processed, SEQ ID NO: 26 polypeptide has 81% sequence identity to processed SEQ ID NO: 12.

Linalool Dehydratase (LinD) from Metagenomics on Activated Sludge (Camp Pendleton): Designated LinD-6.

SEQ ID NO: 27: Native nucleic acid encoding SEQ ID NO: 28, which is unprocessed and includes its signal peptide.

SEQ ID NO: 28: Native, or unprocessed, LinD enzyme, including signal peptide, designated LinD-6.

SEQ ID NO: 29: Nucleic acid encoding processed SEQ ID NO: 30 LinD enzyme, no signal peptide.

SEQ ID NO: 30: Processed LinD-6 LinD enzyme, no signal peptide.

Full length SEQ ID NO: 28 polypeptide has 78% sequence identity to full length SEQ ID NO: 2; and the mature, or processed, SEQ ID NO: 30 polypeptide has 81% sequence identity to processed SEQ ID NO: 5.

Full length SEQ ID NO: 28 polypeptide has 78% sequence identity to full length SEQ ID NO: 9; and the mature, or processed, SEQ ID NO: 30 polypeptide has 81% sequence identity to processed SEQ ID NO: 12.

Linalool Dehydratase (LinD) from Metagenomics on Activated Sludge (Camp Pendleton); Designated LinD-7.

SEQ ID NO: 31: Native nucleic acid encoding SEQ ID NO: 32, which is unprocessed and includes its signal peptide with no identified signal peptide cleavage site.

SEQ ID NO: 32: Native, or unprocessed, LinD enzyme, including signal peptide with no identified signal peptide cleavage site, designated LinD-7.

SEQ ID NO: 33: LinD enzyme LinD-7 having an A196F modification; designated LinD-7B.

Full length SEQ ID NO: 32 polypeptide has 66% sequence identity to full length SEQ ID NO: 2.

Full length SEQ ID NO: 32 polypeptide has 65% sequence identity to full length SEQ ID NO: 9.

Linalool Dehydratase (LinD) (an Engineered Variant of LinD-2, SEQ ID NO: 9, with 7 Mutations (Amino Acid Changes): G74S, G133Q, R171K, I182K, V196F, D200G, G365S); Designated LinD-2T.

SEQ ID NO: 34: Native nucleic acid encoding SEQ ID NO: 35, which is unprocessed and includes its signal peptide SEQ ID NO: 35: Native, or unprocessed, engineered LinD-2 enzyme, including signal peptide, with 7 mutations G74S, G133Q, R171K, I182K, V196F, D200G, G365S; designated LinD-2T.

Linalool Dehydratase (LinD) from Metagenomics on Activated Sludge (Camp Pendleton); Designated LinD-8.

SEQ ID NO: 36: Native nucleic acid encoding SEQ ID NO: 37, which is unprocessed and includes its signal peptide.

SEQ ID NO: 37: Native, or unprocessed, LinD enzyme, designated LinD-8 including signal peptide.

SEQ ID NO: 38: Nucleic acid encoding processed (mature) SEQ ID NO: 39 LinD enzyme, no signal peptide.

SEQ ID NO: 39: Processed (mature) LinD-8 LinD enzyme, no signal peptide.

Linalool Dehydratase (LinD) from Metagenomics on Activated Sludge (Camp Pendleton): Designated LinD-9.

SEQ ID NO: 40: Native nucleic acid encoding SEQ ID NO: 41, which is unprocessed and includes its signal peptide which has no identified signal peptide cleavage site.

SEQ ID NO: 41: Native, or unprocessed, LinD enzyme, designated LinD-9, including signal peptide which has no identified signal peptide cleavage site.

Linalool Dehydratase (LinD) from Metagenomics on Soil Sample (Cottonwood River); Designated LinD-10.

SEQ ID NO: 42: Native nucleic acid encoding SEQ ID NO: 43, which is unprocessed and includes its signal peptide.

SEQ ID NO: 43: Native, or unprocessed, LinD enzyme, designated LinD-10, including signal peptide.

SEQ ID NO: 44: Nucleic acid encoding processed (mature) SEQ ID NO: 45 LinD enzyme, no signal peptide.

SEQ ID NO: 45: Processed (mature) LinD-10 LinD enzyme, no signal peptide.

Linalool Dehydratase (LinD) from Metagenomics on Soil Sample; Designated LinD-11.

SEQ ID NO: 46: Native nucleic acid encoding SEQ ID NO: 47, which is unprocessed and includes its signal peptide.

SEQ ID NO: 47: Native, or unprocessed, LinD enzyme, designated LinD-11 including signal peptide.

SEQ ID NO: 48: Nucleic acid encoding processed (mature) SEQ ID NO: 49 LinD enzyme, no signal peptide.

SEQ ID NO: 49: Processed (mature) LinD-11 LinD enzyme, no signal peptide.

Linalool Dehydratase (LinD) from Metagenomics on Soil Sample (Cottonwood River); Designated LinD-12.

SEQ ID NO 50: Native nucleic acid encoding SEQ ID NO: 51, which is unprocessed and includes its signal peptide.

SEQ ID NO: 51: Native, or unprocessed, LinD enzyme, designated LinD-12 including signal peptide.

SEQ ID NO: 52: Nucleic acid encoding processed (mature) SEQ ID NO: 53 LinD enzyme, no signal peptide.

SEQ ID NO: 53: Processed (mature) LinD-12 LinD enzyme, no signal peptide.

Linalool Dehydratase (LinD) from Metagenomics on Activated Sludge (Sierra Nev.): Designated LinD-13.

SEQ ID NO: 54: Native nucleic acid encoding SEQ ID NO: 55, which is unprocessed and includes its signal peptide.

SEQ ID NO: 55: Native, or unprocessed, LinD enzyme, designated LinD-13 including signal peptide.

SEQ ID NO: 56: Nucleic acid encoding processed (mature) SEQ ID NO: 57 LinD enzyme, no signal peptide.

SEQ ID NO: 57: Processed (mature) LinD-13 LinD enzyme, no signal peptide.

Linalool Dehydratase (LinD) from Metagenomics on Soil Sample (Cottonwood River): Designated LinD-14.

SEQ ID NO: 58: Native nucleic acid encoding SEQ ID NO: 59, which is unprocessed and includes its signal peptide.

SEQ ID NO: 59: Native, or unprocessed, LinD enzyme, designated LinD-14 including signal peptide.

SEQ ID NO: 60: Nucleic acid encoding processed (mature) SEQ ID NO: 61 LinD enzyme, no signal peptide.

SEQ ID NO: 61: Processed (mature) LinD-14 LinD enzyme, no signal peptide.

Linalool Dehydratase LinD-1 with N-Terminal His-Tag and Linker

SEQ ID NO: 62: Nucleic acid encoding native LinD-1 LinD enzyme with N-terminal His-tag and linker (SEQ ID NO: 63).

SEQ ID NO: 63: Native full length LinD-1 LinD enzyme with N-terminal His-tag and linker.

Exemplary Nucleic Acid and Polypeptide Sequences

```
SEQ ID NO: 1: Native nucleic acid sequence from C. defragrans 65Phen
encoding wild type (WT) linalool dehydratase polypeptide SEQ ID NO: 2
ATGCGGTTCACATTGAAGACGACGGCGATTGTGTCGGCCGCCGCCCTGCTGGCCGGTTTCGGGCCGCCGCCCCGC

GCGGCGGAACTGCCGCCGGGGCGGCTCGCCACCACCGAGGACTATTTCGCGCAGCAGGCGAAGCAGGCCGTCACC

CCCGACGTGATGGCCCAGCTGGCCTACATGAACTACATCGATTTCATCTCGCCCTTCTACAGCCGGGGCTGCTCC

TTCGAGGCCTGGGAGCTCAAGCACACGCCGCAGCGGGTCATCAAGTATTCGATCGCCTTCTATGCGTATGGCCTG

GCCAGCGTGGCGCTCATCGACCCGAAGCTGCGTGCGCTCGCCGGCCATGACCTGGACATCGCGGTCTCCAAGATG

AAGTGCAAGCGGGTCTGGGGCGACTGGGAGGAAGACGGGTTCGGCACCGACCCGATCGAGAAAGAGAACATCATG

TACAAGGGCCACCTGAACCTGATGTACGGCCTCTATCAGCTGGTGACCGGCAGCCGCCGGTACGAAGCCGAGCAT

GCCCACCTCACCCGCATCATCCATGACGAGATCGCGGCCAACCCCTTTGCCGGCATCGTCTGCGAGCCGGACAAT

TATTTTGTCCAGTGCAATTCGGTCGCCTACCTGAGCCTGTGGGTCTATGACCGGCTGCATGGCACCGACTACCGG

GCGGCCACCAGGGCCTGGCTGGATTTCATCCAGAAGGACCTGATCGATCCCGAGCGGGGCGCCTTCTACCTGTCC

TATCACCCCGAGTCCGGCGCGGTGAAGCCGTGGATCTCGGCGTATACGACAGCCTGGACGCTCGCCATGGTGCAC

GGCATGGACCCCGCCTTTTCCGAGCGCTACTACCCCCGGTTCAAGCAGACCTTCGTCGAGGTCTACGACGAGGGC

CGCAAGGCCCGGGTGCGCGAGACGGCCGGCACGGACGACGCGGATGGCGGGGTGGGCCTGGCTTCGGCGTTCACC

CTGCTGCTGGCCCGCGAGATGGGCGACCAGCAGCTCTTCGACCAATTGCTGAATCACCTGGAGCCGCCGGCCAAG

CCGAGCATCGTCTCGGCCTCGCTGCGGTACGAGCATCCCGGCAGCCTGCTGTTCGACGAGCTGCTGTTCCTCGCC

AAGGTGCATGCCGGCTTTGGCGCCCTGCTTCGGATGCCGCCTCCGGCGGCCAAGCTCGCAGGGAAATAA

SEQ ID NO: 2: Native full-length wild type linalool dehydratase polypeptide
from C. defragrans 65Phen; designated LinD-1
MRFTLKTTAIVSAAALLAGFGPPPRAAELPPGRLATTEDYFAQQAKQAVTPDVMAQLAYMNYIDFISPFYSRGCS

FEAWELKHTPQRVIKYSIAFYAYGLASVALIDPKLRALAGHDLDIAVSKMKCKRVWGDWEEDGFGTDPIEKENIM

YKGHLNLMYGLYQLVTGSRRYEAEHAHLTRIIHDEIAANPFAGIVCEPDNYFVQCNSVAYLSLWVYDRLHGTDYR

AATRAWLDFIQKDLIDPERGAFYLSYHPESGAVKPWISAYTTAWTLAMVHGMDPAFSERYYPRFKQTFVEVYDEG

RKARVRETAGTDDADGGVGLASAFTLLLAREMGDQQLFDQLLNHLEPPAKPSIVSASLRYEHPGSLLFDELLFLA

KVHAGFGALLRMPPPAAKLAGK

SEQ ID NO: 3: Codon optimized nucleic acid encoding LinD-1
ATGCGCTTTACGTTGAAAACCACCGCCATCGTGTCCGCTGCGGCGTTGCTGGCAGGTTTCGGTCCGCCACCGCGT

GCGGCAGAATTACCACCTGGCCGCCTGGCAACGACCGAAGATTACTTTGCGCAGCAAGCAAAACAAGCCGTTACC

CCGGACGTCATGGCGCAGCTGGCATATATGAACTATATCGATTTCATTTCTCCGTTCTATAGCCGCGGTTGCTCC

TTTGAGGCGTGGGAACTGAAGCATACTCCGCAGCGTGTGATCAAGTATAGCATTGCGTTCTACGCGTACGGTCTG

GCGAGCGTCGCGCTGATTGACCCGAAGTTGAGAGCCCTGGCAGGCCACGATTTGGACATCGCTGTTTCCAAAATG

AAATGTAAACGCGTTTGGGGCGACTGGGAGGAGGACGGTTTCGGTACCGATCCGATCGAGAAAGAAAACATCATG

TACAAGGGCCACCTGAACCTGATGTATGGTCTGTACCAACTGGTCACCGGCTCTCGTCGCTATGAAGCCGAGCAC

GCGCATCTTACCCGCATCATTCATGATGAAATTGCGGCGAACCCGTTCGCGGGTATCGTGTGTGAGCCGGACAAT
```

-continued

TACTTTGTTCAGTGCAATAGCGTTGCCTACCTGAGCCTGTGGGTCTATGACCGTCTGCACGGCACGGACTATCGT

GCGGCGACGCGTGCTTGGCTGGACTTCATTCAGAAAGATTTGATTGATCCGGAGCGTGGCGCCTTTTACCTGAGC

TACCATCCGGAGAGCGGTGCAGTGAAGCCGTGGATCAGCGCTTACACCACCGCTTGGACTCTGGCCATGGTTCAC

GGTATGGACCCGGCGTTTAGCGAGCGTTACTACCCGCGCTTCAAGCAAACGTTTGTCGAGGTGTACGACGAGGGT

CGTAAGGCACGTGTGCGTGAAACCGCGGGTACCGACGACGCGGATGGTGGCGTGGGTCTGGCAAGCGCCTTCACG

CTGCTGCTGGCACGCGAGATGGGTGATCAGCAATTGTTCGATCAGCTGTTGAATCATCTCGAACCGCCAGCGAAG

CCGTCGATTGTGAGCGCCTCCCTGCGTTATGAACACCCGGGTAGCCTGCTGTTTGATGAACTGCTGTTTCTGGCG

AAAGTACACGCGGGCTTCGGCGCACTGCTGCGTATGCCGCCTCCGGCAGCTAAACTGGCGGGTAAATAA

SEQ ID NO: 4: Native nucleic acid encoding processed (mature) form of LinD-1
GCGGAACTGCCGCCGGGGCGGCTCGCCACCACCGAGGACTATTTCGCGCAGCAGGCGAAGCAGGCCGTCACCCCC

GACGTGATGGCCCAGCTGGCCTACATGAACTACATCGATTTCATCTCGCCCTTCTACAGCCGGGGCTGCTCCTTC

GAGGCCTGGGAGCTCAAGCACACGCCGCAGCGGGTCATCAAGTATTCGATCGCCTTCTATGCGTATGGCCTGGCC

AGCGTGGCGCTCATCGACCCGAAGCTGCGTGCGCTCGCCGGCCATGACCTGGACATCGCGGTCTCCAAGATGAAG

TGCAAGCGGGTCTGGGGCGACTGGGAGGAAGACGGGTTCGGCACCGACCCGATCGAGAAGAGAACATCATGTAC

AAGGGCCACCTGAACCTGATGTACGGCCTCTATCAGCTGGTGACCGGCAGCCGCCGGTACGAAGCCGAGCATGCC

CACCTCACCCGCATCATCCATGACGAGATCGCGGCCAACCCCTTTGCCGGCATCGTCTGCGAGCCGGACAATTAT

TTTGTCCAGTGCAATTCGGTCGCCTACCTGAGCCTGTGGGTCTATGACCGGCTGCATGGCACCGACTACCGGGCG

GCCACCAGGGCCTGGCTGGATTTCATCCAGAAGGACCTGATCGATCCCGAGCGGGGCGCCTTCTACCTGTCCTAT

CACCCCGAGTCCGGCGCGGTGAAGCCGTGGATCTCGGCGTATACGACAGCCTGGACGCTCGCCATGGTGCACGGC

ATGGACCCCGCCTTTTCCGAGCGCTACTACCCCCGGTTCAAGCAGACCTTCGTCGAGGTCTACGACGAGGGCCGC

AAGGCCCGGGTGCGCGAGACGGCCGGCACGGACGACGCGGATGGCGGGGTGGGCCTGGCTTCGGCGTTCACCCTG

CTGCTGGCCCGCGAGATGGGCGACCAGCAGCTCTTCGACCAATTGCTGAATCACCTGGAGCCGCCGGCCAAGCCG

AGCATCGTCTCGGCCTCGCTGCGGTACGAGCATCCCGGCAGCCTGCTGTTCGACGAGCTGCTGTTCCTCGCCAAG

GTGCATGCCGGCTTTGGCGCCCTGCTTCGGATGCCGCCTCCGGCGGCCAAGCTCGCAGGGAAATAA

SEQ ID NO: 5: Mature (processed) form of LinD-1, wild type linalool
dehydratase from C. defragrans 65Phen polypeptide
AELPPGRLATTEDYFAQQAKQAVTPDVMAQLAYMNYIDFISPFYSRGCSFEAWELKHTPQRVIKYSIAFYAYGLA

SVALIDPKLRALAGHDLDIAVSKMKCKRVWGDWEEDGFGTDPIEKENIMYKGHLNLMYGLYQLVTGSRRYEAEHA

HLTRIIHDEIAANPFAGIVCEPDNYFVQCNSVAYLSLWVYDRLHGTDYRAATRAWLDFIQKDLIDPERGAFYLSY

HPESGAVKPWISAYTTAWTLAMVHGMDPAFSERYYPRFKQTFVEVYDEGRKARVRETAGTDDADGGVGLASAFTL

LLAREMGDQQLFDQLLNHLEPPAKPSIVSASLRYEHPGSLLFDELLFLAKVHAGFGALLRMPPPAAKLAGK

SEQ ID NO: 6: Nucleic acid encoding SEQ ID NO: 7; differs from SEQ ID NO: 3
by having 12 codon substitutions
ATGCGCTTTACGTTGAAAACCACCGCCATCGTGTCCGCTGCGGCGTTGCTGATTGGTCTGGGTCCGCCACCGCGT

GCGGCAGAACTGCCTCCTGGTCGTCTGGCAACCACCGAAGATTATTTTGCACAGCAGGCAAAACAGGCAGTTACA

CCGGATGTTATGGCACAGCTGGCATATATGAACTATATCGATTTTATCAGCCCGTTTTTTAGCCGCAGCTGTAGC

TTTGAAGCATGGGAACTGAAACATACACCGCAGCGTGTTATCAAATATAGCATTGCCTTTTATGCATATGGTCTG

GCAAGCGTTGCACTGATTGATCCGAAACTGCGTGCACTGGCAGGTCATGATCTGGATATTGCAGTTAGCAAAATG

AAATGCAAACGCGTGTGGATGGATTGGGAAGAAGATGGTTTTGGCACCGATCCGATTGAAAAAGAAACATCATG

TATAAAGGCCATCTGAACCTGATGTATGGTCTGTATCAGCTGGTTACCGGTAGCCGTAAATATGAAGCAGAACAT

GCACATCTGACCCGTCTGATTCATGATGAAATTGCAGCAAATCCGTTTGCCGGTATTTTTTGTGAACCGAACAAC

TATTTTGTGCAGTGTAATAGCGTTGCATATCTGAGCCTGTGGGTTTATGATCGTCTGCATGGTACAGATTATCGT

GCAGCAACCCGTGCATGGCTGGATTTTATTCAGAAAGATCTGATCGATCCGGAACGTGGTGCATTTTATCTGAGC

TATCATCCGGAAAGCGGTGCAGTTAAACCGTGGATTAGCGCATATACCACCGCATGGACCCTGGCAATGGTTCAT

GGTATGGATCCGGCATTTAGCGAACGTTATTATCCGCGTTTTAAACAGACCTTCGTGGAAGTTTATGATGAAGGT

CGTAAAGCACGTGTTCGTGAAACCGCAGGCACCGATGATGCAGATGGTGGTGTTGGTCTGGCCAGTGCAAGCACC

CTGCTGCTGGCACGTGAAATGGGTGATCAGCAGCTGTTTGATCAACTGCTGAATCATCTGGAACCGCCTGCAAAA

CCGAGCATTGTGAGCGCAAGCCTGCGTTATGAACATCCGAGCAGCCTGTTTTTTGATGAGCTGCTGTTTCTGGCA

AAAGTTCATGCAGGTTTTGGTGCACTGCTGCGTATGCCTCCGCCAGCAGCCAAACTGGCAGGCAAATAA

SEQ ID NO: 7: Full-length polypeptide variant of LinD-1, designated LinD-1N, having 12 substitutions: A18I, F20L, Y70F, G73S, G132M, R170K, I181L, V195F, D199N, F324S, G364S, L367F)
MRFTLKTTAIVSAAALLIGLGPPPRAAELPPGRLATTEDYFAQQAKQAVTPDVMAQLAYMNYIDFISPFFSRSCS

FEAWELKHTPQRVIKYSIAFYAYGLASVALIDPKLRALAGHDLDIAVSKMKCKRVWMDWEEDGFGTDPIEKENIM

YKGHLNLMYGLYQLVTGSRKYEAEHAHLTRLIHDEIAANPFAGIFCEPNNYFVQCNSVAYLSLWVYDRLHGTDYR

AATRAWLDFIQKDLIDPERGAFYLSYHPESGAVKPWISAYTTAWTLAMVHGMDPAFSERYYPRFKQTFVEVYDEG

RKARVRETAGTDDADGGVGLASASTLLLAREMGDQQLFDQLLNHLEPPAKPSIVSASLRYEHPSSLFFDELLFLA

KVHAGFGALLRMPPPAAKLAGK

SEQ ID NO: 8: Native nucleic acid encoding novel SEQ ID NO: 9 Linalool dehydratase (LinD) from Castellaniella defragrans 62Car
ATGCGATTCACATTGAAGACGCCGGCGATCGCGTCGGCCGTCGCTGCCCTGCTGGTCGGTCTTGGACAGCCGGCG

CATGCGGCGCCGCTGCCGCTGGGGCGCCTTGCCCCGACCGAGGACTACTTCGCCCAGCAGGCGAAGCAGGCCGTC

ACCCCCGACGTGATGGCCCAGCTGGCCTACATGAACTATATCGATTTCATCTCGCCTTTCTACAGCCGGGGGTGT

TCCTTCGAGGCCTGGGAACTCAAGCACACACCGCAGCGGGTCATCAAGTATTCGATCGCTTTCTATGCGTATGGC

CTGGCCAGCGTGGCGCTCATCGATCCGAATCTGCGCGCGCTCGCCGGCCATGACCTGGACATCGCGGTCTCCAAG

ATGAAATGCAAGCGGGTCTGGGGCGACTGGGAGGAAGACGGGTTCGGCGACGATCCGATCGAGAAAGAGAACATC

ATGTACAAGGGCCACCTGAACCTGATGTACGGCCTCTATCAGCTGGTGACCGGCAGCCGCCGGTACGAAGCCGAG

CATGCGCACCTCACCCGCATCATCCACGACGAGATCGGCGCCAACCCCTTTGCCGGCATCGTCTGTGAGCCGGAT

AATTATTTCGTCCAATGCAACTCGGTCGCCTACCTGAGCCTGTGGGTCTATGACCGCCTGCATGGCACCGATTAT

CGGGCGGCGACCCGGGCCTGGCTGGACTTCATCCAGAAAGACCTGATCGACCCCGAGCGGGGCGCCTTCTACCTG

TCCTATCATCCGGAGTCCGGCGCGGTGAAGCCGTGGATCTCGGCGTATACGACCGCCTGGACGCTCGCCATGGTG

CATGGCATGGATCCCGCCTTTTCCGAGCGCTACTACCCCGCGTTCAAGAAAACCTTCGTCGAGGTCTACGACGGG

GGCCGCAAGGCCCGGGTGCGAGAGACGGCCGGCACGGCCGACGCGGATGGCGGGGTGGGCCTGGCGTCGGCATTT

ACCCTGCTGCTGGCCCGCGAGATGGGCGACCAGACGCTCTTCGACCAGCTGCTGAATCACCTGGAACCGCCGGCC

CAGCCCAGCATCGTCTCGGCCTCATTGCGTTACGAGCATCCCGGCAGCCTGTTGTTCGACGAACTGCTGTTCCTG

GCCAAGGTGCATGCCGGCTTTGGCGCCCTGCTCCAGATGCCGCCTCCGGCGGCGAAATCCGGGGGGAAATGA

SEQ ID NO: 9: Novel full-length wild type LinD, linalool dehydratase-isomerase, from Castellaniella defragrans 62Car, designated LinD-2
MRFTLKTPAIASAVAALLVGLGQPAHAAPLPLGRLAPTEDYFAQQAKQAVTPDVMAQLAYMNYIDFISPFYSRGC

SFEAWELKHTPQRVIKYSIAFYAYGLASVALIDPNLRALAGHDLDIAVSKMKCKRVWGDWEEDGFGDDPIEKENI

MYKGHLNLMYGLYQLVTGSRRYEAEHAHLTRIIHDEIGANPFAGIVCEPDNYFVQCNSVAYLSLWVYDRLHGTDY

RAATRAWLDFIQKDLIDPERGAFYLSYHPESGAVKPWISAYTTAWTLAMVHGMDPAFSERYYPAFKKTFVEVYDG

GRKARVRETAGTADADGGVGLASAFTLLLAREMGDQTLFDQLLNHLEPPAQPSIVSASLRYEHPGSLLFDELLFL

AKVHAGFGALLQMPPPAAKSGGK

SEQ ID NO: 10: codon optimized nucleic acid encoding novel full length LinD-2, designated LinD-2A
ATGCGCTTTACCCTGAAAACACCGGCAATTGCAAGCGCAGTTGCAGCACTGCTGGTTGGTCTGGGTCAGCCTGCA

CATGCAGCACCGCTGCCGCTGGGTCGTCTGGCACCGACCGAAGATTATTTTGCACAGCAGGCAAAACAGGCAGTT

```
ACACCGGATGTTATGGCACAGCTGGCATATATGAACTATATCGATTTTATCAGCCCGTTCTATAGCCGTGGTTGT

AGCTTTGAAGCATGGGAACTGAAACATACACCGCAGCGTGTTATCAAATATAGCATTGCCTTTTATGCATATGGT

CTGGCAAGCGTTGCACTGATTGATCCGAATCTGCGTGCACTGGCAGGTCATGATCTGGATATTGCAGTTAGCAAA

ATGAAATGCAAACGTGTTTGGGGTGATTGGGAAGAGGATGGTTTTGGTGATGATCCGATTGAGAAAGAAAACATC

ATGTATAAAGGCCATCTGAACCTGATGTATGGTCTGTATCAGCTGGTTACCGGTAGCCGTCGTTATGAAGCAGAA

CATGCACATCTGACCCGTATTATTCATGATGAAATTGGTGCAAATCCGTTTGCCGGTATTGTTTGTGAACCGGAT

AACTATTTTGTGCAGTGTAATAGCGTTGCATATCTGAGCCTGTGGGTTTATGATCGTCTGCATGGCACCGATTAT

CGTGCAGCAACCCGTGCATGGCTGGATTTTATTCAGAAAGATCTGATCGATCCGGAACGTGGTGCATTTTATCTG

AGCTATCATCCGGAAAGCGGTGCAGTTAAACCGTGGATTAGCGCATATACCACCGCATGGACCCTGGCAATGGTT

CATGGTATGGATCCGGCATTTAGCGAACGTTATTATCCTGCATTCAAAAAAACCTTTGTCGAGGTGTATGATGGT

GGTCGTAAAGCACGTGTTCGTGAAACCGCAGGCACCGCAGATGCAGATGGTGGTGTGGGTCTGGCCAGTGCATTT

ACCCTGCTGCTGGCACGTGAAATGGGTGATCAGACCCTGTTTGATCAGCTGCTGAATCATCTGGAACCGCCTGCA

CAGCCGAGCATTGTTAGCGCAAGCCTGCGTTATGAACATCCGGGTAGCCTGCTGTTCGATGAACTGCTGTTTCTG

GCAAAAGTTCATGCAGGTTTTGGCGCACTGCTGCAGATGCCTCCGCCTGCAGCAAAAAGCGGTGGTAAATAA

SEQ ID NO: 11: Native nucleic acid encoding processed (mature) form of
LinD-2
GCGCCGCTGCCGCTGGGGCGCCTTGCCCCGACCGAGGACTACTTCGCCCAGCAGGCGAAGCAGGCCGTCACCCCC

GACGTGATGGCCCAGCTGGCCTACATGAACTATATCGATTTCATCTCGCCTTTCTACAGCCGGGGGTGTTCCTTC

GAGGCCTGGGAACTCAAGCACACACCGCAGCGGGTCATCAAGTATTCGATCGCTTTCTATGCGTATGGCCTGGCC

AGCGTGGCGCTCATCGATCCGAATCTGCGCGCGCTCGCCGGCCATGACCTGGACATCGCGGTCTCCAAGATGAAA

TGCAAGCGGGTCTGGGGCGACTGGGAGGAAGACGGGTTCGGCGACGATCCGATCGAGAAAGAGAACATCATGTAC

AAGGGCCACCTGAACCTGATGTACGGCCTCTATCAGCTGGTGACCGGCAGCCGCCGGTACGAAGCCGAGCATGCG

CACCTCACCCGCATCATCCACGACGAGATCGGCGCCAACCCCTTTGCCGGCATCGTCTGTGAGCCGGATAATTAT

TTCGTCCAATGCAACTCGGTCGCCTACCTGAGCCTGTGGGTCTATGACCGCCTGCATGGCACCGATTATCGGGCG

GCGACCCGGGCCTGGCTGGACTTCATCCAGAAAGACCTGATCGACCCCGAGCGGGGCGCCTTCTACCTGTCCTAT

CATCCGGAGTCCGGCGCGGTGAAGCCGTGGATCTCGGCGTATACGACCGCCTGGACGCTCGCCATGGTGCATGGC

ATGGATCCCGCCTTTTCCGAGCGCTACTACCCCGCGTTCAAGAAAACCTTCGTCGAGGTCTACGACGGGGCCGC

AAGGCCCGGGTGCGAGAGACGGCCGGCACGGCCGACGCGGATGGCGGGGTGGGCCTGGCGTCGGCATTTACCCTG

CTGCTGGCCCGCGAGATGGGCGACCAGACGCTCTTCGACCAGCTGCTGAATCACCTGGAACCGCCGGCCCAGCCC

AGCATCGTCTCGGCCTCATTGCGTTACGAGCATCCCGGCAGCCTGTTGTTCGACGAACTGCTGTTCCTGGCCAAG

GTGCATGCCGGCTTTGGCGCCCTGCTCCAGATGCCGCCTCCGGCGGCGAAATCCGGGGGGAAATGA

SEQ ID NO: 12: Mature form of LinD-2
APLPLGRLAPTEDYFAQQAKQAVTPDVMAQLAYMNYIDFISPFYSRGCSFEAWELKHTPQRVIKYSIAFYAYGLA

SVALIDPNLRALAGHDLDIAVSKMKCKRVWGDWEEDGFGDDPIEKENIMYKGHLNLMYGLYQLVTGSRRYEAEHA

HLTRIIHDEIGANPFAGIVCEPDNYFVQCNSVAYLSLWVYDRLHGTDYRAATRAWLDFIQKDLIDPERGAFYLSY

HPESGAVKPWISAYTTAWTLAMVHGMDPAFSERYYPAFKKTFVEVYDGGRKARVRETAGTADADGGVGLASAFTL

LLAREMGDQTLFDQLLNHLEPPAQPSIVSASLRYEHPGSLLFDELLFLAKVHAGFGALLQMPPPAAKSGGK

SEQ ID NO: 13: Nucleic acid encoding full-length engineered variant SEQ ID
NO: 14, differs from wild type SEQ ID NO: 10 by having 11 codon substitutions
ATGCGTTTTACCCTGAAAACACCGGCAATTGCAAGCGCAGTTGCAGCACTGCTGATTGGTCTGGGTCAGCCTGCA

CATGCAGCACCGCTGCCGCTGGGTCGTCTGGCACCGACCGAAGATTATTTTGCACAGCAGGCAAAACAGGCAGTT

ACACCGGATGTTATGGCACAGCTGGCATATATGAACTATATCGATTTTATCAGCCCGTTTTTTAGCCGCAGCTGT

AGCTTTGAAGCATGGGAACTGAAACATACACCGCAGCGTGTTATCAAATATAGCATTGCCTTTTATGCATATGGT
```

```
CTGGCAAGCGTTGCACTGATTGATCCGAATCTGCGTGCACTGGCAGGTCATGATCTGGATATTGCAGTTAGCAAA

ATGAAATGCAAACGCGTGTGGATGGATTGGGAAGAGGATGGTTTTGGTGATGATCCGATTGAGAAAGAAAACATC

ATGTATAAAGGCCATCTGAACCTGATGTATGGTCTGTATCAGCTGGTTACCGGTAGCCGTAAATATGAAGCAGAA

CATGCACATCTGACCCGTCTGATTCATGATGAAATTGGTGCAAATCCGTTTGCCGGTATTTTTTGTGAACCGAAC

AACTATTTTGTGCAGTGTAATAGCGTTGCATATCTGAGCCTGTGGGTTTATGATCGTCTGCATGGCACCGATTAT

CGTGCAGCAACCCGTGCATGGCTGGATTTTATTCAGAAAGATCTGATCGATCCGGAACGTGGTGCATTTTATCTG

AGCTATCATCCGGAAAGCGGTGCAGTTAAACCGTGGATTAGCGCATATACCACCGCATGGACCCTGGCAATGGTT

CATGGTATGGATCCGGCATTTAGCGAACGTTATTATCCTGCATTCAAAAAAACCTTTGTCGAGGTGTATGATGGT

GGTCGTAAAGCACGTGTTCGTGAAACCGCAGGCACCGCAGATGCAGATGGTGGTGTTGGTCTGGCCAGTGCAAGC

ACCCTGCTGCTGGCACGTGAAATGGGTGATCAGACCCTGTTTGATCAGCTGCTGAATCATCTGGAACCGCCTGCA

CAGCCGAGCATTGTTAGCGCAAGCCTGCGTTATGAACATCCGAGCAGCCTGTTTTTTGATGAACTGCTGTTTCTG

GCAAAAGTGCATGCAGGTTTTGGCGCACTGCTGCAGATGCCTCCGCCTGCAGCAAAAAGCGGTGGTAAATAA
```

SEQ ID NO: 14: Full-length engineered variant of novel SEQ ID NO: 9 (LinD-2) with 11 amino acid substitutions V19I, Y71F, G74S, G133M, R171K, I182L, V196F, D200N, F325S, G365S, L368F; designated LinD-2C

MRFTLKTPAIASAVAALLIGLGQPAHAAPLPLGRLAPTEDYFAQQAKQAVTPDVMAQLAYMNYIDFISPFFSRSC

SFEAWELKHTPQRVIKYSIAFYAYGLASVALIDPNLRALAGHDLDIAVSKMKCKRVWMDWEEDGFGDDPIEKENI

MYKGHLNLMYGLYQLVTGSRKYEAEHAHLTRLIHDEIGANPFAGIFCEPNNYFVQCNSVAYLSLWVYDRLHGTDY

RAATRAWLDFIQKDLIDPERGAFYLSYHPESGAVKPWISAYTTAWTLAMVHGMDPAFSERYYPAFKKTFVEVYDG

GRKARVRETAGTADADGGVGLASASTLLLAREMGDQTLFDQLLNHLEPPAQPSIVSASLRYEHPSSLFFDELLFL

AKVHAGFGALLQMPPPAAKSGGK

Linalool Dehydrate (LinD) from Metagenomics on Activated Sludge from Padre Dam Enriched on Myrcene; Designated LinD-3

SEQ ID NO: 15: Native nucleic acid encoding SEQ ID NO: 16; which is unprocessed and includes its signal peptide

ATGCGGTTCACATTGAAGACGACGGCGATCGTGTCGGCCGCCGCCCTGCTGGCCGGTTTCGGGCCGCCGCCCCGC

GCGGCGGAACTGCCGCCGGGGCGGCTCGCCACCACCGAGGACTATTTCGCGCAGCAGGCGAAGCAGGCCGTCACC

CCCGACGTGATGGCCCAGCTGGCCTACATGAACTACATCGATTTCATCTCGCCCTTCTACAGCCGGGGCTGCTCC

TTCGAGGCCTGGGAGCTCAAGCACACGCCGCAGCGGGTCATCAAGTATTCGATCGCCTTCTATGCGTATGGCCTG

GCCAGCGTGGCGCTCATCGACCCGAAGCTGCGTGCGCTCGCCGGCCATGACCTGGACATCGCGGTCTCCAAGATG

AAGTGCAAGCGGGTCTGGGGCGACTGGGAGGAAGACGGGTTCGGCACCGACCCGATCGAGAAAGAGAACATCATG

TACAAGGGCCACCTGAACCTGATGTACGGCCTCTATCAGCTGGTGACCGGCAGCCGCCGGTACGAAGCCGAGCAT

GCCCACCTCACCCGCATCATCCATGACGAGATCGCGGCCAACCCCTTTGCCGGCATCGTCTGCGAGCCGGACAAT

TATTTTGTCCAGTGCAATTCGGTCGCCTACCTGAGCCTGTGGGTCTATGACCGGCTGCATGGCACCGACTACCGG

GCGGCCACCAGGGCCTGGCTGGATTTCATCCAGAAGGACCTGATCGATCCCGAGCGGGGCGCCTTCTACCTGTCC

TATCACCCCGAGTCCGGCGCGGTGAAGCCGTGGATCTCGGCGTATACGACAGCCTGGACGCTCGCCATGGTGCAC

GGCATGGACCCCGCCTTTTCCGAGCGCTACTACCCCCGGTTCAAGCAGACCTTCGTCGAGCTCTACGACGAGGGC

CGCAAGGCCCGGGTGCGCGAGACGGCCGGCACGGACGACGCGGATGGCGGGGTGGGCCTGGCTTCGGCGTTCACC

CTGCTGCTGGCCCGCGAGATGGGCGACCAGCAGCTCTTCGACCAGTTGCTGAATCACCTGGAGCCGCCGGCCAAG

CCCAGCATCGTTTCGGCCTCGCTGCGGTACGAGCATCCCGGCAGCCTGCTGTTCGACGAGCTGCTGTTCCTCGCC

AAGGTGCATGCCGGTTTTGGCGCCCTGCTTCAGATGCCGCCTCCGGCGGCCAAGCTCGCGGGGAAATAA

SEQ ID NO: 16: Native, or unprocessed, LinD enzyme, including signal peptide;
designated LinD-3
MRFTLKTTAIVSAAALLAGFGPPPRAAELPPGRLATTEDYFAQQAKQAVTPDVMAQLAYMNYIDFISPFYSRGCS

FEAWELKHTPQRVIKYSIAFYAYGLASVALIDPKLRALAGHDLDIAVSKMKCKRVWGDWEEDGFGTDPIEKENIM

YKGHLNLMYGLYQLVTGSRRYEAEHAHLTRIIHDEIAANPFAGIVCEPDNYFVQCNSVAYLSLWVYDRLHGTDYR

AATRAWLDFIQKDLIDPERGAFYLSYHPESGAVKPWISAYTTAWTLAMVHGMDPAFSERYYPRFKQTFVELYDEG

RKARVRETAGTDDADGGVGLASAFTLLLAREMGDQQLFDQLLNHLEPPAKPSIVSASLRYEHPGSLLFDELLFLA

KVHAGFGALLQMPPPAAKLAGK

SEQ ID NO: 17: Nucleic acid encoding processed LinD-3 LinD enzyme, no signal
peptide
GCGGAACTGCCGCCGGGGCGGCTCGCCACCACCGAGGACTATTTCGCGCAGCAGGCGAAGCAGGCCGTCACCCCC

GACGTGATGGCCCAGCTGGCCTACATGAACTACATCGATTTCATCTCGCCCTTCTACAGCCGGGGCTGCTCCTTC

GAGGCCTGGGAGCTCAAGCACACGCCGCAGCGGGTCATCAAGTATTCGATCGCCTTCTATGCGTATGGCCTGGCC

AGCGTGGCGCTCATCGACCCGAAGCTGCGTGCGCTCGCCGGCCATGACCTGGACATCGCGGTCTCCAAGATGAAG

TGCAAGCGGGTCTGGGGCGACTGGGAGGAAGACGGGTTCGGCACCGACCCGATCGAGAAGAGAACATCATGTAC

AAGGGCCACCTGAACCTGATGTACGGCCTCTATCAGCTGGTGACCGGCAGCCGCCGGTACGAAGCCGAGCATGCC

CACCTCACCCGCATCATCCATGACGAGATCGCGGCCAACCCCTTTGCCGGCATCGTCTGCGAGCCGGACAATTAT

TTTGTCCAGTGCAATTCGGTCGCCTACCTGAGCCTGTGGGTCTATGACCGGCTGCATGGCACCGACTACCGGGCG

GCCACCAGGGCCTGGCTGGATTTCATCCAGAAGGACCTGATCGATCCCGAGCGGGGCGCCTTCTACCTGTCCTAT

CACCCCGAGTCCGGCGCGGTGAAGCCGTGGATCTCGGCGTATACGACAGCCTGGACGCTCGCCATGGTGCACGGC

ATGGACCCCGCCTTTTCCGAGCGCTACTACCCCCGGTTCAAGCAGACCTTCGTCGAGCTCTACGACGAGGGCCGC

AAGGCCCGGGTGCGCGAGACGGCCGGCACGGACGACGCGGATGGCGGGGTGGGCCTGGCTTCGGCGTTCACCCTG

CTGCTGGCCCGCGAGATGGGCGACCAGCAGCTCTTCGACCAGTTGCTGAATCACCTGGAGCCGCCGGCCAAGCCC

AGCATCGTTTCGGCCTCGCTGCGGTACGAGCATCCCGGCAGCCTGCTGTTCGACGAGCTGCTGTTCCTCGCCAAG

GTGCATGCCGGTTTTGGCGCCCTGCTTCAGATGCCGCCTCCGGCGGCCAAGCTCGCGGGGAAATAA

SEQ ID NO: 18: Processed LinD-3 LinD enzyme, no signal peptide
AELPPGRLATTEDYFAQQAKQAVTPDVMAQLAYMNYIDFISPFYSRGCSFEAWELKHTPQRVIKYSIAFYAYGLA

SVALIDPKLRALAGHDLDIAVSKMKCKRVWGDWEEDGFGTDPIEKENIMYKGHLNLMYGLYQLVTGSRRYEAEHA

HLTRIIHDEIAANPFAGIVCEPDNYFVQCNSVAYLSLWVYDRLHGTDYRAATRAWLDFIQKDLIDPERGAFYLSY

HPESGAVKPWISAYTTAWTLAMVHGMDPAFSERYYPRFKQTFVELYDEGRKARVRETAGTDDADGGVGLASAFTL

LLAREMGDQQLFDQLLNHLEPPAKPSIVSASLRYEHPGSLLFDELLFLAKVHAGFGALLQMPPPAAKLAGK

Linalool Dehydratase (LinD) from Metagenomics on Activated Sludge from Camp Pendleton Enriched on Myrcene (Secondary Enrichment); Designated LinD-4

SEQ ID NO: 19: Native nucleic acid encoding SEQ ID NO: 20, which is unprocessed
and includes its signal peptide
ATGATAAAGCCCCACAGACGATCCGCCGCACGACTTTCCCTAATCATCGCAGCAACCCTCGGTTTCGGCAGTTCC

GCCAGTGCCGAAGACCTGTTCCCCGGCCGCCTCGCCACCACCGCGGACTACTTCGCCCAACGCGAAAAGCACACC

GTGACTCCCGATGTCATGGCGCACCTGGCCTTCATGAACTACACGGATTTCATTTCCCCCTTCTACAGCCGGGGT

TGTGCCTTCGACGCGTGGGACATCAAGAAGACACCGCAACGGATCATCAAGTATTCGCTGGCGTTCTATTCCTAC

GGCCTCGCTAGCGTTGCGCTCACCGATCCCAAACTGCGACCACTTGCCGCGCATGCGATCGATGTCGCCACGTCA

AAGATGAAATGCAAGCGCGTCTGGGAAGACTGGGAAGAAGATGGCTTCGGTAGCGACCCGATCGAGAAGCAAAAC

ATCATGTACAAGGGTCACCTGAACCTGATGTATGGCCTCTACCAGCTGGTCAGCGGAAACCGGCAGTACGAGGCC

```
GAACACAAACATCTGACCAAGATCATCCACGACGAGATCAAGGCCAACCCTTTCGCTGGCGCGCTCTGCGAGCCG

GACAACTATTTTGTCCAATGCAACTCGGTCGCCTATCTGAGCCTGTGGGTGTATGACCGACTCCATGGCACAAGC

TACAAGGCAGCCACCGAACCCTGGCTGAAATTCCTGAAAAAGGATCTGATCGATCCGAAAACGGGCGCCTTCTAT

CTATCCTTTCACCCCGAATCCGGCACAGTGAAACCCTGGCTCTCGGCGTATACCACGGCGTGGACGCTGGCCATG

GTGCACGGCATGGACCCGGCCTTTTCCGAACGCTACTACCCGGCGTTCAAGAAGACCTTTGTCGAAGTCTATGAC

GGCGGCCGAAAGGCACGGGTTCGCGAGACGACCAATACGCCAGACGCCGACGGCGGGGTTGGCGCGGCCTCTGCG

TTCACGTTGCTGCTTGCCCGTGAGATGGGCGACCAGACACTCTTCGACCAGTTGCTCAACCACCTTGAGCCCCCG

GCGAAACCCAAAATCACCTCAGCCATCTTGAACTACGAGGCGCCCAGCAACCTGCTCTTTGATGAGTTGCTGTTC

CTCTCGAAAGTCCATGTCGGCTTTGGTGAACTGCTAAAAGCTACGCCCCGCCGGCGCGCGCAGACAGTCAGAAA

TAA
```

SEQ ID NO: 20: Native, or unprocessed, LinD enzyme, designated LinD-4, including signal peptide
```
MIKPHRRSAARLSLIIAATLGFGSSASAEDLFPGRLATTADYFAQREKHTVTPDVMAHLAFMNYTDFISPFYSRG

CAFDAWDIKKTPQRIIKYSLAFYSYGLASVALTDPKLRPLAAHAIDVATSKMKCKRVWEDWEEDGFGSDPIEKQN

IMYKGHLNLMYGLYQLVSGNRQYEAEHKHLTKIIHDEIKANPFAGALCEPDNYFVQCNSVAYLSLWVYDRLHGTS

YKAATEPWLKFLKKDLIDPKTGAFYLSFHPESGTVKPWLSAYTTAWTLAMVHGMDPAFSERYYPAFKKTFVEVYD

GGRKARVRETTNTPDADGGVGAASAFTLLLAREMGDQTLFDQLLNHLEPPAKPKITSAILNYEAPSNLLFDELLF

LSKVHVGFGELLKATPPPARADSQK
```

SEQ ID NO: 21: Nucleic acid encoding processed LinD-4 LinD enzyme, no signal peptide
```
GAAGACCTGTTCCCCGGCCGCCTCGCCACCACCGCGGACTACTTCGCCCAACGCGAAAAGCACACCGTGACTCCC

GATGTCATGGCGCACCTGGCCTTCATGAACTACACGGATTTCATTTCCCCCTTCTACAGCCGGGGTTGTGCCTTC

GACGCGTGGGACATCAAGAAGACACCGCAACGGATCATCAAGTATTCGCTGGCGTTCTATTCCTACGGCCTCGCT

AGCGTTGCGCTCACCGATCCCAAACTGCGACCACTTGCCGCGCATGCGATCGATGTCGCCACGTCAAAGATGAAA

TGCAAGCGCGTCTGGGAAGACTGGGAAGAAGATGGCTTCGGTAGCGACCCGATCGAGAAGCAAAACATCATGTAC

AAGGGTCACCTGAACCTGATGTATGGCCTCTACCAGCTGGTCAGCGGAAACCGGCAGTACGAGGCCGAACACAAA

CATCTGACCAAGATCATCCACGACGAGATCAAGGCCAACCCTTTCGCTGGCGCGCTCTGCGAGCCGGACAACTAT

TTTGTCCAATGCAACTCGGTCGCCTATCTGAGCCTGTGGGTGTATGACCGACTCCATGGCACAAGCTACAAGGCA

GCCACCGAACCCTGGCTGAAATTCCTGAAAAAGGATCTGATCGATCCGAAAACGGGCGCCTTCTATCTATCCTTT

CACCCCGAATCCGGCACAGTGAAACCCTGGCTCTCGGCGTATACCACGGCGTGGACGCTGGCCATGGTGCACGGC

ATGGACCCGGCCTTTTCCGAACGCTACTACCCGGCGTTCAAGAAGACCTTTGTCGAAGTCTATGACGGCGGCCGA

AAGGCACGGGTTCGCGAGACGACCAATACGCCAGACGCCGACGGCGGGGTTGGCGCGGCCTCTGCGTTCACGTTG

CTGCTTGCCCGTGAGATGGGCGACCAGACACTCTTCGACCAGTTGCTCAACCACCTTGAGCCCCCGGCGAAACCC

AAAATCACCTCAGCCATCTTGAACTACGAGGCGCCCAGCAACCTGCTCTTTGATGAGTTGCTGTTCCTCTCGAAA

GTCCATGTCGGCTTTGGTGAACTGCTAAAAGCTACGCCCCGCCGGCGCGCGCAGACAGTCAGAAATAA
```

SEQ ID NO: 22: Processed LinD-4 LinD enzyme, no signal peptide
```
EDLFPGRLATTADYFAQREKHTVTPDVMAHLAFMNYTDFISPFYSRGCAFDAWDIKKTPQRIIKYSLAFYSYGLA

SVALTDPKLRPLAAHAIDVATSKMKCKRVWEDWEEDGFGSDPIEKQNIMYKGHLNLMYGLYQLVSGNRQYEAEHK

HLTKIIHDEIKANPFAGALCEPDNYFVQCNSVAYLSLWVYDRLHGTSYKAATEPWLKFLKKDLIDPKTGAFYLSF

HPESGTVKPWLSAYTTAWTLAMVHGMDPAFSERYYPAFKKTFVEVYDGGRKARVRETTNTPDADGGVGAASAFTL

LLAREMGDQTLFDQLLNHLEPPAKPKITSAILNYEAPSNLLFDELLFLSKVHVGFGELLKATPPPARADSQK
```

Linalool Dehydratase (LinD) from Metagenomics on Activated Sludge from Camp Pendleton Enriched on Myrcene (Primary Enrichment); Designated LinD-5

SEQ ID NO: 23: Native nucleic acid encoding SEQ ID NO: 24, which is unprocessed and includes its signal peptide
ATGAAGAACATCCAAAAGACGGCTGCCGCGCTGCCCGCCATCCTTGCCGCAGTGCTCGCGTTCAGTGCGCCGGCC

CATTCGGCGGACCTGCCGCCCGGGCGCCTCGCCTCGACCGAGGAATATTTCGCCCAGCGCGAGAAACAGGCCGTC

ACGCCCGACGTCATGGCCCACCTCGCCTACATGAACTACACCGATTTCGTCTCGCCCTTCTACAGCCGGGGCTGC

GCCTTCGACGCCTGGGCGATCAAGAAGACCCCGCAGCGGATCATCAAGTACTCGCTCGCCTTCTACGCCTATGGC

CTGGCCAGCGTCGCGCTCACCGATCCGCAGCTGCGTCCGCTCGCCGGACATGCAATCGACATCGCGACCGCCAAG

ATGAAATGCAAGCAGGTCTGGGGAGACTGGGAGGAAGACGGGTTCGGCGAGGATCCGATCGAGAAAGAGAACATC

ATGTACAAGGGCCACTTGAACCTGATGTACGGCCTCTACCAACTGGTCACCGGCAACCGCCGGTACGAGAAGGAG

CACGCCCGCCTCACGCGGATCATCCACGACGAGATCAAGGCCAATCCCTACGCCGGCATCGTCTGCGAGCCGGAC

AACTATTTCGTTCAGTGCAACTCGGTCGCCTACCTGAGCCTGTGGGTCCATGACCGCCTGCACGGCACCGACTAC

CGGGCGGCGACGGCGGAATGGCTGAAATTCATCGAGCACGACCTGATCGACCCGAAACACGGCGCCTTCCACCTG

TCCTACCATCCGGAATCCCACGCGGTGAAACCGTGGGTCTCCGCATACACCACGGCGTGGACGCTCGCCATGGTG

CACGGCATGGATCCCGCTTTCGCCGAGCGCTACTACCCCCGCTTCAAGGAGACCTTCGTCGAGGTCTACGACGAT

GGCCGCAAGGCCCGGGTCCGCGAGACGACCGGCACCACCGACGCCGATGGCGGCGTCGGCGCGGCCTCCGCGTTC

ACCCTGCTGCTCGCCCGCGAGATGGGCGACCGGCAGCTCTTCGACCAGTTGCTGAACCACCTGGAGCCCCCGGCA

AGACCGAGGATCACCTCGGGCATCCTGGAATACGCGGCCCCAGCAATCTGCTGTTCGACGAGCTGCTGTTCCTC

GCCAAGGTACACGTCGGTTTCGGCCAGTTGCTGCAGGCCGGGTCGGCGCCGCCCCCGCCGGGCCCCGCCAGGGGG

AAATGA

SEQ ID NO: 24: Native, or unprocessed, LinD enzyme, designated LinD-5, including signal peptide
MKNIQKTAAALPAILAAVLAFSAPAHSADLPPGRLASTEEYFAQREKQAVTPDVMAHLAYMNYTDFVSPFYSRGC

AFDAWAIKKTPQRIIKYSLAFYAYGLASVALTDPQLRPLAGHAIDIATAKMKCKQVWGDWEEDGFGEDPIEKENI

MYKGHLNLMYGLYQLVTGNRRYEKEHARLTRIIHDEIKANPYAGIVCEPDNYFVQCNSVAYLSLWVHDRLHGTDY

RAATAEWLKFIEHDLIDPKHGAFHLSYHPESHAVKPWVSAYTTAWTLAMVHGMDPAFAERYYPRFKETFVEVYDD

GRKARVRETTGTTDADGGVGAASAFTLLLAREMGDRQLFDQLLNHLEPPARPRITSGILEYAAPSNLLFDELLFL

AKVHVGFGQLLQAGSAPPPPGPARGK

SEQ ID NO: 25: Nucleic acid encoding processed (mature) LinD-5 LinD enzyme, no signal peptide
GCGGACCTGCCGCCCGGGCGCCTCGCCTCGACCGAGGAATATTTCGCCCAGCGCGAGAAACAGGCCGTCACGCCC

GACGTCATGGCCCACCTCGCCTACATGAACTACACCGATTTCGTCTCGCCCTTCTACAGCCGGGGCTGCGCCTTC

GACGCCTGGGCGATCAAGAAGACCCCGCAGCGGATCATCAAGTACTCGCTCGCCTTCTACGCCTATGGCCTGGCC

AGCGTCGCGCTCACCGATCCGCAGCTGCGTCCGCTCGCCGGACATGCAATCGACATCGCGACCGCCAAGATGAAA

TGCAAGCAGGTCTGGGGAGACTGGGAGGAAGACGGGTTCGGCGAGGATCCGATCGAGAAAGAGAACATCATGTAC

AAGGGCCACTTGAACCTGATGTACGGCCTCTACCAACTGGTCACCGGCAACCGCCGGTACGAGAAGGAGCACGCC

CGCCTCACGCGGATCATCCACGACGAGATCAAGGCCAATCCCTACGCCGGCATCGTCTGCGAGCCGGACAACTAT

TTCGTTCAGTGCAACTCGGTCGCCTACCTGAGCCTGTGGGTCCATGACCGCCTGCACGGCACCGACTACCGGGCG

GCGACGGCGGAATGGCTGAAATTCATCGAGCACGACCTGATCGACCCGAAACACGGCGCCTTCCACCTGTCCTAC

CATCCGGAATCCCACGCGGTGAAACCGTGGGTCTCCGCATACACCACGGCGTGGACGCTCGCCATGGTGCACGGC

ATGGATCCCGCTTTCGCCGAGCGCTACTACCCCCGCTTCAAGGAGACCTTCGTCGAGGTCTACGACGATGGCCGC

AAGGCCCGGGTCCGCGAGACGACCGGCACCACCGACGCCGATGGCGGCGTCGGCGCGGCCTCCGCGTTCACCCTG

-continued

```
CTGCTCGCCCGCGAGATGGGCGACCGGCAGCTCTTCGACCAGTTGCTGAACCACCTGGAGCCCCCGGCAAGACCG

AGGATCACCTCGGGCATCCTGGAATACGCGGCCCCCAGCAATCTGCTGTTCGACGAGCTGCTGTTCCTCGCCAAG

GTACACGTCGGTTTCGGCCAGTTGCTGCAGGCCGGGTCGGCGCCGCCCCGCCGGGCCCCGCCAGGGGGAAATGA
```

SEQ ID NO: 26: Processed (mature) LinD-5 LinD enzyme, no signal peptide
```
ADLPPGRLASTEEYFAQREKQAVTPDVMAHLAYMNYTDFVSPFYSRGCAFDAWAIKKTPQRIIKYSLAFYAYGLA

SVALTDPQLRPLAGHAIDIATAKMKCKQVWGDWEEDGFGEDPIEKENIMYKGHLNLMYGLYQLVTGNRRYEKEHA

RLTRIIHDEIKANPYAGIVCEPDNYFVQCNSVAYLSLWVHDRLHGTDYRAATAEWLKFIEHDLIDPKHGAFHLSY

HPESHAVKPWVSAYTTAWTLAMVHGMDPAFAERYYPRFKETFVEVYDDGRKARVRETTGTTDADGGVGAASAFTL

LLAREMGDRQLFDQLLNHLEPPARPRITSGILEYAAPSNLLFDELLFLAKVHVGFGQLLQAGSAPPPPGPARGK
```
15

Linalool Dehydratase (LinD) from Metagenomics on Activated Sludge (Camp Pendleton); Designated LinD-6

SEQ ID NO: 27: Native nucleic acid encoding SEQ ID NO: 28, which is unprocessed and includes its signal peptide
```
ATGAAGAACATCGCCCGCGCGGCCGCACTGGCAGCCGCCATCATCGCCACGATGCCCGGGCCCGGTACGCCAGCC

CACGCGGCAGAGTTGCTGCCCGGACGCCTCGCCTCGACCGAGGCCTACTTCGCCCAGCGCGAACGGCAGGCCGTC

ACCCCCGACGTGATGGCCCACCTCGCCTACATGAACTACACGGACTTCGTTTCCCCCTTCTACAGCCGGGGCTGC

GCCTTCGATGCGTGGACGATCAAGAAGACCCCGCAGCGGATCATCAAGTACTCGCTGGCCTTCTACGCCTACGGC

CTCGCCAGCGTCGCGCTCATCGACCCGCAGCTGCGCCCACTCGCCGGCCACGCACTCGACATCGCCACGGCCAAG

ATGAAATGCAAGCAGGTCTGGGGAGACTGGGAGGAAGACGGCTTCGGCGACGATCCGATCGAGAAGGAAAACATC

ATGTACAAGGGCCACCTGAACCTGATGTACGCCTCCACCAGCTGGTCACCGGCAACCGGCGGTACGAGAAGGAA

CACGCCCGCCTCACGCAGATCATCCGCGACGAGATCGCGGCCAACCCCTACGCCGGCATCGTCTGCGAGCCCGAC

AACTACTTCGTCCAGTGCAACTCGGTCGCCTACCTGAGCCTGTGGGTCTACGACCGCCTGCACGGCACCAACCAC

AGGGCGGCGACCGCAGCGTGGCTCAAGTTCATCGAGGACGACCTGATCGACCCGAAGCACGGCGTCTTCCACCTC

TCCTACCATCCGGAGTCCGGCGCGGTGAAGCCCTGGGTCTCGGCATACACGACGGCATGGACCCTCGCCATGGTG

CACGGCATGGATCCCGCCTTTGCCGAGCGCTACTACCCCCGCTTCAAGGAAACCTTCGTCGAGGTCTACGACGAC

GGCCGCAAGGCCCGGGTCCGCGAGACGACCGGCACCACCGATGCCGATGGCGGCGTCGGCGCGGCCTCCGCCTTC

ACCCTGCTGCTCGCCCGCGAGATGGGCGACCAGCAGCTCTTCGACCAGTTGCTGAACCACCTCGAGCCGCCGGCA

AGACCGAAGATCACCTCGGGCATCCTGGACTACGAAGCGCCCAGCAACCTGCTGTTCGACGAACTGCTGTTCCTC

GCCAAGGTGCACGTCGGTTTCGGCCAGCTGCTGCAGGCCCGGCCGGATCCCGCCAGGGGGCAATGA
```

SEQ ID NO: 28: Native, or unprocessed, LinD enzyme, designated LinD-6, including signal peptide
```
MKNIARAAALAAAIIATMPGPGTPAHAAELLPGRLASTEAYFAQRERQAVTPDVMAHLAYMNYTDFVSPFYSRGC

AFDAWTIKKTPQRIIKYSLAFYAYGLASVALIDPQLRPLAGHALDIATAKMKCKQVWGDWEEDGFGDDPIEKENI

MYKGHLNLMYGLHQLVTGNRRYEKEHARLTQIIRDEIAANPYAGIVCEPDNYFVQCNSVAYLSLWVYDRLHGTNH

RAATAAWLKFIEDDLIDPKHGVFHLSYHPESGAVKPWVSAYTTAWTLAMVHGMDPAFAERYYPRFKETFVEVYDD

GRKARVRETTGTTDADGGVGAASAFTLLLAREMGDQQLFDQLLNHLEPPARPKITSGILDYEAPSNLLFDELLFL

AKVHVGFGQLLQARPDPARGQ
```

SEQ ID NO: 29: Nucleic acid encoding processed LInD-6 LinD enzyme, no signal peptide
```
GCAGAGTTGCTGCCCGGACGCCTCGCCTCGACCGAGGCCTACTTCGCCCAGCGCGAACGGCAGGCCGTCACCCCC

GACGTGATGGCCCACCTCGCCTACATGAACTACACGGACTTCGTTTCCCCCTTCTACAGCCGGGGCTGCGCCTTC

GATGCGTGGACGATCAAGAAGACCCCGCAGCGGATCATCAAGTACTCGCTGGCCTTCTACGCCTACGGCCTCGCC

AGCGTCGCGCTCATCGACCCGCAGCTGCGCCCACTCGCCGGCCACGCACTCGACATCGCCACGGCCAAGATGAAA
```

-continued
```
TGCAAGCAGGTCTGGGGAGACTGGGAGGAAGACGGCTTCGGCGACGATCCGATCGAGAAGGAAAACATCATGTAC

AAGGGCCACCTGAACCTGATGTACGGCCTCCACCAGCTGGTCACCGGCAACCGGCGGTACGAGAAGGAACACGCC

CGCCTCACGCAGATCATCCGCGACGAGATCGCGGCCAACCCCTACGCCGGCATCGTCTGCGAGCCCGACAACTAC

TTCGTCCAGTGCAACTCGGTCGCCTACCTGAGCCTGTGGGTCTACGACGCCTGCACGGCACCAACCACAGGGCG

GCGACCGCAGCGTGGCTCAAGTTCATCGAGGACGACCTGATCGACCCGAAGCACGGCGTCTTCCACCTCTCCTAC

CATCCGGAGTCCGGCGCGGTGAAGCCCTGGGTCTCGGCATACACGACGGCATGGACCCTCGCCATGGTGCACGGC

ATGGATCCCGCCTTTGCCGAGCGCTACTACCCCCGCTTCAAGGAAACCTTCGTCGAGGTCTACGACGACGGCCGC

AAGGCCCGGGTCCGCGAGACGACCGGCACCACCGATGCCGATGGCGGCGTCGGCGCGGCCTCCGCCTTCACCCTG

CTGCTCGCCCGCGAGATGGGCGACCAGCAGCTCTTCGACCAGTTGCTGAACCACCTCGAGCCGCCGGCAAGACCG

AAGATCACCTCGGGCATCCTGGACTACGAAGCGCCCAGCAACCTGCTGTTCGACGAACTGCTGTTCCTCGCCAAG

GTGCACGTCGGTTTCGGCCAGCTGCTGCAGGCCCGGCCGGATCCCGCCAGGGGGCAATGA
```

SEQ ID NO: 30: Processed (mature) LinD-6 LinD enzyme, no signal peptide
```
AELLPGRLASTEAYFAQRERQAVTPDVMAHLAYMNYTDFVSPFYSRGCAFDAWTIKKTPQRIIKYSLAFYAYGLA

SVALIDPQLRPLAGHALDIATAKMKCKQVWGDWEEDGFGDDPIEKENIMYKGHLNLMYGLHQLVTGNRRYEKEHA

RLTQIIRDEIAANPYAGIVCEPDNYFVQCNSVAYLSLWVYDRLHGTNHRAATAAWLKFIEDDLIDPKHGVFHLSY

HPESGAVKPWVSAYTTAWTLAMVHGMDPAFAERYYPRFKETFVEVYDDGRKARVRETTGTTDADGGVGAASAFTL

LLAREMGDQQLFDQLLNHLEPPARPKITSGILDYEAPSNLLFDELLFLAKVHVGFGQLLQARPDPARGQ
```

Linalool Dehydratase (LinD) from Metagenomics on Activated Sludge (Camp Pendleton): Designated LinD-7

SEQ ID NO: 31: Native nucleic acid encoding SEQ ID NO: 32, which is unprocessed and includes its signal peptide
```
ATGACACAATGGTTATCAACACCCTGCCTGGCGGCGATTTTAAGTGCAATTTTTATTGTTGTACCCAAATTCGGG

TTGACAGAGACATTACTGCCGGGGCGATTAGCCACTACGAAGGCGTATTTTTCACAGCAACGCAACCAAAAACTG

ACGCCGGATATGGATGCCCAGCTGGCCTATATGTCCTACACTGATTTTATTTCACCTTTCTATAGTCGAGGTTGC

GCCTTTGAGGCTTGGGAACTGAAACAGGCTCCCCAGAGAATTATCAAATACTCCCTTGCCTGGTATTCCTACGGC

CTTGCCAGTGTCGCTGTCATTGATCCCAGCCTGCACCGATATGCAGGCCACAATATTGATATTGCCATCGCAAAA

ATGAAGTGCAGACAGGTTTGGGGCGACTGGGAAGAAGACGGCTTTGGCTCCAACCCTATTGCCCACCAAAATATT

ATGTACAAAGGACACTTGAATCTGATGTATGGCCTTTATCAGCTGTTAACGGGCAATACTCAGTATGAAGAGGAA

TTCATCGATCTCTCTAATATCATCTATAGCGAAATCAAGGAAAACCCTTATGCAGGTATTGCTTGCGAGCCGGAC

AATTACTTTCCGCAGTGCAACTCCGTCGCCTATCTCAGCCTGTGGGTTTATGATCGTCTCTACCACACCGACTAC

AAAGCAGTCACAAAACCCTGGCTTGATTTTTTACAGAAAAAACTCATAGATCCTGAAACCGGCACATTTCATGTT

GCCTATCATCCAACATCTCACGCCGTTAAACCCTGGGTTTCCGCCTACACCACGGCCTGGGCGCTAACCATGATT

CATGGTCTGAATCCGGAATTTGCCAAAAAGTACTACCCTAATTTTAAGCAAACCTTTGTTGAGGTTTTTGACAAC

GGCACCAAAGCCAGGGTGCGCGAAACCGCCCACACCACGGATGTTGATGGTGGCGTCGGCGCCGCCTCGATTTTC

ACGCTGGTGTTGGCAAGGGAAATGAATGATCAGGAGCTGTTTGATCAACTATTGAATTATCTCGAACCGCCAGCA

AAGCCTGTGATTTATTCGGGGATTCTGCGATATGAAAATCCAACGAGCCTGCTATTCGATGAACTGCTTTTTGTC

GCCAAGGTGCATGTGGGTTTTGGCGAACTGATCAATCTCAAACCTGTTGAAACAGACTAG
```

SEQ ID NO: 32: Native, or unprocessed, LinD enzyme, designated LinD-7, including signal peptide:
```
MTQWLSTPCLAAILSAIFIVVPKFGLTETLLPGRLATTKAYFSQQRNQKLTPDMDAQLAYMSYTDFISPFYSRGC

AFEAWELKQAPQRIIKYSLAWYSYGLASVAVIDPSLHRYAGHNIDIAIAKMKCRQVWGDWEEDGFGSNPIAHQNI

MYKGHLNLMYGLYQLLTGNTQYEEEFIDLSNITYSEIKENPYAGIACEPDNYFPQCNSVAYLSLWVYDRLYHTDY
```

-continued

```
KAVTKPWLDFLQKKLIDPETGTFHVAYHPTSHAVKPWVSAYTTAWALTMIHGLNPEFAKKYYPNFKQTFVEVFDN

GTKARVRETAHTTDVDGGVGAASIFTLVLAREMNDQELFDQLLNYLEPPAKPVIYSGILRYENPTSLLFDELLFV

AKVHVGFGELINLKPVETD
```

SEQ ID NO: 33: LinD enzyme SEQ ID NO: 32 having an A196F modification,
designated LinD-7B

```
MTQWLSTPCL AAILSAIFIV VPKFGLTETL LPGRLATTKA YFSQQRNQKL TPDMDAQLAY

MSYTDFISPF YSRGCAFEAW ELKQAPQRII KYSLAWYSYG LASVAVIDPS LHRYAGHNID

IAIAKMKCRQ VWGDWEEDGF GSNPIAHQNI MYKGHLNLMY GLYQLLTGNT QYEEEFIDLS

NIIYSEIKEN PYAGIFCEPD

NYFPQCNSVAYLSLWVYDRLYHTDYKAVTKPWLDFLQKKLIDPETGTFHVAYHPTSHAVKPWVSAYTTAWALTMI

HGLNPEFAKKYYPNFKQTFVEVFDNGTKARVRETAHTTDVDGGVGAASIFTLVLAREMNDQELFDQLLNYLEPPA

KPVIYSGILRYENPTSLLFDELLFVAKVHVGFGELINLKPVETD
```

Linalool Dehydratase (LinD) (an Engineered Variant of LinD-2 with the 7 Mutations (Amino Acid Changes): G74S, G133Q, R171K, I182K, V196F, D200G, G365S); Designated LinD-2T SEQ ID NO: 34: Native nucleic acid encoding SEQ ID NO: 35, which is unprocessed
and includes its signal peptide

```
ATGCGCTTTACTCTGAAAACCCCTGCTATCGCTTCCGCCGTTGCTGCACTGTTGGTTGGTCTGGGTCAGCCAGCG

CACGCGGCACCGCTGCCGTTAGGCCGCTTGGCACCGACCGAAGATTACTTTGCCCAACAGGCGAAACAAGCCGTC

ACCCCGGATGTTATGGCCCAGCTGGCGTACATGAATTACATCGACTTCATTAGCCCGTTTTACAGCCGTAGCTGC

AGCTTCGAGGCGTGGGAGTTGAAACACACGCCGCAGCGTGTCATCAAGTATAGCATTGCGTTCTATGCGTACGGC

CTGGCAAGCGTCGCACTGATCGACCCGAATCTGCGTGCTCTGGCGGGTCATGACCTGGATATCGCGGTCAGCAAG

ATGAAATGTAAGCGCGTGTGGCAAGATTGGGAAGAAGATGGCTTTGGTGATGACCCGATTGAGAAGGAAAACATT

ATGTATAAGGGCCACCTGAACCTCATGTACGGTCTGTATCAACTGGTGACCGGTAGCCGTAAATATGAAGCGGAG

CATGCCCACTTGACCCGTTTGATCCACGACGAAATCGGTGCAAACCCGTTCGCGGGTATTTTTTGCGAGCCGGGT

AATTACTTTGTGCAGTGTAACTCTGTCGCGTACCTGAGCCTGTGGGTATATGATCGTCTGCATGGCACCGACTAC

CGTGCAGCGACGCGTGCCTGGCTGGATTTCATCCAGAAAGATCTGATTGACCCGGAGCGCGGTGCGTTTTACCTG

AGCTATCACCCTGAGTCCGGTGCCGTGAAACCGTGGATTAGCGCGTACACTACGGCGTGGACCCTGGCGATGGTG

CATGGCATGGATCCGGCGTTCAGCGAGCGTTATTACCCGGCGTTCAAAAAGACCTTTGTTGAAGTTTACGACGGT

GGCCGCAAGGCACGTGTCCGTGAAACGGCAGGCACGGCAGATGCCGACGGTGGCGTTGGTCTGGCGTCTGCTTTC

ACCCTGCTGCTTGCGCGCGAGATGGGTGACCAAACGCTGTTTGACCAATTGCTGAATCACCTGGAGCCGCCAGCA

CAACCGTCCATCGTGAGCGCTAGCCTGCGTTATGAGCACCCGAGCAGCCTGCTGTTCGACGAACTGCTGTTCTTG

GCCAAGGTTCATGCCGGCTTTGGCGCGCTGCTGCAGATGCCGCCACCGGCAGCTAAATCGGGTGGCAAGTAA
```

SEQ ID NO: 35: Native, or unprocessed, engineered LinD enzyme LinD-2T,
including signal peptide

```
MRFTLKTPAIASAVAALLVGLGQPAHAAPLPLGRLAPTEDYFAQQAKQAVTPDVMAQLAYMNYIDFISPFYSRSC

SFEAWELKHTPQRVIKYSIAFYAYGLASVALIDPNLRALAGHDLDIAVSKMKCKRVWQDWEEDGFGDDPIEKENT

MYKGHLNLMYGLYQLVTGSRKYEAEHAHLTRLIHDEIGANPFAGIFCEPGNYFVQCNSVAYLSLWVYDRLHGTDY

RAATRAWLDFIQKDLIDPERGAFYLSYHPESGAVKPWISAYTTAWTLAMVHGMDPAFSERYYPAFKKTFVEVYDG

GRKARVRETAGTADADGGVGLASAFTLLLAREMGDQTLFDQLLNHLEPPAQPSIVSASLRYEHPSSLLFDELLFL

AKVHAGFGALLQMPPPAAKSGGK
```

Linalool Dehydratase (LinD) from Metagenomics on Activated Sludge (Camp Pendleton); Designated LinD-8

SEQ ID NO: 36: Native nucleic acid encoding SEQ ID NO: 37, which is unprocessed and includes its signal peptide
ATGCGGTTCACATTGAAGACGACGGCGATCGCGTCGGCCGCCGCCCTGCTGGTCGGCCTCGGGCAGCCGCCCCGC

GCGGCGGAACTGCCGCCGGGGCGGCTCGCCACCACCGAGGACTATTTCGCGCAGCAGGCGAAGCAGGCCGTCACC

CCCGACGTGATGGCCCAGCTGGCCTACATGAACTACATCGATTTCATCTCGCCCTTCTACAGCCGGGGCTGCTCC

TTCGAGGCCTGGGAGCTCAAGCACACGCCGCAGCGGGTCATCAAGTATTCGATCGCCTTCTATGCGTATGGCCTG

GCCAGCGTGGCGCTCATCGACCCGAAGCTGCGTGCGCTCGCCGGCCATGACCTGGACATCGCGGTCTCCAAGATG

AAGTGCAAGCGGGTCTGGGGCGACTGGGAGGAAGACGGGTTCGGCACCGACCCGATCGAGAAAGAGAACATCATG

TACAAGGGCCACCTGAACCTGATGTACGGCCTCTATCAGCTGGTGACCGGCAGCCGCCGGTACGAAGCCGAGCAT

GCGCACCTCACCCGCATCATCCATGACGAGATCGCGGCCAACCCCTTTGCCGGCATCGTCTGCGAGCCGGACAAT

TATTTCGTCCAGTGCAATTCGGTCGCCTACCTGAGCCTGTGGGTCTATGACCGGCTGCATGGCACCGACTACCGG

GCGGCCACCAGGGCCTGGCTGGATTTCATCCAGAAGGACCTGATCGATCCCGAGCGGGGCGCCTTCTACCTGTCC

TATCACCCCGAGTCCGGCGCGGTGAAGCCGTGGATCTCGGCGTATACGACGGCCTGGACGCTCGCCATGGTGCAC

GGCATGGACCCCGCCTTTTCCGAGCGCTACTACCCCCGGTTCAAGCAGACCTTCGTCGAGGTCTACGACGAGGGC

CGCAAGGCCCGGGTGCGCGAGACGGCCGGCACGGACGACGCGGATGGCGGGGTGGGCCTGGCTTCGGCGTTCACC

CTGCTGCTGGCCCGCGAGATGGGCGACCAGCAGCTCTTCGACCAGTTGCTGAATCACCTGGAGCCGCCGGCTAAG

CCGAGCATCGTCTCGGCCTCGCTGCGGTACGAGCAACCCGGCAGCCTGCTGTTCGACGAGCTGCTGTTCCTCGCC

AAGGTGCATGCCGGTTTTGGCGCCCTGCTTCGGATGCCGCCTCCGGCGGCCAAGCTCGCGGGGAAATAA

SEQ ID NO: 37: Native, or unprocessed, LinD enzyme, designatend LinD-8, including signal peptide
MRFTLKTTAIASAAALLVGLGQPPRAAELPPGRLATTEDYFAQQAKQAVTPDVMAQLAYMNYIDFISPFYSRGCS

FEAWELKHTPQRVIKYSIAFYAYGLASVALIDPKLRALAGHDLDIAVSKMKCKRVWGDWEEDGFGTDPIEKENIM

YKGHLNLMYGLYQLVTGSRRYEAEHAHLTRIIHDEIAANPFAGIVCEPDNYFVQCNSVAYLSLWVYDRLHGTDYR

AATRAWLDFIQKDLIDPERGAFYLSYHPESGAVKPWISAYTTAWTLAMVHGMDPAFSERYYPRFKQTFVEVYDEG

RKARVRETAGTDDADGGVGLASAFTLLLAREMGDQQLFDQLLNHLEPPAKPSIVSASLRYEQPGSLLFDELLFLA

KVHAGFGALLRMPPPAAKLAGK

SEQ ID NO: 38: Nucleic acid encoding processed (mature) LinD-8 LinD enzyme, no signal peptide
GCGGAACTGCCGCCGGGGCGGCTCGCCACCACCGAGGACTATTTCGCGCAGCAGGCGAAGCAGGCCGTCACCCCC

GACGTGATGGCCCAGCTGGCCTACATGAACTACATCGATTTCATCTCGCCCTTCTACAGCCGGGGCTGCTCCTTC

GAGGCCTGGGAGCTCAAGCACACGCCGCAGCGGGTCATCAAGTATTCGATCGCCTTCTATGCGTATGGCCTGGCC

AGCGTGGCGCTCATCGACCCGAAGCTGCGTGCGCTCGCCGGCCATGACCTGGACATCGCGGTCTCCAAGATGAAG

TGCAAGCGGGTCTGGGGCGACTGGGAGGAAGACGGGTTCGGCACCGACCCGATCGAGAAAGAGAACATCATGTAC

AAGGGCCACCTGAACCTGATGTACGGCCTCTATCAGCTGGTGACCGGCAGCCGCCGGTACGAAGCCGAGCATGCG

CACCTCACCCGCATCATCCATGACGAGATCGCGGCCAACCCCTTTGCCGGCATCGTCTGCGAGCCGGACAATTAT

TTCGTCCAGTGCAATTCGGTCGCCTACCTGAGCCTGTGGGTCTATGACCGGCTGCATGGCACCGACTACCGGGCG

GCCACCAGGGCCTGGCTGGATTTCATCCAGAAGGACCTGATCGATCCCGAGCGGGGCGCCTTCTACCTGTCCTAT

CACCCCGAGTCCGGCGCGGTGAAGCCGTGGATCTCGGCGTATACGACGGCCTGGACGCTCGCCATGGTGCACGGC

ATGGACCCCGCCTTTTCCGAGCGCTACTACCCCCGGTTCAAGCAGACCTTCGTCGAGGTCTACGACGAGGGCCGC

AAGGCCCGGGTGCGCGAGACGGCCGGCACGGACGACGCGGATGGCGGGGTGGGCCTGGCTTCGGCGTTCACCCTG

CTGCTGGCCCGCGAGATGGGCGACCAGCAGCTCTTCGACCAGTTGCTGAATCACCTGGAGCCGCCGGCTAAGCCG

AGCATCGTCTCGGCCTCGCTGCGGTACGAGCAACCCGGCAGCCTGCTGTTCGACGAGCTGCTGTTCCTCGCCAAG

-continued
```
GTGCATGCCGGTTTTGGCGCCCTGCTTCGGATGCCGCCTCCGGCGGCCAAGCTCGCGGGGAAATAA
```

```
SEQ ID NO: 39: Processed (mature) LinD-8 LinD enzyme, no signal peptide
AELPPGRLATTEDYFAQQAKQAVTPDVMAQLAYMNYIDFISPFYSRGCSFEAWELKHTPQRVIKYSIAFYAYGLA

SVALIDPKLRALAGHDLDIAVSKMKCKRVWGDWEEDGFGTDPIEKENIMYKGHLNLMYGLYQLVTGSRRYEAEHA

HLTRIIHDEIAANPFAGIVCEPDNYFVQCNSVAYLSLWVYDRLHGTDYRAATRAWLDFIQKDLIDPERGAFYLSY

HPESGAVKPWISAYTTAWTLAMVHGMDPAFSERYYPRFKQTFVEVYDEGRKARVRETAGTDDADGGVGLASAFTL

LLAREMGDQQLFDQLLNHLEPPAKPSIVSASLRYEQPGSLLFDELLFLAKVHAGFGALLRMPPPAAKLAGK
```

Linalool Dehydratase (LinD) from Metagenomics on Activated Sludge (Camp Pendleton); Designated LinD-9

```
SEQ ID NO: 40: Native nucleic acid encoding SEQ ID NO: 41, which has no defined
signal peptide
ATGACACAATGGTTATCAACACCCTGCCTGGCGGCGATTTTAAGTGCAATTTTTATTGTTGTACCCAAATTCGGG

TTGACAGAGACATTACTGCCGGGGCGATTAGCCACTACGGAGGCGTATTTTTCACAGCAACGCAACCAAAAACTG

ACGCCGGATATGGATGCCCAGCTGGCCTATATGTCCTACACTGATTTTATTTCACCTTTCTATAGTCGAGGTTGC

GCCTTTGAGGCTTGGGAACTGAAACAGGCTCCCCAGAGAATTATCAAATACTCCCTTGCCTGGTATTCCTACGGC

CTTGCCAGTGTCGCTGTCATTGATCCCAGCCTGCACCGATATGCAGGCCACAATATTGATATTGCCATCGCAAAA

ATGAAGTGCAGACAGGTTTGGGGCGACTGGGAAGAAGACGGCTTTGGCTCCAACCCTATTGCCCACCAAAATATT

ATGTACAAAGGACACTTGAATCTGATGTATGGCCTTTATCAGCTGTTAACGGGCAATACTCAGTATGAAGAGGAA

TTCATCGATCTCTCTAATATCATCTATAGCGAAATCAAGGAAAACCCTTATGCAGGTATTGCTTGCGAGCCGGAC

AATTACTTTCCGCAGTGCAACTCCGTCGCCTATCTCAGCCTGTGGGTTTATGATCGTCTCTACCACACCGACTAC

AAAGCAGTCACAAAACCCTGGCTTGATTTTTTACAGAAAAAACTCATAGATCCTGAAACCGGCACATTTCATGTT

GCCTATCATCCAACATCTCACGCCGTTAAACCCTGGGTTTCCGCCTACACCACGGCCTGGGCGCTAACCATGATT

CATGGTCTGAATCCGGAATTTGCCAAAAAGTACTACCCTAATTTTAAGCAAACCTTTGTTGAGGTTTTTGACAAC

GGCACCAAAGCCAGGGTGCGCGAAACCGCCCACACCACGGATGTTGATGGTGGCGTCGGCGCCGCCTCGATTTTC

ACGCTGGTGTTGGCAAGGGAAATGAATGATCAGGAGCTGTTTGATCAACTATTGAATTATCTCGAACCGCCAGCA

AAGCCTGTGATTTATTCGGGGATTCTGCGATATGAAAATCCAACGAGCCTGCTATTCGATGAACTGCTTTTTGTC

GCCAAGGTGCATGTGGGTTTTGGCGAACTGATCAATCTCAAACCTGTTGAAACAGACTAG
```

```
SEQ ID NO: 41: Native, or unprocessed, LinD enzyme, designated LinD-9, no
defined signal peptide
MTQWLSTPCLAAILSAIFIVVPKFGLTETLLPGRLATTEAYFSQQRNQKLTPDMDAQLAYMSYTDFISPFYSRGC

AFEAWELKQAPQRIIKYSLAWYSYGLASVAVIDPSLHRYAGHNIDIAIAKMKCRQVWGDWEEDGFGSNPIAHQNI

MYKGHLNLMYGLYQLLTGNTQYEEEFIDLSNIIYSEIKENPYAGIACEPDNYFPQCNSVAYLSLWVYDRLYHTDY

KAVTKPWLDFLQKKLIDPETGTFHVAYHPTSHAVKPWVSAYTTAWALTMIHGLNPEFAKKYYPNFKQTFVEVFDN

GTKARVRETAHTTDVDGGVGAASIFTLVLAREMNDQELFDQLLNYLEPPAKPVIYSGILRYENPTSLLFDELLFV

AKVHVGFGELINLKPVETD
```

Linalool Dehydratase (LinD) from Metagenomics on Soil Sample (Cottonwood River); Designated LinD-10

```
SEQ ID NO: 42: Native nucleic acid encoding SEQ ID NO: 43, which is unprocessed
and includes its signal peptide
ATGAAGAAACCCGCCCCTTGACCGTCCTGGCCGGCCTGGCCAGCGCCGTCCTGCTCGCCCTTGGCACGCCGGCC

ACGGCAGCCGAGCCGATGCCCGGCCGCCTGGCCTCGACCGACGACTACTTCGCCCAGAGCGCGAAGCACGCCCTG

ACGCCGGACGTGATGGCGCAACTGCGCTACATGAACTACACCGATTTCATTTCGCCGTTCTACAGCCGGGGCTGC

GCCTTCGACGCCTGGACGATGAAGAAGATGCCGCCCCGCATCATCAAATATTCGCTCGCCTGGTACGCCTACGGC
```

```
CTGGCCAGCGTCGCCCTGACCGACCCGGCGATGCGCCCGGTGGCCGGTCACGCGATTGACATCGCGACCGCCAAG

ATGCATTGCAAGCAGGTCTGGGGCGACTGGGAGGAAGACGGTTTCGGCAGCGACCCGATCATCCGCCAGAACGTC

ATGTACAAGGGCCACCTGAACCTGATGTACGGGCTCTACCAGTTGATCACCGGCGACCGCAAGTACGAGAAGGAA

AACACCCGCCTGACCCGCATCATGCACAAGGAGATGAAGAGCAATCCGTACGCCGGCATCGTCTGCGAACCCGAC

AACTACTTCGTCCAGTGCAACTCGGTCGCCTACCTGAGCCTGTGGGTTTACGACCGGCTGCACGGCACCCAGTAC

AAGGCGGCAACCAGGGAGTGGCTGAAATTCATCGAGGACGAACTGATCGACCCGAAGACCGGCAGCTTCTATCTT

TCCTACCACCCCGAAACCGGTGCCGTGAAGCCGTGGCAGTCGGCCTACACGACCGCCTGGACGCTGGCCATGGTG

CATGGCATGGACCCGGCCTTCGCCGAACGCTATTACCCGAAATTCAAGGAAAGCTTCGTCGAGGTCTATGACGAC

GGCCGCAAGGCGCGCGTCCGCGAAATGACCGGCACCACCGACACCGACGGCGGCGTCGGCGCCGCGTCGGCGTTC

ATGCTGGTCCTGGCACGTGAAATGGGCGACAAGCAACTGTTCGACCAGCTGCTGAACCACCTCGAACCGCCAGCC

GGACCGACGATCACTTCGGGCATCCTGCATTACGCGCAGCCGAGCAATCTGCTGTTCGACGAATTGCTGTTCGTC

GGCAAGGTGCATGTCGGCTTCGCCAAGCTGCTCAATGCGCCGCCGGCACCGGCTCGCCCGGCCCTGCAAAAGAAG

AAATGA
```

SEQ ID NO: 43: Native, or unprocessed, LinD enzyme, designated LinD-10, including signal peptide
MKKPRPLTVLAGLASAVLLALGTPATAAEPMPGRLASTDDYFAQSEKHALTPDVMAQLRYMNYTDFISPFYSRGC

AFDAWTMKKMPPRIIKYSLAWYAYGLASVALTDPAMRPVAGHAIDIATAKMHCKQVWGDWEEDGFGSDPIIRQNV

MYKGHLNLMYGLYQLITGDRKYEKENTRLTRIMHKEMKSNPYAGIVCEPDNYFVQCNSVAYLSLWVYDRLHGTQY

KAATREWLKFIEDELIDPKTGSFYLSYHPETGAVKPWQSAYTTAWTLAMVHGMDPAFAERYYPKFKESFVEVYDD

GRKARVREMTGTTDTDGGVGAASAFMLVLAREMGDKQLFDQLLNHLEPPAGPTITSGILHYAQPSNLLFDELLFV

GKVHVGFAKLLNAPPAPARPALQKKK

SEQ ID NO: 44: Nucleic acid encoding processed (mature) LinD-10 LinD enzyme, no signal peptide
```
GCCGAGCCGATGCCCGGCCGCCTGGCCTCGACCGACGACTACTTCGCCCAGAGCGAGAAGCACGCCCTGACGCCG

GACGTGATGGCGCAACTGCGCTACATGAACTACACCGATTTCATTTCGCCGTTCTACAGCCGGGGCTGCGCCTTC

GACGCCTGGACGATGAAGAAGATGCCGCCCCGCATCATCAAATATTCGCTCGCCTGGTACGCCTACGGCCTGGCC

AGCGTCGCCCTGACCGACCCGGCGATGCGCCCGGTGGCCGGTCACGCGATTGACATCGCGACCGCCAAGATGCAT

TGCAAGCAGGTCTGGGGCGACTGGGAGGAAGACGGTTTCGGCAGCGACCCGATCATCCGCCAGAACGTCATGTAC

AAGGGCCACCTGAACCTGATGTACGGGCTCTACCAGTTGATCACCGGCGACCGCAAGTACGAGAAGGAAAACACC

CGCCTGACCCGCATCATGCACAAGGAGATGAAGAGCAATCCGTACGCCGGCATCGTCTGCGAACCCGACAACTAC

TTCGTCCAGTGCAACTCGGTCGCCTACCTGAGCCTGTGGGTTTACGACCGGCTGCACGGCACCCAGTACAAGGCG

GCAACCAGGGAGTGGCTGAAATTCATCGAGGACGAACTGATCGACCCGAAGACCGGCAGCTTCTATCTTTCCTAC

CACCCCGAAACCGGTGCCGTGAAGCCGTGGCAGTCGGCCTACACGACCGCCTGGACGCTGGCCATGGTGCATGGC

ATGGACCCGGCCTTCGCCGAACGCTATTACCCGAAATTCAAGGAAAGCTTCGTCGAGGTCTATGACGACGGCCGC

AAGGCGCGCGTCCGCGAAATGACCGGCACCACCGACACCGACGGCGGCGTCGGCGCCGCGTCGGCGTTCATGCTG

GTCCTGGCACGTGAAATGGGCGACAAGCAACTGTTCGACCAGCTGCTGAACCACCTCGAACCGCCAGCCGGACCG

ACGATCACTTCGGGCATCCTGCATTACGCGCAGCCGAGCAATCTGCTGTTCGACGAATTGCTGTTCGTCGGCAAG

GTGCATGTCGGCTTCGCCAAGCTGCTCAATGCGCCGCCGGCACCGGCTCGCCCGGCCCTGCAAAAGAAGAAATGA
```

SEQ ID NO: 45: Processed (mature) LinD-10 LinD enzyme, no signal peptide.
AEPMPGRLASTDDYFAQSEKHALTPDVMAQLRYMNYTDFISPFYSRGCAFDAWTMKKMPPRIIKYSLAWYAYGLA

SVALTDPAMRPVAGHAIDIATAKMHCKQVWGDWEEDGFGSDPIIRQNVMYKGHLNLMYGLYQLITGDRKYEKENT

RLTRIMHKEMKSNPYAGIVCEPDNYFVQCNSVAYLSLWVYDRLHGTQYKAATREWLKFIEDELIDPKTGSFYLSY

-continued

HPETGAVKPWQSAYTTAWTLAMVHGMDPAFAERYYPKFKESFVEVYDDGRKARVREMTGTTDTDGGVGAASAFML

VLAREMGDKQLFDQLLNHLEPPAGPTITSGILHYAQPSNLLFDELLFVGKVHVGFAKLLNAPPAPARPALQKKK

Linalool Dehydratase (LinD) from Metagenomics on Soil
Sample; Designated LinD-11

SEQ ID NO: 46: Native nucleic acid encoding SEQ ID NO: 47, which is unprocessed
and includes its signal peptide
ATGAAAAAAACACGCTTTTCCGTCGCACTGACCGGCCTGACTGCCGCCACCCTGATCGCATTCGGTTCGCCCGCC

ACGGCCGGCGAATTGCCACCCGGCCGACTGGCTTCGACCGACGACTACTTCACCCAGCGTGAAAAACAGGCACTG

ACGCCCGACGTCATGGCGCAACTGCGCTACATGAACTACACCGATTTCATTTCGCCGTTCTACAGCCGGGGCTGC

GCCTTCGATGCCTGGACGATGAAGAAGATGCCGCCGCGCATCATCAAGTATTCGCTGGCCTTCTACGCCTACGGG

CTGGCCAGCGTCGCCCAGACCGACCCGAAAATGCGTCCCCTCGCCGGCCACGCGATCGACATCGCCACCGCCAAG

ATGCACTGCAAGCAGGTCTGGGGCGACTGGGAGGAAGACGGTTTCGGCAAGGACCCGATCATCAAGGAAAACGTC

ATGTACAAGGGCCATCTGAACCTGATGTACGGGCTGTACCAGATGGTCACCGGCGACCGGAAATACGAGAAGGAA

AATACCCGCCTGACCCAAATCATGCTCAAGGAGATCAAGGCCAATCCGTATGCCGGCATCGTCTGCGAGCCGGAC

AACTACTTCGTGCAATGCAATTCGGTCGCCTACCTGAGCCTGTGGGTCTATGACCGGCTGCACGGCACCAACCAC

AAGGCCGTGACCAAGGAATGGCTGAAGTTCATCGAGGACGAGCTGATCGACCCCAAGAGCGGCAGCTTCTACCTC

TCCTACCATCCCGAGACCGGCGCCGTGAAGCCCTGGCAATCGGCCTACACGTCGGCCTGGGCGCTGGCGATGGTG

CACGGCATGGACCCGGCGTTCACGGAGCGCCATTACCCGAAGTTCAAGGAAACCTTCGTCGAGGTTTATGACGGA

GGCCACAAGGCCCGCGTCCGCGAAATGACCGGCACTCCGGACGCCGATGGCGGGGTCGGCCTGGCCTCGGCCTTC

ACGCTGCTGCTGGCCCGCGAAATGGGTGACAAGGAACTTTTCGACCAGCTGTTGAACCACCTCGAACCGCCAGCC

AAGCCGACGATCACCTCCGGCATCCTGCATTACGGGCAGCCGAGCAGCCTGCTGTTCGACGAATTGCTGTTCGTC

GGCAAGGTGCACGTCGGCTTCGCCAACCTGCTCAATGCGCCGCTGGCCCCGCCCCGCCCTGCCCTGCAAAAGAAG

AAATGA

SEQ ID NO: 47: Native, or unprocessed, LinD enzyme, designated LinD-11,
including signal peptide
MKKTRFSVALTGLTAATLIAFGSPATAGELPPGRLASTDDYFTQREKQALTPDVMAQLRYMNYTDFISPFYSRGC

AFDAWTMKKMPPRIIKYSLAFYAYGLASVAQTDPKMRPLAGHAIDIATAKMHCKQVWGDWEEDGFGKDPIIKENV

MYKGHLNLMYGLYQMVTGDRKYEKENTRLTQIMLKEIKANPYAGIVCEPDNYFVQCNSVAYLSLWVYDRLHGTNH

KAVTKEWLKFIEDELIDPKSGSFYLSYHPETGAVKPWQSAYTSAWALAMVHGMDPAFTERHYPKFKETFVEVYDG

GHKARVREMTGTPDADGGVGLASAFTLLLAREMGDKELFDQLLNHLEPPAKPTITSGILHYGQPSSLLFDELLFV

GKVHVGFANLLNAPLAPPRPALQKKK

SEQ ID NO: 48: Nucleic acid encoding processed (mature) LinD-11 LinD enzyme,
no signal peptide
GGCGAATTGCCACCCGGCCGACTGGCTTCGACCGACGACTACTTCACCCAGCGTGAAAAACAGGCACTGACGCCC

GACGTCATGGCGCAACTGCGCTACATGAACTACACCGATTTCATTTCGCCGTTCTACAGCCGGGGCTGCGCCTTC

GATGCCTGGACGATGAAGAAGATGCCGCCGCGCATCATCAAGTATTCGCTGGCCTTCTACGCCTACGGGCTGGCC

AGCGTCGCCCAGACCGACCCGAAAATGCGTCCCCTCGCCGGCCACGCGATCGACATCGCCACCGCCAAGATGCAC

TGCAAGCAGGTCTGGGGCGACTGGGAGGAAGACGGTTTCGGCAAGGACCCGATCATCAAGGAAAACGTCATGTAC

AAGGGCCATCTGAACCTGATGTACGGGCTGTACCAGATGGTCACCGGCGACCGGAAATACGAGAAGGAAAATACC

CGCCTGACCCAAATCATGCTCAAGGAGATCAAGGCCAATCCGTATGCCGGCATCGTCTGCGAGCCGGACAACTAC

TTCGTGCAATGCAATTCGGTCGCCTACCTGAGCCTGTGGGTCTATGACCGGCTGCACGGCACCAACCACAAGGCC

GTGACCAAGGAATGGCTGAAGTTCATCGAGGACGAGCTGATCGACCCCAAGAGCGGCAGCTTCTACCTCTCCTAC

-continued

```
CATCCCGAGACCGGCGCCGTGAAGCCCTGGCAATCGGCCTACACGTCGGCCTGGCGCTGGCGATGGTGCACGGC

ATGGACCCGGCGTTCACGGAGCGCCATTACCCGAAGTTCAAGGAAACCTTCGTCGAGGTTTATGACGGAGGCCAC

AAGGCCCGCGTCCGCGAAATGACCGGCACTCCGGACGCCGATGGCGGGGTCGGCCTGGCCTCGGCCTTCACGCTG

CTGCTGGCCCGCGAAATGGGTGACAAGGAACTTTTCGACCAGCTGTTGAACCACCTCGAACCGCCAGCCAAGCCG

ACGATCACCTCCGGCATCCTGCATTACGGGCAGCCGAGCAGCCTGCTGTTCGACGAATTGCTGTTCGTCGGCAAG

GTGCACGTCGGCTTCGCCAACCTGCTCAATGCGCCGCTGGCCCCGCCCCGCCCTGCCCTGCAAAAGAAGAAATGA
```

SEQ ID NO: 49: Processed (mature) LinD-11 LinD enzyme, no signal peptide
```
GELPPGRLASTDDYFTQREKQALTPDVMAQLRYMNYTDFISPFYSRGCAFDAWTMKKMPPRIIKYSLAFYAYGLA

SVAQTDPKMRPLAGHAIDIATAKMHCKQVWGDWEEDGFGKDPIIKENVMYKGHLNLMYGLYQMVTGDRKYEKENT

RLTQIMLKEIKANPYAGIVCEPDNYFVQCNSVAYLSLWVYDRLHGTNHKAVTKEWLKFIEDELIDPKSGSFYLSY

HPETGAVKPWQSAYTSAWALAMVHGMDPAFTERHYPKFKETFVEVYDGGHKARVREMTGTPDADGGVGLASAFTL

LLAREMGDKELFDQLLNHLEPPAKPTITSGILHYGQPSSLLFDELLFVGKVHVGFANLLNAPLAPPRPALQKKK
```
20

Linalool Dehydratase (LinD) from Metagenomics on Soil
Sample (Cottonwood River); Designated LinD-12

SEQ ID NO: 50: Native nucleic acid encoding SEQ ID NO:52, which is unprocessed
and includes its signal peptide
```
ATGAAGAAACCCCGCCCCTTGACCGTCCTGGCCGGCCTGGCCAGCGCCGTCCTGCTCGCCCTTGGCACGCCGGCC

ACGGCAGTCGAGCCGATGCCCGGCCGCCTGGCCTCGACCGACGACTACTTCGCCCAGAGCGAGAAGCACGCCCTG

ACGCCCGACGTGATGGCGCAACTGCGCTACATGAACTACACCGATTTCATCTCGCCGTTCTATAGCCGGGGCTGC

GCCTTCGATGCCTGGACGATGAAGAAGATGCCGCCCCGCATCATCAAGTATTCGCTCGCCTGGTACGCCTACGGC

CTGGCCAGCGTCGCCCTGACCGATCCGGCGATGCGGCCGGTGGCCGGCCATGCGATCGACATCGCGACCGCCAAG

ATGCATTGCAAGCAGGTCTGGGGCGACTGGGAGGAAGACGGCTTCGGCAGCGACCCGATCATCCGCGAAAACGTC

ATGTACAAGGGCCACCTGAACCTGATGTACGGTCTCTACCAGCTGATCACCGGCGACCGCAAGTACGAGAAGGAA

AACACCCGCCTGACCCAGATCATGCACAAGGAGATGAAGAGCAATCCGTACGCCGGCATCGTCTGCGAACCCGAC

AACTACTTCGTCCAGTGCAACTCGGTCGCCTACCTGAGCCTGTGGGTTTACGACCGGCTGCACGGCACCCAGTAC

AAGGCGGCAACCAGGGAGTGGCTGAAATTCATCGAGGACGAACTGATCGACCCGAAGACCGGCAGCTTCTATCTT

TCCTACCATCCCGAAACCGGTGCCGTGAAGCCGTGGCAGTCGGCCTACACGACCGCCTGGACGCTGGCCATGGTG

CATGGCATGGACCCGGCCTTCGCCGAACGCTATTACCCGAAATTCAAGGAAAGCTTCGTCGAGGTCTATGACGAC

GGCCGCAAGGCGCGCGTCCGCGAAATGACCGGCACCACCGACACCGACGGCGGCGTCGGCGCCGCGTCGGCGTTC

ATGCTGGTCCTGGCGCGTGAAATGGGCGACAAGCAACTGTTCGACCAGCTGCTGAACCACCTCGAACCGCCAGCC

GGACCGACGATCACTTCGGGCATCCTGCATTACGCGCAGCCGAGCAATCTGCTGTTCGACGAATTGCTGTTCGTC

GGCAAGGTGCATGTCGGCTTCGCCAAACTGCTCAATGCGCCGCCGGCACCGGCCCGCCCCGCCCTGCAAAAGAAG

AAATGA
```

SEQ ID NO: 51: Native, or unprocessed, LinD enzyme, designated LinD-12,
including signal peptide
```
MKKPRPLTVLAGLASAVLLALGTPATAVEPMPGRLASTDDYFAQSEKHALTPDVMAQLRYMNYTDFISPFYSRGC

AFDAWTMKKMPPRIIKYSLAWYAYGLASVALTDPAMRPVAGHAIDIATAKMHCKQVWGDWEEDGFGSDPIIRENV

MYKGHLNLMYGLYQLITGDRKYEKENTRLTRIMHKEMKSNPYAGIVCEPDNYFVQCNSVAYLSLWVYDRLHGTQY

KAATREWLKFIEDELIDPKTGSFYLSYHPETGAVKPWQSAYTTAWTLAMVHGMDPAFAERYYPKFKESFVEVYDD

GRKARVREMTGTTDTDGGVGAASAFMLVLAREMGDKQLFDQLLNHLEPPAGPTITSGILHYAQPSNLLFDELLFV

GKVHVGFAKLLNAPPAPARPALQKKK
```

SEQ ID NO: 52: Nucleic acid encoding processed (mature) LinD-12 LinD enzyme, no signal peptide
GTCGAGCCGATGCCCGGCCGCCTGGCCTCGACCGACGACTACTTCGCCCAGAGCGAGAAGCACGCCCTGACGCCC

GACGTGATGGCGCAACTGCGCTACATGAACTACACCGATTTCATCTCGCCGTTCTATAGCCGGGGCTGCGCCTTC

GATGCCTGGACGATGAAGAAGATGCCGCCCCGCATCATCAAGTATTCGCTCGCCTGGTACGCCTACGGCCTGGCC

AGCGTCGCCCTGACCGATCCGGCGATGCGGCCGGTGGCCGGCCATGCGATCGACATCGCGACCGCCAAGATGCAT

TGCAAGCAGGTCTGGGGCGACTGGGAGGAAGACGGCTTCGGCAGCGACCCGATCATCCGCGAAAACGTCATGTAC

AAGGGCCACCTGAACCTGATGTACGGTCTCTACCAGCTGATCACCGGCGACCGCAAGTACGAGAAGGAAAACACC

CGCCTGACCCGCATCATGCACAAGGAGATGAAGAGCAATCCGTACGCCGGCATCGTCTGCGAACCCGACAACTAC

TTCGTCCAGTGCAACTCGGTCGCCTACCTGAGCCTGTGGGTTTACGACCGGCTGCACGGCACCCAGTACAAGGCG

GCAACCAGGGAGTGGCTGAAATTCATCGAGGACGAACTGATCGACCCGAAGACCGGCAGCTTCTATCTTTCCTAC

CATCCCGAAACCGGTGCCGTGAAGCCGTGGCAGTCGGCCTACACGACCGCCTGGACGCTGGCCATGGTGCATGGC

ATGGACCCGGCCTTCGCCGAACGCTATTACCCGAAATTCAAGGAAAGCTTCGTCGAGGTCTATGACGACGGCCGC

AAGGCGCGCGTCCGCGAAATGACCGGCACCACCGACACCGACGGCGGCGTCGGCGCCGCGTCGGCGTTCATGCTG

GTCCTGGCGCGTGAAATGGGCGACAAGCAACTGTTCGACCAGCTGCTGAACCACCTCGAACCGCCAGCCGGACCG

ACGATCACTTCGGGCATCCTGCATTACGCGCAGCCGAGCAATCTGCTGTTCGACGAATTGCTGTTCGTCGGCAAG

GTGCATGTCGGCTTCGCCAAACTGCTCAATGCGCCGCCGGCACCGGCCCGCCCCGCCCTGCAAAAGAAGAAATGA

SEQ ID NO: 53: Processed (mature) LinD-12 LinD enzyme, no signal peptide.
VEPMPGRLASTDDYFAQSEKHALTPDVMAQLRYMNYTDFISPFYSRGCAFDAWTMKKMPPRIIKYSLAWYAYGLA

SVALTDPAMRPVAGHAIDIATAKMHCKQVWGDWEEDGFGSDPIIRENVMYKGHLNLMYGLYQLITGDRKYEKENT

RLTRIMHKEMKSNPYAGIVCEPDNYFVQCNSVAYLSLWVYDRLHGTQYKAATREWLKFIEDELIDPKTGSFYLSY

HPETGAVKPWQSAYTTAWTLAMVHGMDPAFAERYYPKFKESFVEVYDDGRKARVREMTGTTDTDGGVGAASAFML

VLAREMGDKQLFDQLLNHLEPPAGPTITSGILHYAQPSNLLFDELLFVGKVHVGFAKLLNAPPAPARPALQKKK

Linalool Dehydratase (LinD) from Metagenomics on Activated Sludge (Sierra Nev.); Designated LinD-13

SEQ ID NO: 54: Native nucleic acid encoding SEQ ID NO: 55, which is unprocessed and includes its signal peptide
ATGAAGAACATCCAAAAGGCAGCTGCCGCGCTGCCCGCCATCCTTGCCGCAGTGCTCGCGTTCAGTGCGCCGGCC

CATTCGGCGGACCTGCCGCCCGGCCGCCTCGCCTCGACCGAGGCCTACTTCGCCCAGCGCGAAAGGCAGGCCGTC

ACGCCCGACGTGATGGCCCACCTCGCCTACATGAACTACACCGATTTCGTCTCCCCCTTCTACAGCCGGGGCTGC

GCCTTCGATGCATGGACCATCAAGAAGACGCCGCAGCGGATCATCAAGTACTCGCTCGCCTTCTACGCCTACGGG

CTGGCCAGCGTCGCGCTCACCGATCCGCAGCTGCGTCCGCTCGCCGGCCACGCGATCGACATCGCCACCGCCAAG

ATGCAATGCAAGCAGGTCTGGGGAGACTGGGAGGAAGACGGGTTCGGCGACGATCCGATCGAGAAAGAGAACATC

ATGTACAAGGGCCACTTGAACCTGATGTACGGCCTTTACCAGCTGGTCACCGGCAACCGCCGGTACGAGAAGGAG

CACGCCCGCCTCACGCGGATCATCCACGACGAGATCAAGGCCAATCCCTACGCCGGCATCGTCTGCGAGCCGGAC

AACTATTTCGTCCAGTGCAACTCGGTCGCCTACCTGAGCCTGTGGGTCCATGACCGCCTGCACGGCACCGACTAC

CGGGCGGCGACGGCGGAGTGGCTGAAATTCATCGAGCACGACCTGATCGACCCGAAACACGGCGCCTTCCACCTG

TCCTACCATCCGGAATCCCACGCGGTGAAACCGTGGGTCTCCGCATACACCACGGCGTGGACGCTCGCCATGGTG

CACGGCATGGATCCCGCTTTCGCCGAGCGCTACTACCCCGCTTCAAGGAAACCTTCGTCGAGGTCTACGACGAT

GGCCGCAAGGCCCGGGTCCGCGAGACGACCGGCACCACCGACGCCGATGGCGGCGTCGGCGCGGCCTCCGCGTTC

ACCCTGCTGCTCGCCCGTGAGATGGGCGACCGGCAGCTCTTCGACCAGTTGCTGAACCACCTGGAGCCCCCGGCA

-continued

AGACCGCGGATCACCTCGGGCATCCTGGAATACGAGGCGCCCAGCAACCTGCTGTTCGACGAGTTGCTGTTCCTC

GCCAAGGTGCACGTCGGTTTCGGCCAGTTGCTGGAGGCCGGGTCGGCGCCACCTCGGCCGGGCCCCACCGGGGGG

AAATGA

SEQ ID NO: 55: Native, or unprocessed, LinD enzyme, designated LinD-13, including signal peptide
MKNIQKAAAALPAILAAVLAFSAPAHSADLPPGRLASTEAYFAQRERQAVTPDVMAHLAYMNYTDFVSPFYSRGC

AFDAWTIKKTPQRIIKYSLAFYAYGLASVALTDPQLRPLAGHAIDIATAKMQCKQVWGDWEEDGFGDDPIEKENI

MYKGHLNLMYGLYQLVTGNRRYEKEHARLTRIIHDEIKANPYAGIVCEPDNYFVQCNSVAYLSLWVHDRLHGTDY

RAATAEWLKFIEHDLIDPKHGAFHLSYHPESHAVKPWVSAYTTAWTLAMVHGMDPAFAERYYPRFKETFVEVYDD

GRKARVRETTGTTDADGGVGAASAFTLLLAREMGDRQLFDQLLNHLEPPARPRITSGILEYEAPSNLLFDELLFL

AKVHVGFGQLLEAGSAPPRPGPTGGK

SEQ ID NO: 56: Nucleic acid encoding processed (mature) LinD-13 LinD enzyme, no signal peptide
GCGGACCTGCCGCCCGGCCGCCTCGCCTCGACCGAGGCCTACTTCGCCCAGCGCGAAAGGCAGGCCGTCACGCCC

GACGTGATGGCCCACCTCGCCTACATGAACTACACCGATTTCGTCTCCCCCTTCTACAGCCGGGGCTGCGCCTTC

GATGCATGGACCATCAAGAAGACGCCGCAGCGGATCATCAAGTACTCGCTCGCCTTCTACGCCTACGGGCTGGCC

AGCGTCGCGCTCACCGATCCGCAGCTGCGTCCGCTCGCCGGCCACGCGATCGACATCGCCACCGCCAAGATGCAA

TGCAAGCAGGTCTGGGGAGACTGGGAGGAAGACGGGTTCGGCGACGATCCGATCGAGAAAGAGAACATCATGTAC

AAGGGCCACTTGAACCTGATGTACGGCCTTTACCAGCTGGTCACCGGCAACCGCCGGTACGAGAAGGAGCACGCC

CGCCTCACGCGGATCATCCACGACGAGATCAAGGCCAATCCCTACGCCGGCATCGTCTGCGAGCCGGACAACTAT

TTCGTCCAGTGCAACTCGGTCGCCTACCTGAGCCTGTGGGTCCATGACCGCCTGCACGGCACCGACTACCGGGCG

GCGACGGCGGAGTGGCTGAAATTCATCGAGCACGACCTGATCGACCCGAAACACGGCGCCTTCCACCTGTCCTAC

CATCCGGAATCCCACGCGGTGAAACCGTGGGTCTCCGCATACACCACGGCGTGGACGCTCGCCATGGTGCACGGC

ATGGATCCCGCTTTCGCCGAGCGCTACTACCCCCGCTTCAAGGAAACCTTCGTCGAGGTCTACGACGATGGCCGC

AAGGCCCGGGTCCGCGAGACGACCGGCACCACCGACGCCGATGGCGGCGTCGGCGCGGCCTCCGCGTTCACCCTG

CTGCTCGCCCGTGAGATGGGCGACCGGCAGCTCTTCGACCAGTTGCTGAACCACCTGGAGCCCCGGCAAGACCG

CGGATCACCTCGGGCATCCTGGAATACGAGGCGCCCAGCAACCTGCTGTTCGACGAGTTGCTGTTCCTCGCCAAG

GTGCACGTCGGTTTCGGCCAGTTGCTGGAGGCCGGGTCGGCGCCACCTCGGCCGGGCCCCACCGGGGGGAAATGA

SEQ ID NO: 57: Processed (mature) LinD-13 LinD enzyme, no signal peptide
ADLPPGRLASTEAYFAQRERQAVTPDVMAHLAYMNYTDFVSPFYSRGCAFDAWTIKKTPQRIIKYSLAFYAYGLA

SVALTDPQLRPLAGHAIDIATAKMQCKQVWGDWEEDGFGDDPIEKENIMYKGHLNLMYGLYQLVTGNRRYEKEHA

RLTRIIHDEIKANPYAGIVCEPDNYFVQCNSVAYLSLWVHDRLHGTDYRAATAEWLKFIEHDLIDPKHGAFHLSY

HPESHAVKPWVSAYTTAWTLAMVHGMDPAFAERYYPRFKETFVEVYDDGRKARVRETTGTTDADGGVGAASAFTL

LLAREMGDRQLFDQLLNHLEPPARPRITSGILEYEAPSNLLFDELLFLAKVHVGFGQLLEAGSAPPRPGPTGGK

Linalool Dehydratase (LinD) from Metagenomics on Soil Sample (Cottonwood River); Designated LinD-14.

SEQ ID NO: 58: Native nucleic acid encoding SEQ ID NO: 59, which is unprocessed and includes its signal peptide
ATGAAAAAATTCCGCCCCTTCGCGCCGCTGGCTGCCGCGCTCGCCGGCCTGATCGCCTGCGCCACGCCGGCCGCT

GCGGCCGAGCTGATGCCCGGCCGCCTGGCCTCGACCGAGGATTACTTCGCCCAGCGCGAAAAGCAGGCGCTGACG

CCCGACGTCATGGCCCACCTGCGCTACATGAACTACACCGATTTCATTTCGCCGTTCTACAGCCGGGGCTGCGCC

TTCGATGCCTGGGCGATGAAGAAGACGCCCAACCGCATCATCAAGTATTCGCTCGCCTGGTACGCCTACGGCCTG

GCCAGCGTCGCCCAGACCGATCCGGCCATGCGCCAGGTGGCCGGCCACGCGATCGACATCGCGACCGCCAAGATG

```
CACTGCAAGCAGGTCTGGGGCGACTGGGAGGAAGACCAGTTCGGCAGCGACCCGATCATCCGGGAAAACGTCATG

TACAAGGGTCACCTGAACCTGATGTACGGGCTTTACCAGATGGTGACCGGCGACCGCAAGTACGAGAAGGAAAAC

GCCAGGCTCACCAAAATCATGGCCAGGGAGATCAAGGCCAACCCCTACGCCGGCATCGTCTGCGAACCGGACAAC

TACTTCGTGCAATGCAATTCGGTCGCCTACCTGAGCCTGTGGGTCTATGACCGCCTGCACGGCACCCATTACAAG

GCGCTGACCAAGGACTGGCTGAAGTTCATCGAGGAAGAACTGATCGACCCGAAGACCGGCAGCTTCTATCTCTCC

TACCACCCCGAATCGGGCGCGGTGAAGCCGTGGCAGTCGGCCTACACGACCGCCTGGGCGCTGGCCATGGTGCAC

GGCATGGACCCGGCCTTCTCCGAGCGCTATTACCCGAAGTTCAAGGAAAACTTCGTCGAGGTCTATGACGACGGC

CGCAAGGCGCGCGTCCGCGAAACGACCGGCACGGCGGATACCGACGGCGGCGTCGGCGCAGCCTCGGCGTTCACG

CTGGTGCTAGCCCGCGAAATGGGCGACCAGAAACTCTTCGACCAGTTGCTGAACCATCTCGAACCCCCGGCCGGA

CCGAAAATCACCTCGGGCATCCTGCATTACGCGCAGCCGAGCAACCTGCTGTTCGACGAATTGCTGTTCGTCGGC

AAAGTGCATGTCGGCTTCGCCAATCTGCTCAATGCGCCGCCGGCACCGGCTCGCCCGGTCCTGCAAAAGAAGAAA

TGA

SEQ ID NO: 59: Native, or unprocessed, LinD enzyme, designated LinD-14,
including signal peptide
MKKFRPFAPLAAALAGLIACATPAAAAELMPGRLASTEDYFAQREKQALTPDVMAHLRYMNYTDFISPFYSRGCA

FDAWAMKKTPNRIIKYSLAWYAYGLASVAQTDPAMRQVAGHAIDIATAKMHCKQVWGDWEEDQFGSDPIIRENVM

YKGHLNLMYGLYQMVTGDRKYEKENARLTKIMAREIKANPYAGIVCEPDNYFVQCNSVAYLSLWVYDRLHGTHYK

ALTKDWLKFIEEELIDPKTGSFYLSYHPESGAVKPWQSAYTTAWALAMVHGMDPAFSERYYPKFKENFVEVYDDG

RKARVRETTGTADTDGGVGAASAFTLVLAREMGDQKLFDQLLNHLEPPAGPKITSGILHYAQPSNLLFDELLFVG

KVHVGFANLLNAPPAPARPVLQKKK

SEQ ID NO: 60: Nucleic acid encoding processed (mature) LinD-14 LinD enzyme,
no signal peptide
GCCGAGCTGATGCCCGGCCGCCTGGCCTCGACCGAGGATTACTTCGCCCAGCGCGAAAAGCAGGCGCTGACGCCC

GACGTCATGGCCCACCTGCGCTACATGAACTACACCGATTTCATTTCGCCGTTCTACAGCCGGGGCTGCGCCTTC

GATGCCTGGGCGATGAAGAAGACGCCCAACCGCATCATCAAGTATTCGCTCGCCTGGTACGCCTACGGCCTGGCC

AGCGTCGCCCAGACCGATCCGGCCATGCGCCAGGTGGCCGGCCACGCGATCGACATCGCGACCGCCAAGATGCAC

TGCAAGCAGGTCTGGGGCGACTGGGAGGAAGACCAGTTCGGCAGCGACCCGATCATCCGGGAAAACGTCATGTAC

AAGGGTCACCTGAACCTGATGTACGGGCTTTACCAGATGGTGACCGGCGACCGCAAGTACGAGAAGGAAAACGCC

AGGCTCACCAAAATCATGGCCAGGGAGATCAAGGCCAACCCCTACGCCGGCATCGTCTGCGAACCGGACAACTAC

TTCGTGCAATGCAATTCGGTCGCCTACCTGAGCCTGTGGGTCTATGACCGCCTGCACGGCACCCATTACAAGGCG

CTGACCAAGGACTGGCTGAAGTTCATCGAGGAAGAACTGATCGACCCGAAGACCGGCAGCTTCTATCTCTCCTAC

CACCCCGAATCGGGCGCGGTGAAGCCGTGGCAGTCGGCCTACACGACCGCCTGGGCGCTGGCCATGGTGCACGGC

ATGGACCCGGCCTTCTCCGAGCGCTATTACCCGAAGTTCAAGGAAAACTTCGTCGAGGTCTATGACGACGGCCGC

AAGGCGCGCGTCCGCGAAACGACCGGCACGGCGGATACCGACGGCGGCGTCGGCGCAGCCTCGGCGTTCACGCTG

GTGCTAGCCCGCGAAATGGGCGACCAGAAACTCTTCGACCAGTTGCTGAACCATCTCGAACCCCCGGCCGGACCG

AAAATCACCTCGGGCATCCTGCATTACGCGCAGCCGAGCAACCTGCTGTTCGACGAATTGCTGTTCGTCGGCAAA

GTGCATGTCGGCTTCGCCAATCTGCTCAATGCGCCGCCGGCACCGGCTCGCCCGGTCCTGCAAAAGAAGAAATGA

SEQ ID NO: 61: Processed (mature) LinD-14 LinD enzyme, no signal peptide
AELMPGRLASTEDYFAQREKQALTPDVMAHLRYMNYTDFISPFYSRGCAFDAWAMKKTPNRIIKYSLAWYAYGLA

SVAQTDPAMRQVAGHAIDIATAKMHCKQVWGDWEEDQFGSDPIIRENVMYKGHLNLMYGLYQMVTGDRKYEKENA

RLTKIMAREIKANPYAGIVCEPDNYFVQCNSVAYLSLWVYDRLHGTHYKALTKDWLKFIEEELIDPKTGSFYLSY

HPESGAVKPWQSAYTTAWALAMVHGMDPAFSERYYPKFKENFVEVYDDGRKARVRETTGTADTDGGVGAASAFTL

VLAREMGDQKLFDQLLNHLEPPAGPKITSGILHYAQPSNLLFDELLFVGKVHVGFANLLNAPPAPARPVLQKKK
```

SEQ ID NO: 62: Nucleic acid encoding native LinD-1 LinD enzyme with N-terminal
His-tag and linker (SEQ ID NO: 63)
ATGGGCAGCAGCCATCATCATCATCATCACAGCAGCGGCCTGGTGCCGCGCGGCAGCCATATGCGCTTTACCCTG

AAAACGACCGCCATTGTTAGTGCCGCCGCCCTGCTGGCTGGCTTTGGTCCGCCGCCGCGTGCTGCCGAACTGCCG

CCGGGTCGCCTGGCAACCACGGAAGATTATTTTGCGCAGCAAGCCAAACAGGCAGTCACCCCGGATGTGATGGCT

CAACTGGCGTATATGAACTACATTGACTTTATCAGTCCGTTCTATTCCCGTGGCTGCTCATTTGAAGCCTGGGAA

CTGAAACATACGCCGCAGCGCGTTATTAAATACTCCATCGCCTTCTATGCATACGGTCTGGCTTCAGTCGCGCTG

ATTGATCCGAAACTGCGTGCACTGGCAGGTCACGATCTGGACATCGCAGTGAGCAAAATGAAATGTAAACGCGTT

TGGGGTGATTGGGAAGAAGACGGCTTCGGTACCGATCCGATCGAAAAAGAAAACATCATGTACAAAGGCCATCTG

AATCTGATGTATGGTCTGTACCAGCTGGTGACCGGCTCTCGTCGCTACGAAGCCGAACATGCACACCTGACGCGT

ATTATCCACGATGAAATTGCGGCCAATCCGTTTGCGGGTATCGTCTGCGAACCGGACAACTATTTCGTTCAGTGT

AATTCGGTCGCCTATCTGAGCCTGTGGGTTTACGATCGTCTGCATGGTACCGACTACCGTGCAGCTACGCGTGCA

TGGCTGGATTTTATTCAAAAAGATCTGATCGACCCGGAACGCGGTGCATTCTATCTGTCTTACCATCCGGAAAGT

GGCGCTGTGAAACCGTGGATTTCTGCTTATACCACGGCGTGGACCCTGGCCATGGTTCACGGTATGGACCCGGCA

TTTAGTGAACGTTATTACCCGCGCTTTAAACAGACGTTCGTGGAAGTTTACGATGAAGGCCGTAAAGCTCGTGTC

CGCGAAACCGCCGGTACGGATGACGCTGACGGCGGTGTGGGTCTGGCAAGCGCTTTTACCCTGCTGCTGGCCCGC

GAAATGGGTGATCAGCAACTGTTCGACCAACTGCTGAACCACCTGGAACCGCCGGCAAAACCGTCGATCGTGAGC

GCATCTCTGCGTTATGAACATCCGGGCAGCCTGCTGTTTGATGAACTGCTGTTCCTGGCGAAAGTTCACGCTGGC

TTTGGTGCCCTGCTGCGTATGCCGCCGCCGGCTGCTAAACTGGCTGGTAAATAA

SEQ ID NO: 63: Native full length LinD-1 LinD enzyme with N-terminal His-tag
and linker
MGSSHHHHHHSSGLVPRGSHMRFTLKTTAIVSAAALLAGFGPPPRAAELPPGRLATTEDYFAQQAKQAVTPDVMA

QLAYMNYIDFISPFYSRGCSFEAWELKHTPQRVIKYSIAFYAYGLASVALIDPKLRALAGHDLDIAVSKMKCKRV

WGDWEEDGFGTDPIEKENTMYKGHLNLMYGLYQLVTGSRRYEAEHAHLTRIIHDEIAANPFAGIVCEPDNYFVQC

NSVAYLSLWVYDRLHGTDYRAATRAWLDFIQKDLIDPERGAFYLSYHPESGAVKPWISAYTTAWTLAMVHGMDPA

FSERYYPRFKQTFVEVYDEGRKARVRETAGTDDADGGVGLASAFTLLLAREMGDQQLFDQLLNHLEPPAKPSIVS

ASLRYEHPGSLLFDELLFLAKVHAGFGALLRMPPPAAKLAGK

SEQ ID NO: 64
MMRFTLKTTAIVSAAALLAGFGPPPRAAELPPGRLATTEDYFAQQAKQAVTPDVMAQLAY

MNYIDFISPFYSRGCSFEAWELKHTPQRVIKYSIAFYAYGLASVALIDPKLRALAGHDLD

IAVSKMKCKRVWGDWEEDGFGTDPIEKENIMYKGHLNLMYGLYQLVTGSRRYEAEHAHLT

RIIHDEIAANPFAGIVCEPDNYFVQCNSVAYLSLWVYDRLHGTDYRAATRAWLDFIQKDL

IDPERGAFYLSYHPESGAVKPWISAYTTAWTLAMVHGMDPAFSERYYPRFKQTFVEVYDE

GRKARVRETAGTDDADGGVGLASAFTLLLAREMGDQQLFDQLLNHLEPPAKPSIVSASLR

YEHPGSLLFDELLFLAKVHAGFGALLRMPPPAAKLAGK

SEQ ID NO: 65
MMRFTLKTTAIVSAAALLAGFGPPPRAAELPPGRLATTEDYFAQQAKQAVTPDVMAQLAY

MNYIDFISPFYSRGCSFEAWELKHTPQRVIKYSIAFYAYGLASVALIDPKLRALAGHDLD

IAVSKMKCKRVWGDWEEDGFGTDPIEKENIMYKGHLNLMYGLYQLVTGSRRYEAEHAHLT

RIIHDEIAANPFAGIVCEPDNYFVQCNSVAYLSLWVYDRLHGTDYRAATRAWLDFIQKDL

IDPERGAFYLSYHPESGAVKPWISAYTTAWTLAMVHGMDPAFSERYYPRFKQTFVEVYDE

GRKARVRETAGTDDADGGVGLASAFTLLLAREMGDQQLFDQLLNHLEPPAKPSIVSASLR

YEHPGSLLFDELLFLAKVHAGFGALLRMPPPAAKLAGKGSLEHHHHHH

-continued

SEQ ID NO: 66

MAELPPGRLATTEDYFAQQAKQAVTPDVMAQLAYMNYIDFISPFYSRGCSFEAWELKHTP

QRVIKYSIAFYAYGLASVALIDPKLRALAGHDLDIAVSKMKCKRVWGDWEEDGFGTDPIE

KENIMYKGHLNLMYGLYQLVTGSRRYEAEHAHLTRIIHDEIAANPFAGIVCEPDNYFVQC

NSVAYLSLWVYDRLHGTDYRAATRAWLDFIQKDLIDPERGAFYLSYHPESGAVKPWISAY

TTAWTLAMVHGMDPAFSERYYPRFKQTFVEVYDEGRKARVRETAGTDDADGGVGLASAFT

LLLAREMGDQQLFDQLLNHLEPPAKPSIVSASLRYEHPGSLLFDELLFLAKVHAGFGALL

RMPPPAAKLAGKGSLEHHHHHH

SEQ ID NO: 67

MRFTLKTTAIVSAAALLAGFGPPPRAAELPPGRLATTEDYFAQQAKQAVTPDVMAQLAYM

NYIDFISPFYSRGCSFEAWELKHTPQRVIKYSIAFYAYGLASVALIDPKLRALAGHDLDI

AVSKMKCKRVWGDWEEDGFGTDPIEKENIMYKGHLNLMYGLYQLVTGSRRYEAEHAHLTR

IIHDEIAANPFAGIVCEPDNYFVQCNSVAYLSLWVYDRLHGTDYRAATRAWLDFIQKDLI

DPERGAFYLSYHPESGAVKPWISAYTTAWTLAMVHGMDPAFSERYYPRFKQTFVEVYDEG

RKARVRETAGTDDADGGVGLASAFTLLLAREMGDQQLFDQLLNHLEPPAKPSIVSASLRY

EHPGSLLFDELLFLAKVHAGFGALLRMPPPAAKLAGK

SEQ ID NO: 68

MAELPPGRLATTEDYFAQQAKQAVTPDVMAQLAYMNYIDFISPFYSRGCSFEAWELKHTP

QRVIKYSIAFYAYGLASVALIDPKLRALAGHDLDIAVSKMKCKRVWGDWEEDGFGTDPIE

KENIMYKGHLNLMYGLYQLVTGSRRYEAEHAHLTRIIHDEIAANPFAGIVCEPDNYFVQC

NSVAYLSLWVYDRLHGTDYRAATRAWLDFIQKDLIDPERGAFYLSYHPESGAVKPWISAY

TTAWTLAMVHGMDPAFSERYYPRFKQTFVEVYDEGRKARVRETAGTDDADGGVGLASAFT

LLLAREMGDQQLFDQLLNHLEPPAKPSIVSASLRYEHPGSLLFDELLFLAKVHAGFGALL

RMPPPAAKLAGKGSLE

NUMBERED EMBODIMENTS OF THE DISCLOSURE

Particular subject matter contemplated by the present disclosure is set out in the below numbered embodiments.

1. A recombinant microorganism capable of producing one or more primary alkenes, each primary alkene having a structure as shown in Structure B, from one or more saturated primary or secondary alcohols, each primary or secondary alcohol having a structure as shown in Structure A,

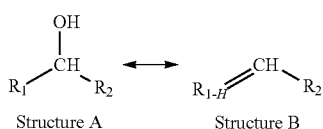

Structure A        Structure B wherein $R_1=C_nH_{2n+1}$ with $1 \leq n \leq 1$; $R_2=C_mH_{2m+1}$ with $0 \leq m \leq 10$ and $n+m \leq 11$; and
wherein the recombinant microorganism expresses one or more exogenous nucleic acid molecules encoding one or more linalool dehydratases/isomerases that catalyzes the conversion of the one or more saturated primary or secondary alcohols to one or more corresponding primary alkenes.

2. The recombinant microorganism of embodiment 1, wherein the recombinant microorganism further expresses one or more endogenous or exogenous nucleic acid molecules encoding one or more enzymes for the production of the one or more saturated primary or secondary alcohols from a renewable feedstock.

3. The recombinant microorganism of embodiment 2, wherein the renewable feedstock is one or more sugars.

4. The recombinant microorganism of any one of embodiments 1-3, wherein the recombinant microorganism is capable of co-producing monoethylene glycol (MEG) and isopropanol from exogenous D-xylose, and wherein the recombinant microorganism expresses one or more of the following:

(a) at least one endogenous or exogenous nucleic acid molecule encoding a D-tagatose 3-epimerase that catalyzes the conversion of D-xylulose to D-ribulose;

(b) at least one endogenous or exogenous nucleic acid molecule encoding a D-ribulokinase that catalyzes the conversion of D-ribulose from (a) to D-ribulose-1-phosphate;

(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

(d) at least one endogenous or exogenous nucleic acid molecule encoding a glycolaldehyde reductase that catalyzes the conversion of glycolaldehyde from (c) to mono ethylene glycol (MEG);

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one endogenous or exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

5. The recombinant microorganism of any one of embodiments 1-3, wherein the recombinant microorganism is capable of co-producing monoethylene glycol (MEG) and isopropanol from exogenous D-xylose, and wherein the recombinant microorganism expresses one or more of the following:

(a) at least one endogenous or exogenous nucleic acid molecule encoding a D-xylulose 1-kinase that catalyzes the conversion of D-xylulose to D-xylulose-1-phosphate;

(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);

(c) at least one endogenous or exogenous nucleic acid molecule encoding a glycolaldehyde reductase that catalyzes the conversion of glycolaldehyde from (b) to MEG;

(d) at least one endogenous or exogenous nucleic acid molecule encoding a thiolase that catalyzes the conversion of acetyl-CoA to acetoacetyl-CoA;

(e) at least one endogenous or exogenous nucleic acid molecule encoding an acetate:acetoacetyl-CoA transferase or hydrolase that catalyzes the conversion of acetoacetyl-CoA from (d) to acetoacetate;

(f) at least one endogenous or exogenous nucleic acid molecule encoding an acetoacetate decarboxylase that catalyzes the conversion of acetoacetate from (e) to acetone; and/or (g) at least one endogenous or exogenous nucleic acid molecule encoding a secondary alcohol dehydrogenase that catalyzes the conversion of acetone from (f) to isopropanol.

6. The recombinant microorganism of any one of embodiments 1-5, wherein the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

7. The recombinant microorganism of any one of embodiments 1-6, wherein an endogenous D-xylose isomerase catalyzes the conversion of D-xylose to D-xylulose.

8. The recombinant microorganism of any one of embodiments 1-3, wherein the recombinant microorganism is capable of co-producing monoethylene glycol (MEG) and isopropanol from exogenous D-xylose, and wherein the recombinant microorganism expresses one or more of the following:

(a) at least one endogenous or exogenous nucleic acid molecule encoding a xylose dehydrogenase that catalyzes the conversion of D-xylose to D-xylonolactone;

(b) at least one endogenous or exogenous nucleic acid molecule encoding a xylonolactonase that catalyzes the conversion of D-xylonolactone from (a) to D-xylonate;

(c) at least one endogenous or exogenous nucleic acid molecule encoding a xylonate dehydratase that catalyzes the conversion of D-xylonate from (b) to 2-keto-3-deoxy-xylonate;

(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;

(e) at least one endogenous or exogenous nucleic acid molecule encoding a glycolaldehyde reductase that catalyzes the conversion of glycolaldehyde from (d) to MEG;

(f) at least one exogenous nucleic acid molecule encoding a thiolase that catalyzes the conversion of acetyl-CoA to acetoacetyl-CoA;

(g) at least one endogenous or exogenous nucleic acid molecule encoding an acetate:acetoacetyl-CoA transferase or hydrolase that catalyzes the conversion of acetoacetyl-CoA from (f) to acetoacetate;

(h) at least one exogenous nucleic acid molecule encoding an acetoacetate decarboxylase that catalyzes the conversion of acetoacetate from (g) to acetone; and/or (i) at least one endogenous or exogenous nucleic acid molecule encoding a secondary alcohol dehydrogenase that catalyzes the conversion of acetone from (h) to isopropanol.

9. The recombinant microorganism of any one of embodiments 1-3, wherein the recombinant microorganism is capable of co-producing monoethylene glycol (MEG) and isopropanol from exogenous D-xylose, and wherein the recombinant microorganism expresses one or more of the following:

(a) at least one endogenous or exogenous nucleic acid molecule encoding a xylose dehydrogenase that catalyzes the conversion of D-xylose to D-xylonate;

(b) at least one endogenous or exogenous nucleic acid molecule encoding a xylonate dehydratase that catalyzes the conversion of D-xylonate from (a) to 2-keto-3-deoxy-xylonate;

(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;

(d) at least one exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

10. The recombinant microorganism of any one of embodiments 1-3 or 8-9, wherein the recombinant microorganism further comprises one or more modifications selected from the group consisting of:

(a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

11. The recombinant microorganism of any one of embodiments 1-3, wherein the recombinant microorganism is capable of co-producing monoethylene glycol (MEG) and isopropanol from exogenous D-xylose and glucose, wherein the recombinant microorganism expresses one or more of the following:

(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;

(b) at least one exogenous nucleic acid molecule encoding a D-xylose isomerase that catalyzes the conversion of D-xylose to D-xylulose, and wherein the microorganism further expresses one or more of the following:

(c) at least one endogenous or exogenous nucleic acid molecule encoding a D-tagatose 3-epimerase that catalyzes the conversion of D-xylulose from (a) or (b) to D-ribulose;

(d) at least one endogenous or exogenous nucleic acid molecule encoding a D-ribulokinase that catalyzes the conversion of D-ribulose from (c) to D-ribulose-1-phosphate;

(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);

(f) at least one endogenous or exogenous nucleic acid molecule encoding a glycolaldehyde reductase or methylglyoxal reductase that catalyzes the conversion of glycolaldehyde from (e) to MEG;

(g) at least one endogenous or exogenous nucleic acid molecule encoding a thiolase that catalyzes the conversion of acetyl-CoA to acetoacetyl-CoA;

(h) at least one endogenous or exogenous nucleic acid molecule encoding an acetate:acetoacetyl-CoA transferase or hydrolase that catalyzes the conversion of acetoacetyl-CoA from (g) to acetoacetate;

(i) at least one endogenous or exogenous nucleic acid molecule encoding an acetoacetate decarboxylase that catalyzes the conversion of acetoacetate from (h) to acetone; and/or (j) at least one endogenous or exogenous nucleic acid molecule encoding a secondary alcohol dehydrogenase that catalyzes the conversion of acetone from (i) to isopropanol.

12. The recombinant microorganism of embodiment 11, wherein the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate; and (b) a deletion, insertion, or loss of function mutation in a gene encoding an alkaline phosphatase that catalyzes the conversion of D-xylulose-5-phosphate to D-xylulose.

13. The recombinant microorganism of any one of embodiments 1-12, wherein the DHAP is converted to acetyl-CoA through the endogenous glycolysis pathway in the microorganism.

14. The recombinant microorganism of any one of embodiments 1-3, wherein the recombinant microorganism is capable of producing isopropanol, and wherein the recombinant microorganism expresses one or more of the following:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and/or (d) at least one endogenous or exogenous nucleic acid molecule encoding a secondary alcohol dehydrogenase that catalyzes the conversion of acetone from (c) to isopropanol.

15. The recombinant microorganism of embodiment 14 further comprising a deletion, insertion, or loss of function mutation in a gene encoding a lactate dehydrogenase that catalyzes the conversion of pyruvate to lactate.

16. The recombinant microorganism of any one of embodiments 1-3, wherein the recombinant microorganism is capable of co-producing n-propanol and isopropanol, wherein the recombinant microorganism expresses one or more of the following:

(a) at least one endogenous or exogenous nucleic acid molecule encoding a methylglyoxal synthase that catalyzes the conversion of dihydroxyacetone phosphate (DHAP) to methylglyoxal;

(b) at least one endogenous or exogenous nucleic acid molecule encoding an aldo-keto reductase that catalyzes the conversion of methylglyoxal from (a) to acetol;

(c) at least one endogenous or exogenous nucleic acid molecule encoding a glyoxylate reductase, a methylglyoxal dehydrogenase or an aldehyde dehydrogenase that catalyzes the conversion of methylglyoxal from (a) to lactaldehyde;

(d) at least one endogenous or exogenous nucleic acid molecule encoding an aldo-keto reductase that catalyzes the conversion of acetol from (b) to 1,2-propanediol;

(e) at least one endogenous or exogenous nucleic acid molecule encoding an aldehyde reductase that catalyzes the conversion of lactaldehyde from (c) to 1,2-propanediol;

(f) at least one endogenous or exogenous nucleic acid molecule encoding a diol-dehydratase that catalyzes the conversion of 1,2-propanediol from (d) or (e) to propanal;

(g) at least one endogenous or exogenous nucleic acid molecule encoding a dehydrogenase that catalyzes the conversion of propanal from (f) to n-propanol;

(h) at least one endogenous or exogenous nucleic acid molecule encoding a pyruvate formate lyase that catalyzes the conversion of pyruvate to acetyl-CoA;

(i) at least one endogenous or exogenous nucleic acid molecule encoding a thiolase that catalyzes the conversion of acetyl-CoA from (h) to acetoacetyl-CoA;

(j) at least one endogenous or exogenous nucleic acid molecule encoding an acetate:acetoacetyl-CoA transferase or hydrolase that catalyzes the conversion of acetoacetyl-CoA from (i) to acetoacetate;

(k) at least one endogenous or exogenous nucleic acid molecule encoding an acetoacetate decarboxylase that catalyzes the conversion of acetoacetate from (j) to acetone; and/or (l) at least one endogenous or exogenous nucleic acid molecule encoding a secondary alcohol dehydrogenase that catalyzes the conversion of acetone from (k) to isopropanol;

and wherein the DHAP and pyruvate are produced from glycolysis in the microorganism.

17. The recombinant microorganism of embodiment 16 further comprising one or more modifications selected from the group consisting of:

(a) a deletion, insertion, or loss of function mutation in a gene encoding an acetaldehyde dehydrogenase that catalyzes the conversion of lactaldehyde to lactate; and (b) a deletion, insertion, or loss of function mutation in a gene encoding a lactate dehydrogenase that catalyzes the conversion of pyruvate to lactate.

18. The recombinant microorganism of any one of embodiments 1-3, wherein the recombinant microorganism is capable of co-producing acetone, butanol and ethanol, wherein the recombinant microorganism expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetaldehyde from (e) to ethanol or butyraldehyde from (i) to butanol;

and wherein the pyruvate is produced from glycolysis in the microorganism.

19. The recombinant microorganism of embodiment 18 further comprising a deletion, insertion, or loss of function mutation in a gene encoding a lactate dehydrogenase that catalyzes the conversion of pyruvate to lactate.

20. The recombinant microorganism of any one of embodiments 1-3, wherein the recombinant microorganism is capable of co-producing isopropanol, butanol and ethanol, wherein the recombinant microorganism expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetone from (d) to isopropanol, acetaldehyde from (e) to ethanol or butyraldehyde from (i) to butanol;

and wherein the pyruvate is produced from glycolysis in the microorganism.

21. The recombinant microorganism of embodiment 20 further comprising a deletion, insertion, or loss of function mutation in a gene encoding a butyrate kinase that catalyzes the conversion of butyryl phosphate to butyrate.

22. The recombinant microorganism of any one of embodiments 1-3, wherein the recombinant microorganism is capable of producing isobutanol, wherein the recombinant microorganism expresses one or more of the following:

(a) at least one endogenous or exogenous nucleic acid molecule encoding an acetohydroxy acid synthase that catalyzes the conversion of pyruvate to acetolactate;

(b) at least one endogenous or exogenous nucleic acid molecule encoding an acetohydroxy acid isomeroreductase that catalyzes the conversion of acetolactate from (a) to 2,3-dihydroxy-isovalerate;

(c) at least one endogenous or exogenous nucleic acid molecule encoding a dihydroxy-acid dehydratase that catalyzes the conversion of 2,3-dihydroxy-isovalerate from (b) to α-keto-isovalerate;

(d) at least one endogenous or exogenous nucleic acid molecule encoding a 2-keto-acid decarboxylase that catalyzes the conversion of α-keto-isovalerate from (c) to isobutyraldehyde; and/or (e) at least one endogenous or exogenous nucleic acid molecule encoding an alcohol dehydrogenase that catalyzes the conversion of isobutyraldehyde from (d) to isobutanol; and wherein the pyruvate is produced from glycolysis in the microorganism. 23. The recombinant microorganism of embodiment 22 further comprising one or more modifications selected from the group consisting of:

(a) a deletion, insertion, or loss of function mutation in a gene encoding an ethanol dehydrogenase that catalyzes the conversion of acetaldehyde to ethanol; and (b) a deletion, insertion, or loss of function mutation in a gene encoding a lactate dehydrogenase that catalyzes the conversion of pyruvate to lactate.

24. The recombinant microorganism of any one of embodiments 1-3, wherein the corresponding primary alkene is propene and the primary alcohol is 1-propanol.

25. The recombinant microorganism of any one of embodiments 1-3, wherein the corresponding primary alkene is propene and the secondary alcohol is 2-propanol.

26. The recombinant microorganism of any one of embodiments 1-3, wherein the corresponding primary alkene is butene and the primary alcohol is 1-butanol.

27. The recombinant microorganism of any one of embodiments 1-3, wherein the corresponding primary alkene is butene and the secondary alcohol is 2-butanol.

28. The recombinant microorganism of any one of embodiments 1-3, wherein the one or more primary alkenes is produced from the one or more saturated primary or secondary alcohols via a single enzymatic step.

29. The recombinant microorganism of any one of embodiments 1-3, wherein the production of one or more corresponding primary alkenes from one or more saturated primary or secondary alcohols comprises a dehydration step.

30. The recombinant microorganism of embodiment 29, wherein the dehydration step is substrate activation independent.

31. The recombinant microorganism of embodiment 29, wherein the dehydration step is cofactor independent.

32. The recombinant microorganism of any one of embodiments 1-3, wherein the linalool dehydratase/isomerase is obtained from a microorganism selected from the group consisting of *Castellaniella defragrans* species.

33. The recombinant microorganism of any one of embodiments 1-3, wherein the linalool dehydratase/isomerase comprises an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63.

34. The recombinant microorganism of any one of embodiments 1-3, wherein the linalool dehydratase/isomerase is encoded by a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62.

35. The recombinant microorganism of any one of embodiments 1-3, wherein the linalool dehydratase/isomerase is LinD.

36. A method of producing one or more primary alkenes, each primary alkene having a structure as shown in Structure B, from one or more saturated primary or secondary alcohols, each primary or secondary alcohol having a structure as shown in Structure A,

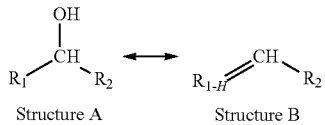

Structure A        Structure B wherein $R_1=C_nH_{2n+1}$ with $1 \leq n \leq 11$; $R_2=C_mH_{2m+1}$ with $0 \leq m \leq 10$ and $n+m \leq 11$; and wherein the method comprises expressing in a recombinant microorganism one or more exogenous nucleic acid molecules encoding one or more linalool dehydratase/isomerases that catalyzes the conversion of the one or more saturated primary or secondary alcohols to one or more corresponding primary alkenes.

37. The method of embodiment 36, further comprising expressing in the recombinant microorganism one or more endogenous or exogenous nucleic acid molecules encoding one or more enzymes for the production of the one or more saturated primary or secondary alcohols from a renewable feedstock.

38. The method of embodiment 37, wherein the renewable feedstock is one or more sugars.

39. The method of any one of embodiments 36-38, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a D-tagatose 3-epimerase that catalyzes the conversion of D-xylulose to D-ribulose;

(b) at least one endogenous or exogenous nucleic acid molecule encoding a D-ribulokinase that catalyzes the conversion of D-ribulose from (a) to D-ribulose-1-phosphate;

(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

(d) at least one endogenous or exogenous nucleic acid molecule encoding a glycolaldehyde reductase that catalyzes the conversion of glycolaldehyde from (c) to mono ethylene glycol (MEG);

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one endogenous or exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

40. The method of any one of embodiments 36-38, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a D-xylulose 1-kinase that catalyzes the conversion of D-xylulose to D-xylulose-1-phosphate;

(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);

(c) at least one endogenous or exogenous nucleic acid molecule encoding a glycolaldehyde reductase that catalyzes the conversion of glycolaldehyde from (b) to MEG;

(d) at least one endogenous or exogenous nucleic acid molecule encoding a thiolase that catalyzes the conversion of acetyl-CoA to acetoacetyl-CoA;

(e) at least one endogenous or exogenous nucleic acid molecule encoding an acetate:acetoacetyl-CoA transferase or hydrolase that catalyzes the conversion of acetoacetyl-CoA from (d) to acetoacetate;

(f) at least one endogenous or exogenous nucleic acid molecule encoding an acetoacetate decarboxylase that catalyzes the conversion of acetoacetate from (e) to acetone; and/or (g) at least one endogenous or exogenous nucleic acid molecule encoding a secondary alcohol dehydrogenase that catalyzes the conversion of acetone from (f) to isopropanol.

41. The method of any one of embodiments 36-40, wherein the method further comprises introducing into the recombinant microorganism one or more modifications selected from the group consisting of:

(a) a deletion, insertion, or loss of function mutation in a gene encoding a D-xylulose-5-kinase that catalyzes the conversion of D-xylulose to D-xylulose-5-phosphate;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

42. The method of any one of embodiments 36-41, wherein an endogenous D-xylose isomerase catalyzes the conversion of D-xylose to D-xylulose.

43. The method of any one of embodiments 36-38, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a xylose dehydrogenase that catalyzes the conversion of D-xylose to D-xylonolactone;

(b) at least one endogenous or exogenous nucleic acid molecule encoding a xylonolactonase that catalyzes the conversion of D-xylonolactone from (a) to D-xylonate;

(c) at least one endogenous or exogenous nucleic acid molecule encoding a xylonate dehydratase that catalyzes the conversion of D-xylonate from (b) to 2-keto-3-deoxy-xylonate;

(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;

(e) at least one endogenous or exogenous nucleic acid molecule encoding a glycolaldehyde reductase that catalyzes the conversion of glycolaldehyde from (d) to MEG;

(f) at least one exogenous nucleic acid molecule encoding a thiolase that catalyzes the conversion of acetyl-CoA to acetoacetyl-CoA;

(g) at least one endogenous or exogenous nucleic acid molecule encoding an acetate:acetoacetyl-CoA transferase or hydrolase that catalyzes the conversion of acetoacetyl-CoA from (f) to acetoacetate;

(h) at least one exogenous nucleic acid molecule encoding an acetoacetate decarboxylase that catalyzes the conversion of acetoacetate from (g) to acetone; and/or (i) at least one endogenous or exogenous nucleic acid molecule encoding a secondary alcohol dehydrogenase that catalyzes the conversion of acetone from (h) to isopropanol.

44. The method of any one of embodiments 36-38, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a xylose dehydrogenase that catalyzes the conversion of D-xylose to D-xylonate;

(b) at least one endogenous or exogenous nucleic acid molecule encoding a xylonate dehydratase that catalyzes the conversion of D-xylonate from (a) to 2-keto-3-deoxy-xylonate;

(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;

(d) at least one exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

45. The method of any one of embodiments 36-38 or 43-44, wherein the method further comprises introducing into the recombinant microorganism one or more modifications selected from the group consisting of:

(a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

46. The method of any one of embodiments 36-38, wherein the recombinant microorganism is capable of co-producing monoethylene glycol (MEG) and isopropanol from exogenous D-xylose and glucose, wherein the recombinant microorganism expresses one or more of the following:

(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;

(b) at least one exogenous nucleic acid molecule encoding a D-xylose isomerase that catalyzes the conversion of D-xylose to D-xylulose, and wherein the microorganism further expresses one or more of the following:

(c) at least one endogenous or exogenous nucleic acid molecule encoding a D-tagatose 3-epimerase that catalyzes the conversion of D-xylulose from (a) or (b) to D-ribulose;

(d) at least one endogenous or exogenous nucleic acid molecule encoding a D-ribulokinase that catalyzes the conversion of D-ribulose from (c) to D-ribulose-1-phosphate;

(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);

(f) at least one endogenous or exogenous nucleic acid molecule encoding a glycolaldehyde reductase or methylglyoxal reductase that catalyzes the conversion of glycolaldehyde from (e) to MEG;

(g) at least one endogenous or exogenous nucleic acid molecule encoding a thiolase that catalyzes the conversion of acetyl-CoA to acetoacetyl-CoA;

(h) at least one endogenous or exogenous nucleic acid molecule encoding an acetate:acetoacetyl-CoA transferase or hydrolase that catalyzes the conversion of acetoacetyl-CoA from (g) to acetoacetate;

(i) at least one endogenous or exogenous nucleic acid molecule encoding an acetoacetate decarboxylase that catalyzes the conversion of acetoacetate from (h) to acetone; and/or (j) at least one endogenous or exogenous nucleic acid molecule encoding a secondary alcohol dehydrogenase that catalyzes the conversion of acetone from (i) to isopropanol.

47. The method of embodiment 46, wherein the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate; and (b) a deletion, insertion, or loss of function mutation in a gene encoding an alkaline phosphatase that catalyzes the conversion of D-xylulose-5-phosphate to D-xylulose.

48. The method of any one of embodiments 36-47, wherein the DHAP is converted to acetyl-CoA through the endogenous glycolysis pathway in the microorganism.

49. The method of any one of embodiments 36-38, wherein the recombinant microorganism is capable of producing isopropanol, and wherein the recombinant microorganism expresses one or more of the following:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and/or (d) at least one endogenous or exogenous nucleic acid molecule encoding a secondary alcohol dehydrogenase that catalyzes the conversion of acetone from (c) to isopropanol.

50. The method of embodiment 49 further comprising a deletion, insertion, or loss of function mutation in a gene encoding a lactate dehydrogenase that catalyzes the conversion of pyruvate to lactate.

51. The method of any one of embodiments 36-38, wherein the recombinant microorganism is capable of co-producing n-propanol and isopropanol, wherein the recombinant microorganism expresses one or more of the following:

(a) at least one endogenous or exogenous nucleic acid molecule encoding a methylglyoxal synthase that catalyzes the conversion of dihydroxyacetone phosphate (DHAP) to methylglyoxal;

(b) at least one endogenous or exogenous nucleic acid molecule encoding an aldo-keto reductase that catalyzes the conversion of methylglyoxal from (a) to acetol;

(c) at least one endogenous or exogenous nucleic acid molecule encoding a glyoxylate reductase, a methylglyoxal dehydrogenase or an aldehyde dehydrogenase that catalyzes the conversion of methylglyoxal from (a) to lactaldehyde;

(d) at least one endogenous or exogenous nucleic acid molecule encoding an aldo-keto reductase that catalyzes the conversion of acetol from (b) to 1,2-propanediol;

(e) at least one endogenous or exogenous nucleic acid molecule encoding an aldehyde reductase that catalyzes the conversion of lactaldehyde from (c) to 1,2-propanediol;

(f) at least one endogenous or exogenous nucleic acid molecule encoding a diol-dehydratase that catalyzes the conversion of 1,2-propanediol from (d) or (e) to propanal;

(g) at least one endogenous or exogenous nucleic acid molecule encoding a dehydrogenase that catalyzes the conversion of propanal from (f) to n-propanol;

(h) at least one endogenous or exogenous nucleic acid molecule encoding a pyruvate formate lyase that catalyzes the conversion of pyruvate to acetyl-CoA;

(i) at least one endogenous or exogenous nucleic acid molecule encoding a thiolase that catalyzes the conversion of acetyl-CoA from (h) to acetoacetyl-CoA;

(j) at least one endogenous or exogenous nucleic acid molecule encoding an acetate:acetoacetyl-CoA transferase or hydrolase that catalyzes the conversion of acetoacetyl-CoA from (i) to acetoacetate;

(k) at least one endogenous or exogenous nucleic acid molecule encoding an acetoacetate decarboxylase that catalyzes the conversion of acetoacetate from (j) to acetone; and/or (l) at least one endogenous or exogenous nucleic acid molecule encoding a secondary alcohol dehydrogenase that catalyzes the conversion of acetone from (k) to isopropanol; wherein the DHAP and pyruvate are produced from glycolysis in the microorganism.

52. The method of embodiment 51 further comprising one or more modifications selected from the group consisting of:

(a) a deletion, insertion, or loss of function mutation in a gene encoding an acetaldehyde dehydrogenase that catalyzes the conversion of lactaldehyde to lactate; and (b) a deletion, insertion, or loss of function mutation in a gene encoding a lactate dehydrogenase that catalyzes the conversion of pyruvate to lactate.

53. The method of any one of embodiments 36-38, wherein the recombinant microorganism is capable of co-producing acetone, butanol and ethanol, wherein the recombinant microorganism expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetaldehyde from (e) to ethanol or butyraldehyde from (i) to butanol;

wherein the pyruvate is produced from glycolysis in the microorganism.

54. The method of embodiment 53 further comprising a deletion, insertion, or loss of function mutation in a gene encoding a lactate dehydrogenase that catalyzes the conversion of pyruvate to lactate.

55. The method of any one of embodiments 36-38, wherein the recombinant microorganism is capable of co-producing isopropanol, butanol and ethanol, wherein the recombinant microorganism expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetone from (d) to isopropanol, acetaldehyde from (e) to ethanol or butyraldehyde from (i) to butanol;

wherein the pyruvate is produced from glycolysis in the microorganism.

56. The method of embodiment 55 further comprising a deletion, insertion, or loss of function mutation in a gene encoding a butyrate kinase that catalyzes the conversion of butyryl phosphate to butyrate.

57. The method of any one of embodiments 36-38, wherein the recombinant microorganism is capable of producing isobutanol, wherein the recombinant microorganism expresses one or more of the following:

(a) at least one endogenous or exogenous nucleic acid molecule encoding an acetohydroxy acid synthase that catalyzes the conversion of pyruvate to acetolactate;

(b) at least one endogenous or exogenous nucleic acid molecule encoding an acetohydroxy acid isomeroreductase that catalyzes the conversion of acetolactate from (a) to 2,3-dihydroxy-isovalerate;

(c) at least one endogenous or exogenous nucleic acid molecule encoding a dihydroxy-acid dehydratase that catalyzes the conversion of 2,3-dihydroxy-isovalerate from (b) to α-keto-isovalerate;

(d) at least one endogenous or exogenous nucleic acid molecule encoding a 2-keto-acid decarboxylase that catalyzes the conversion of α-keto-isovalerate from (c) to isobutyraldehyde; and/or (e) at least one endogenous or exogenous nucleic acid molecule encoding an alcohol dehydrogenase that catalyzes the conversion of isobutyraldehyde from (d) to isobutanol;

wherein the pyruvate is produced from glycolysis in the microorganism.

58. The method of embodiment 57 further comprising one or more modifications selected from the group consisting of:

(a) a deletion, insertion, or loss of function mutation in a gene encoding an ethanol dehydrogenase that catalyzes the conversion of acetaldehyde to ethanol; and (b) a deletion, insertion, or loss of function mutation in a gene encoding a lactate dehydrogenase that catalyzes the conversion of pyruvate to lactate.

59. The method of any one of embodiments 36-38, wherein the corresponding primary alkene is propene and the primary alcohol is 1-propanol.

60. The method of one of embodiments 36-38, wherein the corresponding primary alkene is propene and the secondary alcohol is 2-propanol.

61. The method of one of embodiments 36-38, wherein the corresponding primary alkene is butene and the primary alcohol is 1-butanol.

62. The method of one of embodiments 36-38, wherein the corresponding primary alkene is butene and the primary alcohol is 2-butanol.

63. The method of one of embodiments 36-38, wherein the one or more primary alkenes is produced from the one or more saturated primary or secondary alcohols via a single enzymatic step.

64. The method of any one of embodiments 36-38, wherein the production of one or more corresponding primary alkenes from one or more saturated primary or secondary alcohols comprises a dehydration step.

65. The method of embodiment 64, wherein the dehydration step is substrate activation independent.

66. The method of embodiment 64, wherein the dehydration step is cofactor independent.

67. The method of any one of embodiments 36-38, wherein the linalool dehydratase/isomerase is obtained from a microorganism selected from the group consisting of *Castellaniella defragrans* species.

68. The method of any one of embodiments 36-38, wherein the linalool dehydratase/isomerase comprises an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63.

69. The method of any one of embodiments 36-38, wherein the linalool dehydratase/isomerase is encoded by a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62.

70. The method of any one of embodiments 36-38, wherein the linalool dehydratase/isomerase is LinD.

71. A method of producing a recombinant microorganism that produces or accumulates one or more primary alkenes, each primary alkene having a structure as shown in Structure B, from one or more saturated primary or secondary alcohols, each primary or secondary alcohol having a structure as shown in Structure A,

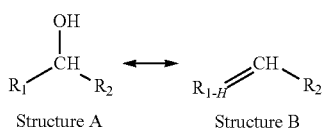

wherein $R_1=C_nH_{2n+1}$ with $1 \leq n \leq 11$; $R_2=C_mH_{2m+1}$ with $0 \leq m \leq 10$ and $n+m \leq 11$; and wherein the method comprises introducing into the recombinant microorganism one or more exogenous nucleic acid molecules encoding a linalool dehydratase/isomerase that catalyzes the conversion of the one or more saturated primary or secondary alcohols to one or more corresponding primary alkenes.

72. The method of embodiment 73, further comprising introducing into the recombinant microorganism and/or expressing in the recombinant microorganism one or more endogenous or exogenous nucleic acid molecules encoding one or more enzymes for the production of the one or more saturated primary or secondary alcohols from a renewable feedstock.

73. The method of embodiment 72, wherein the renewable feedstock is one or more sugars.

74. The method of any one of embodiments 71-73, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a D-tagatose 3-epimerase that catalyzes the conversion of D-xylose to D-ribulose;

(b) at least one endogenous or exogenous nucleic acid molecule encoding a D-ribulokinase that catalyzes the conversion of D-ribulose from (a) to D-ribulose-1-phosphate;

(c) at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

(d) at least one endogenous or exogenous nucleic acid molecule encoding a glycolaldehyde reductase that catalyzes the conversion of glycolaldehyde from (c) to mono ethylene glycol (MEG);

(e) at least one exogenous nucleic acid molecule encoding a thiolase that catalyzes the conversion of acetyl-CoA to acetoacetyl-CoA;

(f) at least one endogenous or exogenous nucleic acid molecule encoding an acetate:acetoacetyl-CoA transferase or hydrolase that catalyzes the conversion of acetoacetyl-CoA from (e) to acetoacetate;

(g) at least one endogenous or exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

75. The method of any one of embodiments 71-73, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a D-xylulose 1-kinase that catalyzes the conversion of D-xylulose to D-xylulose-1-phosphate;

(b) at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);

(c) at least one endogenous or exogenous nucleic acid molecule encoding a glycolaldehyde reductase that catalyzes the conversion of glycolaldehyde from (b) to MEG;

(d) at least one endogenous or exogenous nucleic acid molecule encoding a thiolase that catalyzes the conversion of acetyl-CoA to acetoacetyl-CoA;

(e) at least one endogenous or exogenous nucleic acid molecule encoding an acetate:acetoacetyl-CoA transferase or hydrolase that catalyzes the conversion of acetoacetyl-CoA from (d) to acetoacetate;

(f) at least one endogenous or exogenous nucleic acid molecule encoding an acetoacetate decarboxylase that catalyzes the conversion of acetoacetate from (e) to acetone; and/or (g) at least one endogenous or exogenous nucleic acid molecule encoding a secondary alcohol dehydrogenase that catalyzes the conversion of acetone from (f) to isopropanol.

76. The method of any one of embodiments 71-75, wherein the method further comprises introducing into the recombinant microorganism one or more modifications selected from the group consisting of:

(a) a deletion, insertion, or loss of function mutation in a gene encoding a D-xylulose-5-kinase that catalyzes the conversion of D-xylulose to D-xylulose-5-phosphate;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

77. The method of any one of embodiments 71-76, wherein an endogenous D-xylose isomerase catalyzes the conversion of D-xylose to D-xylulose.

78. The method of any one of embodiments 71-73, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a xylose dehydrogenase that catalyzes the conversion of D-xylose to D-xylonolactone;

(b) at least one endogenous or exogenous nucleic acid molecule encoding a xylonolactonase that catalyzes the conversion of D-xylonolactone from (a) to D-xylonate;

(c) at least one endogenous or exogenous nucleic acid molecule encoding a xylonate dehydratase that catalyzes the conversion of D-xylonate from (b) to 2-keto-3-deoxy-xylonate;

(d) at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;

(e) at least one endogenous or exogenous nucleic acid molecule encoding a glycolaldehyde reductase that catalyzes the conversion of glycolaldehyde from (d) to MEG;

(f) at least one exogenous nucleic acid molecule encoding a thiolase that catalyzes the conversion of acetyl-CoA to acetoacetyl-CoA;

(g) at least one endogenous or exogenous nucleic acid molecule encoding an acetate:acetoacetyl-CoA transferase or hydrolase that catalyzes the conversion of acetoacetyl-CoA from (f) to acetoacetate;

(h) at least one exogenous nucleic acid molecule encoding an acetoacetate decarboxylase that catalyzes the conversion of acetoacetate from (g) to acetone; and/or (i) at least one endogenous or exogenous nucleic acid molecule encoding a secondary alcohol dehydrogenase that catalyzes the conversion of acetone from (h) to isopropanol.

79. The method of any one of embodiments 71-73, wherein the recombinant microorganism is capable of co-producing monoethylene glycol (MEG) and isopropanol from exogenous D-xylose, and wherein expressing one or more endogenous or exogenous nucleic acid molecules encoding one or more enzymes comprises expressing one or more of the following:

(a) at least one endogenous or exogenous nucleic acid molecule encoding a xylose dehydrogenase that catalyzes the conversion of D-xylose to D-xylonate;

(b) at least one endogenous or exogenous nucleic acid molecule encoding a xylonate dehydratase that catalyzes the conversion of D-xylonate from (a) to 2-keto-3-deoxy-xylonate;

(c) at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;

(d) at least one exogenous nucleic acid molecule encoding a glycolaldehyde reductase that catalyzes the conversion of glycolaldehyde from (c) to MEG;

(e) at least one exogenous nucleic acid molecule encoding a thiolase that catalyzes the conversion of acetyl-CoA to acetoacetyl-CoA;

(f) at least one exogenous nucleic acid molecule encoding an acetate:acetoacetyl-CoA transferase or hydrolase that catalyzes the conversion of acetoacetyl-CoA from (e) to acetoacetate;

(g) at least one exogenous nucleic acid molecule encoding an acetoacetate decarboxylase that catalyzes the conversion of acetoacetate from (f) to acetone; and/or (h) at least one endogenous or exogenous nucleic acid molecule encoding a secondary alcohol dehydrogenase that catalyzes the conversion of acetone from (g) to isopropanol.

80. The method of any one of embodiments 71-73 or 78-79, wherein the method further comprises introducing into the recombinant microorganism one or more modifications selected from the group consisting of:

(a) a deletion, insertion, or loss of function mutation in a gene encoding a D-xylose isomerase that catalyzes the conversion of D-xylose to D-xylulose;

(b) a deletion, insertion, or loss of function mutation in a gene encoding a glycolaldehyde dehydrogenase that catalyzes the conversion of glycolaldehyde to glycolic acid; and (c) a deletion, insertion, or loss of function mutation in a gene encoding a lactate dehydrogenase that catalyzes the conversion of pyruvate to lactate.

81. The method of any one of embodiments 71-73, wherein the recombinant microorganism is capable of co-producing monoethylene glycol (MEG) and isopropanol from exogenous D-xylose and glucose, wherein the recombinant microorganism expresses one or more of the following:

(a) at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;

(b) at least one exogenous nucleic acid molecule encoding a D-xylose isomerase that catalyzes the conversion of D-xylose to D-xylulose, and wherein the microorganism further expresses one or more of the following:

(c) at least one endogenous or exogenous nucleic acid molecule encoding a D-tagatose 3-epimerase that catalyzes the conversion of D-xylulose from (a) or (b) to D-ribulose;

(d) at least one endogenous or exogenous nucleic acid molecule encoding a D-ribulokinase that catalyzes the conversion of D-ribulose from (c) to D-ribulose-1-phosphate;

(e) at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);

(f) at least one endogenous or exogenous nucleic acid molecule encoding a glycolaldehyde reductase or methylglyoxal reductase that catalyzes the conversion of glycolaldehyde from (e) to MEG;

(g) at least one endogenous or exogenous nucleic acid molecule encoding a thiolase that catalyzes the conversion of acetyl-CoA to acetoacetyl-CoA;

(h) at least one endogenous or exogenous nucleic acid molecule encoding an acetate:acetoacetyl-CoA transferase or hydrolase that catalyzes the conversion of acetoacetyl-CoA from (g) to acetoacetate;

(i) at least one endogenous or exogenous nucleic acid molecule encoding an acetoacetate decarboxylase that catalyzes the conversion of acetoacetate from (h) to acetone; and/or (j) at least one endogenous or exogenous nucleic acid molecule encoding a secondary alcohol dehydrogenase that catalyzes the conversion of acetone from (i) to isopropanol.

82. The method of embodiment 81, wherein the recombinant microorganism further comprises one or more modifications selected from the group consisting of:

(a) a deletion, insertion, or loss of function mutation in a gene encoding a D-xylulose-5-kinase that catalyzes the conversion of D-xylulose to D-xylulose-5-phosphate; and (b) a deletion, insertion, or loss of function mutation in a gene encoding an alkaline phosphatase that catalyzes the conversion of D-xylulose-5-phosphate to D-xylulose.

83. The method of any one of embodiments 71-82, wherein the DHAP is converted to acetyl-CoA through the endogenous glycolysis pathway in the microorganism.

84. The method of any one of embodiments 71-73, wherein the recombinant microorganism is capable of producing isopropanol, and wherein the recombinant microorganism expresses one or more of the following:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and/or (d) at least one endogenous or exogenous nucleic acid molecule encoding a secondary alcohol dehydrogenase that catalyzes the conversion of acetone from (c) to isopropanol.

85. The method of embodiment 84 further comprising a deletion, insertion, or loss of function mutation in a gene encoding a lactate dehydrogenase that catalyzes the conversion of pyruvate to lactate.

86. The method of any one of embodiments 71-73, wherein the recombinant microorganism is capable of co-producing n-propanol and isopropanol, wherein the recombinant microorganism expresses one or more of the following:

(a) at least one endogenous or exogenous nucleic acid molecule encoding a methylglyoxal synthase that catalyzes the conversion of dihydroxyacetone phosphate (DHAP) to methylglyoxal;

(b) at least one endogenous or exogenous nucleic acid molecule encoding an aldo-keto reductase that catalyzes the conversion of methylglyoxal from (a) to acetol;

(c) at least one endogenous or exogenous nucleic acid molecule encoding a glyoxylate reductase, a methylglyoxal dehydrogenase or an aldehyde dehydrogenase that catalyzes the conversion of methylglyoxal from (a) to lactaldehyde;

(d) at least one endogenous or exogenous nucleic acid molecule encoding an aldo-keto reductase that catalyzes the conversion of acetol from (b) to 1,2-propanediol;

(e) at least one endogenous or exogenous nucleic acid molecule encoding an aldehyde reductase that catalyzes the conversion of lactaldehyde from (c) to 1,2-propanediol;

(f) at least one endogenous or exogenous nucleic acid molecule encoding a diol-dehydratase that catalyzes the conversion of 1,2-propanediol from (d) or (e) to propanal;

(g) at least one endogenous or exogenous nucleic acid molecule encoding a dehydrogenase that catalyzes the conversion of propanal from (f) to n-propanol;

(h) at least one endogenous or exogenous nucleic acid molecule encoding a pyruvate formate lyase that catalyzes the conversion of pyruvate to acetyl-CoA;

(i) at least one endogenous or exogenous nucleic acid molecule encoding a thiolase that catalyzes the conversion of acetyl-CoA from (h) to acetoacetyl-CoA;

(j) at least one endogenous or exogenous nucleic acid molecule encoding an acetate:acetoacetyl-CoA transferase or hydrolase that catalyzes the conversion of acetoacetyl-CoA from (i) to acetoacetate;

(k) at least one endogenous or exogenous nucleic acid molecule encoding an acetoacetate decarboxylase that catalyzes the conversion of acetoacetate from (j) to acetone; and/or (l) at least one endogenous or exogenous nucleic acid molecule encoding a secondary alcohol dehydrogenase that catalyzes the conversion of acetone from (k) to isopropanol; wherein the DHAP and pyruvate are produced from glycolysis in the microorganism.

87. The method of embodiment 86 further comprising one or more modifications selected from the group consisting of:

(a) a deletion, insertion, or loss of function mutation in a gene encoding an acetaldehyde dehydrogenase that catalyzes the conversion of lactaldehyde to lactate; and (b) a deletion, insertion, or loss of function mutation in a gene encoding a lactate dehydrogenase that catalyzes the conversion of pyruvate to lactate.

88. The method of any one of embodiments 71-73, wherein the recombinant microorganism is capable of co-producing acetone, butanol and ethanol, wherein the recombinant microorganism expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetaldehyde from (e) to ethanol or butyraldehyde from (i) to butanol;

wherein the pyruvate is produced from glycolysis in the microorganism.

89. The method of embodiment 88 further comprising a deletion, insertion, or loss of function mutation in a gene encoding a lactate dehydrogenase that catalyzes the conversion of pyruvate to lactate.

90. The method of any one of embodiments 71-73, wherein the recombinant microorganism is capable of co-producing isopropanol, butanol and ethanol, wherein the recombinant microorganism expresses one or more of the following:

(a) at least one endogenous or exogenous nucleic acid molecule encoding a pyruvate ferredoxin oxidoreductase that catalyzes the conversion of pyruvate to acetyl-CoA;

(b) at least one endogenous or exogenous nucleic acid molecule encoding a thiolase that catalyzes the conversion of acetyl-CoA from (a) to acetoacetyl-CoA;

(c) at least one endogenous or exogenous nucleic acid molecule encoding an acetate:acetoacetyl-CoA transferase or hydrolase that catalyzes the conversion of acetoacetyl-CoA from (b) to acetoacetate;

(d) at least one endogenous or exogenous nucleic acid molecule encoding an acetoacetate decarboxylase that catalyzes the conversion of acetoacetate from (c) to acetone;

(e) at least one endogenous or exogenous nucleic acid molecule encoding an acetaldehyde dehydrogenase that catalyzes the conversion of acetyl-CoA from (a) to acetaldehyde;

(f) at least one endogenous or exogenous nucleic acid molecule encoding 3-hydroxybutyryl-CoA dehydrogenase that catalyzes the conversion of acetoacetyl-CoA from (b) to 3-hydroxybutyryl-CoA;

(g) at least one endogenous or exogenous nucleic acid molecule encoding a 3-hydroxybutyryl-CoA dehydratase that catalyzes the conversion of 3-hydroxybutyryl-CoA from (f) to 2-butenoyl-CoA;

(h) at least one endogenous or exogenous nucleic acid molecule encoding a butyryl-CoA dehydrogenase that catalyzes the conversion of 2-butenoyl-CoA from (g) to butyryl-CoA;

(i) at least one endogenous or exogenous nucleic acid molecule encoding a butyraldehyde dehydrogenase that catalyzes the conversion of butyryl-CoA from (h) to butyraldehyde; and/or (j) at least one endogenous or exogenous nucleic acid molecule encoding an alcohol dehydrogenase that catalyzes the conversion of acetone from (d) to isopropanol, acetaldehyde from (e) to ethanol or butyraldehyde from (i) to butanol;

wherein the pyruvate is produced from glycolysis in the microorganism.

91. The method of embodiment 90 further comprising a deletion, insertion, or loss of function mutation in a gene encoding a butyrate kinase that catalyzes the conversion of butyryl phosphate to butyrate.

92. The method of any one of embodiments 71-73, wherein the recombinant microorganism is capable of producing isobutanol, wherein the recombinant microorganism expresses one or more of the following:

(a) at least one endogenous or exogenous nucleic acid molecule encoding an acetohydroxy acid synthase that catalyzes the conversion of pyruvate to acetolactate;

(b) at least one endogenous or exogenous nucleic acid molecule encoding an acetohydroxy acid isomeroreductase that catalyzes the conversion of acetolactate from (a) to 2,3-dihydroxy-isovalerate;

(c) at least one endogenous or exogenous nucleic acid molecule encoding a dihydroxy-acid dehydratase that catalyzes the conversion of 2,3-dihydroxy-isovalerate from (b) to α-keto-isovalerate;

(d) at least one endogenous or exogenous nucleic acid molecule encoding a 2-keto-acid decarboxylase that catalyzes the conversion of α-keto-isovalerate from (c) to isobutyraldehyde; and/or (e) at least one endogenous or exogenous nucleic acid molecule encoding an alcohol dehydrogenase that catalyzes the conversion of isobutyraldehyde from (d) to isobutanol;

wherein the pyruvate is produced from glycolysis in the microorganism.

93. The method of embodiment 92 further comprising one or more modifications selected from the group consisting of:

(a) a deletion, insertion, or loss of function mutation in a gene encoding an ethanol dehydrogenase that catalyzes the conversion of acetaldehyde to ethanol; and (b) a deletion, insertion, or loss of function mutation in a gene encoding a lactate dehydrogenase that catalyzes the conversion of pyruvate to lactate.

94. The method of any one of embodiments 71-73, wherein the corresponding primary alkene is propene and the primary alcohol is 1-propanol.

95. The method of one of embodiments 71-73, wherein the corresponding primary alkene is propene and the secondary alcohol is 2-propanol.

96. The method of one of embodiments 71-73, wherein the corresponding primary alkene is butene and the primary alcohol is 1-butanol.

97. The method of one of embodiments 71-73, wherein the corresponding primary alkene is butene and the primary alcohol is 2-butanol.

98. The method of one of embodiments 71-73, wherein the one or more primary alkenes is produced from the one or more saturated primary or secondary alcohols via a single enzymatic step.

99. The method of any one of embodiments 71-73, wherein the production of one or more corresponding primary alkenes from one or more saturated primary or secondary alcohols comprises a dehydration step.

100. The method of embodiment 99, wherein the dehydration step is substrate activation independent.

101. The method of embodiment 99, wherein the dehydration step is cofactor independent.

102. The method of any one of embodiments 71-73, wherein the linalool dehydratase/isomerase is obtained from a microorganism selected from the group consisting of *Castellaniella defragrans* species.

103. The method of any one of embodiments 71-73, wherein the linalool dehydratase/isomerase comprises an amino acid sequence selected from the group consisting of SEQ ID NOs: 2, 5, 7, 9, 12, 14, 16, 18, 20, 22, 24, 26, 28, 30, 32, 33, 35, 37, 39, 41, 43, 45, 47, 49, 51, 53, 55, 57, 59, 61 and 63.

104. The method of any one of embodiments 71-73, wherein the linalool dehydratase/isomerase is encoded by a nucleic acid sequence selected from the group consisting of SEQ ID NOs: 1, 3, 4, 6, 8, 10, 11, 13, 15, 17, 19, 21, 23, 25, 27, 29, 31, 34, 36, 38, 40, 42, 44, 46, 48, 50, 52, 54, 56, 58, 60 and 62.

105. The method of any one of embodiments 71-73, wherein the linalool dehydratase/isomerase is LinD.

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A recombinant microorganism capable of producing one or more primary alkenes, each primary alkene having a structure as shown in Structure B, from one or more saturated primary or secondary alcohols, each primary or secondary alcohol having a structure as shown in Structure A,

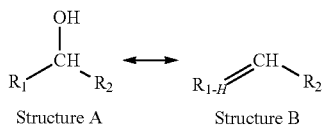

Structure A             Structure B wherein $R_1=C_nH_{2n+1}$ with $1 \leq n \leq 11$; $R_2=C_mH_{2m+1}$ with $0 \leq m \leq 10$ and $n+m \leq 11$; and wherein the recombinant microorganism expresses one or more heterologous nucleic acid molecules encoding one or more linalool dehydratases/isomerases that catalyzes the conversion of the one or more saturated primary or secondary alcohols to one or more corresponding primary alkenes, the linalool dehydratase/isomerase comprising an amino acid sequence selected from the group consisting of SEQ ID NOs: 2, 5, and 26, wherein the recombinant microorganism further expresses one or more exogenous nucleic acid molecules encoding one or more enzymes for the production of the one or more saturated primary or secondary alcohols from a renewable feedstock, and wherein the renewable feedstock is one or more sugars.

2. The recombinant microorganism of claim 1, wherein the corresponding primary alkene is propene and the primary alcohol is 1-propanol.

3. The recombinant microorganism of claim 1, wherein the corresponding primary alkene is propene and the secondary alcohol is 2-propanol.

4. The recombinant microorganism of claim 1, wherein the production of one or more corresponding primary alkenes from one or more saturated primary or secondary alcohols comprises a dehydration step.

5. The recombinant microorganism of claim 4, wherein the dehydration step is substrate activation independent.

6. The recombinant microorganism of claim 4, wherein the dehydration step is cofactor independent.

7. The recombinant microorganism of claim 1, wherein the linalool dehydratase/isomerase is obtained from a microorganism selected from the group consisting of *Castellaniella defragrans* species.

8. The recombinant microorganism of claim 1, wherein the linalool dehydratase/isomerase is encoded by a nucleic acid sequence selected from the group consisting of SEQ ID NOs: 1, 3, 4, and 25.

9. The recombinant microorganism of claim 1, wherein the linalool dehydratase/isomerase is LinD.

10. A method of producing one or more primary alkenes, one or more saturated primary or secondary alcohols, or a combination thereof, wherein the method comprises cultivating the recombinant microorganism of claim 1 in a culture medium containing a feedstock providing a carbon source until one or more primary alkenes, one or more saturated primary or secondary alcohols, or a combination thereof, are produced.

11. The recombinant microorganism of claim 1, wherein Structure A has a formula $C_{n'}H_{2n'+2}O$ wherein $3 \leq n' \leq 12$.

12. The recombinant microorganism of claim 11, wherein the recombinant microorganism expresses:

(a) at least one endogenous or exogenous nucleic acid molecule encoding a thiolase that catalyzes the conversion of acetyl-CoA to acetoacetyl-CoA;

(b) at least one endogenous or exogenous nucleic acid molecule encoding an acetate:acetoacetyl-CoA transferase or hydrolase that catalyzes the conversion of acetoacetyl-CoA from (a) to acetoacetate;

(c) at least one endogenous or exogenous nucleic acid molecule encoding an acetoacetate decarboxylase that catalyzes the conversion of acetoacetate from (b) to acetone; and (d) at least one endogenous or exogenous nucleic acid molecule encoding a secondary alcohol dehydrogenase that catalyzes the conversion of acetone from (c) to isopropanol.

13. A method of producing one or more primary alkenes, one or more saturated primary or secondary alcohols, or a combination thereof, wherein the method comprises cultivating the recombinant microorganism of claim 11 in a culture medium containing a feedstock providing a carbon source until one or more primary alkenes, one or more saturated primary or secondary alcohols, or a combination thereof, are produced.

* * * * *

```
                          SEQUENCE LISTING

<160> NUMBER OF SEQ ID NOS: 190

<210> SEQ ID NO 1
<211> LENGTH: 1194
<212> TYPE: DNA
<213> ORGANISM: Castellaniella defragans

<400> SEQUENCE: 1
atgcggttca cattgaagac gacggcgatt gtgtcggccg ccgccctgct ggccggtttc      60
gggccgccgc cccgcgcggc ggaactgccg ccggggcggc tcgccaccac cgaggactat     120
ttcgcgcagc aggcgaagca ggccgtcacc cccgacgtga tggcccagct ggcctacatg     180
aactacatcg atttcatctc gcccttctac agccggggct gctccttcga ggcctgggag     240
ctcaagcaca cgccgcagcg ggtcatcaag tattcgatcg ccttctatgc gtatggcctg     300
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgccca cctcaccccgc    540 atcatccatg acgagatcgc ggccaacccc tttgccggca tcgtctgcga gccggacaat     600
tattttgtcc agtgcaattc ggtcgcctac ctgagcctgt gggtctatga ccggctgcat     660
ggcaccgact accgggcggc caccagggcc tggctggatt tcatccagaa ggacctgatc     720
gatcccgagc ggggcgcctt ctacctgtcc tatcaccccg agtccggcgc ggtgaagccg     780
tggatctcgg cgtatacgac agcctggacg ctcgccatgg tgcacggcat ggaccccgcc     840
ttttccgagc gctactaccc ccggttcaag cagaccttcg tcgaggtcta cgacgagggc     900
cgcaaggccc gggtgcgcga cggccggc acggacgacg cggatggcgg ggtgggcctg       960
gcttcggcgt tcaccctgct gctggcccgc gagatgggcg accagcagct cttcgaccaa    1020 tgctgaatc acctggagcc gccggccaag ccgagcatcg tctcggcctc gctgcggtac     1080
gagcatcccg gcagcctgct gttcgacgag ctgctgttcc tcgccaaggt gcatgccggc    1140
tttggcgccc tgcttcggat gccgcctccg gcggccaagc tcgcagggaa ataa          1194

<210> SEQ ID NO 2
<211> LENGTH: 397
<212> TYPE: PRT
<213> ORGANISM: Castellaniella defragans

<400> SEQUENCE: 2

Met Arg Phe Thr Leu Lys Thr Thr Ala Ile Val Ser Ala Ala Ala Leu
1               5                   10                  15

Leu Ala Gly Phe Gly Pro Pro Pro Arg Ala Ala Glu Leu Pro Pro Gly
                20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80
```

```
Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
            115                 120                 125

Arg Val Trp Gly Asp Trp Glu Glu Asp Gly Phe Gly Thr Asp Pro Ile
130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
            275                 280                 285

Phe Lys Gln Thr Phe Val Glu Val Tyr Asp Glu Gly Arg Lys Ala Arg
290                 295                 300

Val Arg Glu Thr Ala Gly Thr Asp Ala Asp Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Gly Ser Leu Leu Phe
            355                 360                 365

Asp Glu Leu Leu Phe Leu Ala Lys Val His Ala Gly Phe Gly Ala Leu
370                 375                 380

Leu Arg Met Pro Pro Ala Ala Lys Leu Ala Gly Lys
385                 390                 395

<210> SEQ ID NO 3
<211> LENGTH: 1194
<212> TYPE: DNA
<213> ORGANISM: artificial
<220> FEATURE:
<223> OTHER INFORMATION: Codon optimized nucleic acid encoding LinD-1

<400> SEQUENCE: 3
atgcgcttta cgttgaaaac caccgccatc gtgtccgctg cggcgttgct ggcaggtttc      60
ggtccgccac cgcgtgcggc agaattacca cctggccgcc tggcaacgac cgaagattac     120
tttgcgcagc aagcaaaaca agccgttacc ccggacgtca tggcgcagct ggcatatatg     180
aactatatcg atttcatttc tccgttctat agccgcggtt gctcctttga ggcgtgggaa     240
ctgaagcata ctccgcagcg tgtgatcaag tatagcattg cgttctacgc gtacggtctg     300
```

```
gcgagcgtcg cgctgattga cccgaagttg agagccctgg caggccacga tttggacatc    360 gctgttttcca aaatgaaatg taaacgcgtt tggggcgact gggaggagga cggtttcggt    420
accgatccga tcgagaaaga aaacatcatg tacaagggcc acctgaacct gatgtatggt    480
ctgtaccaac tggtcaccgg ctctcgtcgc tatgaagccg agcacgcgca tcttacccgc    540
atcattcatg atgaaattgc ggcgaacccg ttcgcgggta tcgtgtgtga gccggacaat    600
tactttgttc agtgcaatag cgttgcctac ctgagcctgt gggtctatga ccgtctgcac    660
ggcacggact atcgtgcggc gacgcgtgct ggctggact tcattcagaa agatttgatt    720
gatccggagc gtgcgccctt ttacctgagc taccatccgg agagcggtgc agtgaagccg    780
tggatcagcg cttacaccac cgcttggact ctggccatgg ttcacggtat ggacccggcg    840
tttagcgagc gttactaccc cgcgcttcaag caaacgtttg tcgaggtgta cgacgagggt    900
cgtaaggcac gtgtgcgtga accgcgggt accgacgacg cggatggtgg cgtgggtctg    960
gcaagcgcct tcacgctgct gctggcacgc gagatgggtg atcagcaatt gttcgatcag   1020
ctgttgaatc atctcgaacc gccagcgaag ccgtcgattg tgagcgcctc cctgcgttat   1080
gaacacccgg gtagcctgct gtttgatgaa ctgctgtttc tggcgaaagt acacgcgggc   1140
ttcggcgcac tgctgcgtat gccgcctccg gcagctaaac tggcgggtaa ataa         1194

<210> SEQ ID NO 4
<211> LENGTH: 1116
<212> TYPE: DNA
<213> ORGANISM: Castellaniella defragans

<400> SEQUENCE: 4
gcggaactgc cgccggggcg gctcgccacc accgaggact atttcgcgca gcaggcgaag     60
caggccgtca cccccgacgt gatggcccag ctggcctaca tgaactacat cgatttcatc    120
tcgcccttct acagccgggg ctgctccttc gaggcctggg agctcaagca cacgccgcag    180
cgggtcatca agtattcgat cgccttctat gcgtatggcc tggccagcgt ggcgctcatc    240
gacccgaagc tgcgtgcgct cgccggccat gacctggaca tcgcggtctc caagatgaag    300
tgcaagcggg tctggggcga ctgggaggaa acgggttcg gcaccgaccc gatcgagaaa    360
gagaacatca tgtacaaggg ccacctgaac ctgatgtacg gcctctatca gctggtgacc    420
ggcagccgcc ggtacgaagc cgagcatgcc cacctcaccc gcatcatcca tgacgagatc    480
gcggccaacc cctttgccgg catcgtctgc gagccggaca attattttgt ccagtgcaat    540
tcggtcgcct acctgagcct gtgggtctat gaccggctgc atggcaccga ctaccgggcg    600
gccaccaggg cctggctgga tttcatccag aaggacctga tcgatcccga gcggggcgcc    660
ttctacctgt cctatcaccc cgagtccggc gcggtgaagc cgtggatctc ggcgtatacg    720
acagcctgga cgctcgccat ggtgcacggc atggaccccg ccttttccga gcgctactac    780
ccccggttca gcagaccctt cgtcgaggtc tacgacgagg gccgcaaggc ccgggtgcgc    840
gagacggccg gcacggacga cgcggatggc ggggtgggcc tggcttcggc gttcaccctg    900
ctgctggccc gcgagatggg cgaccagcag ctcttcgacc aattgctgaa tcacctggag    960 ccgcggggcca agccgagcat cgtctcggcc tcgctgcggt acgagcatcc cggcagcctg   1020
ctgttcgacg agctgctgtt cctcgccaag gtgcatgccg gctttggcgc cctgcttcgg   1080
atgccgcctc cggcggccaa gctcgcaggg aaataa                              1116

<210> SEQ ID NO 5
```

```
<211> LENGTH: 371
<212> TYPE: PRT
<213> ORGANISM: Castellaniella defragans

<400> SEQUENCE: 5

Ala Glu Leu Pro Pro Gly Arg Leu Ala Thr Thr Glu Asp Tyr Phe Ala
1               5                   10                  15

Gln Gln Ala Lys Gln Ala Val Thr Pro Asp Val Met Ala Gln Leu Ala
            20                  25                  30

Tyr Met Asn Tyr Ile Asp Phe Ile Ser Pro Phe Tyr Ser Arg Gly Cys
        35                  40                  45

Ser Phe Glu Ala Trp Glu Leu Lys His Thr Pro Gln Arg Val Ile Lys
    50                  55                  60

Tyr Ser Ile Ala Phe Tyr Ala Tyr Gly Leu Ala Ser Val Ala Leu Ile
65                  70                  75                  80

Asp Pro Lys Leu Arg Ala Leu Ala Gly His Asp Leu Asp Ile Ala Val
                85                  90                  95

Ser Lys Met Lys Cys Lys Arg Val Trp Gly Asp Trp Glu Glu Asp Gly
            100                 105                 110

Phe Gly Thr Asp Pro Ile Glu Lys Glu Asn Ile Met Tyr Lys Gly His
        115                 120                 125

Leu Asn Leu Met Tyr Gly Leu Tyr Gln Leu Val Thr Gly Ser Arg Arg
    130                 135                 140

Tyr Glu Ala Glu His Ala His Leu Thr Arg Ile Ile His Asp Glu Ile
145                 150                 155                 160

Ala Ala Asn Pro Phe Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asp Tyr Arg Ala Ala Thr Arg Ala Trp Leu Asp Phe
        195                 200                 205

Ile Gln Lys Asp Leu Ile Asp Pro Glu Arg Gly Ala Phe Tyr Leu Ser
    210                 215                 220

Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Arg Phe Lys Gln Thr Phe Val Glu Val Tyr Asp
            260                 265                 270

Glu Gly Arg Lys Ala Arg Val Arg Glu Thr Ala Gly Thr Asp Asp Ala
        275                 280                 285

Asp Gly Gly Val Gly Leu Ala Ser Ala Phe Thr Leu Leu Leu Ala Arg
    290                 295                 300

Glu Met Gly Asp Gln Gln Leu Phe Asp Gln Leu Leu Asn His Leu Glu
305                 310                 315                 320

Pro Pro Ala Lys Pro Ser Ile Val Ser Ala Ser Leu Arg Tyr Glu His
                325                 330                 335

Pro Gly Ser Leu Leu Phe Asp Glu Leu Leu Phe Leu Ala Lys Val His
            340                 345                 350

Ala Gly Phe Gly Ala Leu Leu Arg Met Pro Pro Ala Ala Lys Leu
        355                 360                 365

Ala Gly Lys
    370
```

<210> SEQ ID NO 6
<211> LENGTH: 1194
<212> TYPE: DNA
<213> ORGANISM: artificial
<220> FEATURE:
<223> OTHER INFORMATION: Nucleic acid encoding SEQ ID NO: 7

<400> SEQUENCE: 6

```
atgcgcttta cgttgaaaac caccgccatc gtgtccgctg cggcgttgct gattggtctg      60
ggtccgccac cgcgtgcggc agaactgcct cctggtcgtc tggcaaccac cgaagattat     120
tttgcacagc aggcaaaaca ggcagttaca ccggatgtta tggcacagct ggcatatatg     180
aactatatcg attttatcag cccgttttt agccgcagct gtagctttga agcatgggaa      240
ctgaaacata caccgcagcg tgttatcaaa tatagcattg cctttatgc atatggtctg      300
gcaagcgttg cactgattga tccgaaactg cgtgcactgg caggtcatga tctggatatt     360
gcagttagca aaatgaaatg caaacgcgtg tggatggatt gggaagaaga tggttttggc     420
accgatccga ttgaaaaaga aaacatcatg tataaaggcc atctgaacct gatgtatggt     480
ctgtatcagc tggttaccgg tagccgtaaa tatgaagcag aacatgcaca tctgacccgt     540
ctgattcatg atgaaattgc agcaaatccg tttgccggta ttttttgtga accgaacaac     600
tattttgtgc agtgtaatag cgttgcatat ctgagcctgt gggtttatga tcgtctgcat     660
ggtacagatt atcgtgcagc aacccgtgca tggctggatt ttattcagaa agatctgatc     720
gatccggaac gtggtgcatt tatctgagc tatcatccgg aaagcggtgc agttaaaccg     780
tggattagcg catataccac cgcatggacc ctggcaatgg ttcatggtat ggatccggca     840
tttagcgaac gttattatcc gcgttttaaa cagaccttcg tggaagttta tgatgaaggt     900
cgtaaagcac gtgttcgtga accgcaggc accgatgatg cagatggtgg tgttggtctg     960
gccagtgcaa gcaccctgct gctggcacgt gaaatgggtg atcagcagct gtttgatcaa    1020
ctgctgaatc atctggaacc gcctgcaaaa ccgagcattg tgagcgcaag cctgcgttat    1080
gaacatccga gcagcctgtt ttttgatgag ctgctgtttc tggcaaaagt tcatgcaggt    1140
tttggtgcac tgctgcgtat gcctccgcca gcagccaaac tggcaggcaa ataa          1194
```

<210> SEQ ID NO 7
<211> LENGTH: 397
<212> TYPE: PRT
<213> ORGANISM: artificial
<220> FEATURE:
<223> OTHER INFORMATION: Full-length polypeptide variant of LinD-1,
    designated LinD-1N, having 12 amino acid substitutions: A18I,
    F20L, Y70F, G73S, G132M, R170K, I181L, V195F, D199N, F324S, G364S,
    L367F

<400> SEQUENCE: 7

```
Met Arg Phe Thr Leu Lys Thr Thr Ala Ile Val Ser Ala Ala Ala Leu
1               5                   10                  15

Leu Ile Gly Leu Gly Pro Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Phe Ser Arg Ser Cys Ser Phe Glu Ala Trp Glu
65                  70                  75                  80

Leu Lys His Thr Pro Gln Arg Val Ile Lys Tyr Ser Ile Ala Phe Tyr
                85                  90                  95
```

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
            115                 120                 125

Arg Val Trp Met Asp Trp Glu Glu Asp Gly Phe Gly Thr Asp Pro Ile
            130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Lys Tyr Glu Ala Glu His Ala
            165                 170                 175

His Leu Thr Arg Leu Ile His Asp Glu Ile Ala Ala Asn Pro Phe Ala
            180                 185                 190

Gly Ile Phe Cys Glu Pro Asn Asn Tyr Phe Val Gln Cys Asn Ser Val
            195                 200                 205

Ala Tyr Leu Ser Leu Trp Val Tyr Asp Arg Leu His Gly Thr Asp Tyr
            210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
            245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
            275                 280                 285

Phe Lys Gln Thr Phe Val Glu Val Tyr Asp Glu Gly Arg Lys Ala Arg
            290                 295                 300

Val Arg Glu Thr Ala Gly Thr Asp Asp Ala Asp Gly Val Gly Leu
305                 310                 315                 320

Ala Ser Ala Ser Thr Leu Leu Leu Ala Arg Glu Met Gly Asp Gln Gln
            325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Ser Ser Leu Phe Phe
            355                 360                 365

Asp Glu Leu Leu Phe Leu Ala Lys Val His Ala Gly Phe Gly Ala Leu
            370                 375                 380

Leu Arg Met Pro Pro Pro Ala Ala Lys Leu Ala Gly Lys
385                 390                 395

<210> SEQ ID NO 8
<211> LENGTH: 1197
<212> TYPE: DNA
<213> ORGANISM: Castellaniella defragans

<400> SEQUENCE: 8

```
atgcgattca cattgaagac gccggcgatc gcgtcggccg tcgctgccct gctggtcggt      60
cttggacagc cggcgcatgc ggcgccgctg ccgctggggc gccttgcccc gaccgaggac     120
tacttcgccc agcaggcgaa gcaggccgtc accccgacg tgatggccca gctggcctac     180
atgaactata tcgatttcat ctcgcctttc tacagccggg ggtgttcctt cgaggcctgg     240
gaactcaagc acacaccgca gcgggtcatc aagtattcga tcgctttcta tgcgtatggc     300
ctggccagcg tggcgctcat cgatccgaat ctgcgcgcgc tcgccggcca tgacctggac     360
atcgcggtct ccaagatgaa atgcaagcgg gtctggggcg actgggagga agacgggttc     420
```

```
ggcgacgatc cgatcgagaa agagaacatc atgtacaagg ccacctgaa cctgatgtac    480 ggcctctatc agctggtgac cggcagccgc cggtacgaag ccgagcatgc gcacctcacc    540
cgcatcatcc acgacgagat cggcgccaac cccttgccg gcatcgtctg tgagccggat    600
aattatttcg tccaatgcaa ctcggtcgcc tacctgagcc tgtgggtcta tgaccgcctg    660
catggcaccg attatcgggc ggcgacccgg gcctggctgg acttcatcca gaaagacctg    720
atcgaccccg agcggggcgc cttctacctg tcctatcatc cggagtccgg cgcggtgaag    780
ccgtggatct cggcgtatac gaccgcctgg acgctcgcca tggtgcatgg catggatccc    840
gccttttccg agcgctacta ccccgcgttc aagaaaacct tcgtcgaggt ctacgacggg    900
ggccgcaagg cccgggtgcg agagacggcc ggcacggccg acgcggatgg cggggtgggc    960
ctggcgtcgg catttaccct gctgctggcc gcgagatgg gcgaccagac gctcttcgac   1020
cagctgctga atcacctgga accgccggcc cagcccagca tcgtctcggc ctcattgcgt   1080
tacgagcatc ccggcagcct gttgttcgac gaactgctgt tcctggccaa ggtgcatgcc   1140
ggctttggcg ccctgctcca gatgccgcct ccggcggcga atccgggggg gaaatga     1197
```

<210> SEQ ID NO 9
<211> LENGTH: 398
<212> TYPE: PRT
<213> ORGANISM: Castellaniella defragans

<400> SEQUENCE: 9

```
Met Arg Phe Thr Leu Lys Thr Pro Ala Ile Ala Ser Ala Val Ala Ala
1               5                   10                  15

Leu Leu Val Gly Leu Gly Gln Pro Ala His Ala Ala Pro Leu Pro Leu
            20                  25                  30

Gly Arg Leu Ala Pro Thr Glu Asp Tyr Phe Ala Gln Gln Ala Lys Gln
        35                  40                  45

Ala Val Thr Pro Asp Val Met Ala Gln Leu Ala Tyr Met Asn Tyr Ile
    50                  55                  60

Asp Phe Ile Ser Pro Phe Tyr Ser Arg Gly Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Asn Leu Arg
            100                 105                 110

Ala Leu Ala Gly His Asp Leu Asp Ile Ala Val Ser Lys Met Lys Cys
        115                 120                 125

Lys Arg Val Trp Gly Asp Trp Glu Glu Asp Gly Phe Gly Asp Asp Pro
    130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Arg Tyr Glu Ala Glu His
                165                 170                 175

Ala His Leu Thr Arg Ile Ile His Asp Glu Ile Gly Ala Asn Pro Phe
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Asp
    210                 215                 220

Tyr Arg Ala Ala Thr Arg Ala Trp Leu Asp Phe Ile Gln Lys Asp Leu
225                 230                 235                 240
```

Ile Asp Pro Glu Arg Gly Ala Phe Tyr Leu Ser Tyr His Pro Glu Ser
            245                 250                 255

Gly Ala Val Lys Pro Trp Ile Ser Ala Tyr Thr Thr Ala Trp Thr Leu
        260                 265                 270

Ala Met Val His Gly Met Asp Pro Ala Phe Ser Glu Arg Tyr Tyr Pro
    275                 280                 285

Ala Phe Lys Lys Thr Phe Val Glu Val Tyr Asp Gly Gly Arg Lys Ala
290                 295                 300

Arg Val Arg Glu Thr Ala Gly Thr Ala Asp Ala Asp Gly Gly Val Gly
305                 310                 315                 320

Leu Ala Ser Ala Phe Thr Leu Leu Leu Ala Arg Glu Met Gly Asp Gln
                325                 330                 335

Thr Leu Phe Asp Gln Leu Leu Asn His Leu Glu Pro Pro Ala Gln Pro
            340                 345                 350

Ser Ile Val Ser Ala Ser Leu Arg Tyr Glu His Pro Gly Ser Leu Leu
        355                 360                 365

Phe Asp Glu Leu Leu Phe Leu Ala Lys Val His Ala Gly Phe Gly Ala
    370                 375                 380

Leu Leu Gln Met Pro Pro Pro Ala Ala Lys Ser Gly Gly Lys
385                 390                 395

<210> SEQ ID NO 10
<211> LENGTH: 1197
<212> TYPE: DNA
<213> ORGANISM: artificial
<220> FEATURE:
<223> OTHER INFORMATION: codon optimized nucleic acid encoding novel
      full length LinD-2, designated LinD-2A

<400> SEQUENCE: 10
atgcgcttta ccctgaaaac accggcaatt gcaagcgcag ttgcagcact gctggttggt      60
ctgggtcagc tgcacatgc agcaccgctg ccgctgggtc gtctggcacc gaccgaagat     120
tattttgcac agcaggcaaa acaggcagtt acaccggatg ttatggcaca gctggcatat     180
atgaactata tcgattttat cagcccgttc tatagccgtg ttgtagcttt gaagcatgg     240
gaactgaaac atacaccgca gcgtgttatc aaatatagca ttgccttta tgcatatggt     300
ctggcaagcg ttgcactgat tgatccgaat ctgcgtgcac tggcaggtca tgatctggat     360
attgcagtta gcaaaatgaa atgcaaacgt gtttggggtg attgggaaga ggatggtttt     420
ggtgatgatc cgattgagaa agaaaacatc atgtataaag ccatctgaa cctgatgtat     480
ggtctgtatc agctggttac cggtagccgt cgttatgaag cagaacatgc acatctgacc     540
cgtattattc atgatgaaat tggtgcaaat ccgtttgccg gtattgtttg tgaaccggat     600
aactatttg tgcagtgtaa tagcgttgca tatctgagcc tgtgggttta tgatcgtctg     660
catggcaccg attatcgtgc agcaacccgt gcatggctgg attttattca gaaagatctg     720
atcgatccgg aacgtggtgc atttttatctg agctatcatc cggaaagcgg tgcagttaaa     780
ccgtggatta gcgcatatac caccgcatgg accctggcaa tggttcatgg tatggatccg     840
gcatttagcg aacgttatta tcctgcattc aaaaaaaccct ttgtcgaggt gtatgatggt     900
ggtcgtaaag cacgtgttcg tgaaaccgca ggcaccgcag atgcagatgg tggtgtgggt     960
ctggccagtg catttacccct gctgctggca cgtgaaatgg gtgatcagac cctgtttgat    1020
cagctgctga atcatctgga accgcctgca cagccgagca ttgttagcgc aagcctgcgt    1080
tatgaacatc cgggtagcct gctgttcgat gaactgctgt ttctggcaaa agttcatgca    1140

```
ggttttggcg cactgctgca gatgcctccg cctgcagcaa aaagcggtgg taaataa       1197
```

<210> SEQ ID NO 11
<211> LENGTH: 1116
<212> TYPE: DNA
<213> ORGANISM: Castellaniella defragans

<400> SEQUENCE: 11

```
gcgccgctgc cgctggggcg ccttgccccg accgaggact acttcgccca gcaggcgaag     60
caggccgtca cccccgacgt gatggcccag ctggcctaca tgaactatat cgatttcatc    120
tcgcctttct acagccgggg gtgttccttc gaggcctggg aactcaagca cacaccgcag    180
cgggtcatca agtattcgat cgcttttctat gcgtatggcc tggccagcgt ggcgctcatc    240
gatccgaatc tgcgcgcgct cgccggccat gacctggaca tcgcggtctc caagatgaaa    300
tgcaagcggg tctggggcga ctggaggaa gacgggttcg gcgacgatcc gatcgagaaa    360
gagaacatca tgtacaaggg ccacctgaac ctgatgtacg gcctctatca gctggtgacc    420
ggcagccgcc ggtacgaagc cgagcatgcg cacctcaccc gcatcatcca cgacgagatc    480
ggcgccaacc cctttgccgg catcgtctgt gagccggata attatttcgt ccaatgcaac    540
tcggtcgcct acctgagcct gtgggtctat gaccgcctgc atggcaccga ttatcgggcg    600
gcgaccgggg cctggctgga cttcatccag aaagacctga tcgacccga gcggggcgcc    660
ttctacctgt cctatcatcc ggagtccggc gcggtgaagc cgtggatctc ggcgtatacg    720
accgcctgga cgctcgccat ggtgcatggc atggatcccg ccttttccga gcgctactac    780
cccgcgttca gaaaaacctt cgtcgaggtc tacgacgggg gccgcaaggc ccgggtgcga    840
gagacggccg gcacggccga cgcggatggc ggggtgggcc tggcgtcggc atttaccctg    900
ctgctggccc gcgagatggg cgaccagacg ctcttcgacc agctgctgaa tcacctggaa    960
ccgccggccc agcccagcat cgtctcggcc tcattgcgtt acgagcatcc cggcagcctg   1020
ttgttcgacg aactgctgtt cctggccaag gtgcatgccg ctttggcgc cctgctccag   1080
atgccgcctc cggcggcgaa atccgggggg aaatga                              1116
```

<210> SEQ ID NO 12
<211> LENGTH: 371
<212> TYPE: PRT
<213> ORGANISM: Castellaniella defragans

<400> SEQUENCE: 12

```
Ala Pro Leu Pro Leu Gly Arg Leu Ala Pro Thr Glu Asp Tyr Phe Ala
1               5                   10                  15

Gln Gln Ala Lys Gln Ala Val Thr Pro Asp Val Met Ala Gln Leu Ala
            20                  25                  30

Tyr Met Asn Tyr Ile Asp Phe Ile Ser Pro Phe Tyr Ser Arg Gly Cys
        35                  40                  45

Ser Phe Glu Ala Trp Glu Leu Lys His Thr Pro Gln Arg Val Ile Lys
    50                  55                  60

Tyr Ser Ile Ala Phe Tyr Ala Tyr Gly Leu Ala Ser Val Ala Leu Ile
65                  70                  75                  80

Asp Pro Asn Leu Arg Ala Leu Ala Gly His Asp Leu Asp Ile Ala Val
                85                  90                  95

Ser Lys Met Lys Cys Lys Arg Val Trp Gly Asp Trp Glu Glu Asp Gly
            100                 105                 110

Phe Gly Asp Asp Pro Ile Glu Lys Glu Asn Ile Met Tyr Lys Gly His
```

115                 120                 125
Leu Asn Leu Met Tyr Gly Leu Tyr Gln Leu Val Thr Gly Ser Arg Arg
    130                 135                 140

Tyr Glu Ala Glu His Ala His Leu Thr Arg Ile Ile His Asp Glu Ile
145                 150                 155                 160

Gly Ala Asn Pro Phe Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asp Tyr Arg Ala Ala Thr Arg Ala Trp Leu Asp Phe
        195                 200                 205

Ile Gln Lys Asp Leu Ile Asp Pro Glu Arg Gly Ala Phe Tyr Leu Ser
    210                 215                 220

Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Ala Phe Lys Lys Thr Phe Val Glu Val Tyr Asp
            260                 265                 270

Gly Gly Arg Lys Ala Arg Val Arg Glu Thr Ala Gly Thr Ala Asp Ala
        275                 280                 285

Asp Gly Gly Val Gly Leu Ala Ser Ala Phe Thr Leu Leu Leu Ala Arg
    290                 295                 300

Glu Met Gly Asp Gln Thr Leu Phe Asp Gln Leu Leu Asn His Leu Glu
305                 310                 315                 320

Pro Pro Ala Gln Pro Ser Ile Val Ser Ala Ser Leu Arg Tyr Glu His
                325                 330                 335

Pro Gly Ser Leu Leu Phe Asp Glu Leu Leu Phe Leu Ala Lys Val His
            340                 345                 350

Ala Gly Phe Gly Ala Leu Leu Gln Met Pro Pro Ala Ala Lys Ser
        355                 360                 365

Gly Gly Lys
    370

<210> SEQ ID NO 13
<211> LENGTH: 1197
<212> TYPE: DNA
<213> ORGANISM: artificial
<220> FEATURE:
<223> OTHER INFORMATION: Nucleic acid encoding full-length engineered
      variant SEQ ID NO: 14

<400> SEQUENCE: 13
atgcgtttta ccctgaaaac accggcaatt gcaagcgcag ttgcagcact gctgattggt     60
ctgggtcagc tgcacatgc agcaccgctg ccgctgggtc gtctggcacc gaccgaagat    120
tattttgcac agcaggcaaa acaggcagtt acaccggatg ttatggcaca gctggcatat    180
atgaactata tcgattttat cagcccgttt tttagccgca gctgtagctt tgaagcatgg    240
gaactgaaac atacaccgca gcgtgttatc aaatatagca ttgccttta tgcatatggt    300 ctggcaagcg ttgcactgat tgatccgaat ctgcgtgcac tggcaggtca tgatctggat    360
attgcagtta gcaaaatgaa atgcaaacgc gtgtggatgg attgggaaga ggatggtttt    420
ggtgatgatc cgattgagaa agaaaacatc atgtataaag ccatctgaa cctgatgtat    480 ggtctgtatc agctggttac cggtagccgt aaatatgaag cagaacatgc acatctgacc    540

```
cgtctgattc atgatgaaat tggtgcaaat ccgtttgccg gtattttttg tgaaccgaac    600
aactattttg tgcagtgtaa tagcgttgca tatctgagcc tgtgggttta tgatcgtctg    660
catggcaccg attatcgtgc agcaacccgt gcatggctgg attttattca gaaagatctg    720
atcgatccgg aacgtggtgc attttatctg agctatcatc cggaaagcgg tgcagttaaa    780
ccgtggatta gcgcatatac caccgcatgg accctggcaa tggttcatgg tatggatccg    840
gcatttagcg aacgttatta tcctgcattc aaaaaaacct ttgtcgaggt gtatgatggt    900
ggtcgtaaag cacgtgttcg tgaaaccgca ggcaccgcag atgcagatgg tggtgttggt    960
ctggccagtg caagcaccct gctgctggca cgtgaaatgg gtgatcagac cctgtttgat    1020
cagctgctga atcatctgga accgcctgca cagccgagca ttgttagcgc aagcctgcgt    1080
tatgaacatc cgagcagcct gttttttgat gaactgctgt ttctggcaaa agtgcatgca    1140
ggttttggcg cactgctgca gatgcctccg cctgcagcaa aaagcggtgg taaataa      1197
```

<210> SEQ ID NO 14
<211> LENGTH: 398
<212> TYPE: PRT
<213> ORGANISM: artificial
<220> FEATURE:
<223> OTHER INFORMATION: Full-length engineered variant of novel SEQ ID
      NO: 9 (LinD-2) with 11 amino acid substitutions V19I, Y71F, G74S,
      G133M, R171K, I182L, V196F, D200N, F325S, G365S, L368F; designated
      LinD-2C

<400> SEQUENCE: 14

```
Met Arg Phe Thr Leu Lys Thr Pro Ala Ile Ala Ser Ala Val Ala Ala
1               5                   10                  15

Leu Leu Ile Gly Leu Gly Gln Pro Ala His Ala Ala Pro Leu Pro Leu
            20                  25                  30

Gly Arg Leu Ala Pro Thr Glu Asp Tyr Phe Ala Gln Gln Ala Lys Gln
        35                  40                  45

Ala Val Thr Pro Asp Val Met Ala Gln Leu Ala Tyr Met Asn Tyr Ile
    50                  55                  60

Asp Phe Ile Ser Pro Phe Phe Ser Arg Ser Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Asn Leu Arg
            100                 105                 110

Ala Leu Ala Gly His Asp Leu Asp Ile Ala Val Ser Lys Met Lys Cys
        115                 120                 125

Lys Arg Val Trp Met Asp Trp Glu Glu Asp Gly Phe Gly Asp Asp Pro
    130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Lys Tyr Glu Ala Glu His
                165                 170                 175

Ala His Leu Thr Arg Leu Ile His Asp Glu Ile Gly Ala Asn Pro Phe
            180                 185                 190

Ala Gly Ile Phe Cys Glu Pro Asn Asn Tyr Phe Val Gln Cys Asn Ser
        195                 200                 205

Val Ala Tyr Leu Ser Leu Trp Val Tyr Asp Arg Leu His Gly Thr Asp
    210                 215                 220

Tyr Arg Ala Ala Thr Arg Ala Trp Leu Asp Phe Ile Gln Lys Asp Leu
225                 230                 235                 240
```

```
Ile Asp Pro Glu Arg Gly Ala Phe Tyr Leu Ser Tyr His Pro Glu Ser
                245                 250                 255
Gly Ala Val Lys Pro Trp Ile Ser Ala Tyr Thr Thr Ala Trp Thr Leu
            260                 265                 270
Ala Met Val His Gly Met Asp Pro Ala Phe Ser Glu Arg Tyr Tyr Pro
        275                 280                 285
Ala Phe Lys Lys Thr Phe Val Glu Val Tyr Asp Gly Gly Arg Lys Ala
    290                 295                 300
Arg Val Arg Glu Thr Ala Gly Thr Ala Asp Ala Asp Gly Gly Val Gly
305                 310                 315                 320
Leu Ala Ser Ala Ser Thr Leu Leu Leu Ala Arg Glu Met Gly Asp Gln
                325                 330                 335
Thr Leu Phe Asp Gln Leu Leu Asn His Leu Glu Pro Pro Ala Gln Pro
            340                 345                 350
Ser Ile Val Ser Ala Ser Leu Arg Tyr Glu His Pro Ser Ser Leu Phe
        355                 360                 365
Phe Asp Glu Leu Leu Phe Leu Ala Lys Val His Ala Gly Phe Gly Ala
    370                 375                 380
Leu Leu Gln Met Pro Pro Pro Ala Ala Lys Ser Gly Gly Lys
385                 390                 395
```

<210> SEQ ID NO 15
<211> LENGTH: 1194
<212> TYPE: DNA
<213> ORGANISM: unknown
<220> FEATURE:
<223> OTHER INFORMATION: Linalool dehydratase (LinD) from Metagenomics
      on Activated sludge from Padre Dam enriched on Myrcene; designated
      LinD-3

<400> SEQUENCE: 15

```
atgcggttca cattgaagac gacggcgatc gtgtcggccg ccgccctgct ggccggtttc      60
gggccgccgc cccgcgcggc ggaactgccg ccggggcggc tcgccaccac cgaggactat     120
ttcgcgcagc aggcgaagca ggccgtcacc cccgacgtga tgcccagct  ggcctacatg     180
aactacatcg atttcatctc gcccttctac agccgggct  gctccttcga ggcctgggag     240
ctcaagcaca cgccgcagcg ggtcatcaag tattcgatcg ccttctatgc gtatggcctg     300
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgccca cctcacccgc     540
atcatccatg acgagatcgc ggccaacccc tttgccggca tcgtctgcga gccggacaat     600
tattttgtcc agtgcaattc ggtcgcctac ctgagcctgt gggtctatga ccggctgcat     660
ggcaccgact accgggcggc caccagggcc tggctggatt tcatccagaa ggacctgatc     720
gatcccgagc ggggcgcctt ctacctgtcc tatcaccccg agtccggcgc ggtgaagccg     780
tggatctcgg cgtatacgac agcctggacg ctcgccatgg tgcacggcat ggaccccgcc     840
ttttccgagc gctactaccc ccggttcaag cagaccttcg tcgagctcta cgacgagggc     900
cgcaaggccc gggtgcgcga cggccggcgc acggacgacg cggatggcgg ggtgggcctg     960
gcttcggcgt tcaccctgct gctggcccgc gagatgggcg accagcagct cttcgaccag    1020
ttgctgaatc acctggagcc gccggccaag cccagcatcg tttcggcctc gctgcggtac    1080
```

```
gagcatcccg gcagcctgct gttcgacgag ctgctgttcc tcgccaaggt gcatgccggt    1140
tttggcgccc tgcttcagat gccgcctccg gcggccaagc tcgcggggaa ataa          1194
```

<210> SEQ ID NO 16
<211> LENGTH: 397
<212> TYPE: PRT
<213> ORGANISM: unknown
<220> FEATURE:
<223> OTHER INFORMATION: unprocessed, LinD enzyme, including signal
      peptide encoded by SEQ ID NO: 15; designated LinD-3

<400> SEQUENCE: 16

```
Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
        115                 120                 125

Arg Val Trp Gly Asp Trp Glu Glu Asp Gly Phe Gly Thr Asp Pro Ile
130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
        195                 200                 205

Ala Tyr Leu Ser Leu Trp Val Tyr Asp Arg Leu His Gly Thr Asp Tyr
    210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
        275                 280                 285

Phe Lys Gln Thr Phe Val Glu Leu Tyr Asp Glu Gly Arg Lys Ala Arg
    290                 295                 300

Val Arg Glu Thr Ala Gly Thr Asp Asp Ala Asp Gly Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
```

```
                340             345             350
Ile Val Ser Ala Ser Leu Arg Tyr Glu His Pro Gly Ser Leu Leu Phe
            355                 360                 365

Asp Glu Leu Leu Phe Leu Ala Lys Val His Ala Gly Phe Gly Ala Leu
    370                 375                 380

Leu Gln Met Pro Pro Pro Ala Ala Lys Leu Ala Gly Lys
385                 390                 395
```

<210> SEQ ID NO 17
<211> LENGTH: 1116
<212> TYPE: DNA
<213> ORGANISM: unknown
<220> FEATURE:
<223> OTHER INFORMATION: Nucleic acid encoding processed LinD-3 LinD
    enzyme, no signal peptide; from Metagenomics on Activated sludge
    from Padre Dam enriched on Myrcene

<400> SEQUENCE: 17

```
gcggaactgc cgccggggcg gctcgccacc accgaggact atttcgcgca gcaggcgaag      60
caggccgtca cccccgacgt gatggcccag ctggcctaca tgaactacat cgatttcatc    120
tcgcccttct acagccgggg ctgctccttc gaggcctggg agctcaagca cacgccgcag    180
cgggtcatca agtattcgat cgccttctat gcgtatggcc tggccagcgt ggcgctcatc    240
gacccgaagc tgcgtgcgct cgccggccat gacctggaca tcgcggtctc caagatgaag    300
tgcaagcggg tctggggcga ctgggaggaa gacgggttcg gcaccgaccc gatcgagaaa    360
gagaacatca tgtacaaggg ccacctgaac ctgatgtacg gcctctatca gctggtgacc    420
ggcagccgcc ggtacgaagc cgagcatgcc cacctcaccc gcatcatcca tgacgagatc    480
gcggccaacc cctttgccgg catcgtctgc gagccggaca ttattttgt ccagtgcaat     540
tcggtcgcct acctgagcct gtgggtctat gaccggctgc atggcaccga ctaccgggcg    600
gccaccaggg cctggctgga tttcatccag aaggacctga tcgatcccga gcggggcgcc    660
ttctacctgt cctatcaccc cgagtccggc gcggtgaagc cgtggatctc ggcgtatacg    720
acagcctgga cgctcgccat ggtgcacggc atggaccccg ccttttccga gcgctactac    780
ccccggttca agcagacctt cgtcgagctc tacgacgagg gccgcaaggc ccgggtgcgc    840
gagacgccg gcacggacga cgcggatggc ggggtgggcc tggcttcggc gttcaccctg    900
ctgctggccc gcgagatggg cgaccagcag ctcttcgacc agttgctgaa tcacctggag    960
ccgccggcca agcccagcat cgtttcggcc tcgctgcggt acgagcatcc cggcagcctg   1020
ctgttcgacg agctgctgtt cctcgccaag gtgcatgccg gttttggcgc cctgcttcag   1080
atgccgcctc cggcggccaa gctcgcgggg aaataa                             1116
```

<210> SEQ ID NO 18
<211> LENGTH: 371
<212> TYPE: PRT
<213> ORGANISM: unknown
<220> FEATURE:
<223> OTHER INFORMATION: Processed LinD-3 LinD enzyme, no signal
    peptide; from Metagenomics on Activated sludge from Padre Dam
    enriched on Myrcene

<400> SEQUENCE: 18

```
Ala Glu Leu Pro Pro Gly Arg Leu Ala Thr Thr Glu Asp Tyr Phe Ala
1               5                   10                  15

Gln Gln Ala Lys Gln Ala Val Thr Pro Asp Val Met Ala Gln Leu Ala
            20                  25                  30
```

Tyr Met Asn Tyr Ile Asp Phe Ile Ser Pro Phe Tyr Ser Arg Gly Cys
            35                  40                  45

Ser Phe Glu Ala Trp Glu Leu Lys His Thr Pro Gln Arg Val Ile Lys
 50                  55                  60

Tyr Ser Ile Ala Phe Tyr Ala Tyr Gly Leu Ala Ser Val Ala Leu Ile
 65                  70                  75                  80

Asp Pro Lys Leu Arg Ala Leu Ala Gly His Asp Leu Asp Ile Ala Val
                 85                  90                  95

Ser Lys Met Lys Cys Lys Arg Val Trp Gly Asp Trp Glu Glu Asp Gly
                100                 105                 110

Phe Gly Thr Asp Pro Ile Glu Lys Glu Asn Ile Met Tyr Lys Gly His
            115                 120                 125

Leu Asn Leu Met Tyr Gly Leu Tyr Gln Leu Val Thr Gly Ser Arg Arg
130                 135                 140

Tyr Glu Ala Glu His Ala His Leu Thr Arg Ile Ile His Asp Glu Ile
145                 150                 155                 160

Ala Ala Asn Pro Phe Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
                180                 185                 190

Leu His Gly Thr Asp Tyr Arg Ala Ala Thr Arg Ala Trp Leu Asp Phe
            195                 200                 205

Ile Gln Lys Asp Leu Ile Asp Pro Glu Arg Gly Ala Phe Tyr Leu Ser
210                 215                 220

Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Arg Phe Lys Gln Thr Phe Val Glu Leu Tyr Asp
                260                 265                 270

Glu Gly Arg Lys Ala Arg Val Arg Glu Thr Ala Gly Thr Asp Asp Ala
            275                 280                 285

Asp Gly Gly Val Gly Leu Ala Ser Ala Phe Thr Leu Leu Leu Ala Arg
290                 295                 300

Glu Met Gly Asp Gln Gln Leu Phe Asp Gln Leu Leu Asn His Leu Glu
305                 310                 315                 320

Pro Pro Ala Lys Pro Ser Ile Val Ser Ala Ser Leu Arg Tyr Glu His
                325                 330                 335

Pro Gly Ser Leu Leu Phe Asp Glu Leu Leu Phe Leu Ala Lys Val His
            340                 345                 350

Ala Gly Phe Gly Ala Leu Leu Gln Met Pro Pro Ala Ala Lys Leu
            355                 360                 365

Ala Gly Lys
370

<210> SEQ ID NO 19
<211> LENGTH: 1203
<212> TYPE: DNA
<213> ORGANISM: unknown
<220> FEATURE:
<223> OTHER INFORMATION: nucleic acid encoding SEQ ID NO: 20, which is
      unprocessed and includes its signal peptide; from Metagenomics on
      Activated sludge from Camp Pendleton enriched on Myrcene
      (Secondary Enrichment); designated LinD-4

<400> SEQUENCE: 19

```
atgataaagc cccacagacg atccgccgca cgactttccc taatcatcgc agcaaccctc    60
ggtttcggca gttccgccag tgccgaagac ctgttccccg ccgcctcgc caccaccgcg    120 gactacttcg cccaacgcga aaagcacacc gtgactcccg atgtcatggc gcacctggcc    180
ttcatgaact acacggattt catttccccc ttctacagcc ggggttgtgc cttcgacgcg    240
tgggacatca agaagacacc gcaacggatc atcaagtatt cgctggcgtt ctattcctac    300
ggcctcgcta gcgttgcgct caccgatccc aaactgcgac cacttgccgc gcatgcgatc    360
gatgtcgcca cgtcaaagat gaaatgcaag cgcgtctggg aagactggga agaagatggc    420
ttcggtagcg acccgatcga aagcaaaac atcatgtaca agggtcacct gaacctgatg    480
tatggcctct accagctggt cagcggaaac cggcagtacg aggccgaaca caaacatctg    540
accaagatca tccacgacga gatcaaggcc aacccttcg ctggcgcgct ctgcgagccg    600
gacaactatt ttgtccaatg caactcggtc gcctatctga gcctgtgggt gtatgaccga    660
ctccatggca caagctacaa ggcagccacc gaacccctggc tgaaattcct gaaaaaggat    720
ctgatcgatc cgaaaacggg cgccttctat ctatcctttc accccgaatc cggcacagtg    780
aaaccctggc tctcggcgta taccacggcg tggacgctgg ccatggtgca cggcatggac    840
ccggcctttt ccgaacgcta ctaccggcg ttcaagaaga cctttgtcga agtctatgac    900
ggcggccgaa aggcacgggt tcgcgagacg accaatacgc cagacgccga cggcggggtt    960
ggcgcggcct ctgcgttcac gttgctgctt gcccgtgaga tgggcgacca gacactcttc    1020
gaccagttgc tcaaccacct tgagcccccg gcgaaaccca aaatcacctc agccatcttg    1080
aactacgagg cgcccagcaa cctgctcttt gatgagttgc tgttcctctc gaaagtccat    1140
gtcggctttg gtgaactgct aaaagctacg ccccccgccgg cgcgcgcaga cagtcagaaa    1200
taa                                                                 1203
```

<210> SEQ ID NO 20
<211> LENGTH: 400
<212> TYPE: PRT
<213> ORGANISM: unknown
<220> FEATURE:
<223> OTHER INFORMATION: unprocessed, LinD enzyme, designated LinD-4,
      including signal peptide; from Metagenomics on Activated sludge
      from Camp Pendleton enriched on Myrcene (Secondary Enrichment)

<400> SEQUENCE: 20

Met Ile Lys Pro His Arg Arg Ser Ala Ala Arg Leu Ser Leu Ile Ile
1               5                   10                  15

Ala Ala Thr Leu Gly Phe Gly Ser Ser Ala Ser Ala Glu Asp Leu Phe
            20                  25                  30

Pro Gly Arg Leu Ala Thr Thr Ala Asp Tyr Phe Ala Gln Arg Glu Lys
        35                  40                  45

His Thr Val Thr Pro Asp Val Met Ala His Leu Ala Phe Met Asn Tyr
    50                  55                  60

Thr Asp Phe Ile Ser Pro Phe Tyr Ser Arg Gly Cys Ala Phe Asp Ala
65                  70                  75                  80

Trp Asp Ile Lys Lys Thr Pro Gln Arg Ile Ile Lys Tyr Ser Leu Ala
                85                  90                  95

Phe Tyr Ser Tyr Gly Leu Ala Ser Val Ala Leu Thr Asp Pro Lys Leu
            100                 105                 110

Arg Pro Leu Ala Ala His Ala Ile Asp Val Ala Thr Ser Lys Met Lys
        115                 120                 125

Cys Lys Arg Val Trp Glu Asp Trp Glu Glu Asp Gly Phe Gly Ser Asp

```
    130                 135                 140
Pro Ile Glu Lys Gln Asn Ile Met Tyr Lys Gly His Leu Asn Leu Met
145                 150                 155                 160

Tyr Gly Leu Tyr Gln Leu Val Ser Gly Asn Arg Gln Tyr Glu Ala Glu
                165                 170                 175

His Lys His Leu Thr Lys Ile Ile His Asp Glu Ile Lys Ala Asn Pro
            180                 185                 190

Phe Ala Gly Ala Leu Cys Glu Pro Asp Asn Tyr Phe Val Gln Cys Asn
        195                 200                 205

Ser Val Ala Tyr Leu Ser Leu Trp Val Tyr Asp Arg Leu His Gly Thr
210                 215                 220

Ser Tyr Lys Ala Ala Thr Glu Pro Trp Leu Lys Phe Leu Lys Lys Asp
225                 230                 235                 240

Leu Ile Asp Pro Lys Thr Gly Ala Phe Tyr Leu Ser Phe His Pro Glu
                245                 250                 255

Ser Gly Thr Val Lys Pro Trp Leu Ser Ala Tyr Thr Thr Ala Trp Thr
            260                 265                 270

Leu Ala Met Val His Gly Met Asp Pro Ala Phe Ser Glu Arg Tyr Tyr
        275                 280                 285

Pro Ala Phe Lys Lys Thr Phe Val Glu Val Tyr Asp Gly Gly Arg Lys
290                 295                 300

Ala Arg Val Arg Glu Thr Thr Asn Thr Pro Asp Ala Asp Gly Val
305                 310                 315                 320

Gly Ala Ala Ser Ala Phe Thr Leu Leu Leu Ala Arg Glu Met Gly Asp
            325                 330                 335

Gln Thr Leu Phe Asp Gln Leu Leu Asn His Leu Glu Pro Pro Ala Lys
        340                 345                 350

Pro Lys Ile Thr Ser Ala Ile Leu Asn Tyr Glu Ala Pro Ser Asn Leu
                355                 360                 365

Leu Phe Asp Glu Leu Leu Phe Leu Ser Lys Val His Val Gly Phe Gly
            370                 375                 380

Glu Leu Leu Lys Ala Thr Pro Pro Ala Arg Ala Asp Ser Gln Lys
385                 390                 395                 400
```

<210> SEQ ID NO 21
<211> LENGTH: 1119
<212> TYPE: DNA
<213> ORGANISM: unknown
<220> FEATURE:
<223> OTHER INFORMATION: Nucleic acid encoding processed LinD-4 LinD enzyme, no signal peptide; from Metagenomics on Activated sludge from Camp Pendleton enriched on Myrcene (Secondary Enrichment)

<400> SEQUENCE: 21

```
gaagacctgt tccccggccg cctcgccacc accgcggact acttcgccca acgcgaaaag    60
cacaccgtga ctcccgatgt catggcgcac ctggccttca tgaactacac ggatttcatt   120
tcccccttct acagccgggg ttgtgccttc gacgcgtggg acatcaagaa gacaccgcaa   180
cggatcatca gtattcgct ggcgttctat tcctacggcc tcgctagcgt tgcgctcacc    240
gatcccaaac tgcgaccact tgccgcgcat gcgatcgatg tcgccacgtc aaagatgaaa   300
tgcaagcgcg tctgggaaga ctgggaagaa gatggcttcg gtagcgaccc gatcgagaag   360
caaaacatca tgtacaaggg tcacctgaac ctgatgtatg gcctctacca gctggtcagc   420 ggaaccggc agtacgaggc cgaacacaaa catctgacca gatcatcca cgacgagatc    480 aaggccaacc ctttcgctgg cgcgctctgc gagccggaca actattttgt ccaatgcaac   540
```

```
tcggtcgcct atctgagcct gtgggtgtat gaccgactcc atggcacaag ctacaaggca    600
gccaccgaac cctggctgaa attcctgaaa aggatctga tcgatccgaa acgggcgcc     660 ttctatctat ccttcaccc cgaatccggc acagtgaaac cctggctctc ggcgtatacc    720
acggcgtgga cgctggccat ggtgcacggc atggacccgg ccttttccga acgctactac    780
ccggcgttca agaagaccttt tgtcgaagtc tatgacggcg ccgaaaggc acgggttcgc    840 gagacgacca atacgccaga cgccgacggc ggggttggcg cggcctctgc gttcacgttg    900
ctgcttgccc gtgagatggg cgaccagaca ctcttcgacc agttgctcaa ccaccttgag    960 ccccccggcga aacccaaaat cacctcagcc atcttgaact acgaggcgcc cagcaacctg   1020
ctctttgatg agttgctgtt cctctcgaaa gtccatgtcg gctttggtga actgctaaaa   1080
gctacgcccc cgccggcgcg cgcagacagt cagaaataa                          1119
```

<210> SEQ ID NO 22
<211> LENGTH: 372
<212> TYPE: PRT
<213> ORGANISM: unknown
<220> FEATURE:
<223> OTHER INFORMATION: Processed LinD-4 LinD enzyme, no signal
      peptide; from Metagenomics on Activated sludge from Camp Pendleton
      enriched on Myrcene (Secondary Enrichment)

<400> SEQUENCE: 22

```
Glu Asp Leu Phe Pro Gly Arg Leu Ala Thr Thr Ala Asp Tyr Phe Ala
1               5                   10                  15

Gln Arg Glu Lys His Thr Val Thr Pro Asp Val Met Ala His Leu Ala
            20                  25                  30

Phe Met Asn Tyr Thr Asp Phe Ile Ser Pro Phe Tyr Ser Arg Gly Cys
        35                  40                  45

Ala Phe Asp Ala Trp Asp Ile Lys Lys Thr Pro Gln Arg Ile Ile Lys
    50                  55                  60

Tyr Ser Leu Ala Phe Tyr Ser Tyr Gly Leu Ala Ser Val Ala Leu Thr
65                  70                  75                  80

Asp Pro Lys Leu Arg Pro Leu Ala Ala His Ala Ile Asp Val Ala Thr
                85                  90                  95

Ser Lys Met Lys Cys Lys Arg Val Trp Glu Asp Trp Glu Glu Asp Gly
            100                 105                 110

Phe Gly Ser Asp Pro Ile Glu Lys Gln Asn Ile Met Tyr Lys Gly His
        115                 120                 125

Leu Asn Leu Met Tyr Gly Leu Tyr Gln Leu Val Ser Gly Asn Arg Gln
    130                 135                 140

Tyr Glu Ala Glu His Lys His Leu Thr Lys Ile Ile His Asp Glu Ile
145                 150                 155                 160

Lys Ala Asn Pro Phe Ala Gly Ala Leu Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Ser Tyr Lys Ala Ala Thr Glu Pro Trp Leu Lys Phe
        195                 200                 205

Leu Lys Lys Asp Leu Ile Asp Pro Lys Thr Gly Ala Phe Tyr Leu Ser
    210                 215                 220

Phe His Pro Glu Ser Gly Thr Val Lys Pro Trp Leu Ser Ala Tyr Thr
225                 230                 235                 240

Thr Ala Trp Thr Leu Ala Met Val His Gly Met Asp Pro Ala Phe Ser
```

|  |  |  | 245 |  |  |  | 250 |  |  |  | 255 |  |
|---|---|---|---|---|---|---|---|---|---|---|---|---|
| Glu | Arg | Tyr | Tyr | Pro | Ala | Phe | Lys | Lys | Thr | Phe | Val | Glu | Val | Tyr | Asp |
|  |  |  | 260 |  |  |  | 265 |  |  |  | 270 |  |

Gly Gly Arg Lys Ala Arg Val Arg Glu Thr Thr Asn Thr Pro Asp Ala
        275                 280                 285

Asp Gly Gly Val Gly Ala Ala Ser Ala Phe Thr Leu Leu Leu Ala Arg
        290                 295                 300

Glu Met Gly Asp Gln Thr Leu Phe Asp Gln Leu Leu Asn His Leu Glu
305                 310                 315                 320

Pro Pro Ala Lys Pro Lys Ile Thr Ser Ala Ile Leu Asn Tyr Glu Ala
                325                 330                 335

Pro Ser Asn Leu Leu Phe Asp Glu Leu Leu Phe Leu Ser Lys Val His
                340                 345                 350

Val Gly Phe Gly Glu Leu Leu Lys Ala Thr Pro Pro Ala Arg Ala
                355                 360                 365

Asp Ser Gln Lys
        370

<210> SEQ ID NO 23
<211> LENGTH: 1206
<212> TYPE: DNA
<213> ORGANISM: unknown
<220> FEATURE:
<223> OTHER INFORMATION: nucleic acid encoding SEQ ID NO: 24, which is
      unprocessed and includes its signal peptide; from Metagenomics on
      Activated sludge from Camp Pendleton  enriched on Myrcene (Primary
      Enrichment)

<400> SEQUENCE: 23
atgaagaaca tccaaaagac ggctgccgcg ctgcccgcca tccttgccgc agtgctcgcg        60
ttcagtgcgc cggcccattc ggcggacctg ccgcccgggc gcctcgcctc gaccgaggaa       120
tatttcgccc agcgcgagaa acaggccgtc acgcccgacg tcatggccca cctcgcctac       180
atgaactaca ccgatttcgt ctcgcccttc tacagccggg gctgcgcctt cgacgcctgg       240
gcgatcaaga agaccccgca gcggatcatc aagtactcgc tcgccttcta cgcctatggc       300
ctggccagcg tcgcgctcac cgatccgcag ctgcgtccgc tcgccggaca tgcaatcgac       360
atcgcgaccg ccaagatgaa atgcaagcag gtctggggag actgggagga agacgggttc       420
ggcgaggatc cgatcgagaa agagaacatc atgtacaagg ccacttgaa cctgatgtac       480 ggcctctacc aactggtcac cggcaaccgc cggtacgaga aggagcacgc ccgcctcacg       540
cggatcatcc acgacgagat caaggccaat ccctacgccg gcatcgtctg cgagccggac       600
aactatttcg ttcagtgcaa ctcggtcgcc tacctgagcc tgtgggtcca tgaccgcctg       660
cacggcaccg actaccgggc ggcgacggcg gaatggctga aattcatcga gcacgacctg       720
atcgacccga acacggcgc cttccacctg tcctaccatc cggaatccca cgcggtgaaa       780
ccgtgggtct ccgcatacac cacggcgtgg acgctcgcca tggtgcacgg catggatccc       840
gctttcgccg agcgctacta ccccgcttc aaggagacct tcgtcgaggt ctacgacgat       900
ggccgcaagg cccgggtccg cgagacgacc ggcaccaccg acgccgatgg cggcgtcggc       960
gcggcctccg cgttcaccct gctgctcgcc cgcgagatgg cgaccggca gctcttcgac      1020 cagttgctga accacctgga gcccccggca agaccgagga tcacctcggg catcctggaa      1080
tacgcggccc ccagcaatct gctgttcgac gagctgctgt tcctcgccaa ggtacacgtc      1140
ggtttcggcc agttgctgca ggccgggtcg gcgccgcccc gccgggccc cgccaggggg      1200 aaatga                                                                1206

<210> SEQ ID NO 24
<211> LENGTH: 401
<212> TYPE: PRT
<213> ORGANISM: unknown
<220> FEATURE:
<223> OTHER INFORMATION: unprocessed, LinD enzyme, designated LinD-5,
      including signal peptide; from Metagenomics on Activated sludge
      from Camp Pendleton  enriched on Myrcene (Primary Enrichment)

<400> SEQUENCE: 24

Met Lys Asn Ile Gln Lys Thr Ala Ala Leu Pro Ala Ile Leu Ala
1               5                   10                  15

Ala Val Leu Ala Phe Ser Ala Pro Ala His Ser Ala Asp Leu Pro Pro
            20                  25                  30

Gly Arg Leu Ala Ser Thr Glu Glu Tyr Phe Ala Gln Arg Glu Lys Gln
            35                  40                  45

Ala Val Thr Pro Asp Val Met Ala His Leu Ala Tyr Met Asn Tyr Thr
        50                  55                  60

Asp Phe Val Ser Pro Phe Tyr Ser Arg Gly Cys Ala Phe Asp Ala Trp
65                  70                  75                  80

Ala Ile Lys Lys Thr Pro Gln Arg Ile Ile Lys Tyr Ser Leu Ala Phe
                85                  90                  95

Tyr Ala Tyr Gly Leu Ala Ser Val Ala Leu Thr Asp Pro Gln Leu Arg
            100                 105                 110

Pro Leu Ala Gly His Ala Ile Asp Ile Ala Thr Ala Lys Met Lys Cys
        115                 120                 125

Lys Gln Val Trp Gly Asp Trp Glu Glu Asp Gly Phe Gly Glu Asp Pro
130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Asn Arg Arg Tyr Glu Lys Glu His
                165                 170                 175

Ala Arg Leu Thr Arg Ile Ile His Asp Glu Ile Lys Ala Asn Pro Tyr
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val His Asp Arg Leu His Gly Thr Asp
210                 215                 220

Tyr Arg Ala Ala Thr Ala Glu Trp Leu Lys Phe Ile Glu His Asp Leu
225                 230                 235                 240

Ile Asp Pro Lys His Gly Ala Phe His Leu Ser Tyr His Pro Glu Ser
                245                 250                 255

His Ala Val Lys Pro Trp Val Ser Ala Tyr Thr Thr Ala Trp Thr Leu
            260                 265                 270

Ala Met Val His Gly Met Asp Pro Ala Phe Ala Glu Arg Tyr Tyr Pro
        275                 280                 285

Arg Phe Lys Glu Thr Phe Val Glu Val Tyr Asp Asp Gly Arg Lys Ala
290                 295                 300

Arg Val Arg Glu Thr Thr Gly Thr Thr Asp Ala Asp Gly Gly Val Gly
305                 310                 315                 320

Ala Ala Ser Ala Phe Thr Leu Leu Ala Arg Glu Met Gly Asp Arg
                325                 330                 335

Gln Leu Phe Asp Gln Leu Leu Asn His Leu Glu Pro Pro Ala Arg Pro
            340                 345                 350

```
Arg Ile Thr Ser Gly Ile Leu Glu Tyr Ala Ala Pro Ser Asn Leu Leu
        355                 360                 365

Phe Asp Glu Leu Leu Phe Leu Ala Lys Val His Val Gly Phe Gly Gln
    370                 375                 380

Leu Leu Gln Ala Gly Ser Ala Pro Pro Pro Gly Pro Ala Arg Gly
385                 390                 395                 400

Lys
```

<210> SEQ ID NO 25
<211> LENGTH: 1125
<212> TYPE: DNA
<213> ORGANISM: unknown
<220> FEATURE:
<223> OTHER INFORMATION: Nucleic acid encoding processed (mature) LinD-5 LinD enzyme, no signal peptide; from Metagenomics on Activated sludge from Camp Pendleton enriched on Myrcene (Primary Enrichment)

<400> SEQUENCE: 25

```
gcggacctgc cgcccgggcg cctcgcctcg accgaggaat atttcgccca gcgcgagaaa      60
caggccgtca cgcccgacgt catggcccac ctcgcctaca tgaactacac cgatttcgtc     120
tcgcccttct acagccgggg ctgcgccttc gacgcctggg cgatcaagaa gaccccgcag     180
cggatcatca gtactcgct cgccttctac gcctatggcc tggccagcgt cgcgctcacc      240
gatccgcagc tgcgtccgct cgccggacat gcaatcgaca tcgcgaccgc caagatgaaa     300
tgcaagcagg tctggggaga ctgggaggaa gacgggttcg gcgaggatcc gatcgagaaa     360
gagaacatca tgtacaaggg ccacttgaac ctgatgtacg gcctctacca actggtcacc     420
ggcaaccgcc ggtacgagaa ggagcacgcc cgcctcacgc ggatcatcca cgacgagatc     480
aaggccaatc cctacgccgg catcgtctgc gagccggaca actatttcgt tcagtgcaac     540
tcggtcgcct acctgagcct gtgggtccat gaccgcctgc acggcaccga ctaccgggcg     600
gcgacggcgg aatggctgaa attcatcgag cacgacctga tcgacccgaa acacggcgcc     660
ttccacctgt cctaccatcc ggaatcccac gcggtgaaac cgtgggtctc cgcatacacc     720
acggcgtgga cgctcgccat ggtgcacggc atggatcccg ctttcgccga cgctactac     780
ccccgcttca aggagacctt cgtcgaggtc tacgacgatg ccgcaaggc ccgggtccgc     840
gagacgaccg gcaccaccga cgccgatggc ggcgtcggcg cggcctccgc gttcaccctg     900
ctgctcgccc gcgagatggg cgaccggcag ctcttcgacc agttgctgaa ccacctggag     960
cccccggcaa gaccgaggat cacctcgggc atcctggaat acgcggcccc cagcaatctg    1020
ctgttcgacg agctgctgtt cctcgccaag gtacacgtcg gtttcggcca gttgctgcag    1080
gccgggtcgg cgccgccccc gccgggcccc gccaggggga aatga                    1125
```

<210> SEQ ID NO 26
<211> LENGTH: 374
<212> TYPE: PRT
<213> ORGANISM: unknown
<220> FEATURE:
<223> OTHER INFORMATION: Processed (mature) LinD-5 LinD enzyme, no signal peptide; from Metagenomics on Activated sludge from Camp Pendleton enriched on Myrcene (Primary Enrichment)

<400> SEQUENCE: 26

```
Ala Asp Leu Pro Pro Gly Arg Leu Ala Ser Thr Glu Glu Tyr Phe Ala
1               5                   10                  15

Gln Arg Glu Lys Gln Ala Val Thr Pro Asp Val Met Ala His Leu Ala
```

```
                    20                  25                  30
Tyr Met Asn Tyr Thr Asp Phe Val Ser Pro Phe Tyr Ser Arg Gly Cys
                35                  40                  45

Ala Phe Asp Ala Trp Ala Ile Lys Lys Thr Pro Gln Arg Ile Ile Lys
 50                  55                  60

Tyr Ser Leu Ala Phe Tyr Ala Tyr Gly Leu Ala Ser Val Ala Leu Thr
 65                  70                  75                  80

Asp Pro Gln Leu Arg Pro Leu Ala Gly His Ala Ile Asp Ile Ala Thr
                85                  90                  95

Ala Lys Met Lys Cys Lys Gln Val Trp Gly Asp Trp Glu Glu Asp Gly
               100                 105                 110

Phe Gly Glu Asp Pro Ile Glu Lys Glu Asn Ile Met Tyr Lys Gly His
               115                 120                 125

Leu Asn Leu Met Tyr Gly Leu Tyr Gln Leu Val Thr Gly Asn Arg Arg
           130                 135                 140

Tyr Glu Lys Glu His Ala Arg Leu Thr Arg Ile Ile His Asp Glu Ile
145                 150                 155                 160

Lys Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val His Asp Arg
                180                 185                 190

Leu His Gly Thr Asp Tyr Arg Ala Ala Thr Ala Glu Trp Leu Lys Phe
            195                 200                 205

Ile Glu His Asp Leu Ile Asp Pro Lys His Gly Ala Phe His Leu Ser
    210                 215                 220

Tyr His Pro Glu Ser His Ala Val Lys Pro Trp Val Ser Ala Tyr Thr
225                 230                 235                 240

Thr Ala Trp Thr Leu Ala Met Val His Gly Met Asp Pro Ala Phe Ala
                245                 250                 255

Glu Arg Tyr Tyr Pro Arg Phe Lys Glu Thr Phe Val Glu Val Tyr Asp
                260                 265                 270

Asp Gly Arg Lys Ala Arg Val Arg Glu Thr Thr Gly Thr Thr Asp Ala
            275                 280                 285

Asp Gly Gly Val Gly Ala Ala Ser Ala Phe Thr Leu Leu Leu Ala Arg
    290                 295                 300

Glu Met Gly Asp Arg Gln Leu Phe Asp Gln Leu Leu Asn His Leu Glu
305                 310                 315                 320

Pro Pro Ala Arg Pro Arg Ile Thr Ser Gly Ile Leu Glu Tyr Ala Ala
                325                 330                 335

Pro Ser Asn Leu Leu Phe Asp Glu Leu Leu Phe Leu Ala Lys Val His
                340                 345                 350

Val Gly Phe Gly Gln Leu Leu Gln Ala Gly Ser Ala Pro Pro Pro
            355                 360                 365

Gly Pro Ala Arg Gly Lys
    370

<210> SEQ ID NO 27
<211> LENGTH: 1191
<212> TYPE: DNA
<213> ORGANISM: unknown
<220> FEATURE:
<223> OTHER INFORMATION: nucleic acid encoding SEQ ID NO: 28, which is
      unprocessed and includes its signal peptide; from Metagenomics on
      activated sludge (Camp Pendleton); designated LinD-6

<400> SEQUENCE: 27
```

```
atgaagaaca tcgcccgcgc ggccgcactg gcagccgcca tcatcgccac gatgccgggg     60
cccggtacgc cagcccacgc ggcagagttg ctgcccggac gcctcgcctc gaccgaggcc    120
tacttcgccc agcgcgaacg gcaggccgtc accccgacg tgatggccca cctcgcctac    180
atgaactaca cggacttcgt ttccccttc tacagccggg gctgcgcctt cgatgcgtgg    240
acgatcaaga agaccccgca gcggatcatc aagtactcgc tggccttcta cgcctacggc    300
ctcgccagcg tcgcgctcat cgacccgcag ctgcgcccac tcgccggcca cgcactcgac    360
atcgccacgg ccaagatgaa atgcaagcag gtctggggag actgggagga agacggcttc    420
ggcgacgatc cgatcgagaa ggaaaacatc atgtacaagg ccacctgaa cctgatgtac    480 ggcctccacc agctggtcac cggcaaccgg cggtacgaga aggaacacgc ccgcctcacg    540
cagatcatcc gcgacgagat cgcggccaac ccctacgccg catcgtctg cgagcccgac    600 aactacttcg tccagtgcaa ctcggtcgcc tacctgagcc tgtgggtcta cgaccgcctg    660
cacggcacca accacagggc ggcgaccgca gcgtggctca agttcatcga ggacgacctg    720
atcgacccga agcacggcgt cttccacctc tcctaccatc cggagtccgg cgcggtgaag    780
ccctgggtct cggcatacac gacggcatgg accctcgcca tggtgcacgg catggatccc    840
gcctttgccg agcgctacta ccccgcttc aaggaaacct tcgtcgaggt ctacgacgac    900
ggccgcaagg cccgggtccg cgagacgacc ggcaccaccg atgccgatgg cggcgtcggc    960
gcggcctccg ccttcaccct gctgctcgcc cgcgagatgg gcgaccagca gctcttcgac   1020
cagttgctga accacctcga gccgccggca agaccgaaga tcacctcggg catcctggac   1080
tacgaagcgc ccagcaacct gctgttcgac gaactgctgt tcctcgccaa ggtgcacgtc   1140
ggtttcggcc agctgctgca ggcccggccg gatcccgcca gggggcaatg a           1191
```

<210> SEQ ID NO 28
<211> LENGTH: 396
<212> TYPE: PRT
<213> ORGANISM: unknown
<220> FEATURE:
<223> OTHER INFORMATION: unprocessed, LinD enzyme, designated LinD-6, including signal peptide; from Metagenomics on activated sludge (Camp Pendleton)

<400> SEQUENCE: 28

```
Met Lys Asn Ile Ala Arg Ala Ala Ala Leu Ala Ala Ile Ile Ala
1               5                   10                  15

Thr Met Pro Gly Pro Gly Thr Pro Ala His Ala Ala Glu Leu Leu Pro
                20                  25                  30

Gly Arg Leu Ala Ser Thr Glu Ala Tyr Phe Ala Gln Arg Glu Arg Gln
            35                  40                  45

Ala Val Thr Pro Asp Val Met Ala His Leu Ala Tyr Met Asn Tyr Thr
        50                  55                  60

Asp Phe Val Ser Pro Phe Tyr Ser Arg Gly Cys Ala Phe Asp Ala Trp
65                  70                  75                  80

Thr Ile Lys Lys Thr Pro Gln Arg Ile Ile Lys Tyr Ser Leu Ala Phe
                85                  90                  95

Tyr Ala Tyr Gly Leu Ala Ser Val Ala Leu Ile Asp Pro Gln Leu Arg
            100                 105                 110

Pro Leu Ala Gly His Ala Leu Asp Ile Ala Thr Ala Lys Met Lys Cys
        115                 120                 125

Lys Gln Val Trp Gly Asp Trp Glu Glu Asp Gly Phe Gly Asp Asp Pro
    130                 135                 140
```

```
Ile Glu Lys Glu Asn Ile Met Tyr Lys Gly His Leu Asn Leu Met Tyr
145                 150                 155                 160

Gly Leu His Gln Leu Val Thr Gly Asn Arg Arg Tyr Glu Lys Glu His
                165                 170                 175

Ala Arg Leu Thr Gln Ile Ile Arg Asp Glu Ile Ala Ala Asn Pro Tyr
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Asn
210                 215                 220

His Arg Ala Ala Thr Ala Ala Trp Leu Lys Phe Ile Glu Asp Asp Leu
225                 230                 235                 240

Ile Asp Pro Lys His Gly Val Phe His Leu Ser Tyr His Pro Glu Ser
                245                 250                 255

Gly Ala Val Lys Pro Trp Val Ser Ala Tyr Thr Thr Ala Trp Thr Leu
            260                 265                 270

Ala Met Val His Gly Met Asp Pro Ala Phe Ala Glu Arg Tyr Tyr Pro
        275                 280                 285

Arg Phe Lys Glu Thr Phe Val Glu Val Tyr Asp Asp Gly Arg Lys Ala
290                 295                 300

Arg Val Arg Glu Thr Thr Gly Thr Thr Asp Ala Asp Gly Gly Val Gly
305                 310                 315                 320

Ala Ala Ser Ala Phe Thr Leu Leu Leu Ala Arg Glu Met Gly Asp Gln
                325                 330                 335

Gln Leu Phe Asp Gln Leu Leu Asn His Leu Glu Pro Pro Ala Arg Pro
            340                 345                 350

Lys Ile Thr Ser Gly Ile Leu Asp Tyr Glu Ala Pro Ser Asn Leu Leu
        355                 360                 365

Phe Asp Glu Leu Leu Phe Leu Ala Lys Val His Val Gly Phe Gly Gln
370                 375                 380

Leu Leu Gln Ala Arg Pro Asp Pro Ala Arg Gly Gln
385                 390                 395
```

<210> SEQ ID NO 29
<211> LENGTH: 1110
<212> TYPE: DNA
<213> ORGANISM: unknown
<220> FEATURE:
<223> OTHER INFORMATION: Nucleic acid encoding processed LInD-6 LinD
      enzyme, no signal peptide; from Metagenomics on activated sludge
      (Camp Pendleton)

<400> SEQUENCE: 29

```
gcagagttgc tgcccggacg cctcgcctcg accgaggcct acttcgccca gcgcgaacgg      60
caggccgtca cccccgacgt gatggcccac ctcgcctaca tgaactacac ggacttcgtt     120 tccccttct acagccgggg ctgcgccttc gatgcgtgga cgatcaagaa gaccccgcag     180
cggatcatca gtactcgct ggccttctac gcctacggcc tcgccagcgt cgcgctcatc     240
gacccgcagc tgcgcccact cgccggccac gcactcgaca tcgccacggc caagatgaaa     300
tgcaagcagg tctggggaga ctgggaggaa cacggcttcg cgacgatcc gatcgagaag     360 gaaaacatca tgtacaaggg ccacctgaac ctgatgtacg gcctccacca gctggtcacc     420
ggcaaccggc ggtacgagaa ggaacacgcc cgcctcacgc agatcatccg cgacgagatc     480
gcggccaacc cctacgccgg catcgtctgc gagcccgaca actacttcgt ccagtgcaac     540
```

```
tcggtcgcct acctgagcct gtgggtctac gaccgcctgc acggcaccaa ccacagggcg    600
gcgaccgcag cgtggctcaa gttcatcgag gacgacctga tcgacccgaa gcacggcgtc    660
ttccacctct cctaccatcc ggagtccggc gcggtgaagc cctgggtctc ggcatacacg    720
acggcatgga ccctcgccat ggtgcacggc atggatcccg cctttgccga gcgctactac    780
ccccgcttca aggaaacctt cgtcgaggtc tacgacgacg gccgcaaggc ccgggtccgc    840
gagacgaccg gcaccaccga tgccgatggc ggcgtcggcg cggcctccgc cttcaccctg    900
ctgctcgccc gcgagatggg cgaccagcag ctcttcgacc agttgctgaa ccacctcgag    960
ccgccggcaa gaccgaagat cacctcgggc atcctggact acgaagcgcc cagcaacctg   1020
ctgttcgacg aactgctgtt cctcgccaag gtgcacgtcg gtttcggcca gctgctgcag   1080
gcccggccgg atcccgccag ggggcaatga                                    1110
```

<210> SEQ ID NO 30
<211> LENGTH: 369
<212> TYPE: PRT
<213> ORGANISM: unknown
<220> FEATURE:
<223> OTHER INFORMATION: Processed (mature) LinD-6 LinD enzyme, no
      signal peptide; from Metagenomics on activated sludge (Camp
      Pendleton)

<400> SEQUENCE: 30

```
Ala Glu Leu Leu Pro Gly Arg Leu Ala Ser Thr Glu Ala Tyr Phe Ala
1               5                   10                  15

Gln Arg Glu Arg Gln Ala Val Thr Pro Asp Val Met Ala His Leu Ala
            20                  25                  30

Tyr Met Asn Tyr Thr Asp Phe Val Ser Pro Phe Tyr Ser Arg Gly Cys
        35                  40                  45

Ala Phe Asp Ala Trp Thr Ile Lys Lys Thr Pro Gln Arg Ile Ile Lys
    50                  55                  60

Tyr Ser Leu Ala Phe Tyr Ala Tyr Gly Leu Ala Ser Val Ala Leu Ile
65                  70                  75                  80

Asp Pro Gln Leu Arg Pro Leu Ala Gly His Ala Leu Asp Ile Ala Thr
                85                  90                  95

Ala Lys Met Lys Cys Lys Gln Val Trp Gly Asp Trp Glu Glu Asp Gly
            100                 105                 110

Phe Gly Asp Asp Pro Ile Glu Lys Glu Asn Ile Met Tyr Lys Gly His
        115                 120                 125

Leu Asn Leu Met Tyr Gly Leu His Gln Leu Val Thr Gly Asn Arg Arg
    130                 135                 140

Tyr Glu Lys Glu His Ala Arg Leu Thr Gln Ile Ile Arg Asp Glu Ile
145                 150                 155                 160

Ala Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asn His Arg Ala Ala Thr Ala Ala Trp Leu Lys Phe
        195                 200                 205

Ile Glu Asp Asp Leu Ile Asp Pro Lys His Gly Val Phe His Leu Ser
    210                 215                 220

Tyr His Pro Glu Ser Gly Ala Val Lys Pro Trp Val Ser Ala Tyr Thr
225                 230                 235                 240

Thr Ala Trp Thr Leu Ala Met Val His Gly Met Asp Pro Ala Phe Ala
                245                 250                 255
```

Glu Arg Tyr Tyr Pro Arg Phe Lys Glu Thr Phe Val Glu Val Tyr Asp
            260                 265                 270

Asp Gly Arg Lys Ala Arg Val Arg Glu Thr Thr Gly Thr Thr Asp Ala
        275                 280                 285

Asp Gly Gly Val Gly Ala Ala Ser Ala Phe Thr Leu Leu Leu Ala Arg
    290                 295                 300

Glu Met Gly Asp Gln Gln Leu Phe Asp Gln Leu Leu Asn His Leu Glu
305                 310                 315                 320

Pro Pro Ala Arg Pro Lys Ile Thr Ser Gly Ile Leu Asp Tyr Glu Ala
                325                 330                 335

Pro Ser Asn Leu Leu Phe Asp Glu Leu Leu Phe Leu Ala Lys Val His
            340                 345                 350

Val Gly Phe Gly Gln Leu Leu Gln Ala Arg Pro Asp Pro Ala Arg Gly
        355                 360                 365

Gln

<210> SEQ ID NO 31
<211> LENGTH: 1185
<212> TYPE: DNA
<213> ORGANISM: unknown
<220> FEATURE:
<223> OTHER INFORMATION: Native nucleic acid encoding SEQ ID NO:32,
      which is unprocessed and includes its signal peptide; from
      Metagenomics on activated sludge (Camp Pendleton); designated
      LinD-7

<400> SEQUENCE: 31

| | | |
|---|---|---|
| atgacacaat ggttatcaac ccctgcctg gcggcgattt taagtgcaat ttttattgtt | 60 |
| gtacccaaat tcgggttgac agagacatta ctgccggggc gattagccac tacgaaggcg | 120 |
| tattttcac agcaacgcaa ccaaaaactg acgccggata tggatgccca gctggcctat | 180 |
| atgtcctaca ctgattttat ttcacctttc tatagtcgag gttgcgcctt tgaggcttgg | 240 |
| gaactgaaac aggctcccca gagaattatc aaatactccc ttgcctggta ttcctacggc | 300 |
| cttgccagtg tcgctgtcat tgatcccagc ctgcaccgat atgcaggcca caatattgat | 360 |
| attgccatcg caaaaatgaa gtgcagacag gtttggggcg actgggaaga agacggcttt | 420 |
| ggctccaacc ctattgccca ccaaaatatt atgtacaaag gacacttgaa tctgatgtat | 480 |
| ggcctttatc agctgttaac gggcaatact cagtatgaag aggaattcat cgatctctct | 540 |
| aatatcatct atagcgaaat caaggaaaac ccttatgcag gtattgcttg cgagccggac | 600 |
| aattactttc gcagtgcaa ctccgtcgcc tatctcagcc tgtgggttta tgatcgtctc | 660 |
| taccacaccg actacaaagc agtcacaaaa ccctggcttg attttttaca gaaaaaactc | 720 |
| atagatcctg aaaccggcac atttcatgtt gcctatcatc aacatctca cgccgttaaa | 780 |
| ccctgggttt ccgcctacac cacggcctgg gcgctaacca tgattcatgg tctgaatccg | 840 |
| gaatttgcca aaagtactac ccctaatttt aagcaaacct tgttgaggt ttttgacaac | 900 |
| ggcaccaaag ccagggtgcg cgaaaccgcc cacaccacgg atgttgatgg tggcgtcggc | 960 |
| gccgcctcga ttttcacgct ggtgttggca agggaaatga atgatcagga gctgttttgat | 1020 |
| caactattga attatctcga accgccagca aagcctgtga tttattcggg gattctgcga | 1080 |
| tatgaaaatc caacgagcct gctattcgat gaactgcttt ttgtcgccaa ggtgcatgtg | 1140 |
| ggttttggcg aactgatcaa tctcaaacct gttgaaacag actag | 1185 |

<210> SEQ ID NO 32

```
<211> LENGTH: 394
<212> TYPE: PRT
<213> ORGANISM: unknown
<220> FEATURE:
<223> OTHER INFORMATION: unprocessed, LinD enzyme, designated LinD-7,
      including signal peptide; from Metagenomics on activated sludge
      (Camp Pendleton)

<400> SEQUENCE: 32
```

| | | | | | | | | | | | | | | | |
|---|---|---|---|---|---|---|---|---|---|---|---|---|---|---|---|
| Met | Thr | Gln | Trp | Leu | Ser | Thr | Pro | Cys | Leu | Ala | Ala | Ile | Leu | Ser | Ala |
| 1 | | | | 5 | | | | | 10 | | | | | 15 | |
| Ile | Phe | Ile | Val | Val | Pro | Lys | Phe | Gly | Leu | Thr | Glu | Thr | Leu | Leu | Pro |
| | | | 20 | | | | | 25 | | | | | 30 | | |
| Gly | Arg | Leu | Ala | Thr | Thr | Lys | Ala | Tyr | Phe | Ser | Gln | Arg | Asn | Gln | |
| | | 35 | | | | | 40 | | | | | 45 | | | |
| Lys | Leu | Thr | Pro | Asp | Met | Asp | Ala | Gln | Leu | Ala | Tyr | Met | Ser | Tyr | Thr |
| 50 | | | | | 55 | | | | | 60 | | | | | |
| Asp | Phe | Ile | Ser | Pro | Phe | Tyr | Ser | Arg | Gly | Cys | Ala | Phe | Glu | Ala | Trp |
| 65 | | | | | 70 | | | | | 75 | | | | | 80 |
| Glu | Leu | Lys | Gln | Ala | Pro | Gln | Arg | Ile | Ile | Lys | Tyr | Ser | Leu | Ala | Trp |
| | | | | 85 | | | | | 90 | | | | | 95 | |
| Tyr | Ser | Tyr | Gly | Leu | Ala | Ser | Val | Ala | Val | Ile | Asp | Pro | Ser | Leu | His |
| | | | 100 | | | | | 105 | | | | | 110 | | |
| Arg | Tyr | Ala | Gly | His | Asn | Ile | Asp | Ile | Ala | Ile | Ala | Lys | Met | Lys | Cys |
| | | 115 | | | | | 120 | | | | | 125 | | | |
| Arg | Gln | Val | Trp | Gly | Asp | Trp | Glu | Glu | Asp | Gly | Phe | Gly | Ser | Asn | Pro |
| 130 | | | | | 135 | | | | | 140 | | | | | |
| Ile | Ala | His | Gln | Asn | Ile | Met | Tyr | Lys | Gly | His | Leu | Asn | Leu | Met | Tyr |
| 145 | | | | | 150 | | | | | 155 | | | | | 160 |
| Gly | Leu | Tyr | Gln | Leu | Leu | Thr | Gly | Asn | Thr | Gln | Tyr | Glu | Glu | Glu | Phe |
| | | | | 165 | | | | | 170 | | | | | 175 | |
| Ile | Asp | Leu | Ser | Asn | Ile | Ile | Tyr | Ser | Glu | Ile | Lys | Glu | Asn | Pro | Tyr |
| | | | 180 | | | | | 185 | | | | | 190 | | |
| Ala | Gly | Ile | Ala | Cys | Glu | Pro | Asp | Asn | Tyr | Phe | Pro | Gln | Cys | Asn | Ser |
| | | 195 | | | | | 200 | | | | | 205 | | | |
| Val | Ala | Tyr | Leu | Ser | Leu | Trp | Val | Tyr | Asp | Arg | Leu | Tyr | His | Thr | Asp |
| 210 | | | | | 215 | | | | | 220 | | | | | |
| Tyr | Lys | Ala | Val | Thr | Lys | Pro | Trp | Leu | Asp | Phe | Leu | Gln | Lys | Lys | Leu |
| 225 | | | | | 230 | | | | | 235 | | | | | 240 |
| Ile | Asp | Pro | Glu | Thr | Gly | Thr | Phe | His | Val | Ala | Tyr | His | Pro | Thr | Ser |
| | | | | 245 | | | | | 250 | | | | | 255 | |
| His | Ala | Val | Lys | Pro | Trp | Val | Ser | Ala | Tyr | Thr | Thr | Ala | Trp | Ala | Leu |
| | | | 260 | | | | | 265 | | | | | 270 | | |
| Thr | Met | Ile | His | Gly | Leu | Asn | Pro | Glu | Phe | Ala | Lys | Lys | Tyr | Tyr | Pro |
| | | 275 | | | | | 280 | | | | | 285 | | | |
| Asn | Phe | Lys | Gln | Thr | Phe | Val | Glu | Val | Phe | Asp | Asn | Gly | Thr | Lys | Ala |
| 290 | | | | | 295 | | | | | 300 | | | | | |
| Arg | Val | Arg | Glu | Thr | Ala | His | Thr | Thr | Asp | Val | Asp | Gly | Gly | Val | Gly |
| 305 | | | | | 310 | | | | | 315 | | | | | 320 |
| Ala | Ala | Ser | Ile | Phe | Thr | Leu | Val | Leu | Ala | Arg | Glu | Met | Asn | Asp | Gln |
| | | | | 325 | | | | | 330 | | | | | 335 | |
| Glu | Leu | Phe | Asp | Gln | Leu | Leu | Asn | Tyr | Leu | Glu | Pro | Pro | Ala | Lys | Pro |
| | | | 340 | | | | | 345 | | | | | 350 | | |
| Val | Ile | Tyr | Ser | Gly | Ile | Leu | Arg | Tyr | Glu | Asn | Pro | Thr | Ser | Leu | Leu |
| | | | 355 | | | | | 360 | | | | | 365 | | |

Phe Asp Glu Leu Leu Phe Val Ala Lys Val His Val Gly Phe Gly Glu
370                 375                 380

Leu Ile Asn Leu Lys Pro Val Glu Thr Asp
385                 390

<210> SEQ ID NO 33
<211> LENGTH: 394
<212> TYPE: PRT
<213> ORGANISM: unknown
<220> FEATURE:
<223> OTHER INFORMATION: LinD enzyme SEQ ID NO: 32 having an A196F
      modification, designated LinD-7B

<400> SEQUENCE: 33

Met Thr Gln Trp Leu Ser Thr Pro Cys Leu Ala Ala Ile Leu Ser Ala
1               5                   10                  15

Ile Phe Ile Val Val Pro Lys Phe Gly Leu Thr Glu Thr Leu Leu Pro
                20                  25                  30

Gly Arg Leu Ala Thr Thr Lys Ala Tyr Phe Ser Gln Gln Arg Asn Gln
            35                  40                  45

Lys Leu Thr Pro Asp Met Asp Ala Gln Leu Ala Tyr Met Ser Tyr Thr
50                  55                  60

Asp Phe Ile Ser Pro Phe Tyr Ser Arg Gly Cys Ala Phe Glu Ala Trp
65                  70                  75                  80

Glu Leu Lys Gln Ala Pro Gln Arg Ile Ile Lys Tyr Ser Leu Ala Trp
                85                  90                  95

Tyr Ser Tyr Gly Leu Ala Ser Val Ala Val Ile Asp Pro Ser Leu His
            100                 105                 110

Arg Tyr Ala Gly His Asn Ile Asp Ile Ala Ile Ala Lys Met Lys Cys
        115                 120                 125

Arg Gln Val Trp Gly Asp Trp Glu Glu Asp Gly Phe Gly Ser Asn Pro
130                 135                 140

Ile Ala His Gln Asn Ile Met Tyr Lys Gly His Leu Asn Leu Met Tyr
145                 150                 155                 160

Gly Leu Tyr Gln Leu Leu Thr Gly Asn Thr Gln Tyr Glu Glu Glu Phe
                165                 170                 175

Ile Asp Leu Ser Asn Ile Ile Tyr Ser Glu Ile Lys Glu Asn Pro Tyr
            180                 185                 190

Ala Gly Ile Phe Cys Glu Pro Asp Asn Tyr Phe Pro Gln Cys Asn Ser
        195                 200                 205

Val Ala Tyr Leu Ser Leu Trp Val Tyr Asp Arg Leu Tyr His Thr Asp
210                 215                 220

Tyr Lys Ala Val Thr Lys Pro Trp Leu Asp Phe Leu Gln Lys Leu
225                 230                 235                 240

Ile Asp Pro Glu Thr Gly Thr Phe His Val Ala Tyr His Pro Thr Ser
                245                 250                 255

His Ala Val Lys Pro Trp Val Ser Ala Tyr Thr Thr Ala Trp Ala Leu
            260                 265                 270

Thr Met Ile His Gly Leu Asn Pro Glu Phe Ala Lys Lys Tyr Tyr Pro
        275                 280                 285

Asn Phe Lys Gln Thr Phe Val Glu Val Phe Asp Asn Gly Thr Lys Ala
290                 295                 300

Arg Val Arg Glu Thr Ala His Thr Thr Asp Val Asp Gly Gly Val Gly
305                 310                 315                 320

Ala Ala Ser Ile Phe Thr Leu Val Leu Ala Arg Glu Met Asn Asp Gln
                325                 330                 335

```
Glu Leu Phe Asp Gln Leu Leu Asn Tyr Leu Glu Pro Pro Ala Lys Pro
            340                 345                 350

Val Ile Tyr Ser Gly Ile Leu Arg Tyr Glu Asn Pro Thr Ser Leu Leu
            355                 360                 365

Phe Asp Glu Leu Leu Phe Val Ala Lys Val His Val Gly Phe Gly Glu
            370                 375                 380

Leu Ile Asn Leu Lys Pro Val Glu Thr Asp
385                 390
```

<210> SEQ ID NO 34
<211> LENGTH: 1197
<212> TYPE: DNA
<213> ORGANISM: artificial
<220> FEATURE:
<223> OTHER INFORMATION: nucleic acid encoding SEQ ID NO: 35, which is
    unprocessed and includes its signal peptide; an engineered variant
    of LinD-2 with the 7 mutations (amino acid changes): G74S, G133Q,
    R171K, I182K, V196F, D200G, G365S); designated LinD-2T

<400> SEQUENCE: 34

```
atgcgcttta ctctgaaaac ccctgctatc gcttccgccg ttgctgcact gttggttggt    60
ctgggtcagc cagcgcacgc ggcaccgctg ccgttaggcc gcttggcacc gaccgaagat   120
tactttgccc aacaggcgaa acaagccgtc accccggatg ttatgggcca gctggcgtac   180
atgaattaca tcgacttcat tagcccgttt tacagccgta gctgcagctt cgaggcgtgg   240
gagttgaaac acacgccgca gcgtgtcatc aagtatagca ttgcgttcta tgcgtacggc   300
ctggcaagcg tcgcactgat cgacccgaat ctgcgtgctc tggcgggtca tgacctggat   360
atcgcggtca gcaagatgaa atgtaagcgc gtgtggcaag attgggaaga agatggcttt   420
ggtgatgacc cgattgagaa agaaaacatt atgtataagg ccacctgaa cctcatgtac    480
ggtctgtatc aactggtgac cggtagccgt aaatatgaag cggagcatgc ccacttgacc   540
cgtttgatcc acgacgaaat cggtgcaaac ccgttcgcgg tattttttg cgagccgggt    600
aattactttg tgcagtgtaa ctctgtcgcg tacctgagcc tgtgggtata tgatcgtctg   660
catggcaccg actaccgtgc agcgacgcgt gcctggctgg atttcatcca gaaagatctg   720
attgacccgg agcgcggtgc gttttacctg agctatcacc ctgagtccgg tgccgtgaaa   780
ccgtggatta gcgcgtacac tacgcgtgg accctggcga tggtgcatgg catggatccg   840
gcgttcagcg agcgttatta cccggcgttc aaaaagacct tgttgaagt ttacgacggt    900
ggccgcaagg cacgtgtccg tgaaacggca ggcacggcag atgccgacgg tggcgttggt   960
ctggcgtctg ctttcaccct gctgcttgcg cgcgagatgg gtgaccaaac gctgtttgac  1020
caattgctga tcacctgga gccgccagca caaccgtcca tcgtgagcgc tagcctgcgt  1080
tatgagcacc cgagcagcct gctgttcgac gaactgctgt tcttggccaa ggttcatgcc  1140
ggctttggcg cgctgctgca gatgccgcca ccggcagcta atcgggtgg caagtaa     1197
```

<210> SEQ ID NO 35
<211> LENGTH: 398
<212> TYPE: PRT
<213> ORGANISM: artificial
<220> FEATURE:
<223> OTHER INFORMATION: unprocessed, engineered LinD enzyme LinD-2T,
    including signal peptide

<400> SEQUENCE: 35

```
Met Arg Phe Thr Leu Lys Thr Pro Ala Ile Ala Ser Ala Val Ala Ala
1               5                   10                  15
```

Leu Leu Val Gly Leu Gly Gln Pro Ala His Ala Ala Pro Leu Pro Leu
            20                  25                  30

Gly Arg Leu Ala Pro Thr Glu Asp Tyr Phe Ala Gln Gln Ala Lys Gln
            35                  40                  45

Ala Val Thr Pro Asp Val Met Ala Gln Leu Ala Tyr Met Asn Tyr Ile
 50                  55                  60

Asp Phe Ile Ser Pro Phe Tyr Ser Arg Ser Cys Ser Phe Glu Ala Trp
 65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Asn Leu Arg
            100                 105                 110

Ala Leu Ala Gly His Asp Leu Asp Ile Ala Val Ser Lys Met Lys Cys
            115                 120                 125

Lys Arg Val Trp Gln Asp Trp Glu Glu Asp Gly Phe Gly Asp Asp Pro
130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Lys Tyr Glu Ala Glu His
                165                 170                 175

Ala His Leu Thr Arg Leu Ile His Asp Glu Ile Gly Ala Asn Pro Phe
            180                 185                 190

Ala Gly Ile Phe Cys Glu Pro Gly Asn Tyr Phe Val Gln Cys Asn Ser
            195                 200                 205

Val Ala Tyr Leu Ser Leu Trp Val Tyr Asp Arg Leu His Gly Thr Asp
 210                 215                 220

Tyr Arg Ala Ala Thr Arg Ala Trp Leu Asp Phe Ile Gln Lys Asp Leu
225                 230                 235                 240

Ile Asp Pro Glu Arg Gly Ala Phe Tyr Leu Ser Tyr His Pro Glu Ser
                245                 250                 255

Gly Ala Val Lys Pro Trp Ile Ser Ala Tyr Thr Thr Ala Trp Thr Leu
            260                 265                 270

Ala Met Val His Gly Met Asp Pro Ala Phe Ser Glu Arg Tyr Tyr Pro
            275                 280                 285

Ala Phe Lys Lys Thr Phe Val Glu Val Tyr Asp Gly Gly Arg Lys Ala
 290                 295                 300

Arg Val Arg Glu Thr Ala Gly Thr Ala Asp Ala Asp Gly Gly Val Gly
305                 310                 315                 320

Leu Ala Ser Ala Phe Thr Leu Leu Leu Ala Arg Glu Met Gly Asp Gln
                325                 330                 335

Thr Leu Phe Asp Gln Leu Leu Asn His Leu Glu Pro Pro Ala Gln Pro
            340                 345                 350

Ser Ile Val Ser Ala Ser Leu Arg Tyr Glu His Pro Ser Ser Leu Leu
            355                 360                 365

Phe Asp Glu Leu Leu Phe Leu Ala Lys Val His Ala Gly Phe Gly Ala
 370                 375                 380

Leu Leu Gln Met Pro Pro Ala Ala Lys Ser Gly Gly Lys
385                 390                 395

<210> SEQ ID NO 36
<211> LENGTH: 1194
<212> TYPE: DNA
<213> ORGANISM: unknown
<220> FEATURE:

<223> OTHER INFORMATION: nucleic acid encoding SEQ ID NO: 37, which is
     unprocessed and includes its signal peptide; from Metagenomics on
     activated sludge (Camp Pendleton); designated LinD-8

<400> SEQUENCE: 36

```
atgcggttca cattgaagac gacggcgatc gcgtcggccg ccgccctgct ggtcggcctc      60
gggcagccgc cccgcgcggc ggaactgccg ccggggcggc tcgccaccac cgaggactat     120
ttcgcgcagc aggcgaagca ggccgtcacc cccgacgtga tggcccagct ggcctacatg     180
aactacatcg atttcatctc gcccttctac agccggggct gctccttcga ggcctgggag     240
ctcaagcaca cgccgcagcg ggtcatcaag tattcgatcg ccttctatgc gtatggcctg     300
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgcgca cctcaccccgc    540
atcatccatg acgagatcgc ggccaacccc tttgccggca tcgtctgcga ccggacaat     600
tatttcgtcc agtgcaattc ggtcgcctac ctgagcctgt gggtctatga ccggctgcat     660
ggcaccgact accgggcggc caccaggggcc tggctggatt tcatccagaa ggacctgatc    720
gatcccgagc ggggcgcctt ctacctgtcc tatcaccccg agtccggcgc ggtgaagccg     780
tggatctcgg cgtatacgac ggcctggacg ctcgccatgg tgcacggcat ggaccccgcc     840
ttttccgagc gctactaccc ccggttcaag cagaccttcg tcgaggtcta cgacgagggc     900
cgcaaggccc gggtgcgcga cggccggc acggacgacg cggatggcgg ggtgggcctg      960
gcttcggcgt tcaccctgct gctggcccgc gagatgggcg accagcagct cttcgaccag    1020
ttgctgaatc acctggagcc gccggctaag ccgagcatgc tctcggcctc gctgcggtac    1080
gagcaacccg gcagcctgct gttcgacgag ctgctgttcc tcgccaaggt gcatgccggt    1140
tttggcgccc tgcttcggat gccgcctccg gcggccaagc tcgcggggaa ataa          1194
```

<210> SEQ ID NO 37
<211> LENGTH: 397
<212> TYPE: PRT
<213> ORGANISM: unknown
<220> FEATURE:
<223> OTHER INFORMATION: unprocessed, LinD enzyme, designatend LinD-8,
     including signal peptide; from Metagenomics on activated sludge
     (Camp Pendleton)

<400> SEQUENCE: 37

```
Met Arg Phe Thr Leu Lys Thr Thr Ala Ile Ala Ser Ala Ala Ala Leu
1               5                   10                  15

Leu Val Gly Leu Gly Gln Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110
```

```
Leu Ala Gly His Asp Leu Asp Ile Ala Val Ser Lys Met Lys Cys Lys
            115                 120                 125

Arg Val Trp Gly Asp Trp Glu Glu Asp Gly Phe Gly Thr Asp Pro Ile
    130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
        195                 200                 205

Ala Tyr Leu Ser Leu Trp Val Tyr Asp Arg Leu His Gly Thr Asp Tyr
    210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
        275                 280                 285

Phe Lys Gln Thr Phe Val Glu Val Tyr Asp Glu Gly Arg Lys Ala Arg
    290                 295                 300

Val Arg Glu Thr Ala Gly Thr Asp Asp Ala Asp Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu Gln Pro Gly Ser Leu Leu Phe
        355                 360                 365

Asp Glu Leu Leu Phe Leu Ala Lys Val His Ala Gly Phe Gly Ala Leu
    370                 375                 380

Leu Arg Met Pro Pro Pro Ala Ala Lys Leu Ala Gly Lys
385                 390                 395

<210> SEQ ID NO 38
<211> LENGTH: 1116
<212> TYPE: DNA
<213> ORGANISM: unknown
<220> FEATURE:
<223> OTHER INFORMATION: Nucleic acid encoding processed (mature) LinD-8
      LinD enzyme, no signal peptide; from Metagenomics on activated
      sludge (Camp Pendleton)

<400> SEQUENCE: 38
gcggaactgc cgccggggcg gctcgccacc accgaggact atttcgcgca gcaggcgaag      60
caggccgtca ccccgacgt gatggcccag ctggcctaca tgaactacat cgatttcatc     120
tcgcccttct acagccgggg ctgctccttc gaggcctggg agctcaagca cacgccgcag     180
cgggtcatca agtattcgat cgccttctat gcgtatggcc tggccagcgt ggcgctcatc     240
gacccgaagc tgcgtgcgct cgccggccat gacctggaca tcgcggtctc caagatgaag     300
tgcaagcggg tctggggcga ctgggaggaa gacgggttcg gcaccgaccc gatcgagaaa     360
gagaacatca tgtacaaggg ccacctgaac ctgatgtacg gcctctatca gctggtgacc     420
```

```
ggcagccgcc ggtacgaagc cgagcatgcg cacctcaccc gcatcatcca tgacgagatc    480
gcggccaacc cctttgccgg catcgtctgc gagccggaca attatttcgt ccagtgcaat    540
tcggtcgcct acctgagcct gtgggtctat gaccggctgc atggcaccga ctaccgggcg    600
gccaccaggg cctggctgga tttcatccag aaggacctga tcgatcccga gcggggcgcc    660
ttctacctgt cctatcaccc cgagtccggc gcggtgaagc cgtggatctc ggcgtatacg    720
acggcctgga cgctcgccat ggtgcacggc atggaccccg ccttttccga gcgctactac    780
ccccggttca agcagacctt cgtcgaggtc tacgacgagg gccgcaaggc ccgggtgcgc    840
gagacggccg cacggacga cgcggatggc ggggtgggcc tggcttcggc gttcaccctg    900
ctgctggccc gcgagatggg cgaccagcag ctcttcgacc agttgctgaa tcacctggag    960
ccgccggcta agccgagcat cgtctcggcc tcgctgcggt acgagcaacc cggcagcctg    1020
ctgttcgacg agctgctgtt cctcgccaag gtgcatgccg gttttggcgc cctgcttcgg    1080
atgccgcctc cggcggccaa gctcgcgggg aaataa                             1116
```

<210> SEQ ID NO 39
<211> LENGTH: 371
<212> TYPE: PRT
<213> ORGANISM: unknown
<220> FEATURE:
<223> OTHER INFORMATION: Processed (mature) LinD-8 LinD enzyme, no signal peptide; from Metagenomics on activated sludge (Camp Pendleton)

<400> SEQUENCE: 39

```
Ala Glu Leu Pro Pro Gly Arg Leu Ala Thr Thr Glu Asp Tyr Phe Ala
1               5                   10                  15

Gln Gln Ala Lys Gln Ala Val Thr Pro Asp Val Met Ala Gln Leu Ala
            20                  25                  30

Tyr Met Asn Tyr Ile Asp Phe Ile Ser Pro Phe Tyr Ser Arg Gly Cys
        35                  40                  45

Ser Phe Glu Ala Trp Glu Leu Lys His Thr Pro Gln Arg Val Ile Lys
    50                  55                  60

Tyr Ser Ile Ala Phe Tyr Ala Tyr Gly Leu Ala Ser Val Ala Leu Ile
65                  70                  75                  80

Asp Pro Lys Leu Arg Ala Leu Ala Gly His Asp Leu Asp Ile Ala Val
                85                  90                  95

Ser Lys Met Lys Cys Lys Arg Val Trp Gly Asp Trp Glu Glu Asp Gly
            100                 105                 110

Phe Gly Thr Asp Pro Ile Glu Lys Glu Asn Ile Met Tyr Lys Gly His
        115                 120                 125

Leu Asn Leu Met Tyr Gly Leu Tyr Gln Leu Val Thr Gly Ser Arg Arg
    130                 135                 140

Tyr Glu Ala Glu His Ala His Leu Thr Arg Ile Ile His Asp Glu Ile
145                 150                 155                 160

Ala Ala Asn Pro Phe Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asp Tyr Arg Ala Ala Thr Arg Ala Trp Leu Asp Phe
        195                 200                 205

Ile Gln Lys Asp Leu Ile Asp Pro Glu Arg Gly Ala Phe Tyr Leu Ser
    210                 215                 220
```

```
Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
            245                 250                 255

Glu Arg Tyr Tyr Pro Arg Phe Lys Gln Thr Phe Val Glu Val Tyr Asp
        260                 265                 270

Glu Gly Arg Lys Ala Arg Val Arg Glu Thr Ala Gly Thr Asp Asp Ala
    275                 280                 285

Asp Gly Gly Val Gly Leu Ala Ser Ala Phe Thr Leu Leu Leu Ala Arg
    290                 295                 300

Glu Met Gly Asp Gln Gln Leu Phe Asp Gln Leu Leu Asn His Leu Glu
305                 310                 315                 320

Pro Pro Ala Lys Pro Ser Ile Val Ser Ala Ser Leu Arg Tyr Glu Gln
            325                 330                 335

Pro Gly Ser Leu Leu Phe Asp Glu Leu Leu Phe Leu Ala Lys Val His
        340                 345                 350

Ala Gly Phe Gly Ala Leu Leu Arg Met Pro Pro Ala Ala Lys Leu
    355                 360                 365

Ala Gly Lys
    370
```

<210> SEQ ID NO 40
<211> LENGTH: 1185
<212> TYPE: DNA
<213> ORGANISM: unknown
<220> FEATURE:
<223> OTHER INFORMATION: nucleic acid encoding SEQ ID NO: 41, which has
  no defined signal peptide; from Metagenomics on activated sludge
  (Camp Pendleton); designated LinD-9

<400> SEQUENCE: 40

```
atgacacaat ggttatcaac ccctgcctg gcggcgattt taagtgcaat ttttattgtt      60
gtacccaaat cgggttgac agagacatta ctgccgggc gattagccac tacgaggcg       120
tattttcac agcaacgcaa ccaaaaactg acgccggata tggatgccca gctggcctat     180
atgtcctaca ctgattttat ttcacctttc tatagtcgag gttgcgcctt tgaggcttgg    240
gaactgaaac aggctcccca gagaattatc aaatactccc ttgcctggta ttcctacggc    300
cttgccagtg tcgctgtcat tgatcccagc ctgcaccgat atgcaggcca caatattgat    360
attgccatcg caaaaatgaa gtgcagacag gtttggggcg actgggaaga agacggcttt    420
ggctccaacc ctattgccca ccaaaatatt atgtacaaag acacttgaa tctgatgtat     480
ggcctttatc agctgttaac gggcaatact cagtatgaag aggaattcat cgatctctct    540
aatatcatct atagcgaaat caaggaaaac ccttatgcag gtattgcttg cgagccggac    600
aattactttc cgcagtgcaa ctccgtcgcc tatctcagcc tgtgggttta tgatcgtctc    660
taccacaccg actacaaagc agtcacaaaa ccctggcttg atttttaca gaaaaaactc    720
atagatcctg aaaccggcac atttcatgtt gcctatcatc aacatctca cgccgttaaa    780
ccctgggttt ccgcctacac cacggcctgg gcgctaacca tgattcatgg tctgaatccg    840
gaatttgcca aaagtactac ccctaatttt aagcaaacct tgttgaggt ttttgacaac    900
ggcaccaaag ccagggtgcg cgaaaccgcc cacaccacgg atgttgatgg tggcgtcggc    960
gccgcctcga ttttcacgct ggtgttggca agggaaatga atgatcagga gctgtttgat   1020
caactattga attatctcga accgccagca aagcctgtga tttattcggg gattctgcga   1080
tatgaaaatc caacgagcct gctattcgat gaactgcttt ttgtcgccaa ggtgcatgtg   1140
```
ggttttggcg aactgatcaa tctcaaacct gttgaaacag actag                                        1185

<210> SEQ ID NO 41
<211> LENGTH: 394
<212> TYPE: PRT
<213> ORGANISM: unknown
<220> FEATURE:
<223> OTHER INFORMATION: unprocessed, LinD enzyme, designated LinD-9, no
      defined signal peptide;) from Metagenomics on activated sludge
      (Camp Pendleton); designated LinD-9

<400> SEQUENCE: 41

Met Thr Gln Trp Leu Ser Thr Pro Cys Leu Ala Ala Ile Leu Ser Ala
1               5                   10                  15

Ile Phe Ile Val Val Pro Lys Phe Gly Leu Thr Glu Thr Leu Leu Pro
            20                  25                  30

Gly Arg Leu Ala Thr Thr Glu Ala Tyr Phe Ser Gln Gln Arg Asn Gln
        35                  40                  45

Lys Leu Thr Pro Asp Met Asp Ala Gln Leu Ala Tyr Met Ser Tyr Thr
50                  55                  60

Asp Phe Ile Ser Pro Phe Tyr Ser Arg Gly Cys Ala Phe Glu Ala Trp
65                  70                  75                  80

Glu Leu Lys Gln Ala Pro Gln Arg Ile Ile Lys Tyr Ser Leu Ala Trp
                85                  90                  95

Tyr Ser Tyr Gly Leu Ala Ser Val Ala Val Ile Asp Pro Ser Leu His
            100                 105                 110

Arg Tyr Ala Gly His Asn Ile Asp Ile Ala Ile Ala Lys Met Lys Cys
        115                 120                 125

Arg Gln Val Trp Gly Asp Trp Glu Glu Asp Gly Phe Gly Ser Asn Pro
130                 135                 140

Ile Ala His Gln Asn Ile Met Tyr Lys Gly His Leu Asn Leu Met Tyr
145                 150                 155                 160

Gly Leu Tyr Gln Leu Leu Thr Gly Asn Thr Gln Tyr Glu Glu Glu Phe
                165                 170                 175

Ile Asp Leu Ser Asn Ile Ile Tyr Ser Glu Ile Lys Glu Asn Pro Tyr
            180                 185                 190

Ala Gly Ile Ala Cys Glu Pro Asp Asn Tyr Phe Pro Gln Cys Asn Ser
        195                 200                 205

Val Ala Tyr Leu Ser Leu Trp Val Tyr Asp Arg Leu Tyr His Thr Asp
210                 215                 220

Tyr Lys Ala Val Thr Lys Pro Trp Leu Asp Phe Leu Gln Lys Lys Leu
225                 230                 235                 240

Ile Asp Pro Glu Thr Gly Thr Phe His Val Ala Tyr His Pro Thr Ser
                245                 250                 255

His Ala Val Lys Pro Trp Val Ser Ala Tyr Thr Thr Ala Trp Ala Leu
            260                 265                 270

Thr Met Ile His Gly Leu Asn Pro Glu Phe Ala Lys Lys Tyr Tyr Pro
        275                 280                 285

Asn Phe Lys Gln Thr Phe Val Glu Val Phe Asp Asn Gly Thr Lys Ala
290                 295                 300

Arg Val Arg Glu Thr Ala His Thr Thr Asp Val Asp Gly Gly Val Gly
305                 310                 315                 320

Ala Ala Ser Ile Phe Thr Leu Val Leu Ala Arg Glu Met Asn Asp Gln
                325                 330                 335

Glu Leu Phe Asp Gln Leu Leu Asn Tyr Leu Glu Pro Pro Ala Lys Pro

```
                340                 345                 350
Val Ile Tyr Ser Gly Ile Leu Arg Tyr Glu Asn Pro Thr Ser Leu Leu
            355                 360                 365

Phe Asp Glu Leu Leu Phe Val Ala Lys Val His Val Gly Phe Gly Glu
        370                 375                 380

Leu Ile Asn Leu Lys Pro Val Glu Thr Asp
385                 390
```

<210> SEQ ID NO 42
<211> LENGTH: 1206
<212> TYPE: DNA
<213> ORGANISM: unknown
<220> FEATURE:
<223> OTHER INFORMATION: nucleic acid encoding SEQ ID NO: 43, which is
      unprocessed and includes its signal peptide; from Metagenomics on
      soil sample (Cottonwood river); designated LinD-10

<400> SEQUENCE: 42

```
atgaagaaac ccgcccctt gaccgtcctg gccggcctgg ccagcgccgt cctgctcgcc      60
cttggcacgc cggccacggc agccgagccg atgcccggcc gcctggcctc gaccgacgac    120
tacttcgccc agagcgagaa gcacgccctg acgccgacg tgatggcgca actgcgctac     180
atgaactaca ccgatttcat ttcgccgttc tacagccggg gctgcgcctt cgacgcctgg    240
acgatgaaga agatgccgcc ccgcatcatc aaatattcgc tcgcctggta cgcctacggc    300
ctggccagcg tcgccctgac cgacccggcg atgcgcccgg tggccggtca cgcgattgac    360
atcgcgaccg ccaagatgca ttgcaagcag gtctggggcg actgggagga agacggtttc    420
ggcagcgacc cgatcatccg ccagaacgtc atgtacaagg ccacctgaa cctgatgtac     480 gggctctacc agttgatcac cggcgaccgc aagtacgaga aggaaaacac ccgcctgacc    540
cgcatcatgc acaaggagat gaagagcaat ccgtacgccg gcatcgtctg cgaacccgac    600
aactacttcg tccagtgcaa ctcggtcgcc tacctgagcc tgtgggttta cgaccggctg    660
cacggcaccc agtacaaggc ggcaaccagg gagtggctga aattcatcga ggacgaactg    720
atcgacccga agaccggcag cttctatctt tcctaccacc ccgaaaccgg tgccgtgaag    780
ccgtggcagt cggcctacac gaccgcctgg acgctggcca tggtgcatgg catggacccg    840
gccttcgccg aacgctatta cccgaaattc aaggaaagct tcgtcgaggt ctatgacgac    900
ggccgcaagg cgcgcgtccg cgaaatgacc ggcaccaccg acaccgacgg cggcgtcggc    960
gccgcgtcgg cgttcatgct ggtcctggca cgtgaaatgg gcgacaagca actgttcgac   1020
cagctgctga accacctcga accgccagcc ggaccgacga tcacttcggg catcctgcat   1080
tacgcgcagc cgagcaatct gctgttcgac gaattgctgt tcgtcggcaa ggtgcatgtc   1140
ggcttcgcca agctgctcaa tgcgccgccg gcaccggctc gcccggccct gcaaagaag    1200 aaatga                                                              1206
```

<210> SEQ ID NO 43
<211> LENGTH: 401
<212> TYPE: PRT
<213> ORGANISM: unknown
<220> FEATURE:
<223> OTHER INFORMATION: unprocessed, LinD enzyme, designated LinD-10,
      including signal peptide; from Metagenomics on soil sample
      (Cottonwood river)

<400> SEQUENCE: 43

```
Met Lys Lys Pro Arg Pro Leu Thr Val Leu Ala Gly Leu Ala Ser Ala
1               5                   10                  15
```

Val Leu Leu Ala Leu Gly Thr Pro Ala Thr Ala Glu Pro Met Pro
            20                  25                  30

Gly Arg Leu Ala Ser Thr Asp Asp Tyr Phe Ala Gln Ser Glu Lys His
         35                  40                  45

Ala Leu Thr Pro Asp Val Met Ala Gln Leu Arg Tyr Met Asn Tyr Thr
 50                  55                  60

Asp Phe Ile Ser Pro Phe Tyr Ser Arg Gly Cys Ala Phe Asp Ala Trp
 65                  70                  75                  80

Thr Met Lys Lys Met Pro Pro Arg Ile Ile Lys Tyr Ser Leu Ala Trp
                 85                  90                  95

Tyr Ala Tyr Gly Leu Ala Ser Val Ala Leu Thr Asp Pro Ala Met Arg
             100                 105                 110

Pro Val Ala Gly His Ala Ile Asp Ile Ala Thr Ala Lys Met His Cys
             115                 120                 125

Lys Gln Val Trp Gly Asp Trp Glu Glu Asp Gly Phe Gly Ser Asp Pro
130                 135                 140

Ile Ile Arg Gln Asn Val Met Tyr Lys Gly His Leu Asn Leu Met Tyr
145                 150                 155                 160

Gly Leu Tyr Gln Leu Ile Thr Gly Asp Arg Lys Tyr Glu Lys Glu Asn
                 165                 170                 175

Thr Arg Leu Thr Arg Ile Met His Lys Glu Met Lys Ser Asn Pro Tyr
             180                 185                 190

Ala Gly Ile Val Cys Glu Pro Asp Asn Tyr Phe Val Gln Cys Asn Ser
             195                 200                 205

Val Ala Tyr Leu Ser Leu Trp Val Tyr Asp Arg Leu His Gly Thr Gln
210                 215                 220

Tyr Lys Ala Ala Thr Arg Glu Trp Leu Lys Phe Ile Glu Asp Glu Leu
225                 230                 235                 240

Ile Asp Pro Lys Thr Gly Ser Phe Tyr Leu Ser Tyr His Pro Glu Thr
                 245                 250                 255

Gly Ala Val Lys Pro Trp Gln Ser Ala Tyr Thr Thr Ala Trp Thr Leu
             260                 265                 270

Ala Met Val His Gly Met Asp Pro Ala Phe Ala Glu Arg Tyr Tyr Pro
             275                 280                 285

Lys Phe Lys Glu Ser Phe Val Glu Val Tyr Asp Asp Gly Arg Lys Ala
290                 295                 300

Arg Val Arg Glu Met Thr Gly Thr Thr Asp Thr Asp Gly Gly Val Gly
305                 310                 315                 320

Ala Ala Ser Ala Phe Met Leu Val Leu Ala Arg Glu Met Gly Asp Lys
                 325                 330                 335

Gln Leu Phe Asp Gln Leu Leu Asn His Leu Glu Pro Pro Ala Gly Pro
             340                 345                 350

Thr Ile Thr Ser Gly Ile Leu His Tyr Ala Gln Pro Ser Asn Leu Leu
             355                 360                 365

Phe Asp Glu Leu Leu Phe Val Gly Lys Val His Val Gly Phe Ala Lys
370                 375                 380

Leu Leu Asn Ala Pro Pro Ala Pro Ala Arg Pro Ala Leu Gln Lys Lys
385                 390                 395                 400

Lys

<210> SEQ ID NO 44
<211> LENGTH: 1125
<212> TYPE: DNA

```
<213> ORGANISM: unknown
<220> FEATURE:
<223> OTHER INFORMATION: Nucleic acid encoding processed (mature)
      LinD-10 LinD enzyme, no signal peptide; from Metagenomics on soil
      sample (Cottonwood river)

<400> SEQUENCE: 44
gccgagccga tgcccggccg cctggcctcg accgacgact acttcgccca gagcgagaag     60
cacgccctga cgccggacgt gatggcgcaa ctgcgctaca tgaactacac cgatttcatt    120
tcgccgttct acagccgggg ctgcgccttc gacgcctgga cgatgaagaa gatgccgccc    180
cgcatcatca aatattcgct cgcctggtac gcctacggcc tggccagcgt cgccctgacc    240
gacccggcga tgcgcccggt ggccggtcac gcgattgaca tcgcgaccgc caagatgcat    300
tgcaagcagg tctggggcga ctgggaggaa gacggtttcg gcagcgaccc gatcatccgc    360
cagaacgtca tgtacaaggg ccacctgaac ctgatgtacg ggctctacca gttgatcacc    420
ggcgaccgca agtacgagaa ggaaaacacc cgcctgaccc gcatcatgca caaggagatg    480
aagagcaatc cgtacgccgg catcgtctgc gaacccgaca actacttcgt ccagtgcaac    540
tcggtcgcct acctgagcct gtgggtttac gaccggctgc acggcaccca gtacaaggcg    600
gcaaccaggg agtggctgaa attcatcgag gacgaactga tcgacccgaa gaccggcagc    660
ttctatcttt cctaccaccc cgaaaccggt gccgtgaagc cgtggcagtc ggcctacacg    720
accgcctgga cgctggccat ggtgcatggc atggacccgg ccttcgccga acgctattac    780
ccgaaattca aggaaagctt cgtcgaggtc tatgacgacg ccgcaaggc gcgcgtccgc    840 gaaatgaccg gcaccaccga caccgacggc ggcgtcggcg ccgcgtcggc gttcatgctg    900
gtcctggcac gtgaaatggg cgacaagcaa ctgttcgacc agctgctgaa ccacctcgaa    960
ccgccagccg gaccgacgat cacttcgggc atcctgcatt acgcgcagcc gagcaatctg   1020
ctgttcgacg aattgctgtt cgtcggcaag gtgcatgtcg gcttcgccaa gctgctcaat   1080
gcgccgccgg caccggctcg cccggccctg caaaagaaga aatga                   1125

<210> SEQ ID NO 45
<211> LENGTH: 374
<212> TYPE: PRT
<213> ORGANISM: unknown
<220> FEATURE:
<223> OTHER INFORMATION: Processed (mature) LinD-10 LinD enzyme, no
      signal peptide; from Metagenomics on soil sample (Cottonwood
      river)

<400> SEQUENCE: 45

Ala Glu Pro Met Pro Gly Arg Leu Ala Ser Thr Asp Asp Tyr Phe Ala
1               5                   10                  15

Gln Ser Glu Lys His Ala Leu Thr Pro Asp Val Met Ala Gln Leu Arg
            20                  25                  30

Tyr Met Asn Tyr Thr Asp Phe Ile Ser Pro Phe Tyr Ser Arg Gly Cys
        35                  40                  45

Ala Phe Asp Ala Trp Thr Met Lys Lys Met Pro Arg Ile Ile Lys
    50                  55                  60

Tyr Ser Leu Ala Trp Tyr Ala Tyr Gly Leu Ala Ser Val Ala Leu Thr
65                  70                  75                  80

Asp Pro Ala Met Arg Pro Val Ala Gly His Ala Ile Asp Ile Ala Thr
                85                  90                  95

Ala Lys Met His Cys Lys Gln Val Trp Gly Asp Trp Glu Glu Asp Gly
            100                 105                 110
```

```
Phe Gly Ser Asp Pro Ile Ile Arg Gln Asn Val Met Tyr Lys Gly His
            115                 120                 125
Leu Asn Leu Met Tyr Gly Leu Tyr Gln Leu Ile Thr Gly Asp Arg Lys
        130                 135                 140
Tyr Glu Lys Glu Asn Thr Arg Leu Thr Arg Ile Met His Lys Glu Met
145                 150                 155                 160
Lys Ser Asn Pro Tyr Ala Gly Ile Val Cys Glu Pro Asp Asn Tyr Phe
                165                 170                 175
Val Gln Cys Asn Ser Val Ala Tyr Leu Ser Leu Trp Val Tyr Asp Arg
            180                 185                 190
Leu His Gly Thr Gln Tyr Lys Ala Ala Thr Arg Glu Trp Leu Lys Phe
        195                 200                 205
Ile Glu Asp Glu Leu Ile Asp Pro Lys Thr Gly Ser Phe Tyr Leu Ser
210                 215                 220
Tyr His Pro Glu Thr Gly Ala Val Lys Pro Trp Gln Ser Ala Tyr Thr
225                 230                 235                 240
Thr Ala Trp Thr Leu Ala Met Val His Gly Met Asp Pro Ala Phe Ala
                245                 250                 255
Glu Arg Tyr Tyr Pro Lys Phe Lys Glu Ser Phe Val Glu Val Tyr Asp
            260                 265                 270
Asp Gly Arg Lys Ala Arg Val Arg Glu Met Thr Gly Thr Thr Asp Thr
        275                 280                 285
Asp Gly Val Gly Ala Ala Ser Ala Phe Met Leu Val Leu Ala Arg
290                 295                 300
Glu Met Gly Asp Lys Gln Leu Phe Asp Gln Leu Leu Asn His Leu Glu
305                 310                 315                 320
Pro Pro Ala Gly Pro Thr Ile Thr Ser Gly Ile Leu His Tyr Ala Gln
                325                 330                 335
Pro Ser Asn Leu Leu Phe Asp Glu Leu Leu Phe Val Gly Lys Val His
            340                 345                 350
Val Gly Phe Ala Lys Leu Leu Asn Ala Pro Pro Ala Pro Ala Arg Pro
        355                 360                 365
Ala Leu Gln Lys Lys Lys
    370

<210> SEQ ID NO 46
<211> LENGTH: 1206
<212> TYPE: DNA
<213> ORGANISM: unknown
<220> FEATURE:
<223> OTHER INFORMATION: nucleic acid encoding SEQ ID NO: 47, which is
      unprocessed and includes its signal peptide; from Metagenomics on
      soil sample; designated LinD-11

<400> SEQUENCE: 46
atgaaaaaaa cacgcttttc cgtcgcactg accggcctga ctgccgccac cctgatcgca      60
ttcggttcgc ccgccacggc cggcgaattg ccacccggcc gactggcttc gaccgacgac     120
tacttcaccc agcgtgaaaa acaggcactg acgcccgacg tcatggcgca actgcgctac     180
atgaactaca ccgatttcat ttcgccgttc tacagccggg gctgcgcctt cgatgcctgg     240
acgatgaaga agatgccgcc gcgcatcatc aagtattcgc tggccttcta cgcctacggg     300
ctggccagcg tcgcccagac cgacccgaaa atgcgtcccc tcgccggcca cgcgatcgac     360
atcgccaccg ccaagatgca ctgcaagcag gtctggggcg actgggagga agacggtttc     420
ggcaaggacc cgatcatcaa ggaaaacgtc atgtacaagg ccatctgaa cctgatgtac     480
```

-continued

```
gggctgtacc agatggtcac cggcgaccgg aaatacgaga aggaaaatac ccgcctgacc    540
caaatcatgc tcaaggagat caaggccaat ccgtatgccg gcatcgtctg cgagccggac    600
aactacttcg tgcaatgcaa ttcggtcgcc tacctgagcc tgtgggtcta tgaccggctg    660
cacggcacca accacaaggc cgtgaccaag gaatggctga agttcatcga ggacgagctg    720
atcgacccca agagcggcag cttctacctc tcctaccatc ccgagaccgg cgccgtgaag    780
ccctggcaat cggcctacac gtcggcctgg gcgctggcga tggtgcacgg catggacccg    840
gcgttcacgg agcgccatta cccgaagttc aaggaaacct tcgtcgaggt ttatgacgga    900
ggccacaagg cccgcgtccg cgaaatgacc ggcactccgg acgccgatgg cggggtcggc    960
ctggcctcgg ccttcacgct gctgctggcc cgcgaaatgg gtgacaagga acttttcgac   1020
cagctgttga accacctcga accgccagcc aagccgacga tcacctccgg catcctgcat   1080
tacgggcagc cgagcagcct gctgttcgac gaattgctgt tcgtcggcaa ggtgcacgtc   1140
ggcttcgcca acctgctcaa tgcgccgctg gccccgcccc ccctgcccct gcaaaagaag   1200
aaatga                                                              1206
```

<210> SEQ ID NO 47
<211> LENGTH: 401
<212> TYPE: PRT
<213> ORGANISM: unknown
<220> FEATURE:
<223> OTHER INFORMATION: unprocessed, LinD enzyme, designated LinD-11, including signal peptide; from Metagenomics on soil sample

<400> SEQUENCE: 47

```
Met Lys Lys Thr Arg Phe Ser Val Ala Leu Thr Gly Leu Thr Ala Ala
1               5                   10                  15

Thr Leu Ile Ala Phe Gly Ser Pro Ala Thr Ala Gly Glu Leu Pro Pro
            20                  25                  30

Gly Arg Leu Ala Ser Thr Asp Asp Tyr Phe Thr Gln Arg Glu Lys Gln
        35                  40                  45

Ala Leu Thr Pro Asp Val Met Ala Gln Leu Arg Tyr Met Asn Tyr Thr
    50                  55                  60

Asp Phe Ile Ser Pro Phe Tyr Ser Arg Gly Cys Ala Phe Asp Ala Trp
65                  70                  75                  80

Thr Met Lys Lys Met Pro Pro Arg Ile Ile Lys Tyr Ser Leu Ala Phe
                85                  90                  95

Tyr Ala Tyr Gly Leu Ala Ser Val Ala Gln Thr Asp Pro Lys Met Arg
            100                 105                 110

Pro Leu Ala Gly His Ala Ile Asp Ile Ala Thr Ala Lys Met His Cys
        115                 120                 125

Lys Gln Val Trp Gly Asp Trp Glu Glu Asp Gly Phe Gly Lys Asp Pro
    130                 135                 140

Ile Ile Lys Glu Asn Val Met Tyr Lys Gly His Leu Asn Leu Met Tyr
145                 150                 155                 160

Gly Leu Tyr Gln Met Val Thr Gly Asp Arg Lys Tyr Glu Lys Glu Asn
                165                 170                 175

Thr Arg Leu Thr Gln Ile Met Leu Lys Glu Ile Lys Ala Asn Pro Tyr
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Asn
    210                 215                 220
```

His Lys Ala Val Thr Lys Glu Trp Leu Lys Phe Ile Glu Asp Glu Leu
225                 230                 235                 240

Ile Asp Pro Lys Ser Gly Ser Phe Tyr Leu Ser Tyr His Pro Glu Thr
            245                 250                 255

Gly Ala Val Lys Pro Trp Gln Ser Ala Tyr Thr Ser Ala Trp Ala Leu
            260                 265                 270

Ala Met Val His Gly Met Asp Pro Ala Phe Thr Glu Arg His Tyr Pro
            275                 280                 285

Lys Phe Lys Glu Thr Phe Val Glu Val Tyr Asp Gly Gly His Lys Ala
    290                 295                 300

Arg Val Arg Glu Met Thr Gly Thr Pro Asp Ala Asp Gly Gly Val Gly
305                 310                 315                 320

Leu Ala Ser Ala Phe Thr Leu Leu Ala Arg Glu Met Gly Asp Lys
                325                 330                 335

Glu Leu Phe Asp Gln Leu Leu Asn His Leu Glu Pro Pro Ala Lys Pro
                340                 345                 350

Thr Ile Thr Ser Gly Ile Leu His Tyr Gly Gln Pro Ser Ser Leu Leu
                355                 360                 365

Phe Asp Glu Leu Leu Phe Val Gly Lys Val His Val Gly Phe Ala Asn
370                 375                 380

Leu Leu Asn Ala Pro Leu Ala Pro Pro Arg Pro Ala Leu Gln Lys Lys
385                 390                 395                 400

Lys

<210> SEQ ID NO 48
<211> LENGTH: 1125
<212> TYPE: DNA
<213> ORGANISM: unknown
<220> FEATURE:
<223> OTHER INFORMATION: Nucleic acid encoding processed (mature)
      LinD-11 LinD enzyme, no signal peptide; from Metagenomics on soil
      sample

<400> SEQUENCE: 48

```
ggcgaattgc acccggccg actggcttcg accgacgact acttcaccca gcgtgaaaaa      60
caggcactga cgcccgacgt catggcgcaa ctgcgctaca tgaactacac cgatttcatt     120
tcgccgttct acagccgggg ctgcgccttc gatgcctgga cgatgaagaa gatgccgccg     180
cgcatcatca gtattcgct ggccttctac gcctacgggc tggccagcgt cgcccagacc      240
gacccgaaaa tgcgtcccct cgccggccac gcgatcgaca tcgccaccgc caagatgcac     300
tgcaagcagg tctggggcga ctgggaggaa gacggtttcg gcaaggaccc gatcatcaag     360
gaaaacgtca tgtacaaggg ccatctgaac ctgatgtacg ggctgtacca gatggtcacc     420
ggcgaccgga atacgagaa ggaaaatacc cgcctgaccc aaatcatgct caaggagatc      480
aaggccaatc cgtatgccgg catcgtctgc gagccggaca actacttcgt gcaatgcaat     540
tcggtcgcct acctgagcct gtgggtctat accggctgc acggcaccaa ccacaaggcc      600
gtgaccaagg aatggctgaa gttcatcgag gacgagctga tcgaccccaa gagcggcagc     660
ttctacctct cctaccatcc cgagaccggc gccgtgaagc cctggcaatc ggcctacacg     720
tcggcctggg cgctggcgat ggtgcacggc atgacccggc gttcacgga gcgccattac      780 ccgaagttca ggaaaccctt cgtcgaggtt tatgacggag ccacaaggc ccgcgtccgc      840 gaaatgaccg gcactccgga cgccgatggc gggtcggcc tggcctcggc cttcacgctg     900
ctgctggccc gcgaaatggg tgacaaggaa cttttcgacc agctgttgaa ccacctcgaa     960
```

```
ccgccagcca agccgacgat cacctccggc atcctgcatt acgggcagcc gagcagcctg    1020
ctgttcgacg aattgctgtt cgtcggcaag gtgcacgtcg gcttcgccaa cctgctcaat    1080
gcgccgctgg ccccgccccg ccctgccctg caaaagaaga aatga                    1125
```

<210> SEQ ID NO 49
<211> LENGTH: 374
<212> TYPE: PRT
<213> ORGANISM: unknown
<220> FEATURE:
<223> OTHER INFORMATION: Processed (mature) LinD-11 LinD enzyme, no
      signal peptide; from Metagenomics on soil sample

<400> SEQUENCE: 49

```
Gly Glu Leu Pro Pro Gly Arg Leu Ala Ser Thr Asp Asp Tyr Phe Thr
1               5                   10                  15

Gln Arg Glu Lys Gln Ala Leu Thr Pro Asp Val Met Ala Gln Leu Arg
            20                  25                  30

Tyr Met Asn Tyr Thr Asp Phe Ile Ser Pro Phe Tyr Ser Arg Gly Cys
        35                  40                  45

Ala Phe Asp Ala Trp Thr Met Lys Lys Met Pro Pro Arg Ile Ile Lys
    50                  55                  60

Tyr Ser Leu Ala Phe Tyr Ala Tyr Gly Leu Ala Ser Val Ala Gln Thr
65                  70                  75                  80

Asp Pro Lys Met Arg Pro Leu Ala Gly His Ala Ile Asp Ile Ala Thr
                85                  90                  95

Ala Lys Met His Cys Lys Gln Val Trp Gly Asp Trp Glu Glu Asp Gly
            100                 105                 110

Phe Gly Lys Asp Pro Ile Ile Lys Glu Asn Val Met Tyr Lys Gly His
        115                 120                 125

Leu Asn Leu Met Tyr Gly Leu Tyr Gln Met Val Thr Gly Asp Arg Lys
    130                 135                 140

Tyr Glu Lys Glu Asn Thr Arg Leu Thr Gln Ile Met Leu Lys Glu Ile
145                 150                 155                 160

Lys Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asn His Lys Ala Val Thr Lys Glu Trp Leu Lys Phe
        195                 200                 205

Ile Glu Asp Glu Leu Ile Asp Pro Lys Ser Gly Ser Phe Tyr Leu Ser
    210                 215                 220

Tyr His Pro Glu Thr Gly Ala Val Lys Pro Trp Gln Ser Ala Tyr Thr
225                 230                 235                 240

Ser Ala Trp Ala Leu Ala Met Val His Gly Met Asp Pro Ala Phe Thr
                245                 250                 255

Glu Arg His Tyr Pro Lys Phe Lys Glu Thr Phe Val Glu Val Tyr Asp
            260                 265                 270

Gly Gly His Lys Ala Arg Val Arg Glu Met Thr Gly Thr Pro Asp Ala
        275                 280                 285

Asp Gly Gly Val Gly Leu Ala Ser Ala Phe Thr Leu Leu Leu Ala Arg
    290                 295                 300

Glu Met Gly Asp Lys Glu Leu Phe Asp Gln Leu Leu Asn His Leu Glu
305                 310                 315                 320

Pro Pro Ala Lys Pro Thr Ile Thr Ser Gly Ile Leu His Tyr Gly Gln
                325                 330                 335
```

```
Pro Ser Ser Leu Leu Phe Asp Glu Leu Leu Phe Val Gly Lys Val His
            340                 345                 350

Val Gly Phe Ala Asn Leu Leu Asn Ala Pro Leu Ala Pro Pro Arg Pro
        355                 360                 365

Ala Leu Gln Lys Lys Lys
    370
```

<210> SEQ ID NO 50
<211> LENGTH: 1206
<212> TYPE: DNA
<213> ORGANISM: unknown
<220> FEATURE:
<223> OTHER INFORMATION: nucleic acid encoding SEQ ID NO:52, which is
      unprocessed and includes its signal peptide; from Metagenomics on
      soil sample (Cottonwood river); designated LinD-12

<400> SEQUENCE: 50

```
atgaagaaac ccgcccctt gaccgtcctg gccggcctgg ccagcgccgt cctgctcgcc    60
cttggcacgc cggccacggc agtcgagccg atgcccggcc gctggcctc gaccgacgac   120 tacttcgccc agagcgagaa gcacgccctg acgcccgacg tgatggcgca actgcgctac   180
atgaactaca ccgatttcat ctcgccgttc tatagccggg gctgcgcctt cgatgcctgg   240
acgatgaaga agatgccgcc ccgcatcatc aagtattcgc tcgcctggta cgcctacggc   300
ctggccagcg tcgccctgac cgatccggcg atgcggccgg tggccggcca tgcgatcgac   360
atcgcgaccg ccaagatgca ttgcaagcag gtctggggcg actgggagga agacggcttc   420
ggcagcgacc cgatcatccg cgaaaacgtc atgtacaagg ccacctgaa cctgatgtac   480 ggtctctacc agctgatcac cggcgaccgc aagtacgaga aggaaaacac ccgcctgacc   540
cgcatcatgc acaaggagat gaagagcaat ccgtacgccg gcatcgtctg cgaacccgac   600
aactacttcg tccagtgcaa ctcggtcgcc tacctgagcc tgtgggttta cgaccggctg   660
cacggcaccc agtacaaggc ggcaaccagg gagtggctga aattcatcga ggacgaactg   720
atcgacccga agaccggcag cttctatctt tcctaccatc ccgaaaccgg tgccgtgaag   780
ccgtggcagt cggcctacac gaccgcctgg acgctggcca tggtgcatgg catggacccg   840
gccttcgccg aacgctatta cccgaaattc aaggaaagct tcgtcgaggt ctatgacgac   900
ggccgcaagg cgcgcgtccg cgaaatgacc ggcaccaccg acaccgacgg cggcgtcggc   960
gccgcgtcgg cgttcatgct ggtcctggcg cgtgaaatgg gcgacaagca actgttcgac  1020
cagctgctga ccaccctcga accgccagcc ggaccgacga tcacttcggg catcctgcat  1080
tacgcgcagc cgagcaatct gctgttcgac gaattgctgt tcgtcggcaa ggtgcatgtc  1140
ggcttcgcca aactgctcaa tgcgccgccg gcaccggccc gccccgccct gcaaagaag  1200 aaatga                                                             1206
```

<210> SEQ ID NO 51
<211> LENGTH: 401
<212> TYPE: PRT
<213> ORGANISM: unknown
<220> FEATURE:
<223> OTHER INFORMATION: unprocessed, LinD enzyme, designated LinD-12,
      including signal peptide; from Metagenomics on soil sample
      (Cottonwood river)

<400> SEQUENCE: 51

```
Met Lys Lys Pro Arg Pro Leu Thr Val Leu Ala Gly Leu Ala Ser Ala
1               5                   10                  15
```

Val Leu Leu Ala Leu Gly Thr Pro Ala Thr Ala Val Glu Pro Met Pro
            20                  25                  30

Gly Arg Leu Ala Ser Thr Asp Asp Tyr Phe Ala Gln Ser Glu Lys His
        35                  40                  45

Ala Leu Thr Pro Asp Val Met Ala Gln Leu Arg Tyr Met Asn Tyr Thr
    50                  55                  60

Asp Phe Ile Ser Pro Phe Tyr Ser Arg Gly Cys Ala Phe Asp Ala Trp
65                  70                  75                  80

Thr Met Lys Lys Met Pro Pro Arg Ile Ile Lys Tyr Ser Leu Ala Trp
                85                  90                  95

Tyr Ala Tyr Gly Leu Ala Ser Val Ala Leu Thr Asp Pro Ala Met Arg
            100                 105                 110

Pro Val Ala Gly His Ala Ile Asp Ile Ala Thr Ala Lys Met His Cys
        115                 120                 125

Lys Gln Val Trp Gly Asp Trp Glu Glu Asp Gly Phe Gly Ser Asp Pro
130                 135                 140

Ile Ile Arg Glu Asn Val Met Tyr Lys Gly His Leu Asn Leu Met Tyr
145                 150                 155                 160

Gly Leu Tyr Gln Leu Ile Thr Gly Asp Arg Lys Tyr Glu Lys Glu Asn
                165                 170                 175

Thr Arg Leu Thr Arg Ile Met His Lys Glu Met Lys Ser Asn Pro Tyr
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Gln
210                 215                 220

Tyr Lys Ala Ala Thr Arg Glu Trp Leu Lys Phe Ile Glu Asp Glu Leu
225                 230                 235                 240

Ile Asp Pro Lys Thr Gly Ser Phe Tyr Leu Ser Tyr His Pro Glu Thr
                245                 250                 255

Gly Ala Val Lys Pro Trp Gln Ser Ala Tyr Thr Thr Ala Trp Thr Leu
            260                 265                 270

Ala Met Val His Gly Met Asp Pro Ala Phe Ala Glu Arg Tyr Tyr Pro
        275                 280                 285

Lys Phe Lys Glu Ser Phe Val Glu Val Tyr Asp Asp Gly Arg Lys Ala
290                 295                 300

Arg Val Arg Glu Met Thr Gly Thr Thr Asp Thr Asp Gly Gly Val Gly
305                 310                 315                 320

Ala Ala Ser Ala Phe Met Leu Val Leu Ala Arg Glu Met Gly Asp Lys
                325                 330                 335

Gln Leu Phe Asp Gln Leu Leu Asn His Leu Glu Pro Pro Ala Gly Pro
            340                 345                 350

Thr Ile Thr Ser Gly Ile Leu His Tyr Ala Gln Pro Ser Asn Leu Leu
        355                 360                 365

Phe Asp Glu Leu Leu Phe Val Gly Lys Val His Val Gly Phe Ala Lys
370                 375                 380

Leu Leu Asn Ala Pro Pro Ala Pro Ala Arg Pro Ala Leu Gln Lys Lys
385                 390                 395                 400

Lys

<210> SEQ ID NO 52
<211> LENGTH: 1125
<212> TYPE: DNA
<213> ORGANISM: unknown

```
<220> FEATURE:
<223> OTHER INFORMATION: Nucleic acid encoding processed (mature)
      LinD-12 LinD enzyme, no signal peptide

<400> SEQUENCE: 52
gtcgagccga tgcccggccg cctggcctcg accgacgact acttcgccca gagcgagaag    60
cacgccctga cgcccgacgt gatggcgcaa ctgcgctaca tgaactacac cgatttcatc   120
tcgccgttct atagccgggg ctgcgccttc gatgcctgga cgatgaagaa gatgccgccc   180
cgcatcatca gtattcgct cgcctggtac gcctacggcc tggccagcgt cgccctgacc    240
gatccggcga tgcggccggt ggccggccat gcgatcgaca tcgcgaccgc caagatgcat   300
tgcaagcagg tctggggcga ctgggaggaa gacggcttcg gcagcgaccc gatcatccgc   360
gaaaacgtca tgtacaaggg ccacctgaac ctgatgtacg gtctctacca gctgatcacc   420
ggcgaccgca agtacgagaa ggaaaacacc cgcctgaccc gcatcatgca aaggagatg    480
aagagcaatc cgtacgccgg catcgtctgc gaacccgaca actacttcgt ccagtgcaac   540
tcggtcgcct acctgagcct gtgggtttac gaccggctgc acggcaccca gtacaaggcg   600
gcaaccaggg agtggctgaa attcatcgag gacgaactga tcgacccgaa gaccggcagc   660
ttctatcttt cctaccatcc cgaaaccggt gccgtgaagc cgtggcagtc ggcctacacg   720
accgcctgga cgctggccat ggtgcatggc atggacccgg ccttcgccga acgctattac   780
ccgaaattca aggaaagctt cgtcgaggtc tatgacgacg ccgcaaggc gcgcgtccgc    840
gaaatgaccg gcaccaccga caccgacggc ggcgtcggcg ccgcgtcggc gttcatgctg   900
gtcctggcgc gtgaaatggg cgacaagcaa ctgttcgacc agctgctgaa ccacctcgaa   960
ccgccagccg gaccgacgat cacttcgggc atcctgcatt acgcgcagcc gagcaatctg  1020
ctgttcgacg aattgctgtt cgtcggcaag gtgcatgtcg gcttcgccaa actgctcaat  1080
gcgccgccgg caccggcccg ccccgcccctg caaaagaaga aatga                 1125

<210> SEQ ID NO 53
<211> LENGTH: 374
<212> TYPE: PRT
<213> ORGANISM: unknown
<220> FEATURE:
<223> OTHER INFORMATION: Processed (mature) LinD-12 LinD enzyme, no
      signal peptide; from Metagenomics on soil sample (Cottonwood
      river)

<400> SEQUENCE: 53

Val Glu Pro Met Pro Gly Arg Leu Ala Ser Thr Asp Asp Tyr Phe Ala
1               5                   10                  15

Gln Ser Glu Lys His Ala Leu Thr Pro Asp Val Met Ala Gln Leu Arg
            20                  25                  30

Tyr Met Asn Tyr Thr Asp Phe Ile Ser Pro Phe Tyr Ser Arg Gly Cys
        35                  40                  45

Ala Phe Asp Ala Trp Thr Met Lys Lys Met Pro Arg Ile Ile Lys
    50                  55                  60

Tyr Ser Leu Ala Trp Tyr Ala Tyr Gly Leu Ala Ser Val Ala Leu Thr
65                  70                  75                  80

Asp Pro Ala Met Arg Pro Val Ala Gly His Ala Ile Asp Ile Ala Thr
                85                  90                  95

Ala Lys Met His Cys Lys Gln Val Trp Gly Asp Trp Glu Glu Asp Gly
            100                 105                 110

Phe Gly Ser Asp Pro Ile Ile Arg Glu Asn Val Met Tyr Lys Gly His
        115                 120                 125
```

-continued

```
Leu Asn Leu Met Tyr Gly Leu Tyr Gln Leu Ile Thr Gly Asp Arg Lys
            130                 135                 140

Tyr Glu Lys Glu Asn Thr Arg Leu Thr Arg Ile Met His Lys Glu Met
145                 150                 155                 160

Lys Ser Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
                180                 185                 190

Leu His Gly Thr Gln Tyr Lys Ala Ala Thr Arg Glu Trp Leu Lys Phe
            195                 200                 205

Ile Glu Asp Glu Leu Ile Asp Pro Lys Thr Gly Ser Phe Tyr Leu Ser
210                 215                 220

Tyr His Pro Glu Thr Gly Ala Val Lys Pro Trp Gln Ser Ala Tyr Thr
225                 230                 235                 240

Thr Ala Trp Thr Leu Ala Met Val His Gly Met Asp Pro Ala Phe Ala
                245                 250                 255

Glu Arg Tyr Tyr Pro Lys Phe Lys Glu Ser Phe Val Glu Val Tyr Asp
                260                 265                 270

Asp Gly Arg Lys Ala Arg Val Arg Glu Met Thr Gly Thr Thr Asp Thr
            275                 280                 285

Asp Gly Gly Val Gly Ala Ala Ser Ala Phe Met Leu Val Leu Ala Arg
290                 295                 300

Glu Met Gly Asp Lys Gln Leu Phe Asp Gln Leu Leu Asn His Leu Glu
305                 310                 315                 320

Pro Pro Ala Gly Pro Thr Ile Thr Ser Gly Ile Leu His Tyr Ala Gln
                325                 330                 335

Pro Ser Asn Leu Leu Phe Asp Glu Leu Leu Phe Val Gly Lys Val His
            340                 345                 350

Val Gly Phe Ala Lys Leu Leu Asn Ala Pro Pro Ala Pro Ala Arg Pro
            355                 360                 365

Ala Leu Gln Lys Lys Lys
        370
```

<210> SEQ ID NO 54
<211> LENGTH: 1206
<212> TYPE: DNA
<213> ORGANISM: unknown
<220> FEATURE:
<223> OTHER INFORMATION: nucleic acid encoding SEQ ID NO: 55, which is unprocessed and includes its signal peptide; from Metagenomics on activated sludge (Sierra Nevada); designated LinD-13

<400> SEQUENCE: 54

```
atgaagaaca tccaaaaggc agctgccgcg ctgcccgcca tccttgccgc agtgctcgcg      60
ttcagtgcgc cggcccattc ggcggacctg ccgcccggcc gcctcgcctc gaccgaggcc     120
tacttcgccc agcgcgaaag gcaggccgtc acgcccgacg tgatggccca cctcgcctac     180
atgaactaca ccgatttcgt ctccccccttc tacagccggg gctgcgcctt cgatgcatgg     240
accatcaaga agacgccgca gcggatcatc aagtactcgc tcgccttcta cgcctacggg     300
ctggccagcg tcgcgctcac cgatccgcag ctgcgtccgc tcgccggcca cgcgatcgac     360
atcgccaccg ccaagatgca atgcaagcag gtctgggagg actgggagga gacgggttc     420
ggcgacgatc cgatcgagaa agagaacatc atgtacaagg ccacttgaa cctgatgtac     480
ggcctttacc agctggtcac cggcaaccgc cggtacgaga aggagcacgc ccgcctcacg     540
```

```
cggatcatcc acgacgagat caaggccaat ccctacgccg gcatcgtctg cgagccggac    600
aactatttcg tccagtgcaa ctcggtcgcc tacctgagcc tgtgggtcca tgaccgcctg    660
cacggcaccg actaccgggc ggcgacggcg gagtggctga attcatcga gcacgacctg     720 atcgacccga aacacggcgc cttccacctg tcctaccatc cggaatccca cgcggtgaaa    780
ccgtgggtct ccgcatacac cacggcgtgg acgctcgcca tggtgcacgg catggatccc    840
gctttcgccg agcgctacta cccccgcttc aaggaaacct tcgtcgaggt ctacgacgat    900
ggccgcaagg cccgggtccg cgagacgacc ggcaccaccg acgccgatgg cggcgtcggc    960
gcggcctccg cgttcaccct gctgctcgcc cgtgagatgg cgaccggca gctcttcgac    1020 cagttgctga accacctgga gccccggca agaccgcgga tcacctcggg catcctggaa    1080
tacgaggcgc ccagcaacct gctgttcgac gagttgctgt tcctcgccaa ggtgcacgtc    1140
ggtttcggcc agttgctgga ggccgggtcg gcgccacctc ggccgggccc caccgggggg    1200
aaatga                                                              1206
```

<210> SEQ ID NO 55
<211> LENGTH: 401
<212> TYPE: PRT
<213> ORGANISM: unknown
<220> FEATURE:
<223> OTHER INFORMATION: unprocessed, LinD enzyme, designated LinD-13, including signal peptide; from Metagenomics on activated sludge (Sierra Nevada)

<400> SEQUENCE: 55

```
Met Lys Asn Ile Gln Lys Ala Ala Ala Leu Pro Ala Ile Leu Ala
1               5                   10                  15

Ala Val Leu Ala Phe Ser Ala Pro Ala His Ser Ala Asp Leu Pro Pro
            20                  25                  30

Gly Arg Leu Ala Ser Thr Glu Ala Tyr Phe Ala Gln Arg Glu Arg Gln
        35                  40                  45

Ala Val Thr Pro Asp Val Met Ala His Leu Ala Tyr Met Asn Tyr Thr
    50                  55                  60

Asp Phe Val Ser Pro Phe Tyr Ser Arg Gly Cys Ala Phe Asp Ala Trp
65                  70                  75                  80

Thr Ile Lys Lys Thr Pro Gln Arg Ile Ile Lys Tyr Ser Leu Ala Phe
                85                  90                  95

Tyr Ala Tyr Gly Leu Ala Ser Val Ala Leu Thr Asp Pro Gln Leu Arg
            100                 105                 110

Pro Leu Ala Gly His Ala Ile Asp Ile Ala Thr Ala Lys Met Gln Cys
        115                 120                 125

Lys Gln Val Trp Gly Asp Trp Glu Glu Asp Gly Phe Gly Asp Pro
    130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Asn Arg Arg Tyr Glu Lys Glu His
                165                 170                 175

Ala Arg Leu Thr Arg Ile Ile His Asp Glu Ile Lys Ala Asn Pro Tyr
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val His Asp Arg Leu His Gly Thr Asp
    210                 215                 220

Tyr Arg Ala Ala Thr Ala Glu Trp Leu Lys Phe Ile Glu His Asp Leu
```

|  |  |  | 225 |  |  |  | 230 |  |  |  | 235 |  |  |  | 240 |
|---|---|---|---|---|---|---|---|---|---|---|---|---|---|---|---|

Ile Asp Pro Lys His Gly Ala Phe His Leu Ser Tyr His Pro Glu Ser
            245                 250                 255

His Ala Val Lys Pro Trp Val Ser Ala Tyr Thr Thr Ala Trp Thr Leu
            260                 265                 270

Ala Met Val His Gly Met Asp Pro Ala Phe Ala Glu Arg Tyr Tyr Pro
            275                 280                 285

Arg Phe Lys Glu Thr Phe Val Glu Val Tyr Asp Asp Gly Arg Lys Ala
    290                 295                 300

Arg Val Arg Glu Thr Thr Gly Thr Thr Asp Ala Asp Gly Val Gly
305                 310                 315                 320

Ala Ala Ser Ala Phe Thr Leu Leu Leu Ala Arg Glu Met Gly Asp Arg
                325                 330                 335

Gln Leu Phe Asp Gln Leu Leu Asn His Leu Glu Pro Pro Ala Arg Pro
            340                 345                 350

Arg Ile Thr Ser Gly Ile Leu Glu Tyr Glu Ala Pro Ser Asn Leu Leu
            355                 360                 365

Phe Asp Glu Leu Leu Phe Leu Ala Lys Val His Val Gly Phe Gly Gln
        370                 375                 380

Leu Leu Glu Ala Gly Ser Ala Pro Pro Arg Pro Gly Pro Thr Gly Gly
385                 390                 395                 400

Lys

<210> SEQ ID NO 56
<211> LENGTH: 1125
<212> TYPE: DNA
<213> ORGANISM: unknown
<220> FEATURE:
<223> OTHER INFORMATION: Nucleic acid encoding processed (mature)
      LinD-13 LinD enzyme, no signal peptide; from Metagenomics on
      activated sludge (Sierra Nevada)

<400> SEQUENCE: 56

| gcggacctgc | cgcccggccg | cctcgcctcg | accgaggcct | acttcgccca | gcgcgaaagg | 60 |
|---|---|---|---|---|---|---|
| caggccgtca | cgcccgacgt | gatggcccac | ctcgcctaca | tgaactacac | cgatttcgtc | 120 |
| tccccttct | acagccgggg | ctgcgccttc | gatgcatgga | ccatcaagaa | gacgccgcag | 180 |
| cggatcatca | gtactcgct | cgccttctac | gcctacgggc | tggccagcgt | cgcgctcacc | 240 |
| gatccgcagc | tgcgtccgct | cgccggccac | gcgatcgaca | tcgccaccgc | caagatgcaa | 300 |
| tgcaagcagg | tctggggaga | ctgggaggaa | gacgggttcg | gcgacgatcc | gatcgagaaa | 360 |
| gagaacatca | tgtacaaggg | ccacttgaac | ctgatgtacg | gccttacca | gctggtcacc | 420 |
| ggcaaccgcc | ggtacgagaa | ggagcacgcc | gcctcacgc | ggatcatcca | cgacgagatc | 480 |
| aaggccaatc | cctacgccgg | catcgtctgc | gagccggaca | actatttcgt | ccagtgcaac | 540 |
| tcggtcgcct | acctgagcct | gtgggtccat | gaccgcctgc | acggcaccga | ctaccgggcg | 600 |
| gcgacggcgg | agtggctgaa | attcatcgag | cacgacctga | tcgacccgaa | acacggcgcc | 660 |
| ttccacctgt | cctaccatcc | ggaatcccac | gcggtgaaac | cgtgggtctc | cgcatacacc | 720 |
| acggcgtgga | cgctcgccat | ggtgcacggc | atggatcccg | ctttcgccga | gcgctactac | 780 |
| ccccgcttca | aggaaaacctt | cgtcgaggtc | tacgacgatg | gccgcaaggc | ccgggtccgc | 840 |
| gagacgaccg | gcaccaccga | cgccgatggc | ggcgtcggcg | cggcctccgc | gttcaccctg | 900 |
| ctgctcgccc | gtgagatggg | cgaccggcag | ctcttcgacc | agttgctgaa | ccacctggag | 960 |
| cccccggcaa | gaccgcggat | cacctcgggc | atcctggaat | acgaggcgcc | cagcaacctg | 1020 |

```
ctgttcgacg agttgctgtt cctcgccaag gtgcacgtcg gtttcggcca gttgctggag    1080
gccgggtcgg cgccacctcg gccgggcccc accgggggga aatga                    1125
```

<210> SEQ ID NO 57
<211> LENGTH: 374
<212> TYPE: PRT
<213> ORGANISM: unknown
<220> FEATURE:
<223> OTHER INFORMATION: Processed (mature) LinD-13 LinD enzyme, no
      signal peptide; from Metagenomics on activated sludge (Sierra
      Nevada)

<400> SEQUENCE: 57

```
Ala Asp Leu Pro Pro Gly Arg Leu Ala Ser Thr Glu Ala Tyr Phe Ala
1               5                   10                  15

Gln Arg Glu Arg Gln Ala Val Thr Pro Asp Val Met Ala His Leu Ala
            20                  25                  30

Tyr Met Asn Tyr Thr Asp Phe Val Ser Pro Phe Tyr Ser Arg Gly Cys
        35                  40                  45

Ala Phe Asp Ala Trp Thr Ile Lys Lys Thr Pro Gln Arg Ile Ile Lys
    50                  55                  60

Tyr Ser Leu Ala Phe Tyr Ala Tyr Gly Leu Ala Ser Val Ala Leu Thr
65                  70                  75                  80

Asp Pro Gln Leu Arg Pro Leu Ala Gly His Ala Ile Asp Ile Ala Thr
                85                  90                  95

Ala Lys Met Gln Cys Lys Gln Val Trp Gly Asp Trp Glu Glu Asp Gly
            100                 105                 110

Phe Gly Asp Asp Pro Ile Glu Lys Glu Asn Ile Met Tyr Lys Gly His
        115                 120                 125

Leu Asn Leu Met Tyr Gly Leu Tyr Gln Leu Val Thr Gly Asn Arg Arg
    130                 135                 140

Tyr Glu Lys Glu His Ala Arg Leu Thr Arg Ile Ile His Asp Glu Ile
145                 150                 155                 160

Lys Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val His Asp Arg
            180                 185                 190

Leu His Gly Thr Asp Tyr Arg Ala Ala Thr Ala Glu Trp Leu Lys Phe
        195                 200                 205

Ile Glu His Asp Leu Ile Asp Pro Lys His Gly Ala Phe His Leu Ser
    210                 215                 220

Tyr His Pro Glu Ser His Ala Val Lys Pro Trp Val Ser Ala Tyr Thr
225                 230                 235                 240

Thr Ala Trp Thr Leu Ala Met Val His Gly Met Asp Pro Ala Phe Ala
                245                 250                 255

Glu Arg Tyr Tyr Pro Arg Phe Lys Glu Thr Phe Val Glu Val Tyr Asp
            260                 265                 270

Asp Gly Arg Lys Ala Arg Val Arg Glu Thr Thr Gly Thr Thr Asp Ala
        275                 280                 285

Asp Gly Gly Val Gly Ala Ala Ser Ala Phe Thr Leu Leu Leu Ala Arg
    290                 295                 300

Glu Met Gly Asp Arg Gln Leu Phe Asp Gln Leu Leu Asn His Leu Glu
305                 310                 315                 320

Pro Pro Ala Arg Pro Arg Ile Thr Ser Gly Ile Leu Glu Tyr Glu Ala
                325                 330                 335
```

Pro Ser Asn Leu Leu Phe Asp Glu Leu Leu Phe Leu Ala Lys Val His
            340                 345                 350

Val Gly Phe Gly Gln Leu Leu Glu Ala Gly Ser Ala Pro Pro Arg Pro
        355                 360                 365

Gly Pro Thr Gly Gly Lys
    370

<210> SEQ ID NO 58
<211> LENGTH: 1203
<212> TYPE: DNA
<213> ORGANISM: unknown
<220> FEATURE:
<223> OTHER INFORMATION: nucleic acid encoding SEQ ID NO: 59, which is
      unprocessed and includes its signal peptide; from Metagenomics on
      soil sample (Cottonwood river); designated LinD-14

<400> SEQUENCE: 58

```
atgaaaaaat tccgcccctt cgcgccgctg gctgccgcgc tcgccggcct gatcgcctgc      60
gccacgccgg ccgctgcggc cgagctgatg cccggccgcc tggcctcgac cgaggattac     120
ttcgcccagc gcgaaaagca ggcgctgacg cccgacgtca tggcccacct gcgctacatg     180
aactacaccg atttcatttc gccgttctac agccggggct gcgccttcga tgcctgggcg     240
atgaagaaga cgcccaaccg catcatcaag tattcgctcg cctggtacgc ctacggcctg     300
gccagcgtcg cccagaccga tccggccatg cgccaggtgg ccggccacgc gatcgacatc     360
gcgaccgcca agatgcactg caagcaggtc tggggcgact gggaggaaga ccagttcggc     420
agcgacccga tcatccggga aaacgtcatg tacaagggtc acctgaacct gatgtacggg     480
ctttaccaga tggtgaccgg cgaccgcaag tacgagaagg aaaacgccag gctcaccaaa     540
atcatggcca gggagatcaa ggccaacccc tacgccggca tcgtctgcga accggacaac     600
tacttcgtgc aatgcaattc ggtcgcctac ctgagcctgt gggtctatga ccgcctgcac     660
ggcacccatt acaaggcgct gaccaaggac tggctgaagt tcatcgagga agaactgatc     720 gaccccgaaga ccggcagctt ctatctctcc taccaccccg aatcgggcgc ggtgaagccg     780
tggcagtcgg cctacacgac cgcctgggcg ctggccatgg tgcacggcat ggacccggcc     840
ttctccgagc gctattaccc gaagttcaag gaaaacttcg tcgaggtcta tgacgacggc     900
cgcaaggcgc gcgtccgcga aacgaccggc acggcggata ccgacggcgg cgtcggcgca     960
gcctcggcgt tcacgctggt gctagcccgc gaaatgggcg accagaaact cttcgaccag    1020
ttgctgaacc atctcgaacc cccggccgga ccgaaaatca cctcgggcat cctgcattac    1080
gcgcagccga gcaacctgct gttcgacgaa ttgctgttcg tcggcaaagt gcatgtcggc    1140
ttcgccaatc tgctcaatgc gccgccggca ccggctcgcc cggtcctgca aagaagaaa    1200 tga                                                                 1203
```

<210> SEQ ID NO 59
<211> LENGTH: 400
<212> TYPE: PRT
<213> ORGANISM: unknown
<220> FEATURE:
<223> OTHER INFORMATION: unprocessed, LinD enzyme, designated LinD-14,
      including signal peptide; from Metagenomics on soil sample
      (Cottonwood river)

<400> SEQUENCE: 59

Met Lys Lys Phe Arg Pro Phe Ala Pro Leu Ala Ala Leu Ala Gly
1               5                   10                  15

Leu Ile Ala Cys Ala Thr Pro Ala Ala Ala Glu Leu Met Pro Gly
            20                  25                  30

Arg Leu Ala Ser Thr Glu Asp Tyr Phe Ala Gln Arg Glu Lys Gln Ala
                35                  40                  45

Leu Thr Pro Asp Val Met Ala His Leu Arg Tyr Met Asn Tyr Thr Asp
 50                  55                  60

Phe Ile Ser Pro Phe Tyr Ser Arg Gly Cys Ala Phe Asp Ala Trp Ala
 65                  70                  75                  80

Met Lys Lys Thr Pro Asn Arg Ile Ile Lys Tyr Ser Leu Ala Trp Tyr
                85                  90                  95

Ala Tyr Gly Leu Ala Ser Val Ala Gln Thr Asp Pro Ala Met Arg Gln
            100                 105                 110

Val Ala Gly His Ala Ile Asp Ile Ala Thr Ala Lys Met His Cys Lys
            115                 120                 125

Gln Val Trp Gly Asp Trp Glu Glu Asp Gln Phe Gly Ser Asp Pro Ile
            130                 135                 140

Ile Arg Glu Asn Val Met Tyr Lys Gly His Leu Asn Leu Met Tyr Gly
145                 150                 155                 160

Leu Tyr Gln Met Val Thr Gly Asp Arg Lys Tyr Glu Lys Glu Asn Ala
                165                 170                 175

Arg Leu Thr Lys Ile Met Ala Arg Glu Ile Lys Ala Asn Pro Tyr Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr His Tyr
210                 215                 220

Lys Ala Leu Thr Lys Asp Trp Leu Lys Phe Ile Glu Glu Leu Ile
225                 230                 235                 240

Asp Pro Lys Thr Gly Ser Phe Tyr Leu Ser Tyr His Pro Glu Ser Gly
                245                 250                 255

Ala Val Lys Pro Trp Gln Ser Ala Tyr Thr Thr Ala Trp Ala Leu Ala
            260                 265                 270

Met Val His Gly Met Asp Pro Ala Phe Ser Glu Arg Tyr Tyr Pro Lys
            275                 280                 285

Phe Lys Glu Asn Phe Val Glu Val Tyr Asp Asp Gly Arg Lys Ala Arg
290                 295                 300

Val Arg Glu Thr Thr Gly Thr Ala Asp Thr Asp Gly Gly Val Gly Ala
305                 310                 315                 320

Ala Ser Ala Phe Thr Leu Val Leu Ala Arg Glu Met Gly Asp Gln Lys
                325                 330                 335

Leu Phe Asp Gln Leu Leu Asn His Leu Glu Pro Pro Ala Gly Pro Lys
            340                 345                 350

Ile Thr Ser Gly Ile Leu His Tyr Ala Gln Pro Ser Asn Leu Leu Phe
            355                 360                 365

Asp Glu Leu Leu Phe Val Gly Lys Val His Val Gly Phe Ala Asn Leu
            370                 375                 380

Leu Asn Ala Pro Pro Ala Pro Ala Arg Pro Val Leu Gln Lys Lys Lys
385                 390                 395                 400

<210> SEQ ID NO 60
<211> LENGTH: 1125
<212> TYPE: DNA
<213> ORGANISM: unknown
<220> FEATURE:
<223> OTHER INFORMATION: Nucleic acid encoding processed (mature)

LinD-14 LinD enzyme, no signal peptide; from Metagenomics on soil sample (Cottonwood river)

<400> SEQUENCE: 60

```
gccgagctga tgcccggccg cctggcctcg accgaggatt acttcgccca gcgcgaaaag      60
caggcgctga cgcccgacgt catggccacc ctgcgctaca tgaactacac cgatttcatt     120
tcgccgttct acagccgggg ctgcgccttc gatgcctggg cgatgaagaa gacgcccaac     180
cgcatcatca gtattcgctc gcctggtac gcctacggcc tggccagcgt cgcccagacc     240
gatccggcca tgcgccaggt ggccggccac gcgatcgaca tcgcgaccgc caagatgcac     300
tgcaagcagg tctggggcga ctgggaggaa gaccagttcg gcagcgaccc gatcatccgg     360
gaaaacgtca tgtacaaggg tcacctgaac ctgatgtacg ggctttacca gatggtgacc     420
ggcgaccgca gtacgagaa ggaaaacgcc aggctcacca aaatcatggc cagggagatc     480
aaggccaacc cctacgccgg catcgtctgc gaaccggaca actacttcgt gcaatgcaat     540
tcggtcgcct acctgagcct gtgggtctat gaccgcctgc acggcaccca ttacaaggcg     600
ctgaccaagg actggctgaa gttcatcgag gaagaactga tcgacccgaa gaccggcagc     660
ttctatctct cctaccaccc cgaatcgggc gcggtgaagc cgtggcagtc ggcctacacg     720
accgcctggg cgctggccat ggtgcacggc atggacccgg ccttctccga gcgctattac     780
ccgaagttca aggaaaactt cgtcgaggtc tatgacgacg ccgcaaggc gcgcgtccgc     840
gaaacgaccg gcacggcgga taccgacggc ggcgtcggcg cagcctcggc gttcacgctg     900
gtgctagccc gcgaaatggg cgaccagaaa ctcttcgacc agttgctgaa ccatctcgaa     960
ccccggccg gaccgaaaat cacctcgggc atcctgcatt acgcgcagcc gagcaacctg    1020
ctgttcgacg aattgctgtt cgtcggcaaa gtgcatgtcg gcttcgccaa tctgctcaat    1080
gcgccgccgg caccggctcg cccggtcctg caaaagaaga aatga                   1125
```

<210> SEQ ID NO 61
<211> LENGTH: 374
<212> TYPE: PRT
<213> ORGANISM: unknown
<220> FEATURE:
<223> OTHER INFORMATION: Processed (mature) LinD-14 LinD enzyme, no signal peptide; from Metagenomics on soil sample (Cottonwood river)

<400> SEQUENCE: 61

```
Ala Glu Leu Met Pro Gly Arg Leu Ala Ser Thr Glu Asp Tyr Phe Ala
1               5                   10                  15

Gln Arg Glu Lys Gln Ala Leu Thr Pro Asp Val Met Ala His Leu Arg
            20                  25                  30

Tyr Met Asn Tyr Thr Asp Phe Ile Ser Pro Phe Tyr Ser Arg Gly Cys
        35                  40                  45

Ala Phe Asp Ala Trp Ala Met Lys Lys Thr Pro Asn Arg Ile Ile Lys
    50                  55                  60

Tyr Ser Leu Ala Trp Tyr Ala Tyr Gly Leu Ala Ser Val Ala Gln Thr
65                  70                  75                  80

Asp Pro Ala Met Arg Gln Val Ala Gly His Ala Ile Asp Ile Ala Thr
                85                  90                  95

Ala Lys Met His Cys Lys Gln Val Trp Gly Asp Trp Glu Glu Asp Gln
            100                 105                 110

Phe Gly Ser Asp Pro Ile Ile Arg Glu Asn Val Met Tyr Lys Gly His
        115                 120                 125
```

```
Leu Asn Leu Met Tyr Gly Leu Tyr Gln Met Val Thr Gly Asp Arg Lys
    130                 135                 140

Tyr Glu Lys Glu Asn Ala Arg Leu Thr Lys Ile Met Ala Arg Glu Ile
145                 150                 155                 160

Lys Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr His Tyr Lys Ala Leu Thr Lys Asp Trp Leu Lys Phe
        195                 200                 205

Ile Glu Glu Glu Leu Ile Asp Pro Lys Thr Gly Ser Phe Tyr Leu Ser
210                 215                 220

Tyr His Pro Glu Ser Gly Ala Val Lys Pro Trp Gln Ser Ala Tyr Thr
225                 230                 235                 240

Thr Ala Trp Ala Leu Ala Met Val His Gly Met Asp Pro Ala Phe Ser
                245                 250                 255

Glu Arg Tyr Tyr Pro Lys Phe Lys Glu Asn Phe Val Glu Val Tyr Asp
            260                 265                 270

Asp Gly Arg Lys Ala Arg Val Arg Glu Thr Thr Gly Thr Ala Asp Thr
        275                 280                 285

Asp Gly Gly Val Gly Ala Ala Ser Ala Phe Thr Leu Val Leu Ala Arg
290                 295                 300

Glu Met Gly Asp Gln Lys Leu Phe Asp Gln Leu Leu Asn His Leu Glu
305                 310                 315                 320

Pro Pro Ala Gly Pro Lys Ile Thr Ser Gly Ile Leu His Tyr Ala Gln
                325                 330                 335

Pro Ser Asn Leu Leu Phe Asp Glu Leu Leu Phe Val Gly Lys Val His
            340                 345                 350

Val Gly Phe Ala Asn Leu Leu Asn Ala Pro Ala Pro Ala Arg Pro
        355                 360                 365

Val Leu Gln Lys Lys Lys
    370
```

<210> SEQ ID NO 62
<211> LENGTH: 1254
<212> TYPE: DNA
<213> ORGANISM: artificial
<220> FEATURE:
<223> OTHER INFORMATION: Nucleic acid encoding native LinD-1 LinD enzyme
      with N-terminal His-tag and linker

<400> SEQUENCE: 62

```
atgggcagca gccatcatca tcatcatcac agcagcggcc tggtgccgcg cggcagccat       60
atgcgcttta ccctgaaaac gaccgccatt gttagtgccg ccgccctgct ggctggcttt      120
ggtccgccgc cgcgtgctgc cgaactgccg ccgggtcgcc tggcaaccac ggaagattat      180
tttgcgcagc aagccaaaca ggcagtcacc ccggatgtga tggctcaact ggcgtatatg      240
aactacattg actttatcag tccgttctat tcccgtggct gctcatttga agcctgggaa      300
ctgaaacata cgccgcagcg cgttattaaa tactccatcg ccttctatgc atacggtctg      360
gcttcagtcg cgctgattga tccgaaactg cgtgcactgg aggtcacga tctggacatc      420
gcagtgagca aaatgaaatg taaacgcgtt tggggtgatt gggaagaaga cggcttcggt      480
accgatccga tcgaaaaaga aaacatcatg tacaaaggcc atctgaatct gatgtatggt      540
ctgtaccagc tggtgaccgg ctctcgtcgc tacgaagccg acatgcaca cctgacgcgt      600
```

```
attatccacg atgaaattgc ggccaatccg tttgcgggta tcgtctgcga accggacaac   660
tatttcgttc agtgtaattc ggtcgcctat ctgagcctgt gggtttacga tcgtctgcat   720
ggtaccgact accgtgcagc tacgcgtgca tggctggatt ttattcaaaa agatctgatc   780
gacccggaac gcggtgcatt ctatctgtct taccatccgg aaagtggcgc tgtgaaaccg   840
tggatttctg cttataccac ggcgtggacc ctggccatgg ttcacggtat ggacccggca   900
tttagtgaac gttattaccc gcgctttaaa cagacgttcg tggaagttta cgatgaaggc   960
cgtaaagctc gtgtccgcga aaccgccggt acggatgacg ctgacggcgg tgtgggtctg  1020
gcaagcgctt ttaccctgct gctggcccgc gaaatgggtg atcagcaact gttcgaccaa  1080
ctgctgaacc acctggaacc gccggcaaaa ccgtcgatcg tgagcgcatc tctgcgttat  1140
gaacatccgg gcagcctgct gtttgatgaa ctgctgttcc tggcgaaagt tcacgctggc  1200
tttggtgccc tgctgcgtat gccgccgccg gctgctaaac tggctggtaa ataa        1254
```

<210> SEQ ID NO 63
<211> LENGTH: 417
<212> TYPE: PRT
<213> ORGANISM: artificial
<220> FEATURE:
<223> OTHER INFORMATION: Native full length LinD-1 LinD enzyme with
      N-terminal His-tag and linker

<400> SEQUENCE: 63

```
Met Gly Ser Ser His His His His His His Ser Ser Gly Leu Val Pro
1               5                   10                  15

Arg Gly Ser His Met Arg Phe Thr Leu Lys Thr Thr Ala Ile Val Ser
            20                  25                  30

Ala Ala Ala Leu Leu Ala Gly Phe Gly Pro Pro Arg Ala Ala Glu
        35                  40                  45

Leu Pro Pro Gly Arg Leu Ala Thr Thr Glu Asp Tyr Phe Ala Gln Gln
    50                  55                  60

Ala Lys Gln Ala Val Thr Pro Asp Val Met Ala Gln Leu Ala Tyr Met
65                  70                  75                  80

Asn Tyr Ile Asp Phe Ile Ser Pro Phe Tyr Ser Arg Gly Cys Ser Phe
                85                  90                  95

Glu Ala Trp Glu Leu Lys His Thr Pro Gln Arg Val Ile Lys Tyr Ser
            100                 105                 110

Ile Ala Phe Tyr Ala Tyr Gly Leu Ala Ser Val Ala Leu Ile Asp Pro
        115                 120                 125

Lys Leu Arg Ala Leu Ala Gly His Asp Leu Asp Ile Ala Val Ser Lys
    130                 135                 140

Met Lys Cys Lys Arg Val Trp Gly Asp Trp Glu Glu Asp Gly Phe Gly
145                 150                 155                 160

Thr Asp Pro Ile Glu Lys Glu Asn Ile Met Tyr Lys Gly His Leu Asn
                165                 170                 175

Leu Met Tyr Gly Leu Tyr Gln Leu Val Thr Gly Ser Arg Arg Tyr Glu
            180                 185                 190

Ala Glu His Ala His Leu Thr Arg Ile Ile His Asp Glu Ile Ala Ala
        195                 200                 205

Asn Pro Phe Ala Gly Ile Val Cys Glu Pro Asp Asn Tyr Phe Val Gln
    210                 215                 220

Cys Asn Ser Val Ala Tyr Leu Ser Leu Trp Val Tyr Asp Arg Leu His
225                 230                 235                 240

Gly Thr Asp Tyr Arg Ala Ala Thr Arg Ala Trp Leu Asp Phe Ile Gln
```

```
                   245                 250                 255

Lys Asp Leu Ile Asp Pro Glu Arg Gly Ala Phe Tyr Leu Ser Tyr His
            260                 265                 270

Pro Glu Ser Gly Ala Val Lys Pro Trp Ile Ser Ala Tyr Thr Thr Ala
        275                 280                 285

Trp Thr Leu Ala Met Val His Gly Met Asp Pro Ala Phe Ser Glu Arg
    290                 295                 300

Tyr Tyr Pro Arg Phe Lys Gln Thr Phe Val Glu Val Tyr Asp Glu Gly
305                 310                 315                 320

Arg Lys Ala Arg Val Arg Glu Thr Ala Gly Thr Asp Asp Ala Asp Gly
                325                 330                 335

Gly Val Gly Leu Ala Ser Ala Phe Thr Leu Leu Ala Arg Glu Met
            340                 345                 350

Gly Asp Gln Gln Leu Phe Asp Gln Leu Leu Asn His Leu Glu Pro Pro
        355                 360                 365

Ala Lys Pro Ser Ile Val Ser Ala Ser Leu Arg Tyr Glu His Pro Gly
    370                 375                 380

Ser Leu Leu Phe Asp Glu Leu Leu Phe Leu Ala Lys Val His Ala Gly
385                 390                 395                 400

Phe Gly Ala Leu Leu Arg Met Pro Pro Ala Ala Lys Leu Ala Gly
                405                 410                 415

Lys

<210> SEQ ID NO 64
<211> LENGTH: 398
<212> TYPE: PRT
<213> ORGANISM: artificial
<220> FEATURE:
<223> OTHER INFORMATION: synthetic linalool dehydratase-isomerase

<400> SEQUENCE: 64

Met Met Arg Phe Thr Leu Lys Thr Thr Ala Ile Val Ser Ala Ala Ala
1               5                   10                  15

Leu Leu Ala Gly Phe Gly Pro Pro Arg Ala Ala Glu Leu Pro Pro
            20                  25                  30

Gly Arg Leu Ala Thr Thr Glu Asp Tyr Phe Ala Gln Gln Ala Lys Gln
        35                  40                  45

Ala Val Thr Pro Asp Val Met Ala Gln Leu Ala Tyr Met Asn Tyr Ile
    50                  55                  60

Asp Phe Ile Ser Pro Phe Tyr Ser Arg Gly Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Lys Leu Arg
            100                 105                 110

Ala Leu Ala Gly His Asp Leu Asp Ile Ala Val Ser Lys Met Lys Cys
        115                 120                 125

Lys Arg Val Trp Gly Asp Trp Glu Glu Asp Gly Phe Gly Thr Asp Pro
    130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Arg Tyr Glu Ala Glu His
                165                 170                 175

Ala His Leu Thr Arg Ile Ile His Asp Glu Ile Ala Ala Asn Pro Phe
            180                 185                 190
```

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Asp
    210                 215                 220

Tyr Arg Ala Ala Thr Arg Ala Trp Leu Asp Phe Ile Gln Lys Asp Leu
225                 230                 235                 240

Ile Asp Pro Glu Arg Gly Ala Phe Tyr Leu Ser Tyr His Pro Glu Ser
                245                 250                 255

Gly Ala Val Lys Pro Trp Ile Ser Ala Tyr Thr Thr Ala Trp Thr Leu
                260                 265                 270

Ala Met Val His Gly Met Asp Pro Ala Phe Ser Glu Arg Tyr Tyr Pro
            275                 280                 285

Arg Phe Lys Gln Thr Phe Val Glu Val Tyr Asp Glu Gly Arg Lys Ala
        290                 295                 300

Arg Val Arg Glu Thr Ala Gly Thr Asp Asp Ala Asp Gly Gly Val Gly
305                 310                 315                 320

Leu Ala Ser Ala Phe Thr Leu Leu Ala Arg Glu Met Gly Asp Gln
                325                 330                 335

Gln Leu Phe Asp Gln Leu Leu Asn His Leu Glu Pro Pro Ala Lys Pro
                340                 345                 350

Ser Ile Val Ser Ala Ser Leu Arg Tyr Glu His Pro Gly Ser Leu Leu
                355                 360                 365

Phe Asp Glu Leu Leu Phe Leu Ala Lys Val His Ala Gly Phe Gly Ala
        370                 375                 380

Leu Leu Arg Met Pro Pro Pro Ala Ala Lys Leu Ala Gly Lys
385                 390                 395

<210> SEQ ID NO 65
<211> LENGTH: 408
<212> TYPE: PRT
<213> ORGANISM: artificial
<220> FEATURE:
<223> OTHER INFORMATION: synthetic linalool dehydratase-isomerase

<400> SEQUENCE: 65

Met Met Arg Phe Thr Leu Lys Thr Thr Ala Ile Val Ser Ala Ala Ala
1               5                   10                  15

Leu Leu Ala Gly Phe Gly Pro Pro Arg Ala Ala Glu Leu Pro Pro
            20                  25                  30

Gly Arg Leu Ala Thr Thr Glu Asp Tyr Phe Ala Gln Gln Ala Lys Gln
        35                  40                  45

Ala Val Thr Pro Asp Val Met Ala Gln Leu Ala Tyr Met Asn Tyr Ile
    50                  55                  60

Asp Phe Ile Ser Pro Phe Tyr Ser Arg Gly Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Lys Leu Arg
                100                 105                 110

Ala Leu Ala Gly His Asp Leu Asp Ile Ala Val Ser Lys Met Lys Cys
            115                 120                 125

Lys Arg Val Trp Gly Asp Trp Glu Glu Asp Gly Phe Gly Thr Asp Pro
        130                 135                 140

Ile Glu Lys Glu Asn Ile Met Tyr Lys Gly His Leu Asn Leu Met Tyr
145                 150                 155                 160

```
Gly Leu Tyr Gln Leu Val Thr Gly Ser Arg Arg Tyr Glu Ala Glu His
                165                 170                 175
Ala His Leu Thr Arg Ile Ile His Asp Glu Ile Ala Ala Asn Pro Phe
            180                 185                 190
Ala Gly Ile Val Cys Glu Pro Asp Asn Tyr Phe Val Gln Cys Asn Ser
            195                 200                 205
Val Ala Tyr Leu Ser Leu Trp Val Tyr Asp Arg Leu His Gly Thr Asp
210                 215                 220
Tyr Arg Ala Ala Thr Arg Ala Trp Leu Asp Phe Ile Gln Lys Asp Leu
225                 230                 235                 240
Ile Asp Pro Glu Arg Gly Ala Phe Tyr Leu Ser Tyr His Pro Glu Ser
                245                 250                 255
Gly Ala Val Lys Pro Trp Ile Ser Ala Tyr Thr Thr Ala Trp Thr Leu
            260                 265                 270
Ala Met Val His Gly Met Asp Pro Ala Phe Ser Glu Arg Tyr Tyr Pro
            275                 280                 285
Arg Phe Lys Gln Thr Phe Val Glu Val Tyr Asp Glu Gly Arg Lys Ala
            290                 295                 300
Arg Val Arg Glu Thr Ala Gly Thr Asp Ala Asp Gly Gly Val Gly
305                 310                 315                 320
Leu Ala Ser Ala Phe Thr Leu Leu Ala Arg Glu Met Gly Asp Gln
            325                 330                 335
Gln Leu Phe Asp Gln Leu Leu Asn His Leu Glu Pro Pro Ala Lys Pro
            340                 345                 350
Ser Ile Val Ser Ala Ser Leu Arg Tyr Glu His Pro Gly Ser Leu Leu
            355                 360                 365
Phe Asp Glu Leu Leu Phe Leu Ala Lys Val His Ala Gly Phe Gly Ala
            370                 375                 380
Leu Leu Arg Met Pro Pro Ala Ala Lys Leu Ala Gly Lys Gly Ser
385                 390                 395                 400
Leu Glu His His His His His His
            405

<210> SEQ ID NO 66
<211> LENGTH: 382
<212> TYPE: PRT
<213> ORGANISM: artificial
<220> FEATURE:
<223> OTHER INFORMATION: synthetic linalool dehydratase-isomerase

<400> SEQUENCE: 66

Met Ala Glu Leu Pro Pro Gly Arg Leu Ala Thr Thr Glu Asp Tyr Phe
1               5                   10                  15
Ala Gln Gln Ala Lys Gln Ala Val Thr Pro Asp Val Met Ala Gln Leu
            20                  25                  30
Ala Tyr Met Asn Tyr Ile Asp Phe Ile Ser Pro Phe Tyr Ser Arg Gly
            35                  40                  45
Cys Ser Phe Glu Ala Trp Glu Leu Lys His Thr Pro Gln Arg Val Ile
    50                  55                  60
Lys Tyr Ser Ile Ala Phe Tyr Ala Tyr Gly Leu Ala Ser Val Ala Leu
65                  70                  75                  80
Ile Asp Pro Lys Leu Arg Ala Leu Ala Gly His Asp Leu Asp Ile Ala
            85                  90                  95
Val Ser Lys Met Lys Cys Lys Arg Val Trp Gly Asp Trp Glu Glu Asp
            100                 105                 110
```

Gly Phe Gly Thr Asp Pro Ile Glu Lys Glu Asn Ile Met Tyr Lys Gly
        115                 120                 125

His Leu Asn Leu Met Tyr Gly Leu Tyr Gln Leu Val Thr Gly Ser Arg
    130                 135                 140

Arg Tyr Glu Ala Glu His Ala His Leu Thr Arg Ile Ile His Asp Glu
145                 150                 155                 160

Ile Ala Ala Asn Pro Phe Ala Gly Ile Val Cys Glu Pro Asp Asn Tyr
                165                 170                 175

Phe Val Gln Cys Asn Ser Val Ala Tyr Leu Ser Leu Trp Val Tyr Asp
            180                 185                 190

Arg Leu His Gly Thr Asp Tyr Arg Ala Ala Thr Arg Ala Trp Leu Asp
        195                 200                 205

Phe Ile Gln Lys Asp Leu Ile Asp Pro Glu Arg Gly Ala Phe Tyr Leu
    210                 215                 220

Ser Tyr His Pro Glu Ser Gly Ala Val Lys Pro Trp Ile Ser Ala Tyr
225                 230                 235                 240

Thr Thr Ala Trp Thr Leu Ala Met Val His Gly Met Asp Pro Ala Phe
                245                 250                 255

Ser Glu Arg Tyr Tyr Pro Arg Phe Lys Gln Thr Phe Val Glu Val Tyr
            260                 265                 270

Asp Glu Gly Arg Lys Ala Arg Val Arg Glu Thr Ala Gly Thr Asp Asp
        275                 280                 285

Ala Asp Gly Gly Val Gly Leu Ala Ser Ala Phe Thr Leu Leu Leu Ala
    290                 295                 300

Arg Glu Met Gly Asp Gln Gln Leu Phe Asp Gln Leu Leu Asn His Leu
305                 310                 315                 320

Glu Pro Pro Ala Lys Pro Ser Ile Val Ser Ala Ser Leu Arg Tyr Glu
                325                 330                 335

His Pro Gly Ser Leu Leu Phe Asp Glu Leu Leu Phe Leu Ala Lys Val
            340                 345                 350

His Ala Gly Phe Gly Ala Leu Leu Arg Met Pro Pro Ala Ala Lys
        355                 360                 365

Leu Ala Gly Lys Gly Ser Leu Glu His His His His His His
    370                 375                 380

<210> SEQ ID NO 67
<211> LENGTH: 397
<212> TYPE: PRT
<213> ORGANISM: Castellaniella defragans

<400> SEQUENCE: 67

Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala

```
              100                 105                 110
Leu Ala Gly His Asp Leu Asp Ile Ala Val Ser Lys Met Lys Cys Lys
            115                 120                 125

Arg Val Trp Gly Asp Trp Glu Glu Asp Gly Phe Gly Thr Asp Pro Ile
130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
        195                 200                 205

Ala Tyr Leu Ser Leu Trp Val Tyr Asp Arg Leu His Gly Thr Asp Tyr
    210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
        275                 280                 285

Phe Lys Gln Thr Phe Val Glu Val Tyr Asp Glu Gly Arg Lys Ala Arg
    290                 295                 300

Val Arg Glu Thr Ala Gly Thr Asp Asp Ala Asp Gly Val Gly Leu
305                 310                 315                 320

Ala Ser Ala Phe Thr Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Gly Ser Leu Leu Phe
        355                 360                 365

Asp Glu Leu Leu Phe Leu Ala Lys Val His Ala Gly Phe Gly Ala Leu
    370                 375                 380

Leu Arg Met Pro Pro Pro Ala Lys Leu Ala Gly Lys
385                 390                 395

<210> SEQ ID NO 68
<211> LENGTH: 376
<212> TYPE: PRT
<213> ORGANISM: artificial
<220> FEATURE:
<223> OTHER INFORMATION: synthetic linalool dehydratase-isomerase

<400> SEQUENCE: 68

Met Ala Glu Leu Pro Pro Gly Arg Leu Ala Thr Thr Glu Asp Tyr Phe
1               5                   10                  15

Ala Gln Gln Ala Lys Gln Ala Val Thr Pro Asp Val Met Ala Gln Leu
            20                  25                  30

Ala Tyr Met Asn Tyr Ile Asp Phe Ile Ser Pro Phe Tyr Ser Arg Gly
        35                  40                  45

Cys Ser Phe Glu Ala Trp Glu Leu Lys His Thr Pro Gln Arg Val Ile
    50                  55                  60

Lys Tyr Ser Ile Ala Phe Tyr Ala Tyr Gly Leu Ala Ser Val Ala Leu
```

```
                65                  70                  75                  80
Ile Asp Pro Lys Leu Arg Ala Leu Ala Gly His Asp Leu Asp Ile Ala
                    85                  90                  95
Val Ser Lys Met Lys Cys Lys Arg Val Trp Gly Asp Trp Glu Glu Asp
                   100                 105                 110
Gly Phe Gly Thr Asp Pro Ile Glu Lys Glu Asn Ile Met Tyr Lys Gly
                   115                 120                 125
His Leu Asn Leu Met Tyr Gly Leu Tyr Gln Leu Val Thr Gly Ser Arg
            130                 135                 140
Arg Tyr Glu Ala Glu His Ala His Leu Thr Arg Ile Ile His Asp Glu
145                 150                 155                 160
Ile Ala Ala Asn Pro Phe Ala Gly Ile Val Cys Glu Pro Asp Asn Tyr
                        165                 170                 175
Phe Val Gln Cys Asn Ser Val Ala Tyr Leu Ser Leu Trp Val Tyr Asp
                    180                 185                 190
Arg Leu His Gly Thr Asp Tyr Arg Ala Ala Thr Arg Ala Trp Leu Asp
                    195                 200                 205
Phe Ile Gln Lys Asp Leu Ile Asp Pro Glu Arg Gly Ala Phe Tyr Leu
            210                 215                 220
Ser Tyr His Pro Glu Ser Gly Ala Val Lys Pro Trp Ile Ser Ala Tyr
225                 230                 235                 240
Thr Thr Ala Trp Thr Leu Ala Met Val His Gly Met Asp Pro Ala Phe
                        245                 250                 255
Ser Glu Arg Tyr Tyr Pro Arg Phe Lys Gln Thr Phe Val Glu Val Tyr
                    260                 265                 270
Asp Glu Gly Arg Lys Ala Arg Val Arg Glu Thr Ala Gly Thr Asp Asp
                    275                 280                 285
Ala Asp Gly Gly Val Gly Leu Ala Ser Ala Phe Thr Leu Leu Leu Ala
            290                 295                 300
Arg Glu Met Gly Asp Gln Gln Leu Phe Asp Gln Leu Leu Asn His Leu
305                 310                 315                 320
Glu Pro Pro Ala Lys Pro Ser Ile Val Ser Ala Ser Leu Arg Tyr Glu
                        325                 330                 335
His Pro Gly Ser Leu Leu Phe Asp Glu Leu Leu Phe Leu Ala Lys Val
                    340                 345                 350
His Ala Gly Phe Gly Ala Leu Leu Arg Met Pro Pro Ala Ala Lys
                    355                 360                 365
Leu Ala Gly Lys Gly Ser Leu Glu
            370                 375

<210> SEQ ID NO 69
<211> LENGTH: 873
<212> TYPE: DNA
<213> ORGANISM: Pseudomonas cichorii

<400> SEQUENCE: 69
gtgaacaaag ttggcatgtt ctacacctac tggtcgactg agtggatggt cgactttccg     60
gcgactgcga agcgcattgc cgggctcggc ttcgacttaa tggaaatctc gctcggcgag    120
tttcacaatc tttccgacgc gaagaagcgt gagctaaaag ccgtggctga tgatctgggg    180
ctcacggtga tgtgctgtat cggactgaag tctgagtacg actttgcctc gccggacaag    240
agcgttcgtg atgccggcac ggaatatgtg aagcgcttgc tcgacgactg tcacctcctc    300
ggcgcgccgg tctttgctgg ccttacgttc tgcgcgtggc cccaatctcc gccgctggac    360
```

-continued

```
atgaaggata agcgccctta cgtcgaccgt gcaatcgaaa gcgttcgtcg tgttatcaag    420
gtagctgaag actacggcat tatttatgca ctggaagtgg tgaaccgatt cgagcagtgg    480
ctttgcaatg acgccaagga agcaattgcg tttgccgacg cggttgacag tccggcgtgc    540
aaggtccagc tcgacacatt ccacatgaat atcgaagaga cttccttccg cgatgcaatc    600
cttgcctgca agggcaagat gggccatttc catttgggcg aagcgaaccg tctgccgccg    660
ggcgagggtc gcctgccgtg ggatgaaata ttcgggcgc tgaaggaaat cggatatgac     720
ggcaccatcg ttatggaacc gttcatgcgc aagggcggct cggtcagccg cgcggtgggc    780
gtatggcggg atatgtcgaa cggtgcgacg gacgaagaga tggacgagcg cgctcgccgc    840
tcgttgcagt ttgttcgtga caagctggcc tga                                 873
```

<210> SEQ ID NO 70
<211> LENGTH: 873
<212> TYPE: DNA
<213> ORGANISM: Pseudomonas cichorii

<400> SEQUENCE: 70

```
atgaacaaag tgggtatgtt ctatacgtac tggtccacgg aatggatggt tgactttccg     60
gcaaccgcga aacgtattgc gggcctgggc ttcgacctga tggaaatttc tctgggcgaa   120
tttcacaacc tgtccgatgc gaaaaagcgt gaactgaaag ccgttgccga cgatctgggt   180
ctgactgtga tgtgctgtat cggcctgaaa tctgaatacg atttcgcgag cccggataaa   240
agcgttcgcg acgccggtac tgaatatgtc aaacgtctgc tggatgactg tcacctgctg   300
ggcgcaccag tgttcgcggg tctgaccttc tgtgcgtggc cgcagtcccc accgctggac   360
atgaaggata aacgtccgta cgtggaccgt gccatcgaaa gcgtgcgccg cgtaatcaaa   420
gtcgctgaag attatggcat tatttacgct ctggaagttg ttaaccgttt cgaacagtgg   480
ctgtgcaacg acgcgaaaga ggccattgcc ttcgctgacg cggtggattc tccggcttgc   540
aaagttcagc tggacacttt ccatatgaac atcgaggaaa cctccttccg tgacgcgatc   600
ctggcttgca gggtaaaat gggccatttc catctgggcg aagcaaaccg cctgccgccg   660
ggcgaaggtc gtctgccgtg ggacgaaatt tttggcgctc tgaaggaaat cggctacgat   720
ggcacgattg ttatggagcc gttcatgcgc aaaggtggct ccgtttcccg tgcagttggt   780
gtttggcgtg atatgtctaa cggtgccacc gatgaagaaa tggacgaacg tgcacgtcgc   840
tccctgcaat tcgttcgcga taaactggcg taa                                 873
```

<210> SEQ ID NO 71
<211> LENGTH: 290
<212> TYPE: PRT
<213> ORGANISM: Pseudomonas cichorii

<400> SEQUENCE: 71

Met Asn Lys Val Gly Met Phe Tyr Thr Tyr Trp Ser Thr Glu Trp Met
1               5                   10                  15

Val Asp Phe Pro Ala Thr Ala Lys Arg Ile Ala Gly Leu Gly Phe Asp
            20                  25                  30

Leu Met Glu Ile Ser Leu Gly Glu Phe His Asn Leu Ser Asp Ala Lys
        35                  40                  45

Lys Arg Glu Leu Lys Ala Val Ala Asp Asp Leu Gly Leu Thr Val Met
    50                  55                  60

Cys Cys Ile Gly Leu Lys Ser Glu Tyr Asp Phe Ala Ser Pro Asp Lys
65                  70                  75                  80

```
Ser Val Arg Asp Ala Gly Thr Glu Tyr Val Lys Arg Leu Leu Asp
                85                  90                  95

Cys His Leu Leu Gly Ala Pro Val Phe Ala Gly Leu Thr Phe Cys Ala
            100                 105                 110

Trp Pro Gln Ser Pro Pro Leu Asp Met Lys Asp Lys Arg Pro Tyr Val
        115                 120                 125

Asp Arg Ala Ile Glu Ser Val Arg Arg Val Ile Lys Val Ala Glu Asp
    130                 135                 140

Tyr Gly Ile Ile Tyr Ala Leu Glu Val Val Asn Arg Phe Glu Gln Trp
145                 150                 155                 160

Leu Cys Asn Asp Ala Lys Glu Ala Ile Ala Phe Ala Asp Ala Val Asp
                165                 170                 175

Ser Pro Ala Cys Lys Val Gln Leu Asp Thr Phe His Met Asn Ile Glu
            180                 185                 190

Glu Thr Ser Phe Arg Asp Ala Ile Leu Ala Cys Lys Gly Lys Met Gly
        195                 200                 205

His Phe His Leu Gly Glu Ala Asn Arg Leu Pro Gly Glu Gly Arg
    210                 215                 220

Leu Pro Trp Asp Glu Ile Phe Gly Ala Leu Lys Glu Ile Gly Tyr Asp
225                 230                 235                 240

Gly Thr Ile Val Met Glu Pro Phe Met Arg Lys Gly Gly Ser Val Ser
                245                 250                 255

Arg Ala Val Gly Val Trp Arg Asp Met Ser Asn Gly Ala Thr Asp Glu
            260                 265                 270

Glu Met Asp Glu Arg Ala Arg Arg Ser Leu Gln Phe Val Arg Asp Lys
        275                 280                 285

Leu Ala
    290

<210> SEQ ID NO 72
<211> LENGTH: 888
<212> TYPE: DNA
<213> ORGANISM: Rhodobacter sphaeroides

<400> SEQUENCE: 72
gtgaaaaatc ctgtcggcat catctcgatg cagttcatcc ggcccttcac ctcggagtcg     60
ctgcatttcc tgaagaagtc ccgggccctg ggcttcgatt tcatcgagct tctcgtgccc    120
gagcccgaag acgggctcga cgcggccgag gtgcggcgca tctgcgaggg cgagggggctg    180 ggcctcgttc tggccgcgcg cgtgaacctc cagcgctcga tcgcgagcga ggaggccgcg    240
gcgcgggccg gcgggcgcga ctatctgaaa tactgcatcg aggccgccga ggcgctcggc    300
gcgaccatcg tcggcggccc gctctatggc gagccgctgg tcttcgccgg ccgcccgccc    360
ttcccctgga cggccgagca gatcgccacc cgcgccgccc gcaccgtcga ggggctggcc    420
gaagtggccc cgctcgccgc gagcgcgggc aaggtcttcg gctcgagcc gctgaaccgc    480 ttcgagaccg acatcgtgaa cacgaccgca caggccatca aggtggtgga tcgcgtgggc    540
tcgcccggtc tcggcgtcat gctcgacacg ttccacatga acatggagga acgctcgatc    600
cccgatgcga tccgcgccac aggcgcgcgc tcgtccatt ttcaggccaa cgagaaccac    660
cgcggcttcc ccggcaccgg caccatggac tggacggcca tcgcgcgggc gctggggcag    720
gcgggctacg cgggtccggt ctcgctcgag cctttccggc gcgacgacga gcgcgtggcg    780
ctgcccatcg cccactggcg cgccccgcac gaggacgagg acgagaagct gcgcgcgggg    840
ctgggtctca tccgctccgc gatcaccctg gcggaggtga cccactga                 888
```

<210> SEQ ID NO 73
<211> LENGTH: 295
<212> TYPE: PRT
<213> ORGANISM: Rhodobacter sphaeroides

<400> SEQUENCE: 73

Met Lys Asn Pro Val Gly Ile Ile Ser Met Gln Phe Ile Arg Pro Phe
1               5                   10                  15

Thr Ser Glu Ser Leu His Phe Leu Lys Lys Ser Arg Ala Leu Gly Phe
            20                  25                  30

Asp Phe Ile Glu Leu Leu Val Pro Glu Pro Glu Asp Gly Leu Asp Ala
        35                  40                  45

Ala Glu Val Arg Arg Ile Cys Glu Gly Glu Gly Leu Gly Leu Val Leu
50                  55                  60

Ala Ala Arg Val Asn Leu Gln Arg Ser Ile Ala Ser Glu Glu Ala Ala
65                  70                  75                  80

Ala Arg Ala Gly Gly Arg Asp Tyr Leu Lys Tyr Cys Ile Glu Ala Ala
                85                  90                  95

Glu Ala Leu Gly Ala Thr Ile Val Gly Gly Pro Leu Tyr Gly Glu Pro
            100                 105                 110

Leu Val Phe Ala Gly Arg Pro Pro Phe Pro Trp Thr Ala Glu Gln Ile
        115                 120                 125

Ala Thr Arg Ala Ala Arg Thr Val Glu Gly Leu Ala Glu Val Ala Pro
130                 135                 140

Leu Ala Ala Ser Ala Gly Lys Val Phe Gly Leu Glu Pro Leu Asn Arg
145                 150                 155                 160

Phe Glu Thr Asp Ile Val Asn Thr Thr Ala Gln Ala Ile Glu Val Val
                165                 170                 175

Asp Ala Val Gly Ser Pro Gly Leu Gly Val Met Leu Asp Thr Phe His
            180                 185                 190

Met Asn Met Glu Glu Arg Ser Ile Pro Asp Ala Ile Arg Ala Thr Gly
        195                 200                 205

Ala Arg Leu Val His Phe Gln Ala Asn Glu Asn His Arg Gly Phe Pro
210                 215                 220

Gly Thr Gly Thr Met Asp Trp Thr Ala Ile Ala Arg Ala Leu Gly Gln
225                 230                 235                 240

Ala Gly Tyr Ala Gly Pro Val Ser Leu Glu Pro Phe Arg Arg Asp Asp
                245                 250                 255

Glu Arg Val Ala Leu Pro Ile Ala His Trp Arg Ala Pro His Glu Asp
            260                 265                 270

Glu Asp Glu Lys Leu Arg Ala Gly Leu Gly Leu Ile Arg Ser Ala Ile
        275                 280                 285

Thr Leu Ala Glu Val Thr His
290                 295

<210> SEQ ID NO 74
<211> LENGTH: 1422
<212> TYPE: DNA
<213> ORGANISM: Escherichia coli

<400> SEQUENCE: 74
atgatgaaac aagaagttat cctggtactc gactgtggcg cgaccaatgt cagggccatc       60
gcggttaatc ggcagggcaa aattgttgcc cgcgcctcaa cgcctaatgc cagcgatatc      120
gcgatggaaa acaacaccct gcaccagtgg tctttagacg ccatttttgca acgctttgct    180

```
gattgctgtc ggcaaatcaa tagtgaactg actgaatgcc acatccgcgg tatcgccgtc      240
accacctttg gtgtggatgg cgctctggta gataagcaag gcaatctgct ctatccgatt      300
attagctgga aatgtccgcg aacagcagcg gttatggaca atattgaacg gttaatctcc      360
gcacagcggt tgcaggctat ttctggcgtc ggagccttta gtttcaatac gttatataag      420
ttggtgtggt tgaaagaaaa tcatccacaa ctgctggaac gcgcgcacgc ctggctcttt      480
atttcgtcgc tgattaacca ccgtttaacc ggcgaattca ctactgatat cacgatggcc      540
ggaaccagcc agatgctgga tatccagcaa cgcgatttca gtccgcaaat tttacaagcc      600
accggtattc cacgccgact cttccctcgt ctggtggaag cgggtgaaca gattggtacg      660
ctacagaaca gcgccgcagc aatgctcggc ttacccgttg gcataccggt gatttccgca      720
ggtcacgata cccagttcgc cctttttggc gctggtgctg aacaaaatga acccgtgctc      780
tcttccggta catgggaaat tttaatggtt cgcagcgccc aggttgatac ttcgctgtta      840
agtcagtacg ccggttccac ctgcgaactg gatagccagg cagggttgta tacccaggt      900 atgcaatggc tggcatccgg cgtgctggaa tgggtgagaa aactgttctg gacggctgaa      960
acaccctggc aaatgttgat tgaagaagct cgtctgatcg cgcctggcgc ggatggcgta     1020
aaaatgcagt gtgatttatt gtcgtgtcag aacgctggct ggcaaggagt gacgcttaat     1080
accacgcggg ggcatttcta tcgcgcggcg ctggaagggt taactgcgca attacagcgc     1140
aatctacaga tgctggaaaa aatcgggcac tttaaggcct ctgaattatt gttagtcggt     1200
ggaggaagtc gcaacacatt gtggaatcag attaaagcca atatgcttga tattccggta     1260
aaagttctcg acgacgccga aacgaccgtc gcaggagctg cgctgttcgg ttggtatggc     1320
gtaggggaat ttaacagccc ggaagaagcc cgcgcacaga ttcattatca gtaccgttat     1380
ttctacccgc aaactgaacc tgaatttata gaggaagtgt ga                       1422
```

<210> SEQ ID NO 75
<211> LENGTH: 1422
<212> TYPE: DNA
<213> ORGANISM: Escherichia coliv

<400> SEQUENCE: 75

```
atgatgaaac aagaagttat cctggtactc gactgtggcg cgaccaatgt cagggccatc       60
gcggttaatc ggcagggcaa aattgttgcc cgcgcctcaa cgcctaatgc cagcgatatc      120
gcgatggaaa acaacacctg gcaccagtgg tctttagacg ccattttgca acgctttgct      180
gattgctgtc ggcaaatcaa tagtgaactg actgaatgcc acatccgcgg tatcgccgtc      240
accacctttg gtgtggatgg cgctctggta gataagcaag gcaatctgct ctatccgatt      300
attagctgga aatgtccgcg aacagcagcg gttatggaca atattgaacg gttaatctcc      360
gcacagcggt tgcaggctat ttctggcgtc ggagccttta gtttcaatac gttatataag      420
ttggtgtggt tgaaagaaaa tcatccacaa ctgctggaac gcgcgcacgc ctggctcttt      480
atttcgtcgc tgattaacca ccgtttaacc ggcgaattca ctactgatat cacgatggcc      540
ggaaccagcc agatgctgga tatccagcaa cgcgatttca gtccgcaaat tttacaagcc      600
accggtattc cacgccgact cttccctcgt ctggtggaag cgggtgaaca gattggtacg      660
ctacagaaca gcgccgcagc aatgctcggc ttacccgttg gcataccggt gatttccgca      720
ggtcacgata cccagttcgc cctttttggc gctggtgctg aacaaaatga acccgtgctc      780
tcttccggta catgggaaat tttaatggtt cgcagcgccc aggttgatac ttcgctgtta      840
```

```
agtcagtacg ccggttccac ctgcgaactg gatagccagg cagggttgta taacccaggt      900
atgcaatggc tggcatccgg cgtgctggaa tgggtgagaa aactgttctg gacggctgaa      960
acaccctggc aaatgttgat tgaagaagct cgtctgatcg cgcctggcgc ggatggcgta     1020
aaaatgcagt gtgatttatt gtcgtgtcag aacgctggct ggcaaggagt gacgcttaat     1080
accacgcggg ggcatttcta tcgcgcggcg ctggaagggt taactgcgca attacagcgc     1140
aatctacaga tgctggaaaa aatcgggcac tttaaggcct ctgaattatt gttagtcggt     1200
ggaggaagtc gcaacacatt gtggaatcag attaaagcca atatgcttga tattccggta     1260
aaagttctcg acgacgccga aacgaccgtc gcaggagctg cgctgttcgg ttggtatggc     1320
gtaggggaat taacagcccc ggaagaagcc cgcgcacaga ttcattatca gtaccgttat     1380
ttctacccgc aaactgaacc tgaatttata gaggaagtgt ga                        1422
```

<210> SEQ ID NO 76
<211> LENGTH: 473
<212> TYPE: PRT
<213> ORGANISM: Escherichia coli

<400> SEQUENCE: 76

| | | | | | | | | | | | | | | |
|---|---|---|---|---|---|---|---|---|---|---|---|---|---|---|
| Met | Met | Lys | Gln | Glu | Val | Ile | Leu | Val | Leu | Asp | Cys | Gly | Ala | Thr | Asn |
| 1 | | | | 5 | | | | | 10 | | | | | 15 | |
| Val | Arg | Ala | Ile | Ala | Val | Asn | Arg | Gln | Gly | Lys | Ile | Val | Ala | Arg | Ala |
| | | | 20 | | | | | 25 | | | | | 30 | | |
| Ser | Thr | Pro | Asn | Ala | Ser | Asp | Ile | Ala | Met | Glu | Asn | Asn | Thr | Trp | His |
| | | 35 | | | | | 40 | | | | | 45 | | | |
| Gln | Trp | Ser | Leu | Asp | Ala | Ile | Leu | Gln | Arg | Phe | Ala | Asp | Cys | Cys | Arg |
| | 50 | | | | | 55 | | | | | 60 | | | | |
| Gln | Ile | Asn | Ser | Glu | Leu | Thr | Glu | Cys | His | Ile | Arg | Gly | Ile | Ala | Val |
| 65 | | | | | 70 | | | | | 75 | | | | | 80 |
| Thr | Thr | Phe | Gly | Val | Asp | Gly | Ala | Leu | Val | Asp | Lys | Gln | Gly | Asn | Leu |
| | | | | 85 | | | | | 90 | | | | | 95 | |
| Leu | Tyr | Pro | Ile | Ile | Ser | Trp | Lys | Cys | Pro | Arg | Thr | Ala | Ala | Val | Met |
| | | | 100 | | | | | 105 | | | | | 110 | | |
| Asp | Asn | Ile | Glu | Arg | Leu | Ile | Ser | Ala | Gln | Arg | Leu | Gln | Ala | Ile | Ser |
| | | | 115 | | | | | 120 | | | | | 125 | | |
| Gly | Val | Gly | Ala | Phe | Ser | Phe | Asn | Thr | Leu | Tyr | Lys | Leu | Val | Trp | Leu |
| | 130 | | | | | 135 | | | | | 140 | | | | |
| Lys | Glu | Asn | His | Pro | Gln | Leu | Leu | Glu | Arg | Ala | His | Ala | Trp | Leu | Phe |
| 145 | | | | | 150 | | | | | 155 | | | | | 160 |
| Ile | Ser | Ser | Leu | Ile | Asn | His | Arg | Leu | Thr | Gly | Glu | Phe | Thr | Thr | Asp |
| | | | | 165 | | | | | 170 | | | | | 175 | |
| Ile | Thr | Met | Ala | Gly | Thr | Ser | Gln | Met | Leu | Asp | Ile | Gln | Gln | Arg | Asp |
| | | | 180 | | | | | 185 | | | | | 190 | | |
| Phe | Ser | Pro | Gln | Ile | Leu | Gln | Ala | Thr | Gly | Ile | Pro | Arg | Arg | Leu | Phe |
| | | 195 | | | | | 200 | | | | | 205 | | | |
| Pro | Arg | Leu | Val | Glu | Ala | Gly | Glu | Gln | Ile | Gly | Thr | Leu | Gln | Asn | Ser |
| | 210 | | | | | 215 | | | | | 220 | | | | |
| Ala | Ala | Ala | Met | Leu | Gly | Leu | Pro | Val | Gly | Ile | Pro | Val | Ile | Ser | Ala |
| 225 | | | | | 230 | | | | | 235 | | | | | 240 |
| Gly | His | Asp | Thr | Gln | Phe | Ala | Leu | Phe | Gly | Ala | Gly | Ala | Glu | Gln | Asn |
| | | | | 245 | | | | | 250 | | | | | 255 | |
| Glu | Pro | Val | Leu | Ser | Ser | Gly | Thr | Trp | Glu | Ile | Leu | Met | Val | Arg | Ser |
| | | | 260 | | | | | 265 | | | | | 270 | | |

Ala Gln Val Asp Thr Ser Leu Leu Ser Gln Tyr Ala Gly Ser Thr Cys
            275                 280                 285

Glu Leu Asp Ser Gln Ala Gly Leu Tyr Asn Pro Gly Met Gln Trp Leu
    290                 295                 300

Ala Ser Gly Val Leu Glu Trp Val Arg Lys Leu Phe Trp Thr Ala Glu
305                 310                 315                 320

Thr Pro Trp Gln Met Leu Ile Glu Glu Ala Arg Leu Ile Ala Pro Gly
                325                 330                 335

Ala Asp Gly Val Lys Met Gln Cys Asp Leu Leu Ser Cys Gln Asn Ala
            340                 345                 350

Gly Trp Gln Gly Val Thr Leu Asn Thr Thr Arg Gly His Phe Tyr Arg
        355                 360                 365

Ala Ala Leu Glu Gly Leu Thr Ala Gln Leu Gln Arg Asn Leu Gln Met
370                 375                 380

Leu Glu Lys Ile Gly His Phe Lys Ala Ser Glu Leu Leu Leu Val Gly
385                 390                 395                 400

Gly Gly Ser Arg Asn Thr Leu Trp Asn Gln Ile Lys Ala Asn Met Leu
                405                 410                 415

Asp Ile Pro Val Lys Val Leu Asp Asp Ala Glu Thr Thr Val Ala Gly
            420                 425                 430

Ala Ala Leu Phe Gly Trp Tyr Gly Val Gly Glu Phe Asn Ser Pro Glu
        435                 440                 445

Glu Ala Arg Ala Gln Ile His Tyr Gln Tyr Arg Tyr Phe Tyr Pro Gln
    450                 455                 460

Thr Glu Pro Glu Phe Ile Glu Glu Val
465                 470

<210> SEQ ID NO 77
<211> LENGTH: 648
<212> TYPE: DNA
<213> ORGANISM: Escherichia coli

<400> SEQUENCE: 77
atggaacgaa ataaacttgc tcgtcagatt attgacactt gcctggaaat gacccgcctg      60
ggactgaacc aggggacagc ggggaacgtc agtgtacgtt atcaggatgg gatgctgatt     120
acgcctacag gcattccata tgaaaaactg acggagtcgc atattgtctt tattgatggc     180
aacggtaaac atgaggaagg aaagctcccc tcaagcgaat ggcgtttcca tatggcagcc     240
tatcaaagca gaccggatgc caacgcggtt gttcacaatc atgccgttca ttgcacggca     300
gtttccattc ttaaccgatc gatccccgct attcactaca tgattgcggc ggctggcggt     360
aattctattc cttgcgcgcc ttatgcgacc tttggaacac gcgaactttc tgaacatgtt     420
gcgctggctc tcaaaaatcg taaggcaact tgttacaac atcatgggct atcgcttgt      480 gaggtgaatc tggaaaaagc gttatggctg gcgcatgaag ttgaagtgct ggcgcaactt     540
tacctgacga ccctggcgat tacgacccg tgccagtgc tgagcgatga agagattgcc      600
gtagtgctgg agaaattcaa aacctatggg ttacgaattg aagagtaa                 648

<210> SEQ ID NO 78
<211> LENGTH: 648
<212> TYPE: DNA
<213> ORGANISM: Escherichia coli

<400> SEQUENCE: 78
atggaacgaa ataaacttgc tcgtcagatt attgacactt gcctggaaat gacccgcctg      60

```
ggactgaacc agggggacagc ggggaacgtc agtgtacgtt atcaggatgg gatgctgatt    120
acgcctacag gcattccata tgaaaaactg acggagtcgc atattgtctt tattgatggc    180
aacggtaaac atgaggaagg aaagctcccc tcaagcgaat ggcgtttcca tatggcagcc    240
tatcaaagca gaccggatgc caacgcggtt gttcacaatc atgccgttca ttgcacggca    300
gtttccattc ttaaccgatc gatccccgct attcactaca tgattgcggc ggctggcggt    360
aattctattc cttgcgcgcc ttatgcgacc tttggaacac gcgaactttc tgaacatgtt    420
gcgctggctc tcaaaaatcg taaggcaact ttgttacaac atcatgggct tatcgcttgt    480
gaggtgaatc tggaaaaagc gttatggctg gcgcatgaag ttgaagtgct ggcgcaactt    540
tacctgacga ccctggcgat tacggacccg gtgccagtgc tgagcgatga agagattgcc    600
gtagtgctgg agaaattcaa aacctatggg ttacgaattg aagagtaa               648
```

```
<210> SEQ ID NO 79
<211> LENGTH: 215
<212> TYPE: PRT
<213> ORGANISM: Escherichia coli

<400> SEQUENCE: 79

Met Glu Arg Asn Lys Leu Ala Arg Gln Ile Ile Asp Thr Cys Leu Glu
1               5                   10                  15
Met Thr Arg Leu Gly Leu Asn Gln Gly Thr Ala Gly Asn Val Ser Val
            20                  25                  30
Arg Tyr Gln Asp Gly Met Leu Ile Thr Pro Thr Gly Ile Pro Tyr Glu
        35                  40                  45
Lys Leu Thr Glu Ser His Ile Val Phe Ile Asp Gly Asn Gly Lys His
    50                  55                  60
Glu Glu Gly Lys Leu Pro Ser Ser Glu Trp Arg Phe His Met Ala Ala
65                  70                  75                  80
Tyr Gln Ser Arg Pro Asp Ala Asn Ala Val Val His Asn His Ala Val
                85                  90                  95
His Cys Thr Ala Val Ser Ile Leu Asn Arg Ser Ile Pro Ala Ile His
            100                 105                 110
Tyr Met Ile Ala Ala Ala Gly Gly Asn Ser Ile Pro Cys Ala Pro Tyr
        115                 120                 125
Ala Thr Phe Gly Thr Arg Glu Leu Ser Glu His Val Ala Leu Ala Leu
    130                 135                 140
Lys Asn Arg Lys Ala Thr Leu Leu Gln His His Gly Leu Ile Ala Cys
145                 150                 155                 160
Glu Val Asn Leu Glu Lys Ala Leu Trp Leu Ala His Glu Val Glu Val
                165                 170                 175
Leu Ala Gln Leu Tyr Leu Thr Thr Leu Ala Ile Thr Asp Pro Val Pro
            180                 185                 190
Val Leu Ser Asp Glu Glu Ile Ala Val Val Leu Glu Lys Phe Lys Thr
        195                 200                 205
Tyr Gly Leu Arg Ile Glu Glu
    210                 215

<210> SEQ ID NO 80
<211> LENGTH: 1104
<212> TYPE: DNA
<213> ORGANISM: Escherichia coli

<400> SEQUENCE: 80
atggaccgca ttattcaatc accgggtaaa tacatccagg gcgctgatgt gattaatcgt    60
```

```
ctgggcgaat acctgaagcc gctggcagaa cgctggttag tggtgggtga caaatttgtt    120
ttaggttttg ctcaatccac tgtcgagaaa agctttaaag atgctggact ggtagtagaa    180
attgcgccgt ttggcggtga atgttcgcaa aatgagatcg accgtctgcg tggcatcgcg    240
gagactgcgc agtgtggcgc aattctcggt atcggtggcg gaaaaaccct cgatactgcc    300
aaagcactgg cacatttcat gggtgttccg gtagcgatcg caccgactat cgcctctacc    360
gatgcaccgt gcagcgcatt gtctgttatc tacaccgatg agggtgagtt tgaccgctat    420
ctgctgttgc caaataaccc gaatatggtc attgtcgaca ccaaaatcgt cgctggcgca    480
cctgcacgtc tgttagcggc gggtatcggc gatgcgctgg caacctggtt tgaagcgcgt    540
gcctgctctc gtagcggcgc gaccaccatg gcgggcggca agtgcaccca ggctgcgctg    600
gcactggctg aactgtgcta acaccctg ctggaagaag gcgaaaaagc gatgcttgct    660
gccgaacagc atgtagtgac tccggcgctg agcgcgtga ttgaagcgaa cacctatttg    720
agcggtgttg gttttgaaag tggtggtctg gctgcggcgc acgcagtgca taacggcctg    780
accgctatcc cggacgcgca tcactattat cacggtgaaa aagtggcatt cggtacgctg    840
acgcagctgt ttctggaaaa tgcgccggtg gaggaaatcg aaaccgtagc tgcccttagc    900
catgcggtag gtttgccaat aactctcgct caactggata ttaaagaaga tgtcccggcg    960
aaaatgcgaa ttgtggcaga agcggcatgt gcagaaggtg aaaccattca caacatgcct   1020
ggcggcgcga cgccagatca ggtttacgcc gctctgctgg tagccgacca gtacggtcag   1080
cgtttcctgc aagagtggga ataa                                          1104

<210> SEQ ID NO 81
<211> LENGTH: 367
<212> TYPE: PRT
<213> ORGANISM: Escherichia coli

<400> SEQUENCE: 81

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
```

```
                    180                 185                 190
Gly Lys Cys Thr Gln Ala Ala Leu Ala Leu Ala Glu Leu Cys Tyr Asn
            195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
                290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 82
<211> LENGTH: 1029
<212> TYPE: DNA
<213> ORGANISM: Saccharomyces cerevisiae

<400> SEQUENCE: 82
atgtcagttt tcgtttcagg tgctaacggg ttcattgccc aacacattgt cgatctcctg      60
ttgaaggaag actataaggt catcggttct gccagaagtc aagaaaaggc cgagaattta     120
acggaggcct ttggtaacaa cccaaaattc tccatggaag ttgtcccaga catatctaag     180
ctggacgcat ttgaccatgt tttccaaaag cacggcaagg atatcaagat agttctacat     240
acggcctctc cattctgctt tgatatcact gacagtgaac gcgatttatt aattcctgct     300
gtgaacggtg ttaagggaat tctccactca attaaaaaat acgccgctga ttctgtagaa     360
cgtgtagttc tcacctcttc ttatgcagct gtgttcgata tggcaaaaga aaacgataag     420
tctttaacat ttaacgaaga atcctggaac ccagctacct gggagagttg ccaaagtgac     480
ccagttaacg cctactgtgg ttctaagaag tttgctgaaa agcagcttgg gaatttcta     540 gaggagaata gagactctgt aaaattcgaa ttaactgccg ttaacccagt ttacgttttt     600
ggtccgcaaa tgtttgacaa agatgtgaaa aaacacttga acacatcttg cgaactcgtc     660
aacagcttga tgcatttatc accagaggac aagataccgg aactatttgg tggatacatt     720
gatgttcgtg atgttgcaaa ggctcattta gttgccttcc aaaagaggga acaattggt     780 caaagactaa tcgtatcgga ggccagattt actatgcagg atgttctcga tatccttaac     840
gaagacttcc ctgttctaaa aggcaatatt ccagtgggga aaccaggttc tggtgctacc     900
cataacaccc ttggtgctac tcttgataat aaaaagagta agaaattgtt aggtttcaag     960
ttcaggaact tgaaagagac cattgacgac actgcctccc aaattttaaa atttgagggc    1020
agaatataa                                                            1029
```

<210> SEQ ID NO 83
<211> LENGTH: 342
<212> TYPE: PRT
<213> ORGANISM: Saccharomyces cerevisiae

<400> SEQUENCE: 83

Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340

<210> SEQ ID NO 84
<211> LENGTH: 984
<212> TYPE: DNA
<213> ORGANISM: Saccharomyces cerevisiae

<400> SEQUENCE: 84

```
atgtcttcac tggttactct taataacggt ctgaaaatgc ccctagtcgg cttagggtgc    60
tggaaaattg acaaaaaagt ctgtgcgaat caaatttatg aagctatcaa attaggctac   120
cgtttattcg atggtgcttg cgactacggc aacgaaaagg aagttggtga aggtatcagg   180
aaagccatct ccgaaggtct tgtttctaga aggatatat ttgttgtttc aaagttatgg    240
aacaattttc accatcctga tcatgtaaaa ttagctttaa agaagacctt aagcgatatg   300
ggacttgatt atttagacct gtattatatt cacttcccaa tcgccttcaa atatgttcca   360
tttgaagaga ataccctcc aggattctat acgggcgcag atgacgagaa aaaggtcac     420
atcaccgaag cacatgtacc aatcatagat acgtaccggg ctctggaaga atgtgttgat   480
gaaggcttga ttaagtctat tggtgtttcc aactttcagg gaagcttgat tcaagattta   540
ttacgtggtt gtagaatcaa gcccgtggct ttgcaaattg aacaccatcc ttatttgact   600
caagaacacc tagttgagtt ttgtaaatta cacgatatcc aagtagttgc ttactcctcc   660
ttcggtcctc aatcattcat tgagatggac ttacagttgg caaaaaccac gccaactctg   720
ttcgagaatg atgtaatcaa gaaggtctca caaaaccatc caggcagtac cacttcccaa   780
gtattgctta gatgggcaac tcagagaggc attgccgtca ttccaaaatc ttccaagaag   840
gaaaggttac ttggcaacct agaaatcgaa aaaaagttca ctttaacgga gcaagaattg   900
aaggatattt ctgcactaaa tgccaacatc agatttaatg atccatggac ctggttggat   960
ggtaaattcc ccacttttgc ctga                                          984
```

<210> SEQ ID NO 85
<211> LENGTH: 327
<212> TYPE: PRT
<213> ORGANISM: Saccharomyces cerevisiae

<400> SEQUENCE: 85

```
Met Ser Ser Leu Val Thr Leu Asn Asn Gly Leu Lys Met Pro Leu Val
  1               5                  10                  15

Gly Leu Gly Cys Trp Lys Ile Asp Lys Lys Val Cys Ala Asn Gln Ile
             20                  25                  30

Tyr Glu Ala Ile Lys Leu Gly Tyr Arg Leu Phe Asp Gly Ala Cys Asp
         35                  40                  45

Tyr Gly Asn Glu Lys Glu Val Gly Glu Gly Ile Arg Lys Ala Ile Ser
     50                  55                  60

Glu Gly Leu Val Ser Arg Lys Asp Ile Phe Val Val Ser Lys Leu Trp
 65                  70                  75                  80

Asn Asn Phe His His Pro Asp His Val Lys Leu Ala Leu Lys Lys Thr
                 85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
```

```
              180                 185                 190
Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
        210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
        290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 86
<211> LENGTH: 1164
<212> TYPE: DNA
<213> ORGANISM: Escherichia coli

<400> SEQUENCE: 86
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaaccccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg gcacattctg     360
caaacgggcg gtaaagagat aaaagcgcc atcccgatgg gctgtgtgct gacgctgcca     420
gcaaccggtt cagaatccaa cgcagaagcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660 tgctgacgc taatcgaaga tggtccgaaa gccctgaaag agccagaaaa ctacgatgtg     720
cgcgccaacg tcatgtgggc ggcgactcag gcgctgaacg gtttgattgg cgctggcgta     780
ccgcaggact gggcaacgca tatgctgggc acgaactga ctgcgatgca cggtctggat     840
cacgcgcaaa cactggctat cgtcctgcct gcactgtgga tgaaaaacg cgataccaag     900 cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa atcatgaca ttacgttgga tgtcagccgc    1140
cgtatatacg aagccgcccg ctaa                                          1164

<210> SEQ ID NO 87
```

<211> LENGTH: 1167
<212> TYPE: DNA
<213> ORGANISM: Escherichia coli

<400> SEQUENCE: 87

```
atgaacaatt ttaatttgca tactccaact agaatattat ttggaaaagg tgcaattgca      60
ggtttaaggg aacaaatacc acatgatgca agggtattaa tcacatacgg tggtggttct     120
gtcaagaaaa ctggtgtatt ggatcaagta ttggatgctt taaagggtat ggatgtcttg     180
gaatttggag gaatcgaacc aaaccctgct tacgagactt taatgaatgc tgtcaaattg     240
gtcagagaac aaaaggtaac attcttattg gctgttggag gtggatcagt attagatggt     300
acaaagttca ttgctgctgc agcaaattat ccagaaaaca ttgatccatg gcatatattg     360
caaactggtg gtaaggaaat aaagtcagct atcccaatgg gatgtgtttt gacattgcct     420
gcaacaggat cagaatcaaa cgctgaagca gtcatctcaa gaaagactac aggtgacaaa     480
caggcattcc attctgccca tgtccaacct gtatttgctg ttttagaccc tgtatacact     540
tacacattac caccaaggca agtcgcaaat ggagttgtcg atgcctttgt tcacactgta     600
gaacagtacg tcaccaaacc agtcgatgca aagatccagg acaggtttgc agaaggtatt     660
ttattgacat taatcgaaga tggaccaaaa gcattgaaag agccagagaa ctatgacgtt     720
agggcaaatg ttatgtgggc tgctacccag gcattgaacg gtttaattgg tgcaggagtt     780
ccacaagatt gggctacaca catgttgggt cacgagttga ccgccatgca cggtttggac     840
catgcacaga ctttagccat tgttttgcct gccttatgga acgagaaaag agatactaag     900
agggctaagt tattacaata cgctgaaagg gtttggaata tcaccgaggg atctgatgat     960
gaaaggattg atgccgctat tgcagccact agaaacttct ttgaacaatt aggtgttcca    1020
actcacttgt ctgactatgg tttagatgga tcatctattc cagctttgtt gaagaaattg    1080
gaagagcacg gtatgaccca gttgggtgag aatcatgata taaccttaga tgtatctagg    1140
agaatctacg aggctgctag ataatga                                         1167
```

<210> SEQ ID NO 88
<211> LENGTH: 387
<212> TYPE: PRT
<213> ORGANISM: Escherichia coli

<400> SEQUENCE: 88

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
```

```
        130                 135                 140
Glu Ser Asn Ala Glu Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 89
<211> LENGTH: 1164
<212> TYPE: DNA
<213> ORGANISM: Escherichia coli

<400> SEQUENCE: 89
atgaacaact ttaatctgca cacccaacc  cgcattctgt tggtaaagg  cgcaatcgct    60 ggtttacgcg aacaaattcc tcacgatgct cgcgtattga ttacctacgg cggcggcagc   120
gtgaaaaaaa ccggcgttct cgatcaagtt ctggatgccc tgaaaggcat ggacgtgctg   180
gaatttggcg gtattgagcc aaacccggct tatgaaacgc tgatgaacgc cgtgaaactg   240
gttcgcgaac agaaagtgac tttcctgctg gcggttggcg gcggttctgt actggacggc   300
accaaattta tcgccgcagc ggctaactat ccggaaaata tcgatccgtg cacattctg    360 caaacgggcg taaagagat  taaaagcgcc atcccgatgg ctgtgtgct  gacgctgcca   420 gcaaccggtt cagaatccaa cgcaggcgcg gtgatctccc gtaaaaccac aggcgacaag   480
caggcgttcc attctgccca tgttcagccg gtatttgccg tgctcgatcc ggtttatacc   540
tacaccctgc cgccgcgtca ggtggctaac ggcgtagtgg acgcctttgt acacaccgtg   600
gaacagtatg ttaccaaacc ggttgatgcc aaaattcagg accgtttcgc agaaggcatt   660
```

```
ttgctgacgc taatcgaaga tggtccgaaa gccctgaaag agccagaaaa ctacgatgtg      720
cgcgccaacg tcatgtgggc ggcgactcag gcgctgaacg gtttgattgg cgctggcgta      780
ccgcaggact gggcaacgca tatgctgggc cacgaactga ctgcgatgca cggtctggat      840
cacgcgcaaa cactggctat cgtcctgcct gcactgtgga atgaaaaacg cgataccaag      900
cgcgctaagc tgctgcaata tgctgaacgc gtctggaaca tcactgaagg ttccgatgat      960
gagcgtattg acgccgcgat tgccgcaacc cgcaatttct ttgagcaatt aggcgtgccg     1020
acccacctct ccgactacgg tctggacggc agctccatcc cggctttgct gaaaaaactg     1080
gaagagcacg gcatgaccca actgggcgaa aatcatgaca ttacgttgga tgtcagccgc     1140
cgtatatacg aagccgcccg ctaa                                            1164

<210> SEQ ID NO 90
<211> LENGTH: 1164
<212> TYPE: DNA
<213> ORGANISM: Escherichia coli

<400> SEQUENCE: 90
atgaacaact ttaatctgca caccccaacc cgcattctgt ttggtaaagg cgcaatcgct       60
ggtttacgcg aacaaattcc tcacgatgct cgcgtattga ttacctacgg cggcggcagc      120
gtgaaaaaaa ccggcgttct cgatcaagtt ctggatgccc tgaaaggcat ggacgtgctg      180
gaatttggcg gtattgagcc aaacccggct tatgaaacgc tgatgaacgc cgtgaaactg      240
gttcgcgaac agaaagtgac tttcctgctg gcggttggcg gcggttctgt actggacggc      300
accaaattta tcgccgcagc ggctaactat ccggaaaata tcgatccgtg gcacattctg      360
caaacgggcg gtaaagagat aaaagcgcc atcccgatgg gctgtgtgct gacgctgcca      420
gcaaccggtt cagaatccaa cgcaggcgcg gtgatctccc gtaaaaccac aggcgacaag      480
caggcgttcc attctgccca tgttcagccg gtatttgccg tgctcgatcc ggtttatacc      540
tacaccctgc cgccgcgtca ggtggctaac ggcgtagtgg acgcctttgt acacaccgtg      600
gaacagtatg ttaccaaacc ggttgatgcc aaaattcagg accgtttcgc agaaggcatt      660
ttgctgacgc taatcgaaga tggtccgaaa gccctgaaag agccagaaaa ctacgatgtg      720
cgcgccaacg tcatgtgggc ggcgactcag gcgctgaacg gtttgattgg cgctggcgta      780
ccgcaggact gggcaacgca tatgctgggc cacgaactga ctgcgatgca cggtctggat      840
cacgcgcaaa cactggctat cgtcctgcct gcactgtgga atgaaaaacg cgataccaag      900
cgcgctaagc tgctgcaata tgctgaacgc gtctggaaca tcactgaagg ttccgatgat      960
gagcgtattg acgccgcgat tgccgcaacc cgcaatttct ttgagcaatt aggcgtgccg     1020
acccacctct ccgactacgg tctggacggc agctccatcc cggctttgct gaaaaaactg     1080
gaagagcacg gcatgaccca actgggcgaa aatcatgaca ttacgttgga tgtcagccgc     1140
cgtatatacg aagccgcccg ctaa                                            1164

<210> SEQ ID NO 91
<211> LENGTH: 387
<212> TYPE: PRT
<213> ORGANISM: Escherichia coli

<400> SEQUENCE: 91

Met Asn Asn Phe Asn Leu His Thr Pro Thr Arg Ile Leu Phe Gly Lys
 1               5                  10                  15

Gly Ala Ile Ala Gly Leu Arg Glu Gln Ile Pro His Asp Ala Arg Val
```

```
            20                  25                  30
Leu Ile Thr Tyr Gly Gly Ser Val Lys Thr Gly Val Leu Asp
            35                  40                  45
Gln Val Leu Asp Ala Leu Lys Gly Met Asp Val Leu Glu Phe Gly Gly
 50                  55                  60
Ile Glu Pro Asn Pro Ala Tyr Glu Thr Leu Met Asn Ala Val Lys Leu
 65                  70                  75                  80
Val Arg Glu Gln Lys Val Thr Phe Leu Leu Ala Val Gly Gly Gly Ser
                85                  90                  95
Val Leu Asp Gly Thr Lys Phe Ile Ala Ala Ala Asn Tyr Pro Glu
            100                 105                 110
Asn Ile Asp Pro Trp His Ile Leu Gln Thr Gly Gly Lys Glu Ile Lys
            115                 120                 125
Ser Ala Ile Pro Met Gly Cys Val Leu Thr Leu Pro Ala Thr Gly Ser
            130                 135                 140
Glu Ser Asn Ala Gly Ala Val Ile Ser Arg Lys Thr Thr Gly Asp Lys
145                 150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
            180                 185                 190
Val Asp Ala Phe Val His Thr Val Glu Gln Tyr Val Thr Lys Pro Val
            195                 200                 205
Asp Ala Lys Ile Gln Asp Arg Phe Ala Glu Gly Ile Leu Leu Thr Leu
            210                 215                 220
Ile Glu Asp Gly Pro Lys Ala Leu Lys Glu Pro Glu Asn Tyr Asp Val
225                 230                 235                 240
Arg Ala Asn Val Met Trp Ala Ala Thr Gln Ala Leu Asn Gly Leu Ile
                245                 250                 255
Gly Ala Gly Val Pro Gln Asp Trp Ala Thr His Met Leu Gly His Glu
            260                 265                 270
Leu Thr Ala Met His Gly Leu Asp His Ala Gln Thr Leu Ala Ile Val
            275                 280                 285
Leu Pro Ala Leu Trp Asn Glu Lys Arg Asp Thr Lys Arg Ala Lys Leu
            290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
            355                 360                 365
Gly Glu Asn His Asp Ile Thr Leu Asp Val Ser Arg Arg Ile Tyr Glu
            370                 375                 380
Ala Ala Arg
385

<210> SEQ ID NO 92
<211> LENGTH: 981
<212> TYPE: DNA
<213> ORGANISM: Escherichia coli

<400> SEQUENCE: 92
```

-continued

```
atgaaaaaga taccttttagg cacaacggat attacgcttt cgcgaatggg gttggggaca      60
tgggccattg gcggcggtcc tgcatggaat ggcgatctcg atcggcaaat atgtattgat     120
acgattcttg aagcccatcg ttgtggcatt aatctgattg atactgcgcc aggatataac     180
tttggcaata gtgaagttat cgtcggtcag gcgttaaaaa aactgccccg tgaacaggtt     240
gtagtagaaa ccaaatgcgg cattgtctgg aacgaaaag gaagtttatt caacaaagtt     300
ggcgatcggc agttgtataa aaaccttccc ccggaatcta ccgcgaaga ggtagcagcg     360
agcttgcaac gtctgggtat tgattacatc gatatctaca tgacgcactg gcagtcggtg     420
ccgccatttt ttacgccgat cgctgaaact gtcgcagtgc ttaatgagtt aaagtctgaa     480
gggaaaattc gcgctatagg cgctgctaac gtcgatgctg accatatccg cgagtatctg     540
caatatggtg aactggatat tattcaggcg aaatacagta tcctcgaccg ggcaatggaa     600
aacgaactgc tgccactatg tcgtgataat ggcattgtgg ttcaggttta ttccccgcta     660
gagcagggat tgttgaccgg caccatcact cgtgattacg ttccgggcgg cgctcgggca     720
aataaagtct ggttccagcg tgaaaacatg ctgaaagtga ttgatatgct gaacagtgg     780
cagccacttt gtgctcgtta tcagtgcaca attcccactc tggcactggc gtggatatta     840
aaacagagtg atttaatctc cattcttagt ggggctactc accggaaca ggtacgcgaa     900
aatgtcgcgg cactgaatat caacttatcg gatgcagacg caacattgat gagggaaatg     960
gcagaggccc tggagcgtta a                                               981
```

<210> SEQ ID NO 93
<211> LENGTH: 326
<212> TYPE: PRT
<213> ORGANISM: Escherichia coli

<400> SEQUENCE: 93

```
Met Lys Lys Ile Pro Leu Gly Thr Thr Asp Ile Thr Leu Ser Arg Met
1               5                  10                  15

Gly Leu Gly Thr Trp Ala Ile Gly Gly Pro Ala Trp Asn Gly Asp
            20                  25                  30

Leu Asp Arg Gln Ile Cys Ile Asp Thr Ile Leu Glu Ala His Arg Cys
        35                  40                  45

Gly Ile Asn Leu Ile Asp Thr Ala Pro Gly Tyr Asn Phe Gly Asn Ser
    50                  55                  60

Glu Val Ile Val Gly Gln Ala Leu Lys Lys Leu Pro Arg Glu Gln Val
65                  70                  75                  80

Val Val Glu Thr Lys Cys Gly Ile Val Trp Glu Arg Lys Gly Ser Leu
                85                  90                  95

Phe Asn Lys Val Gly Asp Arg Gln Leu Tyr Lys Asn Leu Ser Pro Glu
            100                 105                 110

Ser Ile Arg Glu Glu Val Ala Ala Ser Leu Gln Arg Leu Gly Ile Asp
        115                 120                 125

Tyr Ile Asp Ile Tyr Met Thr His Trp Gln Ser Val Pro Pro Phe Phe
    130                 135                 140

Thr Pro Ile Ala Glu Thr Val Ala Val Leu Asn Glu Leu Lys Ser Glu
145                 150                 155                 160

Gly Lys Ile Arg Ala Ile Gly Ala Ala Asn Val Asp Ala Asp His Ile
                165                 170                 175

Arg Glu Tyr Leu Gln Tyr Gly Glu Leu Asp Ile Ile Gln Ala Lys Tyr
            180                 185                 190

Ser Ile Leu Asp Arg Ala Met Glu Asn Glu Leu Leu Pro Leu Cys Arg
```

```
                    195                 200                 205
Asp Asn Gly Ile Val Val Gln Val Tyr Ser Pro Leu Glu Gln Gly Leu
    210                 215                 220

Leu Thr Gly Thr Ile Thr Arg Asp Tyr Val Pro Gly Gly Ala Arg Ala
225                 230                 235                 240

Asn Lys Val Trp Phe Gln Arg Glu Asn Met Leu Lys Val Ile Asp Met
                245                 250                 255

Leu Glu Gln Trp Gln Pro Leu Cys Ala Arg Tyr Gln Cys Thr Ile Pro
            260                 265                 270

Thr Leu Ala Leu Ala Trp Ile Leu Lys Gln Ser Asp Leu Ile Ser Ile
        275                 280                 285

Leu Ser Gly Ala Thr Ala Pro Glu Gln Val Arg Glu Asn Val Ala Ala
    290                 295                 300

Leu Asn Ile Asn Leu Ser Asp Ala Asp Ala Thr Leu Met Arg Glu Met
305                 310                 315                 320

Ala Glu Ala Leu Glu Arg
                325

<210> SEQ ID NO 94
<211> LENGTH: 1149
<212> TYPE: DNA
<213> ORGANISM: Escherichia coli

<400> SEQUENCE: 94
atggctaaca gaatgattct gaacgaaacg gcatggtttg gtcggggtgc tgttggggct      60
ttaaccgatg aggtgaaacg ccgtggttat cagaaggcgc tgatcgtcac cgataaaacg     120
ctggtgcaat gcggcgtggt ggcgaaagtg accgataaga tggatgctgc agggctggca     180
tgggcgattt acgacggcgt agtgcccaac ccaacaatta ctgtcgtcaa agaagggctc     240
ggtgtattcc agaatagcgg cgcggattac ctgatcgcta ttggtggtgg ttctccacag     300
gatacttgta aagcgattgg cattatcagc aacaacccgg agtttgccga tgtgcgtagc     360
ctggaagggc tttccccgac caataaaccc agtgtaccga ttctggcaat tcctaccaca     420
gcaggtactg cggcagaagt gaccattaac tacgtgatca ctgacgaaga gaaacggcgc     480
aagtttgttt gcgttgatcc gcatgatatc ccgcaggtgg cgtttattga cgctgacatg     540
atggatggta tgcctccagc gctgaaagct gcgacgggtg tcgatgcgct cactcatgct     600
attgagggt atattacccg tggcgcgtgg gcgctaaccg atgcactgca cattaaagcg     660
attgaaatca ttgctgggc gctgcgagga tcggttgctg gtgataagga tgccggagaa     720
gaaatggcgc tcgggcagta tgttgcgggt atgggcttct cgaatgttgg gttagggttg     780
gtgcatggta tggcgcatcc actgggcgcg tttataaca ctccacacgg tgttgcgaac      840
gccatcctgt accgcatgt catgcgttat aacgctgact ttaccggtga agtaccgc        900
gatatcgcgc gcgttatggg cgtgaaagtg aaggtatga gcctggaaga ggcgcgtaat      960
gccgctgttg aagcggtgtt tgctctcaac cgtgatgtcg gtattccgcc acatttgcgt    1020
gatgttggtg tacgcaagga agacattccg gcactggcgc aggcggcact ggatgatgtt    1080
tgtaccggtg caacccgcg tgaagcaacg cttgaggata ttgtagagct ttaccatacc    1140
gcctggtaa                                                            1149

<210> SEQ ID NO 95
<211> LENGTH: 1149
<212> TYPE: DNA
<213> ORGANISM: Escherichia coli
```

<400> SEQUENCE: 95

```
atggctaaca gaatgattct gaacgaaacg gcatggtttg gtcggggtgc tgttggggct      60
ttaaccgatg aggtgaaacg ccgtggttat cagaaggcgc tgatcgtcac cgataaaacg     120
ctggtgcaat gcggcgtggt ggcgaaagtg accgataaga tggatgctgc agggctggca     180
tgggcgattt acgacggcgt agtgcccaac ccaacaatta ctgtcgtcaa agaagggctc     240
ggtgtattcc agaatagcgg cgcggattac ctgatcgcta ttggtggtgg ttctccacag     300
gatacttgta aagcgattgg cattatcagc aacaacccgg agtttgccga tgtgcgtagc     360
ctggaagggc tttccccgac caataaaccc agtgtaccga ttctggcaat tcctaccaca     420
gcaggtactg cggcagaagt gaccattaac tacgtgatca ctgacgaaga gaaacggcgc     480
aagtttgttt gcgttgatcc gcatgatatc ccgcaggtgg cgtttattga cgctgacatg     540
atggatggta tgcctccagc gctgaaagct gcgacgggtg tcgatgcgct cactcatgct     600
attgaggggt atattacccg tggcgcgtgg gcgctaaccg atgcactgca cattaaagcg     660
attgaaatca ttgctggggc gctgcgagga tcggttgctg gtgataagga tgccggagaa     720
gaaatggcgc tcgggcagta tgttgcgggt atgggcttct cgaatgttgg gttaggggttg     780
gtgcatggta tggcgcatcc actgggcgcg ttttataaca ctccacacgg tgttgcgaac     840
gccatcctgt taccgcatgt catgcgttat aacgctgact ttaccggtga aagtaccgc      900
gatatcgcgc gcgttatggg cgtgaaagtg gaaggtatga gcctggaaga ggcgcgtaat     960
gccgctgttg aagcggtgtt tgctctcaac cgtgatgtcg gtattccgcc acatttgcgt    1020
gatgttggtg tacgcaagga agacattccg gcactggcgc aggcggcact ggatgatgtt    1080
tgtaccggtg caacccgcg tgaagcaacg cttgaggata ttgtagagct ttaccatacc    1140
gcctggtaa                                                            1149
```

<210> SEQ ID NO 96
<211> LENGTH: 382
<212> TYPE: PRT
<213> ORGANISM: Escherichia coli

<400> SEQUENCE: 96

```
Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
                20                  25                  30

Ala Leu Ile Val Thr Asp Lys Thr Leu Val Gln Cys Gly Val Val Ala
            35                  40                  45

Lys Val Thr Asp Lys Met Asp Ala Ala Gly Leu Ala Trp Ala Ile Tyr
        50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
                100                 105                 110

Pro Glu Phe Ala Asp Val Arg Ser Leu Glu Gly Leu Ser Pro Thr Asn
            115                 120                 125

Lys Pro Ser Val Pro Ile Leu Ala Ile Pro Thr Thr Ala Gly Thr Ala
        130                 135                 140

Ala Glu Val Thr Ile Asn Tyr Val Ile Thr Asp Glu Glu Lys Arg Arg
```

```
            145                 150                 155                 160
Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
                180                 185                 190

Gly Val Asp Ala Leu Thr His Ala Ile Glu Gly Tyr Ile Thr Arg Gly
                195                 200                 205

Ala Trp Ala Leu Thr Asp Ala Leu His Ile Lys Ala Ile Glu Ile Ile
        210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
                260                 265                 270

Asn Thr Pro His Gly Val Ala Asn Ala Ile Leu Leu Pro His Val Met
                275                 280                 285

Arg Tyr Asn Ala Asp Phe Thr Gly Glu Lys Tyr Arg Asp Ile Ala Arg
        290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
                340                 345                 350

Ala Gln Ala Ala Leu Asp Asp Val Cys Thr Gly Gly Asn Pro Arg Glu
                355                 360                 365

Ala Thr Leu Glu Asp Ile Val Glu Leu Tyr His Thr Ala Trp
        370                 375                 380

<210> SEQ ID NO 97
<211> LENGTH: 804
<212> TYPE: DNA
<213> ORGANISM: Escherichia coli

<400> SEQUENCE: 97
atggctatcc ctgcatttgg tttaggtact ttccgtctga agacgacgt tgttatttca     60 tctgtgataa cggcgcttga acttggttat cgcgcaattg ataccgcaca aatctatgat    120
aacgaagccg cagtaggtca ggcgattgca gaaagtggcg tgccacgtca tgaactctac    180
atcaccacta aaatctggat tgaaaatctc agcaaagaca aattgatccc aagtctgaaa    240
gagagcctgc aaaaattgcg taccgattat gttgatctga cgctaatcca ctggccgtca    300
ccaaacgatg aagtctctgt tgaagagttt atgcaggcgc tgctggaagc caaaaaacaa    360
gggctgacgc gtgagatcgg tatttccaac ttcacgatcc cgttgatgga aaaagcgatt    420
gctgctgttg gtgctgaaaa catcgctact aaccagattg aactctctcc ttatctgcaa    480
aaccgtaaag tggttgcctg ggctaaacag cacggcatcc atattacttc ctatatgacg    540
ctggcgtatg gtaaggccct gaaagatgag gttattgctc gtatcgcagc taaacacaat    600
gcgactccgg cacaagtgat tctggcgtgg gctatggggg aaggttactc agtaattcct    660
tcttctacta acgtaaaaaa cctggaaagt aatcttaagg cacaaaattt acagcttgat    720
gccgaagata aaaagcgat cgccgcactg gattgcaacg accgcctggt tagcccggaa    780
ggtctggctc ctgaatggga ttaa                                           804
```

<210> SEQ ID NO 98
<211> LENGTH: 267
<212> TYPE: PRT
<213> ORGANISM: Escherichia coli

<400> SEQUENCE: 98

Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
            20                  25                  30

Ile Asp Thr Ala Gln Ile Tyr Asp Asn Glu Ala Ala Val Gly Gln Ala
        35                  40                  45

Ile Ala Glu Ser Gly Val Pro Arg His Glu Leu Tyr Ile Thr Thr Lys
    50                  55                  60

Ile Trp Ile Glu Asn Leu Ser Lys Asp Lys Leu Ile Pro Ser Leu Lys
65                  70                  75                  80

Glu Ser Leu Gln Lys Leu Arg Thr Asp Tyr Val Asp Leu Thr Leu Ile
                85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
    130                 135                 140

Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
                165                 170                 175

Ser Tyr Met Thr Leu Ala Tyr Gly Lys Ala Leu Lys Asp Glu Val Ile
            180                 185                 190

Ala Arg Ile Ala Ala Lys His Asn Ala Thr Pro Ala Gln Val Ile Leu
        195                 200                 205

Ala Trp Ala Met Gly Glu Gly Tyr Ser Val Ile Pro Ser Ser Thr Lys
    210                 215                 220

Arg Lys Asn Leu Glu Ser Asn Leu Lys Ala Gln Asn Leu Gln Leu Asp
225                 230                 235                 240

Ala Glu Asp Lys Lys Ala Ile Ala Ala Leu Asp Cys Asn Asp Arg Leu
                245                 250                 255

Val Ser Pro Glu Gly Leu Ala Pro Glu Trp Asp
            260                 265

<210> SEQ ID NO 99
<211> LENGTH: 828
<212> TYPE: DNA
<213> ORGANISM: Escherichia coli

<400> SEQUENCE: 99
atggctaatc caaccgttat taagctacag gatggcaatg tcatgcccca gctgggactg     60
ggcgtctggc aagcaagtaa tgaggaagta atcaccgcca ttcaaaaagc gttagaagtg    120
ggttatcgct cgattgatac cgccgcggcc tacaagaacg aagaaggtgt cggcaaagcc    180
ctgaaaaatg cctcagtcaa cagagaagaa ctgttcatca ccactaagct gtggaacgac    240
gaccacaagc gccccgcgaa agccctgctc gacagcctga aaaaactcca gcttgattat    300
atcgacctct acttaatgca ctggcccgtt cccgctatcg accattatgt cgaagcatgg    360

```
aaaggcatga tcgaattgca aaaagaggga ttaatcaaaa gcatcggcgt gtgcaacttc    420
cagatccatc acctgcaacg cctgattgat gaaactggcg tgacgcctgt gataaaccag    480
atcgaacttc atccgctgat gcaacaacgc cagctacacg cctggaacgc gacacacaaa    540
atccagaccg aatcctggag cccattagcg caaggaggga aaggcgtttt cgatcagaaa    600
gtcattcgcg atctggcaga taaatacggc aaaaccccgg cgcagattgt tatccgctgg    660
catctggata gcggcctggt ggtgatcccg aaatcggtca caccttcacg tattgccgaa    720
aactttgatg tctgggattt ccgtctcgac aaagacgaac tcggcgaaat tgcaaaactc    780
gatcagggca agcgtctcgg tcccgatcct gaccagttcg gcggctaa                 828
```

<210> SEQ ID NO 100
<211> LENGTH: 275
<212> TYPE: PRT
<213> ORGANISM: Escherichia coli

<400> SEQUENCE: 100

```
Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
            20                  25                  30

Ala Ile Gln Lys Ala Leu Glu Val Gly Tyr Arg Ser Ile Asp Thr Ala
        35                  40                  45

Ala Ala Tyr Lys Asn Glu Glu Gly Val Gly Lys Ala Leu Lys Asn Ala
    50                  55                  60

Ser Val Asn Arg Glu Glu Leu Phe Ile Thr Thr Lys Leu Trp Asn Asp
65                  70                  75                  80

Asp His Lys Arg Pro Arg Glu Ala Leu Leu Asp Ser Leu Lys Lys Leu
                85                  90                  95

Gln Leu Asp Tyr Ile Asp Leu Tyr Leu Met His Trp Pro Val Pro Ala
            100                 105                 110

Ile Asp His Tyr Val Glu Ala Trp Lys Gly Met Ile Glu Leu Gln Lys
        115                 120                 125

Glu Gly Leu Ile Lys Ser Ile Gly Val Cys Asn Phe Gln Ile His His
    130                 135                 140

Leu Gln Arg Leu Ile Asp Glu Thr Gly Val Thr Pro Val Ile Asn Gln
145                 150                 155                 160

Ile Glu Leu His Pro Leu Met Gln Gln Arg Gln Leu His Ala Trp Asn
                165                 170                 175

Ala Thr His Lys Ile Gln Thr Glu Ser Trp Ser Pro Leu Ala Gln Gly
            180                 185                 190

Gly Lys Gly Val Phe Asp Gln Lys Val Ile Arg Asp Leu Ala Asp Lys
        195                 200                 205

Tyr Gly Lys Thr Pro Ala Gln Ile Val Ile Arg Trp His Leu Asp Ser
    210                 215                 220

Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
            260                 265                 270

Phe Gly Gly
        275
```

<210> SEQ ID NO 101
<211> LENGTH: 1179
<212> TYPE: DNA
<213> ORGANISM: Clostridium acetobutylicum

<400> SEQUENCE: 101

| | | | | | |
|---|---|---|---|---|---|
| atgaaagaag | ttgtaatagc | tagtgcagta | agaacagcga | ttggatctta | tggaaagtct | 60 |
| cttaaggatg | taccagcagt | agatttagga | gctacagcta | taaaggaagc | agttaaaaaa | 120 |
| gcaggaataa | aaccagagga | tgttaatgaa | gtcattttag | gaaatgttct | tcaagcaggt | 180 |
| ttaggacaga | atccagcaag | acaggcatct | tttaaagcag | gattaccagt | tgaaattcca | 240 |
| gctatgacta | ttaataaggt | ttgtggttca | ggacttagaa | cagttagctt | agcagcacaa | 300 |
| attataaaag | caggagatgc | tgacgtaata | atagcaggtg | gtatggaaaa | tatgtctaga | 360 |
| gctccttact | tagcgaataa | cgctagatgg | ggatatagaa | tgggaaacgc | taaatttgtt | 420 |
| gatgaaatga | tcactgacgg | attgtgggat | gcatttaatg | attaccacat | gggaataaca | 480 |
| gcagaaaaca | tagctgagag | atggaacatt | tcaagagaag | aacaagatga | gtttgctctt | 540 |
| gcatcacaaa | aaaagctga | agaagctata | aaatcaggtc | aatttaaaga | tgaaatagtt | 600 |
| cctgtagtaa | ttaaaggcag | aaaggggaaa | actgtagttg | atacagatga | gcaccctaga | 660 |
| tttggatcaa | ctatagaagg | acttgcaaaa | ttaaaacctg | ccttcaaaaa | agatggaaca | 720 |
| gttacagctg | gtaatgcatc | aggattaaat | gactgtgcag | cagtacttgt | aatcatgagt | 780 |
| gcagaaaaag | ctaaagagct | tggagtaaaa | ccacttgcta | agatagtttc | ttatggttca | 840 |
| gcaggagttg | acccagcaat | aatgggatat | ggacctttct | atgcaacaaa | agcagctatt | 900 |
| gaaaaagcag | gttggacagt | tgatgaatta | gatttaatag | aatcaaatga | agcttttgca | 960 |
| gctcaaagtt | tagcagtagc | aaaagattta | aaatttgata | tgaataaagt | aaatgtaaat | 1020 |
| ggaggagcta | ttgcccttgg | tcatccaatt | ggagcatcag | gtgcaagaat | actcgttact | 1080 |
| cttgtacacg | caatgcaaaa | aagagatgca | aaaaaaggct | tagcaacttt | atgtataggt | 1140 |
| ggcggacaag | gaacagcaat | attgctagaa | aagtgctag | | | 1179 |

<210> SEQ ID NO 102
<211> LENGTH: 1179
<212> TYPE: DNA
<213> ORGANISM: Clostridium acetobutylicum

<400> SEQUENCE: 102

| | | | | | |
|---|---|---|---|---|---|
| atgaaagaag | ttgttattgc | gagcgcggtt | cgtaccgcga | ttggcagcta | tggcaagagc | 60 |
| ctgaaggatg | ttccggcggt | ggacctgggt | gcgaccgcga | tcaaagaggc | ggttaagaaa | 120 |
| gcgggcatta | aaccggagga | tgtgaacgaa | gttatcctgg | gtaacgtgct | gcaagcgggt | 180 |
| ctgggccaaa | accggcgcg | tcaggcgagc | ttcaaggcgg | gcctgccggt | tgaaatcccg | 240 |
| gcgatgacca | ttaacaaagt | ttgcggtagc | ggcctgcgta | ccgtgagcct | ggcggcgcaa | 300 |
| atcattaagg | cgggtgacgc | ggatgttatc | attgcgggtg | gcatggagaa | catgagccgt | 360 |
| gcgccgtacc | tggcgaacaa | cgcgcgttgg | ggttatcgta | tgggcaacgc | gaaattcgtg | 420 |
| gacgaaatga | ttaccgacgg | tctgtgggat | gcgtttaacg | actaccacat | gggcatcacc | 480 |
| gcggagaaca | ttgcggaacg | ttggaacatt | agccgtgagg | aacaagatga | gttcgcgctg | 540 |
| gcgagccaga | agaaagcgga | ggaagcgatc | aagagcggcc | agtttaaaga | cgaaatcgtt | 600 |
| ccggtggtta | ttaagggtcg | taagggtgaa | accgtggtgg | acaccgatga | acacccgcgt | 660 |
| ttcggtagca | ccattgaggg | cctggcgaag | ctgaaaccgg | cgtttaagaa | agatggcacc | 720 |

```
gtgaccgcgg gtaacgcgag cggcctgaac gactgcgcgg cggtgctggt tatcatgagc    780
gcggagaagg cgaaagaact gggtgtgaag ccgctggcga aaattgttag ctacggtagc    840
gcgggtgtgg acccggcgat catgggttac ggcccgtttt atgcgaccaa ggcggcgatt    900
gagaaagcgg gttggaccgt ggacgaactg gatctgatcg agagcaacga agcgttcgcg    960
gcgcaaagcc tggcggtggc gaaggatctg aaatttgaca tgaacaaggt gaacgtgaac   1020
ggtggtgcga ttgcgctggg tcacccgatt ggtgcgagcg cgcgcgtat ctggtgacc    1080 ctggttcacg cgatgcagaa acgtgacgcg aagaaaggtc tggcgaccct gtgcattggt   1140
ggtggtcaag gcaccgcgat tctgctggaa aagtgctaa                         1179
```

<210> SEQ ID NO 103
<211> LENGTH: 392
<212> TYPE: PRT
<213> ORGANISM: Clostridium acetobutylicum

<400> SEQUENCE: 103

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285
```

```
Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
            325                 330                 335

Val Asn Val Asn Gly Ala Ile Ala Leu Gly His Pro Ile Gly Ala
            340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 104
<211> LENGTH: 1185
<212> TYPE: DNA
<213> ORGANISM: Escherichia coli

<400> SEQUENCE: 104
atgaaaaatt gtgtcatcgt cagtgcggta cgtactgcta tcggtagttt taacggttca      60
ctcgcttcca ccagcgccat cgacctgggg gcgacagtaa ttaaagccgc cattgaacgt     120
gcaaaaatcg attcacaaca cgttgatgaa gtgattatgg gtaacgtgtt acaagccggg     180
ctggggcaaa atccggcgcg tcaggcactg ttaaaaagcg ggctggcaga acggtgtgc      240 ggattcacgg tcaataaagt atgtggttcg ggtcttaaaa gtgtggcgct tgccgcccag     300
gccattcagg caggtcaggc gcagagcatt gtggcggggg gtatggaaaa tatgagttta     360 gcccctact tactcgatgc aaaagcacgc tctggttatc gtcttggaga cggacaggtt      420
tatgacgtaa tcctgcgcga tggcctgatg tgcgccaccc atggttatca tatggggatt     480
accgccgaaa acgtggctaa agagtacgga attacccgtg aaatgcagga tgaactggcg     540
ctacattcac agcgtaaagc ggcagccgca attgagtccg gtgctttac agccgaaatc      600 gtcccggtaa atgttgtcac tcgaaagaaa accttcgtct tcagtcaaga cgaattcccg     660
aaagcgaatt caacggctga gcgttaggt gcattgcgcc cggccttcga taaagcagga     720
acagtcaccg ctgggaacgc gtctggtatt aacgacggtg ctgccgctct ggtgattatg     780
gaagaatctg cggcgctggc agcaggcctt accccctgg ctcgcattaa agttatgcc      840 agcggtggcg tgccccccgc attgatgggt atggggccag tacctgccac gcaaaaagcg     900
ttacaactgg cggggctgca actggcggat attgatctca ttgaggctaa tgaagcattt     960
gctgcacagt tccttgccgt tgggaaaaac ctgggctttg attctgagaa agtgaatgtc    1020
aacggcgggg ccatcgcgct cgggcatcct atcggtgcca gtggtgctcg tattctggtc    1080
acactattac atgccatgca ggcacgcgat aaaacgctgg gctggcaac actgtgcatt    1140 ggcggcggtc agggaattgc gatggtgatt gaacggttga attaa                   1185

<210> SEQ ID NO 105
<211> LENGTH: 394
<212> TYPE: PRT
<213> ORGANISM: Escherichia coli

<400> SEQUENCE: 105

Met Lys Asn Cys Val Ile Val Ser Ala Val Arg Thr Ala Ile Gly Ser
1               5                   10                  15
```

```
Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
 50                  55                  60

Pro Ala Arg Gln Ala Leu Leu Lys Ser Gly Leu Ala Glu Thr Val Cys
 65                  70                  75                  80

Gly Phe Thr Val Asn Lys Val Cys Gly Ser Gly Leu Lys Ser Val Ala
                 85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285

Met Gly Met Gly Pro Val Pro Ala Thr Gln Lys Ala Leu Gln Leu Ala
290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350

Ala Ser Gly Ala Arg Ile Leu Val Thr Leu Leu His Ala Met Gln Ala
        355                 360                 365

Arg Asp Lys Thr Leu Gly Leu Ala Thr Leu Cys Ile Gly Gly Gly Gln
370                 375                 380

Gly Ile Ala Met Val Ile Glu Arg Leu Asn
385                 390

<210> SEQ ID NO 106
<211> LENGTH: 1197
<212> TYPE: DNA
<213> ORGANISM: Saccharomyces cerevisiae
```

<400> SEQUENCE: 106

```
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttggg taacgttctt     180
tctgccaatt tgggccaagc tccggccaga caagttgctt ggctgccgg  tttgagtaat     240
catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga aagagatggg ttgaacgatg cgtacgatgg tctagccatg     480
ggtgtacacg cagaaaagtg tgcccgtgat tgggatatta ctagagaaca acaagacaat     540
tttgccatcg aatcctacca aaaatctcaa aaatctcaaa aggaaggtaa attcgacaat     600
gaaattgtac ctgttaccat taagggattt agaggtaagc ctgatactca agtcacgaag     660
gacgaggaac ctgctagatt acacgttgaa aaattgagat ctgcaaggac tgttttccaa     720
aaagaaaacg gtactgttac tgccgctaac gcttctccaa tcaacgatgg tgctgcagcc     780
gtcatcttgg tttccgaaaa agttttgaag gaaaagaatt tgaagccttt ggctattatc     840
aaaggttggg gtgaggccgc tcatcaacca gctgatttta catgggctcc atctcttgca     900
gttccaaagg ctttgaaaca tgctggcatc gaagacatca attctgttga ttactttgaa     960
ttcaatgaag ccttttcggt tgtcggtttg gtgaacacta agattttgaa gctagaccca    1020
tctaaggtta atgtatatgg tggtgctgtt gctctaggtc acccattggg ttgttctggt    1080
gctagagtgg ttgttacact gctatccatc ttacagcaag aaggaggtaa gatcggtgtt    1140
gccgccattt gtaatggtgg tggtggtgct tcctctattg tcattgaaaa gatatga       1197
```

<210> SEQ ID NO 107
<211> LENGTH: 1197
<212> TYPE: DNA
<213> ORGANISM: Saccharomyces cerevisiae

<400> SEQUENCE: 107

```
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttggg taacgttctt     180
tctgccaatt tgggccaagc tccggccaga caagttgctt ggctgccgg  tttgagtaat     240
catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga aagagatggg ttgaacgatg cgtacgatgg tctagccatg     480
ggtgtacacg cagaaaagtg tgcccgtgat tgggatatta ctagagaaca acaagacaat     540
tttgccatcg aatcctacca aaaatctcaa aaatctcaaa aggaaggtaa attcgacaat     600
gaaattgtac ctgttaccat taagggattt agaggtaagc ctgatactca agtcacgaag     660
gacgaggaac ctgctagatt acacgttgaa aaattgagat ctgcaaggac tgttttccaa     720
aaagaaaacg gtactgttac tgccgctaac gcttctccaa tcaacgatgg tgctgcagcc     780
gtcatcttgg tttccgaaaa agttttgaag gaaaagaatt tgaagccttt ggctattatc     840
aaaggttggg gtgaggccgc tcatcaacca gctgatttta catgggctcc atctcttgca     900
```

```
gttccaaagg ctttgaaaca tgctggcatc gaagacatca attctgttga ttactttgaa      960
ttcaatgaag cctttcggt tgtcggtttg gtgaacacta agattttgaa gctagaccca     1020
tctaaggtta atgtatatgg tggtgctgtt gctctaggtc acccattggg ttgttctggt    1080
gctagagtgg ttgttacact gctatccatc ttacagcaag aaggaggtaa gatcggtgtt   1140
gccgccattt gtaatggtgg tggtggtgct tcctctattg tcattgaaaa gatatga       1197
```

<210> SEQ ID NO 108
<211> LENGTH: 398
<212> TYPE: PRT
<213> ORGANISM: Saccharomyces cerevisiae

<400> SEQUENCE: 108

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320
```

```
Phe Asn Glu Ala Phe Ser Val Val Gly Leu Val Asn Thr Lys Ile Leu
                325                 330                 335
Lys Leu Asp Pro Ser Lys Val Asn Val Tyr Gly Gly Ala Val Ala Leu
            340                 345                 350
Gly His Pro Leu Gly Cys Ser Gly Ala Arg Val Val Thr Leu Leu
        355                 360                 365
Ser Ile Leu Gln Gln Glu Gly Gly Lys Ile Gly Val Ala Ala Ile Cys
    370                 375                 380
Asn Gly Gly Gly Gly Ala Ser Ser Ile Val Ile Glu Lys Ile
385                 390                 395
```

<210> SEQ ID NO 109
<211> LENGTH: 651
<212> TYPE: DNA
<213> ORGANISM: Escherichia coli

<400> SEQUENCE: 109

```
atggatgcga aacaacgtat tgcgcgccgt gtggcgcaag agcttcgtga tggtgacatc      60
gttaacttag ggatcggttt acccacaatg gtcgccaatt atttaccgga gggtattcat     120
atcactctgc aatcggaaaa cggcttcctc ggtttaggcc cggtcacgac agcgcatcca     180
gatctggtga acgctggcgg gcaaccgtgc ggtgttttac ccggtgcagc catgtttgat     240
agcgccatgt catttgcgct aatccgtggc ggtcatattg atgcctgcgt gctcggcggt     300
ttgcaagtag acgaagaagc aaacctcgcg aactgggtag tgcctgggaa atggtgccc     360
ggtatgggtg gcgcgatgga tctggtgacc gggtcgcgca agtgatcat cgccatggaa     420
cattgcgcca agatggttc agcaaaaatt ttgcgccgct gcaccatgcc actcactgcg     480
caacatgcgg tgcatatgct ggttactgaa ctggctgtct ttcgttttat tgacggcaaa     540
atgtggctca ccgaaattgc cgacgggtgt gatttagcca ccgtgcgtgc caaaacagaa     600
gctcggtttg aagtcgccgc cgatctgaat acgcaacggg gtgatttatg a             651
```

<210> SEQ ID NO 110
<211> LENGTH: 651
<212> TYPE: DNA
<213> ORGANISM: Escherichia coli

<400> SEQUENCE: 110

```
atggatgcga aacaacgtat tgcgcgccgt gtggcgcaag agcttcgtga tggtgacatc      60
gttaacttag ggatcggttt acccacaatg gtcgccaatt atttaccgga gggtattcat     120
atcactctgc aatcggaaaa cggcttcctc ggtttaggcc cggtcacgac agcgcatcca     180
gatctggtga acgctggcgg gcaaccgtgc ggtgttttac ccggtgcagc catgtttgat     240
agcgccatgt catttgcgct aatccgtggc ggtcatattg atgcctgcgt gctcggcggt     300
ttgcaagtag acgaagaagc aaacctcgcg aactgggtag tgcctgggaa atggtgccc     360
ggtatgggtg gcgcgatgga tctggtgacc gggtcgcgca agtgatcat cgccatggaa     420
cattgcgcca agatggttc agcaaaaatt ttgcgccgct gcaccatgcc actcactgcg     480
caacatgcgg tgcatatgct ggttactgaa ctggctgtct ttcgttttat tgacggcaaa     540
atgtggctca ccgaaattgc cgacgggtgt gatttagcca ccgtgcgtgc caaaacagaa     600
gctcggtttg aagtcgccgc cgatctgaat acgcaacggg gtgatttatg a             651
```

<210> SEQ ID NO 111
<211> LENGTH: 216
<212> TYPE: PRT

<213> ORGANISM: Escherichia coli

<400> SEQUENCE: 111

Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
    50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu
        115                 120                 125

Val Thr Gly Ser Arg Lys Val Ile Ile Ala Met Glu His Cys Ala Lys
    130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
        195                 200                 205

Leu Asn Thr Gln Arg Gly Asp Leu
    210                 215

<210> SEQ ID NO 112
<211> LENGTH: 663
<212> TYPE: DNA
<213> ORGANISM: Escherichia coli

<400> SEQUENCE: 112

```
atgaaaacaa aattgatgac attacaagac gccaccggct tctttcgtga cggcatgacc      60
atcatggtgg gcggatttat ggggattggc actccatccc gcctggttga agcattactg     120
gaatctggtg ttcgcgacct gacattgata gccaatgata ccgcgtttgt tgataccggc     180
atcggtccgc tcatcgtcaa tggtcgagtc cgcaaagtga ttgcttcaca tatcggcacc     240
aacccggaaa caggtcggcg catgatatct ggtgagatgg acgtcgttct ggtgccgcaa     300
ggtacgctaa tcgagcaaat cgctgtggt ggagctggac ttggtggttt tctcacccca     360
acgggtgtcg gcaccgtcgt agaggaaggc aaacagacac tgacactcga cggtaaaacc     420
tggctgctcg aacgcccact gcgcgccgac ctggcgctaa ttcgcgctca tcgttgcgac     480
acacttggca acctgaccta tcaacttagc gcccgcaact ttaacccccct gatagccctt     540
gcggctgata tcacgctggt agagccagat gaactggtcg aaaccggcga gctgcaacct     600
gaccatattg tcacccctgg tgccgttatc gaccacatca tcgtttcaca ggagagcaaa     660
taa                                                                    663
```

```
<210> SEQ ID NO 113
<211> LENGTH: 663
<212> TYPE: DNA
<213> ORGANISM: Escherichia coli

<400> SEQUENCE: 113
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat tcgctgtggt ggagctggac ttggtggttt tctcacccca   360
acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaaccccct gatagccctt   540
gcggctgata tcacgctggt agagccagat gaactggtcg aaaccggcga gctgcaacct   600
gaccatattg tcacccctgg tgccgttatc gaccacatca tcgtttcaca ggagagcaaa   660
taa                                                                  663

<210> SEQ ID NO 114
<211> LENGTH: 220
<212> TYPE: PRT
<213> ORGANISM: Escherichia coli

<400> SEQUENCE: 114
```

Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys

<210> SEQ ID NO 115
<211> LENGTH: 735
<212> TYPE: DNA
<213> ORGANISM: Clostridium acetobutylicum

<400> SEQUENCE: 115

```
atgttaaagg atgaagtaat taaacaaatt agcacgccat taacttcgcc tgcatttcct      60
agaggaccct ataaatttca taatcgtgag tattttaaca ttgtatatcg tacagatatg     120
gatgcacttc gtaaagttgt gccagagcct ttagaaattg atgagccctt agtcaggttt     180
gaaattatgg caatgcatga tacgagtgga cttggttgtt atacagaaag cggacaggct     240
attcccgtaa gctttaatgg agttaaggga gattatcttc atatgatgta tttagataat     300
gagcctgcaa ttgcagtagg aagggaatta agtgcatatc ctaaaaagct cgggtatcca     360
aagcttttg tggattcaga tactttagta ggaactttag actatggaaa acttagagtt     420
gcgacagcta caatggggta caaacataaa gccttagatg ctaatgaagc aaaggatcaa     480
atttgtcgcc ctaattatat gttgaaaata tacccaatt atgatggaag ccctagaata     540
tgtgagctta taaatgcgaa aatcacagat gttaccgtac atgaagcttg dacaggacca     600
actcgactgc agttatttga tcacgctatg gcgccactta atgatttgcc agtaaaagag     660
attgtttcta gctctcacat tcttgcagat ataatattgc ctagagctga agttatatat     720
gattatctta agtaa                                                      735
```

<210> SEQ ID NO 116
<211> LENGTH: 735
<212> TYPE: DNA
<213> ORGANISM: Clostridium acetobutylicum

<400> SEQUENCE: 116

```
atgctgaagg acgaggttat taagcagatt agcaccccgc tgaccagccc ggcgttcccg      60
cgtggtccgt acaagttcca taatcgcgaa tacttcaaca ttgtgtatcg taccgacatg     120
gatgcgctgc gtaaggtggt tccggagccg ctggaaattg acgagccgct ggttcgtttc     180
gaaatcatgg cgatgcacga taccagcggt ctgggctgct acaccgagag cggtcaggcg     240
attccggtga gctttaacgg tgttaaaggc gactacctgc acatgatgta tctggataac     300
gaaccggcga ttgcggtggg tcgtgagctg agcgcgtacc cgaagaaact gggctatccg     360
aagctgttcg tggacagcga tacccctggtg ggcaccctgg actacggcaa actgcgtgtt     420
gcgaccgcga ccatgggcta taagcacaaa gcgctggacg cgaacgaagc gaaggatcag     480
atttgccgtc cgaactacat gctgaaaatc attccgaact atgacggtag cccgcgtatc     540
tgcgaactga ttaacgcgaa gatcaccgat gttaccgttc atgaggcgtg gaccggcccg     600
acccgtctgc aactgtttga ccacgcgatg gcgccgctga cgatctgcc ggtgaaagag     660
atcgttagca gcagccacat cctggcggac atcatcctgc cgcgtgcgga agttatctac     720
gattacctga agtaa                                                      735
```

<210> SEQ ID NO 117
<211> LENGTH: 244
<212> TYPE: PRT
<213> ORGANISM: Clostridium acetobutylicum

<400> SEQUENCE: 117

Met Leu Lys Asp Glu Val Ile Lys Gln Ile Ser Thr Pro Leu Thr Ser

```
  1               5                  10                 15
Pro Ala Phe Pro Arg Gly Pro Tyr Lys Phe His Asn Arg Glu Tyr Phe
                 20                 25                 30

Asn Ile Val Tyr Arg Thr Asp Met Asp Ala Leu Arg Lys Val Val Pro
                 35                 40                 45

Glu Pro Leu Glu Ile Asp Pro Leu Val Arg Phe Glu Ile Met Ala
 50                 55                 60

Met His Asp Thr Ser Gly Leu Gly Cys Tyr Thr Glu Ser Gly Gln Ala
 65                 70                 75                 80

Ile Pro Val Ser Phe Asn Gly Val Lys Gly Asp Tyr Leu His Met Met
                 85                 90                 95

Tyr Leu Asp Asn Glu Pro Ala Ile Ala Val Gly Arg Glu Leu Ser Ala
                100                105                110

Tyr Pro Lys Lys Leu Gly Tyr Pro Lys Leu Phe Val Asp Ser Asp Thr
                115                120                125

Leu Val Gly Thr Leu Asp Tyr Gly Lys Leu Arg Val Ala Thr Ala Thr
130                135                140

Met Gly Tyr Lys His Lys Ala Leu Asp Ala Asn Glu Ala Lys Asp Gln
145                150                155                160

Ile Cys Arg Pro Asn Tyr Met Leu Lys Ile Ile Pro Asn Tyr Asp Gly
                165                170                175

Ser Pro Arg Ile Cys Glu Leu Ile Asn Ala Lys Ile Thr Asp Val Thr
                180                185                190

Val His Glu Ala Trp Thr Gly Pro Thr Arg Leu Gln Leu Phe Asp His
                195                200                205

Ala Met Ala Pro Leu Asn Asp Leu Pro Val Lys Glu Ile Val Ser Ser
210                215                220

Ser His Ile Leu Ala Asp Ile Ile Leu Pro Arg Ala Glu Val Ile Tyr
225                230                235                240

Asp Tyr Leu Lys
```

<210> SEQ ID NO 118
<211> LENGTH: 741
<212> TYPE: DNA
<213> ORGANISM: Clostridium beijerinckii

<400> SEQUENCE: 118

| | |
|---|---:|
| atgttagaaa gtgaagtatc taaacaaatt acaactccac ttgctgctcc agcgtttcct | 60 |
| agaggaccat ataggtttca caatagagaa tatctaaaca ttatttatcg aactgattta | 120 |
| gatgctcttc gaaaaatagt accagagcca cttgaattag atagagcata tgttagattt | 180 |
| gaaatgatgg ctatgcctga tacaaccgga ctaggctcat atacagaatg ggtcaagct | 240 |
| attccagtaa atataatgg tgttaagggt gactacttgc atatgatgta tctagataat | 300 |
| gaacctgcta ttgctgttgg aagagaaagt agcgcttatc caaaaaagct tggctatcca | 360 |
| aagctatttg ttgattcaga tactttagtt gggacactta aatatggtac attaccagta | 420 |
| gctactgcaa caatgggata taagcacgag cctctagatc ttaaagaagc ctatgctcaa | 480 |
| attgcaagac ccaattttat gctaaaaatc attcaaggtt acgatggtaa gccaagaatt | 540 |
| tgtgaactaa tatgtgcaga aaatactgat ataactattc acggtgcttg gactggaagt | 600 |
| gcacgtctac aattatttag ccatgcacta gctcctcttg ctgatttacc tgtattagag | 660 |
| attgtatcag catctcatat cctcacagat ttaactcttg aacacctaa ggttgtacat | 720 |
| gattatcttt cagtaaaata a | 741 |

<210> SEQ ID NO 119
<211> LENGTH: 741
<212> TYPE: DNA
<213> ORGANISM: Clostridium beijerinckii

<400> SEQUENCE: 119

```
atgctggaga gcgaagttag caaacaaatc accaccccgc tggcggcgcc ggcgttcccg      60
cgtggcccgt accgttttca taaccgtgag tacctgaaca tcatttatcg taccgacctg     120
gatgcgctgc gtaagattgt gccggagccg ctggaactgg accgtgcgta cgttcgtttc     180
gagatgatgg cgatgccgga taccaccggt ctgggcagct acaccgaatg cggtcaggcg     240
atcccggtga agtataacgg tgttaaaggc gactacctgc acatgatgta tctggataac     300
gagccggcga ttgcggtggg tcgtgaaagc agcgcgtacc cgaagaaact gggctatccg     360
aagctgtttg tggacagcga taccctggtg gcacccctga aatatggcac cctgccggtt     420
gcgaccgcga ccatgggcta caagcacgag ccgctggacc tgaaagaagc gtatgcgcag     480
attgcgcgtc cgaacttcat gctgaagatc attcaaggtt atgacggcaa accgcgtatc     540
tgcgagctga tttgcgcgga aaacaccgat atcaccatcc atggtgcgtg gaccggcagc     600
gcgcgtctgc aactgtttag ccatgcgctg gcgccgctgg cggatctgcc ggtgctggaa     660
atcgttagcg cgagccacat tctgaccgat ctgaccctgg caccccgaa ggttgtgcat     720
gactatctga gcgtgaagta a                                               741
```

<210> SEQ ID NO 120
<211> LENGTH: 246
<212> TYPE: PRT
<213> ORGANISM: Clostridium beijerinckii

<400> SEQUENCE: 120

```
Met Leu Glu Ser Glu Val Ser Lys Gln Ile Thr Thr Pro Leu Ala Ala
1               5                   10                  15

Pro Ala Phe Pro Arg Gly Pro Tyr Arg Phe His Asn Arg Glu Tyr Leu
            20                  25                  30

Asn Ile Ile Tyr Arg Thr Asp Leu Asp Ala Leu Arg Lys Ile Val Pro
        35                  40                  45

Glu Pro Leu Glu Leu Asp Arg Ala Tyr Val Arg Phe Glu Met Met Ala
    50                  55                  60

Met Pro Asp Thr Thr Gly Leu Gly Ser Tyr Thr Glu Cys Gly Gln Ala
65                  70                  75                  80

Ile Pro Val Lys Tyr Asn Gly Val Lys Gly Asp Tyr Leu His Met Met
                85                  90                  95

Tyr Leu Asp Asn Glu Pro Ala Ile Ala Val Gly Arg Glu Ser Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Lys Tyr Gly Thr Leu Pro Val Ala Thr Ala Thr
    130                 135                 140

Met Gly Tyr Lys His Glu Pro Leu Asp Leu Lys Glu Ala Tyr Ala Gln
145                 150                 155                 160

Ile Ala Arg Pro Asn Phe Met Leu Lys Ile Ile Gln Gly Tyr Asp Gly
                165                 170                 175

Lys Pro Arg Ile Cys Glu Leu Ile Cys Ala Glu Asn Thr Asp Ile Thr
            180                 185                 190
```

Ile His Gly Ala Trp Thr Gly Ser Ala Arg Leu Gln Leu Phe Ser His
        195                 200                 205

Ala Leu Ala Pro Leu Ala Asp Leu Pro Val Leu Glu Ile Val Ser Ala
    210                 215                 220

Ser His Ile Leu Thr Asp Leu Thr Leu Gly Thr Pro Lys Val Val His
225                 230                 235                 240

Asp Tyr Leu Ser Val Lys
                245

<210> SEQ ID NO 121
<211> LENGTH: 897
<212> TYPE: DNA
<213> ORGANISM: Homo sapiens

<400> SEQUENCE: 121

| | |
|---|---|
| atggaagaga agcagatcct gtgcgtgggg ctagtggtgc tggacgtcat cagcctggtg | 60 |
| gacaagtacc ctaaggagga ctcggagata aggtgtttgt cccagagatg gcagcgcgga | 120 |
| ggcaacgcgt ccaactcctg caccgttctc tccctgctcg agccccctg tgccttcatg | 180 |
| ggctcaatgg ctcctggcca tgttgctgat tttgtcctgg atgacctccg ccgctattct | 240 |
| gtggacctac gctacacagt ctttcagacc acaggctccg tccccatcgc cacggtcatc | 300 |
| atcaacgagg ccagtggtag ccgcaccatc ctatactatg caggagcct gccagatgtg | 360 |
| tctgctacag actttgagaa ggttgatctg acccagttca gtggatcca cattgagggc | 420 |
| cggaacgcat cggagcaggt gaagatgctg cagcggatag acgcacacaa caccaggcag | 480 |
| cctccagagc agaagatccg ggtgtccgtg gaggtggaga agccacgaga ggagctcttc | 540 |
| cagctgtttg gctacggaga cgtggtgttt gtcagcaaag atgtggccaa gcacttgggg | 600 |
| ttccagtcag cagaggaagc cttgaggggc ttgtatggtc gtgtgaggaa aggggctgtg | 660 |
| cttgtctgtg cctgggctga ggagggcgcc gacgccctgg gccctgatgg caaattgctc | 720 |
| cactcggatg ctttccccgcc accccgcgtg gtggatacac tgggagctgg agacaccttc | 780 |
| aatgcctccg tcatcttcag cctctcccag gggaggagcg tgcaggaagc actgagattc | 840 |
| gggtgccagg tggccggcaa gaagtgtggc ctgcagggct tgatggcat cgtttaa | 897 |

<210> SEQ ID NO 122
<211> LENGTH: 897
<212> TYPE: DNA
<213> ORGANISM: Homo sapiens

<400> SEQUENCE: 122

| | |
|---|---|
| atggaggaaa agcaaattct gtgcgttggt ctggtggttc tggacgtgat tagcctggtt | 60 |
| gataagtacc cgaaagagga tagcgaaatc cgttgcctga ccagcgttg caacgtggt | 120 |
| ggcaacgcga gcaatagctg caccgttctg agcctgctgg gtgcgccgtg cgcgttcatg | 180 |
| ggtagcatgg cgccgggtca tgttgcggac ttcctggtgg cggattttcg tcgtcgtggt | 240 |
| gtggacgtta gccaggttgc gtggcaaagc aagggcgata ccccgagctc ctgctgcatc | 300 |
| attaacaaca gcaacggtaa ccgtaccatt gtgctgcacg acaccagcct gccggatgtt | 360 |
| agcgcgaccg acttcgagaa ggtggatctg acccagttta atggattca cattgagggc | 420 |
| cgtaacgcga gcgaacaggt taaaatgctg caacgtattg atgcgcacaa cacccgtcag | 480 |
| ccgccggaac aaaagattcg tgtgagcgtt gaggtggaaa accgcgtga ggaactgttc | 540 |
| caactgtttg gttacggcga cgtggttttc gttagcaagg atgtggcgaa acacctgggt | 600 |
| tttcaaagcg cggaggaagc gctgcgtggt ctgtatggcc gtgtgcgtaa aggcgcggtt | 660 |

```
ctggtgtgcg cgtgggcgga ggaaggcgcg gatgcgctgg gtccggatgg caaactgctg        720
cacagcgatg cgttcccgcc gccgcgtgtg gttgacaccc tgggtgcggg cgataccttc        780
aacgcgagcg ttatctttag cctgagccag ggccgtagcg tgcaagaggc gctgcgtttc        840
ggctgccaag ttgcgggtaa aaaatgcggt ctgcaaggct tgacggtat cgtgtaa            897
```

<210> SEQ ID NO 123
<211> LENGTH: 298
<212> TYPE: PRT
<213> ORGANISM: Homo sapiens

<400> SEQUENCE: 123

```
Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30

Leu Ser Gln Arg Trp Gln Arg Gly Gly Asn Ala Ser Asn Ser Cys Thr
        35                  40                  45

Val Leu Ser Leu Leu Gly Ala Pro Cys Ala Phe Met Gly Ser Met Ala
    50                  55                  60

Pro Gly His Val Ala Asp Phe Leu Val Ala Asp Phe Arg Arg Arg Gly
65                  70                  75                  80

Val Asp Val Ser Gln Val Ala Trp Gln Ser Lys Gly Asp Thr Pro Ser
                85                  90                  95

Ser Cys Cys Ile Ile Asn Asn Ser Asn Gly Asn Arg Thr Ile Val Leu
            100                 105                 110

His Asp Thr Ser Leu Pro Asp Val Ser Ala Thr Asp Phe Glu Lys Val
        115                 120                 125

Asp Leu Thr Gln Phe Lys Trp Ile His Ile Glu Gly Arg Asn Ala Ser
    130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190

Lys Asp Val Ala Lys His Leu Gly Phe Gln Ser Ala Glu Glu Ala Leu
        195                 200                 205

Arg Gly Leu Tyr Gly Arg Val Arg Lys Gly Ala Val Leu Val Cys Ala
    210                 215                 220

Trp Ala Glu Glu Gly Ala Asp Ala Leu Gly Pro Asp Gly Lys Leu Leu
225                 230                 235                 240

His Ser Asp Ala Phe Pro Pro Arg Val Val Asp Thr Leu Gly Ala
                245                 250                 255

Gly Asp Thr Phe Asn Ala Ser Val Ile Phe Ser Leu Ser Gln Gly Arg
            260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
    290                 295
```

<210> SEQ ID NO 124
<211> LENGTH: 1095
<212> TYPE: DNA
<213> ORGANISM: Homo sapiens

<400> SEQUENCE: 124

```
atggcccacc gatttccagc cctcacccag gagcagaaga aggagctctc agaaattgcc      60
cagagcattg ttgccaatgg aaagggatc ctggctgcag atgaatctgt aggtaccatg     120
gggaaccgcc tgcagaggat caaggtggaa aacactgaag agaaccgccg gcagttccga     180
gaaatcctct tctctgtgga cagttccatc aaccagagca tcggggtgt gatccttttc      240
cacgagaccc tctaccagaa ggacagccag ggaaagctgt tcagaaacat cctcaaggaa     300
aagggatcg tggtgggaat caagttagac caaggaggtg ctcctcttgc aggaacaaac     360
aaagaaacca ccattcaagg gcttgatggc ctctcagagc gctgtgctca gtacaagaaa     420
gatggtgttg actttgggaa gtggcgtgct gtgctgagga ttgccgacca gtgtccatcc     480
agcctcgcta tccaggaaaa cgccaacgcc ctggctcgct acgccagcat ctgtcagcag     540
aatggactgg tacctattgt tgaaccagag gtaattcctg atggagacca tgacctggaa     600
cactgccagt atgttactga aaggtcctg gctgctgtct acaaggccct gaatgaccat      660
catgtttacc tggagggcac cctgctaaag cccaacatgg tgactgctgg acatgcctgc     720
accaagaagt atactccaga caagtagct atggccaccg taacagctct ccaccgtact      780
gttcctgcag ctgttcctgg catctgcttt ttgtctggtg gcatgagtga agaggatgcc     840
actctcaacc tcaatgctat caaccttgc cctctaccaa agccctggaa actaagtttc      900
tcttatggac gggccctgca ggccagtgca ctggctgcct ggggtggcaa ggctgcaaac     960
aaggaggcaa cccaggaggc ttttatgaag cgggccatgg ctaactgcca ggcggccaaa    1020
ggacagtatg ttcacacggg ttcttctggg gctgcttcca cccagtcgct cttcacagcc    1080
tgctatacct actag                                                    1095
```

<210> SEQ ID NO 125
<211> LENGTH: 1095
<212> TYPE: DNA
<213> ORGANISM: Homo sapiens

<400> SEQUENCE: 125

```
atggcgcacc gttttccggc gctgacccaa gagcagaaga aggagctgag cgagattgcg      60
cagagcatcg tggcgaatgg taaaggtatt ctggcggcgg atgagagcgt tggtaccatg     120
ggcaaccgtc tgcagcgtat taaggtggag aacaccgagg aaaaccgtcg tcaattccgt     180
gaaatcctgt ttagcgttga tagcagcatc aaccagagca ttggtggcgt gatcctgttc     240
cacgaaaccc tgtaccagaa ggacagccaa ggtaaactgt tcgtaacat tctgaaggaa      300
aaaggtattg tggttggcat caagctggat caaggtggcg cgccgctggc gggcaccaac     360
aaggaaacca ccatccaggg tctggacggc ctgagcgaac gttgcgcgca atataagaaa     420
gatggtgttg acttcggcaa gtggcgtgcg gtgctgcgta ttgcggacca gtgcccgagc     480
agcctggcga tccaagaaaa cgcgaacgcg ctggcgcgtt acgcgagcat ctgccagcaa     540
aacggtctgg tgccgattgt tgagccggaa gttatcccgg acggcgatca cgacctggag     600
cactgccagt atgtgaccga aaaggttctg gcggcggtgt acaaagcgct gaacgatcac     660
cacgtttatc tggagggtac cctgctgaaa ccgaacatgg tgaccgcggg ccatgcgtgc     720
accaagaaat acaccccgga acaggtggcg atggcgaccg tgaccgcgct gcaccgtacc     780
gttccggcgg cggtgccggg tatttgcttt ctgagcggtg gcatgagcga agaggacgcg     840
accctgaacc tgaacgcgat caacctgtgc ccgctgccga agccgtggaa actgagcttc     900
```

```
agctacggcc gtgcgctgca ggcgagcgcg ctggcggcgt ggggtggcaa ggcggcgaac      960
aaagaggcga cccaagaagc gtttatgaag cgtgcgatgg cgaactgcca ggcggcgaaa     1020
ggtcaatatg tgcataccgg cagcagcggt gcggcgagca cccagagcct gtttaccgcg     1080
tgctatacct attaa                                                      1095
```

<210> SEQ ID NO 126
<211> LENGTH: 364
<212> TYPE: PRT
<213> ORGANISM: Homo sapiens

<400> SEQUENCE: 126

```
Met Ala His Arg Phe Pro Ala Leu Thr Gln Glu Gln Lys Lys Glu Leu
1               5                   10                  15

Ser Glu Ile Ala Gln Ser Ile Val Ala Asn Gly Lys Gly Ile Leu Ala
            20                  25                  30

Ala Asp Glu Ser Val Gly Thr Met Gly Asn Arg Leu Gln Arg Ile Lys
        35                  40                  45

Val Glu Asn Thr Glu Glu Asn Arg Arg Gln Phe Arg Glu Ile Leu Phe
    50                  55                  60

Ser Val Asp Ser Ser Ile Asn Gln Ser Ile Gly Gly Val Ile Leu Phe
65                  70                  75                  80

His Glu Thr Leu Tyr Gln Lys Asp Ser Gln Gly Lys Leu Phe Arg Asn
                85                  90                  95

Ile Leu Lys Glu Lys Gly Ile Val Val Gly Ile Lys Leu Asp Gln Gly
            100                 105                 110

Gly Ala Pro Leu Ala Gly Thr Asn Lys Glu Thr Thr Ile Gln Gly Leu
        115                 120                 125

Asp Gly Leu Ser Glu Arg Cys Ala Gln Tyr Lys Lys Asp Gly Val Asp
    130                 135                 140

Phe Gly Lys Trp Arg Ala Val Leu Arg Ile Ala Asp Gln Cys Pro Ser
145                 150                 155                 160

Ser Leu Ala Ile Gln Glu Asn Ala Asn Ala Leu Ala Arg Tyr Ala Ser
                165                 170                 175

Ile Cys Gln Gln Asn Gly Leu Val Pro Ile Val Glu Pro Glu Val Ile
            180                 185                 190

Pro Asp Gly Asp His Asp Leu Glu His Cys Gln Tyr Val Thr Glu Lys
        195                 200                 205

Val Leu Ala Ala Val Tyr Lys Ala Leu Asn Asp His His Val Tyr Leu
    210                 215                 220

Glu Gly Thr Leu Leu Lys Pro Asn Met Val Thr Ala Gly His Ala Cys
225                 230                 235                 240

Thr Lys Lys Tyr Thr Pro Glu Gln Val Ala Met Ala Thr Val Thr Ala
                245                 250                 255

Leu His Arg Thr Val Pro Ala Ala Val Pro Gly Ile Cys Phe Leu Ser
            260                 265                 270

Gly Gly Met Ser Glu Glu Asp Ala Thr Leu Asn Leu Asn Ala Ile Asn
        275                 280                 285

Leu Cys Pro Leu Pro Lys Pro Trp Lys Leu Ser Phe Ser Tyr Gly Arg
    290                 295                 300

Ala Leu Gln Ala Ser Ala Leu Ala Ala Trp Gly Gly Lys Ala Ala Asn
305                 310                 315                 320

Lys Glu Ala Thr Gln Glu Ala Phe Met Lys Arg Ala Met Ala Asn Cys
                325                 330                 335
```

Gln Ala Ala Lys Gly Gln Tyr Val His Thr Gly Ser Ser Gly Ala Ala
                340                 345                 350

Ser Thr Gln Ser Leu Phe Thr Ala Cys Tyr Thr Tyr
        355                 360

<210> SEQ ID NO 127
<211> LENGTH: 747
<212> TYPE: DNA
<213> ORGANISM: Caulobacter crescentus

<400> SEQUENCE: 127

| | | | | | |
|---|---|---|---|---|---|
| atgtcctcag | ccatctatcc | cagcctgaag | ggcaagcgcg | tcgtcatcac | cggcggcggc | 60 |
| tcgggcatcg | gggccggcct | caccgccggc | ttcgcccgtc | agggcgcgga | ggtgatcttc | 120 |
| ctcgacatcg | ccgacgagga | ctccagggct | cttgaggccg | agctggccgg | ctcgccgatc | 180 |
| ccgccggtct | acaagcgctg | cgacctgatg | aacctcgagg | cgatcaaggc | ggtcttcgcc | 240 |
| gagatcggcg | acgtcgacgt | gctggtcaac | aacgccggca | tgacgaccg | ccacaagctg | 300 |
| gccgacgtga | ccggcgccta | tgggacgag | cggatcaacg | tcaacctgcg | ccacatgctg | 360 |
| ttctgcaccc | aggccgtcgc | gccgggcatg | aagaagcgtg | gcggcgggc | ggtgatcaac | 420 |
| ttcggttcga | tcagctggca | cctggggctt | gaggacctcg | tcctctacga | aaccgccaag | 480 |
| gccggcatcg | aaggcatgac | ccgcgcgctg | gcccgggagc | tgggtcccga | cgacatccgc | 540 |
| gtcacctgcg | tggtgccggg | caacgtcaag | accaagcgcc | aggagaagtg | gtacacgccc | 600 |
| gaaggcgagg | cccagatcgt | ggcggcccaa | tgcctgaagg | ccgcatcgt | cccggagaac | 660 |
| gtcgccgcgc | tggtgctgtt | cctggcctcg | gatgacgcgt | cgctctgcac | cggccacgaa | 720 |
| tactggatcg | acgccggctg | gcgttga | | | | 747 |

<210> SEQ ID NO 128
<211> LENGTH: 747
<212> TYPE: DNA
<213> ORGANISM: Caulobacter crescentus

<400> SEQUENCE: 128

| | | | | | |
|---|---|---|---|---|---|
| atgagcagcg | cgatctaccc | gagcctgaaa | ggtaaacgtg | tggtgattac | cggcggcggc | 60 |
| agcggcattg | gtgcgggcct | gaccgcgggc | ttcgcgcgtc | agggtgcgga | agtgatcttt | 120 |
| ctggacattg | cggacgaaga | tagccgtgcg | ctggaggcgg | aactggcggg | cagcccgatc | 180 |
| ccgccggtgt | acaagcgttg | cgatctgatg | aacctggagg | cgatcaaagc | ggttttcgcg | 240 |
| gaaattggcg | acgtggatgt | tctggtgaac | aacgcgggta | acgacgaccg | tcacaagctg | 300 |
| gcggatgtga | ccggtgcgta | ttgggatgag | cgtattaacg | ttaacctgcg | tcacatgctg | 360 |
| ttctgcaccc | aggcggtggc | gccgggtatg | aagaaacgtg | gtggcggtgc | ggttatcaac | 420 |
| tttggcagca | ttagctggca | cctgggtctg | gaggacctgg | tgctgtacga | aaccgcgaaa | 480 |
| gcgggcatcg | agggtatgac | ccgtgcgctg | gcgcgtgaac | tgggtccgga | cgatattcgt | 540 |
| gtgacctgcg | tggttccggg | taacgttaag | accaaacgtc | aagagaagtg | gtataccccg | 600 |
| gagggtgaag | cgcagattgt | tgcggcgcaa | tgcctgaaag | gtcgtattgt | tccggaaaac | 660 |
| gtggcggcgc | tggttctgtt | tctggcgagc | gatgatgcga | gcctgtgcac | cggccatgag | 720 |
| tattggattg | atgcgggctg | gcgttaa | | | | 747 |

<210> SEQ ID NO 129
<211> LENGTH: 248
<212> TYPE: PRT
<213> ORGANISM: Caulobacter crescentus

<400> SEQUENCE: 129

Met Ser Ser Ala Ile Tyr Pro Ser Leu Lys Gly Lys Arg Val Val Ile
1               5                   10                  15

Thr Gly Gly Ser Gly Ile Gly Ala Gly Leu Thr Ala Gly Phe Ala
            20                  25                  30

Arg Gln Gly Ala Glu Val Ile Phe Leu Asp Ile Ala Asp Glu Asp Ser
        35                  40                  45

Arg Ala Leu Glu Ala Glu Leu Ala Gly Ser Pro Ile Pro Pro Val Tyr
    50                  55                  60

Lys Arg Cys Asp Leu Met Asn Leu Glu Ala Ile Lys Ala Val Phe Ala
65                  70                  75                  80

Glu Ile Gly Asp Val Asp Val Leu Val Asn Asn Ala Gly Asn Asp Asp
                85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
        115                 120                 125

Gly Met Lys Lys Arg Gly Gly Ala Val Ile Asn Phe Gly Ser Ile
    130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Gln Ile Val Ala
        195                 200                 205

Ala Gln Cys Leu Lys Gly Arg Ile Val Pro Glu Asn Val Ala Ala Leu
    210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245

<210> SEQ ID NO 130
<211> LENGTH: 1173
<212> TYPE: DNA
<213> ORGANISM: Haloferax volcanii

<400> SEQUENCE: 130
atgagccccg ccccaccga catcgtcgag gagttcacgc gccgcgactg gcagggagac     60
gacgtgacgg gcaccgtgcg ggtcgccatg atcggcctcg gctggtggac ccgcgacgag    120
gcgattcccg cggtcgaggc gtccgagttc tgcgagacga cggtcgtcgt cagcagttcg    180
aaggagaaag ccgagggcgc gacggcgttg accgagtcga taacccacgg cctcaccatc    240
gacgagttcc acgagggggt cgccgccgac gcctacgacg cggtgtacgt cgtcacgccg    300
aacggtctgc atctcccgta cgtcgagacc gccgccgagt tggggaaggc ggtcctctgc    360
gagaaaccgc tggaagcgtc ggtcgagcgg gccgaaaagc tcgtcgccgc ctgcgaccgc    420
gccgacgtgc ccctgatggt cgcctatcgg atgcagaccg agccggccgt ccggcgcgcc    480
cgcgaactcg tcgaggccgg cgtcatcggc gagccggtgt cgtccacgg ccacatgtcc    540 cagcgcctgc tcgacgaggt cgtccccgac cccgaccagt ggcggctcga ccccgaactc    600

-continued

```
tccggcggcg cgaccgtcat ggacatcggg ctctacccgc tgaacaccgc ccggttcgtc      660
ctcgacgccg accccgtccg cgtcagggcg accgcccgcg tcgacgacga ggcgttcgag      720
gccgtcggcg acgagcacgt cagtttcggc gtcgacttcg acgacggcac gctcgcggtc      780
tgcaccgcca gccagtcggc ttaccagttg agccacctcc gggtgaccgg caccgagggc      840
gaactcgaaa tcgagcccgc gttctacaac cgccaaaagc ggggattccg actgtcgtgg      900
ggggaccagt ccgccgacta cgacttcgag caggtaaacc agatgacgga ggagttcgac      960
tacttcgcgt cccggctcct gtcggattcc gaccccgcgc ccgacggcga ccacgcgctc     1020
gtggacatgc gcgcgatgga cgcgatttac gccgcggcgg agcgcgggac cgatgtcgcc     1080
gtcgacgccg ccgactccga ttccgccgac tccgattccg ccgacgctgc cgccgccaac     1140
cacgacgccg accccgattc cgacgggacg tag                                  1173
```

<210> SEQ ID NO 131
<211> LENGTH: 390
<212> TYPE: PRT
<213> ORGANISM: Haloferax volcanii

<400> SEQUENCE: 131

```
Met Ser Pro Ala Pro Thr Asp Ile Val Glu Glu Phe Thr Arg Arg Asp
1               5                   10                  15

Trp Gln Gly Asp Asp Val Thr Gly Thr Val Arg Val Ala Met Ile Gly
            20                  25                  30

Leu Gly Trp Trp Thr Arg Asp Glu Ala Ile Pro Ala Val Glu Ala Ser
        35                  40                  45

Glu Phe Cys Glu Thr Thr Val Val Ser Ser Lys Glu Lys Ala
    50                  55                  60

Glu Gly Ala Thr Ala Leu Thr Glu Ser Ile Thr His Gly Leu Thr Tyr
65                  70                  75                  80

Asp Glu Phe His Glu Gly Val Ala Ala Asp Ala Tyr Asp Ala Val Tyr
                85                  90                  95

Val Val Thr Pro Asn Gly Leu His Leu Pro Tyr Val Glu Thr Ala Ala
            100                 105                 110

Glu Leu Gly Lys Ala Val Leu Cys Glu Lys Pro Leu Glu Ala Ser Val
        115                 120                 125

Glu Arg Ala Glu Lys Leu Val Ala Ala Cys Asp Arg Ala Asp Val Pro
    130                 135                 140

Leu Met Val Ala Tyr Arg Met Gln Thr Glu Pro Ala Val Arg Arg Ala
145                 150                 155                 160

Arg Glu Leu Val Glu Ala Gly Val Ile Gly Glu Pro Val Phe Val His
                165                 170                 175

Gly His Met Ser Gln Arg Leu Leu Asp Glu Val Val Pro Asp Pro Asp
            180                 185                 190

Gln Trp Arg Leu Asp Pro Glu Leu Ser Gly Gly Ala Thr Val Met Asp
        195                 200                 205

Ile Gly Leu Tyr Pro Leu Asn Thr Ala Arg Phe Val Leu Asp Ala Asp
    210                 215                 220

Pro Val Arg Val Arg Ala Thr Ala Arg Val Asp Asp Glu Ala Phe Glu
225                 230                 235                 240

Ala Val Gly Asp Glu His Val Ser Phe Gly Val Asp Phe Asp Gly
                245                 250                 255

Thr Leu Ala Val Cys Thr Ala Ser Gln Ser Ala Tyr Gln Leu Ser His
            260                 265                 270
```

```
Leu Arg Val Thr Gly Thr Glu Gly Glu Leu Glu Ile Glu Pro Ala Phe
            275                 280                 285

Tyr Asn Arg Gln Lys Arg Gly Phe Arg Leu Ser Trp Gly Asp Gln Ser
        290                 295                 300

Ala Asp Tyr Asp Phe Glu Gln Val Asn Gln Met Thr Glu Glu Phe Asp
305                 310                 315                 320

Tyr Phe Ala Ser Arg Leu Leu Ser Asp Ser Asp Pro Ala Pro Asp Gly
                325                 330                 335

Asp His Ala Leu Val Asp Met Arg Ala Met Asp Ala Ile Tyr Ala Ala
                340                 345                 350

Ala Glu Arg Gly Thr Asp Val Ala Val Asp Ala Ala Asp Ser Asp Ser
            355                 360                 365

Ala Asp Ser Asp Ser Ala Asp Ala Ala Ala Asn His Asp Ala Asp
        370                 375                 380

Pro Asp Ser Asp Gly Thr
385                 390

<210> SEQ ID NO 132
<211> LENGTH: 1176
<212> TYPE: DNA
<213> ORGANISM: Trichoderma reesei

<400> SEQUENCE: 132
atggcgtctg aaacccctta caccctgaaa tggggcatca tggccaccgg cggaatcgca      60
gagaccttct gcaaggatct cctgtgcaac cccgcgattc gaggcgccga tgatgtgcgc     120
cacgagattg tggccgtggc ctcttccagc agcagcaaga gagcagagga gttcctccag     180
agaatcgacg gtgcctttga cgccaagacg tacggatcat acccggaact tgtggcagac     240
cccaacgtcg acatcgtcta tgtggcaact ccccacagcc accacttcca gaacaccatg     300
ctggcgctgg aagccggcaa gaacgtcttg tgcgaaaagg ctttcaccgt gacggccgcg     360
caggcccgaa agctggttga cggccaag gccagaagc tcttcctgat ggaagctgtg     420
tggacacggt actttccgct gagtatcaag attcgagagc tcattgccgc cggcgagatt     480
ggcactgtct ttcgaacaat cgccgacttg tccatcaacg caaactcaga gcagggtcaa     540
gccctgaaat cgcagactc acatcgaatg gtcaacccgg acctcgcagg cggtgccacc     600
ttggatctcg agtctatcc cttgacctgg gtgttccaga ccctgtatca tttgcaaccg     660
gaggaagaca aggaggctcc caccgtggtt gcttccagca caagtacac cactggcgca     720 gacgagaata ccgccatcat ctgcagcttc cctcgccaca acagcattgg aattgcttcg     780
acgacgatga gggcggacac cgaccccgag aaggacacca ttccggcggt ccgaattcaa     840
ggatccaagg gagaaatcca agtcttcttc ccgacctacc gaccgctcaa gtacaaggtg     900
gtgaagacga acggcgaggc gcagacggtt gactgcccca tccccggaga ccccgcgcgc     960
aagggctcgg ccacggaat gttctgggag gcggacgagt gtgctcgatg ccttcgcgat    1020
ggcaagttgg agagtgccac gttgccatgg aaggagagca ttgtcattat ggaaacgatg    1080
gaggaggcgc tgaggcaggg tggcgtcacg tatccggagc tgattaccac ggatgtctat    1140
gatcccaaga gccctctcaa cacggggaat cagtag                              1176

<210> SEQ ID NO 133
<211> LENGTH: 391
<212> TYPE: PRT
<213> ORGANISM: Trichoderma reesei

<400> SEQUENCE: 133
```

```
Met Ala Ser Gly Asn Pro Tyr Thr Leu Lys Trp Gly Ile Met Ala Thr
  1               5                  10                  15

Gly Gly Ile Ala Glu Thr Phe Cys Lys Asp Leu Leu Cys Asn Pro Ala
             20                  25                  30

Ile Arg Gly Ala Asp Asp Val Arg His Glu Ile Val Ala Val Ala Ser
         35                  40                  45

Ser Ser Ser Ser Lys Arg Ala Glu Glu Phe Leu Gln Arg Ile Asp Gly
 50                      55                  60

Ala Phe Asp Ala Lys Thr Tyr Gly Ser Tyr Pro Glu Leu Val Ala Asp
 65                  70                  75                  80

Pro Asn Val Asp Ile Val Tyr Val Ala Thr Pro His Ser His His Phe
                 85                  90                  95

Gln Asn Thr Met Leu Ala Leu Glu Ala Gly Lys Asn Val Leu Cys Glu
             100                 105                 110

Lys Ala Phe Thr Val Thr Ala Ala Gln Ala Arg Lys Leu Val Glu Thr
             115                 120                 125

Ala Lys Ala Lys Lys Leu Phe Leu Met Glu Ala Val Trp Thr Arg Tyr
130                 135                 140

Phe Pro Leu Ser Ile Lys Ile Arg Glu Leu Ile Ala Ala Gly Glu Ile
145                 150                 155                 160

Gly Thr Val Phe Arg Thr Ile Ala Asp Leu Ser Ile Asn Ala Asn Ser
                165                 170                 175

Glu Gln Gly Gln Ala Leu Lys Phe Ala Asp Ser His Arg Met Val Asn
                180                 185                 190

Pro Asp Leu Ala Gly Gly Ala Thr Leu Asp Leu Gly Val Tyr Pro Leu
            195                 200                 205

Thr Trp Val Phe Gln Thr Leu Tyr His Leu Gln Pro Glu Glu Asp Lys
210                 215                 220

Glu Ala Pro Thr Val Val Ala Ser Ser Asn Lys Tyr Thr Thr Gly Ala
225                 230                 235                 240

Asp Glu Asn Thr Ala Ile Ile Cys Ser Phe Pro Arg His Asn Ser Ile
                245                 250                 255

Gly Ile Ala Ser Thr Thr Met Arg Ala Asp Thr Asp Pro Glu Lys Asp
                260                 265                 270

Thr Ile Pro Ala Val Arg Ile Gln Gly Ser Lys Gly Glu Ile Gln Val
            275                 280                 285

Phe Phe Pro Thr Tyr Arg Pro Leu Lys Tyr Lys Val Val Lys Thr Asn
290                 295                 300

Gly Glu Ala Gln Thr Val Asp Cys Pro Ile Pro Gly Asp Pro Ala Arg
305                 310                 315                 320

Lys Gly Ser Gly His Gly Met Phe Trp Glu Ala Asp Glu Cys Ala Arg
                325                 330                 335

Cys Leu Arg Asp Gly Lys Leu Glu Ser Ala Thr Leu Pro Trp Lys Glu
                340                 345                 350

Ser Ile Val Ile Met Glu Thr Met Glu Glu Ala Leu Arg Gln Gly Gly
            355                 360                 365

Val Thr Tyr Pro Glu Leu Ile Thr Thr Asp Val Tyr Asp Pro Lys Ser
370                 375                 380

Pro Leu Asn Thr Gly Asn Gln
385                 390

<210> SEQ ID NO 134
<211> LENGTH: 870
```

<212> TYPE: DNA
<213> ORGANISM: Caulobacter crescentus

<400> SEQUENCE: 134

```
atgaccgctc aagtcacttg cgtatgggat ctgaaggcca cgttgggcga aggcccgatc    60
tggcatggcg acaccctgtg gttcgtcgac atcaagcagc gtaaaatcca caactaccac   120
cccgccaccg gcgagcgctt cagcttcgac gcgccggatc aggtgacctt cctcgcgccg   180
atcgtcggcg cgaccggctt tgtcgtcggt ctgaagaccg ggattcaccg cttccacccg   240
gccacgggct tcagcctgct gctcgaggtc gaggacgcgg cgctgaacaa ccgccccaac   300
gacgccacgg tcgacgcgca aggccgtctg tggttcggca ccatgcacga cggggaagag   360
aacaatagcg gctcgctcta tcggatggac ctcaccggcg tcgcccggat ggaccgcgac   420
atctgcatca ccaacggccc gtgcgtctcg cccgacggca agaccttcta ccacaccgac   480
accctggaaa agacgatcta cgccttcgac ctggccgagg acggcctgct gtcgaacaag   540
cgcgtcttcg tgcagttcgc cctgggcgac gatgtctatc cggacggttc ggtcgtcgat   600
tccgaaggct atctgtggac cgccctgtgg ggcggtttcg gcgcggtccg cttctcgccg   660
caaggcgacg ccgtgacgcg catcgaactg cccgccccca acgtcaccaa gccctgcttc   720
ggcgggcctg acctgaagac cctctatttc accaccgccc gcaagggcct gagcgacgag   780
accctggccc agtacccgct ggccggcggt gtgttcgccg ttccggtcga tgtggccggc   840
caaccccagc atgaggtccg ccttgtctaa                                    870
```

<210> SEQ ID NO 135
<211> LENGTH: 289
<212> TYPE: PRT
<213> ORGANISM: Caulobacter crescentus

<400> SEQUENCE: 135

```
Met Thr Ala Gln Val Thr Cys Val Trp Asp Leu Lys Ala Thr Leu Gly
1               5                   10                  15
Glu Gly Pro Ile Trp His Gly Asp Thr Leu Trp Phe Val Asp Ile Lys
            20                  25                  30
Gln Arg Lys Ile His Asn Tyr His Pro Ala Thr Gly Glu Arg Phe Ser
        35                  40                  45
Phe Asp Ala Pro Asp Gln Val Thr Phe Leu Ala Pro Ile Val Gly Ala
    50                  55                  60
Thr Gly Phe Val Val Gly Leu Lys Thr Gly Ile His Arg Phe His Pro
65                  70                  75                  80
Ala Thr Gly Phe Ser Leu Leu Leu Glu Val Glu Asp Ala Ala Leu Asn
                85                  90                  95
Asn Arg Pro Asn Asp Ala Thr Val Asp Ala Gln Gly Arg Leu Trp Phe
            100                 105                 110
Gly Thr Met His Asp Gly Glu Glu Asn Asn Ser Gly Ser Leu Tyr Arg
        115                 120                 125
Met Asp Leu Thr Gly Val Ala Arg Met Asp Arg Asp Ile Cys Ile Thr
    130                 135                 140
Asn Gly Pro Cys Val Ser Pro Asp Gly Lys Thr Phe Tyr His Thr Asp
145                 150                 155                 160
Thr Leu Glu Lys Thr Ile Tyr Ala Phe Asp Leu Ala Glu Asp Gly Leu
                165                 170                 175
Leu Ser Asn Lys Arg Val Phe Val Gln Phe Ala Leu Gly Asp Asp Val
            180                 185                 190
```

```
Tyr Pro Asp Gly Ser Val Val Asp Ser Glu Gly Tyr Leu Trp Thr Ala
        195                 200                 205

Leu Trp Gly Gly Phe Gly Ala Val Arg Phe Ser Pro Gln Gly Asp Ala
    210                 215                 220

Val Thr Arg Ile Glu Leu Pro Ala Pro Asn Val Thr Lys Pro Cys Phe
225                 230                 235                 240

Gly Gly Pro Asp Leu Lys Thr Leu Tyr Phe Thr Thr Ala Arg Lys Gly
                245                 250                 255

Leu Ser Asp Glu Thr Leu Ala Gln Tyr Pro Leu Ala Gly Gly Val Phe
            260                 265                 270

Ala Val Pro Val Asp Val Ala Gly Gln Pro Gln His Glu Val Arg Leu
        275                 280                 285

Val

<210> SEQ ID NO 136
<211> LENGTH: 1776
<212> TYPE: DNA
<213> ORGANISM: Caulobacter crescentus

<400> SEQUENCE: 136
ttgtctaacc gcacgccccg ccggttccgg tcccgcgatt ggttcgataa ccccgaccat      60
atcgacatga ccgcgctcta tctggagcgc ttcatgaact acgggatcac gccggaggag     120
ctgcgcagcg gcaagccgat catcggcatc gcccagaccg cagcgacat  ctcgccctgc     180
aaccgcatcc acctggacct ggtccagcgg gtgcgggacg ggatccgcga cgccgggggc     240
atccccatgg agttcccggt ccatccgatc ttcgagaact gccgtcgccc gacggcggcg     300
ctggaccgga acctctcgta cctgggtctc gtcgagaccc tgcacggcta tccgatcgac     360
gccgtggttc tgaccaccgg ctgcgacaag accaccccgg ccgggatcat ggccgccacc     420
acggtcaata tcccggccat cgtgctgtcg ggcggcccga tgctggacgg ctggcacgag     480
aacgagctcg tgggctcggg caccgtgatc tggcgctcgc gccgcaagct ggcggccggc     540
gagatcaccg aggaagagtt catcgaccgc gccgcagct  cggcgccgtc ggcgggccac     600
tgcaacacca tgggcacggc ctcgaccatg aacgccgtgg ccgaggcgct gggcctgtcg     660
ctgaccggct gcgcggccat ccccgccccc taccgcgagc gcggccagat ggcctacaag     720
accggccagc gcatcgtcga tctggcctat gacgacgtca aaccgctcga catcctgacc     780
aagcaagcct tcgagaacgc catcgccctg gtggcggcgg ccggcggctc gaccaacgcc     840
cagccgcaca tcgtggccat ggcccgtcac gccggcgtcg agataccgc  cgacgactgg     900
cgcgcggcct atgacatccc gctgatcgtc aacatgcagc cggccggcaa gtatctgggc     960
gagcgcttcc accgagccgg cggcgcgccg gcggtgctgt gggagctgtt gcagcaaggc    1020
cgcctgcacg gcgacgtgct gaccgtcacc ggcaagacga tgagcgagaa cctgcaaggc    1080
cgcgaaacca gcgaccgcga ggtgatcttc ccgtaccacg agccgctggc cgagaaggcc    1140
gggttcctgg ttctcaaggg caacctcttc gacttcgcga tcatgaagtc cagcgtgatc    1200
ggcgaggagt tccgcaagcg ctacctgtcg cagcccggcc aggaaggcgt gttcgaagcc    1260
cgcgccatcg tgttcgacgg ctcggacgac tatcacaagc ggatcaacga tccggccctg    1320
gagatcgacg agcgctgcat cctggtgatc cgcggcgcgg gtccgatcgg ctggcccggc    1380
tcggccgagg tcgtcaacat gcagccgccg gatcaccttc tgaagaaggg gatcatgagc    1440
ctgcccaccc tgggcgatgg ccgtcagtcg ggcaccgccg acagcccctc gatcctgaac    1500
gcctcgcccg aaagcgcgat cggcggcggc ctgtcgtggc tgcgcaccgg cgacaccatc    1560
```

```
cgcatcgacc tcaacaccgg ccgctgcgac gccctggtcg acgaggcgac gatcgccgcg    1620
cgcaagcagg acggcatccc ggcggttccc gccaccatga cgccctggca ggaaatctac    1680
cgcgcccacg ccagtcagct cgacaccggc ggcgtgctgg agttcgcggt caagtaccag    1740
gacctggcgg ccaagctgcc ccgccacaac cactga                              1776
```

<210> SEQ ID NO 137
<211> LENGTH: 591
<212> TYPE: PRT
<213> ORGANISM: Caulobacter crescentus

<400> SEQUENCE: 137

```
Met Ser Asn Arg Thr Pro Arg Arg Phe Arg Ser Arg Asp Trp Phe Asp
1               5                   10                  15

Asn Pro Asp His Ile Asp Met Thr Ala Leu Tyr Leu Glu Arg Phe Met
            20                  25                  30

Asn Tyr Gly Ile Thr Pro Glu Glu Leu Arg Ser Gly Lys Pro Ile Ile
        35                  40                  45

Gly Ile Ala Gln Thr Gly Ser Asp Ile Ser Pro Cys Asn Arg Ile His
    50                  55                  60

Leu Asp Leu Val Gln Arg Val Arg Asp Gly Ile Arg Asp Ala Gly Gly
65                  70                  75                  80

Ile Pro Met Glu Phe Pro Val His Pro Ile Phe Glu Asn Cys Arg Arg
                85                  90                  95

Pro Thr Ala Ala Leu Asp Arg Asn Leu Ser Tyr Leu Gly Leu Val Glu
            100                 105                 110

Thr Leu His Gly Tyr Pro Ile Asp Ala Val Val Leu Thr Thr Gly Cys
        115                 120                 125

Asp Lys Thr Thr Pro Ala Gly Ile Met Ala Ala Thr Thr Val Asn Ile
    130                 135                 140

Pro Ala Ile Val Leu Ser Gly Gly Pro Met Leu Asp Gly Trp His Glu
145                 150                 155                 160

Asn Glu Leu Val Gly Ser Gly Thr Val Ile Trp Arg Ser Arg Arg Lys
                165                 170                 175

Leu Ala Ala Gly Glu Ile Thr Glu Glu Phe Ile Asp Arg Ala Ala
            180                 185                 190

Ser Ser Ala Pro Ser Ala Gly His Cys Asn Thr Met Gly Thr Ala Ser
        195                 200                 205

Thr Met Asn Ala Val Ala Glu Ala Leu Gly Leu Ser Leu Thr Gly Cys
    210                 215                 220

Ala Ala Ile Pro Ala Pro Tyr Arg Glu Arg Gly Gln Met Ala Tyr Lys
225                 230                 235                 240

Thr Gly Gln Arg Ile Val Asp Leu Ala Tyr Asp Val Lys Pro Leu
                245                 250                 255

Asp Ile Leu Thr Lys Gln Ala Phe Glu Asn Ala Ile Ala Leu Val Ala
            260                 265                 270

Ala Ala Gly Gly Ser Thr Asn Ala Gln Pro His Ile Val Ala Met Ala
        275                 280                 285

Arg His Ala Gly Val Glu Ile Thr Ala Asp Asp Trp Arg Ala Ala Tyr
    290                 295                 300

Asp Ile Pro Leu Ile Val Asn Met Gln Pro Ala Gly Lys Tyr Leu Gly
305                 310                 315                 320

Glu Arg Phe His Arg Ala Gly Gly Ala Pro Ala Val Leu Trp Glu Leu
                325                 330                 335
```

Leu Gln Gln Gly Arg Leu His Gly Asp Val Leu Thr Val Thr Gly Lys
                340                 345                 350

Thr Met Ser Glu Asn Leu Gln Gly Arg Glu Thr Ser Asp Arg Glu Val
            355                 360                 365

Ile Phe Pro Tyr His Glu Pro Leu Ala Glu Lys Ala Gly Phe Leu Val
370                 375                 380

Leu Lys Gly Asn Leu Phe Asp Phe Ala Ile Met Lys Ser Ser Val Ile
385                 390                 395                 400

Gly Glu Glu Phe Arg Lys Arg Tyr Leu Ser Gln Pro Gly Gln Glu Gly
                405                 410                 415

Val Phe Glu Ala Arg Ala Ile Val Phe Asp Gly Ser Asp Tyr His
            420                 425                 430

Lys Arg Ile Asn Asp Pro Ala Leu Glu Ile Asp Glu Arg Cys Ile Leu
                435                 440                 445

Val Ile Arg Gly Ala Gly Pro Ile Gly Trp Pro Gly Ser Ala Glu Val
450                 455                 460

Val Asn Met Gln Pro Pro Asp His Leu Leu Lys Lys Gly Ile Met Ser
465                 470                 475                 480

Leu Pro Thr Leu Gly Asp Gly Arg Gln Ser Gly Thr Ala Asp Ser Pro
                485                 490                 495

Ser Ile Leu Asn Ala Ser Pro Glu Ser Ala Ile Gly Gly Leu Ser
            500                 505                 510

Trp Leu Arg Thr Gly Asp Thr Ile Arg Ile Asp Leu Asn Thr Gly Arg
            515                 520                 525

Cys Asp Ala Leu Val Asp Glu Ala Thr Ile Ala Ala Arg Lys Gln Asp
530                 535                 540

Gly Ile Pro Ala Val Pro Ala Thr Met Thr Pro Trp Gln Glu Ile Tyr
545                 550                 555                 560

Arg Ala His Ala Ser Gln Leu Asp Thr Gly Gly Val Leu Glu Phe Ala
                565                 570                 575

Val Lys Tyr Gln Asp Leu Ala Ala Lys Leu Pro Arg His Asn His
            580                 585                 590

<210> SEQ ID NO 138
<211> LENGTH: 1968
<212> TYPE: DNA
<213> ORGANISM: Escherichia coli

<400> SEQUENCE: 138
atgtctgttc gcaatatttt tgctgacgag agccacgata tttacaccgt cagaacgcac    60
gccgatggcc cggacggcga actcccatta accgcagaga tgcttatcaa ccgcccgagc   120
ggggatctgt tcggtatgac catgaatgcc ggaatgggtt ggtctccgga cgagctggat   180
cgggacggta tttactgct cagtacactc ggtggcttac gcggcgcaga cggtaaaccc   240
gtggcgctgg cgttgcacca ggggcattac gaactggaca tccagatgaa agcggcggcc   300
gaggttatta aagccaacca tgccctgccc tatgccgtgt acgtctccga tccttgtgac   360
gggcgtactc agggtacaac ggggatgttt gattcgctac ataccgaaa tgacgcatcg   420 atggtaatgc gccgccttat tcgctctctg cccgacgcga agcagttat ggtgtggcg   480 agttgcgata aggggcttcc ggccaccatg atggcactcg ccgcgcagca acatcgca   540 accgtgctgg tccccggcgg cgcgacgctg cccgcaaagg atggagaaga caacggcaag   600
gtgcaaacca ttggcgcacg cttcgccaat ggcgaattat ctctacagga cgcacgccgt   660

```
gcgggctgta aagcctgtgc ctcttccggc ggcggctgtc aattttggg cactgccggg    720 acatctcagg tggtggccga aggattggga ctggcaatcc cacattcagc cctggcccct    780
tccggtgagc ctgtgtggcg ggagatcgcc agagcttccg cgcgagctgc gctgaacctg    840
agtcaaaaag gcataccac ccgggaaatt ctcaccgata aagcgataga gaatgcgatg    900
acggtccatg ccgcgttcgg tggttcaaca aacctgctgt tacacatccc ggcaattgct    960
caccaggcag gttgccatat cccgaccgtt gatgactgga tccgcatcaa caagcgcgtg   1020
ccccgactgg tgagcgtact gcctaatggc ccggtttatc atccaacggt caatgccttt   1080
atggcaggtg gtgtgccgga agtcatgttg catctgcgca gcctcggatt gttgcatgaa   1140
gacgttatga cggttaccgg cagcacgctg aaagaaaacc tcgactggtg ggagcactcc   1200
gaacggcgtc agcggttcaa gcaactcctg ctcgatcagg aacaaatcaa cgctgacgaa   1260
gtgatcatgt ctccgcagca agcaaaagcg cgcggattaa cctcaactat caccttcccg   1320
gtgggcaata ttgcgccaga aggttcggtg atcaaatcca ccgccattga cccctcgatg   1380
attgatgagc aaggtatcta ttaccataaa ggtgtggcga aggtttatct gtccgagaaa   1440
agtgcgattt acgatatcaa acatgacaag atcaaggcgg gcgatattct ggtcattatt   1500
ggcgttggac cttcaggtac agggatggaa gaaacctacc aggttaccag tgccctgaag   1560
catctgtcat acggtaagca tgtttcgtta atcaccgatg cacgtttctc gggcgtttct   1620
actggcgcgt gcatcggcca tgtggggcca gaagcgctgg ccggaggccc catcggtaaa   1680
ttacgcaccg gggatttaat tgaaattaaa attgattgtc gcgagcttca cggcgaagtc   1740
aatttcctcg gaacccgtag cgatgaacaa ttaccttcac aggaggaggc aactgcaata   1800
ttaaatgcca gacccagcca tcaggattta cttcccgatc ctgaattgcc agatgatacc   1860
cggctatggg caatgcttca ggccgtgagt ggtgggacat ggaccggttg tatttatgat   1920
gtaaacaaaa ttggcgcggc tttgcgcgat tttatgaata aaaactga                1968

<210> SEQ ID NO 139
<211> LENGTH: 1968
<212> TYPE: DNA
<213> ORGANISM: Escherichia coli

<400> SEQUENCE: 139
atgtctgttc gcaatatttt tgctgacgag agccacgata tttacaccgt cagaacgcac     60
gccgatggcc cggacggcga actcccatta accgcagaga tgcttatcaa ccgcccgagc    120
ggggatctgt tcggtatgac catgaatgcc ggaatgggtt ggtctccgga cgagctggat    180
cgggacggta ttttactgct cagtacactc ggtggcttac gcggcgcaga cggtaaaccc    240
gtggcgctgg cgttgcacca ggggcattac gaactggaca tccagatgaa agcggcggcc    300
gaggttatta aagccaacca tgccctgccc tatgccgtgt acgtctccga tccttgtgac    360
gggcgtactc agggtacaac ggggatgttt gattcgctac ataccgaaa tgacgcatcg    420 atggtaatgc gccgccttat tcgctctctg cccgacgcga aagcagttat tggtgtggcg    480
agttgcgata agggcttcc ggccaccatg atggcactcg ccgcgcagca caacatcgca    540
accgtgctgt tccccggcgg cgcgacgctg cccgcaaagg atggagaaga caacggcaag    600
gtgcaaacca ttggcgcacg cttcgccaat ggcgaattat ctctacagga cgcacgccgt    660
gcgggctgta aagcctgtgc ctcttccggc ggcggctgtc aattttggg cactgccggg    720 acatctcagg tggtggccga aggattggga ctggcaatcc cacattcagc cctggcccct    780
tccggtgagc ctgtgtggcg ggagatcgcc agagcttccg cgcgagctgc gctgaacctg    840
```

```
agtcaaaaag gcatcaccac ccgggaaatt ctcaccgata aagcgataga gaatgcgatg    900
acggtccatg ccgcgttcgg tggttcaaca aacctgctgt tacacatccc ggcaattgct    960
caccaggcag gttgccatat cccgaccgtt gatgactgga tccgcatcaa caagcgcgtg   1020
ccccgactgg tgagcgtact gcctaatggc ccggtttatc atccaacggt caatgccttt   1080
atggcaggtg gtgtgccgga agtcatgttg catctgcgca gcctcggatt gttgcatgaa   1140
gacgttatga cggttaccgg cagcacgctg aaagaaaacc tcgactggtg ggagcactcc   1200
gaacggcgtc agcggttcaa gcaactcctg ctcgatcagg aacaaatcaa cgctgacgaa   1260
gtgatcatgt ctccgcagca agcaaaagcg cgcggattaa cctcaactat caccttcccg   1320
gtgggcaata ttgcgccaga aggttcggtg atcaaatcca ccgccattga cccctcgatg   1380
attgatgagc aagtatcta ttaccataaa ggtgtggcga aggtttatct gtccgagaaa   1440
agtgcgattt acgatatcaa acatgacaag atcaaggcgg gcgatattct ggtcattatt   1500
ggcgttggac cttcaggtac agggatggaa gaaacctacc aggttaccag tgccctgaag   1560
catctgtcat acggtaagca tgtttcgtta atcaccgatg cacgtttctc gggcgtttct   1620
actgcgcgt gcatcggcca tgtggggcca gaagcgctgg ccgaggccc catcggtaaa   1680
ttacgcaccg gggatttaat tgaaattaaa attgattgtc gcgagcttca cggcgaagtc   1740
aatttcctcg gaacccgtag cgatgaacaa ttaccttcac aggaggaggc aactgcaata   1800
ttaaatgcca gacccagcca tcaggattta cttcccgatc ctgaattgcc agatgatacc   1860
cggctatggg caatgcttca ggccgtgagt ggtgggacat ggaccggttg tatttatgat   1920
gtaaacaaaa ttggcgcggc tttgcgcgat tttatgaata aaaactga                1968
```

<210> SEQ ID NO 140
<211> LENGTH: 655
<212> TYPE: PRT
<213> ORGANISM: Escherichia coli

<400> SEQUENCE: 140

```
Met Ser Val Arg Asn Ile Phe Ala Asp Glu Ser His Asp Ile Tyr Thr
1               5                   10                  15

Val Arg Thr His Ala Asp Gly Pro Asp Gly Glu Leu Pro Leu Thr Ala
            20                  25                  30

Glu Met Leu Ile Asn Arg Pro Ser Gly Asp Leu Phe Gly Met Thr Met
        35                  40                  45

Asn Ala Gly Met Gly Trp Ser Pro Asp Glu Leu Asp Arg Asp Gly Ile
    50                  55                  60

Leu Leu Leu Ser Thr Leu Gly Gly Leu Arg Gly Ala Asp Gly Lys Pro
65                  70                  75                  80

Val Ala Leu Ala Leu His Gln Gly His Tyr Glu Leu Asp Ile Gln Met
                85                  90                  95

Lys Ala Ala Ala Glu Val Ile Lys Ala Asn His Ala Leu Pro Tyr Ala
            100                 105                 110

Val Tyr Val Ser Asp Pro Cys Asp Gly Arg Thr Gln Gly Thr Thr Gly
        115                 120                 125

Met Phe Asp Ser Leu Pro Tyr Arg Asn Asp Ala Ser Met Val Met Arg
    130                 135                 140

Arg Leu Ile Arg Ser Leu Pro Asp Ala Lys Ala Val Ile Gly Val Ala
145                 150                 155                 160

Ser Cys Asp Lys Gly Leu Pro Ala Thr Met Met Ala Leu Ala Ala Gln
                165                 170                 175
```

-continued

```
His Asn Ile Ala Thr Val Leu Val Pro Gly Ala Thr Leu Pro Ala
            180                 185                 190
Lys Asp Gly Glu Asp Asn Gly Lys Val Gln Thr Ile Gly Ala Arg Phe
        195                 200                 205
Ala Asn Gly Glu Leu Ser Leu Gln Asp Ala Arg Arg Ala Gly Cys Lys
        210                 215                 220
Ala Cys Ala Ser Ser Gly Gly Cys Gln Phe Leu Gly Thr Ala Gly
225                 230                 235                 240
Thr Ser Gln Val Val Ala Glu Gly Leu Gly Leu Ala Ile Pro His Ser
                245                 250                 255
Ala Leu Ala Pro Ser Gly Glu Pro Val Trp Arg Glu Ile Ala Arg Ala
            260                 265                 270
Ser Ala Arg Ala Ala Leu Asn Leu Ser Gln Lys Gly Ile Thr Thr Arg
        275                 280                 285
Glu Ile Leu Thr Asp Lys Ala Ile Glu Asn Ala Met Thr Val His Ala
        290                 295                 300
Ala Phe Gly Gly Ser Thr Asn Leu Leu Leu His Ile Pro Ala Ile Ala
305                 310                 315                 320
His Gln Ala Gly Cys His Ile Pro Thr Val Asp Asp Trp Ile Arg Ile
                325                 330                 335
Asn Lys Arg Val Pro Arg Leu Val Ser Val Leu Pro Asn Gly Pro Val
            340                 345                 350
Tyr His Pro Thr Val Asn Ala Phe Met Ala Gly Val Pro Glu Val
        355                 360                 365
Met Leu His Leu Arg Ser Leu Gly Leu Leu His Glu Asp Val Met Thr
        370                 375                 380
Val Thr Gly Ser Thr Leu Lys Glu Asn Leu Asp Trp Trp Glu His Ser
385                 390                 395                 400
Glu Arg Arg Gln Arg Phe Lys Gln Leu Leu Asp Gln Glu Gln Ile
                405                 410                 415
Asn Ala Asp Glu Val Ile Met Ser Pro Gln Gln Ala Lys Ala Arg Gly
            420                 425                 430
Leu Thr Ser Thr Ile Thr Phe Pro Val Gly Asn Ile Ala Pro Glu Gly
        435                 440                 445
Ser Val Ile Lys Ser Thr Ala Ile Asp Pro Ser Met Ile Asp Glu Gln
        450                 455                 460
Gly Ile Tyr Tyr His Lys Gly Val Ala Lys Val Tyr Leu Ser Glu Lys
465                 470                 475                 480
Ser Ala Ile Tyr Asp Ile Lys His Asp Lys Ile Lys Ala Gly Asp Ile
                485                 490                 495
Leu Val Ile Ile Gly Val Gly Pro Ser Gly Thr Gly Met Glu Glu Thr
            500                 505                 510
Tyr Gln Val Thr Ser Ala Leu Lys His Leu Ser Tyr Gly Lys His Val
        515                 520                 525
Ser Leu Ile Thr Asp Ala Arg Phe Ser Gly Val Ser Thr Gly Ala Cys
        530                 535                 540
Ile Gly His Val Gly Pro Glu Ala Leu Ala Gly Gly Pro Ile Gly Lys
545                 550                 555                 560
Leu Arg Thr Gly Asp Leu Ile Glu Ile Lys Ile Asp Cys Arg Glu Leu
                565                 570                 575
His Gly Glu Val Asn Phe Leu Gly Thr Arg Ser Asp Glu Gln Leu Pro
            580                 585                 590
```

```
Ser Gln Glu Glu Ala Thr Ala Ile Leu Asn Ala Arg Pro Ser His Gln
            595                 600                 605

Asp Leu Leu Pro Asp Pro Glu Leu Pro Asp Asp Thr Arg Leu Trp Ala
610                 615                 620

Met Leu Gln Ala Val Ser Gly Gly Thr Trp Thr Gly Cys Ile Tyr Asp
625                 630                 635                 640

Val Asn Lys Ile Gly Ala Ala Leu Arg Asp Phe Met Asn Lys Asn
            645                 650                 655

<210> SEQ ID NO 141
<211> LENGTH: 1968
<212> TYPE: DNA
<213> ORGANISM: Escherichia coli

<400> SEQUENCE: 141
```

| | | | | | |
|---|---|---|---|---|---|
| atgaccattg | agaaaatttt | cacccccgcag | gacgacgcgt | tttatgcggt | gatcacccac | 60
| gcggcgggc | cgcagggcgc | tctgccgctg | accccgcaga | tgctgatgga | atctcccagc | 120
| ggcaacctgt | tcggcatgac | gcagaacgcc | gggatgggct | ggacgccaa | caagctcacc | 180
| ggcaaagagg | tgctgattat | cggcactcag | gcggcatcc | gcgccggaga | cggacgccca | 240
| atcgcgctgg | gctaccacac | cgggcattgg | gagatcggca | tgcagatgca | gcggcggcg | 300
| aaggagatca | cccgcaatgg | cgggatcccg | ttcgcggcct | tcgtcagcga | tccgtgcgac | 360
| gggcgctcgc | agggcacgca | cggtatgttc | gattccctgc | cgtaccgcaa | cgacgcgggcg | 420
| atcgtgtttc | gccgcctgat | ccgctccctg | ccgacgcggc | gggcggtgat | cggcgtagcg | 480
| acctgcgata | aagggctgcc | cgccaccatg | attgcgctgg | ccgcgatgca | cgacctgccg | 540
| actattctgg | tgccgggcgg | ggcgacgctg | ccgccgaccg | tcggggaaga | cgcgggcaag | 600
| gtgcagacca | tcggcgcgcg | tttcgccaac | cacgaactct | ccctgcagga | ggccgccgaa | 660
| ctgggctgtc | gcgcctgcgc | ctcgccgggc | ggcgggtgtc | agttcctcgg | cacggcgggc | 720
| acctcgcagg | tggtcgcgga | ggcgctgggt | ctggcgctgc | cgcactccgc | gctggcgccg | 780
| tccgggcagg | cggtgtggct | ggagatcgcc | cgccagtcgg | cgcgcgcggt | cagcgagctg | 840
| gatagccgcg | gcatcaccac | gcgggatatc | ctctccgata | aagccatcga | aaacgcgatg | 900
| gtgatccacg | cggcgttcgg | cggctccacc | aatttactgc | tgcacattcc | ggccatcgcc | 960
| cacgcggcgg | gctgcacgat | cccggacgtt | gagcactgga | cgcgcatcaa | ccgtaaagtg | 1020
| ccgcgtctgg | tgagcgtgct | gcccaacggc | ccggactatc | acccgaccgt | gcgcgccttc | 1080
| ctcgcgggcg | gcgtgccgga | ggtgatgctc | cacctgcgcg | acctcggcct | gctgcatctg | 1140
| gacgccatga | ccgtgaccgg | ccagacggtg | ggcgagaacc | ttgaatggtg | gcaggcgtcc | 1200
| gagcgccggg | cgcgcttccg | ccagtgcctg | cgcgagcagg | acggcgtaga | gccggatgac | 1260
| gtgatcctgc | cgccggagaa | ggcaaaagcg | aaagggctga | cctcgacggt | ctgcttcccg | 1320
| acgggcaaca | tcgctccgga | aggttcggtg | atcaaggcca | cggcgatcga | cccgtcggtg | 1380
| gtgggcgaag | atgcgtata | ccaccacacc | ggccgggtgc | gggtgtttgt | ctcggaagcg | 1440
| caggcgatca | aggcgatcaa | gcgggaagag | attgtgcagg | gcgatatcat | ggtggtgatc | 1500
| ggcgcgggc | cgtccggcac | cggcatggaa | gagacctacc | agctcacctc | cgcgctaaag | 1560
| catatctcgt | ggggcaagac | ggtgtcgctc | atcaccgatg | cgcgcttctc | gggcgtgtcg | 1620
| acgggcgcct | gcttcggcca | cgtgtcgccg | gaggcgctgg | cggcggggcc | gattggcaag | 1680
| ctgcgcgata | cgacatcat | cgagattgcc | gtggatcgtc | tgacgttaac | tggcagcgtg | 1740
| aacttcatcg | gcaccgcgga | caacccgctg | acgccggaag | agggcgcgcg | cgagctggcg | 1800

-continued

| | |
|---|---|
| cggcggcaga cgcacccgga cctgcacgcc cacgactttt tgccggacga cacccggctg | 1860 |
| tgggcggcac tgcagtcggt gagcggcggc acctggaaag gctgtattta tgacaccgat | 1920 |
| aaaattatcg aggtaattaa cgccggtaaa aaagcgctcg gaatttaa | 1968 |

<210> SEQ ID NO 142
<211> LENGTH: 1968
<212> TYPE: DNA
<213> ORGANISM: Escherichia coli

<400> SEQUENCE: 142

| | |
|---|---|
| atgaccattg agaaaatttt caccccgcag gacgacgcgt tttatgcggt gatcacccac | 60 |
| gcggcgggc cgcagggcgc tctgccgctg accccgcaga tgctgatgga atctcccagc | 120 |
| ggcaacctgt tcggcatgac gcagaacgcc gggatgggct gggacgccaa caagctcacc | 180 |
| ggcaaagagg tgctgattat cggcactcag ggcggcatcc gcgccggaga cggacgccca | 240 |
| atcgcgctgg gctaccacac cgggcattgg gagatcggca tgcagatgca ggcggcggcg | 300 |
| aaggagatca cccgcaatgg cgggatcccg ttcgcggcct tcgtcagcga tccgtgcgac | 360 |
| gggcgctcgc agggcacgca cggtatgttc gattccctgc cgtaccgcaa cgacgcggcg | 420 |
| atcgtgtttc gccgcctgat ccgctccctg ccgacgcggc gggcggtgat cggcgtagcg | 480 |
| acctgcgata aagggctgcc cgccaccatg attgcgctgg ccgcgatgca cgacctgccg | 540 |
| actattctgg tgccgggcgg ggcgacgctg ccgccgaccg tcggggaaga cgcgggcaag | 600 |
| gtgcagacca tcgcgcgcg tttcgccaac cacgaactct ccctgcagga ggccgccgaa | 660 |
| ctgggctgtc gcgcctgcgc ctcgccgggc ggcgggtgtc agttcctcgg cacggcgggc | 720 |
| acctcgcagg tggtcgcgga ggcgctgggc ctggcgctgc cgcactccgc gctggcgccg | 780 |
| tccgggcagg cggtgtggct ggagatcgcc cgccagtcgg cgcgcgcggt cagcgagctg | 840 |
| gatagccgcg gcatcaccac gcgggatatc ctctccgata aagccatcga aaacgcgatg | 900 |
| gtgatccacg cggcgttcgg cggctccacc aatttactgc tgcacattcc ggccatcgcc | 960 |
| cacgcggcgg gctgcacgat cccggacgtt gagcactgga cgcgcatcaa ccgtaaagtg | 1020 |
| ccgcgtctgg tgagcgtgct gcccaacggc ccggactatc acccgaccgt gcgcgccttc | 1080 |
| ctcgcgggcg gcgtgccgga ggtgatgctc cacctgcgcg acctcggcct gctgcatctg | 1140 |
| gacgccatga ccgtgaccgg ccagacggtg ggcgagaacc ttgaatggtg gcaggcgtcc | 1200 |
| gagcgccggg cgcgcttccg ccagtgcctg cgcgagcagg acggcgtaga gccggatgac | 1260 |
| gtgatcctgc cgccggagaa ggcaaaagcg aaagggctga cctcgacggt ctgcttcccg | 1320 |
| acgggcaaca tcgctccgga aggttcggtg atcaaggcca cggcgatcga cccgtcggtg | 1380 |
| gtgggcgaag atggcgtata ccaccacacc ggccgggtgc gggtgtttgt ctcggaagcg | 1440 |
| caggcgatca aggcgatcaa gcgggaagag attgtgcagg gcgatatcat ggtggtgatc | 1500 |
| ggcggcgggc cgtccggcac cggcatggaa gagacctacc agctcacctc cgcgctaaag | 1560 |
| catatctcgt ggggcaagac ggtgtcgctc atcaccgatg cgcgcttctc gggcgtgtcg | 1620 |
| acgggcgcct gcttcggcca cgtgtcgccg gaggcgctgg cggcggggcc gattggcaag | 1680 |
| ctgcgcgata cgacatcat cgagattgcc gtggatcgtc tgacgttaac tggcagcgtg | 1740 |
| aacttcatcg gcaccgcgga caacccgctg acgccggaag agggcgcgcg cgagctggcg | 1800 |
| cggcggcaga cgcacccgga cctgcacgcc cacgactttt tgccggacga cacccggctg | 1860 |
| tgggcggcac tgcagtcggt gagcggcggc acctggaaag gctgtattta tgacaccgat | 1920 |

-continued

```
aaaattatcg aggtaattaa cgccggtaaa aaagcgctcg gaatttaa            1968
```

<210> SEQ ID NO 143
<211> LENGTH: 655
<212> TYPE: PRT
<213> ORGANISM: Escherichia coli

<400> SEQUENCE: 143

```
Met Thr Ile Glu Lys Ile Phe Thr Pro Gln Asp Asp Ala Phe Tyr Ala
1               5                   10                  15

Val Ile Thr His Ala Ala Gly Pro Gln Gly Ala Leu Pro Leu Thr Pro
            20                  25                  30

Gln Met Leu Met Glu Ser Pro Ser Gly Asn Leu Phe Gly Met Thr Gln
        35                  40                  45

Asn Ala Gly Met Gly Trp Asp Ala Asn Lys Leu Thr Gly Lys Glu Val
    50                  55                  60

Leu Ile Ile Gly Thr Gln Gly Gly Ile Arg Ala Gly Asp Gly Arg Pro
65                  70                  75                  80

Ile Ala Leu Gly Tyr His Thr Gly His Trp Glu Ile Gly Met Gln Met
                85                  90                  95

Gln Ala Ala Ala Lys Glu Ile Thr Arg Asn Gly Gly Ile Pro Phe Ala
            100                 105                 110

Ala Phe Val Ser Asp Pro Cys Asp Gly Arg Ser Gln Gly Thr His Gly
        115                 120                 125

Met Phe Asp Ser Leu Pro Tyr Arg Asn Asp Ala Ala Ile Val Phe Arg
    130                 135                 140

Arg Leu Ile Arg Ser Leu Pro Thr Arg Arg Ala Val Ile Gly Val Ala
145                 150                 155                 160

Thr Cys Asp Lys Gly Leu Pro Ala Thr Met Ile Ala Leu Ala Ala Met
                165                 170                 175

His Asp Leu Pro Thr Ile Leu Val Pro Gly Gly Ala Thr Leu Pro Pro
            180                 185                 190

Thr Val Gly Glu Asp Ala Gly Lys Val Gln Thr Ile Gly Ala Arg Phe
        195                 200                 205

Ala Asn His Glu Leu Ser Leu Gln Glu Ala Ala Glu Leu Gly Cys Arg
    210                 215                 220

Ala Cys Ala Ser Pro Gly Gly Gly Cys Gln Phe Leu Gly Thr Ala Gly
225                 230                 235                 240

Thr Ser Gln Val Val Ala Glu Ala Leu Gly Leu Ala Leu Pro His Ser
                245                 250                 255

Ala Leu Ala Pro Ser Gly Gln Ala Val Trp Leu Glu Ile Ala Arg Gln
            260                 265                 270

Ser Ala Arg Ala Val Ser Glu Leu Asp Ser Arg Gly Ile Thr Thr Arg
        275                 280                 285

Asp Ile Leu Ser Asp Lys Ala Ile Glu Asn Ala Met Val Ile His Ala
    290                 295                 300

Ala Phe Gly Gly Ser Thr Asn Leu Leu Leu His Ile Pro Ala Ile Ala
305                 310                 315                 320

His Ala Ala Gly Cys Thr Ile Pro Asp Val Glu His Trp Thr Arg Ile
                325                 330                 335

Asn Arg Lys Val Pro Arg Leu Val Ser Val Leu Pro Asn Gly Pro Asp
            340                 345                 350

Tyr His Pro Thr Val Arg Ala Phe Leu Ala Gly Gly Val Pro Glu Val
        355                 360                 365
```

```
Met Leu His Leu Arg Asp Leu Gly Leu Leu His Leu Asp Ala Met Thr
    370                 375                 380
Val Thr Gly Gln Thr Val Gly Glu Asn Leu Glu Trp Trp Gln Ala Ser
385                 390                 395                 400
Glu Arg Arg Ala Arg Phe Arg Gln Cys Leu Arg Glu Gln Asp Gly Val
                405                 410                 415
Glu Pro Asp Asp Val Ile Leu Pro Pro Glu Lys Ala Lys Ala Lys Gly
                420                 425                 430
Leu Thr Ser Thr Val Cys Phe Pro Thr Gly Asn Ile Ala Pro Glu Gly
                435                 440                 445
Ser Val Ile Lys Ala Thr Ala Ile Asp Pro Ser Val Val Gly Glu Asp
450                 455                 460
Gly Val Tyr His His Thr Gly Arg Val Arg Val Phe Val Ser Glu Ala
465                 470                 475                 480
Gln Ala Ile Lys Ala Ile Lys Arg Glu Glu Ile Val Gln Gly Asp Ile
                485                 490                 495
Met Val Val Ile Gly Gly Gly Pro Ser Gly Thr Gly Met Glu Glu Thr
                500                 505                 510
Tyr Gln Leu Thr Ser Ala Leu Lys His Ile Ser Trp Gly Lys Thr Val
                515                 520                 525
Ser Leu Ile Thr Asp Ala Arg Phe Ser Gly Val Ser Thr Gly Ala Cys
530                 535                 540
Phe Gly His Val Ser Pro Glu Ala Leu Ala Gly Gly Pro Ile Gly Lys
545                 550                 555                 560
Leu Arg Asp Asn Asp Ile Ile Glu Ile Ala Val Asp Arg Leu Thr Leu
                565                 570                 575
Thr Gly Ser Val Asn Phe Ile Gly Thr Ala Asp Asn Pro Leu Thr Pro
                580                 585                 590
Glu Glu Gly Ala Arg Glu Leu Ala Arg Arg Gln Thr His Pro Asp Leu
                595                 600                 605
His Ala His Asp Phe Leu Pro Asp Asp Thr Arg Leu Trp Ala Ala Leu
610                 615                 620
Gln Ser Val Ser Gly Gly Thr Trp Lys Gly Cys Ile Tyr Asp Thr Asp
625                 630                 635                 640
Lys Ile Ile Glu Val Ile Asn Ala Gly Lys Lys Ala Leu Gly Ile
                645                 650                 655

<210> SEQ ID NO 144
<211> LENGTH: 906
<212> TYPE: DNA
<213> ORGANISM: Escherichia coli

<400> SEQUENCE: 144
atgaaaaaat tcagcggcat tattccaccg gtatccagca cgtttcatcg tgacggaacc        60
cttgataaaa aggcaatgcg cgaagttgcc gacttcctga ttaataaagg ggtcgacggg       120
ctgttttatc tgggtaccgg tggtgaattt agccaaatga atacagccca gcgcatggca       180
ctcgccgaag aagctgtaac cattgtcgac gggcgagtgc cggtattgat tggcgtcggt       240 tcccccttcca ctgacgaagc ggtcaaactg gcgcagcatg cgcaagccta cggcgctgat       300
ggtatcgtcg ccatcaaccc ctactactgg aaagtcgcac acgaaatctc tgacgactat       360
taccagcaga tcgcccgtag cgtcacccta ccggtgatcc tgtacaactt ccggatctg        420 acgggtcagg acttaacccc ggaaaccgtg acgcgtctgg ctctgcaaaa cgagaatatc       480
gttggcatca agacaccat cgacagcgtt ggtcacttgc gtacgatgat caacacagtt       540
```

```
aagtcggtac gcccgtcgtt ttcggtattc tgcggttacg atgatcattt gctgaatacg    600
atgctgctgg gcggcgacgg tgcgataacc gccagcgcta actttgctcc ggaactctcc    660
gtcggcatct accgcgcctg gcgtgaaggc gatctggcga ccgctgcgac gctgaataaa    720
aaactactac aactgcccgc tatttacgcc ctcgaaacac cgtttgtctc actgatcaaa    780
tacagcatgc agtgtgtcgg gctgcctgta gagacatatt gcttaccacc gattcttgaa    840
gcatctgaag aagcaaaaga taaagtccac gtgctgctta ccgcgcaggg cattttacca    900
gtctga                                                                906
```

<210> SEQ ID NO 145
<211> LENGTH: 906
<212> TYPE: DNA
<213> ORGANISM: Escherichia coli

<400> SEQUENCE: 145

```
atgaaaaaat tcagcggcat tattccaccg gtatccagca cgtttcatcg tgacggaacc     60
cttgataaaa aggcaatgcg cgaagttgcc gacttcctga ttaataaagg ggtcgacggg    120
ctgttttatc tgggtaccgg tgtgaattt agccaaatga atacagccca gcgcatggca    180
ctcgccgaag aagctgtaac cattgtcgac gggcgagtgc cggtattgat tggcgtcggt    240
tccccttcca ctgacgaagc ggtcaaactg gcgcagcatg cgcaagccta cggcgctgat    300
ggtatcgtcg ccatcaaccc ctactactgg aaagtcgcac cacgaaatct tgacgactat    360
taccagcaga tcgcccgtag cgtcacccta ccggtgatcc tgtacaactt ccggatctg    420 acgggtcagg acttaacccc ggaaaccgtg acgcgtctgg ctctgcaaaa cgagaatatc    480
gttggcatca agacaccat cgacagcgtt ggtcacttgc gtacgatgat caacacagtt    540
aagtcggtac gcccgtcgtt ttcggtattc tgcggttacg atgatcattt gctgaatacg    600
atgctgctgg gcggcgacgg tgcgataacc gccagcgcta actttgctcc ggaactctcc    660
gtcggcatct accgcgcctg gcgtgaaggc gatctggcga ccgctgcgac gctgaataaa    720
aaactactac aactgcccgc tatttacgcc ctcgaaacac cgtttgtctc actgatcaaa    780
tacagcatgc agtgtgtcgg gctgcctgta gagacatatt gcttaccacc gattcttgaa    840
gcatctgaag aagcaaaaga taaagtccac gtgctgctta ccgcgcaggg cattttacca    900
gtctga                                                                906
```

<210> SEQ ID NO 146
<211> LENGTH: 301
<212> TYPE: PRT
<213> ORGANISM: Escherichia coli

<400> SEQUENCE: 146

```
Met Lys Lys Phe Ser Gly Ile Ile Pro Pro Val Ser Ser Thr Phe His
1               5                   10                  15

Arg Asp Gly Thr Leu Asp Lys Lys Ala Met Arg Glu Val Ala Asp Phe
            20                  25                  30

Leu Ile Asn Lys Gly Val Asp Gly Leu Phe Tyr Leu Gly Thr Gly Gly
        35                  40                  45

Glu Phe Ser Gln Met Asn Thr Ala Gln Arg Met Ala Leu Ala Glu Glu
    50                  55                  60

Ala Val Thr Ile Val Asp Gly Arg Val Pro Val Leu Ile Gly Val Gly
65                  70                  75                  80

Ser Pro Ser Thr Asp Glu Ala Val Lys Leu Ala Gln His Ala Gln Ala
```

```
            85                  90                  95
Tyr Gly Ala Asp Gly Ile Val Ala Ile Asn Pro Tyr Tyr Trp Lys Val
                100                 105                 110

Ala Pro Arg Asn Leu Asp Asp Tyr Tyr Gln Gln Ile Ala Arg Ser Val
            115                 120                 125

Thr Leu Pro Val Ile Leu Tyr Asn Phe Pro Asp Leu Thr Gly Gln Asp
        130                 135                 140

Leu Thr Pro Glu Thr Val Thr Arg Leu Ala Leu Gln Asn Glu Asn Ile
145                 150                 155                 160

Val Gly Ile Lys Asp Thr Ile Asp Ser Val Gly His Leu Arg Thr Met
                165                 170                 175

Ile Asn Thr Val Lys Ser Val Arg Pro Ser Phe Ser Val Phe Cys Gly
            180                 185                 190

Tyr Asp Asp His Leu Leu Asn Thr Met Leu Leu Gly Gly Asp Gly Ala
        195                 200                 205

Ile Thr Ala Ser Ala Asn Phe Ala Pro Glu Leu Ser Val Gly Ile Tyr
    210                 215                 220

Arg Ala Trp Arg Glu Gly Asp Leu Ala Thr Ala Thr Leu Asn Lys
225                 230                 235                 240

Lys Leu Leu Gln Leu Pro Ala Ile Tyr Ala Leu Glu Thr Pro Phe Val
                245                 250                 255

Ser Leu Ile Lys Tyr Ser Met Gln Cys Val Gly Leu Pro Val Glu Thr
            260                 265                 270

Tyr Cys Leu Pro Pro Ile Leu Glu Ala Ser Glu Glu Ala Lys Asp Lys
        275                 280                 285

Val His Val Leu Leu Thr Ala Gln Gly Ile Leu Pro Val
290                 295                 300
```

<210> SEQ ID NO 147
<211> LENGTH: 909
<212> TYPE: DNA
<213> ORGANISM: Escherichia coli

<400> SEQUENCE: 147

```
atgccgcagt ccgcgttgtt cacgggaatc attccccctg tctccaccat ttttaccgcc     60
gacggccagc tcgataagcc gggcaccgcc gcgctgatcg acgatctgat caaagcaggc    120
gttgacggcc tgttcttcct gggcagcggt ggcgagttct cccagctcgg cgccgaagag    180
cgtaaagcca ttgcccgctt tgctatcgat catgtcgatc gtcgcgtgcc ggtgctgatc    240
ggcaccggcg gcaccaacgc ccgggaaacc atcgaactca gccagcacgc gcagcaggcg    300
ggcgcggacg gcatcgtggt gatcaacccc tactactgga agtgtcggaa gcgaacctg     360
atccgctatt cgagcaggt ggccgacagc gtcacgctgc cggtgatgct ctataacttc    420
ccggcgctga ccgggcagga tctgactccg gcgctggtga aaaccctcgc cgactcgcgc    480
agcaatatta tcggcatcaa agacaccatc gactccgtcg cccacctgcg cagcatgatc    540
cataccgtca aggtgcccca tccgcacttc accgtgctct gcggctacga cgatcatctg    600
ttcaataccc tgctgctcgg cggcgacggg gcgatatcgg cgagcggcaa ctttgccccg    660
caggtgtcgg tgaatcttct gaaagcctgg cgcgacgggg acgtggcgaa gcggccgggg    720
tatcatcaga ccttgctgca aattccgcag atgtatcagc tggatacgcc gtttgtgaac    780
gtgattaaag aggcgatcgt gctctgcggt cgtcctgtct ccacgcacgt gctgccgccc    840
gcctcgccgc tggacgagcc gcgcaaggcg cagctgaaaa ccctgctgca acagctcaag    900
```

-continued

```
ctttgctga                                                               909
```

<210> SEQ ID NO 148
<211> LENGTH: 909
<212> TYPE: DNA
<213> ORGANISM: Escherichia coli

<400> SEQUENCE: 148

```
atgccgcagt ccgcgttgtt cacgggaatc attcccctg tctccaccat ttttaccgcc        60
gacggccagc tcgataagcc gggcaccgcc gcgctgatcg acgatctgat caaagcaggc      120
gttgacggcc tgttcttcct gggcagcggt ggcgagttct cccagctcgg cgccgaagag      180
cgtaaagcca ttgcccgctt tgctatcgat catgtcgatc gtcgcgtgcc ggtgctgatc      240
ggcaccggcg gcaccaacgc ccgggaaacc atcgaactca gccagcacgc gcagcaggcg      300
ggcgcggacg gcatcgtggt gatcaacccc tactactgga agtgtcgga agcgaacctg       360
atccgctatt tcgagcaggt ggccgacagc gtcacgctgc cggtgatgct ctataacttc      420
ccggcgctga ccgggcagga tctgactccg gcgctggtga aaaccctcgc cgactcgcgc      480
agcaatatta tcggcatcaa agacaccatc gactccgtcg cccacctgcg cagcatgatc      540
cataccgtca aggtgccca tccgcacttc accgtgctct gcggctacga cgatcatctg       600
ttcaataccc tgctgctcgg cggcgacggg gcgatatcgg cgagcggcaa ctttgccccg      660
caggtgtcgg tgaatcttct gaaagcctgg cgcgacgggg acgtggcgaa agcggccggg      720
tatcatcaga ccttgctgca aattccgcag atgtatcagc tggatacgcc gtttgtgaac      780
gtgattaaag aggcgatcgt gctctgcggt cgtcctgtct ccacgcacgt gctgccgccc      840
gcctcgccgc tggacgagcc gcgcaaggcg cagctgaaaa ccctgctgca acagctcaag      900
ctttgctga                                                               909
```

<210> SEQ ID NO 149
<211> LENGTH: 302
<212> TYPE: PRT
<213> ORGANISM: Escherichia coli

<400> SEQUENCE: 149

```
Met Pro Gln Ser Ala Leu Phe Thr Gly Ile Ile Pro Val Ser Thr
1               5                   10                  15

Ile Phe Thr Ala Asp Gly Gln Leu Asp Lys Pro Gly Thr Ala Ala Leu
                20                  25                  30

Ile Asp Asp Leu Ile Lys Ala Gly Val Asp Gly Leu Phe Phe Leu Gly
            35                  40                  45

Ser Gly Gly Glu Phe Ser Gln Leu Gly Ala Glu Glu Arg Lys Ala Ile
    50                  55                  60

Ala Arg Phe Ala Ile Asp His Val Asp Arg Arg Val Pro Val Leu Ile
65                  70                  75                  80

Gly Thr Gly Gly Thr Asn Ala Arg Glu Thr Ile Glu Leu Ser Gln His
                85                  90                  95

Ala Gln Gln Ala Gly Ala Asp Gly Ile Val Val Ile Asn Pro Tyr Tyr
            100                 105                 110

Trp Lys Val Ser Glu Ala Asn Leu Ile Arg Tyr Phe Glu Gln Val Ala
        115                 120                 125

Asp Ser Val Thr Leu Pro Val Met Leu Tyr Asn Phe Pro Ala Leu Thr
    130                 135                 140

Gly Gln Asp Leu Thr Pro Ala Leu Val Lys Thr Leu Ala Asp Ser Arg
145                 150                 155                 160
```

```
Ser Asn Ile Ile Gly Ile Lys Asp Thr Ile Asp Ser Val Ala His Leu
            165                 170                 175

Arg Ser Met Ile His Thr Val Lys Gly Ala His Pro His Phe Thr Val
            180                 185                 190

Leu Cys Gly Tyr Asp Asp His Leu Phe Asn Thr Leu Leu Leu Gly Gly
            195                 200                 205

Asp Gly Ala Ile Ser Ala Ser Gly Asn Phe Ala Pro Gln Val Ser Val
            210                 215                 220

Asn Leu Leu Lys Ala Trp Arg Asp Gly Asp Val Ala Lys Ala Ala Gly
225                 230                 235                 240

Tyr His Gln Thr Leu Leu Gln Ile Pro Gln Met Tyr Gln Leu Asp Thr
            245                 250                 255

Pro Phe Val Asn Val Ile Lys Glu Ala Ile Val Leu Cys Gly Arg Pro
            260                 265                 270

Val Ser Thr His Val Leu Pro Pro Ala Ser Pro Leu Asp Glu Pro Arg
            275                 280                 285

Lys Ala Gln Leu Lys Thr Leu Leu Gln Gln Leu Lys Leu Cys
            290                 295                 300
```

<210> SEQ ID NO 150
<211> LENGTH: 957
<212> TYPE: DNA
<213> ORGANISM: Scheffersomyces stipitis

<400> SEQUENCE: 150

```
atgccttcta ttaagttgaa ctctggttac gacatgccag ccgtcggttt cggctgttgg    60
aaagtcgacg tcgacacctg ttctgaacag atctaccgtg ctatcaagac cggttacaga   120
ttgttcgacg tgccgaaga ttacgccaac gaaaagttag ttggtgccgg tgtcaagaag   180
gccattgacg aaggtatcgt caagcgtgaa gatttgttcc ttacctccaa gttgtggaac   240
aactaccacc cccagacaa cgtcgaaaag gccttgaaca gaacccttc tgacttgcaa   300
gttgactacg ttgacttgtt cttgatccac ttcccagtca ccttcaagtt cgttccatta   360
gaagaaaagt accccaccag gattctactgt ggtaagggtg acaacttcga ctacgaagat   420
gttccaattt tagagacttg gaaggctctt gaaaagttgg tcaaggccgg taagatcaga   480
tctatcggtg tttctaactt cccaggtgct tgctcttgg acttgttgag aggtgctacc   540
atcaagccat ctgtcttgca agttgaacac caccatact tgcaacaacc aagattgatc   600
gaattcgctc aatcccgtgg tattgctgtc accgcttact cttcgttcgg tcctcaatct   660
ttcgttgaat tgaaccaagg tagagctttg aacacttctc cattgttcga gaacgaaact   720
atcaaggcta tcgctgctaa gcacggtaag tctccagctc aagtcttgtt gagatggtca   780
tcccaaagag gcattgccat cattccaaag tccaacactg tcccaagatt gttggaaaac   840
aaggacgtca acagcttcga cttggacgaa caagatttcg ctgacattgc caagttggac   900
atcaacttga gattcaacga cccatgggac tgggacaaga ttcctatctt cgtctaa       957
```

<210> SEQ ID NO 151
<211> LENGTH: 957
<212> TYPE: DNA
<213> ORGANISM: Scheffersomyces stipitis

<400> SEQUENCE: 151

```
atgccatcta tcaagttaaa ttccggttac gacatgcctg ctgttggttt cggttgctgg    60
aaggttgatg tcgatacttg ttccgagcaa atttaccgtg ctatcaagac tggttacaga   120
```

```
ttgttcgatg gtgctgaaga ctacgccaac gaaaagttag tcggtgctgg tgttaaaaag    180
gctatcgacg aaggtattgt taaaagagaa gacttgttct tgacttctaa gttgtggaac    240
aactaccacc atcctgataa cgtcgaaaaa gctttgaacc gtaccttgtc cgatttgcaa    300
gtcgattacg ttgatttgtt cttgattcat ttcccagtta ccttcaagtt cgttccattg    360
gaagagaagt atccaccagg tttctactgt ggtaagggtg ataacttcga ttacgaagat    420
gtcccaatct tagaaacctg gaaggcttta gaaaagttgg ttaaggctgg taagatcaga    480
tccatcggtg tttctaactt cccaggtgcc ttattgttag acttattgag aggtgctacc    540
attaagcctt ccgttttgca agttgaacat catccttact tgcaacaacc aagattgatc    600
gaattcgctc aatctagagg tatcgctgtt actgcctact cttccttcgg tccacaatct    660
ttcgttgagt tgaaccaagg tagagctttg aacacctctc cattgttcga aaacgaaact    720
attaaggcca ttgctgctaa gcatggtaag tctccagccc aagttttgtt gagatggtct    780
tctcaaagag gtatcgctat tatcccaaag tctaatactg tcccaagatt gttggaaaac    840
aaggacgtta actcctttga tttggatgaa caagactttg ctgacatcgc taaattggac    900
atcaacttga gattcaacga cccatgggac tgggacaaga ttccaatttt tgtttaa     957
```

<210> SEQ ID NO 152  
<211> LENGTH: 318  
<212> TYPE: PRT  
<213> ORGANISM: Scheffersomyces stipitis

<400> SEQUENCE: 152

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220
```

```
Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
            245                 250                 255

Leu Arg Trp Ser Ser Gln Arg Gly Ile Ala Ile Pro Lys Ser Asn
                260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 153
<211> LENGTH: 984
<212> TYPE: DNA
<213> ORGANISM: Saccharomyces cerevisiae

<400> SEQUENCE: 153

```
atgtcttcac tggttactct taataacggt ctgaaaatgc cctagtcgg cttagggtgc      60
tggaaaattg acaaaaaagt ctgtgcgaat caaatttatg aagctatcaa attaggctac    120
cgtttattcg atggtgcttg cgactacggc aacgaaaagg aagttggtga aggtatcagg    180
aaagccatct ccgaaggtct tgtttctaga aggatatat tgttgtttc aaagttatgg      240
aacaattttc accatcctga tcatgtaaaa ttagctttaa agaagacctt aagcgatatg    300
ggacttgatt atttagacct gtattatatt cacttcccaa tcgccttcaa atatgttcca    360
tttgaagaga ataccctcc aggattctat acgggcgcag atgacgagaa gaaaggtcac    420
atcaccgaag cacatgtacc aatcatagat acgtaccggg ctctggaaga atgtgttgat    480
gaaggcttga ttaagtctat tggtgttcc aactttcagg gaagcttgat tcaagattta    540
ttacgtggtt gtagaatcaa gcccgtggct ttgcaaattg aacaccatcc ttatttgact    600
caagaacacc tagttgagtt ttgtaaatta acgatatcc aagtagttgc ttactcctcc     660
ttcggtcctc aatcattcat tgagatggac ttacagttgg caaaaaccac gccaactctg    720
ttcgagaatg atgtaatcaa gaaggtctca caaaaccatc caggcagtac cacttcccaa    780
gtattgctta gatgggcaac tcagagaggc attgccgtca ttccaaaatc ttccaagaag    840
gaaaggttac ttggcaacct agaaatcgaa aaaagttca ctttaacgga gcaagaattg     900
aaggatattt ctgcactaaa tgccaacatc agatttaatg atccatggac ctggttggat    960
ggtaaaattcc ccactttgc ctga                                          984
```

<210> SEQ ID NO 154
<211> LENGTH: 984
<212> TYPE: DNA
<213> ORGANISM: Saccharomyces cerevisiae

<400> SEQUENCE: 154

```
atgtcttcac tggttactct taataacggt ctgaaaatgc cctagtcgg cttagggtgc      60
tggaaaattg acaaaaaagt ctgtgcgaat caaatttatg aagctatcaa attaggctac    120
cgtttattcg atggtgcttg cgactacggc aacgaaaagg aagttggtga aggtatcagg    180
aaagccatct ccgaaggtct tgtttctaga aggatatat tgttgtttc aaagttatgg      240
aacaattttc accatcctga tcatgtaaaa ttagctttaa agaagacctt aagcgatatg    300
ggacttgatt atttagacct gtattatatt cacttcccaa tcgccttcaa atatgttcca    360
```

```
tttgaagaga aatacccctcc aggattctat acgggcgcag atgacgagaa gaaaggtcac    420
atcaccgaag cacatgtacc aatcatagat acgtaccggg ctctggaaga atgtgttgat    480
gaaggcttga ttaagtctat tggtgttttcc aactttcagg gaagcttgat tcaagattta    540
ttacgtggtt gtagaatcaa gcccgtggct ttgcaaattg aacaccatcc ttatttgact    600
caagaacacc tagttgagtt ttgtaaatta cacgatatcc aagtagttgc ttactcctcc    660
ttcggtcctc aatcattcat tgagatggac ttacagttgg caaaaaccac gccaactctg    720
ttcgagaatg atgtaatcaa gaaggtctca caaaaccatc caggcagtac cacttcccaa    780
gtattgctta gatgggcaac tcagagaggc attgccgtca ttccaaaatc ttccaagaag    840
gaaaggttac ttggcaacct agaaatcgaa aaaagttca ctttaacgga gcaagaattg     900
aaggatattt ctgcactaaa tgccaacatc agatttaatg atccatggac ctggttggat    960
ggtaaattcc ccactttgc ctga                                             984
```

<210> SEQ ID NO 155
<211> LENGTH: 327
<212> TYPE: PRT
<213> ORGANISM: Saccharomyces cerevisiae

<400> SEQUENCE: 155

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255
```

```
Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 156
<211> LENGTH: 1092
<212> TYPE: DNA
<213> ORGANISM: Scheffersomyces stipitis

<400> SEQUENCE: 156
atgactgcta acccttcctt ggtgttgaac aagatcgacg acatttcgtt cgaaacttac      60
gatgccccag aaatctctga acctaccgat gtcctcgtcc aggtcaagaa aaccggtatc     120
tgtggttccg acatccactt ctacgcccat ggtagaatcg gtaacttcgt tttgaccaag     180
ccaatggtct tgggtcacga atccgccggt actgttgtcc aggttggtaa gggtgtcacc     240
tctcttaagg ttggtgacaa cgtcgctatc gaaccaggta ttccatccag attctccgac     300
gaatacaaga gcggtcacta caacttgtgt cctcacatgg ccttcgccgc tactcctaac     360
tccaaggaag gcgaaccaaa cccaccaggt accttatgta agtacttcaa gtcgccagaa     420
gacttcttgg tcaagttgcc agaccacgtc agcttggaac tcggtgctct tgttgagcca     480
ttgtctgttg gtgtccacgc ctctaagttg ggttccgttg ctttcggcga ctacgttgcc     540
gtctttggtg ctggtcctgt tggtcttttg gctgctgctg tcgccaagac cttcggtgct     600
aagggtgtca tcgtcgttga cattttcgac aacaagttga agatggccaa ggacattggt     660
gctgctactc acaccttcaa ctccaagacc ggtggttctg aagaattgat caaggctttc     720
ggtggtaacg tgccaaacgt cgttttggaa tgtactggtg ctgaaccttg tatcaagttg     780
ggtgttgacg ccattgcccc aggtggtcgt ttcgttcaag tcggtaacgc tgctggtcca     840
gtcagcttcc caatcaccgt tttcgccatg aaggaattga ctttgttcgg ttctttcaga     900
tacggattca cgactacaa gactgctgtt ggaatctttg acactaacta ccaaaacggt     960
agagaaaatg ctccaattga ctttgaacaa ttgatcaccc acagatacaa gttcaaggac    1020
gctattgaag cctacgactt ggtcagagcc ggtaagggtg ctgtcaagtg tctcattgac    1080
ggccctgagt aa                                                       1092

<210> SEQ ID NO 157
<211> LENGTH: 1092
<212> TYPE: DNA
<213> ORGANISM: Scheffersomyces stipitis

<400> SEQUENCE: 157
atgactgcta acccttcctt ggtgttgaac aagatcgacg acatttcgtt cgaaacttac      60
gatgccccag aaatctctga acctaccgat gtcctcgtcc aggtcaagaa aaccggtatc     120
tgtggttccg acatccactt ctacgcccat ggtagaatcg gtaacttcgt tttgaccaag     180
ccaatggtct tgggtcacga atccgccggt actgttgtcc aggttggtaa gggtgtcacc     240
tctcttaagg ttggtgacaa cgtcgctatc gaaccaggta ttccatccag attctccgac     300
```

-continued

```
gaatacaaga gcggtcacta caacttgtgt cctcacatgg ccttcgccgc tactcctaac       360
tccaaggaag gcgaaccaaa cccaccaggt accttatgta agtacttcaa gtcgccagaa       420
gatttcttgg tcaagttgcc agaccacgtc agcttggaac tcggtgctct tgttgagcca       480
ttgtctgttg gtgtccacgc ctctaagttg ggttccgttg ctttcggcga ctacgttgcc       540
gtctttggag caggtcctgt tggtcttttg gctgctgctg tcgccaagac cttcggtgct       600
aagggtgtca tcgtcgttga catttttcgac aacaagttga agatggccaa ggacattgga      660
gctgctactc acaccttcaa ctccaagacc ggtggttctg aagaattgat caaggctttc       720
ggtggtaacg tgccaaacgt cgttttggaa tgtacaggtg cagaaccttg tatcaagttg       780
ggtgttgacg ccattgcccc aggtggtcgt ttcgttcaag tcggtaacgc tgctggtcca       840
gtcagcttcc caataccgt tttcgccatg aaggaattga ctttgttcgg ttcttttcaga       900 tacggattca acgactacaa gactgctgtt ggaatctttg acactaacta ccaaaacggt       960
agagaaaatg ctccaattga ctttgaacaa ttgatcaccc acagatacaa gttcaaggac      1020
gctattgaag cctacgactt ggtcagagcc ggtaagggtg ctgtcaagtg tctcattgac      1080
ggccctgagt aa                                                          1092
```

<210> SEQ ID NO 158
<211> LENGTH: 363
<212> TYPE: PRT
<213> ORGANISM: Scheffersomyces stipitis

<400> SEQUENCE: 158

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
```

```
              225                 230                 235                 240
Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360
```

<210> SEQ ID NO 159
<211> LENGTH: 1092
<212> TYPE: DNA
<213> ORGANISM: Trichoderma reesei

<400> SEQUENCE: 159

```
atggcgactc aaacgatcaa caaggatgcg atcagcaacc tctccttcgt cctcaacaag      60
cccggcgacg tgacctttga ggagcggccg aagccgacca tcacggaccc caacgacgtc     120
ctcgtcgccg tcaactacac gggcatctgc ggctccgacg tgcactactg ggtgcacggc     180
gccatcgggc acttcgtcgt caaggacccg atggtgctgg ccacgagtc ggccggcacc     240
gtcgtcgagg tcggcccggc cgtcaagagc ctcaagcccg cgaccgcgt cgccctcgag     300
cccggctacc cgtgccggcg tgctccttc tgccgcgccg caaatacaa cctgtgcccg     360
gacatggtct cgccgccac gccgccgtac cacggcaccc tgacgggcct gtgggcggcg     420
cccgccgact tctgctacaa gctgccggac ggcgtgtcgc tgcaggaggg cgcgctgatc     480
gagccgctgg ccgtggccgt ccacattgtc aagcaggccc gcgtccagcc gggccagtcc     540
gtcgtcgtca tgggcgccgg cccgtcggc ctgctgtgcg ccgccgtggc caaggcgtac     600
ggcgcctcca ccattgtcag cgtcgacatc gtgcagtcca agctcgactt gcgcgcgggc     660
ttctgctcga cgcacacgta cgtctcgcag cgcatctcgg ctgaggacaa cgcaaaggcc     720
atcaaggagc tggcgggcct gccgggcggc gccgacgtcg tgattgacgc cagcggcgcg     780
gagccgtcga tccagacgag cattcacgtc gtccgcatgg cggcacgta cgtccagggc     840
ggcatgggca agagcgacat cacgttcccc atcatggcca tgtgcctcaa ggaggtgacg     900
gtccgggct cgttccgcta cggcgccggc gactacgagc tggcggtcga gctggtccgg     960
acggggcggg tggacgtcaa gaagctgatt acgggcaccg tcagcttcaa gcaggcggag    1020
gaggcgttcc aaaaggtcaa gtctggggag gccatcaaga ttctgattgc cgggcccaac    1080
gagaaggtgt aa                                                        1092
```

<210> SEQ ID NO 160
<211> LENGTH: 363
<212> TYPE: PRT
<213> ORGANISM: Trichoderma reesei

<400> SEQUENCE: 160

```
Met Ala Thr Gln Thr Ile Asn Lys Asp Ala Ile Ser Asn Leu Ser Phe
1               5                   10                  15

Val Leu Asn Lys Pro Gly Asp Val Thr Phe Glu Glu Arg Pro Lys Pro
            20                  25                  30

Thr Ile Thr Asp Pro Asn Asp Val Leu Val Ala Val Asn Tyr Thr Gly
        35                  40                  45

Ile Cys Gly Ser Asp Val His Tyr Trp Val His Gly Ala Ile Gly His
    50                  55                  60

Phe Val Val Lys Asp Pro Met Val Leu Gly His Glu Ser Ala Gly Thr
65                  70                  75                  80

Val Val Glu Val Gly Pro Ala Val Lys Ser Leu Lys Pro Gly Asp Arg
                85                  90                  95

Val Ala Leu Glu Pro Gly Tyr Pro Cys Arg Arg Cys Ser Phe Cys Arg
            100                 105                 110

Ala Gly Lys Tyr Asn Leu Cys Pro Asp Met Val Phe Ala Ala Thr Pro
        115                 120                 125

Pro Tyr His Gly Thr Leu Thr Gly Leu Trp Ala Ala Pro Ala Asp Phe
130                 135                 140

Cys Tyr Lys Leu Pro Asp Gly Val Ser Leu Gln Glu Gly Ala Leu Ile
145                 150                 155                 160

Glu Pro Leu Ala Val Ala Val His Ile Val Lys Gln Ala Arg Val Gln
            165                 170                 175

Pro Gly Gln Ser Val Val Val Met Gly Ala Gly Pro Val Gly Leu Leu
        180                 185                 190

Cys Ala Val Ala Lys Ala Tyr Gly Ala Ser Thr Ile Val Ser Val
            195                 200                 205

Asp Ile Val Gln Ser Lys Leu Asp Phe Ala Arg Gly Phe Cys Ser Thr
210                 215                 220

His Thr Tyr Val Ser Gln Arg Ile Ser Ala Glu Asp Asn Ala Lys Ala
225                 230                 235                 240

Ile Lys Glu Leu Ala Gly Leu Pro Gly Gly Ala Asp Val Val Ile Asp
            245                 250                 255

Ala Ser Gly Ala Glu Pro Ser Ile Gln Thr Ser Ile His Val Val Arg
        260                 265                 270

Met Gly Gly Thr Tyr Val Gln Gly Gly Met Gly Lys Ser Asp Ile Thr
275                 280                 285

Phe Pro Ile Met Ala Met Cys Leu Lys Glu Val Thr Val Arg Gly Ser
290                 295                 300

Phe Arg Tyr Gly Ala Gly Asp Tyr Glu Leu Ala Val Glu Leu Val Arg
305                 310                 315                 320

Thr Gly Arg Val Asp Val Lys Lys Leu Ile Thr Gly Thr Val Ser Phe
            325                 330                 335

Lys Gln Ala Glu Glu Ala Phe Gln Lys Val Lys Ser Gly Glu Ala Ile
        340                 345                 350

Lys Ile Leu Ile Ala Gly Pro Asn Glu Lys Val
            355                 360
```

<210> SEQ ID NO 161
<211> LENGTH: 1314
<212> TYPE: DNA
<213> ORGANISM: Pyromyces sp.

<400> SEQUENCE: 161
atggctaagg aatatttccc acaaattcaa aagattaagt tcgaaggtaa ggattctaag     60

```
aatccattag ccttccacta ctacgatgct gaaaaggaag tcatgggtaa gaaaatgaag      120
gattggttac gtttcgccat ggcctggtgg cacactcttt gcgccgaagg tgctgaccaa      180
ttcggtggag gtacaaagtc tttcccatgg aacgaaggta ctgatgctat tgaaattgcc      240
aagcaaaagg ttgatgctgg tttcgaaatc atgcaaaagc ttggtattcc atactactgt      300
ttccacgatg ttgatcttgt ttccgaaggt aactctattg aagaatacga atccaacctt      360
aaggctgtcg ttgcttacct caaggaaaag caaaaggaaa ccggtattaa gcttctctgg      420
agtactgcta acgtcttcgg tcacaagcgt acatgaacg gtgcctccac taacccagac       480
tttgatgttg tcgcccgtgc tattgttcaa attaagaacg ccatagacgc cggtattgaa      540
cttggtgctg aaaactacgt cttctggggt ggtcgtgaag gttacatgag tctccttaac      600
actgaccaaa agcgtgaaaa ggaacacatg gccactatgc ttaccatggc tcgtgactac      660
gctcgttcca agggattcaa gggtactttc ctcattgaac caaagccaat ggaaccaacc      720
aagcaccaat acgatgttga cactgaaacc gctattggtt tccttaaggc ccacaactta      780
gacaaggact tcaaggtcaa cattgaagtt aaccacgcta ctcttgctgg tcacactttc      840
gaacacgaac ttgcctgtgc tgttgatgct ggtatgctcg gttccattga tgctaaccgt      900
ggtgactacc aaaacggttg ggatactgat caattcccaa ttgatcaata cgaactcgtc      960
caagcttgga tggaaatcat ccgtggtggt ggtttcgtta ctggtggtac caacttcgat     1020
gccaagactc gtcgtaactc tactgacctc gaagacatca tcattgccca cgtttctggt     1080
atggatgcta tggctcgtgc tcttgaaaac gctgccaagc tcctccaaga atctccatac     1140
accaagatga agaaggaacg ttacgcttcc ttcgacagtg gtattggtaa ggactttgaa     1200
gatggtaagc tcaccctcga acaagtttac gaatacggta agaagaacgg tgaaccaaag     1260
caaacttctg gtaagcaaga actctacgaa gctattgttg ccatgtacca ataa           1314
```

<210> SEQ ID NO 162
<211> LENGTH: 1314
<212> TYPE: DNA
<213> ORGANISM: Pyromyces sp.

<400> SEQUENCE: 162

```
atggccaagg aatacttccc acaaatccaa aagattaaat cgaaggtaa agattccaag        60 aacccattgg cttttcacta ctacgatgct gagaaggaag ttatgggtaa gaagatgaag      120
gattggttga gattcgctat ggcttggtgg cacacttttgt gcgctgaagg tgctgaccaa     180
ttcggtggtg gtactaagtc tttcccatgg aacgaaggta ctgatgctat tgaaatcgct     240
aagcaaaaag tcgatgctgg ttttgagatt atgcaaaaat gggtatccc atactactgt      300 ttccacgacg tcgacttggt ttctgaaggt aattctatcg aagaatacga atctaatttg     360
aaggctgttg tcgcttactt aaaagaaaag caaaggaga ctggtattaa gttgttgtgg     420
tccaccgcta acgtctttgg tcataaaaga tacatgaacg gtgcttccac caacccagac     480
ttcgatgtcg tcgccagagc tatcgttcaa attaaaaacg ccatcgacgc tggtattgaa    540
ttgggtgctg aaaattacgt cttttgggt ggtcgtgaag gttacatgtc tttgttgaac     600
actgaccaaa agagagaaaa agaacacatg gccactatgt tgaccatggc cagagattac    660
gccagatcta agggtttcaa gggtaccttc ttaattgaac caaaacctat ggaaccaact    720
aagcaccaat acgacgttga cactgaaact gctatcggtt ttttgaaggc tcacaacttg    780
gataaggatt ttaaagtcaa cattgaagtt aaccatgcta ctttggctgg tcacactttt    840
```

```
gaacatgaat tggcctgtgc tgttgatgct ggtatgttgg gttctatcga tgctaataga      900
ggtgactatc aaaacggttg ggacactgat caattcccaa tcgatcaata tgaattagtt      960
caagcttgga tggaaattat cagaggtggt ggtttcgtta ctggtggtac taacttcgat     1020
gctaagacca aagaaactc tactgatttg aagatatta tcattgccca cgtttccggt       1080
atggatgcca tggccagagc tttggaaaac gccgccaagt tattgcaaga gtccccatac     1140
accaagatga aaaaggaacg ttacgcttct ttcgactctg gtatcggtaa agacttcgaa     1200
gatggtaagt tgaccttgga acaagtttac gaatacggta agaagaacgg tgaacctaaa     1260
caaacctctg gtaaacaaga attgtatgaa gctattgttg ccatgtacca ataa            1314
```

<210> SEQ ID NO 163
<211> LENGTH: 437
<212> TYPE: PRT
<213> ORGANISM: Pyromyces sp.

<400> SEQUENCE: 163

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
```

```
                290                 295                 300
Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
                340                 345                 350

Ile Ile Ile Ala His Val Ser Gly Met Asp Ala Met Ala Arg Ala Leu
            355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Tyr Gly Lys Lys Asn
                405                 410                 415

Gly Glu Pro Lys Gln Thr Ser Gly Lys Gln Glu Leu Tyr Glu Ala Ile
                420                 425                 430

Val Ala Met Tyr Gln
        435

<210> SEQ ID NO 164
<211> LENGTH: 657
<212> TYPE: DNA
<213> ORGANISM: Clostridium acetobutylicum

<400> SEQUENCE: 164
atgaactcta aataattag atttgaaaat ttaaggtcat tctttaaaga tgggatgaca      60
attatgattg gaggttttt aaactgtggc actccaacca aattaattga ttttttagtt     120
aatttaaata taagaatttt aacgattata agtaatgata catgttatcc taatacaggt    180
attggtaagt taatatcaaa taatcaagta aaaaagctta ttgcttcata taggcagc      240 aacccagata ctgcaaaaa acttttttaat aatgaacttg aagtagagct ctctccccaa    300
ggaactctag tggaaagaat acgtgcaggc ggatctggct taggtggtgt actaactaaa    360
acaggtttag gaactttgat tgaaaaagga agaaaaaaaa tatctataaa tggaacggaa    420
tatttgttag agctacctct tacagccgat gtagcattaa ttaaaggtag tattgtagat    480
gaggccggaa acaccttcta taaggtact actaaaaact ttaatcccta tatggcaatg    540
gcagctaaaa ccgtaatagt tgaagctgaa aatttagtta gctgtgaaaa actagaaaag    600
gaaaaagcaa tgaccccgg agttcttata aattatatag taaggagcc tgcataa       657

<210> SEQ ID NO 165
<211> LENGTH: 218
<212> TYPE: PRT
<213> ORGANISM: Clostridium acetobutylicum

<400> SEQUENCE: 165

Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
                20                  25                  30

Thr Lys Leu Ile Asp Phe Leu Val Asn Leu Asn Ile Lys Asn Leu Thr
            35                  40                  45

Ile Ile Ser Asn Asp Thr Cys Tyr Pro Asn Thr Gly Ile Gly Lys Leu
        50                  55                  60
```

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
            115                 120                 125

Lys Gly Lys Lys Lys Ile Ser Ile Asn Gly Thr Glu Tyr Leu Leu Glu
130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
            180                 185                 190

Val Ser Cys Glu Lys Leu Glu Lys Ala Met Thr Pro Gly Val
            195                 200                 205

Leu Ile Asn Tyr Ile Val Lys Glu Pro Ala
    210                 215

<210> SEQ ID NO 166
<211> LENGTH: 666
<212> TYPE: DNA
<213> ORGANISM: Clostridium acetobutylicum

<400> SEQUENCE: 166
atgattaatg ataaaaacct agcgaaagaa ataatagcca aaagagttgc aagagaatta      60
aaaaatggtc aacttgtaaa cttaggtgta ggtcttccta ccatggttgc agattatata     120
ccaaaaaatt tcaaaattac tttccaatca gaaacggaa tagttggaat gggcgctagt      180
cctaaaataa atgaggcaga taagatgta gtaaatgcag aggagacta tacaacagta       240 cttcctgacg gcacattttt cgatagctca gtttcgtttt cactaatccg tggtggtcac     300
gtagatgtta ctgttttagg ggctctccag gtagatgaaa agggtaatat agccaattgg     360
attgttcctg gaaaaatgct ctctggtatg ggtggagcta tggatttagt aaatggagct     420
aagaaagtaa taattgcaat gagacataca aataaaggtc aacctaaaat tttaaaaaaa     480
tgtacacttc ccctcacggc aaagtctcaa gcaaatctaa ttgtaacaga acttggagta     540
attgaggtta ttaatgatgg tttacttctc actgaaatta ataaaaacac aaccattgat     600
gaaataaggt ctttaactgc tgcagattta ctcatatcca atgaacttag acccatggct     660
gtttag                                                               666

<210> SEQ ID NO 167
<211> LENGTH: 221
<212> TYPE: PRT
<213> ORGANISM: Clostridium acetobutylicum

<400> SEQUENCE: 167

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
 65                  70                  75                  80

Leu Pro Asp Gly Thr Phe Phe Asp Ser Ser Val Ser Phe Ser Leu Ile
                 85                  90                  95

Arg Gly Gly His Val Asp Val Thr Val Leu Gly Ala Leu Gln Val Asp
                100                 105                 110

Glu Lys Gly Asn Ile Ala Asn Trp Ile Val Pro Gly Lys Met Leu Ser
                115                 120                 125

Gly Met Gly Gly Ala Met Asp Leu Val Asn Gly Ala Lys Lys Val Ile
            130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
                180                 185                 190

Ile Asn Lys Asn Thr Thr Ile Asp Glu Ile Arg Ser Leu Thr Ala Ala
                195                 200                 205

Asp Leu Leu Ile Ser Asn Glu Leu Arg Pro Met Ala Val
210                 215                 220

<210> SEQ ID NO 168
<211> LENGTH: 651
<212> TYPE: DNA
<213> ORGANISM: Escherichia coli

<400> SEQUENCE: 168
atggatgcga acaacgtat tgcgcgccgt gtggcgcaag agcttcgtga tggtgacatc       60
gttaacttag ggatcggttt acccacaatg gtcgccaatt atttaccgga gggtattcat      120
atcactctgc aatcggaaaa cggcttcctc ggtttaggcc cggtcacgac agcgcatcca      180
gatctggtga acgctggcgg gcaaccgtgc ggtgttttac ccggtgcagc catgtttgat      240
agcgccatgt catttgcgct aatccgtggc ggtcatattg atgcctgcgt gctcggcggt      300
ttgcaagtag acgaagaagc aaaccctcgc aactgggtag tgcctgggaa atggtgccc      360 ggtatgggtg gcgcgatgga tctggtgacc gggtcgcgca agtgatcat cgccatggaa       420 cattgcgcca agatggttc agcaaaaatt ttgcgccgct gcaccatgcc actcactgcg       480
caacatgcgg tgcatatgct ggttactgaa ctggctgtct ttcgttttat tgacggcaaa      540
atgtggctca ccgaaattgc cgacgggtgt gatttagcca ccgtgcgtgc caaaacagaa      600
gctcggtttg aagtcgccgc cgatctgaat acgcaacggg gtgatttatg a              651

<210> SEQ ID NO 169
<211> LENGTH: 216
<212> TYPE: PRT
<213> ORGANISM: Escherichia coli

<400> SEQUENCE: 169

Met Asp Ala Lys Gln Arg Ile Ala Arg Arg Val Ala Gln Glu Leu Arg
 1               5                  10                  15

Asp Gly Asp Ile Val Asn Leu Gly Ile Gly Leu Pro Thr Met Val Ala
                20                  25                  30

Asn Tyr Leu Pro Glu Gly Ile His Ile Thr Leu Gln Ser Glu Asn Gly
            35                  40                  45

```
Phe Leu Gly Leu Gly Pro Val Thr Thr Ala His Pro Asp Leu Val Asn
     50                  55                  60
Ala Gly Gly Gln Pro Cys Gly Val Leu Pro Gly Ala Ala Met Phe Asp
 65                  70                  75                  80
Ser Ala Met Ser Phe Ala Leu Ile Arg Gly Gly His Ile Asp Ala Cys
                 85                  90                  95
Val Leu Gly Gly Leu Gln Val Asp Glu Glu Ala Asn Leu Ala Asn Trp
            100                 105                 110
Val Val Pro Gly Lys Met Val Pro Gly Met Gly Ala Met Asp Leu
        115                 120                 125
Val Thr Gly Ser Arg Lys Val Ile Ile Ala Met Glu His Cys Ala Lys
130                 135                 140
Asp Gly Ser Ala Lys Ile Leu Arg Arg Cys Thr Met Pro Leu Thr Ala
145                 150                 155                 160
Gln His Ala Val His Met Leu Val Thr Glu Leu Ala Val Phe Arg Phe
                165                 170                 175
Ile Asp Gly Lys Met Trp Leu Thr Glu Ile Ala Asp Gly Cys Asp Leu
            180                 185                 190
Ala Thr Val Arg Ala Lys Thr Glu Ala Arg Phe Glu Val Ala Ala Asp
        195                 200                 205
Leu Asn Thr Gln Arg Gly Asp Leu
    210                 215

<210> SEQ ID NO 170
<211> LENGTH: 663
<212> TYPE: DNA
<213> ORGANISM: Escherichia coli

<400> SEQUENCE: 170
atgaaaacaa aattgatgac attacaagac gccaccggct tctttcgtga cggcatgacc      60
atcatggtgg gcggatttat ggggattggc actccatccc gctggttgaa agcattactg     120
gaatctggtg ttcgcgacct gacattgata gccaatgata ccgcgtttgt tgataccggc     180
atcggtccgc tcatcgtcaa tggtcgagtc cgcaaagtga ttgcttcaca tatcggcacc     240
aacccggaaa caggtcggcg catgatatct ggtgagatgg acgtcgttct ggtgccgcaa     300
ggtacgctaa tcgagcaaat cgctgtggt ggagctggac ttggtggttt ctctcacccca     360
acgggtgtcg gcaccgtcgt agaggaaggc aaacagacac tgacactcga cggtaaaacc     420
tggctgctcg aacgcccact gcgcgccgac ctggcgctaa ttcgcgctca tcgttgcgac     480
acacttggca acctgaccta tcaacttagc gcccgcaact ttaaccccct gatagccctt     540
gcggctgata tcacgctggt agagccagat gaactggtcg aaaccggcga gctgcaacct     600
gaccatattg tcaccctgg tgccgttatc gaccacatca tcgtttcaca ggagagcaaa     660
taa                                                                   663

<210> SEQ ID NO 171
<211> LENGTH: 220
<212> TYPE: PRT
<213> ORGANISM: Escherichia coli

<400> SEQUENCE: 171

Met Lys Thr Lys Leu Met Thr Leu Gln Asp Ala Thr Gly Phe Phe Arg
 1               5                  10                  15
Asp Gly Met Thr Ile Met Val Gly Gly Phe Met Gly Ile Gly Thr Pro
            20                  25                  30
```

```
Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys
    210                 215                 220
```

<210> SEQ ID NO 172
<211> LENGTH: 1056
<212> TYPE: DNA
<213> ORGANISM: Clostridium beijerinckii

<400> SEQUENCE: 172

```
atgaaaggtt ttgcaatgct aggtattaat aagttaggat ggatcgaaaa agaaaggcca    60
gttgcgggtt catatgatgc tattgtacgc ccattagcag tatctccgtg tacatcagat   120
atacatactg ttttttgaggg agctcttgga gataggaaga atatgatttt agggcatgaa   180
gctgtaggtg aagttgttga agtaggaagt gaagtgaagg attttaaacc tggtgacaga   240
gttatagttc cttgtacaac tccagattgg agatctttgg aagttcaagc tggttttcaa   300
cagcactcaa acggtatgct cgcaggatgg aaattttcaa atttcaagga tggagttttt   360
ggtgaatatt tcatgtaaa tgatgcggat atgaatcttg cgattctacc taaagacatg   420
ccattagaaa tgctgttat gataacagat atgatgacta ctggatttca tggagcagaa   480
cttgcagata ttcaaatggg ttcaagtgtt gtggtaattg cattggagc tgttggctta   540 atgggaatag caggtgctaa attacgtgga gcaggtagaa taattggagt ggggagcagg   600
ccgatttgtg ttgaggctgc aaaatttat ggagcaacag atattctaaa ttataaaaat   660
ggtcatatag ttgatcaagt tatgaaatta cgaatggaa aaggcgttga ccgcgtaatt   720
atggcaggcg gtggttctga acattatcc caagcagtat ctatggttaa accaggagga   780
ataatttcta atataaatta tcatggaagt ggagatgctt tactaatacc acgtgtagaa   840
tggggatgtg gaatggctca aagactata aaaggaggtc tttgtcctgg gggacgtttg   900
agagcagaaa tgttaagaga tatggtagta tataatcgtg ttgatctaag taaattagtt   960
acacatgtat atcatggatt tgatcacata gaagaagcac tgttattaat gaaagacaag  1020
```

```
ccaaaagact taattaaagc agtagttata ttataa                              1056
```

<210> SEQ ID NO 173
<211> LENGTH: 1056
<212> TYPE: DNA
<213> ORGANISM: Clostridium beijerinckii

<400> SEQUENCE: 173

```
atgaaagggt tgccatgtt aggtatcaat aaactgggct ggattgaaaa agagcgcccg      60
gtggcgggtt catacgatgc aattgttcgt ccgctggccg tcagtccgtg caccagcgac    120
atccatacag tctttgaagg tgccctgggt gatcggaaaa acatgattct ggccatgaa    180
gccgtaggcg aagtagtgga agtgggcagc gaggtaaagg atttcaaacc gggtgatcgc    240
gtaattgttc cttgcacgac cccagattgg cgctcactgg aagttcaggc tggttttcag    300
cagcatagta acggtatgtt agcaggctgg aagtttagca attttaaaga cggggtgttc    360
ggggagtatt ttcatgtcaa cgatgcggac atgaatctgg ctatttacc taaagatatg    420
ccgctggaga acgcagtgat gattaccgac atgatgacga caggcttca cggtgcagaa    480
ctggctgaca tccaaatggg ctccagtgtg gtggttatcg gtattggtgc ggtcgggctg    540
atgggtatcg cgggcgcgaa attacggggc gctggtcgca tcatcggtgt cggcagccgt    600
ccaatttgcg ttgaagcagc taaattctat ggtgccacgg acattctgaa ctataaaat    660
ggtcacatcg tcgatcaggt gatgaaactg accaatggca aggtgtgga ccgcgtgatc    720
atggcgggcg gcggctcaga gactttatct caagcggtgt ctatggttaa acctgggggc    780
atcatttcta atattaacta tcatggctcc ggcgacgcat tactgatccc gcgtgttgaa    840
tggggctgtg ggatggccca caaaaccatt aagggggt tatgtccggg tggtcgcctg    900
cgtgccgaaa tgctgcgtga catggtggtt tacaaccgtg tggatctgtc caaactggta    960
actcacgtat accacggttt cgatcacatt gaagaggcgc tgctgctgat gaaggataag   1020
ccaaaggatc tgattaaggc ggttgttatc ctgtaa                             1056
```

<210> SEQ ID NO 174
<211> LENGTH: 351
<212> TYPE: PRT
<213> ORGANISM: Clostridium beijerinckii

<400> SEQUENCE: 174

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
```

-continued

```
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
            340                 345                 350

<210> SEQ ID NO 175
<211> LENGTH: 2580
<212> TYPE: DNA
<213> ORGANISM: Clostridium carboxidivorans

<400> SEQUENCE: 175
atgaaggtaa ctaatgttga agaactgatg aaaaaaatgc aggaagtgca aaatgctcaa      60
aaaaaatttg ggagttttac tcaggaacaa gtagatgaaa ttttcaggca agcagcacta     120
gcagctaaca gtgccagaat agatctagct aaaatggcag tggaagaaac taaaatggga     180
attgtagagg ataaggttat aaaaaatcat tttgttgcag aatacatata taataagtat     240
aaaaatgaaa aaacttgtgg gattttggaa gaagatgaag gctttggaat ggttaaaatt     300
gcagaacctg taggtgtgat tgcagcagta attccaacaa caaatccaac atctacagca     360
atatttaaag cattattagc tttgaaaaca agaaatggta taattttttc accacatcca     420
agagcaaaaa agtgtactat tgcagcagct aagttagttc ttgatgctgc agttaaagca     480
ggtgctccta aaggaattat aggttggata gatgaacctt ctattgaact ttcacagata     540
gtaatgaaag aagctgatat aatccttgca acaggtggtc caggtatggt taaagcagct     600
tattcttcag gtaaacctgc tataggggtt ggtcctggta acacacctgc tttaattgat     660
gaaagtgctg atattaaaat ggcagtaaat tcaatacttc tttccaaaac ttttgataat     720
ggtatgattt gtgcttcaga gcagtcggta gtagttgtag attcaatata tgaagaagtt     780
aagaaagaat ttgctcatag aggagcttat attttaagta aggatgaaac aactaaagtt     840
ggaaaaatac tcttagttaa tggtacatta aatgctggta tcgttggtca gagtgcttat     900
```

```
aaaatagcag aaatggcagg agttaaagtt ccagaagatg ctaaagttct tataggagaa    960
gtaaaatcag tggagcattc agaagagcca ttttcacatg aaaagttatc tccagtttta   1020
gctatgtata gagctaaaaa ttttgatgaa gctcttttaa agctggaag attagttgaa    1080
ctcggtggaa tggtcatac atctgtatta tatgtaaatg caataactga aaaagtaaaa    1140
gtagaaaaat ttagagaaac tatgaagact ggtagaacat taataaatat gccttcagca   1200
caaggtgcta taggagacat ataacttt aaactagctc cttcattaac attaggttgt    1260
ggttcatggg gaggaaactc cgtatcagaa aatgttggac ctaaacactt attaaatata   1320
aaaagtgttg ctgagaggag agaaaatatg ctttggttta gagttcctga aaaggtttat   1380
tttaaatatg gtagtcttgg agttgcatta aaagaattag atattttgga taagaaaaaa   1440
gtatttatag taacagataa agttctttat caattaggtt atatagatag agttacaaag   1500
attcttgaag aattgaaaat ttcatataaa atatttacag atgtagaacc agatccaacc   1560
ctagctacag ctaaaaaagg tgcagaagaa ttgttatcat ttaatccaga tactattata   1620
gcagttggtg gtggttcagc aatggatgct gctaagatta tgtgggtaat gtatgaacat   1680
ccggaagtaa gatttgaaga tttagctatg agatttatgg atataagaaa gagagtatat   1740
acttttccta agatgggtga aaaagcaatg atgatttctg ttgcaacatc agcaggaaca   1800
ggatcagaag taacacccttt tgcagtaatt actgatgaaa aaacaggagc taaatatcca   1860
ttagctgatt atgaattaac tccaaatatg gctataattg atgctgaact tatgatgggt   1920
atgccaaaag gattaacagc agcttcagga atagatgcac taactcatgc aatagaagct   1980
tatgtatcaa taatggcttc agaatatact aatggattag cgttagaagc aataagattg   2040
atatttaagt atttaccaat agcttacagt gaaggaacaa caagtataaa ggcaagagaa   2100
aaaatggcgc atgcttcaac aatagctggt atggcatttg ctaatgcatt tttaggagta   2160
tgtcattcaa tggcacataa attaggatca actcatcacg taccacatgg cattgccaat   2220
gcactactta taaatgaagt tataaaattt aatgcagtag aaaatccaag aaaacaagct   2280
gcatttccac aatataagta tccaaatata aaaagagat atgctagaat agcagattac    2340
cttaacttag gtgggtcaac agacgatgaa aaagtacaat tattaataaa tgctatagat   2400
gaattaaaag ctaagataaa tattccagaa agtattaaag aagcaggagt aacagaagaa   2460
aaattttatg ctactttaga taaaatgtca gaattagctt ttgatgatca atgtacaggt   2520
gcaaacccta gatatccatt aataagtgaa ataaaacaaa tgtatgtaaa tgcattttaa   2580
```

<210> SEQ ID NO 176
<211> LENGTH: 859
<212> TYPE: PRT
<213> ORGANISM: Clostridium carboxidivorans

<400> SEQUENCE: 176

Met Lys Val Thr Asn Val Glu Glu Leu Met Lys Met Gln Glu Val
1               5                   10                  15

Gln Asn Ala Gln Lys Lys Phe Gly Ser Phe Thr Gln Glu Gln Val Asp
            20                  25                  30

Glu Ile Phe Arg Gln Ala Ala Leu Ala Ala Asn Ser Ala Arg Ile Asp
        35                  40                  45

Leu Ala Lys Met Ala Val Glu Glu Thr Lys Met Gly Ile Val Glu Asp
    50                  55                  60

Lys Val Ile Lys Asn His Phe Val Ala Glu Tyr Ile Tyr Asn Lys Tyr
65                  70                  75                  80

-continued

```
Lys Asn Glu Lys Thr Cys Gly Ile Leu Glu Glu Asp Glu Gly Phe Gly
                85                  90                  95

Met Val Lys Ile Ala Glu Pro Val Gly Val Ile Ala Ala Val Ile Pro
            100                 105                 110

Thr Thr Asn Pro Thr Ser Thr Ala Ile Phe Lys Ala Leu Leu Ala Leu
        115                 120                 125

Lys Thr Arg Asn Gly Ile Ile Phe Ser Pro His Pro Arg Ala Lys Lys
    130                 135                 140

Cys Thr Ile Ala Ala Lys Leu Val Leu Asp Ala Ala Val Lys Ala
145                 150                 155                 160

Gly Ala Pro Lys Gly Ile Ile Gly Trp Ile Asp Glu Pro Ser Ile Glu
                165                 170                 175

Leu Ser Gln Ile Val Met Lys Glu Ala Asp Ile Ile Leu Ala Thr Gly
            180                 185                 190

Gly Pro Gly Met Val Lys Ala Ala Tyr Ser Ser Gly Lys Pro Ala Ile
        195                 200                 205

Gly Val Gly Pro Gly Asn Thr Pro Ala Leu Ile Asp Glu Ser Ala Asp
    210                 215                 220

Ile Lys Met Ala Val Asn Ser Ile Leu Leu Ser Lys Thr Phe Asp Asn
225                 230                 235                 240

Gly Met Ile Cys Ala Ser Glu Gln Ser Val Val Val Asp Ser Ile
                245                 250                 255

Tyr Glu Glu Val Lys Lys Glu Phe Ala His Arg Gly Ala Tyr Ile Leu
            260                 265                 270

Ser Lys Asp Glu Thr Thr Lys Val Gly Lys Ile Leu Leu Val Asn Gly
        275                 280                 285

Thr Leu Asn Ala Gly Ile Val Gly Gln Ser Ala Tyr Lys Ile Ala Glu
    290                 295                 300

Met Ala Gly Val Lys Val Pro Glu Asp Ala Lys Val Leu Ile Gly Glu
305                 310                 315                 320

Val Lys Ser Val Glu His Ser Glu Glu Pro Phe Ser His Glu Lys Leu
                325                 330                 335

Ser Pro Val Leu Ala Met Tyr Arg Ala Lys Asn Phe Asp Glu Ala Leu
            340                 345                 350

Leu Lys Ala Gly Arg Leu Val Glu Leu Gly Gly Met Gly His Thr Ser
        355                 360                 365

Val Leu Tyr Val Asn Ala Ile Thr Glu Lys Val Lys Val Glu Lys Phe
    370                 375                 380

Arg Glu Thr Met Lys Thr Gly Arg Thr Leu Ile Asn Met Pro Ser Ala
385                 390                 395                 400

Gln Gly Ala Ile Gly Asp Ile Tyr Asn Phe Lys Leu Ala Pro Ser Leu
                405                 410                 415

Thr Leu Gly Cys Gly Ser Trp Gly Gly Asn Ser Val Ser Glu Asn Val
            420                 425                 430

Gly Pro Lys His Leu Leu Asn Ile Lys Ser Val Ala Glu Arg Arg Glu
        435                 440                 445

Asn Met Leu Trp Phe Arg Val Pro Glu Lys Val Tyr Phe Lys Tyr Gly
    450                 455                 460

Ser Leu Gly Val Ala Leu Lys Glu Leu Asp Ile Leu Asp Lys Lys Lys
465                 470                 475                 480

Val Phe Ile Val Thr Asp Lys Val Leu Tyr Gln Leu Gly Tyr Ile Asp
                485                 490                 495

Arg Val Thr Lys Ile Leu Glu Glu Leu Lys Ile Ser Tyr Lys Ile Phe
```

```
                500             505             510
Thr Asp Val Glu Pro Asp Pro Thr Leu Ala Thr Ala Lys Lys Gly Ala
            515                 520             525
Glu Glu Leu Leu Ser Phe Asn Pro Asp Thr Ile Ile Ala Val Gly Gly
            530                 535             540
Gly Ser Ala Met Asp Ala Ala Lys Ile Met Trp Val Met Tyr Glu His
545                 550                 555                 560
Pro Glu Val Arg Phe Glu Asp Leu Ala Met Arg Phe Met Asp Ile Arg
                565                 570                 575
Lys Arg Val Tyr Thr Phe Pro Lys Met Gly Glu Lys Ala Met Met Ile
            580                 585                 590
Ser Val Ala Thr Ser Ala Gly Thr Gly Ser Glu Val Thr Pro Phe Ala
            595                 600                 605
Val Ile Thr Asp Glu Lys Thr Gly Ala Lys Tyr Pro Leu Ala Asp Tyr
            610                 615                 620
Glu Leu Thr Pro Asn Met Ala Ile Ile Asp Ala Glu Leu Met Met Gly
625                 630                 635                 640
Met Pro Lys Gly Leu Thr Ala Ala Ser Gly Ile Asp Ala Leu Thr His
                645                 650                 655
Ala Ile Glu Ala Tyr Val Ser Ile Met Ala Ser Glu Tyr Thr Asn Gly
                660                 665                 670
Leu Ala Leu Glu Ala Ile Arg Leu Ile Phe Lys Tyr Leu Pro Ile Ala
            675                 680                 685
Tyr Ser Glu Gly Thr Thr Ser Ile Lys Ala Arg Glu Lys Met Ala His
            690                 695                 700
Ala Ser Thr Ile Ala Gly Met Ala Phe Ala Asn Ala Phe Leu Gly Val
705                 710                 715                 720
Cys His Ser Met Ala His Lys Leu Gly Ser Thr His His Val Pro His
                725                 730                 735
Gly Ile Ala Asn Ala Leu Leu Ile Asn Glu Val Ile Lys Phe Asn Ala
                740                 745                 750
Val Glu Asn Pro Arg Lys Gln Ala Ala Phe Pro Gln Tyr Lys Tyr Pro
            755                 760                 765
Asn Ile Lys Lys Arg Tyr Ala Arg Ile Ala Asp Tyr Leu Asn Leu Gly
            770                 775                 780
Gly Ser Thr Asp Asp Glu Lys Val Gln Leu Leu Ile Asn Ala Ile Asp
785                 790                 795                 800
Glu Leu Lys Ala Lys Ile Asn Ile Pro Glu Ser Ile Lys Glu Ala Gly
                805                 810                 815
Val Thr Glu Glu Lys Phe Tyr Ala Thr Leu Asp Lys Met Ser Glu Leu
            820                 825                 830
Ala Phe Asp Asp Gln Cys Thr Gly Ala Asn Pro Arg Tyr Pro Leu Ile
            835                 840                 845
Ser Glu Ile Lys Gln Met Tyr Val Asn Ala Phe
850                 855
```

<210> SEQ ID NO 177
<211> LENGTH: 1401
<212> TYPE: DNA
<213> ORGANISM: Escherichia coli

<400> SEQUENCE: 177
atgccacatt cctacgatta cgatgccata gtaataggtt ccggccccgg cggcgaaggc       60
gctgcaatgg gcctggttaa gcaaggtgcg cgcgtcgcag ttatcgagcg ttatcaaaat      120

-continued

```
gttggcggcg gttgcaccca ctggggcacc atcccgtcga agctctccg tcacgccgtc    180 agccgcatta tagaattcaa tcaaaaccca ctttacagcg accattcccg actgctccgc    240
tcttcttttg ccgatatcct taaccatgcc gataacgtga ttaatcaaca aacgcgcatg    300
cgtcagggat tttacgaacg taatcactgt gaaatattgc agggaaacgc tcgctttgtt    360
gacgagcata cgttggcgct ggattgcccg gacggcagcg ttgaaacact aaccgctgaa    420
aaatttgtta ttgcctgcgg ctctcgtcca tatcatccaa cagatgttga tttcacccat    480
ccacgcattt acgacagcga ctcaattctc agcatgcacc acgaaccgcg ccatgtactt    540
atctatggtg ctggagtgat cggctgtgaa tatgcgtcga tcttccgcgg tatggatgta    600
aaagtggatc tgatcaacac ccgcgatcgc ctgctggcat ttctcgatca agagatgtca    660
gattctctct cctatcactt ctggaacagt ggcgtagtga ttcgtcacaa cgaagagtac    720
gagaagatcg aaggctgtga cgatggtgtg atcatgcatc tgaagtcggg taaaaaactg    780
aaagctgact gcctgctcta tgccaacggt cgcaccggta ataccgattc gctggcgtta    840
cagaacattg ggctagaaac tgacagccgc ggacagctga aggtcaacag catgtatcag    900
accgcacagc cacacgttta cgcggtgggc gacgtgattg gttatccgag cctggcgtcg    960
gcggcctatg accaggggcg cattgccgcg caggcgctgg taaaaggcga agccaccgca    1020
catctgattc aagatatccc taccggtatt tacaccatcc cggaaatcag ctctgtgggc    1080
aaaaccgaac agcagctgac cgcaatgaaa gtgccatatg aagtgggccg cgcccagttt    1140
aaacatctgg cacgcgcaca atcgtcggc atgaacgtgg cacgctgaa aattttgttc    1200 catcgggaaa caaaagagat tctgggtatt cactgctttg gcgagcgcgc tgccgaaatt    1260
attcatatcg gtcaggcgat tatggaacag aaaggtggcg gcaacactat tgagtacttc    1320
gtcaacacca cctttaacta cccgacgatg gcggaagcct atcgggtagc tgcgttaaac    1380
ggtttaaacc gcctgtttta a                                             1401
```

<210> SEQ ID NO 178
<211> LENGTH: 466
<212> TYPE: PRT
<213> ORGANISM: Escherichia coli

<400> SEQUENCE: 178

```
Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140
```

```
Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
            165                 170                 175

Arg His Val Leu Ile Tyr Gly Ala Gly Val Ile Gly Cys Glu Tyr Ala
        180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Glu Gln Gln Leu Thr Ala
        355                 360                 365

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415

Ala Ala Glu Ile Ile His Ile Gly Gln Ala Ile Met Glu Gln Lys Gly
            420                 425                 430

Gly Gly Asn Thr Ile Glu Tyr Phe Val Asn Thr Thr Phe Asn Tyr Pro
        435                 440                 445

Thr Met Ala Glu Ala Tyr Arg Val Ala Ala Leu Asn Gly Leu Asn Arg
    450                 455                 460

Leu Phe
465

<210> SEQ ID NO 179
<211> LENGTH: 41
<212> TYPE: DNA
<213> ORGANISM: artificial
<220> FEATURE:
<223> OTHER INFORMATION: Forward primer to amplify fucA and fucO

<400> SEQUENCE: 179
cctttaataa ggagatatac catggaacga aataaacttg c                                41

<210> SEQ ID NO 180
<211> LENGTH: 56
```

-continued

<212> TYPE: DNA
<213> ORGANISM: artificial
<220> FEATURE:
<223> OTHER INFORMATION: Reverse primer to amplify fucA and fucO

<400> SEQUENCE: 180
ggttattcct ccttatttag agctctaaac gaattcttac caggcggtat ggtaaa         56

<210> SEQ ID NO 181
<211> LENGTH: 56
<212> TYPE: DNA
<213> ORGANISM: artificial
<220> FEATURE:
<223> OTHER INFORMATION: Forward primer to amplify fucK

<400> SEQUENCE: 181
gaattcgttt agagctctaa ataaggagga ataaccatga tgaaacaaga agttat         56

<210> SEQ ID NO 182
<211> LENGTH: 40
<212> TYPE: DNA
<213> ORGANISM: artificial
<220> FEATURE:
<223> OTHER INFORMATION: Reverse primer to amplify fucK

<400> SEQUENCE: 182
gagctcggta cccgggggatc caaaaaaccc ctcaagaccc                          40

<210> SEQ ID NO 183
<211> LENGTH: 39
<212> TYPE: DNA
<213> ORGANISM: artificial
<220> FEATURE:
<223> OTHER INFORMATION: Forward primer to amplify thl

<400> SEQUENCE: 183
ctgttgttat attgtaatga tgtatgcaag agggataaa                            39

<210> SEQ ID NO 184
<211> LENGTH: 38
<212> TYPE: DNA
<213> ORGANISM: artificial
<220> FEATURE:
<223> OTHER INFORMATION: Reverse primer to amplify thl

<400> SEQUENCE: 184
tatatctcct tcttaaagtt cataaatcac cccgttgc                             38

<210> SEQ ID NO 185
<211> LENGTH: 21
<212> TYPE: DNA
<213> ORGANISM: artificial
<220> FEATURE:
<223> OTHER INFORMATION: Forward primer to amplify fucO

<400> SEQUENCE: 185
atggctaaca gaatgattct g                                               21

<210> SEQ ID NO 186
<211> LENGTH: 23
<212> TYPE: DNA
<213> ORGANISM: artificial
<220> FEATURE:
<223> OTHER INFORMATION: Reverse primer to amplify fucO

<400> SEQUENCE: 186
ttaccaggcg gtatggtaaa gct                                              23

<210> SEQ ID NO 187
<211> LENGTH: 39
<212> TYPE: DNA
<213> ORGANISM: artificial
<220> FEATURE:
<223> OTHER INFORMATION: Forward primer to amplify atoA/D

<400> SEQUENCE: 187
ctgttgttat attgtaatga tgtatgcaag agggataaa                             39

<210> SEQ ID NO 188
<211> LENGTH: 38
<212> TYPE: DNA
<213> ORGANISM: artificial
<220> FEATURE:
<223> OTHER INFORMATION: Reverse primer to amplify atoA/D

<400> SEQUENCE: 188
tatatctcct tcttaaagtt cataaatcac cccgttgc                              38

<210> SEQ ID NO 189
<211> LENGTH: 1323
<212> TYPE: DNA
<213> ORGANISM: Escherichia coli

<400> SEQUENCE: 189
atgcaagcct attttgacca gctcgatcgc gttcgttatg aaggctcaaa atcctcaaac      60
ccgttagcat tccgtcacta caatcccgac gaactggtgt tgggtaagcg tatggaagag     120
cacttgcgtt ttgccgcctg ctactggcac accttctgct ggaacggggc ggatatgttt     180
ggtgtggggg cgtttaatcg tccgtggcag cagcctggtg aggcactggc gttggcgaag     240
cgtaaagcag atgtcgcatt tgagttttc cacaagttac atgtgccatt ttattgcttc     300
cacgatgtgg atgtttcccc tgagggcgcg tcgttaaaag agtacatcaa taattttgcg     360
caaatggttg atgtcctggc aggcaagcaa gaagagagcg gcgtgaagct gctgtgggga     420
acggccaact gctttacaaa ccctcgctac ggcgcgggtg cggcgacgaa cccagatcct     480
gaagtcttca gctgggcggc aacgcaagtt gttacagcga tggaagcaac ccataaattg     540
ggcggtgaaa actatgtcct gtggggcggt cgtgaaggtt acgaaacgct gttaaatacc     600
gacttgcgtc aggagcgtga acaactgggc cgctttatgc agatggtggt tgagcataaa     660
cataaaatcg gtttccaggg cacgttgctt atcgaaccga accgcaaga accgaccaaa     720 catcaatatg attacgatgc cgcgacggtc tatggcttcc tgaaacagtt tggtctggaa     780
aaagagatta aactgaacat tgaagctaac cacgcgacgc tggcaggtca ctcttttccat     840 catgaaatag ccaccgccat tgcgcttggc ctgttcggtt ctgtcgacgc caaccgtggc     900
gatgcgcaac tgggctggga caccgaccag ttcccgaaca gtgtggaaga gaatgcgctg     960
gtgatgtatg aaattctcaa agcaggcggt ttcaccaccg tggtctgaa cttcgatgcc    1020 aaagtacgtc gtcaaagtac tgataaatat gatctgtttt acggtcatat cggcgcgatg    1080
gatacgatgg cactggcgct gaaaattgca gcgcgcatga ttgaagatgg cgagctggat    1140
aaacgcatcg cgcagcgtta ttccggctgg aatagcgaat tgggccagca aatcctgaaa    1200
ggccaaatgt cactggcaga tttagccaaa tatgctcagg aacatcattt gtctccggtg    1260
catcagagtg tcgccagga acaactggaa aatctggtaa accattatct gttcgacaaa    1320
taa                                                                  1323

<210> SEQ ID NO 190
<211> LENGTH: 440
<212> TYPE: PRT
<213> ORGANISM: Escherichia coli

<400> SEQUENCE: 190

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

Ile Ala Ala Arg Met Ile Glu Asp Gly Glu Leu Asp Lys Arg Ile Ala

```
        370                 375                 380
Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
            405                 410                 415

Leu Ser Pro Val His Gln Ser Gly Arg Gln Glu Gln Leu Glu Asn Leu
            420                 425                 430

Val Asn His Tyr Leu Phe Asp Lys
            435                 440
```